US009801868B2

(12) United States Patent
Muller et al.

(10) Patent No.: US 9,801,868 B2
(45) Date of Patent: Oct. 31, 2017

(54) 5-SUBSTITUTED ISOINDOLINE COMPOUNDS

(71) Applicant: Celgene Corporation, Summit, NJ (US)

(72) Inventors: George W. Muller, Rancho Santa Fe, CA (US); Roger Shen-Chu Chen, Edison, NJ (US); Alexander L. Ruchelman, Cream Ridge, NJ (US)

(73) Assignee: Celgene Corporation, Summit, NJ (US)

( * ) Notice: Subject to any disclaimer, the term of this patent is extended or adjusted under 35 U.S.C. 154(b) by 0 days.

(21) Appl. No.: 15/233,803

(22) Filed: Aug. 10, 2016

(65) Prior Publication Data

US 2016/0346264 A1     Dec. 1, 2016

Related U.S. Application Data

(60) Division of application No. 14/490,554, filed on Sep. 18, 2014, now Pat. No. 9,447,070, which is a continuation of application No. 12/130,445, filed on May 30, 2008, now Pat. No. 8,877,780, which is a continuation-in-part of application No. 11/897,339, filed on Aug. 29, 2007, now abandoned.

(60) Provisional application No. 60/937,782, filed on Jun. 28, 2007, provisional application No. 60/925,513, filed on Apr. 20, 2007, provisional application No. 60/841,365, filed on Aug. 30, 2006.

(51) Int. Cl.

| | |
|---|---|
| *A61K 31/454* | (2006.01) |
| *C07D 401/04* | (2006.01) |
| *C07D 401/14* | (2006.01) |
| *C07D 405/14* | (2006.01) |
| *C07D 409/14* | (2006.01) |
| *C07D 413/14* | (2006.01) |
| *A61K 31/4545* | (2006.01) |
| *A61K 31/4709* | (2006.01) |
| *A61K 31/4725* | (2006.01) |
| *A61K 31/496* | (2006.01) |
| *A61K 31/501* | (2006.01) |
| *A61K 31/5377* | (2006.01) |

(52) U.S. Cl.
CPC ........ *A61K 31/454* (2013.01); *A61K 31/4545* (2013.01); *A61K 31/4709* (2013.01); *A61K 31/4725* (2013.01); *A61K 31/496* (2013.01); *A61K 31/501* (2013.01); *A61K 31/5377* (2013.01); *C07D 401/04* (2013.01); *C07D 401/14* (2013.01); *C07D 405/14* (2013.01); *C07D 409/14* (2013.01); *C07D 413/14* (2013.01)

(58) Field of Classification Search
None
See application file for complete search history.

(56) References Cited

U.S. PATENT DOCUMENTS

| | | | |
|---|---|---|---|
| 5,635,517 A | 6/1997 | Muller et al. | |
| 5,955,476 A | 9/1999 | Muller et al. | |
| 6,335,349 B1 | 1/2002 | Muller et al. | |
| 6,395,754 B1 | 5/2002 | Muller et al. | |
| 7,091,353 B2 | 8/2006 | Robarge et al. | |
| 7,576,104 B2 | 8/2009 | Robarge et al. | |
| 7,964,354 B2 | 6/2011 | Ferguson et al. | |
| 8,012,997 B2 | 9/2011 | Robarge et al. | |
| 2003/0096841 A1 | 5/2003 | Robarge et al. | |
| 2004/0077685 A1 | 4/2004 | Figg et al. | |
| 2008/0161328 A1 | 7/2008 | Muller et al. | |
| 2009/0142297 A1 | 6/2009 | Muller et al. | |
| 2011/0144158 A1 | 6/2011 | Muller et al. | |

FOREIGN PATENT DOCUMENTS

| | | |
|---|---|---|
| JP | 2000-159761 | 6/2000 |
| WO | 02/059106 A1 | 8/2002 |
| WO | 2004/103274 A2 | 12/2004 |
| WO | 2005/028436 A2 | 3/2005 |
| WO | 2008/027542 A2 | 3/2008 |
| WO | 2008/039489 A2 | 4/2008 |

OTHER PUBLICATIONS

Federal Register, "Examination guidelines update: developments in obviousness inquiry after KSR v. Teleflex," pp. 1-34 (2010).
Jonsson et al., "Chemical structure and teratogenic properties. II. Synthesis and teratogenic activity in rabbits of some derivatives of phthalmide, isoindoline-1-one, 1,2-benzisothiazoline-3-one-1,1-dioxide and 4(3H)-quinazolinone," Acta Pharm. Suec., 9:431-446 (1972).
Morrisette et al., "High-throughput crystallization: polymorphs, salts, co-crystals and solvates of pharmaceutical solids," Adv. Drug Del. Rev., 56:275-300 (2004).
Muller et al., "Amino-substituted thalidomide analogs: potent inhibitors of TNF-α production," Bioorg. Med. Chem. Lett., 9:1625-1630 (1999).
Ruchelman et al., "Isosteric analogs of lenalidomide and pomalidomide: synthesis and biological activity," Bioorg. Med. Chem. Lett., 23:360-365 (2013).
Souillac et al., "Characterization of delivery systems, differential scanning calorimetry," in Encyclopedia of controlled Drug Delivery, John Wiley & Sons, pp. 212-227 (1999).
Vippagunta et al., "Crystalline solids," Adv. Drug Del. Rev., 48:3-26 (2001).

*Primary Examiner* — Heidi Reese
(74) *Attorney, Agent, or Firm* — Jones Day

(57) ABSTRACT

This invention relates to 5-substituted isoindoline compounds, and pharmaceutically acceptable salts, solvates, stereoisomers, and prodrugs thereof. Methods of use, and pharmaceutical compositions of these compounds are disclosed.

3 Claims, No Drawings

5-SUBSTITUTED ISOINDOLINE COMPOUNDS

This application is a divisional of U.S. application Ser. No. 14/490,554, filed Sep. 18, 2014, which is a continuation of U.S. application Ser. No. 12/130,445, filed May 30, 2008, now U.S. Pat. No. 8,877,780, issued Nov. 4, 2014, which is a continuation-in-part of U.S. application Ser. No. 11/897,339, filed Aug. 29, 2007, which claims priority to U.S. Provisional Application Nos. 60/841,365, filed Aug. 30, 2006, 60/925,513, filed Apr. 20, 2007, and 60/937,782, filed Jun. 28, 2007, all of which are incorporated herein by reference in their entireties.

1. FIELD OF THE INVENTION

This invention relates to 5-substituted isoindole compounds. Pharmaceutical compositions comprising the compounds and methods for treating, preventing and managing various disorders are also disclosed.

2. BACKGROUND OF THE INVENTION

2.1 Pathobiology of Cancer and Other Diseases

Cancer is characterized primarily by an increase in the number of abnormal cells derived from a given normal tissue, invasion of adjacent tissues by these abnormal cells, or lymphatic or blood-borne spread of malignant cells to regional lymph nodes and to distant sites (metastasis). Clinical data and molecular biologic studies indicate that cancer is a multistep process that begins with minor pre-neoplastic changes, which may under certain conditions progress to neoplasia. The neoplastic lesion may evolve clonally and develop an increasing capacity for invasion, growth, metastasis, and heterogeneity, especially under conditions in which the neoplastic cells escape the host's immune surveillance. Roitt, I., Brostoff, J and Kale, D., *Immunology*, 17.1-17.12 (3rd ed., Mosby, St. Louis, Mo., 1993).

There is an enormous variety of cancers which are described in detail in the medical literature. Examples includes cancer of the lung, colon, rectum, prostate, breast, brain, and intestine. The incidence of cancer continues to climb as the general population ages, as new cancers develop, and as susceptible populations (e.g., people infected with AIDS or excessively exposed to sunlight) grow. However, options for the treatment of cancer are limited. For example, in the case of blood cancers (e.g., multiple myeloma), few treatment options are available, especially when conventional chemotherapy fails and bone-marrow transplantation is not an option. A tremendous demand therefore exists for new methods and compositions that can be used to treat patients with cancer.

Many types of cancers are associated with new blood vessel formation, a process known as angiogenesis. Several of the mechanisms involved in tumor-induced angiogenesis have been elucidated. The most direct of these mechanisms is the secretion by the tumor cells of cytokines with angiogenic properties. Examples of these cytokines include acidic and basic fibroblastic growth factor (a,b-FGF), angiogenin, vascular endothelial growth factor (VEGF), and TNFα. Alternatively, tumor cells can release angiogenic peptides through the production of proteases and the subsequent breakdown of the extracellular matrix where some cytokines are stored (e.g., b-FGF). Angiogenesis can also be induced indirectly through the recruitment of inflammatory cells (particularly macrophages) and their subsequent release of angiogenic cytokines (e.g., TNF-α, bFGF).

A variety of other diseases and disorders are also associated with, or characterized by, undesired angiogenesis. For example, enhanced or unregulated angiogenesis has been implicated in a number of diseases and medical conditions including, but not limited to, ocular neovascular diseases, choroidal neovascular diseases, retina neovascular diseases, rubeosis (neovascularization of the angle), viral diseases, genetic diseases, inflammatory diseases, allergic diseases, and autoimmune diseases. Examples of such diseases and conditions include, but are not limited to: diabetic retinopathy; retinopathy of prematurity; corneal graft rejection; neovascular glaucoma; retrolental fibroplasia; arthritis; and proliferative vitreoretinopathy.

Accordingly, compounds that can control angiogenesis or inhibit the production of certain cytokines, including TNFα, may be useful in the treatment and prevention of various diseases and conditions.

2.2 Methods of Treating Cancer

Current cancer therapy may involve surgery, chemotherapy, hormonal therapy and/or radiation treatment to eradicate neoplastic cells in a patient (see, e.g., Stockdale, 1998, *Medicine*, vol. 3, Rubenstein and Federman, eds., Chapter 12, Section IV). Recently, cancer therapy could also involve biological therapy or immunotherapy. All of these approaches pose significant drawbacks for the patient. Surgery, for example, may be contraindicated due to the health of a patient or may be unacceptable to the patient. Additionally, surgery may not completely remove neoplastic tissue. Radiation therapy is only effective when the neoplastic tissue exhibits a higher sensitivity to radiation than normal tissue. Radiation therapy can also often elicit serious side effects. Hormonal therapy is rarely given as a single agent. Although hormonal therapy can be effective, it is often used to prevent or delay recurrence of cancer after other treatments have removed the majority of cancer cells. Biological therapies and immunotherapies are limited in number and may produce side effects such as rashes or swellings, flu-like symptoms, including fever, chills and fatigue, digestive tract problems or allergic reactions.

With respect to chemotherapy, there are a variety of chemotherapeutic agents available for treatment of cancer. A majority of cancer chemotherapeutics act by inhibiting DNA synthesis, either directly, or indirectly by inhibiting the biosynthesis of deoxyribonucleotide triphosphate precursors, to prevent DNA replication and concomitant cell division. Gilman et al., Goodman and Gilman's: *The Pharmacological Basis of Therapeutics*, Tenth Ed. (McGraw Hill, New York).

Despite availability of a variety of chemotherapeutic agents, chemotherapy has many drawbacks. Stockdale, *Medicine*, vol. 3, Rubenstein and Federman, eds., ch. 12, sect. 10, 1998. Almost all chemotherapeutic agents are toxic, and chemotherapy causes significant, and often dangerous side effects including severe nausea, bone marrow depression, and immunosuppression. Additionally, even with administration of combinations of chemotherapeutic agents, many tumor cells are resistant or develop resistance to the chemotherapeutic agents. In fact, those cells resistant to the particular chemotherapeutic agents used in the treatment protocol often prove to be resistant to other drugs, even if those agents act by different mechanism from those of the drugs used in the specific treatment. This phenomenon is referred to as pleiotropic drug or multidrug resistance.

Because of the drug resistance, many cancers prove or become refractory to standard chemotherapeutic treatment protocols.

Other diseases or conditions associated with, or characterized by, undesired angiogenesis are also difficult to treat. However, some compounds such as protamine, hepain and steroids have been proposed to be useful in the treatment of certain specific diseases. Taylor et al., *Nature* 297:307 (1982); Folkman et al., *Science* 221:719 (1983); and U.S. Pat. Nos. 5,001,116 and 4,994,443.

Still, there is a significant need for effective methods of treating, preventing and managing cancer and other diseases and conditions, particularly for diseases that are refractory to standard treatments, such as surgery, radiation therapy, chemotherapy and hormonal therapy, while reducing or avoiding the toxicities and/or side effects associated with the conventional therapies.

3. SUMMARY OF THE INVENTION

This invention is directed, in part, to 5-substituted isoindole compounds, and pharmaceutically acceptable salts, solvates (e.g., hydrates), prodrugs, or stereoisomers thereof.

This invention also encompasses methods of treating and managing various diseases or disorders. The methods comprise administering to a patient in need of such treatment or management a therapeutically effective amount of a compound of this invention, or a pharmaceutically acceptable salt, solvate, stereoisomer, or prodrug thereof.

The invention also encompasses methods of preventing various diseases and disorders, which comprise administering to a patient in need of such prevention a prophylactically effective amount of a compound of this invention, or a pharmaceutically acceptable salt, solvate, hydrate, stereoisomer, or prodrug thereof.

This invention also encompasses pharmaceutical compositions, single unit dosage forms, dosing regimens and kits which comprise a compound of this invention, or a pharmaceutically acceptable salt, solvate, hydrate, stereoisomer, clathrate, or prodrug thereof.

4. DETAILED DESCRIPTION OF THE INVENTION

In one embodiment, this invention encompasses 5-substituted isoindole compounds, and pharmaceutically acceptable salts, solvates, stereoisomers and prodrugs thereof.

In another embodiment, this invention encompasses methods of treating, managing, and preventing various diseases and disorders, which comprise administering to a patient in need of such treatment or prevention a therapeutically or prophylactically effective amount of a compound of this invention, or a pharmaceutically acceptable salt, solvate, stereoisomer or prodrug thereof. Examples of diseases and disorders are described herein.

In particular embodiments, a compound of this invention, or a pharmaceutically acceptable salt, solvate, stereoisomer, or prodrug thereof, is administered in combination with another drug ("second active agent") or treatment. Second active agents include small molecules and large molecules (e.g., proteins and antibodies), examples of which are provided herein, as well as stem cells. Methods, or therapies, that can be used in combination with the administration of compounds of this invention include, but are not limited to, surgery, blood transfusions, immunotherapy, biological therapy, radiation therapy, and other non-drug based therapies presently used to treat, prevent or manage various disorders described herein.

This invention also encompasses pharmaceutical compositions (e.g., single unit dosage forms) that can be used in methods disclosed herein. Particular pharmaceutical compositions comprise a compound of this invention, or a pharmaceutically acceptable salt, solvate, stereoisomer, or prodrug thereof, and optionally a second active agent.

4.1 Compounds

In one embodiment, this invention encompasses compounds of formula (I):

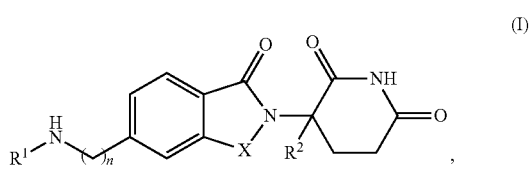

and pharmaceutically acceptable salts, solvates, stereoisomers, and prodrugs thereof, wherein:

n is 0 or 1;

X is $CH_2$, $C=O$, or $C=S$;

$R^1$ is:

a) —$(CH_2)_m R^3$ or —$CO(CH_2)_m R^3$, wherein m is 0, 1, 2, or 3; and $R^3$ is 5-10 membered aryl or heteroaryl, optionally substituted with one or more halogen;

b) —$C=YR^4$, wherein

Y is O or S; and $R^4$ is:

($C_1$-$C_{10}$)alkyl; ($C_1$-$C_{10}$)alkoxy;

($C_0$-$C_{10}$)alkyl-(5 to 10 membered heteroaryl or heterocycle), said heteroaryl or heterocycle optionally substituted with one or more of ($C_1$-$C_6$)alkyl, halogen, oxo, ($C_1$-$C_6$)alkoxy, or —Z—($C_1$-$C_6$)alkyl, wherein Z is S or $SO_2$, and wherein said ($C_1$-$C_6$)alkyl may be optionally substituted with one or more halogen;

($C_0$-$C_{10}$)alkyl-(5 to 10 membered aryl), said aryl optionally substituted with one or more of: halogen; ($C_1$-$C_6$)alkoxy, itself optionally substituted with one or more halogen; ($C_1$-$C_6$)alkyl, itself optionally substituted with one or more halogen; or —Z—($C_1$-$C_6$)alkyl, wherein Z is S or $SO_2$, and wherein said ($C_1$-$C_6$)alkyl may be optionally substituted with one or more halogen; or ($C_1$-$C_6$)alkyl-CO—O—$R^{12}$, wherein $R^{12}$ is H or ($C_1$-$C_6$)alkyl; or c) —$C=ZNHR^6$, wherein Z is O or S; and $R^6$ is:

($C_1$-$C_{10}$)alkyl; ($C_1$-$C_{10}$)alkoxy;

5 to 10 membered aryl or heteroaryl, optionally substituted with one or more of: halogen; cyano; ($C_1$-$C_6$)alkylenedioxy; ($C_1$-$C_6$)alkoxy, itself optionally substituted with one or more halogen; ($C_1$-$C_6$)alkyl, itself optionally substituted with one or more halogen; or ($C_1$-$C_6$)alkylthio, itself optionally substituted with one or more halogen; and $R^2$ is H or ($C_1$-$C_6$)alkyl.

In one specific embodiment, this invention encompasses compounds of formula (II):

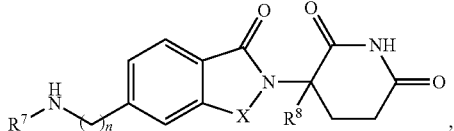

(II)

and pharmaceutically acceptable salts, solvates, stereoisomers, and prodrugs thereof, wherein:
n is 0 or 1;
X is $CH_2$ or C=O;
$R^7$ is $-(CH_2)_m R^9$, wherein m is 0, 1, 2, or 3, and $R^9$ is 5-10 membered aryl or heteroaryl, optionally substituted with one or more halogen; and
$R^8$ is H or $(C_1-C_6)$alkyl.

In one embodiment, X is C=O. In another embodiment, X is $CH_2$.

In one embodiment, n is 0. In another embodiment, n is 1.

In one embodiment, m is 0. In another embodiment, m is 1. In another embodiment, m is 2. In another embodiment, m is 3.

In one embodiment, $R^9$ is 5-10 membered aryl. In certain specific embodiments, $R^9$ is phenyl, optionally substituted with one or more halogen.

In one embodiment, $R^9$ is 5-10 membered heteroaryl. In certain specific embodiments, R9 is furyl or benzofuryl.

In one embodiment, $R^8$ is H. In another embodiment, $R^8$ is $(C_1-C_6)$alkyl. In certain specific embodiments, $R^8$ is methyl.

All of the combinations of the above embodiments are encompassed by this invention.

Examples include, but are not limited to, those listed below, or a pharmaceutically acceptable salt, solvate (e.g., hydrate), prodrug or stereoisomer thereof:

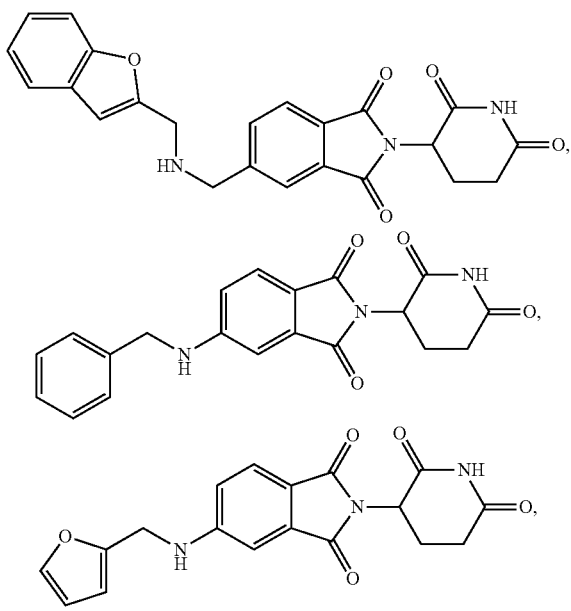

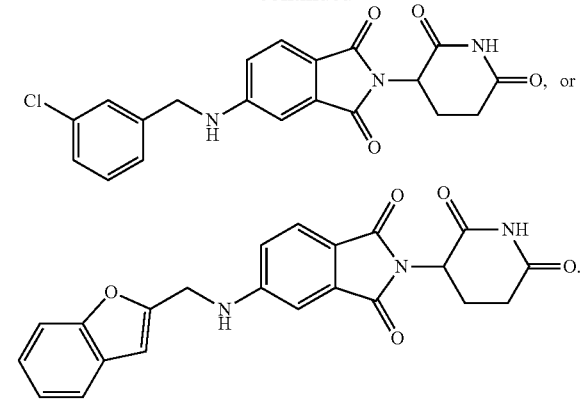

In another embodiment, this invention encompasses compounds of formula (III):

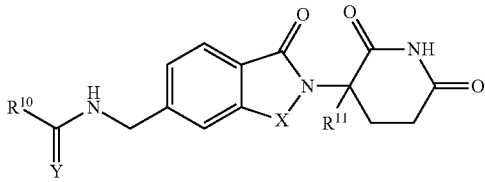

(III)

and pharmaceutically acceptable salts, solvates, stereoisomers, and prodrugs thereof, wherein:
X is $CH_2$ or C=O;
Y is O or S;
$R^{10}$ is:
  $(C_1-C_{10})$alkyl; $(C_1-C_{10})$alkoxy;
  $(C_0-C_{10})$alkyl-(5 to 10 membered heteroaryl or heterocycle), said heteroaryl or heterocycle optionally substituted with one or more of: $(C_1-C_6)$alkyl, itself substituted with one or more halogen; halogen; oxo; $(C_1-C_6)$alkoxy, itself substituted with one or more halogen; or $-Z-(C_1-C_6)$alkyl, wherein Z is S or $SO_2$, and wherein said $(C_1-C_6)$alkyl may be optionally substituted with one or more halogen;
  $(C_0-C_{10})$alkyl-(5 to 10 membered aryl), said aryl optionally substituted with one or more of: halogen; $(C_1-C_6)$alkoxy, itself optionally substituted with one or more halogen; $(C_1-C_6)$alkyl, itself optionally substituted with one or more halogen; or $-Z-(C_1-C_6)$alkyl, wherein Z is S or $SO_2$, and wherein said $(C_1-C_6)$alkyl may be optionally substituted with one or more halogen; or
  $(C_1-C_6)$alkyl-CO-O-$R^{12}$, wherein $R^{12}$ is H or $(C_1-C_6)$alkyl; and
$R^{11}$ is H or $(C_1-C_6)$alkyl.

In one embodiment, X is $CH_2$. In another embodiment, X is C=O.

In one embodiment, Y is O. In another embodiment, Y is S.

In one embodiment, $R^{10}$ is $(C_1-C_{10})$alkyl. In certain specific embodiments, $R^{10}$ is $(C_5-C_{10})$alkyl. In certain specific embodiments, $R^{10}$ is pentyl or hexyl.

In one embodiment, $R^{10}$ is $(C_1-C_{10})$alkoxy. In certain specific embodiments, $R^{10}$ is $(C_5-C_{10})$alkoxy. In certain specific embodiments, $R^{10}$ is pentyloxy or hexyloxy.

In one embodiment, $R^{10}$ is 5 to 10 membered heteroaryl. In certain specific embodiments, $R^{10}$ is thiopheneyl or furyl.

In one embodiment, $R^{10}$ is 5 to 10 membered aryl, optionally substituted with one or more halogen. In certain specific embodiments, $R^{10}$ is phenyl, optionally substituted with one or more halogen.

In one embodiment, $R^{10}$ is 5 to 10 membered aryl or heteroaryl, optionally substituted with $(C_1-C_6)$alkyl or $(C_1-C_6)$alkoxy, themselves optionally substituted with one or more halogen. In certain specific embodiments, $R^{10}$ is phenyl substituted with $(C_1-C_3)$alkyl or $(C_1-C_3)$alkoxy, substituted with one or more halogen. In certain specific embodiments, $R^{10}$ is phenyl substituted with methyl or methoxy, substituted with 1, 2, or 3 halogens.

In one embodiment, $R^{10}$ is aryl or heteroaryl substituted with $-S-(C_1-C_6)$alkyl, wherein said alkyl itself optionally substituted with one or more halogen. In another embodiment, $R^{10}$ is aryl or heteroaryl substituted with $-SO_2-(C_1-C_6)$alkyl, wherein said alkyl itself optionally substituted with one or more halogen.

In one embodiment, $R^{10}$ is $(C_1-C_6)$alkyl-CO-O-$R^{12}$, and $R^{12}$ is $(C_1-C_6)$alkyl. In one specific embodiment, $R^{10}$ is butyl-CO-O-tBu.

In one embodiment, $R^{10}$ is $(C_1-C_6)$alkyl-CO-O-$R^{12}$, and $R^{12}$ is H. In one specific embodiment, $R^{10}$ is butyl-COOH.

In one embodiment, $R^{11}$ is H. In another embodiment, $R^{11}$ is $(C_1-C_6)$alkyl. In certain specific embodiments, $R^{11}$ is methyl.

All of the combinations of the above embodiments are encompassed by this invention.

Examples include, but are not limited to, those listed below, or a pharmaceutically acceptable salt, solvate (e.g., hydrate), or stereoisomer thereof:

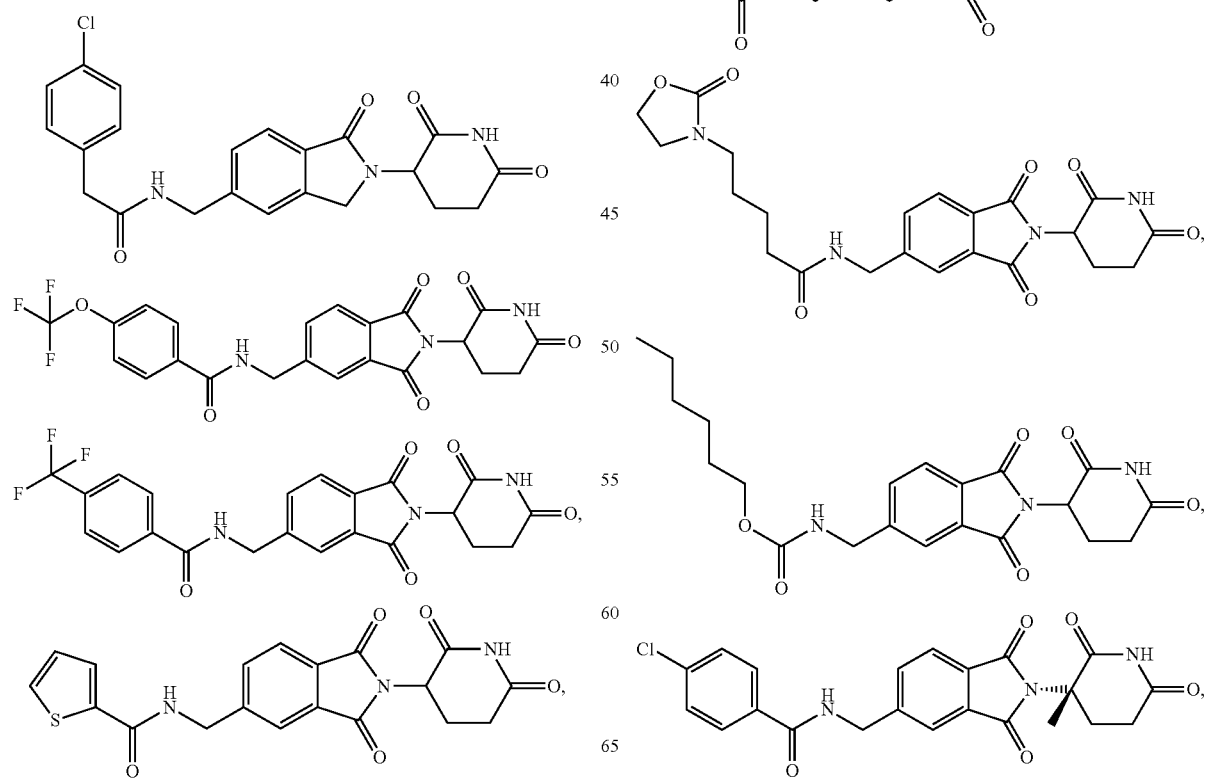

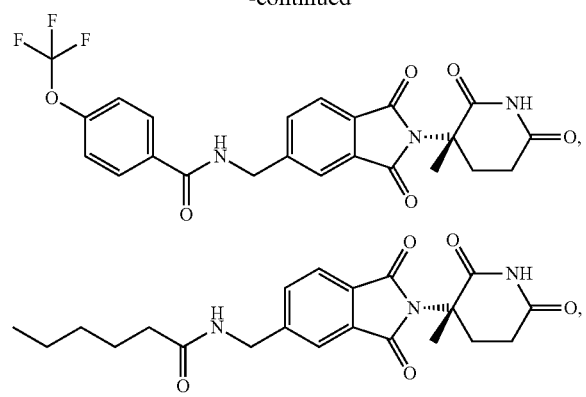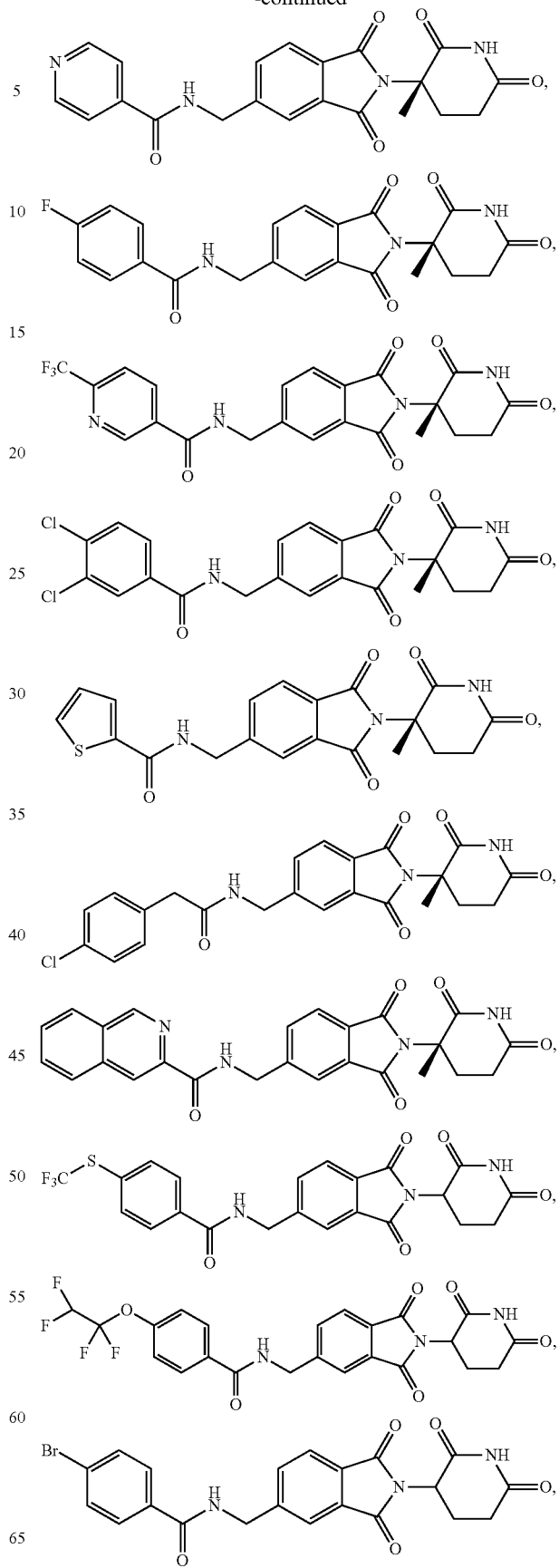

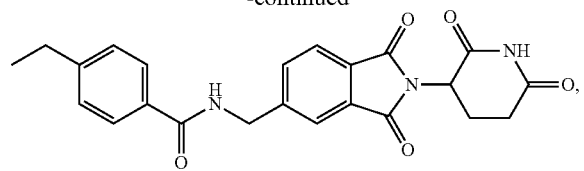
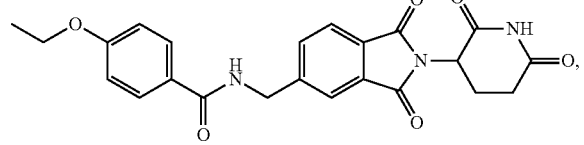
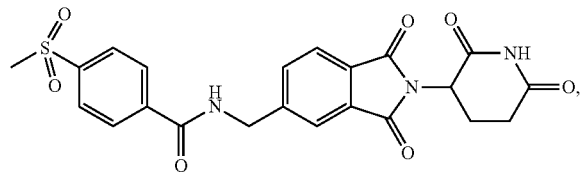
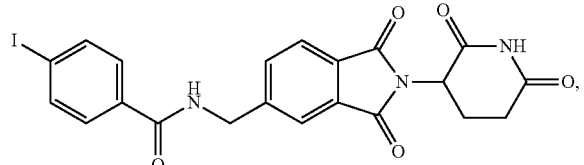
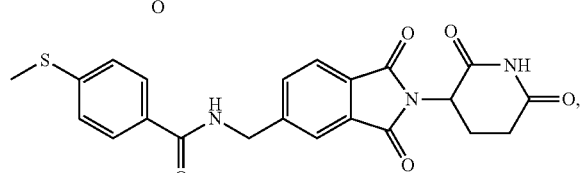
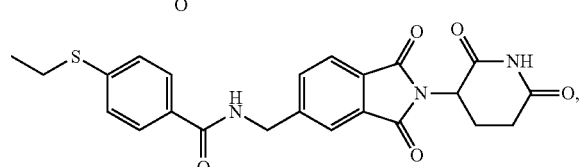
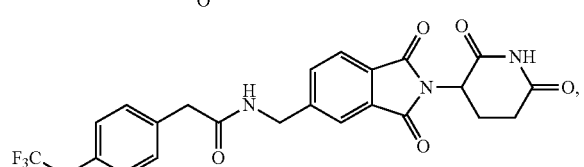
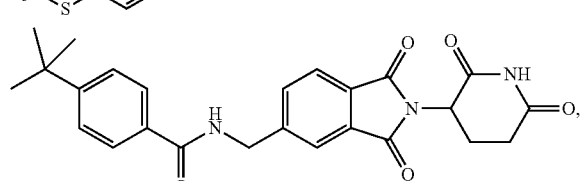
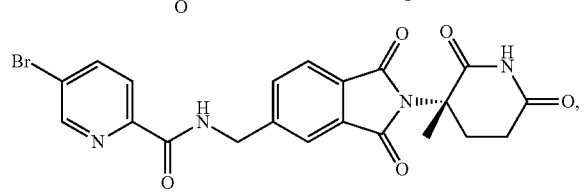
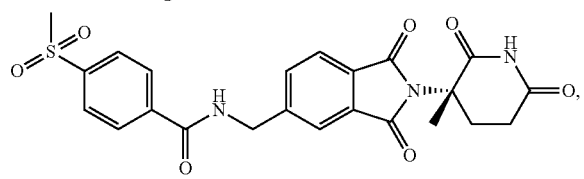
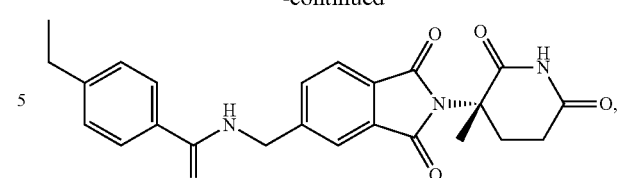
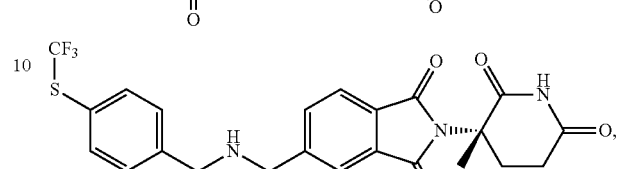
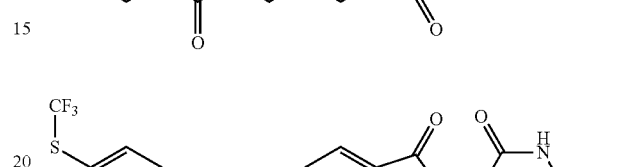
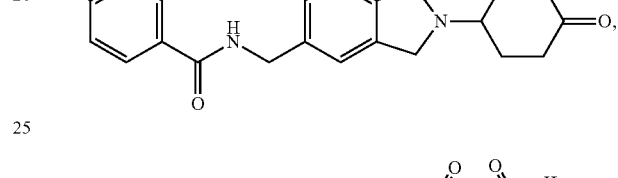
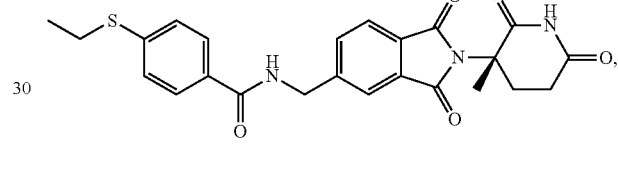
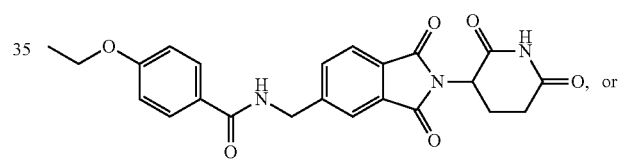
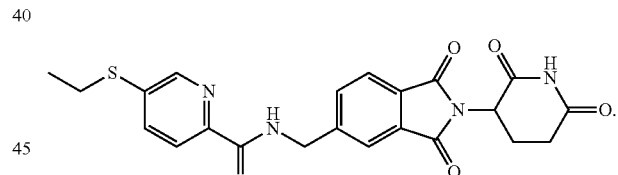
Other examples include, but are not limited to, those listed below, or a pharmaceutically acceptable salt, solvate (e.g., hydrate), or stereoisomer thereof:
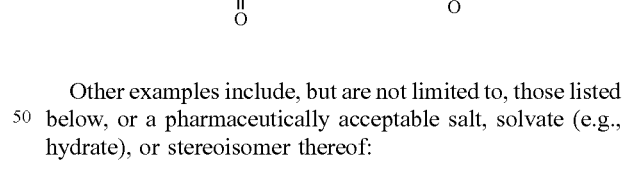
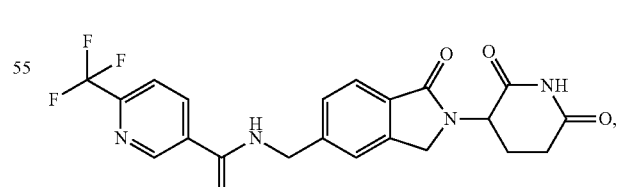
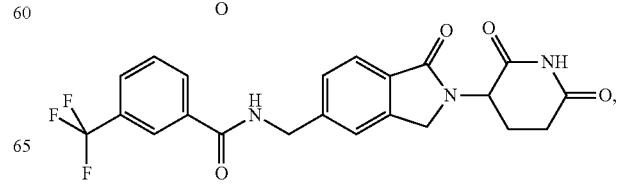

-continued
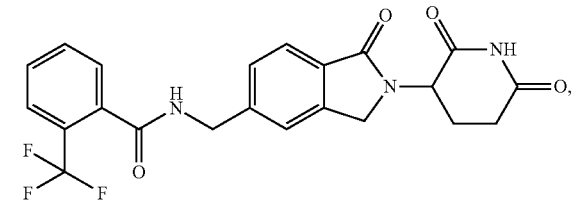
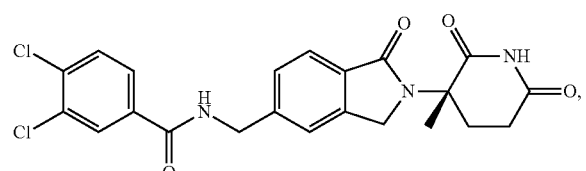
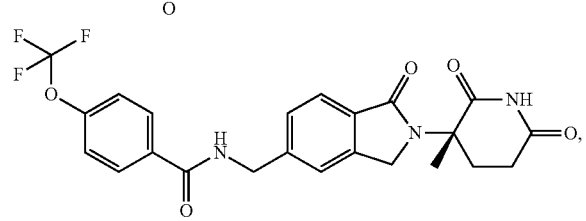
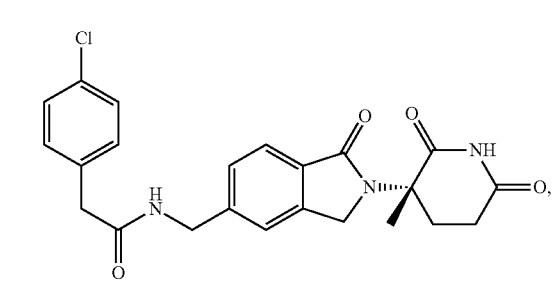
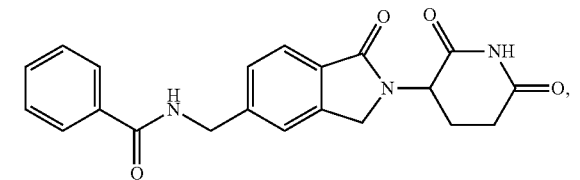
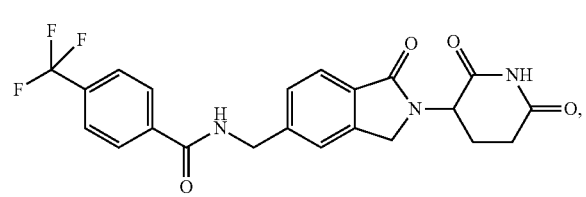
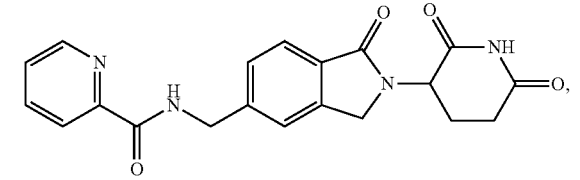
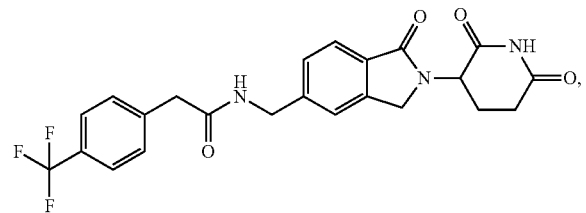
-continued
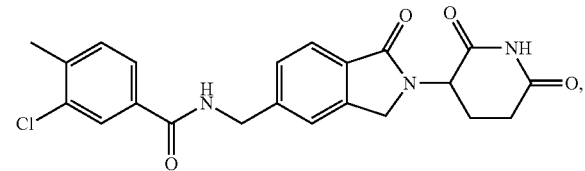
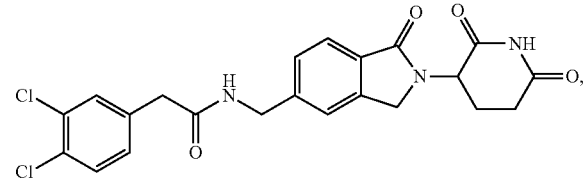
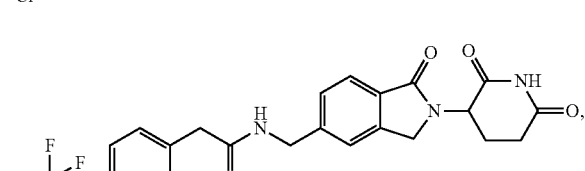
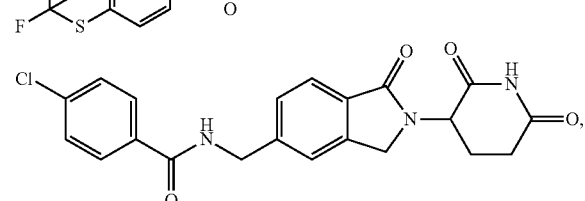
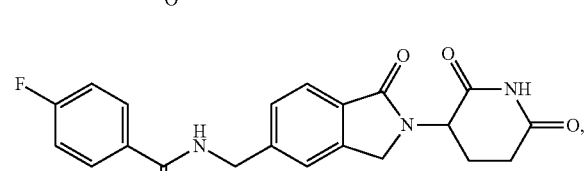
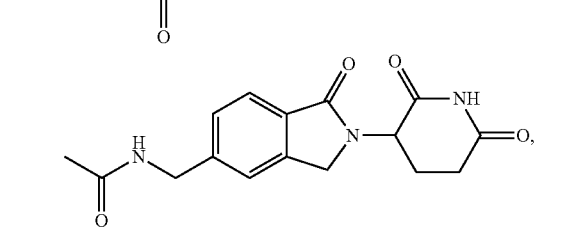
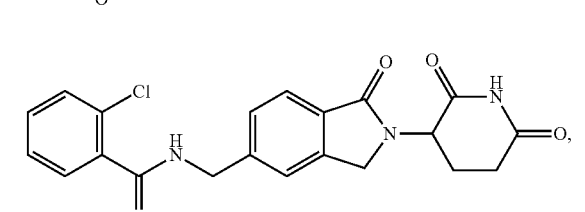
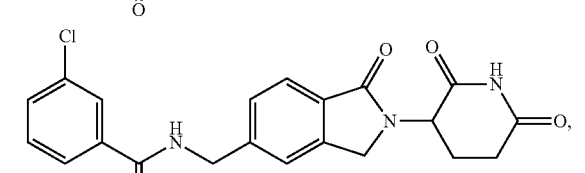
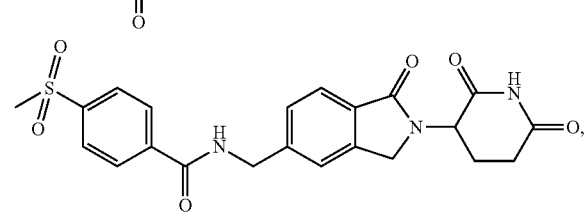

-continued
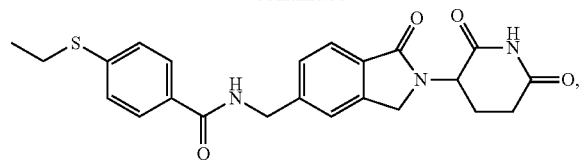
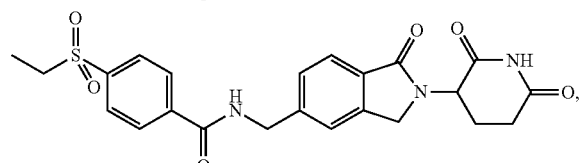
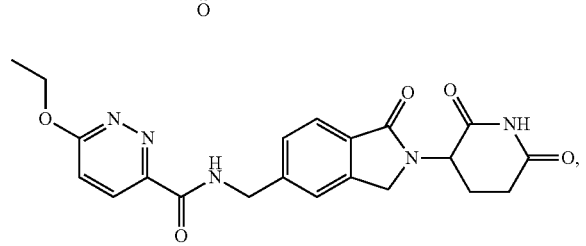
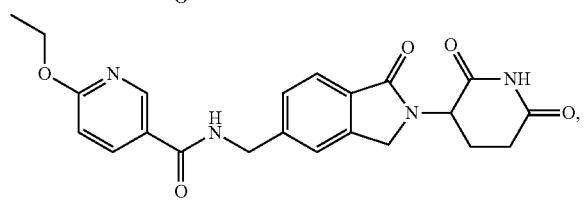
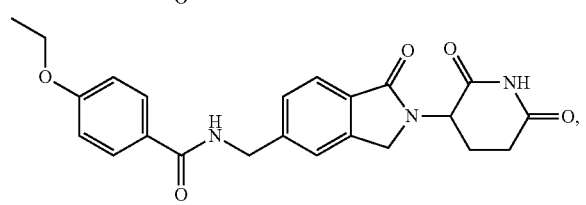
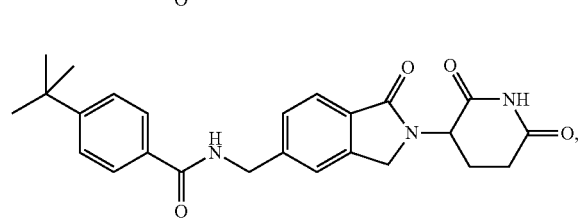
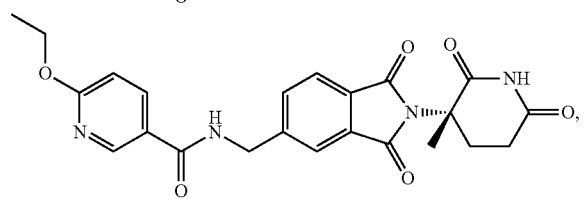
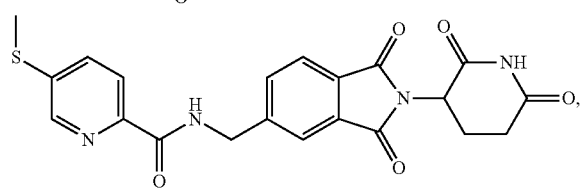
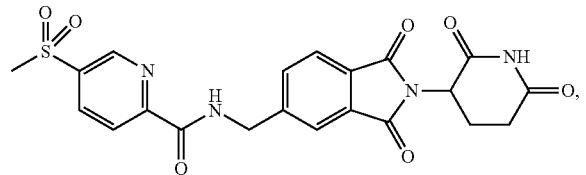
-continued
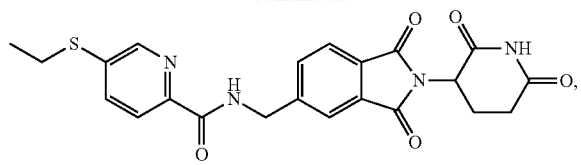
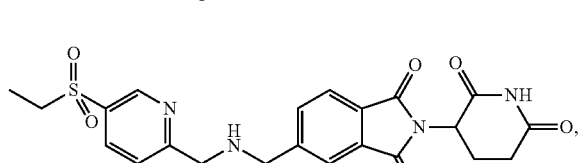
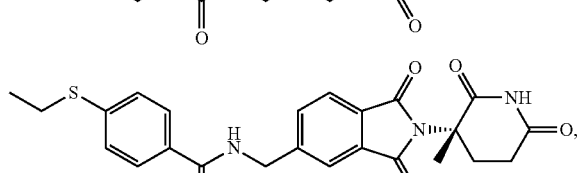
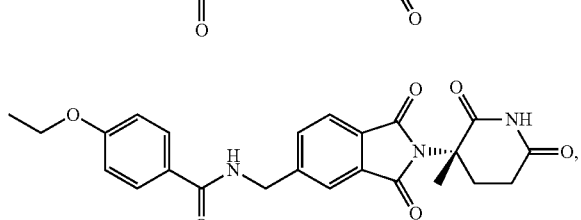
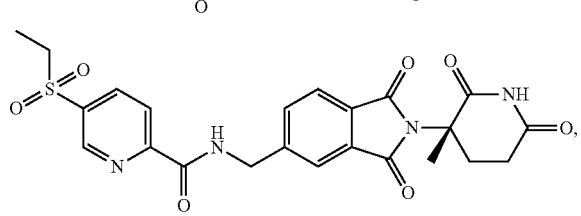
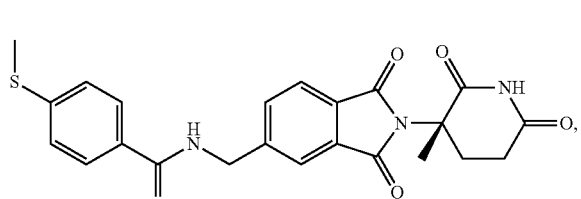
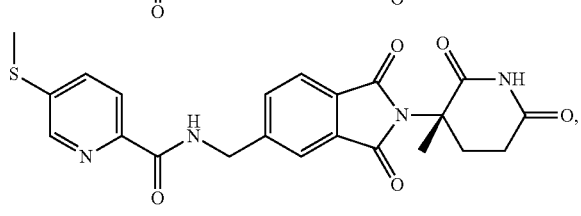
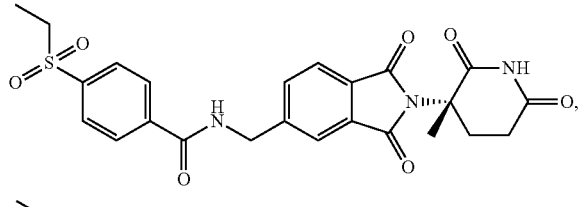
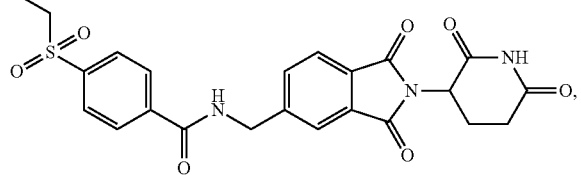

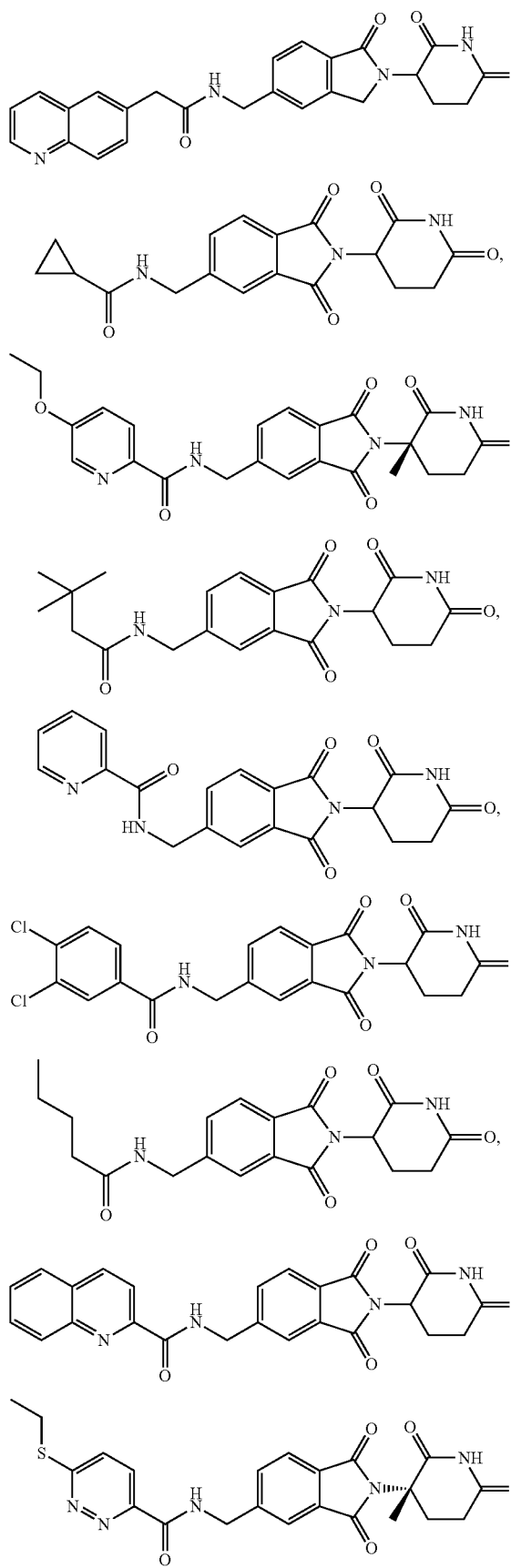
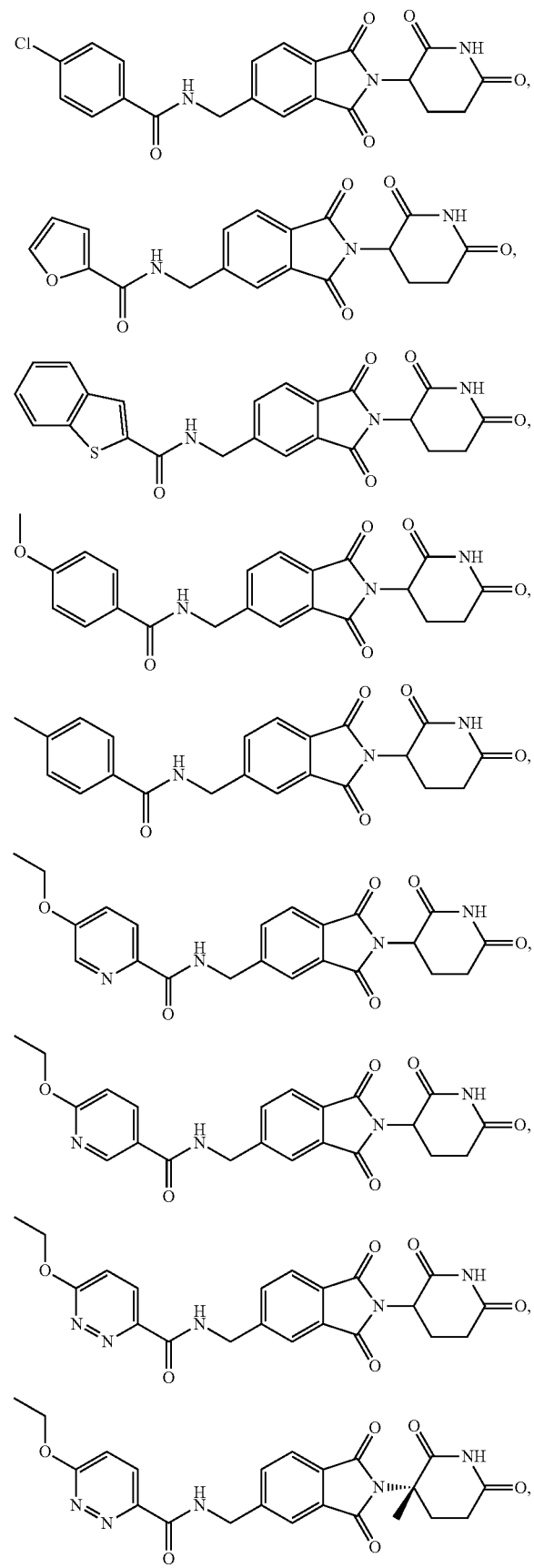

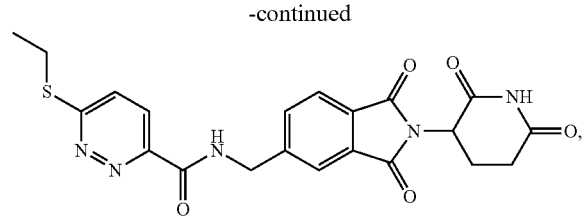
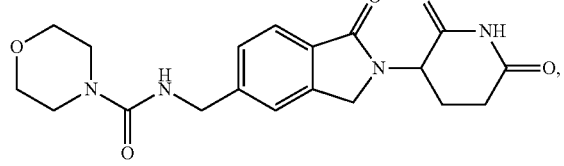
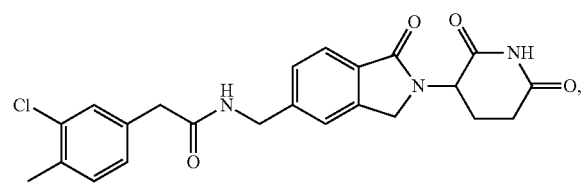
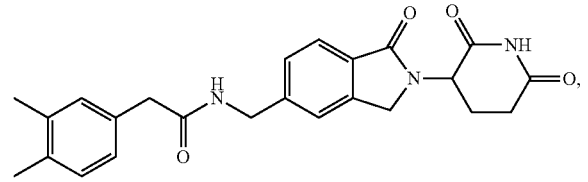
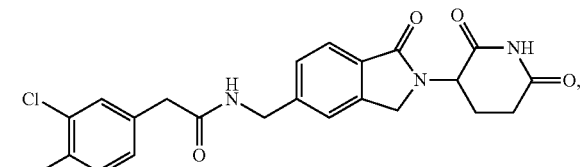
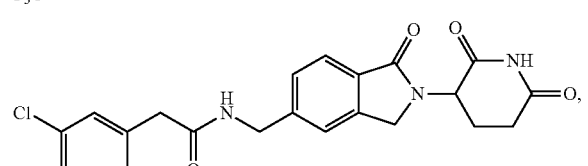
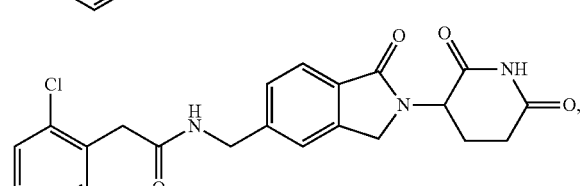
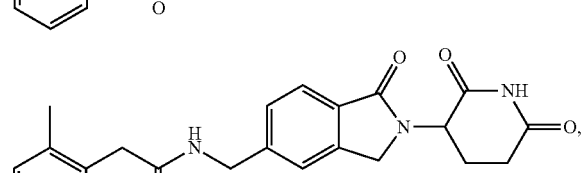
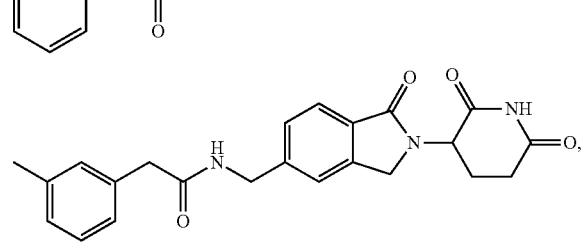
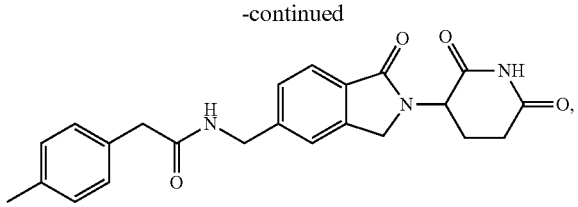
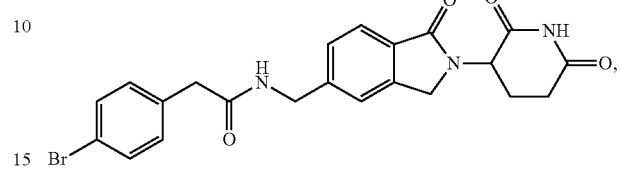
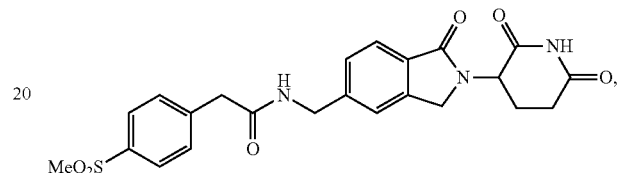
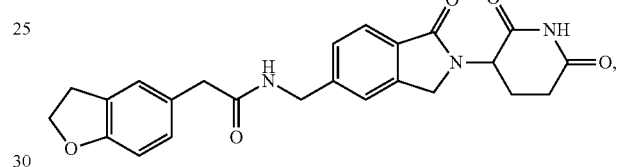
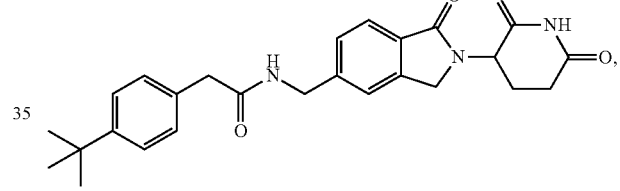
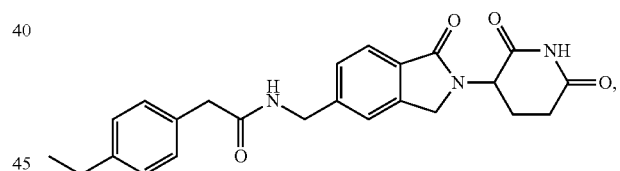
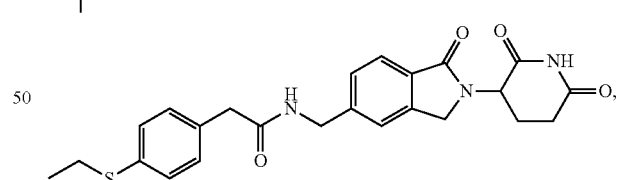
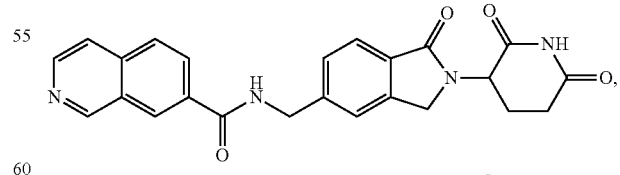
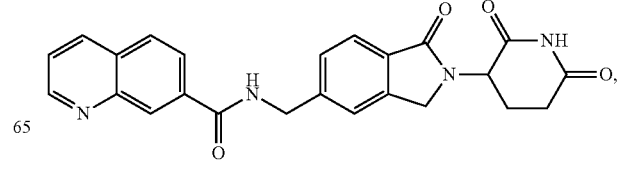

-continued

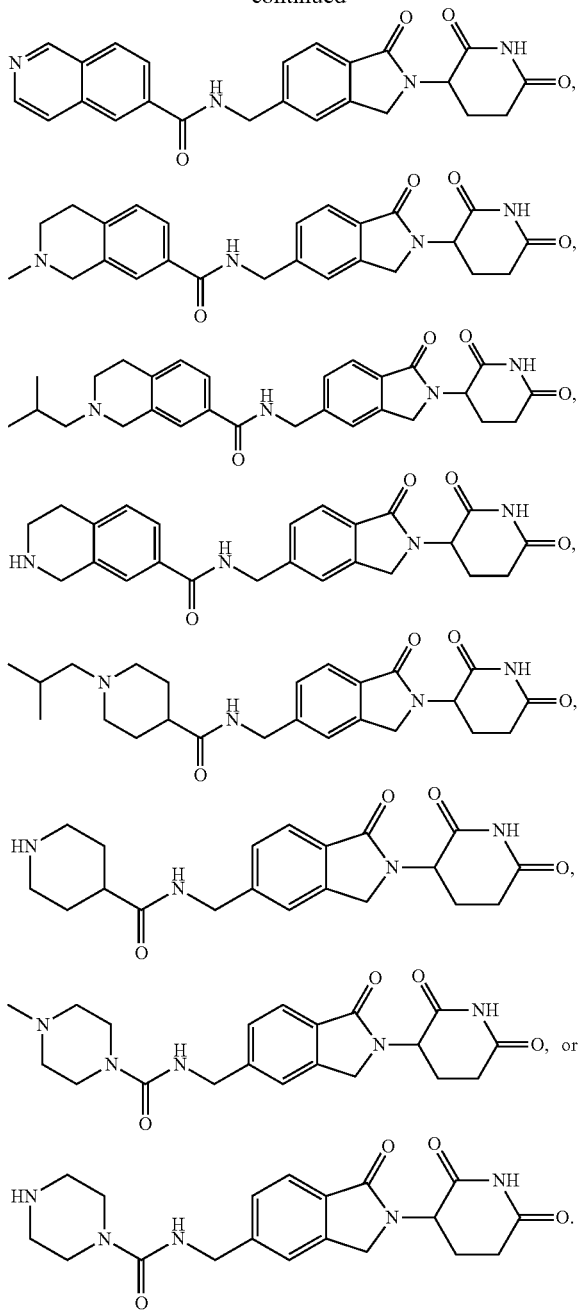

In another embodiment, this invention encompasses compounds of formula (IV):

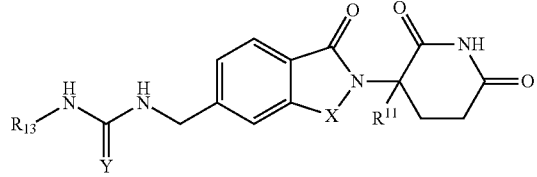

(IV)

and pharmaceutically acceptable salts, solvates, stereoisomers, and prodrugs thereof, wherein:
X is $CH_2$ or C=O;
Y is O or S;

$R^{13}$ is:
($C_1$-$C_{10}$)alkyl; ($C_1$-$C_{10}$)alkoxy;
5 to 10 membered aryl or heteroaryl, optionally substituted with one or more of: halogen; cyano; ($C_1$-$C_6$)alkylenedioxy; ($C_1$-$C_6$)alkoxy, itself optionally substituted with one or more halogen; ($C_1$-$C_6$)alkyl, itself optionally substituted with one or more halogen; or ($C_1$-$C_6$)alkylthio, itself optionally substituted with one or more halogen; and
$R^{14}$ is H or ($C_1$-$C_6$)alkyl.

In one embodiment, X is $CH_2$. In another embodiment, X is C=O.

In one embodiment, Y is O. In another embodiment, Y is S.

In one embodiment, $R^{13}$ is ($C_1$-$C_{10}$)alkyl. In certain specific embodiments, $R^{13}$ is ($C_1$-$C_6$)alkyl. In certain specific embodiments, $R^{13}$ is propyl, butyl, pentyl, or hexyl.

In one embodiment, $R^{13}$ is ($C_1$-$C_{10}$)alkoxy.

In one embodiment, $R^{13}$ is 5 to 10 membered aryl or heteroaryl, optionally substituted with cyano. In certain specific embodiments, $R^{13}$ is phenyl, optionally substituted with cyano.

In one embodiment, $R^{13}$ is 5 to 10 membered aryl or heteroaryl, optionally substituted with ($C_1$-$C_6$)alkylenedioxy. In certain specific embodiments, $R^{13}$ is phenyl, optionally substituted with methylenedioxy.

In one embodiment, $R^{13}$ is 5 to 10 membered aryl or heteroaryl, optionally substituted with one or more halogen. In certain specific embodiments, $R^{13}$ is phenyl, optionally substituted with one or more halogen.

In another embodiment, $R^{13}$ is 5 to 10 membered aryl or heteroaryl, optionally substituted with ($C_1$-$C_6$)alkyl or ($C_1$-$C_6$)alkoxy, themselves optionally substituted with one or more halogens. In certain specific embodiments, $R^{13}$ is phenyl, optionally substituted with methyl or methoxy, themselves optionally substituted with 1, 2, or 3 halogens.

In another embodiment, $R^{13}$ is 5 to 10 membered aryl or heteroaryl, optionally substituted with ($C_1$-$C_6$)alkylthio, itself optionally substituted with one or more halogens.

In another embodiment, $R^{14}$ is H. In another embodiment, $R^{14}$ is ($C_1$-$C_6$)alkyl. In certain specific embodiments, $R^{14}$ is methyl.

All of the combinations of the above embodiments are encompassed by this invention.

Examples include, but are not limited to, those listed below, or a pharmaceutically acceptable salt, solvate (e.g., hydrate), prodrug or stereoisomer thereof:

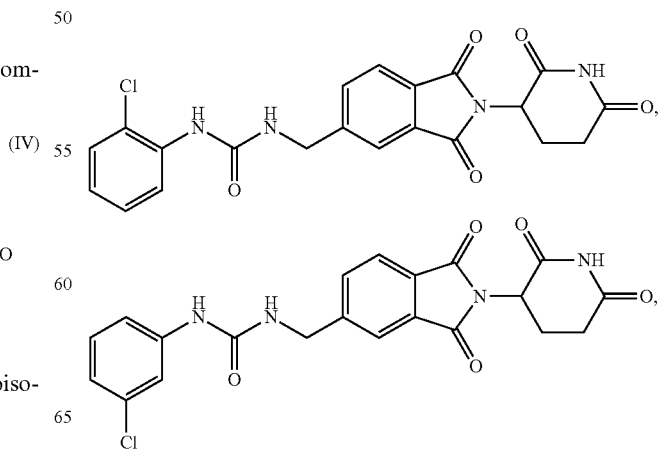

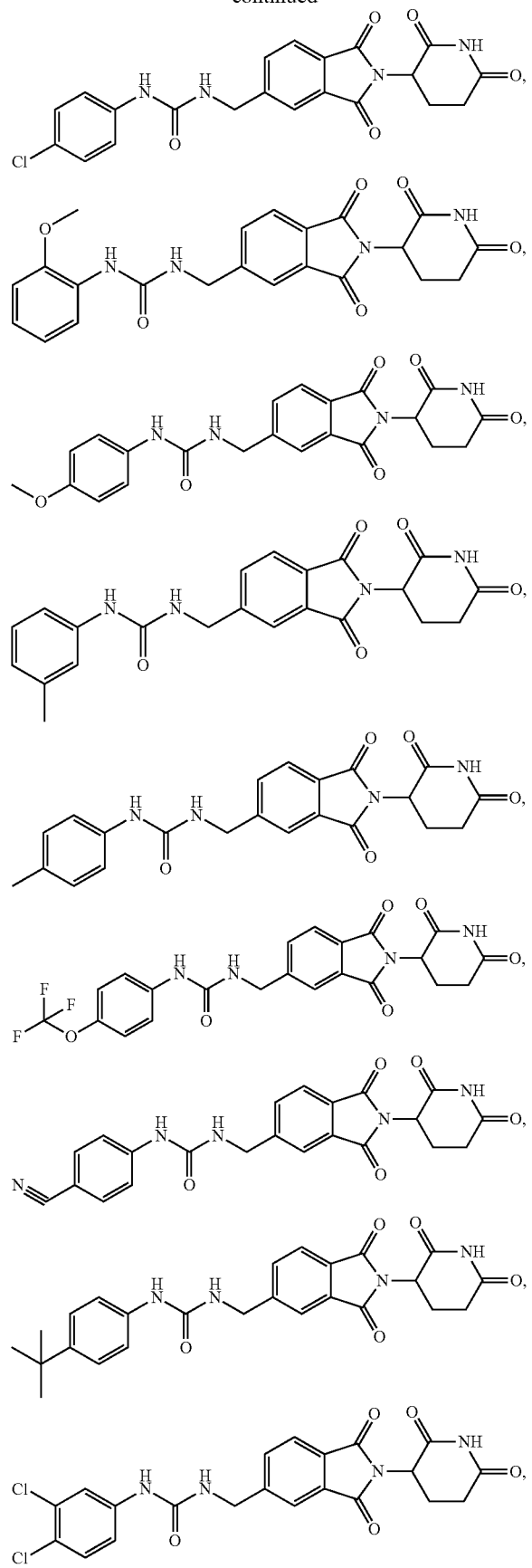
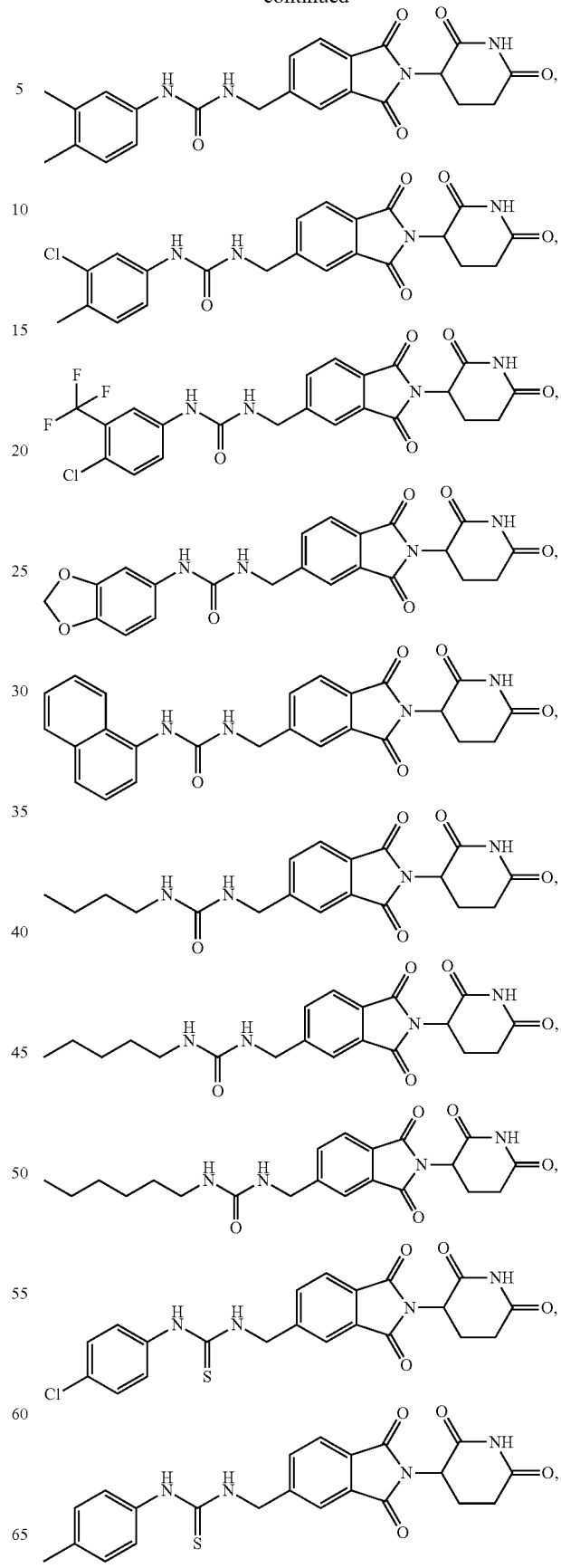

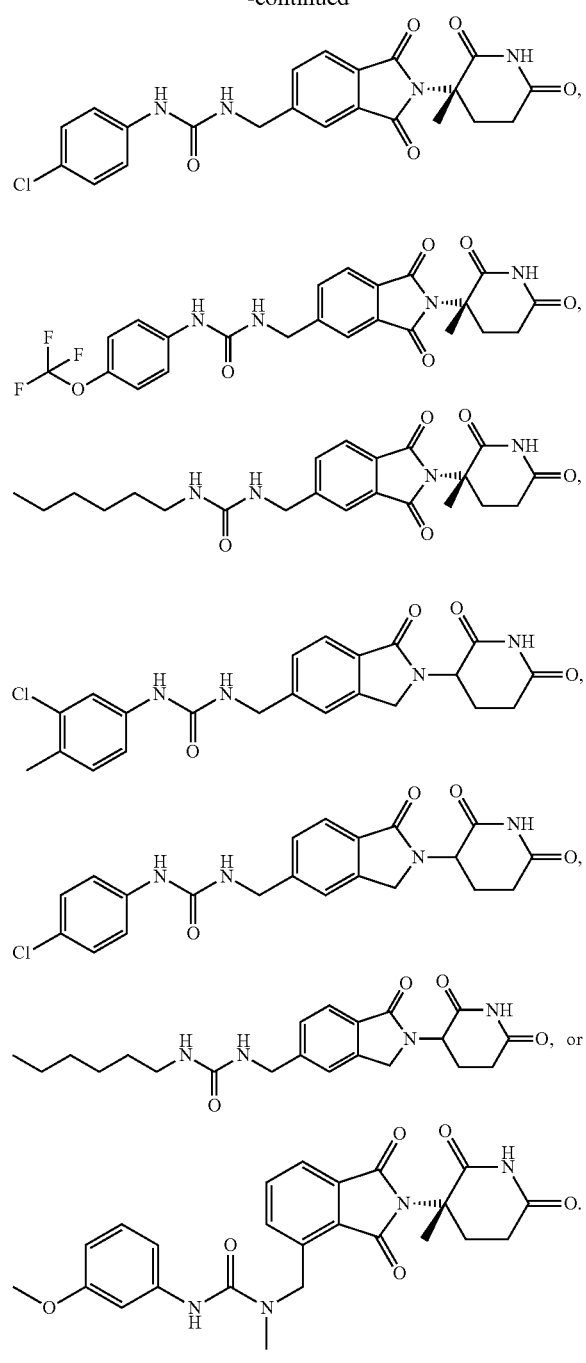
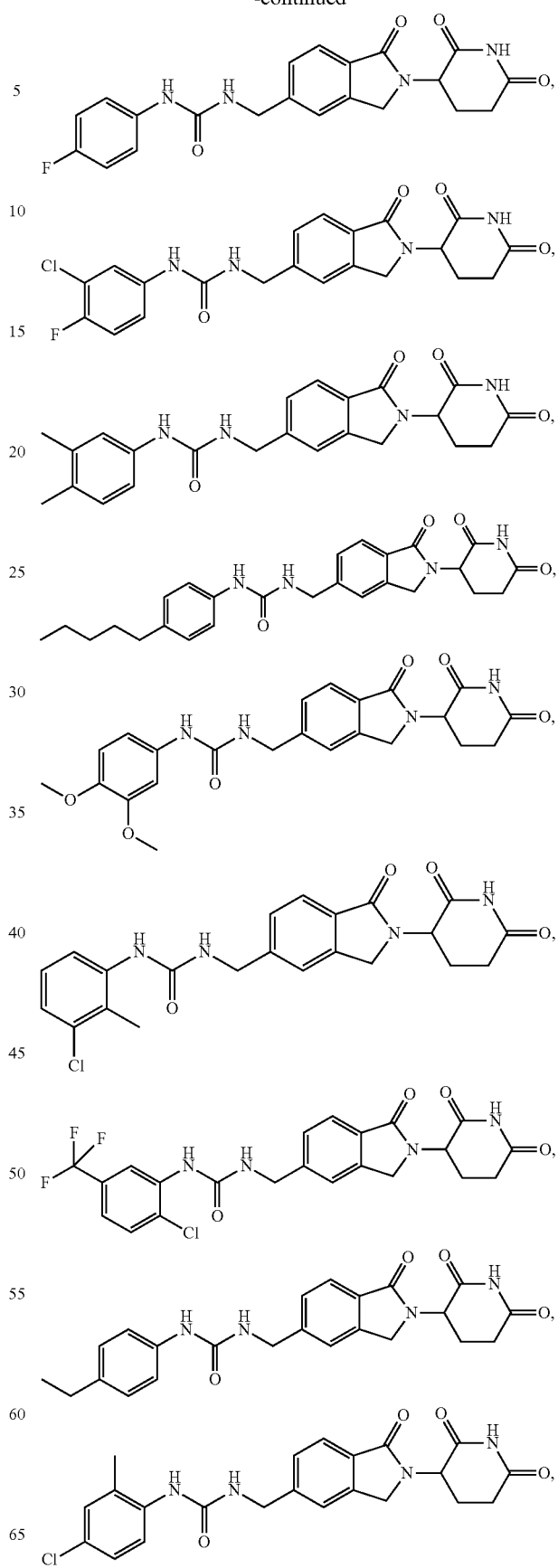
Other examples include, but are not limited to, those listed below, or a pharmaceutically acceptable salt, solvate (e.g., hydrate), prodrug or stereoisomer thereof:
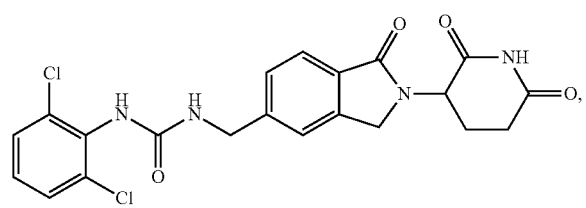

27
-continued
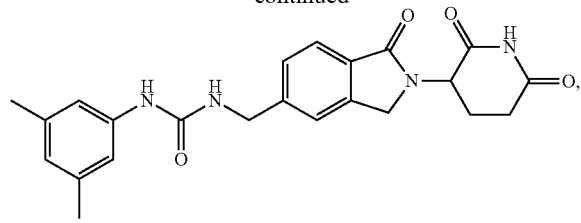
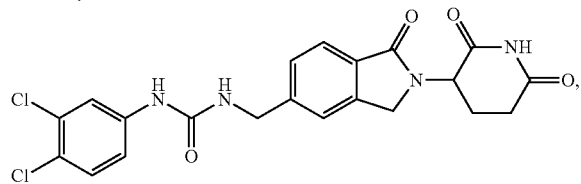
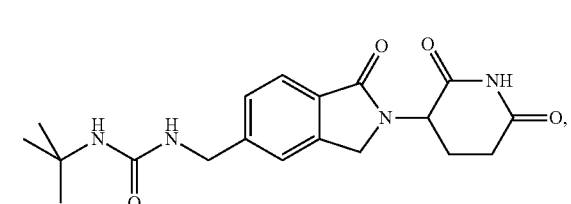
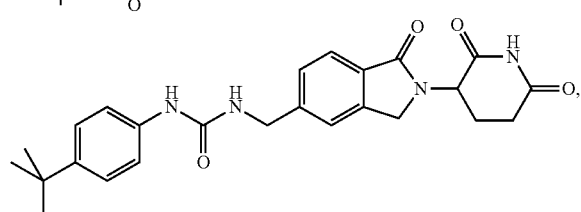
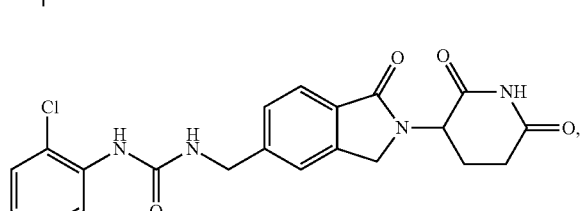
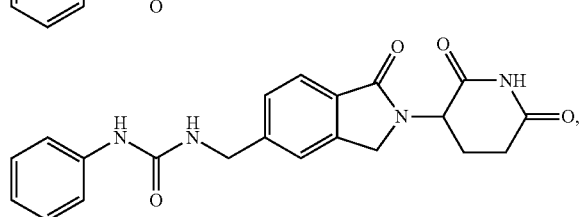
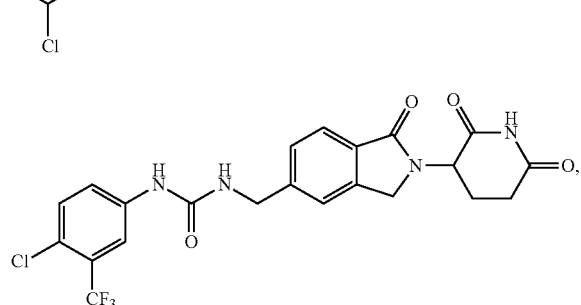
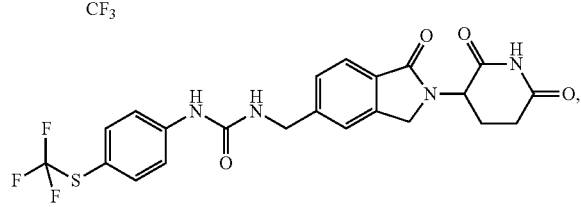
28
-continued
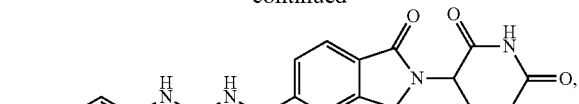
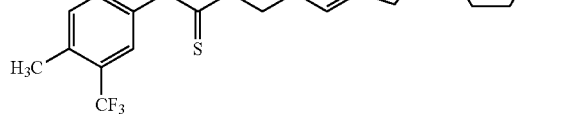
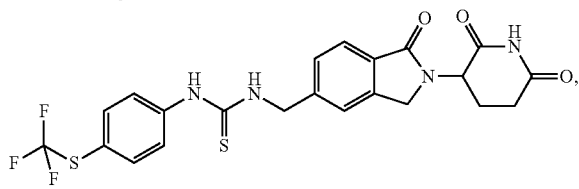
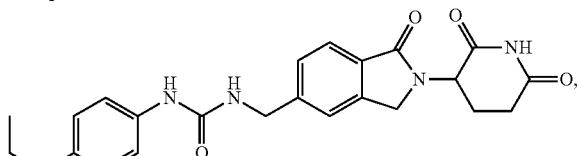
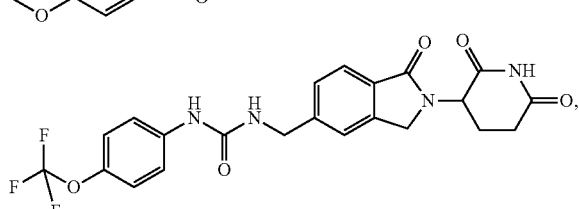
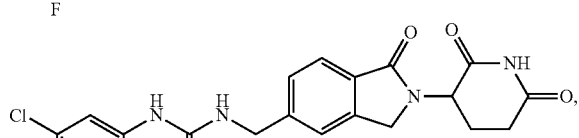
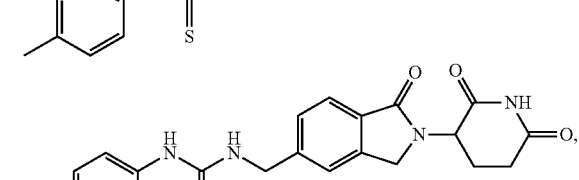
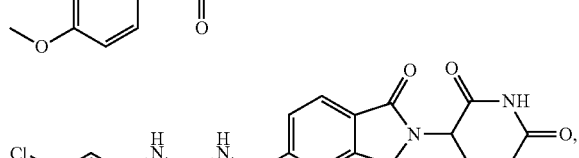
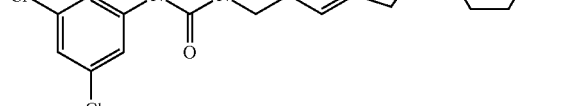
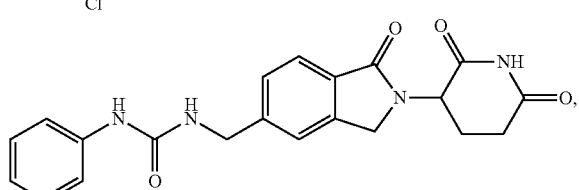
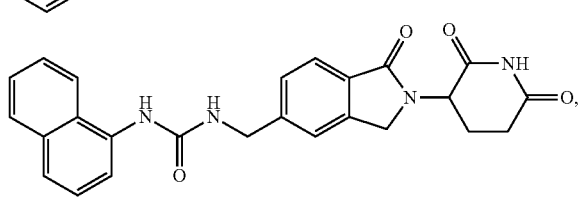

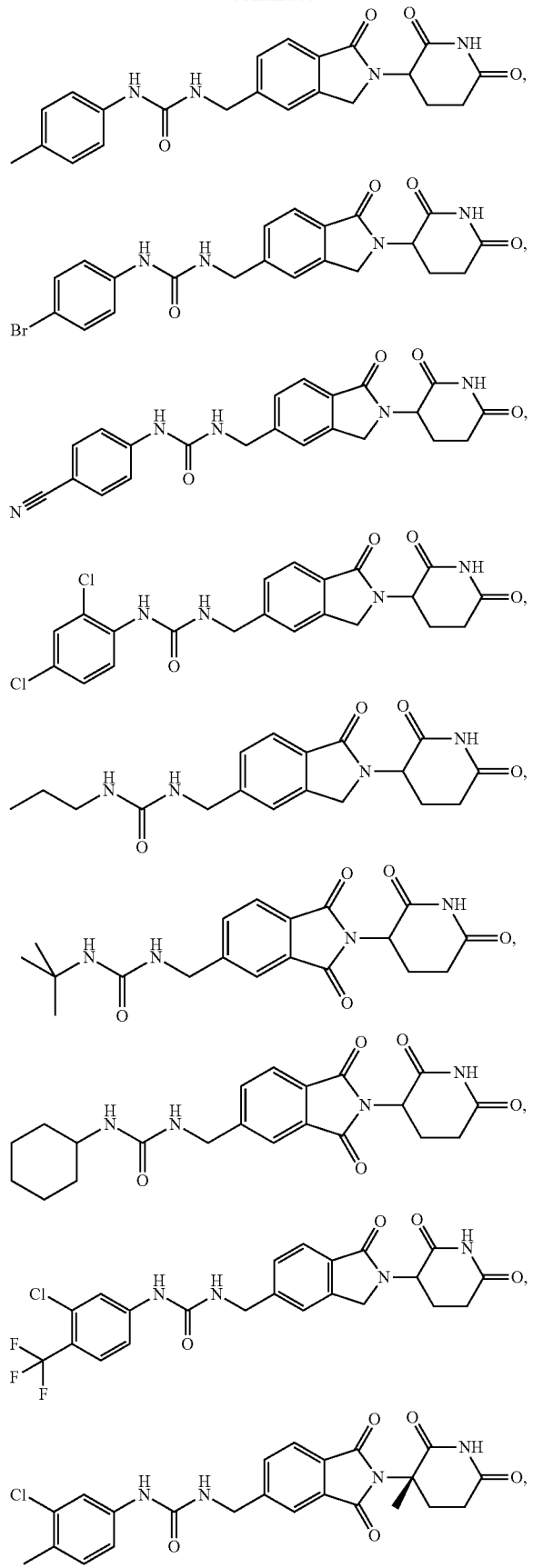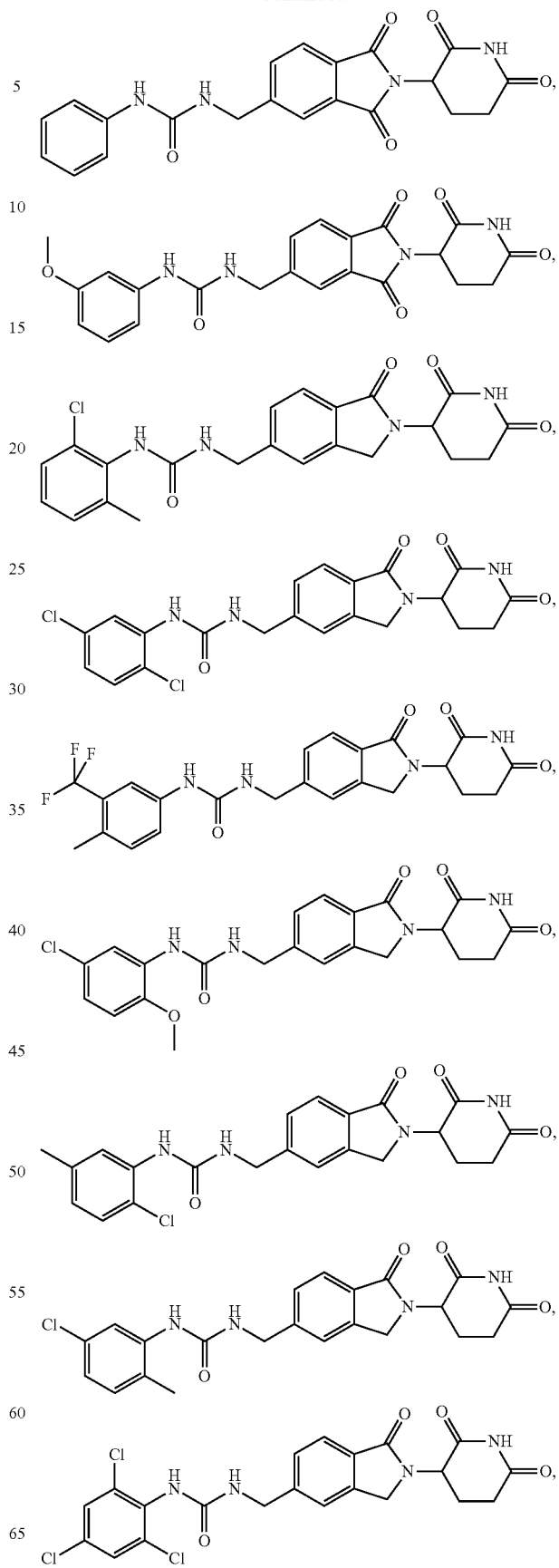

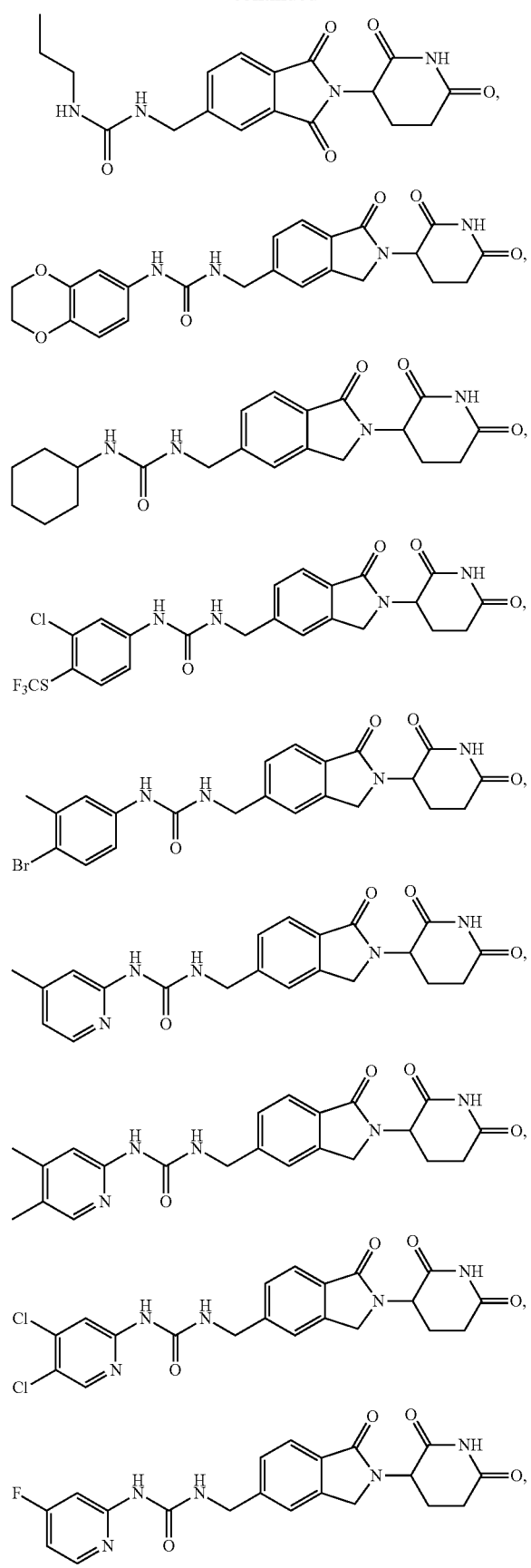
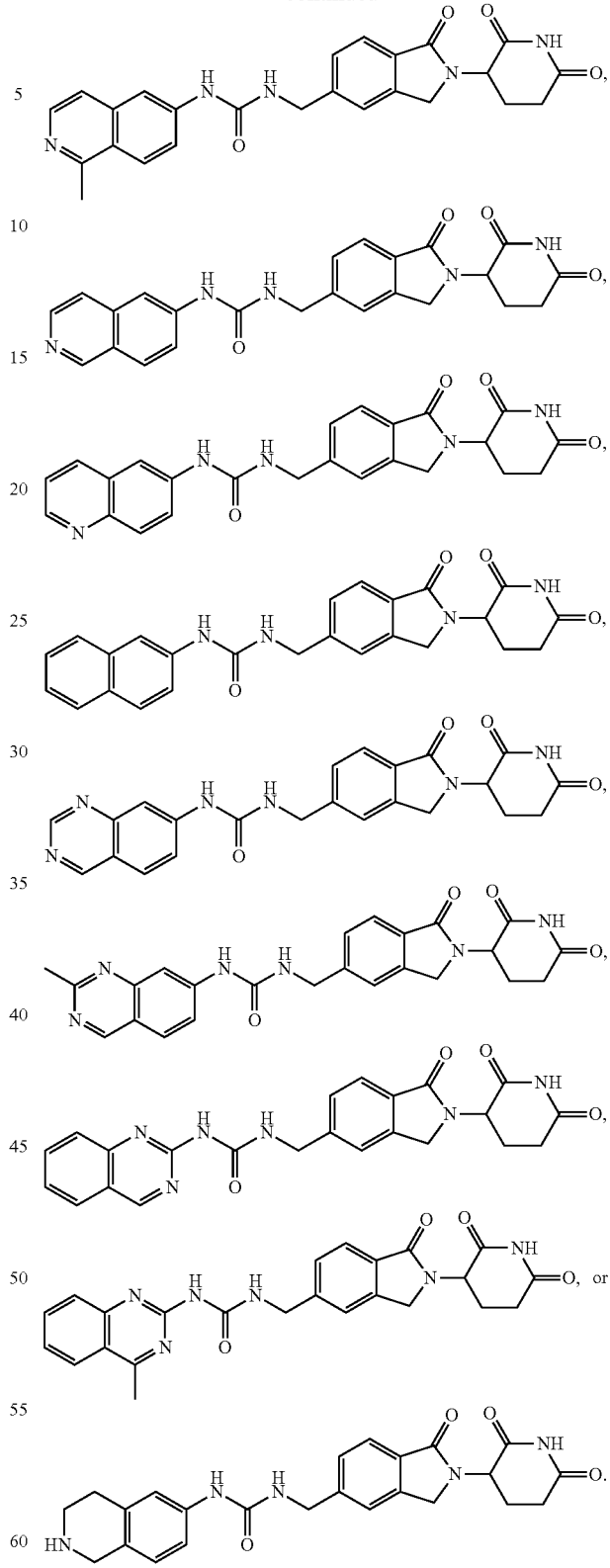
As used herein, and unless otherwise specified, the term "pharmaceutically acceptable salt" refers to salts prepared from pharmaceutically acceptable non-toxic acids, including inorganic acids and organic acids. Suitable non-toxic acids include inorganic and organic acids such as, but not limited to, acetic, alginic, anthranilic, benzenesulfonic, benzoic, camphorsulfonic, citric, ethenesulfonic, formic, fumaric, furoic, gluconic, glutamic, glucorenic, galacturonic, glycidic, hydrobromic, hydrochloric, isethionic, lactic, maleic, malic, mandelic, methanesulfonic, mucic, nitric, pamoic, pantothenic, phenylacetic, propionic, phosphoric, salicylic, stearic, succinic, sulfanilic, sulfuric, tartaric acid, p-toluenesulfonic and the like. Suitable are hydrochloric, hydrobromic, phosphoric, and sulfuric acids.

As used herein, and unless otherwise specified, the term "solvate" means a compound of the present invention or a salt thereof, that further includes a stoichiometric or non-stoichiometric amount of solvent bound by non-covalent intermolecular forces. Where the solvent is water, the solvate is a hydrate.

As used herein, and unless otherwise specified, the term "prodrug" means a derivative of a compound that can hydrolyze, oxidize, or otherwise react under biological conditions (in vitro or in vivo) to provide the compound. Examples of prodrugs include, but are not limited to, compounds that comprise biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Other examples of prodrugs include compounds that comprise —NO, —NO$_2$, —ONO, or —ONO$_2$ moieties. Prodrugs can typically be prepared using well-known methods, such as those described in *Burger's Medicinal Chemistry and Drug Discovery*, 172-178, 949-982 (Manfred E. Wolff ed., 5th ed. 1995), and *Design of Prodrugs* (H. Bundgaard ed., Elsevier, N.Y. 1985).

As used herein, and unless otherwise specified, the terms "biohydrolyzable carbamate," "biohydrolyzable carbonate," "biohydrolyzable ureide" and "biohydrolyzable phosphate" mean a carbamate, carbonate, ureide and phosphate, respectively, of a compound that either: 1) does not interfere with the biological activity of the compound but can confer upon that compound advantageous properties in vivo, such as uptake, duration of action, or onset of action; or 2) is biologically inactive but is converted in vivo to the biologically active compound. Examples of biohydrolyzable carbamates include, but are not limited to, lower alkylamines, substituted ethylenediamines, aminoacids, hydroxyalkylamines, heterocyclic and heteroaromatic amines, and polyether amines.

As used herein, and unless otherwise specified, the term "stereoisomer" encompasses all enantiomerically/stereomerically pure and enantiomerically/stereomerically enriched compounds of this invention.

As used herein and unless otherwise indicated, the term "stereomerically pure" means a composition that comprises one stereoisomer of a compound and is substantially free of other stereoisomers of that compound. For example, a stereomerically pure composition of a compound having one chiral center will be substantially free of the opposite enantiomer of the compound. A stereomerically pure composition of a compound having two chiral centers will be substantially free of other diastereomers of the compound. A typical stereomerically pure compound comprises greater than about 80% by weight of one stereoisomer of the compound and less than about 20% by weight of other stereoisomers of the compound, more preferably greater than about 90% by weight of one stereoisomer of the compound and less than about 10% by weight of the other stereoisomers of the compound, even more preferably greater than about 95% by weight of one stereoisomer of the compound and less than about 5% by weight of the other stereoisomers of the compound, and most preferably greater than about 97% by weight of one stereoisomer of the compound and less than about 3% by weight of the other stereoisomers of the compound.

As used herein and unless otherwise indicated, the term "stereomerically enriched" means a composition that comprises greater than about 55% by weight of one stereoisomer of a compound, greater than about 60% by weight of one stereoisomer of a compound, preferably greater than about 70% by weight, more preferably greater than about 80% by weight of one stereoisomer of a compound.

As used herein, and unless otherwise indicated, the term "enantiomerically pure" means a stereomerically pure composition of a compound having one chiral center. Similarly, the term "enantiomerically enriched" means a stereomerically enriched composition of a compound having one chiral center.

As used herein, and unless otherwise indicated, the term "alkyl" refers to a saturated straight chain or branched hydrocarbon having number of carbon atoms as specified herein. Representative saturated straight chain alkyls include -methyl, -ethyl, -n-propyl, -n-butyl, -n-pentyl, and -n-hexyl; while saturated branched alkyls include -isopropyl, -sec-butyl, -isobutyl, -tert-butyl, -isopentyl, 2-methylbutyl, 3-methylbutyl, 2-methylpentyl, 3-methylpentyl, 4-methylpentyl, 2-methylhexyl, 3-methylhexyl, 4-methylhexyl, 5-methylhexyl, 2,3-dimethylbutyl, and the like. The term "alkyl" also encompasses cycloalkyl.

As used herein, and unless otherwise specified, the term "cycloalkyl" means a specie of alkyl containing from 3 to 15 carbon atoms, without alternating or resonating double bonds between carbon atoms. It may contain from 1 to 4 rings. Examples of unsubstituted cycloalkyls include, but are not limited to, cyclopropyl, cyclobutyl, cyclopentyl, cyclohexyl, and adamantyl. A cycloalkyl may be substituted with one or more of the substituents as defined below.

As used herein, and unless otherwise specified, the term "alkoxy" refers to —O-(alkyl), wherein alkyl is defined herein. Examples of alkoxy include, but are not limited to, —OCH$_3$, —OCH$_2$CH$_3$, —O(CH$_2$)$_2$CH$_3$, —O(CH$_2$)$_3$CH$_3$, —O(CH$_2$)$_4$CH$_3$, and —O(CH$_2$)$_5$CH$_3$.

As used herein, the term "aryl" means a carbocyclic aromatic ring containing from 5 to 14 ring atoms. The ring atoms of a carbocyclic aryl group are all carbon atoms. Aryl ring structures include compounds having one or more ring structures such as mono-, bi-, or tricyclic compounds as well as benzo-fused carbocyclic moieties such as 5,6,7,8-tetrahydronaphthyl and the like. Representative aryl groups include phenyl, anthracenyl, fluorenyl, indenyl, azulenyl, phenanthrenyl and naphthyl.

As used herein, and unless otherwise specified, the term "heteroaryl" means an aromatic ring containing from 5 to 14 ring atoms, of which at least one (e.g., one, two, or three) is a heteroatom (e.g., nitrogen, oxygen, or sulfur). Heteroaryl ring structures include compounds having one or more ring structures such as mono-, bi-, or tricyclic compounds, as well as fused heterocyclic moieties. Examples of heteroaryls include, but are not limited to, triazolyl, tetrazolyl, oxadiazolyl, pyridyl, furyl, benzofuranyl, thiophenyl, thiazolyl, benzothiophenyl, benzoisoxazolyl, benzoisothiazolyl, quinolinyl, isoquinolinyl, pyrrolyl, indolyl, oxazolyl, benzoxazolyl, imidazolyl, benzimidazolyl, thiazolyl, benzothiazolyl, isoxazolyl, pyrazolyl, isothiazolyl, pyridazinyl, pyrimidinyl, pyrazinyl, triazinyl, cinnolinyl, phthalazinyl, quinazolinyl, benzoquinazolinyl, quinoxalinyl, acridinyl, pyrimidyl, oxazolyl, benzo[1,3]dioxole and 2,3-dihydrobenzo[1,4]dioxine.

As used herein, and unless otherwise indicated, the term "heterocycle" means a monocyclic or polycyclic ring comprising carbon and hydrogen atoms, optionally having 1 or 2 multiple bonds, and the ring atoms contain at least one heteroatom, specifically 1 to 3 heteroatoms, independently selected from nitrogen, oxygen, and sulfur. Heterocycle ring structures include, but are not limited to, mono-, bi-, and tri-cyclic compounds. Specific heterocycles are monocyclic or bicyclic. Representative heterocycles include morpholinyl, pyrrolidinonyl, pyrrolidinyl, piperidinyl, piperazinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl and tetrahydrothiopyranyl. A heterocyclic ring may be unsubstituted or substituted.

As used herein, and unless otherwise specified, the term "heterocycloalkyl" refers to a cycloalkyl group in which at least one of the carbon atoms in the ring is replaced by a heteroatom (e.g., O, S or N).

It should be noted that if there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it.

4.2 Methods of Treatment, Prevention and Management

This invention encompasses methods of treating, preventing, and/or managing various diseases or disorders using a compound of this invention, or a pharmaceutically acceptable salt, solvate, stereoisomer or prodrug thereof.

Examples of diseases or disorders include, but are not limited to, cancer, disorders associated with angiogenesis, pain including Complex Regional Pain Syndrome ("CRPS"), Macular Degeneration ("MD") and related syndromes, skin diseases, pulmonary disorders, asbestos-related disorders, parasitic diseases, immunodeficiency disorders, CNS disorders, CNS injury, atherosclerosis and related disorders, dysfunctional sleep and related disorders, hemoglobinopathy and related disorders (e.g., anemia), TNFα related disorders, and other various diseases and disorders.

As used herein, and unless otherwise specified, the terms "treat," "treating" and "treatment" refer to the eradication or amelioration of a disease or disorder, or of one or more symptoms associated with the disease or disorder. In certain embodiments, the terms refer to minimizing the spread or worsening of the disease or disorder resulting from the administration of one or more prophylactic or therapeutic agents to a subject with such a disease or disorder.

As used herein, and unless otherwise specified, the terms "prevent," "preventing" and "prevention" refer to the prevention of the onset, recurrence or spread of a disease or disorder, or of one or more symptoms thereof.

As used herein, and unless otherwise specified, the terms "manage," "managing" and "management" refer to preventing or slowing the progression, spread or worsening of a disease or disorder, or of one or more symptoms thereof. Often, the beneficial effects that a subject derives from a prophylactic or therapeutic agent do not result in a cure of the disease or disorder.

As used herein, and unless otherwise specified, a "therapeutically effective amount" of a compound is an amount sufficient to provide a therapeutic benefit in the treatment or management of a disease or disorder, or to delay or minimize one or more symptoms associated with the disease or disorder. A therapeutically effective amount of a compound means an amount of therapeutic agent, alone or in combination with other therapies, which provides a therapeutic benefit in the treatment or management of the disease or disorder. The term "therapeutically effective amount" can encompass an amount that improves overall therapy, reduces or avoids symptoms or causes of disease or disorder, or enhances the therapeutic efficacy of another therapeutic agent.

As used herein, and unless otherwise specified, a "prophylactically effective amount" of a compound is an amount sufficient to prevent a disease or disorder, or prevent its recurrence. A prophylactically effective amount of a compound means an amount of therapeutic agent, alone or in combination with other agents, which provides a prophylactic benefit in the prevention of the disease. The term "prophylactically effective amount" can encompass an amount that improves overall prophylaxis or enhances the prophylactic efficacy of another prophylactic agent.

In one embodiment, the compounds provided herein are used for treatment, prevention, and/or management of cancer or precancerous condition. As provided herein otherwise, and without being limited by a particular theory, it was found that certain compounds provided herein exhibit antiproliferative effects on various cancer cells as determined by methods described herein as well as those known in the art. Examples of cancer cells include, but are not limited to, Namalwa, HN 5q (oral calcinoma), HT-1080 (fibrosarcoma), SK-MES-1 (5q; lung), U87MG (glioblastoma; astrocytoma), T98G (mutant p53; glioblastoma), SH-SY5Y (neuroblastoma), SK-N-MC (neuroblastoma), PC-3 (prostate), MCF-7 (breast), T-47D (breast), SF-268 (CNS), HCT-116 (colon), 786-O (kidney), A498 (kidney), SN12C (kidney), TK-10 (kidney), CCRF-CEM (leukemia), HL-60 (leukemia), K0562 (leukemia), A549 (lung), Hop 92 (lung), NCI-H1650 (lung), NCI-H522 (lung), GRANTA-519 (mantle cell lymphoma), REC-1 (mantle cell lymphoma), Malme-3M (melanoma), MDA-MB-435 (melanoma), SK-MEL-28 (melanoma), M14 (melanoma), SK-MEL-2 (melanoma), U266B1 (multiple myeloma), KARPAS-1106P (non-Hodgkins lymphoma), KARPAS-422 (non-Hodgkins lymphoma), OCI-LY-19 (non-Hodgkins lymphoma), and WSU-DLCL2 (non-Hodgkins lymphoma).

Examples of cancer and precancerous conditions include, but are not limited to, those described in U.S. Pat. Nos. 6,281,230 and 5,635,517 to Muller et al., in various U.S. patent publications to Zeldis, including publication nos. 2004/0220144A1, published Nov. 4, 2004 (Treatment of Myelodysplastic Syndrome); 2004/0029832A1, published Feb. 12, 2004 (Treatment of Various Types of Cancer); and 2004/0087546, published May 6, 2004 (Treatment of Myeloproliferative Diseases). Examples also include those described in PCT/US04/14004, filed May 5, 2004. All of these references are incorporated herein in their entireties by reference.

Specific examples of cancer include, but are not limited to, cancers of the skin, such as melanoma; lymph node; breast; cervix; uterus; gastrointestinal tract; lung; ovary; prostate; colon; rectum; mouth; brain; head and neck; throat; testes; kidney; pancreas; bone; spleen; liver; bladder; larynx; nasal passages; and AIDS-related cancers. The compounds are particularly useful for treating cancers of the blood and bone marrow, such as multiple myeloma and acute and chronic leukemias, for example, lymphoblastic, myelogenous, lymphocytic, and myelocytic leukemias. The compounds of the invention can be used for treating, preventing or managing either primary or metastatic tumors.

Other specific cancers include, but are not limited to, advanced malignancy, amyloidosis, neuroblastoma, meningioma, hemangiopericytoma, multiple brain metastase, glioblastoma multiforms, glioblastoma, brain stem glioma, poor prognosis malignant brain tumor, malignant glioma, recurrent malignant glioma, anaplastic astrocytoma, anaplastic oligodendroglioma, neuroendocrine tumor, rectal adenocarcinoma, Dukes C & D colorectal cancer, unresectable colorectal carcinoma, metastatic hepatocellular carcinoma, Kaposi's sarcoma, karotype acute myeloblastic leukemia, chronic lymphocytic leukemia (CLL), Hodgkin's lymphoma, non-Hodgkin's lymphoma, cutaneous T-Cell lymphoma, cutaneous B-Cell lymphoma, diffuse large B-Cell lymphoma, low grade follicular lymphoma, metastatic melanoma (localized melanoma, including, but not limited to, ocular melanoma), malignant mesothelioma, malignant pleural effusion mesothelioma syndrome, peritoneal carcinoma, papillary serous carcinoma, gynecologic sarcoma, soft tissue sarcoma, scleroderma, cutaneous vasculitis, Langerhans cell histiocytosis, leiomyosarcoma, fibrodysplasia ossificans progressive, hormone refractory prostate cancer, resected high-risk soft tissue sarcoma, unrescectable hepatocellular carcinoma, Waldenstrom's macroglobulinemia, smoldering myeloma, indolent myeloma, fallopian tube cancer, androgen independent prostate cancer, androgen dependent stage IV non-metastatic prostate cancer, hormone-insensitive prostate cancer, chemotherapy-insensitive prostate cancer, papillary thyroid carcinoma, follicular thyroid carcinoma, medullary thyroid carcinoma, and leiomyoma. In a specific embodiment, the cancer is metastatic. In another embodiment, the cancer is refractory or resistance to chemotherapy or radiation.

In one specific embodiment, this invention encompasses methods of treating, preventing or managing various forms of leukemias such as chronic lymphocytic leukemia, chronic myelocytic leukemia, acute lymphoblastic leukemia, acute myelogenous leukemia and acute myeloblastic leukemia, including leukemias that are relapsed, refractory or resistant, as disclosed in U.S. publication no. 2006/0030594, published Feb. 9, 2006, which is incorporated in its entirety by reference.

The term "leukemia" refers malignant neoplasms of the blood-forming tissues. The leukemia includes, but is not limited to, chronic lymphocytic leukemia, chronic myelocytic leukemia, acute lymphoblastic leukemia, acute myelogenous leukemia and acute myeloblastic leukemia. The leukemia can be relapsed, refractory or resistant to conventional therapy. The term "relapsed" refers to a situation where patients who have had a remission of leukemia after therapy have a return of leukemia cells in the marrow and a decrease in normal blood cells. The term "refractory or resistant" refers to a circumstance where patients, even after intensive treatment, have residual leukemia cells in their marrow.

In another specific embodiment, this invention encompasses methods of treating, preventing or managing various types of lymphomas, including Non-Hodgkin's lymphoma (NHL). The term "lymphoma" refers a heterogenous group of neoplasms arising in the reticuloendothelial and lymphatic systems. "NHL" refers to malignant monoclonal proliferation of lymphoid cells in sites of the immune system, including lymph nodes, bone marrow, spleen, liver and gastrointestinal tract. Examples of NHL include, but are not limited to, mantle cell lymphoma, MCL, lymphocytic lymphoma of intermediate differentiation, intermediate lymphocytic lymphoma, ILL, diffuse poorly differentiated lymphocytic lymphoma, PDL, centrocytic lymphoma, diffuse small-cleaved cell lymphoma, DSCCL, follicular lymphoma, and any type of the mantle cell lymphomas that can be seen under the microscope (nodular, diffuse, blastic and mentle zone lymphoma).

Examples of diseases and disorders associated with, or characterized by, undesired angiogenesis include, but are not limited to, inflammatory diseases, autoimmune diseases, viral diseases, genetic diseases, allergic diseases, bacterial diseases, ocular neovascular diseases, choroidal neovascular diseases, retina neovascular diseases, and rubeosis (neovascularization of the angle). Specific examples of the diseases and disorders associated with, or characterized by, undesired angiogenesis include, but are not limited to, endometriosis, Crohn's disease, heart failure, advanced heart failure, renal impairment, endotoxemia, toxic shock syndrome, osteoarthritis, retrovirus replication, wasting, meningitis, silica-induced fibrosis, asbestos-induced fibrosis, veterinary disorder, malignancy-associated hypercalcemia, stroke, circulatory shock, periodontitis, gingivitis, macrocytic anemia, refractory anemia, and 5q-deletion syndrome.

Examples of pain include, but are not limited to those described in U.S. patent publication no. 2005/0203142, published Sep. 15, 2005, which is incorporated herein by reference. Specific types of pain include, but are not limited to, nociceptive pain, neuropathic pain, mixed pain of nociceptive and neuropathic pain, visceral pain, migraine, headache and post-operative pain.

Examples of nociceptive pain include, but are not limited to, pain associated with chemical or thermal burns, cuts of the skin, contusions of the skin, osteoarthritis, rheumatoid arthritis, tendonitis, and myofascial pain.

Examples of neuropathic pain include, but are not limited to, CRPS type I, CRPS type II, reflex sympathetic dystrophy (RSD), reflex neurovascular dystrophy, reflex dystrophy, sympathetically maintained pain syndrome, causalgia, Sudeck atrophy of bone, algoneurodystrophy, shoulder hand syndrome, post-traumatic dystrophy, trigeminal neuralgia, post herpetic neuralgia, cancer related pain, phantom limb pain, fibromyalgia, chronic fatigue syndrome, spinal cord injury pain, central post-stroke pain, radiculopathy, diabetic neuropathy, post-stroke pain, luetic neuropathy, and other painful neuropathic conditions such as those induced by drugs such as vincristine and velcade.

As used herein, the terms "complex regional pain syndrome," "CRPS" and "CRPS and related syndromes" mean a chronic pain disorder characterized by one or more of the following: pain, whether spontaneous or evoked, including allodynia (painful response to a stimulus that is not usually painful) and hyperalgesia (exaggerated response to a stimulus that is usually only mildly painful); pain that is disproportionate to the inciting event (e.g., years of severe pain after an ankle sprain); regional pain that is not limited to a single peripheral nerve distribution; and autonomic dysregulation (e.g., edema, alteration in blood flow and hyperhidrosis) associated with trophic skin changes (hair and nail growth abnormalities and cutaneous ulceration).

Examples of macular degeneration (MD) and related syndromes include, but are not limited to, those described in U.S. patent publication no. 2004/0091455, published May 13, 2004, which is incorporated herein by reference. Specific examples include, but are not limited to, atrophic (dry) MD, exudative (wet) MD, age-related maculopathy (ARM), choroidal neovascularisation (CNVM), retinal pigment epithelium detachment (PED), and atrophy of retinal pigment epithelium (RPE).

Examples of skin diseases include, but are not limited to, those described in U.S. publication no. 2005/0214328A1, published Sep. 29, 2005, which is incorporated herein by reference. Specific examples include, but are not limited to, keratoses and related symptoms, skin diseases or disorders characterized with overgrowths of the epidermis, acne, and wrinkles.

As used herein, the term "keratosis" refers to any lesion on the epidermis marked by the presence of circumscribed overgrowths of the horny layer, including but not limited to actinic keratosis, seborrheic keratosis, keratoacanthoma, keratosis follicularis (Darier disease), inverted follicular keratosis, palmoplantar keratoderma (PPK, keratosis palmaris et plantaris), keratosis pilaris, and stucco keratosis. The term "actinic keratosis" also refers to senile keratosis, keratosis senilis, verruca senilis, plana senilis, solar keratosis, keratoderma or keratoma. The term "seborrheic keratosis" also refers to seborrheic wart, senile wart, or basal cell papilloma. Keratosis is characterized by one or more of the following symptoms: rough appearing, scaly, erythematous papules, plaques, spicules or nodules on exposed surfaces (e.g., face, hands, ears, neck, legs and thorax), excrescences of keratin referred to as cutaneous horns, hyperkeratosis, telangiectasias, elastosis, pigmented lentigines, acanthosis, parakeratosis, dyskeratoses, papillomatosis, hyperpigmentation of the basal cells, cellular atypia, mitotic figures, abnormal cell-cell adhesion, dense inflammatory infiltrates and small prevalence of squamous cell carcinomas.

Examples of skin diseases or disorders characterized with overgrowths of the epidermis include, but are not limited to, any conditions, diseases or disorders marked by the presence of overgrowths of the epidermis, including but not limited to, infections associated with papilloma virus, arsenical keratoses, sign of Leser-Trélat, warty dyskeratoma (WD), trichostasis spinulosa (TS), erythrokeratodermia variabilis (EKV), ichthyosis fetalis (harlequin ichthyosis), knuckle pads, cutaneous melanoacanthoma, porokeratosis, psoriasis, squamous cell carcinoma, confluent and reticulated papillomatosis (CRP), acrochordons, cutaneous horn, cowden disease (multiple hamartoma syndrome), dermatosis papulosa nigra (DPN), epidermal nevus syndrome (ENS), ichthyosis vulgaris, molluscum contagiosum, prurigo nodularis, and acanthosis nigricans (AN).

Examples of pulmonary disorders include, but are not limited to, those described in U.S. publication no. 2005/0239842A1, published Oct. 27, 2005, which is incorporated herein by reference. Specific examples include pulmonary hypertension and related disorders. Examples of pulmonary hypertension and related disorders include, but are not limited to: primary pulmonary hypertension (PPH); secondary pulmonary hypertension (SPH); familial PPH; sporadic PPH; precapillary pulmonary hypertension; pulmonary arterial hypertension (PAH); pulmonary artery hypertension; idiopathic pulmonary hypertension; thrombotic pulmonary arteriopathy (TPA); plexogenic pulmonary arteriopathy; functional classes I to IV pulmonary hypertension; and pulmonary hypertension associated with, related to, or secondary to, left ventricular dysfunction, mitral valvular disease, constrictive pericarditis, aortic stenosis, cardiomyopathy, mediastinal fibrosis, anomalous pulmonary venous drainage, pulmonary venoocclusive disease, collagen vascular disease, congenital heart disease, HIV virus infection, drugs and toxins such as fenfluramines, congenital heart disease, pulmonary venous hypertension, chronic obstructive pulmonary disease, interstitial lung disease, sleep-disordered breathing, alveolar hypoventilation disorder, chronic exposure to high altitude, neonatal lung disease, alveolar-capillary dysplasia, sickle cell disease, other coagulation disorder, chronic thromboemboli, connective tissue disease, lupus including systemic and cutaneous lupus, schistosomiasis, sarcoidosis or pulmonary capillary hemangiomatosis.

Examples of asbestos-related disorders include, but not limited to, those described in U.S. publication no. 2005/0100529, published May 12, 2005, which is incorporated herein by reference. Specific examples include, but are not limited to, mesothelioma, asbestosis, malignant pleural effusion, benign exudative effusion, pleural plaques, pleural calcification, diffuse pleural thickening, rounded atelectasis, fibrotic masses, and lung cancer.

Examples of parasitic diseases include, but are not limited to, those described in U.S. application Ser. No. 11/271,963, filed Nov. 14, 2005, which is incorporated herein by reference. Parasitic diseases include diseases and disorders caused by human intracellular parasites such as, but not limited to, *P. falcifarium, P. ovale, P. vivax, P. malariae, L. donovari, L. infantum, L. aethiopica, L. major, L. tropica, L. mexicana, L. braziliensis, T. Gondii, B. microti, B. divergens, B. coli, C. parvum, C. cayetanensis, E. histolytica, I. belli, S. mansonii, S. haematobium, Trypanosoma* ssp., *Toxoplasma* ssp., and *O. volvulus*. Other diseases and disorders caused by non-human intracellular parasites such as, but not limited to, *Babesia bovis, Babesia canis, Babesia Gibsoni, Besnoitia darlingi, Cytauxzoon fells, Eimeria* ssp., *Hammondia* ssp., and *Theileria* ssp., are also encompassed. Specific examples include, but are not limited to, malaria, babesiosis, trypanosomiasis, leishmaniasis, toxoplasmosis, meningoencephalitis, keratitis, amebiasis, giardiasis, cryptosporidiosis, isosporiasis, cyclosporiasis, microsporidiosis, ascariasis, trichuriasis, ancylostomiasis, strongyloidiasis, toxocariasis, trichinosis, lymphatic filariasis, onchocerciasis, filariasis, schistosomiasis, and dermatitis caused by animal schistosomes.

Examples of immunodeficiency disorders include, but are not limited to, those described in U.S. application Ser. No. 11/289,723, filed Nov. 30, 2005. Specific examples include, but not limited to, adenosine deaminase deficiency, antibody deficiency with normal or elevated Igs, ataxia-tenlangiectasia, bare lymphocyte syndrome, common variable immunodeficiency, Ig deficiency with hyper-IgM, Ig heavy chain deletions, IgA deficiency, immunodeficiency with thymoma, reticular dysgenesis, Nezelof syndrome, selective IgG subclass deficiency, transient hypogammaglobulinemia of infancy, Wistcott-Aldrich syndrome, X-linked agammaglobulinemia, X-linked severe combined immunodeficiency.

Examples of CNS disorders include, but are not limited to, those described in U.S. publication no. 2005/0143344A1, published Jun. 30, 2005, which is incorporated herein by reference. Specific examples include, but are not limited to, include, but are not limited to, Amyotrophic Lateral Sclerosis, Alzheimer Disease, Parkinson Disease, Huntington's Disease, Multiple Sclerosis other neuroimmunological disorders such as Tourette Syndrome, delerium, or disturbances in consciousness that occur over a short period of time, and amnestic disorder, or discreet memory impairments that occur in the absence of other central nervous system impairments.

Examples of CNS injuries and related syndromes include, but are not limited to, those described in U.S. application Ser. No. 11/284,403, filed Nov. 18, 2005, which is incorporated herein by reference. Specific examples include, but are not limited to, CNS injury/damage and related syndromes, include, but are not limited to, primary brain injury, secondary brain injury, traumatic brain injury, focal brain injury, diffuse axonal injury, head injury, concussion, post-concussion syndrome, cerebral contusion and laceration, subdural hematoma, epidermal hematoma, post-traumatic epilepsy, chronic vegetative state, complete SCI, incomplete SCI, acute SCI, subacute SCI, chronic SCI, central cord syndrome, Brown-Sequard syndrome, anterior cord syndrome, conus medullaris syndrome, cauda equina syndrome, neurogenic shock, spinal shock, altered level of consciousness, headache, nausea, emesis, memory loss, dizziness, diplopia, blurred vision, emotional lability, sleep disturbances, irritability, inability to concentrate, nervousness, behavioral impairment, cognitive deficit, and seizure.

Other disease or disorders include, but not limited to, viral, genetic, allergic, and autoimmune diseases. Specific examples include, but not limited to, HIV, hepatitis, adult respiratory distress syndrome, bone resorption diseases, chronic pulmonary inflammatory diseases, dermatitis, cystic fibrosis, septic shock, sepsis, endotoxic shock, hemodynamic shock, sepsis syndrome, post ischemic reperfusion injury, meningitis, psoriasis, fibrotic disease, cachexia, graft versus host disease, graft rejection, auto-immune disease, rheumatoid spondylitis, Crohn's disease, ulcerative colitis, inflammatory-bowel disease, multiple sclerosis, systemic lupus erythrematosus, ENL in leprosy, radiation damage, cancer, asthma, or hyperoxic alveolar injury.

Examples of atherosclerosis and related conditions include, but not limited to, those disclosed in U.S. publication no. 2002/0054899, published May 9, 2002, which is incorporated herein by reference. Specific examples include, but are not limited to, all forms of conditions involving atherosclerosis, including restenosis after vascular intervention such as angioplasty, stenting, atherectomy and grafting. All forms of vascular intervention are contemplated by the invention including diseases of the cardiovascular and renal system, such as, but not limited to, renal angioplasty, percutaneous coronary intervention (PCI), percutaneous transluminal coronary angioplasty (PTCA), carotid percutaneous transluminal angioplasty (PTA), coronary by-pass grafting, angioplasty with stent implantation, peripheral percutaneous transluminal intervention of the iliac, femoral or popliteal arteries, and surgical intervention using impregnated artificial grafts. The following chart provides a listing of the major systemic arteries that may be in need of treatment, all of which are contemplated by the invention:

| Artery | Body Areas Supplied |
| --- | --- |
| Axillary | Shoulder and axilla |
| Brachial | Upper arm |
| Brachiocephalic | Head, neck, and arm |
| Celiac | Divides into left gastric, splenic, and hepatic arteries |
| Common carotid | Neck |
| Common iliac | Divides into external and internal iliac arteries |
| Coronary | Heart |
| Deep femoral | Thigh |
| Digital | Fingers |
| Dorsalis pedis | Foot |
| External carotid | Neck and external head regions |
| External iliac | Femoral artery |
| Femoral | Thigh |
| Gastric | Stomach |
| Hepatic | Liver, gallbladder, pancreas, and duodenum |
| Inferior mesenteric | Descending colon, rectum, and pelvic wall |
| Internal carotid | Neck and internal head regions |
| Internal iliac | Rectum, urinary bladder, external genitalia, buttocks muscles, uterus and vagina |
| Left gastric | Esophagus and stomach |
| Middle sacral | Sacrum |
| Ovarian | Ovaries |
| Palmar arch | Hand |
| Peroneal | Calf |
| Popliteal | Knee |
| Posterior tibial | Calf |
| Pulmonary | Lungs |
| Radial | Forearm |
| Renal | Kidney |
| Splenic | Stomach, pancreas, and spleen |
| Subclavian | Shoulder |
| Superior mesenteric | Pancreas, small intestine, ascending and transverse colon |
| Testicular | Testes |
| Ulnar | Forearm |

Examples of dysfunctional sleep and related syndromes include, but are not limited to, those disclosed in U.S. publication no. 2005/0222209A1, published Oct. 6, 2005, which is incorporated herein by reference. Specific examples include, but are not limited to, snoring, sleep apnea, insomnia, narcolepsy, restless leg syndrome, sleep terrors, sleep walking sleep eating, and dysfunctional sleep associated with chronic neurological or inflammatory conditions. Chronic neurological or inflammatory conditions, include, but are not limited to, Complex Regional Pain Syndrome, chronic low back pain, musculoskeletal pain, arthritis, radiculopathy, pain associated with cancer, fibromyalgia, chronic fatigue syndrome, visceral pain, bladder pain, chronic pancreatitis, neuropathies (diabetic, post-herpetic, traumatic or inflammatory), and neurodegenerative disorders such as Parkinson's Disease, Alzheimer's Disease, amyotrophic lateral sclerosis, multiple sclerosis, Huntington's Disease, bradykinesia; muscle rigidity; parkinsonian tremor; parkinsonian gait; motion freezing; depression; defective long-term memory, Rubinstein-Taybi syndrome (RTS); dementia; postural instability; hypokinetic disorders; synuclein disorders; multiple system atrophies; striatonigral degeneration; olivopontocerebellar atrophy; Shy-Drager syndrome; motor neuron disease with parkinsonian features; Lewy body dementia; Tau pathology disorders; progressive supranuclear palsy; corticobasal degeneration; frontotemporal dementia; amyloid pathology disorders; mild cognitive impairment; Alzheimer disease with parkinsonism; Wilson disease; Hallervorden-Spatz disease; Chediak-Hagashi disease; SCA-3 spinocerebellar ataxia; X-linked dystonia parkinsonism; prion disease; hyperkinetic disorders; chorea; ballismus; dystonia tremors; Amyotrophic Lateral Sclerosis (ALS); CNS trauma and myoclonus.

Examples of hemoglobinopathy and related disorders include, but are not limited to, those described in U.S. publication no. 2005/0143420A1, published Jun. 30, 2005, which is incorporated herein by reference. Specific examples include, but are not limited to, hemoglobinopathy, sickle cell anemia, and any other disorders related to the differentiation of CD34+ cells.

Examples of TNFα related disorders include, but are not limited to, those described in WO 98/03502 and WO 98/54170, both of which are incorporated herein in their entireties by reference. Specific examples include, but are not limited to: endotoxemia or toxic shock syndrome; cachexia; adult respiratory distress syndrome; bone resorption diseases such as arthritis; hypercalcemia; Graft versus Host Reaction; cerebral malaria; inflammation; tumor growth; chronic pulmonary inflammatory diseases; reperfusion injury; myocardial infarction; stroke; circulatory shock; rheumatoid arthritis; Crohn's disease; HIV infection and AIDS; other disorders such as rheumatoid arthritis, rheumatoid spondylitis, osteoarthritis and other arthritic conditions, septic shock, septis, endotoxic shock, graft versus host disease, wasting, Crohn's disease, ulcerative colitis, multiple sclerosis, systemic lupus erythromatosis, ENL in leprosy, HIV, AIDS, and opportunistic infections in AIDS; cAMP related disorders such as septic shock, sepsis, endotoxic shock, hemodynamic shock and sepsis syndrome, post ischemic reperfusion injury, malaria, mycobacterial infection, meningitis, psoriasis, congestive heart failure, fibrotic disease, cachexia, graft rejection, oncogenic or cancerous conditions, asthma, autoimmune disease, radiation damages, and hyperoxic alveolar injury; viral infections, such as those caused by the herpes viruses; viral conjunctivitis; or atopic dermatitis.

In other embodiments, the use of compounds of this invention in various immunological applications, in particular, as vaccine adjuvants, particularly anticancer vaccine adjuvants, as disclosed in U.S. Provisional Application No. 60/712,823, filed Sep. 1, 2005, which is incorporated herein in its entirety by reference, is also encompassed. This aspect of the invention also relates to the uses of compounds of this invention in combination with vaccines to treat or prevent cancer or infectious diseases, and other various uses of immunomodulatory compounds such as reduction or desensitization of allergic reactions.

Doses of a compound of this invention, or a pharmaceutically acceptable salt, solvate, stereoisomer or prodrug thereof, vary depending on factors such as: specific indication to be treated, prevented, or managed; age and condition of a patient; and amount of second active agent used, if any. Generally, a compound of this invention, or a pharmaceutically acceptable salt, solvate, stereoisomer or prodrug thereof, may be used in an amount of from about 0.1 mg to about 500 mg per day, and can be adjusted in a conventional fashion (e.g., the same amount administered each day of the treatment, prevention or management period), in cycles (e.g., one week on, one week off), or in an amount that increases or decreases over the course of treatment, prevention, or management.

In other embodiments, the dose can be from about 1 mg to about 300 mg, from about 0.1 mg to about 150 mg, from about 1 mg to about 200 mg, from about 10 mg to about 100 mg, from about 0.1 mg to about 50 mg, from about 1 mg to about 50 mg, from about 10 mg to about 50 mg, from about 10 mg to about 25 mg, from about 20 mg to about 30 mg, or from about 1 mg to about 20 mg.

4.3 Second Active Agents

A compound of this invention, or a pharmaceutically acceptable salt, solvate, stereoisomer or prodrug thereof, can be combined with other pharmacologically active compounds ("second active agents") in methods and compositions of the invention. It is believed that certain combinations may work synergistically in the treatment of particular types of diseases or disorders, and conditions and symptoms associated with such diseases or disorders. A compound of this invention, or a pharmaceutically acceptable salt, solvate, stereoisomer or prodrug thereof, can also work to alleviate adverse effects associated with certain second active agents, and vice versa.

One or more second active ingredients or agents can be used in the methods and compositions of the invention. Second active agents can be large molecules (e.g., proteins) or small molecules (e.g., synthetic inorganic, organometallic, or organic molecules).

Examples of large molecule active agents include, but are not limited to, hematopoietic growth factors, cytokines, and monoclonal and polyclonal antibodies. Specific examples of the active agents are anti-CD40 monoclonal antibodies (such as, for example, SGN-40); histone deacetlyase inhibitors (such as, for example, SAHA and LAQ 824); heat-shock protein-90 inhibitors (such as, for example, 17-AAG); insulin-like growth factor-1 receptor kinase inhibitors; vascular endothelial growth factor receptor kinase inhibitors (such as, for example, PTK787); insulin growth factor receptor inhibitors; lysophosphatidic acid acyltransferase inhibitors; IkB kinase inhibitors; p38MAPK inhibitors; EGFR inhibitors (such as, for example, gefitinib and erlotinib HCL); HER-2 antibodies (such as, for example, trastuzumab (Herceptin®) and pertuzumab (Omnitarg™)); VEGFR antibodies (such as, for example, bevacizumab (Avastin™)); VEGFR inhibitors (such as, for example, flk-1 specific kinase inhibitors, SU5416 and ptk787/zk222584); P13K inhibitors (such as, for example, wortmannin); C-Met inhibitors (such as, for example, PHA-665752); monoclonal antibodies (such as, for example, rituximab (Rituxan®), tositumomab (Bexxar®), edrecolomab (Panorex®) and G250); and anti-TNF-α antibodies. Examples of small molecule active agents include, but are not limited to, small molecule anti-cancer agents and antibiotics (e.g., clarithromycin).

Specific second active compounds that can be combined with compounds of this invention vary depending on the specific indication to be treated, prevented or managed.

For instance, for the treatment, prevention or management of cancer, second active agents include, but are not limited to: semaxanib; cyclosporin; etanercept; doxycycline; bortezomib; acivicin; aclarubicin; acodazole hydrochloride; acronine; adozelesin; aldesleukin; altretamine; ambomycin; ametantrone acetate; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; celecoxib; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; iproplatin; irinotecan; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride;

pyrazofurin; riboprine; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; taxotere; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; and zorubicin hydrochloride.

Other second agents include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; doxorubicin; droloxifene; dronabinol; duocarmycin SA; ebselen; ecomustine; edelfosine; edrecolomab; eflornithine; elemene; emitefur; epirubicin; episteride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imatinib (Gleevec®), imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mitoguazone; mitolactol; mitomycin analogues; mitonafide; mitotoxin fibroblast growth factor-saporin; mitoxantrone; mofarotene; molgramostim; Erbitux, human chorionic gonadotrophin; monophosphoryl lipid A+myobacterium cell wall sk; mopidamol; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; nilutamide; nisamycin; nitric oxide modulators; nitroxide antioxidant; nitrullyn; oblimersen (Genasense®); O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RH retinamide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stipiamide; stromelysin inhibitors; sulfinosine; superactive vasoactive intestinal peptide antagonist; suradista; suramin; swainsonine; tallimustine; tamoxifen methiodide; tauromustine; tazarotene; tecogalan sodium; tegafur; tellurapyrylium; telomerase inhibitors; temoporfin; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; translation inhibitors; tretinoin; triacetyluridine; triciribine; trimetrexate; triptorelin; tropisetron; turosteride; tyrosine kinase inhibitors; tyrphostins; UBC inhibitors; ubenimex;

urogenital sinus-derived growth inhibitory factor; urokinase receptor antagonists; vapreotide; variolin B; velaresol; veramine; verdins; verteporfin; vinorelbine; vinxaltine; vitaxin; vorozole; zanoterone; zeniplatin; zilascorb; and zinostatin stimalamer.

Specific second active agents include, but are not limited to, 2-methoxyestradiol, telomestatin, inducers of apoptosis in multiple myeloma cells (such as, for example, TRAIL), statins, semaxanib, cyclosporin, etanercept, doxycycline, bortezomib, oblimersen (Genasense®), remicade, docetaxel, celecoxib, melphalan, dexamethasone (Decadron®), steroids, gemcitabine, cisplatinum, temozolomide, etoposide, cyclophosphamide, temodar, carboplatin, procarbazine, gliadel, tamoxifen, topotecan, Tykerb® (lapatinib), methotrexate, Arisa®, taxol, taxotere, fluorouracil, leucovorin, irinotecan, xeloda, CPT-11, interferon alpha, pegylated interferon alpha (e.g., PEG INTRON-A), capecitabine, cisplatin, thiotepa, fludarabine, carboplatin, liposomal daunorubicin, cytarabine, doxetaxol, pacilitaxel, vinblastine, IL-2, GM-CSF, dacarbazine, vinorelbine, zoledronic acid, palmitronate, biaxin, busulphan, prednisone, bisphosphonate, arsenic trioxide, vincristine, doxorubicin (Doxil®), pacilitaxel, ganciclovir, adriamycin, estramustine sodium phosphate (Emcyt®), sulindac, and etoposide.

Similarly, examples of specific second agents according to the indications to be treated, prevented, or managed can be found in the following references, all of which are incorporated herein in their entireties: U.S. Pat. Nos. 6,281,230 and 5,635,517; U.S. application Ser. Nos. 10/411,649, 10/483,213, 10/411,656, 10/693,794, 10/699,154, and 10/981,189; and U.S. provisional application Nos. 60/554,923, 60/565,172, 60/626,975, 60/630,599, 60/631,870, and 60/533,862.

Examples of second active agents that may be used for the treatment, prevention and/or management of pain include, but are not limited to, conventional therapeutics used to treat or prevent pain such as antidepressants, anticonvulsants, antihypertensives, anxiolytics, calcium channel blockers, muscle relaxants, non-narcotic analgesics, opioid analgesics, anti-inflammatories, cox-2 inhibitors, immunomodulatory agents, alpha-adrenergic receptor agonists or antagonists, immunosuppressive agents, corticosteroids, hyperbaric oxygen, ketamine, other anesthetic agents, NMDA antagonists, and other therapeutics found, for example, in the *Physician's Desk Reference* 2003. Specific examples include, but are not limited to, salicylic acid acetate (Aspirin®), celecoxib (Celebrex®), Enbrel®, ketamine, gabapentin (Neurontin®), phenytoin (Dilantin®), carbamazepine (Tegretol®), oxcarbazepine (Trileptal®), valproic acid (Depakene®), morphine sulfate, hydromorphone, prednisone, griseofulvin, penthonium, alendronate, dyphenhydramide, guanethidine, ketorolac (Acular®), thyrocalcitonin, dimethylsulfoxide (DMSO), clonidine (Catapress®), bretylium, ketanserin, reserpine, droperidol, atropine, phentolamine, bupivacaine, lidocaine, acetaminophen, nortriptyline)(Pamelor®), amitriptyline (Elavir®), imipramine (Tofranil®), doxepin (Sinequan®), clomipramine (Anafranil®), fluoxetine (Prozac®), sertraline (Zoloft®), nefazodone (Serzone®), venlafaxine (Effexor®), trazodone (Desyrel®), bupropion (Wellbutrin®), mexiletine, nifedipine, propranolol, tramadol, lamotrigine, ziconotide, ketamine, dextromethorphan, benzodiazepines, baclofen, tizanidine and phenoxybenzamine.

Examples of second active agents that may be used for the treatment, prevention and/or management of MD and related syndromes include, but are not limited to, a steroid, a light sensitizer, an integrin, an antioxidant, an interferon, a xanthine derivative, a growth hormone, a neutrotrophic factor, a regulator of neovascularization, an anti-VEGF antibody, a prostaglandin, an antibiotic, a phytoestrogen, an anti-inflammatory compound or an antiangiogenesis compound, or a combination thereof. Specific examples include, but are not limited to, verteporfin, purlytin, an angiostatic steroid, rhuFab, interferon-2α, pentoxifylline, tin etiopurpurin, motexafin lutetium, 9-fluoro-11,21-dihydroxy-16, 17-1-methylethylidinebis(oxy)pregna-1,4-diene-3,20-dione, latanoprost (see U.S. Pat. No. 6,225,348), tetracycline and its derivatives, rifamycin and its derivatives, macrolides, metronidazole (U.S. Pat. Nos. 6,218,369 and 6,015,803), genistein, genistin, 6'-O-Mal genistin, 6'-O—Ac genistin, daidzein, daidzin, 6'-O-Mal daidzin, 6'-O—Ac daidzin, glycitein, glycitin, 6'-O-Mal glycitin, biochanin A, formononetin (U.S. Pat. No. 6,001,368), triamcinolone acetomide, dexamethasone (U.S. Pat. No. 5,770,589), thalidomide, glutathione (U.S. Pat. No. 5,632,984), basic fibroblast growth factor (bFGF), transforming growth factor b (TGF-b), brain-derived neurotrophic factor (BDNF), plasminogen activator factor type 2 (PAI-2), EYE 101 (Eyetech Pharmaceuticals), LY333531 (Eli Lilly), Miravant, and RETISERT implant (Bausch & Lomb). All of the references cited above are incorporated herein in their entireties by reference.

Examples of second active agents that may be used for the treatment, prevention and/or management of skin diseases include, but are not limited to, keratolytics, retinoids, α-hydroxy acids, antibiotics, collagen, botulinum toxin, interferon, steroids, and immunomodulatory agents. Specific examples include, but are not limited to, 5-fluorouracil, masoprocol, trichloroacetic acid, salicylic acid, lactic acid, ammonium lactate, urea, tretinoin, isotretinoin, antibiotics, collagen, botulinum toxin, interferon, corticosteroid, transretinoic acid and collagens such as human placental collagen, animal placental collagen, Dermalogen, AlloDerm, Fascia, Cymetra, Autologen, Zyderm, Zyplast, Resoplast, and Isolagen.

Examples of second active agents that may be used for the treatment, prevention and/or management of pulmonary hepertension and related disorders include, but are not limited to, anticoagulants, diuretics, cardiac glycosides, calcium channel blockers, vasodilators, prostacyclin analogues, endothelin antagonists, phosphodiesterase inhibitors (e.g., PDE V inhibitors), endopeptidase inhibitors, lipid lowering agents, thromboxane inhibitors, and other therapeutics known to reduce pulmonary artery pressure. Specific examples include, but are not limited to, warfarin (Coumadin), a diuretic, a cardiac glycoside, digoxin-oxygen, diltiazem, nifedipine, a vasodilator such as prostacyclin (e.g., prostaglandin I2 (PGI2), epoprostenol (EPO, Floran®), treprostinil (Remodulin®), nitric oxide (NO), bosentan (Tracleer®), amlodipine, epoprostenol (Floran®), treprostinil (Remodulin®), prostacyclin, tadalafil (Cialis®), simvastatin (Zocor®), omapatrilat (Vanlev®), irbesartan (Avapro®), pravastatin (Pravachol®), digoxin, L-arginine, iloprost, betaprost, and sildenafil (Viagra®).

Examples of second active agents that may be used for the treatment, prevention and/or management of asbestos-related disorders include, but are not limited to, anthracycline, platinum, alkylating agent, oblimersen (Genasense®), cisplatinum, cyclophosphamide, temodar, carboplatin, procarbazine, gliadel, tamoxifen, topotecan, methotrexate, taxotere, irinotecan, capecitabine, cisplatin, thiotepa, fludarabine, carboplatin, liposomal daunorubicin, cytarabine, doxetaxol, pacilitaxel, vinblastine, IL-2, GM-CSF, dacarbazine, vinorelbine, zoledronic acid, palmitronate, biaxin, busulphan, prednisone, bisphosphonate, arsenic trioxide, vincristine, doxorubicin (Doxil®), paclitaxel, ganciclovir, adriamycin, bleomycin, hyaluronidase, mitomycin C, mepacrine, thiotepa, tetracycline and gemcitabine.

Examples of second active agents that may be used for the treatment, prevention and/or management of parasitic diseases include, but are not limited to, chloroquine, quinine, quinidine, pyrimethamine, sulfadiazine, doxycycline, clindamycin, mefloquine, halofantrine, primaquine, hydroxychloroquine, proguanil, atovaquone, azithromycin, suramin, pentamidine, melarsoprol, nifurtimox, benznidazole, amphotericin B, pentavalent antimony compounds (e.g., sodium stiboglucuronate), interfereon gamma, itraconazole, a combination of dead promastigotes and BCG, leucovorin, corticosteroids, sulfonamide, spiramycin, IgG (serology), trimethoprim, and sulfamethoxazole.

Examples of second active agents that may be used for the treatment, prevention and/or management of immunodeficiency disorders include, but are not limited to: antibiotics (therapeutic or prophylactic) such as, but not limited to, ampicillin, clarithromycin, tetracycline, penicillin, cephalosporins, streptomycin, kanamycin, and erythromycin; antivirals such as, but not limited to, amantadine, rimantadine, acyclovir, and ribavirin; immunoglobulin; plasma; immunologic enhancing drugs such as, but not limited to, levami sole and isoprinosine; biologics such as, but not limited to, gammaglobulin, transfer factor, interleukins, and interferons; hormones such as, but not limited to, thymic; and other immunologic agents such as, but not limited to, B cell stimulators (e.g., BAFF/BlyS), cytokines (e.g., IL-2, IL-4, and IL-5), growth factors (e.g., TGF-α), antibodies (e.g., anti-CD40 and IgM), oligonucleotides containing unmethylated CpG motifs, and vaccines (e.g., viral and tumor peptide vaccines).

Examples of second active agents that may be used for the treatment, prevention and/or management of CNS disorders include, but are not limited to: a dopamine agonist or antagonist, such as, but not limited to, Levodopa, L-DOPA, cocaine, α-methyl-tyrosine, reserpine, tetrabenazine, benzotropine, pargyline, fenodolpam mesylate, cabergoline, pramipexole dihydrochloride, ropinorole, amantadine hydrochloride, selegiline hydrochloride, carbidopa, pergolide mesylate, Sinemet CR, and Symmetrel; a MAO inhibitor, such as, but not limited to, iproniazid, clorgyline, phenelzine and isocarboxazid; a COMT inhibitor, such as, but not limited to, tolcapone and entacapone; a cholinesterase inhibitor, such as, but not limited to, physostigmine saliclate, physostigmine sulfate, physostigmine bromide, meostigmine bromide, neostigmine methylsulfate, ambenonim chloride, edrophonium chloride, tacrine, pralidoxime chloride, obidoxime chloride, trimedoxime bromide, diacetyl monoxim, endrophonium, pyridostigmine, and demecarium; an anti-inflammatory agent, such as, but not limited to, naproxen sodium, diclofenac sodium, diclofenac potassium, celecoxib, sulindac, oxaprozin, diflunisal, etodolac, meloxicam, ibuprofen, ketoprofen, nabumetone, refecoxib, methotrexate, leflunomide, sulfasalazine, gold salts, Rho-D Immune Globulin, mycophenylate mofetil, cyclosporine, azathioprine, tacrolimus, basiliximab, daclizumab, salicylic acid, acetylsalicylic acid, methyl salicylate, diflunisal, salsalate, olsalazine, sulfasalazine, acetaminophen, indomethacin, sulindac, mefenamic acid, meclofenamate sodium, tolmetin, ketorolac, dichlofenac, flurbinprofen, oxaprozin, piroxicam, meloxicam, ampiroxicam, droxicam, pivoxicam, tenoxicam, phenylbutazone, oxyphenbutazone, antipyrine, aminopyrine, apazone, zileuton, aurothioglucose, gold sodium thiomalate, auranofin, methotrexate, colchicine, allopurinol, probenecid, sulfinpyrazone and benzbromarone or betamethasone and other glucocorticoids; and an antiemetic agent, such as, but not limited to, metoclopromide, domperidone, prochlorperazine, promethazine, chlorpromazine, trimethobenzamide, ondansetron, granisetron, hydroxyzine, acetylleucine monoethanolamine, alizapride, azasetron, benzquinamide, bietanautine, bromopride, buclizine, clebopride, cyclizine, dimenhydrinate, diphenidol, dolasetron, meclizine, methallatal, metopimazine, nabilone, oxyperndyl, pipamazine, scopolamine, sulpiride, tetrahydrocannabinol, thiethylperazine, thioproperazine, tropisetron, and a mixture thereof.

Examples of second active agents that may be used for the treatment, prevention and/or management of CNS injuries and related syndromes include, but are not limited to, immunomodulatory agents, immunosuppressive agents, antihypertensives, anticonvulsants, fibrinolytic agents, antiplatelet agents, antipsychotics, antidepressants, benzodiazepines, buspirone, amantadine, and other known or conventional agents used in patients with CNS injury/damage and related syndromes. Specific examples include, but are not limited to: steroids (e.g., glucocorticoids, such as, but not limited to, methylprednisolone, dexamethasone and betamethasone); an anti-inflammatory agent, including, but not limited to, naproxen sodium, diclofenac sodium, diclofenac potassium, celecoxib, sulindac, oxaprozin, diflunisal, etodolac, meloxicam, ibuprofen, ketoprofen, nabumetone, refecoxib, methotrexate, leflunomide, sulfasalazine, gold salts, RHo-D Immune Globulin, mycophenylate mofetil, cyclosporine, azathioprine, tacrolimus, basiliximab, daclizumab, salicylic acid, acetylsalicylic acid, methyl salicylate, diflunisal, salsalate, olsalazine, sulfasalazine, acetaminophen, indomethacin, sulindac, mefenamic acid, meclofenamate sodium, tolmetin, ketorolac, dichlofenac, flurbinprofen, oxaprozin, piroxicam, meloxicam, ampiroxicam, droxicam, pivoxicam, tenoxicam, phenylbutazone, oxyphenbutazone, antipyrine, aminopyrine, apazone, zileuton, aurothioglucose, gold sodium thiomalate, auranofin, methotrexate, colchicine, allopurinol, probenecid, sulfinpyrazone and benzbromarone; a cAMP analog including, but not limited to, db-cAMP; an agent comprising a methylphenidate drug, which comprises l-threo-methylphenidate, d-threo-methylphenidate, dl-threo-methylphenidate, l-erythro-methylphenidate, d-erythro-methylphenidate, dl-erythro-methylphenidate, and a mixture thereof; and a diuretic agent such as, but not limited to, mannitol, furosemide, glycerol, and urea.

Examples of second active agent that may be used for the treatment, prevention and/or management of dysfunctional sleep and related syndromes include, but are not limited to, a tricyclic antidepressant agent, a selective serotonin reuptake inhibitor, an antiepileptic agent (gabapentin, pregabalin, carbamazepine, oxcarbazepine, levitiracetam, topiramate), an antiaryhthmic agent, a sodium channel blocking agent, a selective inflammatory mediator inhibitor, an opioid agent, a second immunomodulatory compound, a combination agent, and other known or conventional agents used in sleep therapy. Specific examples include, but are not limited to, Neurontin, oxycontin, morphine, topiramate, amitryptiline, nortryptiline, carbamazepine, Levodopa, L-DOPA, cocaine, α-methyl-tyrosine, reserpine, tetrabenazine, benzotropine, pargyline, fenodolpam mesylate, cabergoline, pramipexole dihydrochloride, ropinorole, amantadine hydrochloride, selegiline hydrochloride, carbidopa, pergolide mesylate, Sinemet CR, Symmetrel, iproniazid, clorgyline, phenelzine, isocarboxazid, tolcapone, entacapone, physostigmine saliclate, physostigmine sulfate, physostigmine bromide, meostigmine bromide, neostigmine methylsulfate, ambenonim chloride, edrophonium chloride, tacrine, pralidoxime chloride, obidoxime chloride, trimedoxime bromide, diacetyl monoxim, endrophonium, pyridostigmine, demecarium, naproxen sodium, diclofenac sodium, diclofenac potassium, celecoxib, sulindac, oxaprozin, diflunisal, etodolac, meloxicam, ibuprofen, ketoprofen, nabumetone, refecoxib, methotrexate, leflunomide, sulfasalazine, gold salts, RHo-D Immune Globulin, mycophenylate mofetil, cyclosporine, azathioprine, tacrolimus, basiliximab, daclizumab, salicylic acid, acetylsalicylic acid, methyl salicylate, diflunisal, salsalate, olsalazine, sulfasalazine, acetaminophen, indomethacin, sulindac, mefenamic acid, meclofenamate sodium, tolmetin, ketorolac, dichlofenac, flurbinprofen, oxaprozin, piroxicam, meloxicam, ampiroxicam, droxicam, pivoxicam, tenoxicam, phenylbutazone, oxyphenbutazone, antipyrine, aminopyrine, apazone, zileuton, aurothioglucose, gold sodium thiomalate, auranofin, methotrexate, colchicine, allopurinol, probenecid, sulfinpyrazone, benzbromarone, betamethasone and other glucocorticoids, metoclopromide, domperidone, prochlorperazine, promethazine, chlorpromazine, trimethobenzamide, ondansetron, granisetron, hydroxyzine, acetylleucine monoethanolamine, alizapride, azasetron, benzquinamide, bietanautine, bromopride, buclizine, clebopride, cyclizine, dimenhydrinate, diphenidol, dolasetron, meclizine, methallatal, metopimazine, nabilone, oxyperndyl, pipamazine, scopolamine, sulpiride, tetrahydrocannabinol, thiethylperazine, thioproperazine, tropisetron, and a mixture thereof.

Examples of second active agents that may be used for the treatment, prevention and/or management of hemoglobinopathy and related disorders include, but are not limited to: interleukins, such as IL-2 (including recombinant IL-II ("rIL2") and canarypox IL-2), IL-10, IL-12, and IL-18; interferons, such as interferon alfa-2a, interferon alfa-2b, interferon alfa-n1, interferon alfa-n3, interferon beta-I a, and interferon gamma-I b; and G-CSF; hydroxyurea; butyrates or butyrate derivatives; nitrous oxide; HEMOXIN™ (NIPRISAN™; see U.S. Pat. No. 5,800,819); Gardos channel antagonists such as clotrimazole and triaryl methane derivatives; Deferoxamine; protein C; and transfusions of blood, or of a blood substitute such as Hemospan™ or Hemospan™ PS (Sangart).

Administration of a compound of this invention, or a pharmaceutically acceptable salt, solvate, stereoisomer or prodrug thereof, and the second active agents to a patient can occur simultaneously or sequentially by the same or different routes of administration. The suitability of a particular route of administration employed for a particular active agent will depend on the active agent itself (e.g., whether it can be administered orally without decomposing prior to entering the blood stream) and the disease being treated. A preferred route of administration for compounds of this invention is oral. Preferred routes of administration for the second active agents or ingredients of the invention are known to those of ordinary skill in the art. See, e.g., *Physicians' Desk Reference,* 1755-1760 (56th ed., 2002).

In one embodiment of the invention, the second active agent is administered intravenously or subcutaneously and once or twice daily in an amount of from about 1 to about 1000 mg, from about 5 to about 500 mg, from about 10 to about 350 mg, or from about 50 to about 200 mg. The specific amount of the second active agent will depend on the specific agent used, the type of disease being treated or managed, the severity and stage of disease, and the amount(s) of compounds of the invention and any optional additional active agents concurrently administered to the patient.

As discussed elsewhere herein, the invention encompasses a method of reducing, treating and/or preventing adverse or undesired effects associated with conventional therapy including, but not limited to, surgery, chemotherapy, radiation therapy, hormonal therapy, biological therapy and immunotherapy. Compounds of the invention and other active ingredients can be administered to a patient prior to, during, or after the occurrence of the adverse effect associated with conventional therapy.

4.4 Cycling Therapy

In certain embodiments, the prophylactic or therapeutic agents of the invention are cyclically administered to a patient. Cycling therapy involves the administration of an active agent for a period of time, followed by a rest for a period of time, and repeating this sequential administration. Cycling therapy can reduce the development of resistance to one or more of the therapies, avoid or reduce the side effects of one of the therapies, and/or improves the efficacy of the treatment.

Consequently, in one specific embodiment of the invention, a compound of the invention is administered daily in a single or divided doses in a four to six week cycle with a rest period of about a week or two weeks. The invention further allows the frequency, number, and length of dosing cycles to be increased. Thus, another specific embodiment of the invention encompasses the administration of a compound of the invention for more cycles than are typical when it is administered alone. In yet another specific embodiment of the invention, a compound of the invention is administered for a greater number of cycles that would typically cause dose-limiting toxicity in a patient to whom a second active ingredient is not also being administered.

In one embodiment, a compound of the invention is administered daily and continuously for three or four weeks at a dose of from about 0.1 mg to about 500 mg per day, followed by a break of one or two weeks. In other embodiments, the dose can be from about 1 mg to about 300 mg, from about 0.1 mg to about 150 mg, from about 1 mg to about 200 mg, from about 10 mg to about 100 mg, from about 0.1 mg to about 50 mg, from about 1 mg to about 50 mg, from about 10 mg to about 50 mg, from about 20 mg to about 30 mg, or from about 1 mg to about 20 mg, followed by a break.

In one embodiment of the invention, a compound of the invention and a second active ingredient are administered orally, with administration of the compound of the invention occurring 30 to 60 minutes prior to the second active ingredient, during a cycle of four to six weeks. In another embodiment of the invention, the combination of a compound of the invention and a second active ingredient is administered by intravenous infusion over about 90 minutes every cycle.

Typically, the number of cycles during which the combinatorial treatment is administered to a patient will be from about one to about 24 cycles, more typically from about two to about 16 cycles, and even more typically from about four to about three cycles.

4.5 Pharmaceutical Compositions and Dosage Forms

Pharmaceutical compositions can be used in the preparation of individual, single unit dosage forms. Pharmaceutical compositions and dosage forms of the invention comprise a compound of the invention, or a pharmaceutically acceptable salt, solvate, stereoisomer, or prodrug thereof. Pharmaceutical compositions and dosage forms of the invention can further comprise one or more excipients.

Pharmaceutical compositions and dosage forms of the invention can also comprise one or more additional active ingredients. Examples of optional second, or additional, active ingredients are disclosed in Section 4.3, above.

Single unit dosage forms of the invention are suitable for oral, mucosal (e.g., nasal, sublingual, vaginal, buccal, or rectal), parenteral (e.g., subcutaneous, intravenous, bolus injection, intramuscular, or intraarterial), topical (e.g., eye drops or other ophthalmic preparations), transdermal or transcutaneous administration to a patient. Examples of dosage forms include, but are not limited to: tablets; caplets; capsules, such as soft elastic gelatin capsules; cachets; troches; lozenges; dispersions; suppositories; powders; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; eye drops or other ophthalmic preparations suitable for topical administration; and sterile solids (e.g., crystalline or amorphous solids) that can be reconstituted to provide liquid dosage forms suitable for parenteral administration to a patient.

The composition, shape, and type of dosage forms of the invention will typically vary depending on their use. For example, a dosage form used in the acute treatment of a disease may contain larger amounts of one or more of the active ingredients it comprises than a dosage form used in the chronic treatment of the same disease. Similarly, a parenteral dosage form may contain smaller amounts of one or more of the active ingredients it comprises than an oral dosage form used to treat the same disease. These and other ways in which specific dosage forms encompassed by this invention will vary from one another will be readily apparent to those skilled in the art. See, e.g., *Remington's Pharmaceutical Sciences*, 18th ed., Mack Publishing, Easton Pa. (1990).

Typical pharmaceutical compositions and dosage forms comprise one or more excipients. Suitable excipients are well known to those skilled in the art of pharmacy, and non-limiting examples of suitable excipients are provided herein. Whether a particular excipient is suitable for incorporation into a pharmaceutical composition or dosage form depends on a variety of factors well known in the art including, but not limited to, the way in which the dosage form will be administered to a patient. For example, oral dosage forms such as tablets may contain excipients not suited for use in parenteral dosage forms. The suitability of a particular excipient may also depend on the specific active ingredients in the dosage form. For example, the decomposition of some active ingredients may be accelerated by some excipients such as lactose, or when exposed to water. Active ingredients that comprise primary or secondary amines are particularly susceptible to such accelerated decomposition. Consequently, this invention encompasses pharmaceutical compositions and dosage forms that contain little, if any, lactose other mono- or di-saccharides. As used herein, the term "lactose-free" means that the amount of lactose present, if any, is insufficient to substantially increase the degradation rate of an active ingredient.

Lactose-free compositions of the invention can comprise excipients that are well known in the art and are listed, for example, in the *U.S. Pharmacopeia* (USP) 25-NF20 (2002). In general, lactose-free compositions comprise active ingredients, a binder/filler, and a lubricant in pharmaceutically compatible and pharmaceutically acceptable amounts. Preferred lactose-free dosage forms comprise active ingredients, microcrystalline cellulose, pre-gelatinized starch, and magnesium stearate.

This invention further encompasses anhydrous pharmaceutical compositions and dosage forms comprising active ingredients, since water can facilitate the degradation of some compounds. For example, the addition of water (e.g., 5%) is widely accepted in the pharmaceutical arts as a means of simulating long-term storage in order to determine characteristics such as shelf-life or the stability of formulations over time. See, e.g., Jens T. Carstensen, *Drug Stability: Principles & Practice,* 2d. Ed., Marcel Dekker, NY, N.Y., 1995, pp. 379-80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous pharmaceutical compositions and dosage forms of the invention can be prepared using anhydrous or low moisture containing ingredients and low moisture or low humidity conditions. Pharmaceutical compositions and dosage forms that comprise lactose and at least one active ingredient that comprises a primary or secondary amine are preferably anhydrous if substantial contact with moisture and/or humidity during manufacturing, packaging, and/or storage is expected.

An anhydrous pharmaceutical composition should be prepared and stored such that its anhydrous nature is maintained. Accordingly, anhydrous compositions are preferably packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The invention further encompasses pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers, or salt buffers.

Like the amounts and types of excipients, the amounts and specific types of active ingredients in a dosage form may differ depending on factors such as, but not limited to, the route by which it is to be administered to patients. However, typical dosage forms of the invention comprise a compound of the invention in an amount of from about 0.10 to about 500 mg. Typical dosage forms comprise a compound of the invention in an amount of about 0.1, 1, 2, 5, 7.5, 10, 12.5, 15, 17.5, 20, 25, 50, 100, 150, 200, 250, 300, 350, 400, 450, or 500 mg.

Typical dosage forms comprise the second active ingredient in an amount of 1 to about 1000 mg, from about 5 to about 500 mg, from about 10 to about 350 mg, or from about 50 to about 200 mg. Of course, the specific amount of the second active agent will depend on the specific agent used, the type of cancer being treated or managed, and the amount(s) of a compound of the invention and any optional additional active agents concurrently administered to the patient.

4.5.1 Oral Dosage Forms

Pharmaceutical compositions of the invention that are suitable for oral administration can be presented as discrete dosage forms, such as, but are not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art.

See generally, *Remington's Pharmaceutical Sciences,* 18th ed., Mack Publishing, Easton Pa. (1990).

Typical oral dosage forms of the invention are prepared by combining the active ingredients in an intimate admixture with at least one excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, micro-crystalline cellulose, diluents, granulating agents, lubricants, binders, and disintegrating agents.

Because of their ease of administration, tablets and capsules represent the most advantageous oral dosage unit forms, in which case solid excipients are employed. If desired, tablets can be coated by standard aqueous or non-aqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

For example, a tablet can be prepared by compression or molding Compressed tablets can be prepared by compressing in a suitable machine the active ingredients in a free-flowing form such as powder or granules, optionally mixed with an excipient. Molded tablets can be made by molding in a suitable machine a mixture of the powdered compound moistened with an inert liquid diluent.

Examples of excipients that can be used in oral dosage forms of the invention include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof.

Suitable forms of microcrystalline cellulose include, but are not limited to, the materials sold as AVICEL-PH-101, AVICEL-PH-103 AVICEL RC-581, AVICEL-PH-105 (available from FMC Corporation, American Viscose Division, Avicel Sales, Marcus Hook, Pa.), and mixtures thereof. An specific binder is a mixture of microcrystalline cellulose and sodium carboxymethyl cellulose sold as AVICEL RC-581. Suitable anhydrous or low moisture excipients or additives include AVICEL-PH-103™ and Starch 1500 LM.

Examples of fillers suitable for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. The binder or filler in pharmaceutical compositions of the invention is typically present in from about 50 to about 99 weight percent of the pharmaceutical composition or dosage form.

Disintegrants are used in the compositions of the invention to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients should be used to form solid oral dosage forms of the invention. The amount of disintegrant used varies based upon the type of formulation, and is readily discernible to those of ordinary skill in the art. Typical pharmaceutical compositions comprise from about 0.5 to about 15 weight percent of disintegrant, preferably from about 1 to about 5 weight percent of disintegrant.

Disintegrants that can be used in pharmaceutical compositions and dosage forms of the invention include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums, and mixtures thereof.

Lubricants that can be used in pharmaceutical compositions and dosage forms of the invention include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL200, manufactured by W.R. Grace Co. of Baltimore, Md.), a coagulated aerosol of synthetic silica (marketed by Degussa Co. of Plano, Tex.), CAB-O-SIL (a pyrogenic silicon dioxide product sold by Cabot Co. of Boston, Mass.), and mixtures thereof. If used at all, lubricants are typically used in an amount of less than about 1 weight percent of the pharmaceutical compositions or dosage forms into which they are incorporated.

A solid oral dosage form of the invention comprises a compound of the invention, anhydrous lactose, microcrystalline cellulose, polyvinylpyrrolidone, stearic acid, colloidal anhydrous silica, and gelatin.

4.5.2 Controlled Release Dosage Forms

Active ingredients of the invention can be administered by controlled release means or by delivery devices that are well known to those of ordinary skill in the art. Examples include, but are not limited to, those described in U.S. Pat. Nos. 3,845,770; 3,916,899; 3,536,809; 3,598,123; and U.S. Pat. Nos. 4,008,719, 5,674,533, 5,059,595, 5,591,767, 5,120,548, 5,073,543, 5,639,476, 5,354,556, and 5,733,566, each of which is incorporated herein by reference. Such dosage forms can be used to provide slow or controlled-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein, can be readily selected for use with the active ingredients of the invention. The invention thus encompasses single unit dosage forms suitable for oral administration such as, but not limited to, tablets, capsules, gelcaps, and caplets that are adapted for controlled-release.

All controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

Most controlled-release formulations are designed to initially release an amount of drug (active ingredient) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or compounds.

4.5.3 Parenteral Dosage Forms

Parenteral dosage forms can be administered to patients by various routes including, but not limited to, subcutaneous, intravenous (including bolus injection), intramuscular, and intraarterial. Because their administration typically bypasses patients' natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions.

Suitable vehicles that can be used to provide parenteral dosage forms of the invention are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Compounds that increase the solubility of one or more of the active ingredients disclosed herein can also be incorporated into the parenteral dosage forms of the invention. For example, cyclodextrin and its derivatives can be used to increase the solubility of an immunomodulatory compound of the invention and its derivatives. See, e.g., U.S. Pat. No. 5,134,127, which is incorporated herein by reference.

4.5.4 Topical and Mucosal Dosage Forms

Topical and mucosal dosage forms of the invention include, but are not limited to, sprays, aerosols, solutions, emulsions, suspensions, eye drops or other ophthalmic preparations, or other forms known to one of skill in the art. See, e.g., *Remington's Pharmaceutical Sciences,* 16th and 18th eds., Mack Publishing, Easton Pa. (1980 & 1990); and *Introduction to Pharmaceutical Dosage Forms,* 4th ed., Lea & Febiger, Philadelphia (1985). Dosage forms suitable for treating mucosal tissues within the oral cavity can be formulated as mouthwashes or as oral gels.

Suitable excipients (e.g., carriers and diluents) and other materials that can be used to provide topical and mucosal dosage forms encompassed by this invention are well known to those skilled in the pharmaceutical arts, and depend on the particular tissue to which a given pharmaceutical composition or dosage form will be applied. With that fact in mind, typical excipients include, but are not limited to, water, acetone, ethanol, ethylene glycol, propylene glycol, butane-1,3-diol, isopropyl myristate, isopropyl palmitate, mineral oil, and mixtures thereof to form solutions, emulsions or gels, which are non-toxic and pharmaceutically acceptable. Moisturizers or humectants can also be added to pharmaceutical compositions and dosage forms if desired. Examples of such additional ingredients are well known in the art. See, e.g., *Remington's Pharmaceutical Sciences,* 16th and 18th eds., Mack Publishing, Easton Pa. (1980 & 1990).

The pH of a pharmaceutical composition or dosage form may also be adjusted to improve delivery of one or more active ingredients. Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery-enhancing or penetration-enhancing agent. Different salts, hydrates or solvates of the active ingredients can be used to further adjust the properties of the resulting composition.

4.6 Kits

In one embodiment, active ingredients of the invention are preferably not administered to a patient at the same time or by the same route of administration. This invention therefore encompasses kits which, when used by the medical practitioner, can simplify the administration of appropriate amounts of active ingredients to a patient.

A kit of the invention comprises a dosage form of a compound of the invention. Kits encompassed by this invention can further comprise additional active ingredients such as oblimersen (Genasense®), melphalan, G-CSF, GM-CSF, EPO, topotecan, dacarbazine, irinotecan, taxotere, IFN, COX-2 inhibitor, pentoxifylline, ciprofloxacin, dexamethasone, IL2, IL8, IL18, Ara-C, vinorelbine, isotretinoin, 13 cis-retinoic acid, or a pharmacologically active mutant or derivative thereof, or a combination thereof. Examples of the additional active ingredients include, but are not limited to, those disclosed herein (see, e.g., section 4.3).

Kits of the invention can further comprise devices that are used to administer the active ingredients. Examples of such devices include, but are not limited to, syringes, drip bags, patches, and inhalers.

Kits of the invention can further comprise cells or blood for transplantation as well as pharmaceutically acceptable vehicles that can be used to administer one or more active ingredients. For example, if an active ingredient is provided in a solid form that must be reconstituted for parenteral administration, the kit can comprise a sealed container of a suitable vehicle in which the active ingredient can be dissolved to form a particulate-free sterile solution that is suitable for parenteral administration. Examples of pharmaceutically acceptable vehicles include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

5. EXAMPLES

Certain embodiments of the invention are illustrated by the following non-limiting examples.

5.1 5-{[(benzofuran-2-ylmethyl)-amino]-methyl}-2-(2,6-dioxo-piperidin-3-yl)-isoindole-1,3-dione

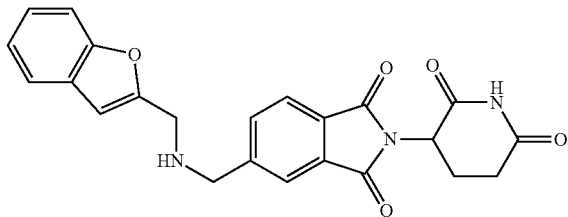 [SMILES: O=C1CCC(N2C(=O)c3ccc(CNCc4cc5ccccc5o4)cc3C2=O)C(=O)N1]

To a mixture of 5-aminomethyl-2-(2,6-dioxo-piperidin-3-yl)-isoindole-1,3-dione hydrochloride (0.97 g, 3.0 mmol) in $CH_2Cl_2$ (20 mL), were added diisopropylethylamine (0.52 mL, 3.0 mmol), 2-benzofurancarboxaldehyde (0.36 mL, 3.0 mmol) and glacial acetic acid (0.17 mL, 3.0 mmol). The reaction mixture was stirred at room temperature for 2 hours. Sodium triacetoxyborohydride (1.27 g, 6.0 mmol) was added, and the mixture was stirred at room temperature overnight. Water (20 mL) was added to quench the reaction, and the mixture was extracted with $CH_2Cl_2$ (2×50 mL). The organic layer was washed with dilute aqueous HCl (2×150 mL) and water (2×150 mL), and dried ($MgSO_4$) and evaporated under vacuum. The residue was chromatographed using an ethyl acetate-hexanes gradient, eluting the 0.38 g of the product at 83:17 ethyl acetate-hexanes, in 30% yield; mp 133-135° C.; HPLC, Waters Xterra RP18, 3.9×150 mm, 5 μm, 1 mL/min, 240 nm, 40/60 $CH_3CN/0.1\%$ $HCO_2(NH_4)$, 5.11 min (98.22%); $^1H$ NMR (DMSO-$d_6$) δ 2.04-2.10 (m, 1H), 2.50-2.63 (m, 2H), 2.84-2.96 (m, 1H), 3.20 (br, 1H), 3.85 (s, 2H), 3.94 (s, 2H), 5.14 (dd, J=12.6 Hz, 5.1 Hz, 1H), 6.73 (s, 1H), 7.17-7.27 (m, 2H), 7.48-7.58 (m, 2H), 7.84 (t, J=7.8 Hz, 2H), 7.93 (s, 1H), 11.12 (s, 1H); $^{13}C$ NMR (DMSO-$d_6$) δ 22.0, 30.9, 45.0, 48.9, 51.5, 103.6, 110.8, 120.7, 122.6, 123.2, 123.6, 128.2, 129.6, 131.4, 134.1, 148.8, 154.1, 157.3, 167.1, 167.2, 169.8, 172.7; Anal. Calcd for $C_{23}H_{19}N_3O_5$: C, 66.18; H, 4.59; N, 10.07. Found: C, 66.02; H, 4.27; N, 9.94.

5.2 5-benzylamino-2-(2,6-dioxo-piperidin-3-yl)-isoindole-1,3-dione

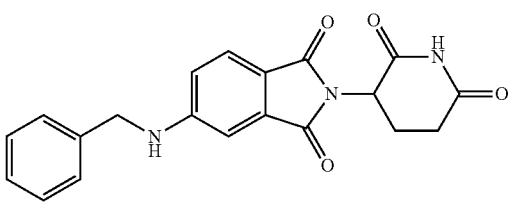 [SMILES: O=C1CCC(N2C(=O)c3ccc(NCc4ccccc4)cc3C2=O)C(=O)N1]

Step 1: A mixture of dimethyl-4-nitrophthalate (15.0 g, 62.7 mmol) and 10% Pd—C (1.5 g) in ethyl acetate (100 mL) was hydrogenated at 50 psi overnight. The reaction mixture was filtered through Celite, and the filter was washed with additional ethyl acetate (50 mL). The solvent was evaporated, and the residue was stirred in hexanes. The solid was filtered, washed with additional hexanes and dried to give 12.77 g of 4-amino-phthalic acid dimethyl ester as a pale orange solid, in 97% yield; $^1H$ NMR (DMSO-$d_6$) δ 3.71 (s, 3H), 3.75 (s, 3H), 6.17 (s, 2H), 6.58-6.65 (m, 2H), 7.57 (d, J=8.4 Hz, 1H).

Step 2: A mixture of 4-amino-phthalic acid dimethyl ester (0.84 g, 4.0 mmol), benzaldehyde (0.81 mL, 8.0 mmol) and acetic acid (1.37 mL, 24.0 mmol) in $CH_2Cl_2$ (40 mL) was stirred at room temperature for 10 minutes. Sodium triacetoxyborohydride (2.54 g, 12.0 mmol) was added, and the mixture was stirred overnight. The reaction mixture was diluted with $CH_2Cl_2$ (20 mL), washed with water (2×100 mL), saturated sodium bicarbonate (1×100 mL), and brine (1×100 mL), and dried ($MgSO_4$) and evaporated under vacuum. The resulting oil was chromatographed using an ethyl acetate-hexanes gradient, eluting the product at 20:80 ethyl acetate-hexanes, 1.1 g of 4-benzylamino-phthalic acid dimethyl ester, in 93% yield; $^1H$ NMR (DMSO-$d_6$) δ 3.70 (s, 3H), 3.74 (s, 3H), 4.36 (d, J=6.0 Hz, 2H), 6.57-6.69 (m, 2H), 7.22-7.39 (m, 6H), 7.60 (d, J=8.4 Hz, 1H).

Step 3: A mixture of 4-benzylamino-phthalic acid dimethyl ester (1.11 g, 3.71 mmol) and 3N sodium hydroxide (50 mL) in ethanol (100 mL) was refluxed for one hour. The reaction mixture was cooled to room temperature, and the solvent was removed under vacuum. The residue was dissolved in water (100 mL), washed with $CH_2Cl_2$ (2×100 mL) and acidified (HCl), and resulting mixture was extracted with ethyl acetate (2×100 mL). The combined organic extracts were washed with water (2×100 mL), and dried ($MgSO_4$) and evaporated under vacuum. The resulting solid was stirred in ether for 2 hours. The solid was filtered and dried, providing 0.50 g of 4-benzylamino-phthalic acid, in 74% yield; $^1H$ NMR (DMSO-$d_6$) δ 4.35 (d, J=5.7 Hz, 2H), 6.59-6.62 (m, 2H), 7.10-7.34 (m, 6H), 7.54-7.57 (m, 1H), 12.48 (br, 2H).

Step 4: A mixture of 4-benzylamino-phthalic acid (0.47 g, 1.7 mmol) and rac-α-aminoglutarimide hydrochloride (0.29 g, 1.7 mmol) in pyridine (10 mL) was heated at reflux overnight. The reaction mixture was cooled to room temperature, and the solvent was removed under vacuum. The residue was partitioned between ethyl acetate (150 mL) and dilute aqueous HCl (150 mL). The aqueous phase was extracted with ethyl acetate (100 mL). The combined organic phases were washed with dilute aqueous HCl (2×150 mL) and water (2×150 mL), and the solvent was removed under vacuum. The residue was chromatographed using a methanol-$CH_2Cl_2$ gradient, eluting the product at 2:98 methanol-$CH_2Cl_2$. The solid thereby obtained was stirred in ether for 30 minutes and filtered, washed with additional ether, and dried, providing 0.49 g of the product as a yellow solid, 78% yield; mp 239-241° C.; HPLC, Waters Symmetry C-18, 3.9×150 mm, 5 μm, 1 mL/min, 240 nm, 40/60 $CH_3CN/0.1\%$ $H_3PO_4$, 9.15 (95.32%); $^1H$ NMR (DMSO-$d_6$) δ 1.94-2.01 (m, 1H), 2.43-2.59 (m, 2H), 2.81-2.93 (m, 1H), 4.46 (d, J=6.0 Hz, 2H), 5.02 (dd, J=12.9 Hz, J=5.4 Hz, 1H), 6.89 (dd, J=8.4 Hz, J=1.8 Hz, 1H), 6.96 (d, J=1.5 Hz, 1H), 7.23-7.33 (m, 1H), 7.35 (d, J=4.2 Hz, 4H), 7.56 (d, J=8.4 Hz, 1H), 7.71 (t, J=5.7 Hz, 1H), 11.06 (s, 1H); $^{13}C$ NMR (DMSO-$d_6$) δ 22.2, 30.9, 45.9, 48.6, 105.7, 115.9, 116.5, 125.0, 127.0, 127.1, 128.5, 134.0, 138.6, 154.2, 167.1, 167.6, 170.1, 172.8; Anal. Calcd for $C_{20}H_{17}N_3O_4$+ 0.1$H_2O$: C, 65.78; H, 4.75; N, 11.51. Found: C, 65.49; H, 4.71; N, 11.45.

5.3 2-(2,6-dioxo-piperidin-3-yl)-5-[(furan-2-ylmethyl)-amino]-isoindole-1,3-dione

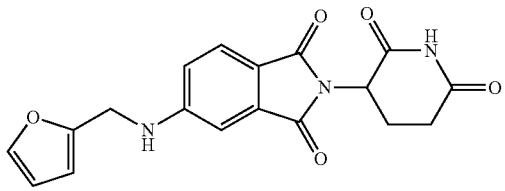 [SMILES: O=C1CCC(N2C(=O)c3ccc(NCc4ccco4)cc3C2=O)C(=O)N1]

Step 1: A mixture of 4-amino-phthalic acid dimethyl ester (0.84 g, 4.0 mmol), 2-furaldehyde (0.66 mL, 8.0 mmol) and acetic acid (1.37 mL, 24.0 mmol) in $CH_2Cl_2$ (40 mL) was stirred at room temperature for 10 minutes. Sodium triacetoxyborohydride (2.54 g, 12.0 mmol) was added, and the mixture was stirred overnight. The reaction mixture was diluted with $CH_2Cl_2$ (20 mL), washed with water (2×100 mL), saturated sodium bicarbonate (100 mL), and brine (100 mL), and dried ($MgSO_4$) and evaporated under vacuum. The resulting oil was chromatographed using a ethyl acetate-hexanes gradient, eluting the product at 40:60 ethyl acetate-hexanes, 1.11 g of 4-[(furan-2-ylmethyl)-amino]-phthalic acid dimethyl ester, in 96% yield; $^1H$ NMR (DMSO-$d_6$) δ 3.71 (s, 3H), 3.76 (s, 3H), 4.34 (d, J=5.7 Hz, 2H), 6.27-6.40 (m, 2H), 6.62-6.78 (m, 2H), 7.18 (t, J=5.7 Hz, 1H), 7.59-7.64 (m, 2H).

Step 2: A mixture of 4-[(furan-2-ylmethyl)-amino]-phthalic acid dimethyl ester (1.11 g, 3.84 mmol) and 3N sodium hydroxide (50 mL) in ethanol (100 mL) was refluxed for one hour. The reaction mixture was cooled to room temperature, and the solvent was removed under vacuum. The residue was dissolved in water (100 mL), washed with $CH_2Cl_2$ (2×100 mL) and acidified (HCl). The resulting mixture was extracted with ethyl acetate (2×100 mL), and the organic phase was washed with water (2×100 mL), and dried ($MgSO_4$) and evaporated. The resulting solid was stirred in ether for 2 hours. The solid was filtered to give the 0.44 g of 4-[(furan-2-ylmethyl)-amino]-phthalic acid, in 44% yield; $^1H$ NMR (DMSO-$d_6$) δ 4.33 (d, J=5.1 Hz, 2H), 6.31 (d, J=3.0 Hz, 1H), 6.39 (dd, J=3.0 Hz, 1.8 Hz, 1H), 6.65-6.71 (m, 2H), 7.00 (t, J=5.7 Hz, 1H), 7.57-7.60 (m, 2H), 12.51 (br, 2H).

Step 3: A mixture of 4-[(furan-2-ylmethyl)-amino]-phthalic acid (0.43 g, 1.7 mmol) and rac-α-aminoglutarimide hydrochloride (0.27 g, 1.7 mmol) in pyridine (10 mL) was heated at reflux overnight. The reaction mixture was cooled to room temperature, and the solvent was removed under vacuum. The residue was partitioned between ethyl acetate (150 mL) and dilute aqueous HCl (150 mL). The aqueous phase was extracted with ethyl acetate (100 mL). The combined organic phases were washed with dilute aqueous HCl (2×150 mL) and water (2×150 mL), and the solvent was removed under vacuum. The residue was chromatographed using a methanol-$CH_2Cl_2$ gradient, eluting the product at 4:96 methanol-$CH_2Cl_2$. The resulting solid was stirred in ether overnight. The solid was filtered, washed with additional ether, and dried. It was purified by preparative HPLC using an acetonitrile-water isocrat, eluting the product at 45:55 acetonitrile:water and providing the 0.24 g of the product as a yellow solid, in 41% yield; mp 143-145° C.; HPLC, Waters Symmetry C-18, 3.9×150 mm, 5 μm, 1 mL/min, 240 nm, 40/60 $CH_3CN/0.1\%$ $H_3PO_4$, 4.96 (96.16%); $^1H$ NMR (DMSO-$d_6$) δ 1.96-2.03 (m, 1H), 2.44-2.60 (m, 2H), 2.82-2.94 (m, 1H), 4.44 (d, J=5.7 Hz, 2H), 5.03 (dd, J=12.6 Hz, J=5.1 Hz, 1H), 6.35-6.42 (m, 2H), 6.94-7.07 (m, 2H), 7.53-7.61 (m, 3H), 11.06 (s, 1H); $^{13}C$ NMR (DMSO-$d_6$) δ 22.2, 30.9, 39.3, 48.6, 105.7, 107.5, 110.4, 116.0, 116.8, 124.9, 134.0, 142.5, 151.8, 154.0, 167.1, 167.6, 170.1, 172.8; Anal. Calcd for $C_{18}H_{15}N_3O_5+0.1H_2O$: C, 60.88; H, 4.31; N, 11.83. Found: C, 60.58; H, 3.87; N, 11.59.

5.4 5-(3-chloro-benzylamino)-2-(2,6-dioxo-piperidin-3-yl)-isoindole-1,3-dione

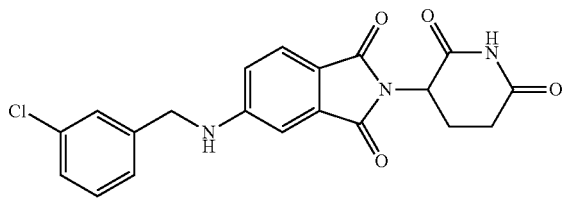 [SMILES: O=C1CCC(N2C(=O)c3ccc(NCc4cccc(Cl)c4)cc3C2=O)C(=O)N1]

Step 1: A mixture of 4-amino-phthalic acid dimethyl ester (0.84 g, 4.0 mmol), 3-chloro-benzaldehyde (0.91 mL, 8.0 mmol) and acetic acid (1.37 mL, 24.0 mmol) in $CH_2Cl_2$ (40 mL) was stirred at room temperature for 10 minutes. Sodium triacetoxyborohydride (2.54 g, 12.0 mmol) was added, and the mixture was stirred overnight. The reaction mixture was diluted with $CH_2Cl_2$ (20 mL), washed with water (2×100 mL), saturated sodium bicarbonate (100 mL), and brine (100 mL), and dried ($MgSO_4$) and evaporated. The resulting oil was chromatographed using an ethyl acetate-hexanes gradient, eluting the product at 35:65 ethyl acetate-hexanes, 1.10 g of 4-(3-chloro-benzylamino)-phthalic acid dimethyl ester, in 82% yield; $^1H$ NMR (DMSO-$d_6$) δ 3.71 (s, 3H), 3.75 (s, 3H), 4.39 (d, J=6.0 Hz, 2H), 6.66-6.70 (m, 2H), 7.28-7.39 (m, 5H), 7.61 (d, J=9.0 Hz, 1H).

Step 2: A mixture of 4-(3-chloro-benzylamino)-phthalic acid dimethyl ester (1.10 g, 3.30 mmol) and 3N sodium hydroxide (50 mL) in ethanol (100 mL) was refluxed for one hour. The reaction mixture was cooled to room temperature, and the solvent was removed under vacuum. The residue was dissolved in water (100 mL), washed with $CH_2Cl_2$ (2×100 mL), and acidified (HCl). The resulting mixture was extracted with ethyl acetate (2×100 mL), and the organic phase was washed with water (2×100 mL), dried ($MgSO_4$), and evaporated, providing 1.00 g of 4-(3-chloro-benzylamino)-phthalic acid, in 99% yield; $^1H$ NMR (DMSO-$d_6$) δ 4.37 (d, J=5.7 Hz, 2H), 6.59-6.62 (m, 2H), 7.18 (t, J=6.0 Hz, 1H), 7.28-7.39 (m, 4H), 7.56-7.61 (m, 1H), 12.51 (br, 2H).

Step 3: A mixture of 4-(3-chloro-benzylamino)-phthalic acid (0.97 g, 3.2 mmol) and rac-α-aminoglutarimide hydrochloride (0.52 g, 3.2 mmol) in pyridine (20 mL) was heated at reflux overnight. The reaction mixture was cooled to room temperature, and the solvent was removed under vacuum. The residue was partitioned between ethyl acetate (150 mL) and dilute aqueous HCl (150 mL). The aqueous phase was extracted with ethyl acetate (100 mL). The combined organic phases were washed with dilute aqueous HCl (2×150 mL) and water (2×150 mL), and the solvent was removed under vacuum. The residue was chromatographed using a methanol-$CH_2Cl_2$ gradient, eluting the product at 5:95 methanol-$CH_2Cl_2$. The resulting solid was stirred in methanol (5 mL) overnight. The solid was filtered, washed with additional methanol, and dried to give 0.96 g of the product as a yellow solid, in 76% yield; mp 250-252° C.;

HPLC, Waters Symmetry C-18, 3.9×150 mm, 5 μm, 1 mL/min, 240 nm, 50/50 CH$_3$CN/0.1% H$_3$PO$_4$, 6.46 (99.41%); $^1$H NMR (DMSO-d$_6$) δ 1.95-2.03 (m, 1H), 2.42-2.59 (m, 2H), 2.81-2.93 (m, 1H), 4.49 (d, J=6.0 Hz, 2H), 5.02 (dd, J=12.9 Hz, J=5.4 Hz, 1H), 6.88-6.98 (m, 2H), 7.30-7.42 (m, 4H), 7.58 (d, J=8.4 Hz, 1H), 7.72 (t, J=6.0 Hz, 1H), 11.06 (s, 1H); $^{13}$C NMR (DMSO-d$_6$) δ 22.1, 30.9, 45.2, 48.6, 105.7, 116.0, 116.8, 125.1, 125.7, 126.9, 127.0, 130.4, 133.2, 134.1, 141.5, 154.0, 167.0, 167.5, 170.1, 172.8; Anal. Calcd for C$_{20}$H$_{16}$N$_3$O$_4$Cl+0.15H$_2$O: C, 59.98; H, 4.10; N, 10.49. Found: C, 59.61; H, 3.84; N, 10.36.

5.5 5-[(benzofuran-2-ylmethyl)-amino]-2-(2,6-di-oxo-piperidin-3-yl)-isoindole-1,3-dione

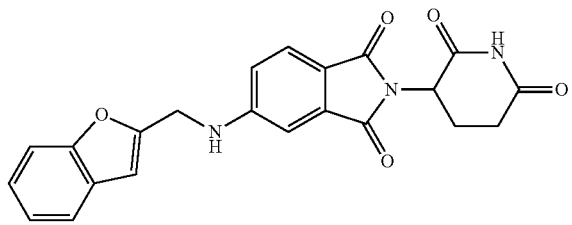 [SMILES: O=C1CCC(N2C(=O)c3ccc(NCc4cc5ccccc5o4)cc3C2=O)C(=O)N1]

Step 1: A mixture of 4-amino-phthalic acid dimethyl ester (0.84 g, 4.0 mmol), 2-benzofurancarboxaldehyde (0.83 mL, 8.0 mmol) and acetic acid (1.37 mL, 24.0 mmol) in CH$_2$Cl$_2$ (40 mL) was stirred at room temperature for 10 minutes. Sodium triacetoxyborohydride (2.54 g, 12.0 mmol) was added, and the mixture was stirred overnight. The reaction mixture was diluted with CH$_2$Cl$_2$ (20 mL), washed with water (2×100 mL), saturated sodium bicarbonate (100 mL), and brine (100 mL), and dried (MgSO$_4$) and evaporated. The resulting oil was chromatographed using an ethyl acetate-hexanes gradient, eluting the product at 25:75 ethyl acetate, 0.89 g of 4-[(benzofuran-2-ylmethyl)-amino]-phthalic acid dimethyl ester, in 65% yield; $^1$H NMR (DMSO-d$_6$) δ 3.71 (s, 3H), 3.76 (s, 3H), 4.56 (d, J=5.7 Hz, 2H), 6.76-6.83 (m, 3H), 7.20-7.29 (m, 2H), 7.35 (t, J=6.0 Hz, 1H), 7.51-7.65 (m, 3H).

Step 2: A mixture of 4-[(benzofuran-2-ylmethyl)-amino]-phthalic acid dimethyl ester (0.89 g, 3.30 mmol) and 3N sodium hydroxide (50 mL) in ethanol (100 mL) was refluxed for one hour. The reaction mixture was cooled to room temperature, and the solvent was removed under vacuum. The residue was dissolved in water (100 mL), washed with CH$_2$Cl$_2$ (2×100 mL), and acidified (HCl). The resulting mixture was extracted with ethyl acetate (2×100 mL), and the combined organic layers were washed with water (2×100 mL), dried (MgSO$_4$), and evaporated, providing 0.80 g of 4-[(benzofuran-2-ylmethyl)amino]-phthalic acid, in 98% yield; $^1$H NMR (DMSO-d$_6$) δ 4.54 (d, J=4.5 Hz, 2H), 6.71-6.77 (m, 3H), 7.18-7.29 (m, 3H), 7.51-7.61 (m, 3H), 12.52 (br, 2H).

Step 3: A mixture of 4-[(benzofuran-2-ylmethyl)amino]-phthalic acid (0.80 g, 2.6 mmol) and rac-α-aminoglutarimide hydrochloride (0.42 g, 2.6 mmol) in pyridine (20 mL) was heated at reflux overnight. The reaction mixture was cooled to room temperature, and the solvent was removed under vacuum. The residue was partitioned between ethyl acetate (150 mL) and dilute aqueous HCl (150 mL). The aqueous phase was extracted with ethyl acetate (100 mL). The combined organic phases were washed with dilute aqueous HCl (2×150 mL) and water (2×150 mL), and the solvent was removed under vacuum. The residue was chromatographed using a methanol-CH$_2$Cl$_2$ gradient, eluting the product at 5:95 methanol-CH$_2$Cl$_2$. The appropriate fractions were pooled and treated with decolorizing carbon (1.5 g), filtered through Celite, and evaporated to give 0.68 g the product as a yellow solid, in 66% yield; mp 259-261° C.; HPLC, Waters Symmetry C-18, 3.9×150 mm, 5 μm, 1 mL/min, 240 nm, 50/50 CH$_3$CN/0.1% H$_3$PO$_4$, 5.14 (99.16%); $^1$H NMR (DMSO-d$_6$) δ 1.95-2.01 (m, 1H), 2.43-2.60 (m, 2H), 2.81-2.93 (m, 1H), 4.66 (d, J=6.0 Hz, 2H), 5.03 (dd, J=12.9 Hz, J=5.4 Hz, 1H), 6.81 (s, 1H), 7.01 (dd, J=8.4 Hz, J=2.1 Hz, 1H), 7.12 (d, J=1.8 Hz, 1H), 7.18-7.29 (m, 2H), 7.52-7.61 (m, 3H), 7.72 (t, J=5.7 Hz, 1H), 11.06 (s, 1H); $^{13}$C NMR (DMSO-d$_6$) δ 22.2, 30.9, 48.6, 104.0, 105.8, 110.9, 116.1, 117.1, 120.9, 122.8, 124.0, 125.0, 127.9, 134.0, 153.9, 154.2, 155.1, 167.1, 167.5, 170.1, 172.8; Anal. Calcd for C$_{22}$H$_{17}$N$_3$O$_5$+0.1H$_2$O: C, 65.21; H, 4.28; N, 10.37. Found: C, 65.07; H, 4.29; N, 10.32.

5.6 2-(4-chloro-phenyl)-n-[2-(2,6-dioxo-piperidin-3-yl)-1-oxo-2,3-dihydro-1H-isoindol-5-ylmethyl]-acetamide

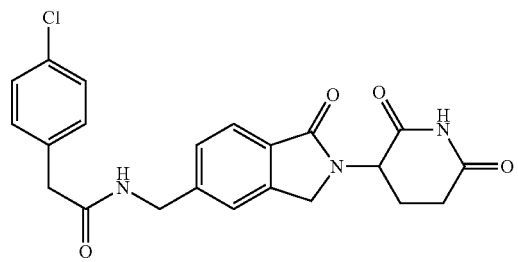 [SMILES: O=C(Cc1ccc(Cl)cc1)NCc1ccc2c(c1)CN(C1CCC(=O)NC1=O)C2=O]

A mixture of 3-(5-aminomethyl-1-oxo-1,3-dihydro-isoindol-2-yl)-piperidine-2,6-dione hydrochloride (0.40 g, 1.29 mmol), 4-chorophenylacetyl chloride (0.19 mL, 1.29 mmol) and diisopropylethyl amine (0.41 mL, 2.37 mmol) in acetonitrile (20 mL) was stirred at room temperature for 2 days. Additional 4-chorophenylacetyl chloride (0.04 mL) was added, and the reaction mixture was stirred for 2 hours. The solid was filtered, washed with additional acetonitrile and water to give 0.13 g of the product, in 24% yield; mp 264-266° C.; HPLC, Waters Symmetry C-18, 3.9×150 mm, 5 μm, 1 mL/min, 240 nm, 40/60 CH$_3$CN/0.1% H$_3$PO$_4$, 3.23 (98.97%); $^1$H NMR (DMSO-d$_6$) δ 1.96-2.03 (m, 1H), 2.32-2.46 (m, 1H), 2.53-2.63 (m, 1H), 2.86-2.98 (m, 1H), 3.51 (s, 2H), 4.25-4.45 (m, 4H), 5.11 (dd, J=13.2 Hz, J=5.1 Hz, 1H), 7.29-7.42 (m, 6H), 7.67 (d, J=7.8 Hz, 1H), 8.67 (t, J=6.0 Hz, 1H), 10.99 (s, 1H); $^{13}$C NMR (DMSO-d$_6$) δ 22.5, 31.2, 41.5, 42.2, 47.1, 51.6, 122.0, 122.9, 127.0, 128.1, 130.4, 130.9, 131.1, 135.3, 142.3, 143.7, 167.9, 169.9, 171.0, 172.9; Anal. Calcd for C$_{22}$H$_{20}$N$_3$O$_4$Cl+0.2H$_2$O: C, 61.53; H, 4.79; N, 9.78. Found: C, 61.52; H, 4.44; N, 9.40.

5.7 N-[2-(2,6-dioxo-piperidin-3-yl)-1,3-dioxo-2,3-dihydro-1H-isoindol-5-ylmethyl]-4-trifluoromethoxybenzamide

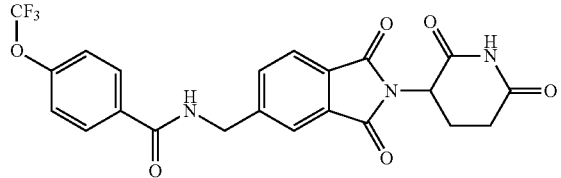 [SMILES: O=C1CCC(N2C(=O)c3ccc(CNC(=O)c4ccc(OC(F)(F)F)cc4)cc3C2=O)C(=O)N1]

A mixture of 5-aminomethyl-2-(2,6-dioxo-piperidin-3-yl)-isoindole-1,3-dione hydrochloride (1.0 g, 3.1 mmol), 4-trifluoromethoxybenzoyl chloride (0.70 g, 3.1 mmol), and triethylamine (0.63 g, 6.2 mmol) in DMF (20 mL) was stirred under N$_2$ at room temperature for 1 hour. The mixture was partitioned between ethyl acetate (75 mL) and water (75 mL), and the aqueous phase was extracted with ethyl acetate (75 mL). The combined organic layers were washed with water (3×100 mL), and evaporated. The residue was chromatographed in ethyl acetate, providing 1.1 g of the product, in 75% yield; mp 200-202° C.; HPLC, Waters Symmetry C-18, 3.9×150 mm, 5 μm, 1 mL/min, 240 nm, 50/50 CH$_3$CN/0.1% H$_3$PO$_4$, 4.85 (97.90%); $^1$H NMR (DMSO-d$_6$) δ 2.02-2.10 (m, 1H), 2.46-2.63 (m, 2H), 2.83-2.95 (m, 1H), 4.66 (d, J=6.0 Hz, 2H), 5.15 (dd, J=12.9 Hz, J=5.4 Hz, 1H), 7.48-7.51 (m, 2H), 7.81-7.91 (m, 3H), 8.02-8.05 (m, 2H), 9.34 (t, J=6.0 Hz, 1H), 11.13 (s, 1H); $^{13}$C NMR (DMSO-d$_6$) δ 22.0, 30.9, 42.7, 48.9, 119.9 (q, J=255), 120.7, 122.0, 123.5, 129.6, 129.8, 131.6, 133.0, 133.4, 147.3, 150.4, 165.2, 167.0, 167.1, 169.8, 172.7; Anal. Calcd for C$_{22}$H$_{16}$F$_3$N$_3$O$_6$: C, 55.58; H, 3.39; N, 8.84. Found: C, 55.38; H, 3.18; N, 8.69.

5.8 N-[2-(2,6-dioxo-piperidin-3-yl)-1,3-dioxo-2,3-dihydro-1H-isoindol-5-ylmethyl]-4-methyl-benzamide

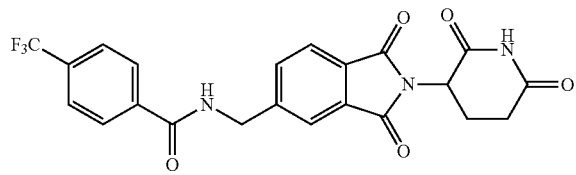 [SMILES: O=C1CCC(N2C(=O)c3ccc(CNC(=O)c4ccc(C(F)(F)F)cc4)cc3C2=O)C(=O)N1]

A mixture of 5-aminomethyl-2-(2,6-dioxo-piperidin-3-yl)-isoindole-1,3-dione hydrochloride (0.97 g, 3.0 mmol), 4-(trifluoromethyl)-benzoyl chloride (0.45 mL, 3.0 mmol) and N,N-diisopropylethylamine (1.05 mL, 6.00 mmol) in acetonitrile (20 mL) was stirred at room temperature for 1 hour. The reaction mixture was concentrated; and the residue was dissolved in ethyl acetate (100 mL). The organic phase was washed with dilute aqueous HCl (2×150 mL) and water (2×150 mL), dried (MgSO$_4$), and evaporated under vacuum. The residue was chromatographed using a methanol-CH$_2$Cl$_2$ gradient, eluting the product at 5:95 methanol-CH$_2$Cl$_2$. The resulting solid was stirred in ether overnight, filtered and dried to give 0.66 g of the product, in 48% yield; mp 168-170° C.; HPLC, Waters Symmetry C-18, 3.9×150 mm, 5 μm, 1 mL/min, 240 nm, 40/60 CH$_3$CN/0.1% H$_3$PO$_4$, 8.49 (95.33%); $^1$H NMR (DMSO-d$_6$) δ 2.02-2.09 (m, 1H), 2.46-2.63 (m, 2H), 2.84-2.96 (m, 1H), 4.68 (d, J=6.0 Hz, 2H), 5.15 (dd, J=12.6 Hz, J=5.1 Hz, 1H), 7.71-8.12 (m, 7H), 9.46 (t, J=6.0 Hz, 1H), 11.13 (s, 1H); $^{13}$C NMR (DMSO-d$_6$) δ 22.0, 30.9, 42.7, 49.0, 122.0, 123.6, 123.9 (q, J=270.8 Hz), 125.4 (q, J=3.75 Hz), 128.2, 129.9, 131.3 (q, J=31.5 Hz), 131.6, 133.5, 137.7, 147.2, 165.3, 167.0, 167.1, 169.8, 172.7; Anal. Calcd for C$_{22}$H$_{16}$N$_3$O$_5$F$_3$: C, 57.52; H, 3.51; N, 9.15. Found: C, 57.27; H, 3.35; N, 9.00.

5.9 thiophene-2-carboxylic acid [2-(2,6-dioxo-piperidin-3-yl)-1,3-dioxo-2,3-dihydro-1H-isoindol-5-ylmethyl]-amide

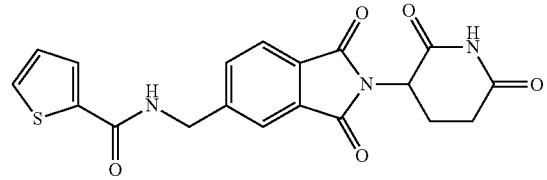 [SMILES: O=C1CCC(N2C(=O)c3ccc(CNC(=O)c4cccs4)cc3C2=O)C(=O)N1]

A mixture of 5-aminomethyl-2-(2,6-dioxo-piperidin-3-yl)-isoindole-1,3-dione hydrochloride (0.97 g, 3.0 mmol), 2-thiophenecarbonyl chloride (0.32 mL, 3.0 mmol) and N,N-diisopropylethylamine (1.05 mL, 6.00 mmol) in CH$_2$Cl$_2$ (20 mL) was stirred at room temperature for 2 days. The organic phase was washed with dilute aqueous HCl (2×50 mL) and water (2×50 mL), dried (MgSO$_4$), and evaporated under vacuum. The residue was chromatographed using a methanol-CH$_2$Cl$_2$ gradient, eluting the product at 3:97 methanol-CH$_2$Cl$_2$. The resulting solid was stirred in ethyl acetate for 1 hour and filtered to give 0.69 g of the product, in 58% yield; mp 219-221° C.; HPLC, Waters Symmetry C-18, 3.9×150 mm, 5 μm, 1 mL/min, 240 nm, 30/70 CH$_3$CN/0.1% H$_3$PO$_4$, 5.84 (95.85%); $^1$H NMR (DMSO-d$_6$) δ 1.99-2.09 (m, 1H), 2.46-2.63 (m, 2H), 2.83-2.95 (m, 1H), 4.62 (d, J=6.0 Hz, 2H), 5.15 (dd, J=12.9 Hz, J=5.4 Hz, 1H), 7.18 (dd, J=5.1 Hz, J=3.6 Hz, 1H), 7.79-7.84 (m, 4H), 7.91 (d, J=7.8 Hz, 1H), 9.23 (t, J=6.0 Hz, 1H), 11.13 (s, 1H); $^{13}$C NMR (DMSO-d$_6$) δ 22.0, 30.9, 42.4, 49.0, 121.9, 123.6, 128.0, 128.4, 129.8, 131.2, 131.6, 133.4, 139.3, 147.4, 161.4, 167.0, 167.1, 169.8, 172.7; Anal. Calcd for C$_{19}$H$_{15}$N$_3$O$_5$S: C, 57.42; H, 3.80; N, 10.57. Found: C, 57.49; H, 3.42; N, 10.28.

5.10 hexanoic acid [2-(2,6-dioxo-piperidin-3-yl)-1,3-dioxo-2,3-dihydro-1H-isoindol-5-ylmethyl]-amide

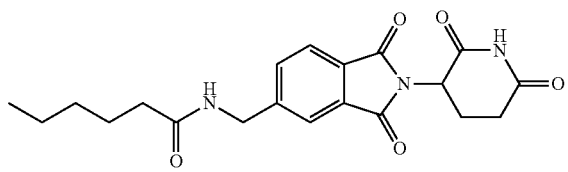 [SMILES: CCCCCC(=O)NCc1ccc2c(c1)C(=O)N(C1CCC(=O)NC1=O)C2=O]

A mixture of 5-aminomethyl-2-(2,6-dioxo-piperidin-3-yl)-isoindole-1,3-dione hydrochloride (0.97 g, 3.0 mmol), hexanoyl chloride (0.42 mL, 3.0 mmol) and N,N-diisopropylethylamine (1.05 mL, 6.00 mmol) in THF (20 mL) was stirred at 40° C. overnight. The reaction mixture was cooled to room temperature, and the solvent was removed under vacuum. The residue was dissolved in ethyl acetate (150 mL), washed with dilute aqueous HCl (2×150 mL) and water (2×150 mL), dried (MgSO$_4$), and evaporated under vacuum. The residue was stirred in ether (20 mL) overnight. The resulting solid was filtered and dried under vacuum, to give 0.71 g of the product, in 61% yield; mp 178-180° C.; HPLC, Waters Symmetry C-18, 3.9×150 mm, 5 μm, 1 mL/min, 240 nm, 30/70 CH$_3$CN/0.1% H$_3$PO$_4$, 8.83 (98.70%); $^1$H NMR (DMSO-d$_6$) δ 0.86 (t, J=6.6 Hz, 3H), 1.27-1.33 (m, 4H), 1.48-1.58 (m, 2H), 2.02-2.09 (m, 1H), 2.16 (t, J=7.5 Hz, 2H), 2.46-2.63 (m, 2H), 2.83-2.96 (m, 1H), 4.43 (d, J=6.0 Hz, 2H), 5.14 (dd, J=12.9 Hz, J=5.4 Hz, 1H), 7.72-7.90 (m, 3H), 8.51 (t, J=6.0 Hz, 1H), 11.13 (s, 1H); $^{13}$C NMR (DMSO-$d_6$) δ 13.8, 21.8, 22.0, 24.9, 30.9, 30.9, 35.2, 41.8, 49.0, 121.8, 123.5, 129.7, 131.6, 133.3, 147.8, 167.0, 167.1, 169.8, 172.5, 172.7; Anal. Calcd for $C_{20}H_{23}N_3O_5$: C, 62.33; H, 6.02; N, 10.90. Found: C, 62.20; H, 5.99; N, 10.84.

5.11 heptanoic acid [2-(2,6-dioxo-piperidin-3-yl)-1,3-dioxo-2,3-dihydro-1H-isoindol-5-ylmethyl]-amide

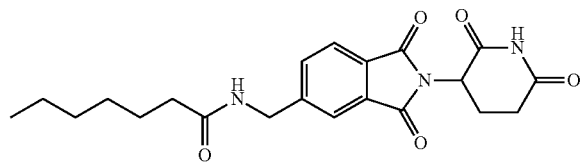 [SMILES: CCCCCCC(=O)NCc1ccc2c(c1)C(=O)N(C1CCC(=O)NC1=O)C2=O]

A mixture of 5-aminomethyl-2-(2,6-dioxo-piperidin-3-yl)-isoindole-1,3-dione hydrochloride (0.97 g, 3.0 mmol), heptanoyl chloride (0.46 mL, 3.0 mmol) and diisopropyl-ethylamine (1.05 mL, 6.0 mmol) in acetonitrile (20 mL) was stirred at room temperature for 1 hour. The residue was dissolved in ethyl acetate (100 mL), washed with dilute aqueous HCl (2×150 mL) and water (2×150 mL), dried (MgSO$_4$), and evaporated under vacuum. The residue was purified by preparative HPLC using a 45:65 acetonitrile-water isocrat, affording 0.60 g of the product, in 50% yield; mp 141-143° C.; HPLC, Waters Symmetry C-18, 3.9×150 mm, 5 μm, 1 mL/min, 240 nm, 50/50 CH$_3$CN/0.1% H$_3$PO$_4$, 3.99 (98.05%); $^1$H NMR (DMSO-$d_6$) δ 0.84 (t, J=6.6 Hz, 3H), 1.24-1.30 (m, 6H), 1.48-1.54 (m, 2H), 2.02-2.09 (m, 1H), 2.16 (t, J=7.2 Hz, 3H), 2.51-2.63 (m, 2H), 2.83-2.96 (m, 1H), 4.43 (d, J=6.0 Hz, 2H), 5.14 (dd, J=5.4, 12.9 Hz, 1H), 7.72-7.89 (m, 3H), 8.50 (t, J=6.0 Hz, 1H), 11.12 (s, 1H); $^{13}$C NMR (DMSO-$d_6$) δ 13.9, 22.0, 25.2, 28.3, 30.9, 31.0, 35.3, 41.8, 49.0, 121.8, 123.4, 129.7, 131.6, 133.3, 147.8, 167.0, 167.1, 169.8, 172.5, 172.7; Anal. Calcd for $C_{21}H_{25}N_3O_5$+0.1H$_2$O: C, 62.86; H, 6.33; N, 10.47. Found: C, 62.54; H, 6.21; N, 10.38.

5.12 5-{[2-(2,6-dioxo-piperidin-3-yl)-1,3-dioxo-2,3-dihydro-1H-isoindol-5-ylmethyl]-carbamoyl}-pentanoic acid tert-butyl ester

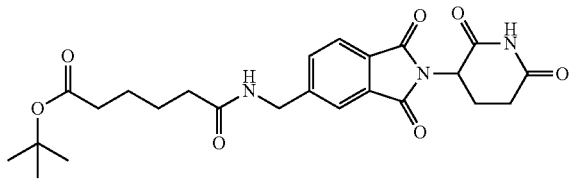 [SMILES: CC(C)(C)OC(=O)CCCCC(=O)NCc1ccc2c(c1)C(=O)N(C1CCC(=O)NC1=O)C2=O]

Step 1: To a solution of adipic acid monomethyl ester (4.8 g, 30 mmol) in DMF (30 mL), was added CDI (4.9 g, 30 mmol), and the resulting mixture was stirred under N$_2$ at 40° C. for 1 hour. t-Butanol (4.4 g, 60 mmol) and DBU (4.6 g, 30 mmol) were added, and stirring proceeded at 40° C. for 70 hours. The mixture was poured into ether (100 mL), and this mixture was washed with 10% aq. HOAc (100 mL), 10% aq. K$_2$CO$_3$ (100 mL), and water (3×100 mL), dried (MgSO$_4$), and evaporated, providing 5.1 g of hexanedioic acid tert-butyl ester methyl ester, in 78% yield; $^1$H NMR (CDCl$_3$) δ 1.44 (s, 9H), 1.59-1.67 (m, 4H), 2.21-2.26 (m, 2H), 3.67 (s, 3H).

Step 2: Lithium hydroxide (0.53 g, 22 mmol) was added to a solution of hexanedioic acid tert-butyl ester methyl ester (4.8 g, 22 mmol) in 3:1 methanol-water (80 mL), and the resulting mixture was stirred at room temperature for 16 hours. The mixture was evaporated under vacuum. The residue was partitioned between water (60 mL) and methylene chloride (75 mL), and the aqueous phase was washed with methylene chloride (3×75 mL) and evaporated, providing 4.0 g of hexanedioic acid mono-tert-butyl ester, lithium salt; $^1$H NMR (D$_2$O) δ 1.45 (s, 9H), 1.54-1.58 (m, 4H), 2.15-2.20 (m, 2H), 2.25-2.34 (m, 2H).

Step 3: DBU (1.9 g, 12.3 mmol) was added to a stirred suspension of 5-aminomethyl-2-(2,6-dioxo-piperidin-3-yl)-isoindole-1,3-dione hydrochloride (2.5 g, 7.7 mmol) in acetonitrile (75 mL), resulting in the formation of a clear solution. The mixture was stirred at room temperature for 10 minutes, and then, hexanedioic acid mono-tert-butyl ester, lithium salt (1.9 g, 9.2 mmol) and HOBt (1.2 g, 9.2 mmol) were added, followed by EDC (2.2 g, 11.6 mmol). The mixture was stirred under N$_2$ for 1 hour, and DMF (20 mL) was added. After stirring for an additional 16 hours, the mixture was evaporated under vacuum. The residue was partitioned between ethyl acetate (100 mL) and water (100 mL), and the aqueous phase was extracted with ethyl acetate (2×100 mL). The combined organic layers were washed with water (3×100 mL) and evaporated. The residue was chromatographed on silica, eluting with ethyl acetate, providing 2.1 g of the product, in 58% yield; mp 108-110° C.; HPLC, Waters Symmetry C-18, 3.9×150 mm, 5 μm, 1 mL/min, 240 nm, 35/65 CH$_3$CN/0.1% H$_3$PO$_4$, 7.64 (96.65%); $^1$H NMR (DMSO-$d_6$) δ 1.38 (s, 9H), 1.45-1.55 (m, 4H), 2.02-2.08 (m, 1H), 2.15-2.21 (m, 4H), 2.46-2.63 (m, 2H), 2.83-2.95 (m, 1H), 4.43 (d, J=5.8 Hz, 2H), 5.14 (dd, J=12.9 Hz, J=5.4 Hz, 1H), 7.72-7.76 (m, 2H), 7.87 (d, J=7.5 Hz, 1H), 8.51 (t, J=5.8 Hz, 1H), 11.12 (s, 1H); $^{13}$C NMR (DMSO-$d_6$) δ 22.0, 24.2, 24.6, 27.7, 30.9, 34.5, 34.9, 41.9, 49.0, 79.4, 121.9, 123.4, 129.7, 131.6, 133.3, 147.8, 167.0, 167.1, 169.8, 172.1, 172.2, 172.8; Anal. Calcd for $C_{24}H_{29}N_3O_7$+0.2H$_2$O: C, 60.67; H, 6.24; N, 8.84. Found: C, 60.60; H, 6.16; N, 8.65.

5.13 5-{[2-(2,6-dioxo-piperidin-3-yl)-1,3-dioxo-2,3-dihydro-1H-isoindol-5-ylmethyl]-carbamoyl}-pentanoic acid

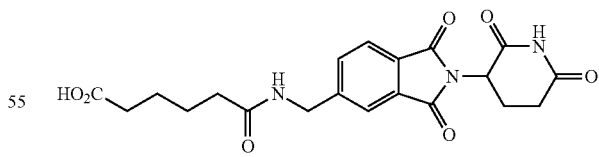

A solution of 5-{[2-(2,6-dioxo-piperidin-3-yl)-1,3-dioxo-2,3-dihydro-1H-isoindol-5-ylmethyl]-carbamoyl}-pentanoic acid tert-butyl ester (0.85 g, 1.8 mmol) in formic acid (25 mL) was stirred at room temperature for 90 minutes. The mixture was evaporated under vacuum, and the residue was triturated in ether/ethyl acetate and filtered, providing 0.66 g, in 88% yield; mp 144-146° C.; HPLC, Waters Symmetry C-18, 3.9×150 mm, 5 μm, 1 mL/min, 240 nm, 20/80 CH$_3$CN/0.1% H$_3$PO$_4$, 4.15 (95.81%); $^1$H NMR (DMSO-$d_6$)

δ 1.44-1.59 (m, 4H), 2.02-2.09 (m, 1H), 2.16-2.24 (m, 4H), 2.46-2.63 (m, 2H), 2.83-2.95 (m, 1H), 4.43 (d, J=6.0 Hz, 2H), 5.14 (dd, J=12.9 Hz, J=5.4 Hz, 1H), 7.72-7.77 (m, 2H), 7.87 (d, J=7.8 Hz, 1H), 8.51 (t, J=6.0 Hz, 1H), 11.12 (s, 1H), 12.00 (s, 1H); $^{13}$C NMR (DMSO-d$_6$) δ 22.0, 24.1, 24.7, 30.9, 33.3, 34.9, 41.9, 48.9, 121.9, 123.5, 129.7, 131.6, 133.3, 147.8, 167.0, 167.1, 169.8, 172.2, 172.7, 174.3; Anal. Calcd for $C_{20}H_{21}N_3O_7+0.2H_2O$: C, 57.33; H, 5.13; N, 10.03. Found: C, 57.33; H, 4.89; N, 9.81.

5.14 6-(2-oxo-oxazolidin-3-yl)-hexanoic acid [2-(2,6-dioxo-piperidin-3-yl)-1,3-dioxo-2,3-dihydro-1H-isoindol-5-yl-methyl]-amide

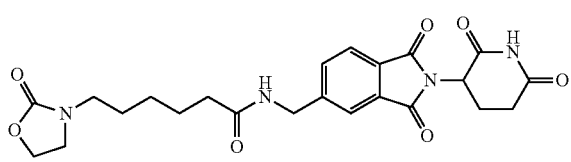 [SMILES: O=C(CCCCCN1CCOC1=O)NCc1ccc2c(c1)C(=O)N(C1CCC(=O)NC1=O)C2=O]

Step 1: A mixture of 2-oxazolidinone (1.74 g, 20.0 mmol), ethyl 6-bromohexanoate (4.46 g, 20.0 mmol), and sodium hydride (0.80 g of a 60% dispersion, 20 mmol), in acetonitrile (10 mL) was heated to 160° C. in a microwave reactor for 15 minutes. The mixture was cooled, and the solvent was removed under reduced pressure. The crude product, 6-(2-oxo-oxazolidin-3-yl)-hexanoic acid ethyl ester, was used directly in the next step.

Step 2: Lithium hydroxide (0.48 g, 20 mmol) was added to the crude product from Step 1 in 2:1 methanol-water (30 mL), and the resulting mixture was stirred at room temperature for 70 hours. The mixture was evaporated under vacuum. The residue was dissolved in water (75 mL), washed with methylene chloride (3×75 mL), and acidified (HCl). The resulting mixture was extracted with methylene chloride (6×50 mL), and the combined extracts were dried (MgSO$_4$) and evaporated, providing 2.0 g of 6-(2-oxo-oxazolidin-3-yl)-hexanoic acid, in 49% combined yield over two steps; $^1$H NMR (CDCl$_3$) δ 1.36-1.44 (m, 2H), 1.51-1.74 (m, 4H), 2.38 (t, J=7.4 Hz, 2H), 3.28 (t, J=7.2 Hz, 2H), 3.56 (t, J=8.0 Hz, 2H), 4.33 (t, J=8.0 Hz, 2H).

Step 3: DBU (1.2 g, 8.1 mmol) was added to a stirred suspension of 5-aminomethyl-2-(2,6-dioxo-piperidin-3-yl)-isoindole-1,3-dione hydrochloride (1.0 g, 3.1 mmol) in acetonitrile (35 mL), resulting in the formation of a clear solution. The mixture was stirred at room temperature for 10 minutes, and then, 6-(2-oxo-oxazolidin-3-yl)-hexanoic acid (2.0 g, 10 mmol) and HOBt (0.5 g, 3.7 mmol) were added, followed by EDC (0.89 g, 4.7 mmol). After stirring for an additional 16 hours, the mixture was evaporated under vacuum. The residue was partitioned between ethyl acetate (50 mL) and water (100 mL), and the aqueous phase was extracted with ethyl acetate (3×50 mL). The combined organic layers were evaporated. The residue was chromatographed on silica, using a methylene chloride-methanol gradient, eluting 0.61 g of the product at 93:7 methylene chloride-methanol, in 42% yield; mp 178-180° C.; HPLC, Waters Symmetry C-18, 3.9×150 mm, 5 μm, 1 mL/min, 240 nm, 25/75 CH$_3$CN/0.1% H$_3$PO$_4$, 3.36 (98.33%); $^1$H NMR (DMSO-d$_6$) δ 1.26-1.28 (m, 2H), 1.43-1.61 (m, 4H), 2.04-2.08 (m, 1H), 2.18 (t, J=7.4 Hz, 2H), 2.46-2.63 (m, 2H), 2.83-2.96 (m, 1H), 3.12 (t, J=7.1 Hz, 2H), 3.49 (t, J=8.0 Hz, 2H), 4.42 (t, J=8.0 Hz, 2H), 4.43 (d, J=5.8 Hz, 2H), 5.15 (dd, J=12.9 Hz, J=5.4 Hz, 1H), 7.72-7.77 (m, 2H), 7.89 (d, J=7.8 Hz, 1H), 8.51 (t, J=5.8 Hz, 1H), 11.12 (s, 1H); $^{13}$C NMR (DMSO-d$_6$) δ 22.0, 24.8, 25.7, 26.4, 30.9, 35.1, 41.9, 43.3, 43.8, 49.0, 61.5, 121.8, 123.5, 129.7, 131.6, 133.3, 147.8, 157.8, 167.0, 167.1, 169.8, 172.4, 172.7; Anal. Calcd for $C_{23}H_{26}N_4O_7+0.3H_2O$: C, 58.05; H, 5.63; N, 11.77. Found: C, 58.05; H, 5.42; N, 11.62.

5.15 [2-(2,6-dioxo-piperidin-3-yl)-1,3-dioxo-2,3-dihydro-1H-isoindol-5-ylmethyl]-carbamic acid hexyl ester

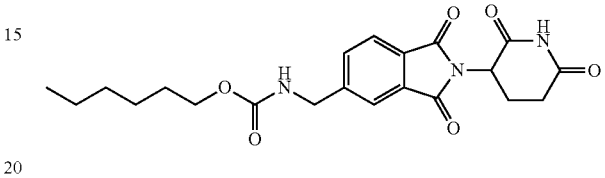

A mixture of 5-aminomethyl-2-(2,6-dioxo-piperidin-3-yl)-isoindole-1,3-dione hydrochloride (1.0 g, 3.1 mmol), hexyl chloroformate (0.51 g, 3.1 mmol), and triethylamine (0.63 g, 6.2 mmol) in THF (35 mL) was stirred at 40° C. under nitrogen for 3 hours. The mixture was cooled and diluted with ethyl acetate (100 mL), washed with water (3×100 mL), and evaporated. The residue was chromatographed in methylene chloride-methanol gradient, eluting the product at 19:1 methylene chloride-methanol. This material was further purified by preparative HPLC, using a 50-50 acetonitrile-water isocrat, and providing 0.40 g as a white solid, in 31% yield; mp 111-113° C.; HPLC, Waters Symmetry C-18, 3.9×150 mm, 5 μm, 1 mL/min, 240 nm, 50/50 CH$_3$CN/0.1% H$_3$PO$_4$, 5.08 (99.11%); $^1$H NMR (DMSO-d$_6$) δ 1.11-1.57 (m, 11H), 2.02-2.07 (m, 1H), 2.46-2.63 (m, 2H), 2.84-2.96 (m, 1H), 3.97 (t, J=8.3 Hz, 2H), 4.35 (d, J=6.0 Hz, 2H), 5.15 (dd, J=12.9 Hz, J=5.4 Hz, 1H), 7.72-7.77 (m, 2H), 7.84-7.90 (m, 2H), 11.13 (s, 1H); $^{13}$C NMR (DMSO-d$_6$) δ 13.8, 22.0, 25.0, 28.6, 30.8, 30.9, 43.5, 49.0, 64.0, 121.6, 123.5, 129.8, 131.6, 133.2, 147.9, 156.6, 167.0, 167.1, 169.8, 172.7; Anal. Calcd for $C_{21}H_{15}N_3O_6$: C, 60.71; H, 6.07; N, 10.11. Found: C, 60.49; H, 6.13; N, 9.91.

5.16 4-chloro-N-[2-[(3S)-3-methyl-2,6-dioxo-piperidin-3-yl]-1,3-dioxo-2,3-dihydro-1H-isoindol-5-ylmethyl]-benzamide

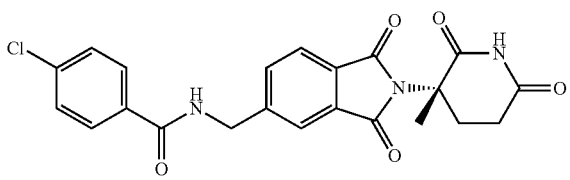 [SMILES: C[C@]1(N2C(=O)c3ccc(CNC(=O)c4ccc(Cl)cc4)cc3C2=O)CCC(=O)NC1=O]

A mixture of 5-aminomethyl-2-[(3S)-3-methyl-2,6-dioxo-piperidin-3-yl]-isoindole-1,3-dione hydrochloride (0.40 g, 1.18 mmol), 4-chlorobenzoyl chloride (0.15 mL, 1.18 mmol) and diisopropylethylamine (0.41 mL, 2.37 mmol) in acetonitrile (20 mL) was stirred at room temperature for 1 hour. The reaction mixture was concentrated, and the residue was dissolved in ethyl acetate (100 mL), washed with dilute aqueous HCl (2×150 mL) and water (2×150 mL), dried (MgSO$_4$), and evaporated under vacuum, providing 0.49 g of the product, in 94% yield; mp 163-165° C.; HPLC, Waters Symmetry C-18, 3.9×150 mm, 5 μm, 1 mL/min, 240 nm, 50/50 CH₃CN/0.1% H₃PO₄, 3.38 (98.94%); ¹H NMR (DMSO-d₆) δ 1.89 (s, 3H), 2.02-2.08 (m, 1H), 2.53-2.60 (m, 2H), 2.63-2.71 (m, 1H), 4.62 (d, J=6.0 Hz, 2H), 7.56-7.59 (m, 2H), 7.77-7.83 (m, 3H), 7.90-7.94 (m, 2H), 9.30 (t, J=5.7 Hz, 1H), 11.02 (s, 1H); ¹³C NMR (DMSO-d₆) δ 21.0, 28.5, 29.1, 42.6, 58.7, 121.6, 123.2, 128.5, 129.2, 129.6, 131.4, 132.6, 133.4, 136.3, 147.2, 165.4, 167.7, 167.9, 172.1, 172.2; Anal. Calcd for C₂₂H₁₈N₃O₅Cl: C, 60.08; H, 4.12; N, 9.55. Found: C, 59.70; H, 3.94; N, 9.43.

5.17 N-[2-[(3S)-3-methyl-2,6-dioxo-piperidin-3-yl]-1,3-dioxo-2,3-dihydro-1H-isoindol-5-ylmethyl]-4-trifluoromethoxy-benzamide

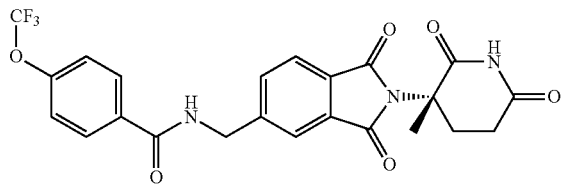

A mixture of 5-aminomethyl-2-[(3S)-3-methyl-2,6-dioxo-piperidin-3-yl]-isoindole-1,3-dione hydrochloride (0.40 g, 1.18 mmol), 4-(trifluoromethoxy)benzoyl chloride (0.19 mL, 1.18 mmol) and diisopropylethylamine (0.41 mL, 2.37 mmol) in acetonitrile (20 mL) was stirred at room temperature for 1 hour. The reaction mixture was concentrated, and the residue was dissolved in ethyl acetate (100 mL), washed with dilute aqueous HCl (2×150 mL) and water (2×150 mL), dried (MgSO₄), and evaporated under vacuum. The residue was stirred in ether (20 mL). The solid was filtered to give 0.42 g of the product, in 72% yield; mp 161-163° C.; HPLC, Waters Symmetry C-18, 3.9×150 mm, 5 μm, 1 mL/min, 240 nm, 50/50 CH₃CN/0.1% H₃PO₄, 5.58 (97.42%); ¹H NMR (DMSO-d₆) δ 1.89 (s, 3H), 2.02-2.08 (m, 1H), 2.49-2.60 (m, 2H), 2.63-2.72 (m, 1H), 4.63 (d, J=6.0 Hz, 2H), 7.48-7.51 (m, 2H), 7.78-7.84 (m, 3H), 8.00-8.05 (m, 2H), 9.34 (t, J=5.7 Hz, 1H), 11.02 (s, 1H); ¹³C NMR (DMSO-d₆) δ 21.0, 28.5, 29.1, 42.6, 58.7, 119.9 (q, J=255), 120.7, 121.6, 123.2, 125.0, 129.6, 131.4, 133.0, 133.4, 147.2, 150.4, 165.2, 167.7, 167.8, 172.1, 172.2; Anal. Calcd for C₂₃H₁₈N₃O₆F₃: C, 56.45; H, 3.71; N, 8.59. Found: C, 56.16; H, 3.39; N, 8.45.

5.18 hexanoic acid [2-[(3S)-3-methyl-2,6-dioxo-piperidin-3-yl]-1,3-dioxo-2,3-dihydro-1H-isoindol-5-ylmethyl]-amide

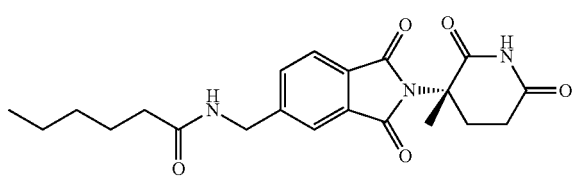 [SMILES: CCCCCC(=O)NCc1ccc2c(c1)C(=O)N([C@@]1(C)CCC(=O)NC1=O)C2=O]

A mixture of 5-aminomethyl-2-[(3S)-3-methyl-2,6-dioxo-piperidin-3-yl]-isoindole-1,3-dione hydrochloride (0.40 g, 1.2 mmol), hexanoyl chloride (0.17 mL, 1.2 mmol) and N,N-diisopropylethylamine (0.41 mL, 2.4 mmol) in anhydrous acetonitrile (20 mL) was stirred at room temperature for 1 hour. The reaction mixture was concentrated, and the residue was dissolved in ethyl acetate (100 mL), washed with dilute aqueous HCl (2×150 mL) and water (2×150 mL), dried (MgSO₄), and evaporated under vacuum. The resulting solid was stirred in ether overnight, filtered and dried to give 0.36 g of the product, in 77% yield; mp 154-156° C.; HPLC, Waters Symmetry C-18, 3.9×150 mm, 5 μm, 1 mL/min, 240 nm, 40/60 CH₃CN/0.1% H₃PO₄, 4.51 (97.79%); ¹H NMR (DMSO-d₆) δ 0.85 (t, J=6.9 Hz, 3H), 1.19-1.32 (m, 4H), 1.48-1.57 (m, 2H), 1.89 (s, 3H), 2.02-2.08 (m, 1H), 2.15 (t, J=7.5 Hz, 2H), 2.53-2.60 (m, 2H), 2.63-2.72 (m, 1H), 4.41 (d, J=6.0 Hz, 2H), 7.68-7.81 (m, 3H), 8.49 (t, J=6.0 Hz, 1H), 11.02 (s, 1H); ¹³C NMR (DMSO-d₆) δ 13.8, 21.0, 21.8, 24.9, 28.6, 29.1, 30.9, 35.2, 41.8, 58.7, 121.4, 123.1, 129.5, 131.3, 133.2, 147.7, 167.7, 167.9, 172.1, 172.2, 172.4; Anal. Calcd for C₂₁H₂₅N₃O₅: C, 63.15; H, 6.31; N, 10.52. Found: C, 63.06; H, 6.14; N, 10.48.

5.19 {2-[(3S)-3-methyl-2,6-dioxo-piperidin-3-yl]-1,3-dioxo-2,3-dihydro-1H-isoindol-5-ylmethyl}-carbamic acid hexyl ester

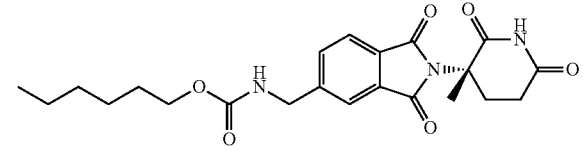 [SMILES: CCCCCCOC(=O)NCc1ccc2c(c1)C(=O)N([C@@]1(C)CCC(=O)NC1=O)C2=O]

A mixture of 5-aminomethyl-2-[(3S)-3-methyl-2,6-dioxo-piperidin-3-yl]-isoindole-1,3-dione hydrochloride (0.40 g, 1.18 mmol), hexyl chloroformate (0.19 mL, 1.18 mmol) and diisopropylethyl amine (0.41 mL, 2.37 mmol) in acetonitrile (20 mL) was stirred at room temperature for 1 hour. The reaction mixture was concentrated, and the residue was dissolved in ethyl acetate (100 mL), washed with dilute aqueous HCl (2×150 mL) and water (2×150 mL), dried (MgSO₄), and evaporated under vacuum, providing 0.45 g of the product, in 88% yield; mp 95-97° C.; HPLC, Waters Symmetry C-18, 3.9×150 mm, 5 μm, 1 mL/min, 240 nm, 50/50 CH₃CN/0.1% H₃PO₄, 6.94 (97.26%); ¹H NMR (DMSO-d₆) δ 0.78-0.86 (m, 3H), 1.09-1.26 (m, 6H), 1.52-1.54 (m, 2H), 1.89 (s, 3H), 1.99-2.08 (m, 1H), 2.54-2.59 (m, 2H), 2.64-2.72 (m, 1H), 3.96 (t, J=6.6 Hz, 2H), 4.33 (d, J=6.0 Hz, 2H), 7.70-7.87 (m, 4H), 11.02 (s, 1H); ¹³C NMR (DMSO-d₆) δ 13.8, 21.0, 22.0, 25.0, 28.6, 29.1, 30.9, 43.5, 58.7, 64.0, 121.3, 123.1, 129.6, 131.4, 133.1, 147.7, 156.6, 167.7, 167.8, 172.1, 172.2; Anal. Calcd for C₂₂H₂₇N₃O₆: C, 61.53; H, 6.34; N, 9.78. Found: C, 61.73; H, 6.33; N, 9.58.

5.20 3,4-dichloro-N-[2-(2,6-dioxo-piperidin-3-yl)-1-oxo-2,3-dihydro-1H-isoindol-5-ylmethyl]-benzamide

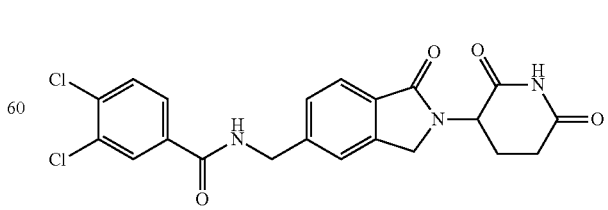

A mixture of 3-(5-aminomethyl-1-oxo-1,3-dihydro-isoindol-2-yl)-piperidine-2,6-dione hydrochloride (0.50 g, 1.6 mmol), 3,4-dichlorobenzoyl chloride (0.34 g, 1.6 mmol) and TEA (0.32 g, 3.2 mmol) in THF (25 mL) was heated to 40° C. with stirring under N₂, for 2.5 hours. The mixture was filtered, and the filtered solid was loaded onto a silica gel column, which was run using with a methylene chloride-methanol gradient. The product eluted at 93:7 methylene chloride-methanol, 0.42 g, in 58% yield; mp 260-262° C.; HPLC, Waters Symmetry C-18, 3.9×150 mm, 5 μm, 1 mL/min, 240 nm, 40/60 CH₃CN/0.1% H₃PO₄, 3.36 (99.65%); ¹H NMR (DMSO-d₆) δ 1.96-2.03 (m, 1H), 2.31-2.43 (m, 1H), 2.56-2.62 (m, 1H), 2.85-2.97 (m, 1H), 4.30 (d, J=17.4 Hz, 1H), 4.44 (d, J=17.4 Hz, 1H), 4.59 (d, J=6.0 Hz, 2H), 5.11 (dd, J=13.4 Hz, J=5.0 Hz, 1H), 7.45-7.55 (m, 2H), 7.70 (d, J=7.8, 1H), 7.78 (d, J=8.4 Hz, 1H), 7.88 (dd, J=8.4 Hz, J=1.8 Hz, 1H), 8.14 (d, J=2.1 Hz, 1H), 9.33 (t, J=6.0 Hz, 1H), 10.98 (s, 1H); ¹³C NMR (DMSO-d₆) δ 22.5, 31.2, 42.9, 47.1, 51.6, 122.2, 123.0, 127.2, 127.6, 129.2, 130.4, 130.7, 131.3, 134.1, 134.4, 142.4, 143.4, 164.0, 167.9, 171.0, 172.8; Anal. Calcd for C₂₁H₁₇Cl₂N₃O₄+0.25H₂O: C, 55.95; H, 3.91; N, 9.32. Found: C, 55.98; H, 3.55; N, 9.32.

5.21 N-[2-(2,6-dioxo-piperidin-3-yl)-1-oxo-2,3-dihydro-1H-isoindol-5-ylmethyl]-4-trifluoromethoxy-benzamide

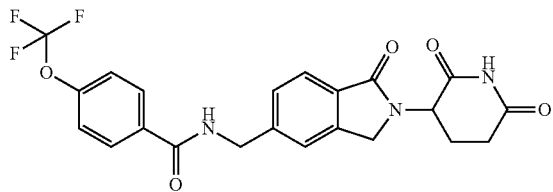 [SMILES: O=C1CCC(N2Cc3cc(CNC(=O)c4ccc(OC(F)(F)F)cc4)ccc3C2=O)C(=O)N1]

A mixture of 3-(5-aminomethyl-1-oxo-1,3-dihydro-isoindol-2-yl)-piperidine-2,6-dione hydrochloride (0.40 g, 1.29 mmol), 4-(trifluoromethoxy)benzoyl chloride (0.20 mL, 1.29 mmol) and diisopropylethylamine (0.41 mL, 2.37 mmol) in acetonitrile (20 mL) was stirred at room temperature for 1 hour. The solid was filtered, washed with additional acetonitrile (20 mL), and dried to give 0.41 g of the product, in 68% yield; mp 133-135° C.; HPLC, Waters Symmetry C-18, 3.9×150 mm, 5 μm, 1 mL/min, 240 nm, 40/60 CH₃CN/0.1% H₃PO₄, 5.44 (98.98%); ¹H NMR (DMSO-d₆) δ 1.98-2.01 (m, 1H), 2.27-2.45 (m, 1H), 2.57-2.62 (m, 1H), 2.85-2.97 (m, 1H), 4.30 (d, J=17.1 Hz, 1H), 4.45 (d, J=17.4 Hz, 1H), 4.60 (d, J=5.7 Hz, 2H), 5.11 (dd, J=13.5 Hz, J=5.1 Hz, 1H), 7.46-7.55 (m, 4H), 7.70 (d, J=7.8 Hz, 1H), 8.04 (d, J=8.7 Hz, 2H), 9.27 (t, J=5.7 Hz, 1H), 10.98 (s, 1H); ¹³C NMR (DMSO-d₆) δ 22.5, 31.2, 42.8, 47.1, 51.6, 119.9 (q, J=255.8 Hz), 120.7, 122.1, 122.9, 127.1, 129.6, 130.4, 133.2, 142.4, 143.7, 150.3, 165.1, 167.9, 171.0, 172.8; Anal. Calcd for C₂₂H₁₈N₃O₅F₃+0.15H₂O: C, 56.94; H, 3.97; N, 9.05. Found: C, 56.54; H, 3.63; N, 8.95.

5.22 furan-2-carboxylic acid [2-(2,6-dioxo-piperidin-3-yl)-1-oxo-2,3-dihydro-1H-isoindol-5-ylmethyl]amide

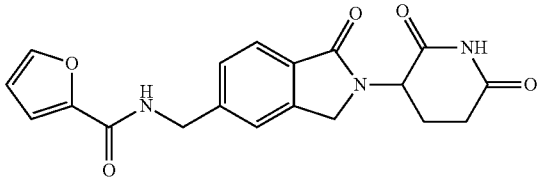 [SMILES: O=C1CCC(N2Cc3cc(CNC(=O)c4ccco4)ccc3C2=O)C(=O)N1]

A mixture of 3-(5-aminomethyl-1-oxo-1,3-dihydro-isoindol-2-yl)-piperidine-2,6-dione hydrochloride (0.40 g, 1.29 mmol), 2-furoyl chloride (0.13 mL, 1.29 mmol) and diisopropylethylamine (0.41 mL, 2.37 mmol) in acetonitrile (20 mL) was stirred at room temperature for 1 hour. The reaction mixture was filtered, and the solid was washed with additional acetonitrile (20 mL) and dried, providing 0.33 g of the product, in 71% yield; mp 338-340° C.; HPLC, Waters Symmetry C-18, 3.9×150 mm, 5 μm, 1 mL/min, 240 nm, 20/80 CH₃CN/0.1% H₃PO₄, 5.65 (96.68%); ¹H NMR (DMSO-d₆) δ 1.97-2.10 (m, 1H), 2.19-2.45 (m, 1H), 2.50-2.62 (m, 1H), 2.73-3.03 (m, 1H), 4.30 (d, J=17.1 Hz, 1H), 4.44 (d, J=17.4 Hz, 1H), 4.53 (d, J=5.7 Hz, 2H), 5.10 (dd, J=13.2 Hz, J=5.1 Hz, 1H), 6.64-8.20 (m, 6H), 9.04 (t, J=6.0 Hz, 1H), 10.98 (s, 1H); ¹³C NMR (DMSO-d₆) δ 22.5, 31.2, 42.0, 47.1, 51.6, 111.9, 113.6, 122.1, 122.9, 127.1, 130.4, 142.4, 143.7, 145.1, 147.7, 157.8, 167.9, 171.0, 172.8; Anal. Calcd for C₁₉H₁N₃O₅+0.1H₂O: C, 61.82; H, 4.70; N, 11.38. Found: C, 61.45; H, 4.46; N, 11.37.

5.23 hexanoic acid [2-(2,6-dioxo-piperidin-3-yl)-1-oxo-2,3-dihydro-1H-isoindol-5-ylmethyl]-amide

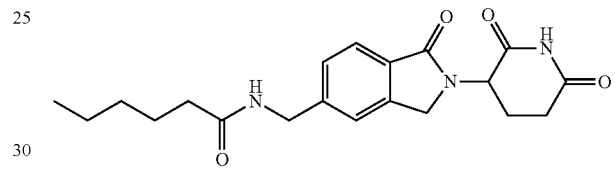

A mixture of 3-(5-aminomethyl-1-oxo-1,3-dihydro-isoindol-2-yl)-piperidine-2,6-dionehydrochloride (0.40 g, 1.29 mmol), hexanoyl chloride (0.18 mL, 1.29 mmol) and diisopropylethylamine (0.41 mL, 2.37 mmol) in acetonitrile (20 mL) was stirred at room temperature for 1 hour. The solid was filtered and washed with additional acetonitrile to give 0.26 g of the product, in 55% yield; mp 206-208° C.; HPLC, Waters Symmetry C-18, 3.9×150 mm, 5 μm, 1 mL/min, 240 nm, 30/70 CH₃CN/0.1% H₃PO₄, 5.30 (98.77%); ¹H NMR (DMSO-d₆) δ 0.86 (t, J=6.6 Hz, 3H), 1.25-1.29 (m, 4H), 1.48-1.58 (m, 2H), 1.98-2.01 (m, 1H), 2.14 (t, J=7.2 Hz, 2H), 2.33-2.42 (m, 1H), 2.57-2.63 (m, 1H), 2.86-2.98 (m, 1H), 4.27-4.47 (m, 4H), 5.11 (dd, J=13.2 Hz, J=4.8 Hz, 1H), 7.37-7.45 (m, 2H), 7.68 (d, J=7.8 Hz, 1H), 8.40 (t, J=5.4 Hz, 1H), 10.98 (s, 1H); ¹³C NMR (DMSO-d₆) δ 13.8, 21.8, 22.5, 24.9, 30.9, 31.2, 35.3, 42.0, 47.1, 51.6, 122.0, 122.9, 127.0, 130.3, 142.3, 144.1, 167.9, 171.0, 172.2, 172.8; Anal. Calcd for C₂₀H₂₅N₃O₄+0.1H₂O: C, 64.36; H, 6.81; N, 11.26. Found: C, 64.16; H, 6.80; N, 11.17.

5.24 pyridine-2-carboxylic acid [2-[(3S)-3-methyl-2,6-dioxo-piperidin-3-yl]-1,3-dioxo-2,3-dihydro-1H-isoindol-5-ylmethyl]-amide

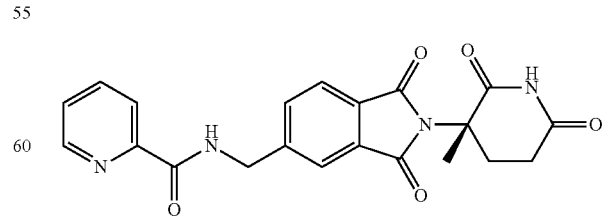

A mixture of 5-aminomethyl-2-[(3S)-3-methyl-2,6-dioxo-piperidin-3-yl]-isoindole-1,3-dione hydrochloride (0.85 g, 2.5 mmol), picolinoyl chloride hydrochloride (0.45 g, 2.5 mmol) and triethylamine (0.76 g, 7.5 mmol) in anhydrous acetonitrile (20 mL) was stirred at room temperature for 13 hours. The reaction mixture was filtered. The filtrate was concentrated in vacuo, and the residue was dissolved in ethyl acetate (100 mL). The organic phase was washed with 4 N aqueous HCl (150 mL) and neutralized with sodium bicarbonate. The solid precipitate was isolated by filtration, rinsed with water (200 mL) and dried to give the product as a white solid (0.47 g, 46% yield); mp 365-367° C.; HPLC, Waters Symmetry C-18, 3.9×150 mm, 5 μm, 1 mL/min, 240 nm, 30/70 $CH_3CN$/0.1% $H_3PO_4$, 6.59 (96.15%); $^1$H NMR (DMSO-$d_6$) δ 1.88 (s, 3H), 2.01-2.07 (m, 1H), 2.54-2.74 (m, 3H), 4.64 (d, J=6.3 Hz, 2H), 7.61-7.65 (m, 1H), 7.79-7.83 (m, 3H), 7.98-8.06 (m, 2H), 8.68 (d, J=4.8 Hz, 1H), 9.61 (t, J=6.3 Hz, 1H), 11.01 (s, 1H); $^{13}$C NMR (DMSO-$d_6$) δ 21.0, 28.5, 29.1, 42.3, 58.7, 121.8, 122.0, 123.1, 126.7, 129.6, 131.3, 133.5, 137.8, 147.3, 148.5, 149.7, 164.2, 167.7, 167.9, 172.1, 172.2; Anal. Calcd for $C_{21}H_{18}N_4O_5$+0.3$H_2O$: C, 61.25; H, 4.55; N, 13.61. Found: C, 60.88; H, 4.22; N, 13.33.

5.25 N-[2-[(3S)-3-methyl-2,6-dioxo-piperidin-3-yl]-1,3-dioxo-2,3-dihydro-1H-isoindol-5-ylmethyl]-4-trifluoromethyl-benzamide

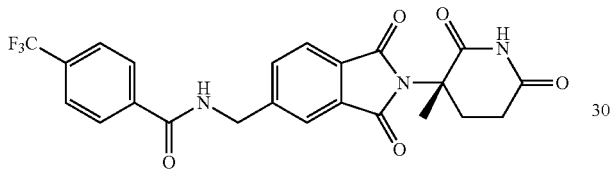

A mixture of 5-aminomethyl-2-[(3S)-3-methyl-2,6-dioxo-piperidin-3-yl)-isoindole-1,3-dione hydrochloride (0.85 g, 2.5 mmol), 4-(trifluoromethyl)-benzoyl chloride (0.52 g, 2.5 mmol) and triethylamine (0.51 g, 5.0 mmol) in anhydrous acetonitrile (20 mL) was stirred at room temperature for 13 hours. The reaction mixture was filtered. The filtrate was concentrated, and the resulting yellow residue was chromatographed on silica gel using a methanol-methylene chloride gradient, eluting the product at 3:97 methanol-methylene chloride to give the product as a white solid (0.94 g, 80% yield); mp 188-190° C.; HPLC, Waters Symmetry C-18, 3.9×150 mm, 5 μm, 1 mL/min, 240 nm, 50/50 $CH_3CN$/0.1% $H_3PO_4$, 3.82 (99.33%); $^1$H NMR (DMSO-$d_6$) δ 1.89 (s, 3H), 2.02-2.08 (m, 1H), 2.53-2.72 (m, 3H), 4.65 (d, J=6.0 Hz, 2H), 7.79-8.11 (m, 7H), 9.46 (t, J=6.0 Hz, 1H), 11.02 (s, 1H); $^{13}$C NMR (DMSO-$d_6$) δ 21.0, 28.6, 29.1, 42.7, 58.8, 121.7, 123.2, 123.9 (q, J=271 Hz), 125.5 (q, J=3.8 Hz), 128.2, 129.7, 131.3 (q, J=31.5 Hz), 131.4, 133.5, 137.7, 147.0, 165.3, 167.7, 167.9, 172.1, 172.2; Anal. Calcd for $C_{23}H_{18}N_3O_5F_3$: C, 58.35; H, 3.83; N, 8.88. Found: C, 58.05; H, 3.64; N, 8.65.

5.26 N-[2-[(3S)-3-methyl-2,6-dioxo-piperidin-3-yl]-1,3-dioxo-2,3-dihydro-1H-isoindol-5-ylmethyl]-isonicotinamide

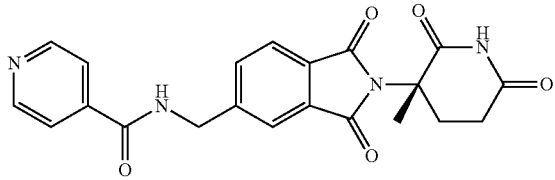 [SMILES: C[C@]1(N2C(=O)c3ccc(CNC(=O)c4ccncc4)cc3C2=O)CCC(=O)NC1=O]

A mixture of 5-aminomethyl-2-[(3S)-3-methyl-2,6-dioxo-piperidin-3-yl)-isoindole-1,3-dione hydrochloride (0.85 g, 2.5 mmol), isonicotinoyl chloride hydrochloride (0.45 g, 2.5 mmol) and triethylamine (0.76 g, 7.5 mmol) in anhydrous acetonitrile (20 mL) was stirred at room temperature for 2 hours. The reaction mixture was concentrated, and the resulting yellow residue was chromatographed on silica gel using a methanol-methylene chloride gradient, eluting the product at 5:95 methanol-methylene chloride. The crude product was stirred in water (20 mL) for 15 hours. The resulting solid was filtered and rinsed with additional water (20 mL). The solid was then stirred in methanol (20 mL) for two days, filtered, and washed with additional methanol (20 mL), providing the product as a white solid (0.23 g, 23% yield); mp 186-188° C.; HPLC, Waters Symmetry C-18, 3.9×150 mm, 5 μm, 1 mL/min, 240 nm, 25/75 $CH_3CN$/$H_2O$, 3.06 (97.62%); $^1$H NMR (DMSO-$d_6$) δ 1.89 (s, 3H), 2.02-2.08 (m, 1H), 2.53-2.76 (m, 3H), 4.65 (d, J=5.7 Hz, 2H), 7.79-7.84 (m, 5H), 8.76 (d, J=6.0 Hz, 2H), 9.51 (t, J=6.0 Hz, 1H), 11.02 (s, 1H); $^{13}$C NMR (DMSO-$d_6$) δ 21.0, 28.5, 29.1, 42.6, 58.8, 121.2, 121.7, 123.2, 129.7, 131.4, 133.5, 140.9, 146.8, 150.3, 164.9, 167.7, 167.8, 172.1, 172.2; Anal. Calcd for $C_{21}H_{18}N_4O_5$+0.2$H_2O$: C, 61.52; H, 4.52; N, 13.66. Found: C, 61.28; H, 4.36; N, 13.55.

5.27 4-fluoro-N-[2-[(3S)-3-methyl-2,6-dioxo-piperidin-3-yl]-1,3-dioxo-2,3-dihydro-1H-isoindol-5-ylmethyl]-benzamide

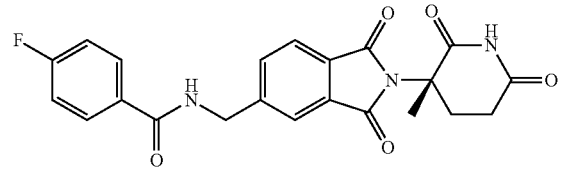 [SMILES: C[C@]1(N2C(=O)c3ccc(CNC(=O)c4ccc(F)cc4)cc3C2=O)CCC(=O)NC1=O]

A mixture of 5-aminomethyl-2-[(3S)-3-methyl-2,6-dioxo-piperidin-3-yl)-isoindole-1,3-dione hydrochloride (0.85 g, 2.5 mmol), 4-fluorobenzoyl chloride (0.40 g, 2.5 mmol) and triethylamine (0.51 g, 5.0 mmol) in anhydrous acetonitrile (20 mL) was stirred at room temperature for 2 hours. The reaction mixture was filtered. The filtrate was concentrated in vacuo, and the residue was chromatographed on silica gel using a methanol-methylene chloride gradient, eluting the product at 5:95 methanol-methylene chloride. The combined fractions were concentrated, and the resulting solid was stirred in ether for 2 hours. The suspension was filtered and the solid washed with additional ether to give the product as a white solid (0.41 g, 38% yield); mp 231-233° C.; HPLC, Waters Symmetry C-18, 3.9×150 mm, 5 μm, 1 mL/min, 240 nm, 40/60 $CH_3CN$/0.1% $H_3PO_4$, 3.90 (96.87%); $^1$H NMR (DMSO-$d_6$) δ 1.89 (s, 3H), 2.02-2.06 (m, 1H), 2.54-2.75 (m, 3H), 4.62 (d, J=5.7 Hz, 2H), 7.30-7.36 (m, 2H), 7.77-7.83 (m, 3H), 7.95-7.99 (m, 2H), 9.24 (t, J=6.0 Hz, 1H), 11.02 (s, 1H); $^{13}$C NMR (DMSO-$d_6$) δ 21.0, 28.5, 29.1, 42.6, 58.7, 115.3 (d, J=21 Hz), 121.6, 123.2, 129.6, 129.9 (d, J=8.3 Hz), 130.4 (d, J=3.0 Hz), 131.4, 133.4, 147.3, 164.0 (d, J=247 Hz), 165.3, 167.7, 167.9, 172.1, 172.2; Anal. Calcd for $C_{22}H_{18}N_3O_5F$: C, 62.41; H, 4.29; N, 9.92. Found: C, 62.46; H, 4.12; N, 9.88.

5.28 N-[2-(3S)-(3-methyl-2,6-dioxo-piperidin-3-yl)-1,3-dioxo-2,3-dihydro-1H-isoindol-5-ylmethyl]-6-trifluoromethyl nicotinamide

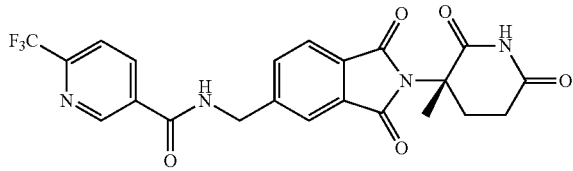 [SMILES: C[C@]1(N2C(=O)c3ccc(CNC(=O)c4ccc(C(F)(F)F)nc4)cc3C2=O)CCC(=O)NC1=O]

A mixture of 5-aminomethyl-2-[(3S)-3-methyl-2,6-dioxo-piperidin-3-yl]-isoindole-1,3-dione hydrochloride (0.65 g, 1.9 mmol), 6-(trifluoromethyl)nicotinoyl chloride (0.40 g, 1.9 mmol) and triethylamine (0.39 g, 3.8 mmol) in acetonitrile (20 mL) was stirred at room temperature for 1 hour. The reaction mixture was concentrated in vacuo, and the residue was dissolved in ethyl acetate (100 mL) and washed with 4 N HCl (2×150 mL) and water (2×150 mL), dried (MgSO$_4$) and evaporated under vacuum. The residue was chromatographed on silica gel (ethyl acetate) providing 0.58 g of the product, in 65% yield as a white solid; mp 358-360° C.; HPLC, Waters Symmetry C-18, 3.9×150 mm, 5 μm, 1 mL/min, 240 nm, 40/60 CH$_3$CN/0.1% H$_3$PO$_4$, 5.10 (99.34%); $^1$H NMR (DMSO-d$_6$) δ 1.89 (s, 3H), 2.00-2.08 (m, 1H), 2.55-2.72 (m, 3H), 4.69 (d, J=6.0 Hz, 2H), 7.83 (s, 3H), 8.08 (d, J=8.1 Hz, 1H), 8.51 (dd, J=8.1 Hz and 1.8 Hz, 1H), 9.21 (d, J=1.2 Hz, 1H), 9.61 (t, J=6.0 Hz, 1H), 11.02 (s, 1H); $^{13}$C NMR (DMSO-d$_6$) δ 21.0, 28.6, 29.1, 42.7, 58.8, 120.7 (q, J=3.0 Hz), 121.4 (q, J=273 Hz), 121.8, 123.2, 129.8, 131.4, 132.6, 133.5, 137.5, 146.6, 148.2 (q, J=33.8 Hz), 149.0, 163.9, 167.7, 167.8, 172.1, 172.2; Anal. Calcd for C$_{22}$H$_{17}$N$_4$O$_5$F$_3$+0.1H$_2$O: C, 55.49; H, 3.64; N, 11.77. Found: C, 55.11; H, 3.35; N, 11.64.

5.29 3,4-dichloro-N-[2-[(3S)-3-methyl-2,6-dioxo-piperidin-3-yl]-1,3-dioxo-2,3-dihydro-1H-isoindol-5-ylmethyl]-benzamide

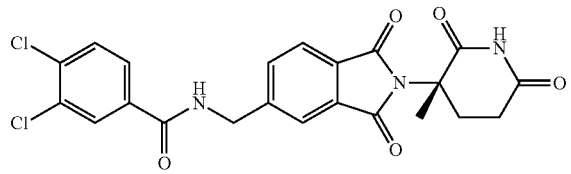 [SMILES: C[C@]1(N2C(=O)c3ccc(CNC(=O)c4ccc(Cl)c(Cl)c4)cc3C2=O)CCC(=O)NC1=O]

A mixture of 5-aminomethyl-2-[(3S)-3-methyl-2,6-dioxo-piperidin-3-yl]-isoindole-1,3-dione hydrochloride (0.65 g, 1.9 mmol), 3,4-dichlorobenzoyl chloride (0.40 g, 1.9 mmol) and triethylamine (0.39 g, 3.8 mmol) in anhydrous acetonitrile (20 mL) was stirred at room temperature for 1 hour. The reaction mixture was concentrated in vacuo, and the residue was dissolved in ethyl acetate (100 mL) and washed with 4 N HCl (2×150 mL), water (2×150 mL), dried (MgSO$_4$), and evaporated under vacuum. The solid was stirred in ether overnight and then filtered. The solid was chromatographed on silica gel using an ethyl acetate-hexane gradient, eluting the product at 90:10 ethyl acetate-hexane. The combined fractions were concentrated in vacuo, and the resulting solid was stirred in ether for 2 hours. The suspension was filtered and the solid washed with additional ether to afford the product as a white solid (0.54 g, 60% yield); mp 162-164° C.; HPLC, Waters Symmetry C-18, 3.9×150 mm, 5 μm, 1 mL/min, 240 nm, 50/50 CH$_3$CN/0.1% H$_3$PO$_4$, 4.89 (98.63%); $^1$H NMR (DMSO-d$_6$) δ 1.89 (s, 3H), 1.99-2.08 (m, 1H), 2.55-2.75 (m, 3H), 4.63 (d, J=6.0 Hz, 2H), 7.78-7.89 (m, 5H), 8.13 (d, J=2.1 Hz, 1H), 9.39 (t, J=6.0 Hz, 1H), 11.01 (s, 1H); $^{13}$C NMR (DMSO-d$_6$) δ 21.0, 28.6, 29.1, 42.7, 58.8, 121.7, 123.2, 127.6, 129.2, 129.7, 130.8, 131.3, 131.4, 133.5, 134.2, 134.3, 146.9, 164.2, 167.7, 167.8, 172.1, 172.2; Anal. Calcd for C$_{22}$H$_{17}$N$_3$O$_5$Cl$_2$: C, 55.71; H, 3.61; N, 8.86. Found: C, 55.34; H, 3.66; N, 8.67.

5.30 thiophene-2-carboxylic acid [2-[(3S)-3-methyl-2,6-dioxo-piperidin-3-yl]-1,3-dioxo-2,3-dihydro-1H-isoindol-5-ylmethyl]-amide

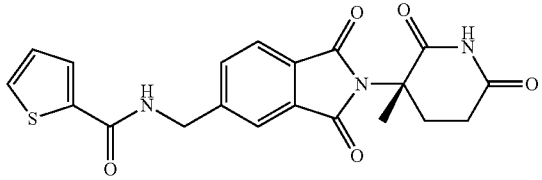 [SMILES: C[C@]1(N2C(=O)c3ccc(CNC(=O)c4cccs4)cc3C2=O)CCC(=O)NC1=O]

A mixture of 5-aminomethyl-2-[(3S)-3-methyl-2,6-dioxo-piperidin-3-yl]-isoindole-1,3-dione hydrochloride (0.85 g, 2.5 mmol), 2-thiophenecarbonyl chloride (0.37 g, 2.5 mmol) and triethylamine (0.51 g, 5.0 mmol) in anhydrous acetonitrile (20 mL) was stirred at room temperature for 1 hour. The reaction mixture was then concentrated in vacuo, and the residue was chromatographed on silica gel using a methanol-methylene chloride gradient, eluting the product at 5:95 methanol-methylene chloride. The solvent was concentrated in vacuo, and the resulting solid was dissolved in DMF (4 mL) and the mixture was warmed to 95° C. for 1 hour. Water (5 mL) was then added drop-wise and the mixture was then allowed to cool to room temperature and stirred overnight. The resulting suspension was filtered and rinsed with additional water to give the product as a white solid (0.62 g, 60% yield); mp 222-224° C.; HPLC, Waters Symmetry C-18, 3.9×150 mm, 5 μm, 1 mL/min, 240 nm, 30/70 CH$_3$CN/0.1% H$_3$PO$_4$, 6.67 (96.69%); $^1$H NMR (DMSO-d$_6$) δ 1.89 (s, 3H), 2.02-2.08 (m, 1H), 2.53-2.73 (m, 3H), 4.60 (d, J=6.0 Hz, 2H), 7.16-7.19 (m, 1H), 7.76-7.84 (m, 5H), 9.22 (t, J=6.0 Hz, 1H), 11.01 (s, 1H); $^{13}$C NMR (DMSO-d$_6$) δ 21.0, 28.5, 29.1, 42.4, 58.7, 121.6, 123.2, 128.0, 128.4, 129.6, 131.1, 131.4, 133.4, 139.3, 147.3, 161.3, 167.7, 167.9, 172.1, 172.2; Anal. Calcd for C$_{20}$H$_{17}$N$_3$O$_5$S: C, 58.39; H, 4.16; N, 10.21. Found: C, 58.55; H, 3.98; N, 10.06.

5.31 2-(4-chloro-phenyl)-N-[2-[(3S)-3-methyl-2,6-dioxo-piperidin-3-yl]-1,3-dioxo-2,3-dihydro-1H-isoindol-5-ylmethyl]-acetamide

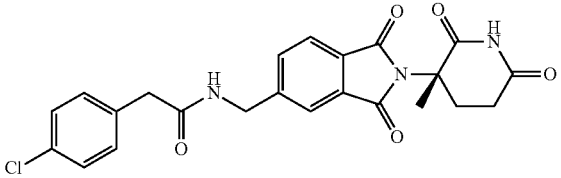 [SMILES: C[C@]1(N2C(=O)c3ccc(CNC(=O)Cc4ccc(Cl)cc4)cc3C2=O)CCC(=O)NC1=O]

A mixture of 5-aminomethyl-2-[(3S)-3-methyl-2,6-dioxo-piperidin-3-yl]-isoindole-1,3-dione hydrochloride (0.65 g, 1.9 mmol), 4-chlorophenylacetyl chloride (0.36 g, 1.9 mmol) and triethylamine (0.39 g, 3.8 mmol) in acetonitrile (20 mL) was stirred at room temperature for 1 hour. Additional 4-chlorophenylacetyl chloride (0.36 g, 1.9 mmol) and triethylamine (0.39 g, 3.8 mmol) were added to the reaction mixture, and stirring proceeded for an additional 3 hours. The reaction mixture was filtered, and the filtrate was concentrated. The residue was dissolved in ethyl acetate (100 mL) and washed with 4 N HCl (2×150 mL) and water (2×150 mL), dried (MgSO$_4$) and concentrated in vacuo. The residue was chromatographed on silica gel using a methanol-CH$_2$Cl$_2$ gradient, eluting the product at 5:95 methanol-CH$_2$Cl$_2$, and providing 0.60 g of the product as a white solid in a 69% yield; mp 156-158° C.; HPLC, Waters Symmetry C-18, 3.9×150 mm, 5 urn, 1 mL/min, 240 nm, 40/60 CH$_3$CN/0.1% H$_3$PO$_4$, 6.09 (95.59%); $^1$H NMR (DMSO-d$_6$) δ 1.89 (s, 3H), 2.02-2.08 (m, 1H), 2.53-2.76 (m, 3H), 4.42 (d, J=6.0 Hz, 2H), 7.28-7.44 (m, 4H), 7.68-7.80 (m, 3H), 8.73 (t, J=6.0 Hz, 1H), 11.03 (s, 1H); $^{13}$C NMR (DMSO-d$_6$) δ 21.0, 28.6, 29.1, 41.4, 42.1, 58.8, 121.5, 123.1, 128.2, 129.6, 130.9, 131.2, 131.4, 133.3, 135.1, 147.3, 167.7, 167.8, 170.1, 172.1, 172.2; Anal. Calcd for C$_{22}$K$_7$N$_4$O$_5$F$_3$+0.10H$_2$O+0.15 EtOAc: C, 60.45; H, 4.60; N, 8.96. Found: C, 60.37; H, 4.21; N, 8.56.

5.32 isoquinoline-3-carboxylic acid [2-[(3S)-3-methyl-2,6-dioxo-piperidin-3-yl]-1,3-dioxo-2,3-dihydro-1H-isoindol-5-ylmethyl]-amide

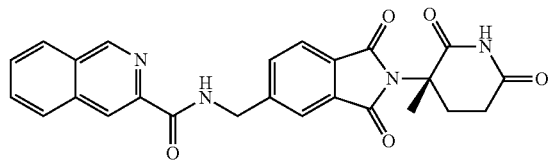 [SMILES: C[C@]1(N2C(=O)c3ccc(CNC(=O)c4cc5ccccc5cn4)cc3C2=O)CCC(=O)NC1=O]

3-Isoquinolinecarboxylic acid hydrate (0.33 g, 1.9 mmol) was dissolved in DMF (20 mL) and CDI (0.34 g, 2.1 mmol) was added. The mixture was stirred at 40° C. for 1 hour. 5-Aminomethyl-2-[(3S)-3-methyl-2,6-dioxo-piperidin-3-yl]-isoindole-1,3-dione hydrochloride (0.65 g, 1.9 mmol) and triethylamine (0.39 g, 3.8 mmol) were then added, and the reaction mixture was stirred at 40° C. for an additional 90 minutes. The mixture was cooled to room temperature and stirred overnight. Water (30 mL) was added and a solid precipitated. The precipitated solid was isolated by filtration, washed with additional water, and dried to afford 0.66 g of the product in a 76% yield; mp 259-261° C.; HPLC, Waters Symmetry C-18, 3.9×150 mm, 5 μm, 1 mL/min, 240 nm, 50/50 CH$_3$CN/0.1% H$_3$PO$_4$, 3.24 (97.97%); $^1$H NMR (DMSO-d$_6$) δ 1.88 (s, 3H), 2.01-2.07 (m, 1H), 2.53-2.74 (m, 3H), 4.71 (d, J=6.3 Hz, 2H), 7.80-7.92 (m, 5H), 8.19-8.28 (m, 2H), 8.58 (s, 1H), 9.42 (s, 1H), 9.75 (t, J=6.3 Hz, 1H), 11.02 (s, 1H); $^{13}$C NMR (DMSO-d$_6$) δ 21.0, 28.5, 29.1, 42.4, 58.7, 120.0, 121.8, 123.1, 127.8, 128.0, 129.2, 129.3, 129.6, 131.4, 133.6, 135.3, 143.5, 147.5, 151.6, 164.5, 167.7, 167.9, 172.1, 172.2; Anal. Calcd for C$_{22}$H$_{20}$N$_4$O$_5$+0.20H$_2$O: C, 65.27; H, 4.47; N, 12.18. Found: C, 64.98; H, 4.33; N, 12.18.

5.33 N-((2-(2,6-dioxopiperidin-3-yl)-1,3-dioxoisoindolin-5-yl)methyl)-4-(trifluoromethylthio)benzamide

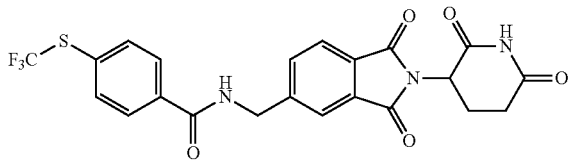 [SMILES: O=C1CCC(N2C(=O)c3ccc(CNC(=O)c4ccc(SC(F)(F)F)cc4)cc3C2=O)C(=O)N1]

TEA was added to a stirred mixture of 5-aminomethyl-2-(2,6-dioxo-piperidin-3-yl)-isoindole-1,3-dione hydrochloride (1.0 g, 3.1 mmol) and 4-(trifluoromethylthio)benzoyl chloride (0.75 g, 3.1 mmol) in acetonitrile (30 mL), and the resulting mixture was stirred at room temperature for 1 hour. The mixture was diluted with water (100 mL) and ethyl acetate (100 mL). The organic phase was separated and concentrated in vacuo. The residue was chromatographed on silica gel using a hexanes-ethyl acetate gradient, eluting 1.2 g of the product at 60-70% ethyl acetate, in 76% yield as a white solid; mp 171-173° C.; HPLC, Waters Symmetry C-18, 3.9×150 mm, 5 μm, 1 mL/min, 240 nm, 50/50 CH$_3$CN/0.1% H$_3$PO$_4$, 4.72 (97.94%); $^1$H NMR (DMSO-d$_6$) δ 2.02-2.10 (m, 1H), 2.46-2.63 (m, 2H), 2.83-2.95 (m, 1H), 4.66 (d, J=5.8 Hz, 2H), 5.15 (dd, J=12.8 Hz, J=5.3 Hz, 1H), 7.81-7.92 (m, 5H), 8.00-8.03 (m, 2H), 9.41 (t, J=5.8 Hz, 1H), 11.13 (s, 1H); $^{13}$C NMR (DMSO-d$_6$) δ 22.0, 30.9, 42.7, 49.0, 122.0, 123.6, 126.4, 128.7, 129.5 (q, J=306 Hz), 129.9, 131.6, 133.5, 135.9, 136.5, 147.2, 165.5, 167.0, 167.1, 169.8, 172.7; Anal. Calcd for C$_{22}$H$_{16}$N$_3$O$_5$F$_3$S: C, 53.77; H, 3.28; N, 8.55. Found: C, 53.55; H, 3.14; N, 8.37.

5.34 N-((2-(2,6-dioxopiperidin-3-yl)-1,3-dioxoisoindolin-5-yl)methyl)-4-(1,1,2,2-tetrafluoroethoxy)benzamide

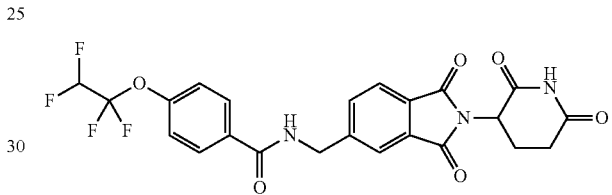

A mixture of 4-(1,1,2,2-tetrafluoroethoxy)benzoic acid (0.73 g, 3.1 mmol), and CDI (0.55 g, 3.4 mmol) in DMF (20 mL) was stirred at 40° C. for 2 hours, and then 5-aminomethyl-2-(2,6-dioxo-piperidin-3-yl)-isoindole-1,3-dione hydrochloride (1.0 g, 3.1 mmol) was added. After 2 hours, the mixture was cooled to room temperature, poured into ethyl acetate (100 mL), and then washed with NaHCO$_3$ (3×75 mL) and then concentrated. The residue was chromatographed on silica gel (ethyl acetate) affording 0.79 g of the product as a white solid in a 51% yield; mp 148-150° C.; HPLC, Waters Symmetry C-18, 3.9×150 mm, 5 μm, 1 mL/min, 240 nm, 50/50 CH$_3$CN/0.1% H$_3$PO$_4$, 4.72 (98.94%); $^1$H NMR (DMSO-d$_6$) δ 1.99-2.10 (m, 1H), 2.48-2.63 (m, 2H), 2.84-2.96 (m, 1H), 4.66 (d, J=5.8 Hz, 2H), 5.15 (dd, J=12.9 Hz, J=5.4 Hz, 1H), 6.85 (tt, J=51.9, J=3.1, 1H), 7.42 (d, J=8.7 Hz, 2H), 7.81-7.92 (m, 3H), 8.00-8.04 (m, 2H), 9.32 (t, J=5.8 Hz, 1H), 11.13 (s, 1H); $^{13}$C NMR (DMSO-d$_6$) δ 22.0, 30.9, 42.7, 49.0, 107.7 (tt, J=247, J=40), 116.4 (tt, J=269, J=27), 121.2, 122.0, 123.5, 129.5, 129.8, 131.6, 132.5, 133.4, 147.4, 150.3, 165.4, 167.0, 167.1, 169.8, 172.7; Anal. Calcd for C$_{23}$H$_{17}$N$_3$O$_6$F$_4$: C, 54.44; H, 3.38; N, 8.28. Found: C, 54.24; H, 3.28; N, 8.15.

5.35 4-bromo-N-[2-(2,6-dioxo-piperidin-3-yl)-1,3-dioxo-2,3-dihydro-1H-isoindol-5-ylmethyl]-benzamide

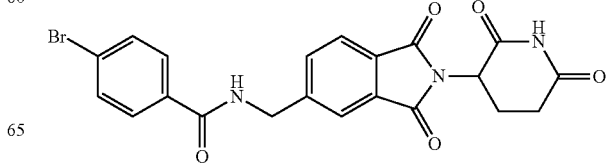

A mixture of 5-aminomethyl-2-(2,6-dioxo-piperidin-3-yl)-isoindole-1,3-dione hydrochloride (1.0 g, 3.1 mmol), 4-bromobenzoyl chloride (0.68 g, 3.1 mmol) and triethylamine (0.63 g, 6.2 mmol) in acetonitrile (20 mL) was stirred for 3 hours at room temperature. The reaction mixture was filtered, and the filtrate was concentrated. The residue was chromatographed on silica gel (ethyl acetate) providing 1.2 g of the product as a white solid in an 83% yield; mp 166-168° C.; HPLC, Waters Symmetry C-18, 3.9×150 mm, 5 μm, 1 mL/min, 240 nm, 40/60 $CH_3CN/0.1\%$ $H_3PO_4$, 6.07 (97.97%); $^1H$ NMR (DMSO-$d_6$) δ 2.02-2.10 (m, 1H), 2.46-2.63 (m, 2H), 2.83-2.95 (m, 1H), 4.64 (d, J=6.0 Hz, 2H), 5.15 (dd, J=12.6 Hz, J=5.1 Hz, 1H), 7.69-7.74 (m, 2H), 7.80-7.91 (m, 5H), 9.30 (t, J=6.0 Hz, 1H), 11.12 (s, 1H); $^{13}C$ NMR (DMSO-$d_6$) δ 22.0, 30.9, 42.7, 49.0, 122.0, 123.5, 125.2, 129.4, 129.8, 131.4, 131.6, 133.0, 133.5, 147.4, 165.5, 167.0, 167.1, 169.8, 172.7; Anal. Calcd for $C_{21}H_{16}N_3O_5Br$: C, 53.63; H, 3.43; N, 8.94; Br, 16.99. Found: C, 53.61; H, 3.14; N, 8.84; Br, 16.80.

5.36 N-[2-(2,6-dioxo-piperidin-3-yl)-1,3-dioxo-2,3-dihydro-1H-isoindol-5-ylmethyl]-4-ethyl-benzamide

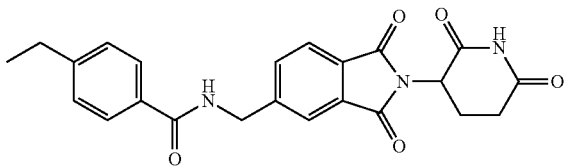 [SMILES: CCc1ccc(C(=O)NCc2ccc3c(c2)C(=O)N(C2CCC(=O)NC2=O)C3=O)cc1]

A mixture of 5-aminomethyl-2-(2,6-dioxo-piperidin-3-yl)-isoindole-1,3-dione hydrochloride (1.00 g, 3.1 mmol), 4-ethylbenzoyl chloride (0.52 g, 3.1 mmol) and triethylamine (0.63 g, 6.2 mmol) in acetonitrile (20 mL) was stirred for 3 hours at room temperature. The reaction suspension was filtered, and the solid washed with additional acetonitrile. The solid was then stirred in water for 2 hours, filtered and dried to give 0.51 g of the product. The filtrate of the reaction mixture was concentrated down. The residue was chromatographed on silica gel (ethyl acetate). The combined fraction were concentrated, and the resulting solid was stirred in ether overnight, filtered and dried to give 0.59 g of the product, overall yield 85% yield. The product was a white solid; mp 191-193° C.; HPLC, Waters Symmetry C-18, 3.9×150 mm, 5 μm, 1 mL/min, 240 nm, 40/60 $CH_3CN/0.1\%$ $H_3PO_4$, 6.56 (99.32%); $^1H$ NMR (DMSO-$d_6$) δ 1.20 (t, J=5.7 Hz, 3H), 2.02-2.10 (m, 1H), 2.47-2.70 (m, 2H), 2.83-2.95 (m, 1H), 4.64 (d, J=5.7 Hz, 2H), 5.16 (dd, J=12.9 Hz, J=5.1 Hz, 1H), 7.33 (d, J=8.1 Hz, 2H), 7.79-7.91 (m, 5H), 9.15 (t, J=6.0 Hz, 1H), 11.12 (s, 1H); $^{13}C$ NMR (DMSO-$d_6$) δ 15.3, 22.0, 28.0, 30.9, 42.5, 49.0, 121.9, 123.5, 127.3, 127.7, 129.8, 131.4, 131.6, 133.4, 147.5, 147.7, 166.3, 167.0, 167.1, 169.8, 172.7; Anal. Calcd for $C_{23}H_{21}N_3O_5$: C, 65.86; H, 5.05; N, 10.02. Found: C, 65.73; H, 4.86; N, 9.91.

5.37 N-[2-(2,6-dioxo-piperidin-3-yl)-1,3-dioxo-2,3-dihydro-1H-isoindol-5-ylmethyl]-4-ethoxy-benzamide

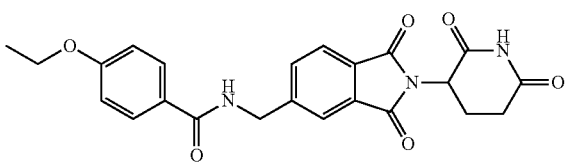

4-Ethoxybenzoic acid (0.51 g, 3.1 mmol) was dissolved in DMF (20 mL) and CDI (0.55 g, 3.4 mmol) was added. The mixture was stirred at 40° C. for 1 hour. 5-Aminomethyl-2-(2,6-dioxo-piperidin-3-yl)-isoindole-1,3-dione hydrochloride (1.00 g, 3.1 mmol) and triethylamine (0.63 g, 6.2 mmol) were then added, and the reaction mixture was stirred at 40° C. for an additional 90 minutes. The mixture was then cooled to room temperature and stirred overnight. Water (30 mL) was then added and a solid precipitated. The solid was isolated by filtration, washed with additional water and the resulting solid was chromatographed on silica gel (ethyl acetate) providing 0.21 g of the product, in 16% yield as a white solid; mp 213-215° C.; HPLC, Waters Symmetry C-18, 3.9×150 mm, 5 μm, 1 mL/min, 240 nm, 40/60 $CH_3CN/0.1\%$ $H_3PO_4$, 3.71 (99.35%); $^1H$ NMR (DMSO-$d_6$) δ 1.34 (t, J=6.9 Hz, 3H), 2.02-2.09 (m, 1H), 2.46-2.62 (m, 2H), 2.83-2.95 (m, 1H), 4.06-4.13 (m, 2H), 4.62 (d, J=6.0 Hz, 2H), 5.14 (dd, J=12.9 Hz, J=5.4 Hz, 1H), 6.98-7.03 (m, 2H), 7.79-7.91 (m, 5H), 9.07 (t, J=5.7 Hz, 1H), 11.12 (s, 1H); $^{13}C$ NMR (DMSO-$d_6$) δ 14.5, 22.0, 30.9, 42.5, 49.0, 63.3, 114.0, 121.9, 123.5, 125.9, 129.1, 129.7, 131.6, 133.4, 147.9, 161.0, 165.9, 167.0, 167.1, 169.8, 172.7; Anal. Calcd for $C_{23}H_{21}N_3O_6$: C, 63.44; H, 4.86; N, 9.65. Found: C, 63.41; H, 4.76; N, 9.41.

5.38 N-[2-(2,6-dioxo-piperidin-3-yl)-1,3-dioxo-2,3-dihydro-1H-isoindol-5-ylmethyl]-4-methanesulfonyl-benzamide

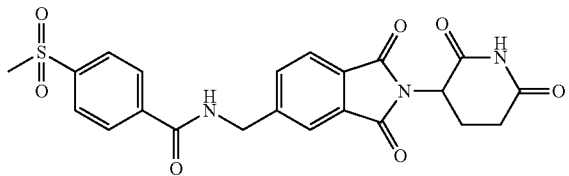 [SMILES: CS(=O)(=O)c1ccc(C(=O)NCc2ccc3c(c2)C(=O)N(C2CCC(=O)NC2=O)C3=O)cc1]

4-(Methylsulfonyl)-benzoic acid (0.62 g, 3.1 mmol) was dissolved in DMF (20 mL) and CDI (0.55 g, 3.4 mmol) was added. The mixture was stirred at 40° C. for 1 hour. 5-aminomethyl-2-(2,6-dioxo-piperidin-3-yl)-isoindole-1,3-dione hydrochloride (1.0 g, 3.1 mmol) and triethylamine (0.63 g, 6.2 mmol) were added, and the reaction mixture was stirred at 40° C. for an additional 90 minutes. The mixture was cooled to room temperature and stirred overnight. The reaction mixture was concentrated, and the residue was chromatographed on silica gel (ethyl acetate) providing 0.83 g of the product in a 57% yield as a white solid; mp 241-243° C.; HPLC, Waters Symmetry C-18, 3.9×150 mm, 5 μm, 1 mL/min, 240 nm, 30/70 $CH_3CN/0.1\%$ $H_3PO_4$, 3.48 (98.80%); $^1H$ NMR (DMSO-$d_6$) δ 2.03-2.08 (m, 1H), 2.49-2.63 (m, 2H), 2.83-2.91 (m, 1H), 3.27 (s, 3H), 4.68 (d, J=6.0 Hz, 2H), 5.15 (dd, J=12.6 Hz, J=5.1 Hz, 1H), 7.82-7.92 (m, 3H), 8.04-8.07 (m, 2H), 8.12-8.15 (m, 2H), 9.49 (t, J=5.7 Hz, 1H), 11.12 (s, 1H); $^{13}C$ NMR (DMSO-$d_6$) δ 22.0, 30.9, 42.8, 43.3, 49.0, 122.0, 123.6, 127.1, 128.3, 129.9, 131.6, 133.5, 138.3, 143.1, 147.1, 165.2, 167.0, 167.1, 169.8, 172.7; Anal. Calcd for $C_{22}H_{19}N_3O_7S$: C, 56.28; H, 4.08; N, 8.95. Found: C, 56.13; H, 3.90; N, 8.74.

5.39 N-[2-(2,6-dioxo-piperidin-3-yl)-1,3-dioxo-2,3-dihydro-1H-isoindol-5-ylmethyl]-4-iodo-benzamide

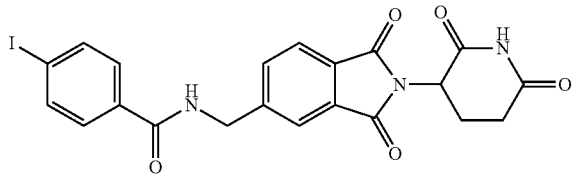 [SMILES: O=C1CCC(N2C(=O)c3ccc(CNC(=O)c4ccc(I)cc4)cc3C2=O)C(=O)N1]

4-Iodobenzoic acid (0.77 g, 3.1 mmol) was dissolved in DMF (20 mL), and CDI (0.55 g, 3.4 mmol) was added. The mixture stirred at 40° C. for 1 hour. 5-aminomethyl-2-(2,6-dioxo-piperidin-3-yl)-isoindole-1,3-dione hydrochloride (1.00 g, 3.1 mmol) and triethylamine (0.63 g, 6.2 mmol) were added, and the reaction mixture was stirred at 40° C. for an additional 90 minutes. The mixture was cooled to room temperature and stirred overnight. The reaction mixture was then concentrated, and the residue was chromatographed on silica gel (ethyl acetate) to afford a solid that was stirred in ether overnight, filtered and dried to give 1.33 g of the product, in 83% yield as a white solid; mp 163-165° C.; HPLC, Waters Symmetry C-18, 3.9×150 mm, 5 µm, 1 mL/min, 240 nm, 50/50 $CH_3CN/0.1\%$ $H_3PO_4$, 3.27 (97.68%); $^1$H NMR (DMSO-$d_6$) δ 2.03-2.09 (m, 1H), 2.46-2.63 (m, 2H), 2.83-2.95 (m, 1H), 4.63 (d, J=6.0 Hz, 2H), 5.14 (dd, J=12.9 Hz, J=5.4 Hz, 1H), 7.67-7.91 (m, 7H), 9.29 (t, J=5.7 Hz, 1H), 11.12 (s, 1H); $^{13}$C NMR (DMSO-$d_6$) δ 22.0, 30.9, 42.6, 49.0, 99.1, 122.0, 123.5, 129.2, 129.8, 131.6, 133.3, 133.5, 137.3, 147.4, 165.8, 167.0, 167.1, 169.8, 172.7; Anal. Calcd for $C_{21}H_{16}N_3O_5I$: C, 48.76; H, 3.12; N, 8.12. Found: C, 48.64; H, 2.77; N, 7.85.

5.40 N-[2-(2,6-dioxo-piperidin-3-yl)-1,3-dioxo-2,3-dihydro-1H-isoindol-5-ylmethyl]-4-methylsulfanyl-benzamide

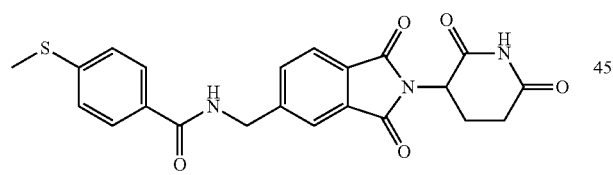

4-(Methylthio)-benzoic acid (0.52 g, 3.1 mmol) was dissolved in DMF (20 mL), and CDI (0.55 g, 3.4 mmol) was added. The mixture was stirred at 40° C. for 1 hour. 5-aminomethyl-2-(2,6-dioxo-piperidin-3-yl)-isoindole-1,3-dione hydrochloride (1.00 g, 3.1 mmol) and triethylamine (0.63 g, 6.2 mmol) were then added, and the reaction mixture was stirred at 40° C. for an additional 90 minutes. The mixture was cooled to room temperature and stirred overnight. The reaction mixture was concentrated, and the residue was chromatographed on silica gel (ethyl acetate) affording 0.75 g of the product in a 56% yield as a white solid; mp 187-189° C.; HPLC, Waters Symmetry C-18, 3.9×150 mm, 5 µm, 1 mL/min, 240 nm, 40/60 $CH_3CN/0.1\%$ $H_3PO_4$, 4.61 (95.58%); $^1$H NMR (DMSO-$d_6$) δ 2.03-2.10 (m, 1H), 2.46-2.63 (m, 2H), 2.52 (s, 3H), 2.83-2.95 (m, 1H), 4.63 (d, J=6.0 Hz, 2H), 5.14 (dd, J=12.6 Hz, J=5.1 Hz, 1H), 7.35 (d, J=8.4 Hz, 2H), 7.80-7.91 (m, 5H), 9.18 (t, J=6.0 Hz, 1H), 11.12 (s, 1H); $^{13}$C NMR (DMSO-$d_6$) δ 14.1, 22.0, 30.9, 42.6, 49.0, 121.9, 123.5, 124.9, 127.7, 129.8, 129.9, 131.6, 133.4, 142.8, 147.7, 165.9, 167.0, 167.1, 169.8, 172.7; Anal. Calcd for $C_{22}H_{19}N_3O_5S+0.1H_2O$: C, 60.15; H, 4.41; N, 9.57. Found: C, 59.98; H, 4.32; N, 9.61.

5.41 N-[2-(2,6-dioxo-piperidin-3-yl)-1,3-dioxo-2,3-dihydro-1H-isoindol-5-ylmethyl]-4-ethylsulfanyl-benzamide

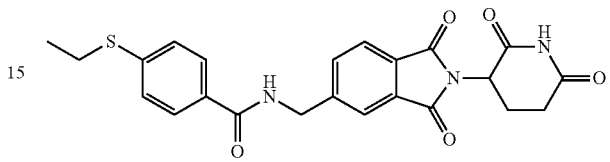

4-(Ethylthio)-benzoic acid (0.56 g, 3.1 mmol) was dissolved in DMF (20 mL) and CDI (0.55 g, 3.4 mmol) was added. The mixture was stirred at 40° C. for 1 hour. 5-aminomethyl-2-(2,6-dioxo-piperidin-3-yl)-isoindole-1,3-dione hydrochloride (1.00 g, 3.1 mmol) and triethylamine (0.63 g, 6.2 mmol) were added, and the reaction mixture was stirred at 40° C. for an additional 90 minutes. The mixture was cooled to room temperature and stirred overnight. The reaction mixture was concentrated, and the residue was chromatographed on silica gel using an ethyl acetate-hexane gradient, eluting the product at 80:20 ethyl acetate-hexanes, providing 1.1 g of the product in an 81% yield as a white solid; mp 175-177° C.; HPLC, Waters Symmetry C-18, 3.9×150 mm, 5 µm, 1 mL/min, 240 nm, 40/60 $CH_3CN/0.1\%$ $H_3PO_4$, 6.93 (99.44%); $^1$H NMR (DMSO-$d_6$) δ 1.27 (t, J=7.5 Hz, 3H), 2.02-2.09 (m, 1H), 2.47-2.63 (m, 2H), 2.83-2.95 (m, 1H), 3.06 (q, J=7.5 Hz, 2H), 4.63 (d, J=5.7 Hz, 2H), 5.14 (dd, J=12.9 Hz, J=5.4 Hz, 1H), 7.37-7.39 (m, 2H), 7.80-7.91 (m, 5H), 9.18 (t, J=6.0 Hz, 1H), 11.12 (s, 1H); $^{13}$C NMR (DMSO-$d_6$) δ 13.9, 22.0, 25.2, 30.9, 42.6, 49.0, 121.9, 123.5, 126.3, 127.8, 129.8, 130.4, 131.6, 133.4, 141.2, 147.6, 165.9, 167.0, 167.1, 169.8, 172.7; Anal. Calcd for $C_{23}H_{21}N_3O_5S$: C, 61.19; H, 4.69; N, 9.31. Found: C, 60.80; H, 4.34; N, 9.21.

5.42 N-((2-(2,6-dioxopiperidin-3-yl)-1,3-dioxoisoindolin-5-yl)methyl)-2-(4-(trifluoromethylthio)phenyl)acetamide

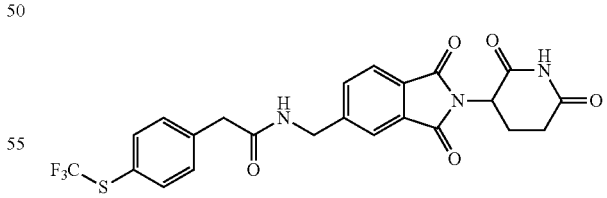

A mixture of 4-(trifluoromethylthio)phenylacetic acid (0.73 g, 3.1 mmol), and CDI (0.55 g, 3.4 mmol) in DMF (20 mL) was stirred at 40° C. for 2 hours, and then 5-aminomethyl-2-(2,6-dioxo-piperidin-3-yl)-isoindole-1,3-dione hydrochloride (1.0 g, 3.1 mmol) was added. After 2 hours, the mixture was cooled to room temperature, poured into ethyl acetate (100 mL), and washed with $NaHCO_3$ (3×75 mL) and concentrated. The residue was chromatographed on silica gel (ethyl acetate) affording 1.2 g of the product in a 77% yield as a white solid; mp 140-142° C.; HPLC, Waters Symmetry C-18, 3.9×150 mm, 5 μm, 1 mL/min, 240 nm, 50/50 CH$_3$CN/0.1% H$_3$PO$_4$, 3.87 (98.06%); $^1$H NMR (DMSO-d$_6$) δ 2.02-2.09 (m, 1H), 2.47-2.63 (m, 2H), 2.84-2.96 (m, 1H), 3.62 (s, 2H), 4.46 (d, J=5.8 Hz, 2H), 5.15 (dd, J=12.9 Hz, J=5.4 Hz, 1H), 7.45 (d, J=8.4 Hz, 2H), 7.65-7.77 (m, 4H), 7.87 (d, J=7.5 Hz, 1H), 8.82 (t, J=5.8 Hz, 1H), 11.13 (s, 1H); $^{13}$C NMR (DMSO-d$_6$) δ 21.2, 30.1, 40.9, 41.3, 48.2, 119.9, 120.0, 121.1, 122.6, 128.8 (q, J=306 Hz), 129.0, 129.9, 130.8, 132.5, 135.3, 139.2, 146.5, 166.1, 166.2, 167.0, 171.9; Anal. Calcd for C$_{23}$H$_{18}$N$_3$O$_5$F$_3$S: C, 54.65; H, 3.59; N, 8.31. Found: C, 54.45; H, 3.73; N, 7.93.

5.43 4-tert-butyl-N-((2-(2,6-dioxopiperidin-3-yl)-1,3-dioxoisoindolin-5-yl)methyl)benzamide

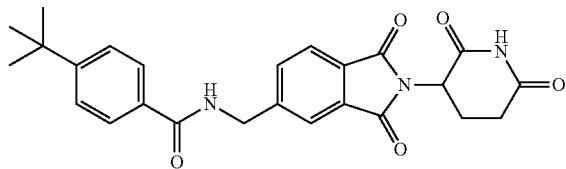 [SMILES: CC(C)(C)c1ccc(C(=O)NCc2ccc3c(c2)C(=O)N(C2CCC(=O)NC2=O)C3=O)cc1]

TEA was added to a mixture of 5-aminomethyl-2-(2,6-dioxo-piperidin-3-yl)-isoindole-1,3-dione hydrochloride (1.0 g, 3.1 mmol) and 4-(t-butyl)benzoyl chloride (0.61 g, 3.1 mmol) in acetonitrile (35 mL), and the resulting mixture was stirred at room temperature for 1 hour. The mixture was diluted with water (100 mL) and ethyl acetate (100 mL), and the organic phase separated and concentrated. The residue was chromatographed on silica gel using a hexanes-ethyl acetate gradient, eluting 1.1 g of the product at 80-90% ethyl acetate, in 80% yield as a white solid; mp 164-166° C.; HPLC, Waters Symmetry C-18, 3.9×150 mm, 5 μm, 1 mL/min, 240 nm, 50/50 CH$_3$CN/0.1% H$_3$PO$_4$, 4.26 (99.57%), $^1$H NMR (DMSO-d$_6$) δ 1.30 (s, 9H), 2.01-2.09 (m, 1H), 2.46-2.63 (m, 2H), 2.84-2.96 (m, 1H), 4.65 (d, J=6.0 Hz, 2H), 5.15 (dd, J=12.9 Hz, J=5.4 Hz, 1H), 7.49-7.52 (m, 2H), 7.79-7.91 (m, 5H), 9.16 (t, J=6.0 Hz, 1H), 11.13 (s, 1H); $^{13}$C NMR (DMSO-d$_6$) δ 22.0, 30.9, 34.6, 42.5, 49.0, 121.9, 123.5, 125.1, 127.1, 129.7, 131.1, 131.6, 133.3, 147.8, 154.3, 166.3, 167.0, 167.1, 169.8, 172.7; Anal. Calcd for C$_{25}$H$_{25}$N$_3$O$_5$.0.25H$_2$O: C, 66.43; H, 5.69; N, 9.30. Found: C, 66.49; H, 5.62; N, 8.96.

5.44 5-bromo-N-[[2-[(3S)-3-methyl-2,6-dioxopiperidin-3-yl]-1,3-dioxoisoindolin-5-yl]methyl]picolinamide

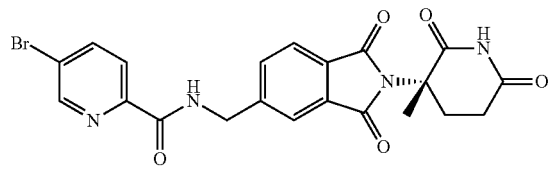 [SMILES: C[C@]1(N2C(=O)c3ccc(CNC(=O)c4ccc(Br)cn4)cc3C2=O)CCC(=O)NC1=O]

A mixture of 5-bromopicolinic acid (0.40 g, 2.0 mmol) and CDI (0.36 g, 2.2 mmol) in DMF (20 mL) was stirred under nitrogen at 40° C. for 2 hours. Then, 5-aminomethyl-2-[(3S)-3-methyl-2,6-dioxo-piperidin-3-yl]-isoindole-1,3-dione hydrochloride (0.67 g, 2.0 mmol) was added, and the mixture was stirred at this temperature for an additional 2 hours. The mixture was cooled to room temperature, and the solvent was evaporated under vacuum. The residue was dissolved in ethyl acetate (100 mL) and washed with saturated aqueous sodium bicarbonate solution (2×100 mL). The organic phase was evaporated. The residue was chromatographed on silica gel using methylene chloride as the mobile phase. A pale red solid was obtained; this material was triturated in 10 mL of acetonitrile for 16 hours. The solid was filtered and washed with an additional 7 mL of acetonitrile. The product was dried under vacuum, providing 0.55 g (57% yield) as a white solid; mp 260-262° C.; HPLC, Waters Symmetry C-18, 3.9×150 mm, 5 μm, 1 mL/min, 240 nm, 45/55 CH$_3$CN/0.1% H$_3$PO$_4$, 3.61 (96.62%); $^1$H NMR (DMSO-d$_6$) δ 1.88 (s, 3H), 2.00-2.08 (m, 1H), 2.49-2.62 (m, 2H), 2.65-2.73 (m, 1H), 4.62 (d, J=6.3 Hz, 2H), 7.76-7.82 (m, 3H), 7.97 (dd, J=8.4 Hz, J=0.6 Hz, 1H), 8.26 (dd, J=8.4 Hz, J=2.3 Hz, 1H), 8.81 (dd, J=2.3 Hz, J=0.6 Hz, 1H), 9.63 (t, J=6.3 Hz, 1H), 11.00 (s, 1H); $^{13}$C NMR (DMSO-d$_6$) δ 21.0, 28.5, 29.1, 42.4, 58.7, 121.8, 123.1, 123.5, 123.9, 129.6, 131.3, 133.6, 140.5, 147.1, 148.5, 149.3, 163.5, 167.7, 167.8, 172.0, 172.1; Anal. Calcd for C$_{21}$H$_{17}$BrN$_4$O$_5$: C, 51.97; H, 3.53; N, 11.55. Found: C, 52.05; H, 3.44; N, 11.39.

5.45 N-[[2-[(3S)-3-methyl-2,6-dioxopiperidin-3-yl]-1,3-dioxoisoindolin-5-yl]methyl]-4-(methylsulfonyl)benzamide

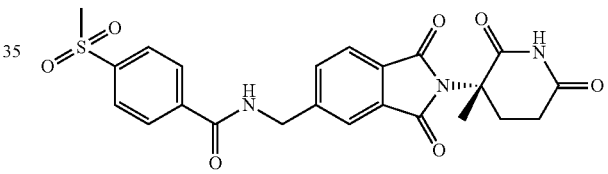

A mixture of 4-(methylsulfonyl)benzoic acid (0.40 g, 2.0 mmol) and CDI (0.36 g, 2.2 mmol) in DMF (20 mL) was stirred under nitrogen at 40° C. for 2 hours. Then, 5-aminomethyl-2-[(3S)-3-methyl-2,6-dioxo-piperidin-3-yl]-isoindole-1,3-dione hydrochloride (0.67 g, 2.0 mmol) was added, and stirring proceeded at this temperature for an additional 2 hours. The mixture was cooled to room temperature, and was partitioned between ethyl acetate (100 mL) and saturated aqueous sodium bicarbonate solution (100 mL). The organic phase was washed with saturated aqueous sodium bicarbonate solution (2×100 mL) and evaporated. The residue was chromatographed on silica gel using 99:1 methylene chloride-methanol as the mobile phase, providing 0.30 g, in 32% yield. The product was obtained as a white solid; mp 165.5-167.5° C.; HPLC, Waters Symmetry C-18, 3.9× 150 mm, 5 μm, 1 mL/min, 240 nm, 30/70 CH$_3$CN/0.1% H$_3$PO$_4$, 4.08 (96.23%); $^1$H NMR (DMSO-d$_6$) δ 2.09 (s, 3H), 2.22-2.28 (m, 1H), 2.73-2.95 (m, 3H), 3.47 (s, 3H), 4.86 (d, J=5.7 Hz, 2H), 7.98-8.04 (m, 3H), 8.25 (d, J=8.7 Hz, 2H), 8.32 (d, J=8.7 Hz, 2H), 9.58 (t, J=5.7 Hz, 1H), 11.21 (s, 1H); $^{13}$C NMR (DMSO-d$_6$) δ 23.0, 30.6, 31.1, 44.8, 45.6, 60.8, 123.7, 125.2, 129.2, 130.3, 131.7, 133.4, 135.5, 140.4, 145.2, 149.0, 167.2, 169.7, 169.9, 174.1, 174.2; Anal. Calcd for C$_{23}$H$_{21}$N$_3$O$_7$S+0.3H$_2$O: C, 56.50; H, 4.45; N, 8.59. Found: C, 56.61; H, 4.42; N, 8.30.

5.46 4-ethyl-N-[[2-[(3S)-3-methyl-2,6-dioxopiperidin-3-yl]-1,3-dioxoisoindolin-5-yl]methyl]benzamide

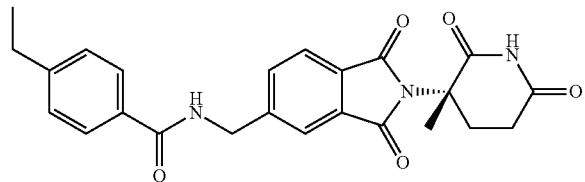 [SMILES: CCc1ccc(C(=O)NCc2ccc3c(c2)C(=O)N([C@@]2(C)CCC(=O)NC2=O)C3=O)cc1]

TEA (0.44 g, 4.4 mmol) was added to a mixture of 4-ethylbenzoyl chloride (0.34 g, 2.0 mmol) and 5-aminomethyl-2-[(3S)-3-methyl-2,6-dioxo-piperidin-3-yl]-isoindole-1,3-dione hydrochloride (0.67 g, 2.0 mmol) in acetonitrile (20 mL). The mixture was stirred at room temperature for 2 hours, and was evaporated under vacuum. The residue was partitioned between water (100 mL) and ethyl acetate (100 mL), and the organic phase was evaporated. The residue was chromatographed on silica gel using ethyl acetate as the mobile phase, providing 0.65 g, in 76% yield. The product was obtained as a white solid; mp 160-162° C.; HPLC, Waters Symmetry C-18, 3.9×150 mm, 5 μm, 1 mL/min, 240 nm, 45/55 CH$_3$CN/0.1% H$_3$PO$_4$, 4.20 (97.47%); $^1$H NMR (DMSO-d$_6$) δ 1.19 (t, J=7.7 Hz, 3H), 1.89 (s, 3H), 2.02-2.08 (m, 1H), 2.54-2.62 (m, 2H), 2.65-2.78 (m, 3H), 4.61 (d, J=6.0 Hz, 2H), 7.32 (d, J=8.1 Hz, 2H), 7.76-7.84 (m, 5H), 9.14 (t, J=6.0 Hz, 1H), 11.01 (s, 1H); $^{13}$C NMR (DMSO-d$_6$) δ 15.4, 21.1, 28.1, 28.6, 29.2, 42.6, 58.8, 121.6, 123.2, 127.4, 127.8, 129.6, 131.4, 131.5, 133.4, 147.6, 147.7, 166.4, 167.8, 167.9, 172.2, 172.3; Anal. Calcd for C$_{24}$H$_{23}$N$_3$O$_5$: C, 66.50; H, 5.35; N, 9.69. Found: C, 66.30; H, 5.26; N, 9.56.

5.47 N-[[2-[(3S)-3-methyl-2,6-dioxopiperidin-3-yl]-1,3-dioxoisoindolin-5-yl]methyl]-4-(trifluoromethylthio) benzamide

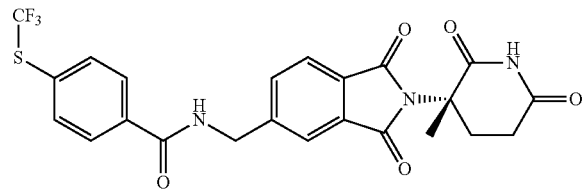 [SMILES: C[C@]1(N2C(=O)c3ccc(CNC(=O)c4ccc(SC(F)(F)F)cc4)cc3C2=O)CCC(=O)NC1=O]

TEA (0.44 g, 4.4 mmol) was added to a mixture of 4-(trifluoromethylthio)benzoyl chloride (0.48 g, 2.0 mmol) and 5-aminomethyl-2-[(3S)-3-methyl-2,6-dioxo-piperidin-3-yl]-isoindole-1,3-dione hydrochloride (0.67 g, 2.0 mmol) in acetonitrile (15 mL). The mixture was stirred at room temperature for 2 hours, and was evaporated under vacuum. The residue was partitioned between water (75 mL) and ethyl acetate (75 mL), and the organic phase was washed with water (2×75 mL) and evaporated. The residue was chromatographed on silica gel using ethyl acetate as the mobile phase, providing 0.62 g of the product, in 62% yield. The product was obtained as a white solid; mp 138-140° C.; HPLC, Waters Symmetry C-18, 3.9×150 mm, 5 μm, 1 mL/min, 240 nm, 50/50 CH$_3$CN/0.1% H$_3$PO$_4$, 4.77 (96.89%); $^1$H NMR (DMSO-d$_6$) δ 1.89 (s, 3H), 2.02-2.08 (m, 1H), 2.54-2.60 (m, 2H), 2.63-2.75 (m, 1H), 4.64 (d, J=6.0 Hz, 2H), 7.78-7.86 (m, 5H), 7.99-8.03 (m, 2H), 9.40 (t, J=6.0 Hz, 1H), 11.01 (s, 1H); $^{13}$C NMR (DMSO-d$_6$) δ 21.0, 28.5, 29.0, 42.7, 58.8, 121.7, 123.2, 126.5, 128.7, 129.5 (q, J=306), 129.7, 131.4, 133.4, 135.9, 136.5, 147.0, 165.4, 167.7, 167.8, 172.1, 172.2; Anal. Calcd for C$_{23}$H$_{18}$F$_3$N$_3$O$_5$S: C, 54.65; H, 3.59; N, 8.31. Found: C, 54.56; H, 3.36; N, 8.24.

5.48 N-[[2-(2,6-dioxopiperidin-3-yl)-1-oxoisoindolin-5-yl]methyl]-4-(trifluoromethylthio)benzamide

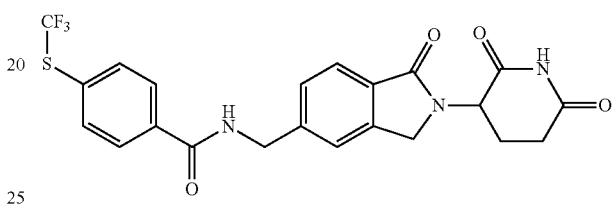

TEA (0.65 g, 6.4 mmol) was added to a mixture of 4-(trifluoromethylthio)benzoyl chloride (0.77 g, 3.2 mmol) and 3-(5-aminomethyl-1-oxo-1,3-dihydro-isoindol-2-yl)-piperidine-2,6-dione hydrochloride (1.0 g, 3.2 mmol) in DMF (25 mL). The mixture was stirred at room temperature for 1 hour, and was then diluted with water (40 mL) and stirred for 15 minutes. The precipitated solid was filtered and washed with additional water (40 mL). This material was stirred in 4% aqueous HCl (15 mL) and filtered, and the solid was washed with additional 4% aqueous HCl (15 mL) and water (15 mL). The solid was dried under vacuum, affording 0.90 g of the product as a cream-colored solid, in 59% yield; mp 203-205° C.; HPLC, Waters Symmetry C-18, 3.9×150 mm, 5 μm, 1 mL/min, 240 nm, 50/50 CH$_3$CN/0.1% H$_3$PO$_4$, 2.91 (96.41%); $^1$H NMR (DMSO-d$_6$) δ 1.96-2.03 (m, 1H), 2.31-2.45 (m, 1H), 2.54-2.63 (m, 1H), 2.85-2.98 (m, 1H), 4.31 (d, J=17.4 Hz, 1H), 4.45 (d, J=17.4 Hz, 1H), 4.61 (d, J=5.9 Hz, 2H), 5.11 (dd, J=13.2 Hz, J=5.1 Hz, 1H), 7.50 (d, J=7.8 Hz, 1H), 7.56 (s, 1H), 7.70 (d, J=7.8 Hz, 1H), 7.84 (d, J=8.1 Hz, 1H), 8.02 (d, J=8.1 Hz, 1H), 9.35 (t, J=5.9 Hz, 1H), 10.98 (s, 1H); $^{13}$C NMR (DMSO-d$_6$) δ 22.5, 31.2, 42.8, 47.1, 51.6, 122.1, 122.9, 126.3, 127.1, 128.7, 129.5 (q, J=306), 130.4, 135.9, 136.8, 142.4, 143.6, 165.3, 167.9, 171.0, 172.8; Anal. Calcd for C$_{22}$H$_{18}$F$_3$N$_3$O$_4$S+0.4H$_2$O: C, 54.52; H, 3.91; N, 8.65. Found: C, 54.51; H, 3.61; N, 8.64.

5.49 4-ethylsulfanyl-N-[[2-[(3S)-3-methyl-2,6-dioxopiperidin-3-yl]-1,3-dioxo-2,3-dihydro-1H-isoindol-5-ylmethyl]-benzamide

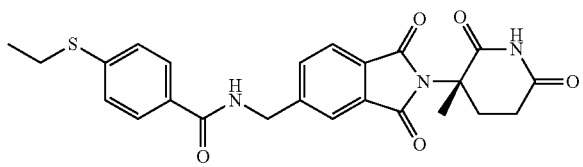 [SMILES: CCSc1ccc(C(=O)NCc2ccc3c(c2)C(=O)N([C@@]2(C)CCC(=O)NC2=O)C3=O)cc1]

A mixture of, 4-(ethylthio)benzoic acid (0.36 g, 2.0 mmol) and CDI (0.34 g, 2.1 mmol) in DMF (20 mL) was stirred at 40° C. under N$_2$ for 2 hours. Then, 5-aminomethyl-2-[(3S)-3-methyl-2,6-dioxo-piperidin-3yl]-isoindole-1,3-dione hydrochloride (0.67 g, 2.0 mmol) was added and stirring proceeded at 40° C. under N$_2$ for an additional 3 hours. The mixture was partitioned between ethyl acetate (75 mL) and saturated aqueous sodium bicarbonate (100 mL); the aqueous phase was extracted with ethyl acetate (75 mL). The combined organic phases were then washed with saturated aqueous sodium bicarbonate (3×100 mL), dried (MgSO$_4$), and evaporated. The residue was chromatographed (silica gel) using an ethyl acetate/hexanes gradient, providing 0.92 g of the product in 61% yield, as a white solid; mp 135-137° C.; HPLC, Waters Symmetry C-18, 3.9×150 mm, 5 µm, 1 ml/min, 240 nm, 50/50 CH$_3$CN/0.1% H$_3$PO$_4$, 4.03 (99.73%); $^1$H NMR (DMSO-d$_6$) δ 1.27 (t, 3H, J=7.3 Hz), 1.99 (s, 3H), 2.00-2.02 (m, 1H), 2.49-2.65 (m, 3H), 3.06 (q, 2H, J=7.25 Hz), 4.61 (d, 2H, J=6.0 Hz), 7.38 (dd, 2H, J=6.0 Hz, J=3.0 Hz), 7.76-7.85 (m, 5H), 9.17 (t, 1H, J=6.0 Hz), 11.01 (s, 1H); $^{13}$C NMR (DMSO-d$_6$) δ 13.9, 21.0, 25.2, 28.5, 29.1, 42.6, 58.7, 121.6, 123.2, 126.3, 127.8, 129.6, 130.4, 131.4, 133.4, 141.2, 147.5, 165.9, 167.7, 167.9, 172.1, 172.2. Anal. Calcd for C$_{24}$H$_{23}$N$_3$O$_5$S. 0.3H$_2$O: C, 61.21; H, 5.05; N, 8.92. Found: C, 61.27; H, 5.13; N, 8.80.

5.50 4-ethoxy-N-[[2-[(3S)-3-methyl-2,6-dioxopiperidin-3-yl]-1,3-dioxo-2,3-dihydro-1H-isoindol-5-ylmethyl]-benzamide

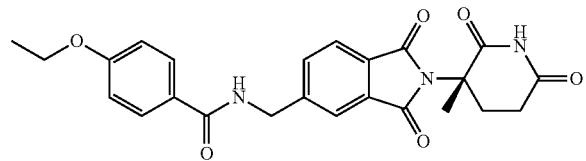

A mixture of 4-(ethoxy)benzoic acid (0.33 g, 2.0 mmol) and CDI (0.34 g, 2.1 mmol) in DMF (20 mL) was stirred at 40° C. under N$_2$ for 2 hours. Then, 5-aminomethyl-2-[(3S)-3-methyl-2,6-dioxo-piperidin-3yl]-isoindole-1,3-dione hydrochloride (0.67 g, 2.0 mmol) was added and stirring proceeded at 40° C. for an additional 2 hours. The reaction mixture was partitioned between ethyl acetate (75 mL) and saturated aqueous sodium bicarbonate (100 mL). The aqueous phase was extracted with ethyl acetate (75 mL). The combined organic phases were then washed with saturated aqueous sodium bicarbonate (3×100 mL), dried (MgSO$_4$), and evaporated. The residue was chromatographed (silica gel) using an ethyl acetate/hexanes gradient, providing 0.27 g of the product in 31% yield, as a white solid; mp 163-165° C.; HPLC, Waters Symmetry C-18, 3.9×150 mm, 5 µm, 1 ml/min, 240 nm, 40/60 CH$_3$CN/0.1% H$_3$PO$_4$, 5.73 (97.04%); $^1$H NMR (DMSO-d$_6$) δ 1.34 (t, 3H, J=6.0 Hz), 2.01 (s, 3H), 2.03-2.06 (m, 1H), 2.49-2.71 (m, 3H), 4.09 (q, 2H, J=7.0 Hz), 4.60 (d, 2H, J=6.0 Hz), 7.00 (d, 2H, J=9.0), 7.75-7.87 (m, 5H), 9.06 (t, 1H, J=6.0 Hz), 11.01 (s, 1H); $^{13}$C NMR (DMSO-d$_6$) δ 14.5, 21.0, 28.5, 29.1, 42.5, 58.7, 63.3, 114.0, 121.5, 123.1, 125.9, 129.1, 129.5, 131.4, 133.3, 147.7, 161.0, 165.9, 167.7, 167.9, 172.1, 172.2; Anal. Calcd for C$_{24}$H$_{23}$N$_3$O$_6$. 0.75H$_2$O: C, 62.26; H, 5.33; N, 9.08. Found: C, 62.25; H, 5.13; N, 9.17.

5.51 N-((2-(2,6-dioxopiperidin-3-yl)-1,3-dioxoisoindolin-5-yl)methyl)-5-(ethylthio)picolinamide

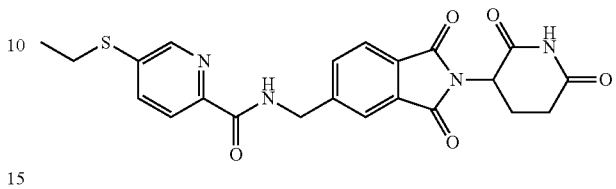

Step 1: A mixture of 2-chloro-5-nitropyridine (25.0 g, 158 mmol) and dimethyl malonate (21.9 g, 166 mmol) in DMF (150 mL) was cooled to 0° C., and sodium hydride (6.50 g of a 60% dispersion in mineral oil, 162 mmol) was added in small portions. The mixture was stirred at 0° C. for 1 hour following completion of the addition. Then, another equivalent of sodium hydride (6.5 g of a 60% dispersion in mineral oil, 162 mmol) was added in small portions. The reaction was quenched by the addition of acetic acid (10 mL), and the mixture was evaporated to dryness. The residue was triturated with diethyl ether (150 mL) overnight and filtered, providing crude dimethyl 2-(5-nitropyridin-2-yl)malonate as an orange solid.

Step 2: The crude product from Step 1 was slurried in 250 mL of water in an ice bath, and 10N NaOH (15 mL) was added. A hot solution of KMnO$_4$ (33.3 g, 210 mmol) in water (140 mL) and 10N NaOH (8 mL) was added via addition funnel Additional solid KMnO$_4$ (110 g, 690 mmol) was added portionwise along with 10N NaOH. Following completion of the addition, the mixture was heated to 95° C. for 90 minutes. Celite was added to the mixture, which was filtered while still hot, through a pad of Celite. The filter was washed with hot 2N NaOH (200 mL). The filtrate was cooled and adjusted to pH 3-4 with concentrated HCl. The solid precipitate was filtered and dried, providing 9.4 g of 5-nitropicolinic acid as a cream-colored solid, in 35% yield over 2 steps; $^1$H NMR (DMSO-d$_6$) δ 8.26 (dd, 1H, J=8.7 Hz, J=0.6 Hz), 8.74 (dd, 1H, J=8.7 Hz, J=2.7 Hz), 9.44 (dd, 1H, J=2.7 Hz, J=0.6 Hz), 13.92 (br, 1H).

Step 3: A suspension of 5-nitropicolinic acid (6.0 g, 36 mmol) in methanolic HCl (1.25 M) was heated to reflux and stirred for 16 hours. The mixture was cooled to ambient temperature. The product was filtered and rinsed with additional methanol (20 mL) and dried under vacuum, providing 6.1 g of methyl 5-nitropicolinate, in 94% yield; $^1$H NMR (DMSO-d$_6$) δ 3.95 (s, 3H), 8.29 (dd, 1H, J=8.4 Hz, J=0.6 Hz), 8.75 (dd, 1H, J=8.4 Hz, J=2.7 Hz), 9.46 (dd, 1H, J=2.7 Hz, J=0.6 Hz).

Step 4: Sodium ethanethiolate (1.6 g, 17.2 mmol) was added to a solution of methyl 5-nitropicolinate (2.8 g, 16 mmol) in DMF (30 mL), and the resulting mixture was stirred a room temperature. After 3 hours, acetic acid (1 mL) was added, and the mixture was evaporated to dryness. The residue was suspended in methanol (50 mL) and treated with 3N NaOH. The resulting mixture was stirred at room temperature for 16 hours and then evaporated. The residue was dissolved in water (100 mL), washed with ethyl acetate (2×100 mL), and acidified to pH 3-4 (conc. HCl), resulting in precipitation of the product. The precipitate was filtered, rinsed with water (100 mL) and dried under vacuum, providing 2.3 g of 5-(ethylthio)picolinic acid, in 79% yield; $^1$H NMR (DMSO-$d_6$) δ 1.23 (t, 3H, J=7.3 Hz), 3.14 (q, 2H, J=7.3 Hz), 7.86 (dd, 1H, J=8.4 Hz, J=2.4 Hz), 7.95 (dd, 1H, J=8.4 Hz, J=0.9 Hz), 8.57 (dd, 1H, J=2.4 Hz, J=0.9 Hz), 13.09 (br, 1H).

Step 5: CDI (0.44 g, 2.7 mmol) was added to a mixture of 5-(ethylthio)picolinic acid (0.48 g, 2.6 mmol) in DMF (20 mL), and the resulting mixture was stirred at 40° C. for 2 hours. Then, 5-aminomethyl-2-(2,6-dioxo-piperidin-3-yl)-isoindole-1,3-dione methanesulfonate (1.00 g, 2.6 mmol) was added, and stirring proceeded at 40° C. under $N_2$ for an additional 3 hours. The mixture was partitioned between ethyl acetate (75 mL) and saturated aqueous sodium bicarbonate (100 mL); the aqueous phase was extracted with ethyl acetate (75 mL). The combined organic phases were then washed with saturated aqueous sodium bicarbonate (3×100 mL), dried (MgSO$_4$) and evaporated. The residue was chromatographed (silica gel) using an ethyl acetate/hexanes gradient, providing 0.65 g of the product in 60% yield, as a white solid; mp 198-200° C.; HPLC, Waters Symmetry C-18, 3.9×150 mm, 5 μm, 1 ml/min, 240 nm, 40/60 CH$_3$CN/0.1% H$_3$PO$_4$, 7.53 (97.70%); $^1$H NMR (DMSO-$d_6$) δ 1.28 (t, 3H, J=7.3 Hz), 2.02-2.08 (m, 1H), 2.45-2.62 (m, 2H), 2.83-2.95 (m, 1H), 3.13 (q, 2H, J=7.3 Hz), 4.65 (d, 2H, J=6.3 Hz), 5.14 (dd, 1H, J=12.9 Hz, J=5.4 Hz), 7.83-7.95 (m, 5H), 8.54 (dd, 1H, J=2.3 Hz, J=0.8 Hz), 9.53 (t, 1H, J=6.3 Hz), 11.12 (s, 1H); $^{13}$C NMR (DMSO-$d_6$) δ 13.8, 22.0, 25.2, 30.9, 42.3, 49.0, 122.1, 122.2, 123.5, 129.8, 131.5, 133.5, 135.4, 138.0, 146.3, 146.4, 147.5, 164.1, 167.0, 167.1, 169.8, 172.7; Anal. Calcd for C$_{22}$H$_{20}$N$_4$O$_5$S: C, 58.40; H, 4.46; N, 12.38. Found: C, 58.27; H, 4.35; N, 12.30.

5.52 N-[2-(2,6-dioxo-piperidin-3-yl)-1-oxo-2,3-dihydro-1H-isoindol-5-ylmethyl]-6-trifluoromethyl-nicotinamide

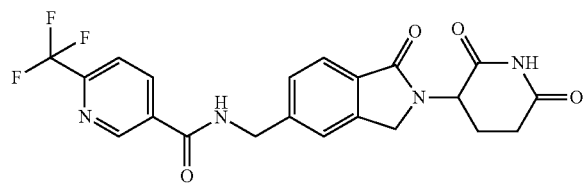 [SMILES: O=C1CCC(N2Cc3cc(CNC(=O)c4ccc(C(F)(F)F)nc4)ccc3C2=O)C(=O)N1]

To a stirred mixture of 3-(5-Aminomethyl-1-oxo-1,3-dihydro-isoindol-2-yl)-piperidine-2,6-dione hydrochloride (1.00 g, 3.20 mmol) and 6-trifluoromethylnicotinoyl chloride (0.65 g, 3.10 mmol) in N,N-dimethylformamide (25 mL), was added triethylamine (0.88 mL, 6.20 mmol) at room temperature under nitrogen. After 1 h, 1N aq. HCl (50 mL) was added and the mixture was stirred for 10 min. The mixture was neutralized with sat. aq. NaHCO$_3$. The product was isolated by filtration, washed with water (50 mL) and dried overnight in vacuo to give N-[2-(2,6-dioxo-piperidin-3-yl)-1-oxo-2,3-dihydro-1H-isoindol-5-ylmethyl]-6-trifluoromethyl-nicotinamide as a white solid (0.73 g, 51% yield): HPLC: Waters Symmetry C$_{18}$, 5 μm, 3.9×150 mm, 1 mL/min, 240 nm, 40/60 CH$_3$CN/0.1% H$_3$PO$_4$, 2.39 min (97.69%); mp: 240-242° C.; $^1$H NMR (DMSO-$d_6$) δ 1.92-2.12 (m, 1H), 2.29-2.44 (m, 1H), 2.54-2.70 (m, 1H), 2.81-3.09 (m, 1H), 4.32 (d, J=17.4 Hz, 1H), 4.45 (d, J=17.6 Hz, 1H), 4.65 (d, J=5.7 Hz, 2H), 5.11 (dd, J=5.0, 13.1 Hz, 1H), 7.51 (d, J=7.9 Hz, 1H), 7.59 (s, 1H), 7.71 (d, J=7.7 Hz, 1H), 8.07 (d, J=8.1 Hz, 1H), 8.40-8.60 (m, 1H), 9.22 (s, 1H), 9.56 (t, J=5.8 Hz, 1H), 10.98 (s, 1H); $^{13}$C NMR (DMSO-$d_6$) δ 22.49, 31.21, 42.87, 47.14, 51.60, 120.60 (q, J=2.9 Hz), 121.41 (q, J=272 Hz), 122.23, 123.00, 127.20, 130.54, 132.78, 137.49, 142.45, 143.13, 148.1 (q, J=34 Hz), 149.02, 163.74, 167.89, 170.98, 172.85; LCMS: MH=447; Anal Calcd for C$_{21}$H$_{17}$N$_4$O$_4$F$_3$+0.25H$_2$O: C, 55.94; H, 3.91; N, 12.43. Found: C, 55.97; H, 3.49; N, 12.28.

5.53 N-[2-(2,6-dioxo-piperidin-3-yl)-1-oxo-2,3-dihydro-1H-isoindol-5-ylmethyl]-3-trifluoromethyl-benzamide

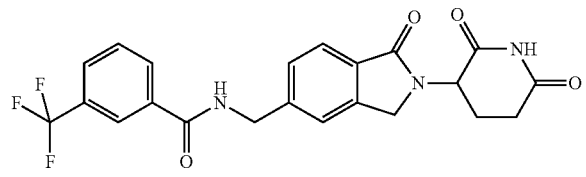 [SMILES: O=C1CCC(N2Cc3cc(CNC(=O)c4cccc(C(F)(F)F)c4)ccc3C2=O)C(=O)N1]

To a stirred mixture of 3-(5-Aminomethyl-1-oxo-1,3-dihydro-isoindol-2-yl)-piperidine-2,6-dione hydrochloride (1.00 g, 3.20 mmol) and 3-(trifluoromethyl)benzoyl chloride (0.67 g, 3.20 mmol) in N,N-dimethylformamide (25 mL), was added triethylamine (0.90 mL, 6.40 mmol) at room temperature under nitrogen. After 1 h, 1N aq. HCl (50 mL) was added and the mixture was stirred for 10 min. The product was isolated by filtration, washed with 1N aq. HCl (50 mL) and water (50 mL). The solids were dissolved in EtOAc (75 mL) and washed with water (75 mL). The organic layer was separated, dried (MgSO$_4$) and concentrated in vacuo to give N-[2-(2,6-dioxo-piperidin-3-yl)-1-oxo-2,3-dihydro-1H-isoindol-5-ylmethyl]-3-trifluoromethyl-benzamide as an off-white solid (0.95 g, 66% yield): HPLC: Waters Symmetry C$_{18}$, 5 μm, 3.9×150 mm, 1 mL/min, 240 nm, 40/60 CH$_3$CN/0.1% H$_3$PO$_4$, 3.69 min (98.71%); mp: 244-246° C.; $^1$H NMR (DMSO-$d_6$) δ 1.94-2.06 (m, 1H), 2.27-2.46 (m, 1H), 2.53-2.68 (m, 1H), 2.80-3.04 (m, 1H), 4.32 (d, J=17.4 Hz, 1H), 4.45 (d, J=17.4 Hz, 1H), 4.63 (d, J=5.9 Hz, 2H), 5.11 (dd, J=5.0, 13.3 Hz, 1H), 7.49 (d, J=7.7 Hz, 1H), 7.57 (s, 1H), 7.66-7.82 (m, 2H), 7.94 (d, J=7.7 Hz, 1H), 8.16-8.34 (m, 2H), 9.42 (t, J=5.8 Hz, 1H), 10.98 (s, 1H); $^{13}$C NMR (DMSO-$d_6$) δ 22.50, 31.19, 42.90, 47.14, 51.59, 122.21, 122.99, 123.86 (q, J=3.6 Hz), 123.90 (q, J=270 Hz), 127.18, 127.94 (q, J=3.5 Hz), 129.2 (q, J=32 Hz), 129.71, 130.47, 131.44, 134.97, 142.42, 143.50, 164.79, 167.91, 170.98, 172.85. LCMS: MH=446; Anal Calcd for C$_{22}$H$_{18}$N$_3$O$_4$F$_3$+0.6H$_2$O: C, 57.92; H, 4.24; N, 9.21. Found: C, 57.87; H, 4.08; N, 9.16.

5.54 N-[2-(2,6-dioxo-piperidin-3-yl)-1-oxo-2,3-dihydro-1H-isoindol-5-ylmethyl]-2-trifluoromethyl-benzamide

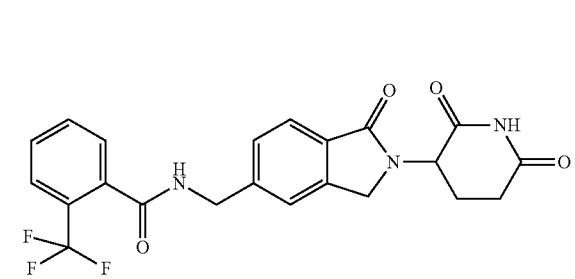 [SMILES: O=C1CCC(N2Cc3cc(CNC(=O)c4ccccc4C(F)(F)F)ccc3C2=O)C(=O)N1]

To a stirred mixture of 3-(5-Aminomethyl-1-oxo-1,3-dihydro-isoindol-2-yl)-piperidine-2,6-dione hydrochloride (1.00 g, 3.20 mmol) and 3-(trifluoromethyl)benzoyl chloride (0.67 g, 3.20 mmol) in N,N-dimethylformamide (25 mL), was added triethylamine (0.90 mL, 6.40 mmol) at room temperature under nitrogen. After 1 h, the solvent was removed in vacuo and the residue was dissolved in ethyl acetate (100 mL). The ethyl acetate layer was washed with 1N aq. HCl (2×100 mL) and water (100 mL), then dried (MgSO$_4$) and concentrated in vacuo to give N-[2-(2,6-dioxo-piperidin-3-yl)-1-oxo-2,3-dihydro-1H-isoindol-5-yl-methyl]-2-trifluoromethyl-benzamide as an off-white solid (0.61 g, 43% yield): HPLC: Waters Symmetry C$_{18}$, 5 μm, 3.9×150 mm, 1 mL/min, 240 nm, 30/70 CH$_3$CN/0.1% H$_3$PO$_4$, 4.89 min (97.35%); mp: 303-305° C.; $^1$H NMR (DMSO-d$_6$) δ 1.93-2.11 (m, 1H), 2.31-2.46 (m, 1H), 2.55-2.71 (m, 1H), 2.83-3.03 (m, 1H), 4.33 (d, J=17.4 Hz, 1H), 4.47 (d, J=17.4 Hz, 1H), 4.56 (d, J=5.9 Hz, 2H), 5.12 (dd, J=5.0, 13.1 Hz, 1H), 7.49 (d, J=7.7 Hz, 1H), 7.54-7.87 (m, 6H), 9.15 (t, J=5.9 Hz, 1H), 10.99 (s, 1H); $^{13}$C NMR (DMSO-d$_6$) δ 22.49, 31.21, 42.61, 47.13, 51.59, 122.14, 122.94, 123.61 (q, J=272 Hz), 125.94 (q, J=31.2 Hz), 126.25 (q, J=4.7 Hz), 127.13, 128.61, 129.82, 130.47, 132.48, 136.18, 142.38, 143.35, 167.16, 167.92, 171.03, 172.88; LCMS: MH=446; Anal Calcd for C$_{22}$H$_{18}$N$_3$O$_4$F$_3$+0.3H$_2$O: C, 58.62; H, 4.16; N, 9.32. Found: C, 58.60; H, 3.82; N, 9.20.

5.55 3,4-dichloro-N-[2-(3-methyl-2,6-dioxo-piperidin-3-yl)-1-oxo-2,3-dihydro-1H-isoindol-5-ylmethyl]-benzamide

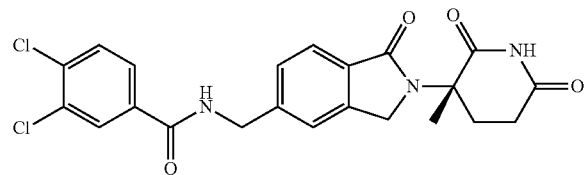 [SMILES: C[C@]1(N2Cc3cc(CNC(=O)c4ccc(Cl)c(Cl)c4)ccc3C2=O)CCC(=O)NC1=O]

Step 1: A stirred mixture of 4-bromo-2-bromomethyl-benzoic acid methyl ester (3.0 g, 10.0 mmol), 3-amino-3-methyl-piperidine-2,6-dione hydrobromide (2.2 g, 10.0 mmol) and triethylamine (2.0 g, 20 mmol) in N,N-dimethylformamide (10 mL) was heated to 90° C. under nitrogen. After 1 h, the mixture was cooled to rt and the solvent was removed in vacuo. The crude residue was purified by column chromatography (95:5 CH$_2$Cl$_2$: MeOH) providing 3-(5-bromo-1-oxo-1,3-dihydro-isoindol-2-yl)-3-methyl-piperidine-2,6-dione (2.0 g, 61% yield); $^1$H NMR (DMSO-d$_6$) δ 1.67 (s, 3H), 1.87-1.93 (m, 1H), 2.54-2.80 (m, 3H), 4.64 (d, J=17.9 Hz, 1H), 4.73 (d, J=17.9 Hz, 1H), 7.58 (d, J=8.1 Hz, 1H), 7.69 (dd, J=8.1, 1.5 Hz, 1H), 7.88 (d, J=1.5 Hz, 1H), 10.89 (s, 1H).

Step 2: A stirred mixture of 3-(5-bromo-1-oxo-1,3-dihydro-isoindol-2-yl)-3-methyl-piperidine-2,6-dione (1.40 g, 4.00 mmol), Zn(CN)$_2$ (0.28 g, 2.40 mmol), Pd$_2$(dba)$_3$ (0.07 g, 0.08 mmol) and dppf (0.09 g, 0.16 mmol) in deoxygenated N,N-dimethylformamide (30 mL) was heated to 130° C. under nitrogen. After 2 h, the solvent was removed in vacuo and the residue was triturated in water (30 mL) then ethyl acetate/hexanes (1:1, 30 mL). The product was isolated by filtration, washed with ethyl acetate/hexanes (1:1) and dried in vacuo providing 2-(3-methyl-2,6-dioxo-piperidin-3-yl)-1-oxo-2,3-dihydro-1H-isoindole-5-carbonitrile (1.2 g, 99% yield); $^1$H NMR (DMSO-d$_6$) δ 1.67 (s, 3H), 1.89-1.95 (m, 1H), 2.55-2.81 (m, 3H), 4.73 (d, J=18.2 Hz, 1H), 7.82 (d, J=7.8 Hz, 1H), 7.97 (d, J=7.8 Hz, 1H), 8.17 (s, 1H), 10.93 (s, 1H).

Step 3: A mixture of 2-(3-methyl-2,6-dioxo-piperidin-3-yl)-1-oxo-2,3-dihydro-1H-isoindole-5-carbonitrile (1.20 g, 4.00 mmol) and PtO$_2$ (0.4 g) in 5-6 N HCl in iPrOH was hydrogenated (55 psi, rt) for 24 h. The resulting mixture was diluted with water (30 mL) and filtered through celite. The celite was washed with water (30 mL) and the combined filtrates were concentrated in vacuo. The residue was triturated in acetonitrile (50 mL) and the product was isolated by filtration and dried in vacuo providing 3-(5-aminomethyl-1-oxo-1,3-dihydro-isoindol-2-yl)-3-methyl-piperidine-2,6-dione hydrochloride (1.2 g, 92% yield); $^1$H NMR (DMSO-d$_6$) δ 1.70 (s, 3H), 1.87-1.93 (m, 1H), 2.55-2.82 (m, 3H), 4.14 (s, 2H), 4.66 (d, J=17.7 Hz, 1H), 4.75 (d, J=17.7 Hz, 1H), 7.61-7.74 (m, 3H), 8.60 (br, 3H), 10.88 (s, 1H).

Step 4: To a stirred mixture of 3-(5-aminomethyl-1-oxo-1,3-dihydro-isoindol-2-yl)-piperidine-2,6-dione hydrochloride (0.4 g, 1.20 mmol) and 3,4-dichlorobenzoyl chloride (0.26 g, 1.20 mmol) in N,N-dimethylformamide (15 mL), was added triethylamine (0.34 mL, 2.40 mmol) at room temperature under nitrogen. After 2 h, the mixture was diluted with water (40 mL) and stirred for 1 h. The product was isolated by filtration, washed with water (50 mL) and dried in vacuo providing 3,4-dichloro-N-[2-(3-methyl-2,6-dioxo-piperidin-3-yl)-1-oxo-2,3-dihydro-1H-isoindol-5-yl-methyl]-benzamide as an off-white solid (0.44 g, 79% yield): HPLC: Waters Symmetry C$_{18}$, 5 μm, 3.9×150 mm, 1 mL/min, 240 nm, 45/55 CH$_3$CN/0.1% H$_3$PO$_4$, 3.46 min (96.23%); mp: 220-222° C.; $^1$H NMR (DMSO-d$_6$) δ 1.66 (s, 3H), 1.80-1.98 (m, 1H), 2.52-2.82 (m, 3H), 4.51-4.72 (m, 4H), 7.45 (d, J=7.7 Hz, 1H), 7.54 (s, 1H), 7.61 (d, J=7.7 Hz, 1H), 7.78 (d, J=8.3 Hz, 1H), 7.88 (d, J=7.7 Hz, 1H), 8.14 (s, 1H), 9.34 (t, J=5.2 Hz, 1H), 10.86 (br. s., 1H); $^{13}$C NMR (DMSO-d$_6$) δ 20.74, 27.81, 29.01, 42.89, 47.65, 57.12, 121.92, 122.59, 127.13, 127.61, 129.24, 130.76, 131.08, 131.31, 134.15, 134.49, 142.41, 143.28, 164.04, 166.97, 172.43, 173.53; LCMS: MH=460/462; Anal Calcd for C$_{22}$H$_{19}$Cl$_2$N$_3$O$_4$+1.15H$_2$O: C, 54.93; H, 4.46; N, 8.74. Found: C, 54.60; H, 4.07; N, 8.70.

5.56 N-[2-(3-methyl-2,6-dioxo-piperidin-3-yl)-1-oxo-2,3-dihydro-1H-isoindol-5-ylmethyl]-4-trifluoromethoxy-benzamide

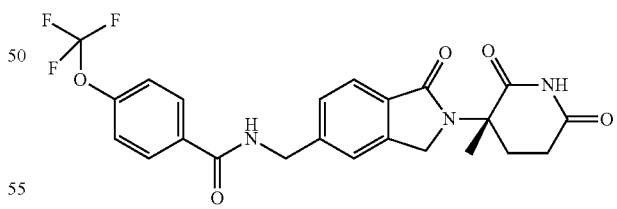

To a stirred mixture of 3-(5-aminomethyl-1-oxo-1,3-dihydro-isoindol-2-yl)-piperidine-2,6-dione hydrochloride (0.4 g, 1.20 mmol) and 4-(trifluoromethoxy)benzoyl chloride (0.27 g, 1.20 mmol) in N,N-dimethylformamide (15 mL), was added triethylamine (0.34 mL, 2.40 mmol) at room temperature under nitrogen. After 2 h, the mixture was diluted with water (60 mL) and stirred for 1 h. The product was isolated by filtration, washed with water (50 mL) and dried in vacuo providing N-[2-(3-methyl-2,6-dioxo-piperidin-3-yl)-1-oxo-2,3-dihydro-1H-isoindol-5-ylmethyl]-4-trifluoromethoxy-benzamide as an off-white solid (0.41 g, 71% yield): HPLC: Waters Symmetry $C_{18}$, 5 μm, 3.9×150 mm, 1 mL/min, 240 nm, 40/60 $CH_3CN/0.1\%$ $H_3PO_4$, 4.81 min (95.39%); mp: 224-226° C.; $^1H$ NMR (DMSO-$d_6$) δ 1.66 (s, 3H), 1.82-1.94 (m, 1H), 2.52-2.82 (m, 3H), 4.48-4.69 (m, 4H), 7.38-7.56 (m, 4H), 7.61 (d, J=7.9 Hz, 1H), 8.04 (d, J=8.7 Hz, 2H), 9.28 (t, J=5.5 Hz, 1H), 10.86 (s, 1H); $^{13}C$ NMR (DMSO-$d_6$) δ 20.74, 27.81, 29.01, 42.78, 47.64, 57.12, 119.9 (q, J=256 Hz), 120.68, 121.82, 122.58, 127.04, 129.60, 131.02, 133.36, 142.41, 143.57, 150.34, 165.06, 167.00, 172.44, 173.55; LCMS: MH=476; Anal Calcd for $C_{23}H_{20}F_3N_3O_5+0.7H_2O$: C, 56.61; H, 4.42; N, 8.61. Found: C, 56.60; H, 4.11; N, 8.61.

5.57 2-(4-chloro-phenyl)-N-[2-(3-methyl-2,6-dioxo-piperidin-3-yl)-1-oxo-2,3-dihydro-1H-isoindol-5-ylmethyl]-acetamide

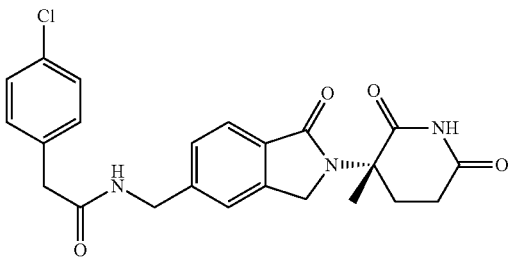 [SMILES: C[C@]1(N2Cc3cc(CNC(=O)Cc4ccc(Cl)cc4)ccc3C2=O)CCC(=O)NC1=O]

To a stirred mixture of 3-(5-aminomethyl-1-oxo-1,3-dihydro-isoindol-2-yl)-piperidine-2,6-dione hydrochloride (0.4 g, 1.20 mmol) and 4-chlorophenylacetyl chloride (0.23 g, 1.20 mmol) in N,N-dimethylformamide (15 mL), was added triethylamine (0.34 mL, 2.40 mmol) at room temperature under nitrogen. After 2 h, the mixture was diluted with water (10 mL) and the product was extracted with ethyl acetate (3×50 mL). The combined organic layers were washed with water (3×100 mL), dried ($MgSO_4$) and concentrated in vacuo. The residue was triturated in acetonitrile (20 mL) for 2 h. The solids were isolated by filtration and washed with acetonitrile (10 mL) providing 2-(4-chloro-phenyl)-N-[2-(3-methyl-2,6-dioxo-piperidin-3-yl)-1-oxo-2,3-dihydro-1H-isoindol-5-ylmethyl]-acetamide as a white solid (0.24 g, 44% yield): HPLC: Waters Symmetry $C_{18}$, 5 μm, 3.9×150 mm, 1 mL/min, 240 nm, 50/50 $CH_3CN/0.1\%$ $H_3PO_4$, 1.87 min (96.81%); mp: 230-232° C.; $^1H$ NMR (DMSO-$d_6$) δ 1.67 (s, 3H), 1.81-1.95 (m, 1H), 2.52-2.82 (m, 3H), 3.50 (s, 2H), 4.37 (d, J=5.9 Hz, 2H), 4.52-4.74 (m, 2H), 7.25-7.44 (m, 6H), 7.57 (d, J=7.7 Hz, 1H), 8.67 (t, J=5.8 Hz, 1H), 10.85 (s, 1H); $^{13}C$ NMR (DMSO-$d_6$) δ 20.75, 27.81, 29.01, 41.49, 42.24, 47.60, 57.12, 121.78, 122.55, 127.00, 128.15, 130.92, 130.98, 131.14, 135.28, 142.33, 143.59, 166.91, 169.87, 172.43, 173.55; Anal Calcd for $C_{23}H_{22}ClN_3O_4+0.3H_2O$: C, 62.04; H, 5.12; N, 9.44. Found: C, 61.98; H, 4.80; N, 9.17.

5.58 N-[2-(2,6-dioxo-piperidin-3-yl)-1-oxo-2,3-dihydro-1H-isoindol-5-ylmethyl]-benzamide

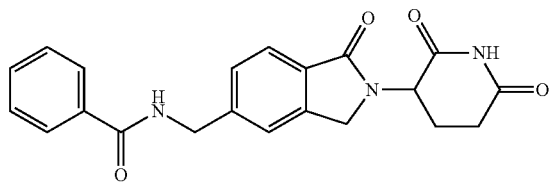 [SMILES: O=C1CCC(N2Cc3cc(CNC(=O)c4ccccc4)ccc3C2=O)C(=O)N1]

To a stirred mixture of 3-(5-aminomethyl-1-oxo-1,3-dihydro-isoindol-2-yl)-piperidine-2,6-dione methane sulfonate (0.50 g, 1.80 mmol) and benzoyl chloride (0.25 g, 1.80 mmol) in acetonitrile (20 mL), was added triethylamine (0.51 mL, 3.60 mmol) at room temperature under nitrogen. After 1 h, 1N aq. HCl (20 mL) was added and the mixture was stirred for 10 min. The product was isolated by filtration, washed with 1N aq. HCl (20 mL), acetonitrile (20 mL) and dried overnight in vacuo to give N-[2-(2,6-dioxo-piperidin-3-yl)-1-oxo-2,3-dihydro-1H-isoindol-5-ylmethyl]-benzamide as a white solid (0.43 g, 64% yield): HPLC: Waters Symmetry $C_{18}$, 5 μm, 3.9×150 mm, 1 mL/min, 240 nm, 30/70 $CH_3CN/0.1\%$ $H_3PO_4$, 3.17 min (99.25%); mp: 266-268° C.; $^1H$ NMR (DMSO-$d_6$) δ 1.93-2.06 (m, 1H), 2.27-2.47 (m, 1H), 2.53-2.68 (m, 1H), 2.79-3.05 (m, 1H), 4.31 (d, J=17.4 Hz, 1H), 4.45 (d, J=17.4 Hz, 1H), 4.60 (d, J=5.9 Hz, 2H), 5.11 (dd, J=5.0, 13.1 Hz, 1H), 7.42-7.62 (m, 5H), 7.70 (d, J=7.7 Hz, 1H), 7.91 (d, J=7.0 Hz, 2H), 9.16 (t, J=5.9 Hz, 1H), 10.99 (s, 1H); $^{13}C$ NMR (DMSO-$d_6$) δ 22.5, 31.2, 42.7, 47.1, 51.6, 122.1, 122.9, 127.1, 127.2, 128.3, 130.3, 131.3, 134.2, 142.4, 144.0, 166.3, 167.9, 171.0, 172.8; LCMS: MH=378; Anal Calcd for $C_{21}H_{19}N_3O_4$: C, 66.83; H, 5.07; N, 11.13. Found: C, 66.75; H, 5.08; N, 11.18.

5.59 N-[2-(2,6-dioxo-piperidin-3-yl)-1-oxo-2,3-dihydro-1H-isoindol-5-ylmethyl]-4-trifluoromethyl-benzamide

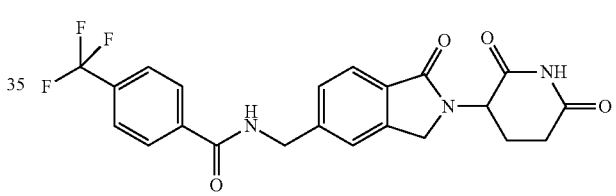

To a stirred mixture of 3-(5-Aminomethyl-1-oxo-1,3-dihydro-isoindol-2-yl)-piperidine-2,6-dione hydrochloride (1.00 g, 3.20 mmol) and 4-(trifluoromethyl)benzoyl chloride (0.67 g, 3.20 mmol) in N,N-dimethylformamide (25 mL), was added triethylamine (0.90 mL, 6.40 mmol) at room temperature under nitrogen. After 1 h, 1N aq. HCl (50 mL) was added and the mixture was stirred for 10 min. The product was isolated by filtration, washed with 1N aq. HCl (50 mL), ethyl acetate (50 mL) and dried overnight in vacuo to give N-[2-(2,6-dioxo-piperidin-3-yl)-1-oxo-2,3-dihydro-1H-isoindol-5-ylmethyl]-4-trifluoromethyl-benzamide as a white solid (0.70 g, 49% yield): HPLC: Waters Symmetry $C_{18}$, 5 μm, 3.9×150 mm, 1 mL/min, 240 nm, 40/60 $CH_3CN/0.1\%$ $H_3PO_4$, 3.75 min (95.6%); mp: 241-243° C.; $^1H$ NMR (DMSO-$d_6$) δ 1.92-2.14 (m, 1H), 2.29-2.48 (m, 1H), 2.54-2.67 (m, 1H), 2.80-3.04 (m, 1H), 4.31 (d, J=17.4 Hz, 1H), 4.45 (d, J=17.6 Hz, 1H), 4.62 (d, J=5.9 Hz, 2H), 5.11 (dd, J=5.1, 13.2 Hz, 1H), 7.49 (d, J=7.9 Hz, 1H), 7.56 (s, 1H), 7.71 (d, J=7.7 Hz, 1H), 7.88 (d, J=8.3 Hz, 2H), 8.11 (d, J=8.1 Hz, 2H), 9.39 (s, 1H), 10.99 (s, 1H); $^{13}C$ NMR (DMSO-$d_6$) δ 22.50, 31.19, 42.87, 47.13, 51.59, 122.15, 122.97, 123.90 (q, J=270 Hz), 125.38 (q, J=3.5 Hz), 127.13, 128.21, 130.47, 131.23 (q, J=31.6), 137.92, 142.42, 143.53, 165.14, 167.91, 170.98, 172.85; LCMS: MH=446; Anal Calcd for $C_{22}H_{18}N_3O_4F_3+0.35H_2O$: C, 58.50; H, 4.17; N, 9.30. Found: C, 58.55; H, 3.81; N, 9.18.

5.60 pyridine-2-carboxylic acid [2-(2,6-dioxo-piperidin-3-yl)-1-oxo-2,3-dihydro-1H-isoindol-5-ylmethyl]-amide

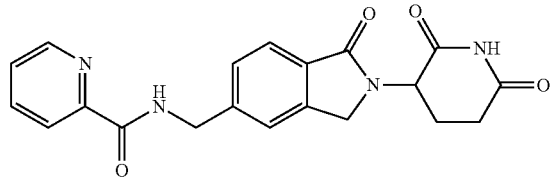 [SMILES: O=C1CCC(N2Cc3cc(CNC(=O)c4ccccn4)ccc3C2=O)C(=O)N1]

To a stirred mixture of 3-(5-Aminomethyl-1-oxo-1,3-dihydro-isoindol-2-yl)-piperidine-2,6-dione hydrochloride (0.50 g, 1.60 mmol) and picolinoyl chloride hydrochloride (0.29 g, 1.60 mmol) in N,N-dimethylformamide (20 mL), was added triethylamine (0.67 mL, 4.80 mmol) at room temperature under nitrogen. After 18 h, water (100 mL) was added and the product was extracted with $CH_2Cl_2$ (3×150 mL). The organic layers were combined, washed with water (3×150 mL), dried ($MgSO_4$) and concentrated in vacuo. The resulting residue was triturated in $Et_2O$ (50 mL) for 18 h. The product was isolated by filtration, washed with $Et_2O$ (25 mL) and dried in vacuo to give pyridine-2-carboxylic acid [2-(2,6-dioxo-piperidin-3-yl)-1-oxo-2,3-dihydro-1H-isoindol-5-ylmethyl]-amide as a white solid (0.31 g, 51% yield): HPLC: Waters Symmetry $C_{18}$, 5 μm, 3.9×150 mm, 1 mL/min, 240 nm, 20/80 $CH_3CN$/0.1% $H_3PO_4$, 5.52 min (97.80%); mp: 229-231° C.; $^1$H NMR (DMSO-$d_6$) δ 1.86-2.11 (m, 1H, CHH), 2.24-2.47 (m, 1H, CHH), 2.59 (d, J=17.0 Hz, 1H, CHH), 2.79-3.06 (m, 1H, CHH), 4.30 (d, J=17.4 Hz, 1H, CHH), 4.44 (d, J=17.4 Hz, 1H, CHH), 4.61 (d, J=6.4 Hz, 2H, $CH_2$), 5.10 (dd, J=4.9, 13.2 Hz, 1H, CH), 7.48 (d, J=7.7 Hz, 1H, Ar), 7.54 (s, 1H, Ar), 7.58-7.65 (m, 1H, Ar), 7.68 (d, J=7.9 Hz, 1H, Ar), 7.89-8.19 (m, 2H, Ar), 8.67 (d, J=4.5 Hz, 1H, Ar), 9.49 (t, J=6.3 Hz, 1H, NH), 10.98 (s, 1H, NH); $^{13}$C NMR (DMSO-$d_6$) δ 22.50, 31.19, 42.51, 47.11, 51.58, 122.02, 122.18, 122.93, 126.62, 127.20, 130.36, 137.81, 142.35, 143.82, 148.47, 149.89, 164.07, 167.92, 170.98, 172.85; LCMS: MH=379; Anal Calcd for $C_{20}H_{18}N_4O_4$+0.1$H_2O$: C, 63.18; H, 4.83; N, 14.74. Found: C, 62.80; H, 4.86; N, 14.69.

5.61 N-[2-(2,6-dioxo-piperidin-3-yl)-1-oxo-2,3-dihydro-1H-isoindol-5-ylmethyl]-2-(4-trifluoromethyl-phenyl)-acetamide

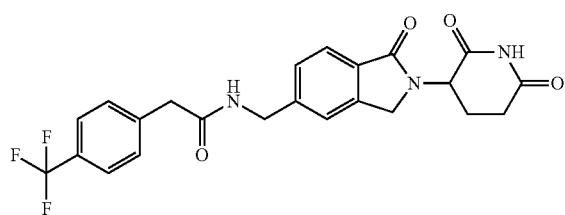 [SMILES: O=C(Cc1ccc(C(F)(F)F)cc1)NCc1ccc2c(c1)CN(C1CCC(=O)NC1=O)C2=O]

A mixture of (α, α, α-trifluoro-p-tolyl) acetic acid (0.33 g, 1.6 mmol) and CDI (0.27 g, 1.7 mmol) was stirred in DMF (20 ml) at 40° C. under $N_2$ for 2 hours. After 2 hours, 3-(5-(aminomethyl)-1-oxoisoindolin-2-yl)piperidine-2,6-dione hydrochloride (0.50 g, 1.6 mmol) was added. After 2 h, TEA (0.16 g, 1.6 mmol) was added to the mixture and stirring continued for 16 h at this temperature. Water (40 mL) was added, resulting in precipitation of the product. The solids were filtered, washed with water (50 mL) and dried in vacuo providing N-[2-(2,6-dioxo-piperidin-3-yl)-1-oxo-2,3-dihydro-1H-isoindol-5-ylmethyl]-2-(4-trifluoromethyl-phenyl)-acetamide as an off-white solid (0.22 g, 29% yield); mp 217-219° C.; HPLC, Waters Symmetry $C_{18}$, 5 μm, 3.9×150 mm, 1 ml/min, 240 nm, 40/60 $CH_3CN$/0.1% $H_3PO_4$, 3.95 (96.06%); $^1$H NMR (DMSO-d6) δ 1.98-2.02 (m, 1H), 2.32-2.46 (m, 1H), 2.57-2.63 (m, 1H), 2.86-2.98 (m, 1H), 3.63 (s, 2H), 4.25 (d, 1H, J=17.4), 4.31-4.45 (m, 3H), 5.11 (dd, 1H, J=13.2, J=5.1), 7.37-7.43 (m, 2H), 7.51 (d, 2H, J=7.8), 7.67-7.70 (m, 3H), 8.74 (t, 1H, J=5.7), 10.99 (s, 1H); $^{13}$C NMR (DMSO-$d_6$) δ 22.5, 31.2, 41.9, 42.3, 47.0, 51.6, 122.0, 122.9, 124.4 (q, J=269.3), 125.0 (q, J=3.75), 127.1, 127.2 (q, J=31.5), 129.9, 130.4, 141.1, 142.3, 143.6, 167.9, 169.5, 171.0, 172.9; LCMS: MH=460; Anal. Calcd for $C_{23}H_{20}F_3N_3O_4$+0.5 $CH_2Cl_2$: C, 56.24; H, 4.22; N, 8.37. Found: C, 56.10; H, 3.92; N, 8.50.

5.62 3-chloro-N-[2-(2,6-dioxo-piperidin-3-yl)-1-oxo-2,3-dihydro-1H-isoindol-5-ylmethyl]-4-methyl-benzamide

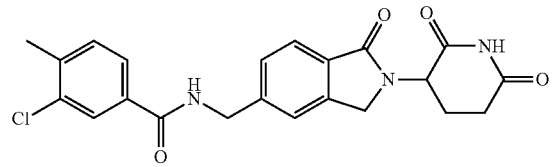 [SMILES: Cc1ccc(C(=O)NCc2ccc3c(c2)CN(C2CCC(=O)NC2=O)C3=O)cc1Cl]

A mixture of 3-chloro-4-methylbenzoic acid (0.17 g, 1.0 mmol) and CDI (0.17 g, 1.1 mmol) was stirred in DMF (20 mL) at 40° C. under $N_2$ for 4 hours. 3-(5-(Aminomethyl)-1-oxoisoindolin-2-yl)piperidine-2,6-dione hydrochloride (0.31 g, 1.0 mmol) was added and stirring continued for 1 h at this temperature. Water (40 mL) was added and the resulting precipitate was filtered, washed with 4% aqueous HCl (40 mL) and dried in vacuo providing 3-chloro-N-[2-(2,6-dioxo-piperidin-3-yl)-1-oxo-2,3-dihydro-1H-isoindol-5-ylmethyl]-4-methyl-benzamide as a white solid (0.28 g, 65% yield); mp 229-231° C.; HPLC, Waters Symmetry $C_{18}$, 5 μm, 3.9×150 mm, 1 ml/min, 240 nm, 40/60 $CH_3CN$/0.1% $H_3PO_4$, 4.29 (97.85%); $^1$H NMR (DMSO-$d_6$) δ 1.97-2.01 (m, 1H), 2.32-2.45 (m, 4H), 2.57-2.62 (m, 1H), 2.85-2.96 (m, 1H), 4.31 (d, 1H, J=17.4), 4.45 (d, 1H, J=17.4), 4.58 (d, 2H, J=6.0), 5.11 (dd, 1H, J=13.2, J=5.1), 7.47-7.49 (m, 2H), 7.54 (s, 1H), 7.70 (d, 1H, J=7.8), 7.79 (dd, 1H, J=7.8, J=1.5), 7.95 (d, 1H, J=1.5), 9.21 (t, 1H, J=5.7), 10.99 (s, 1H); $^{13}$C NMR (DMSO-$d_6$) δ 19.5, 22.5, 31.2, 42.8, 47.1, 51.6, 122.1, 122.9, 126.0, 127.1, 127.5, 130.4, 131.2, 133.3, 133.6, 138.9, 142.4, 143.7, 164.8, 167.9, 171.0, 172.9; LCMS: MH=426, 428; Anal. Calcd for $C_{22}H_{20}ClN_3O_4$+0.36 $CH_2Cl_2$: C, 58.84; H, 4.58; N, 9.21. Found: C, 58.49; H, 4.45; N, 8.91.

5.63 2-(3,4-dichloro-phenyl)-N-[2-(2,6-dioxo-piperidin-3-yl)-1-oxo-2,3-dihydro-1H-isoindol-5-ylmethyl]-acetamide

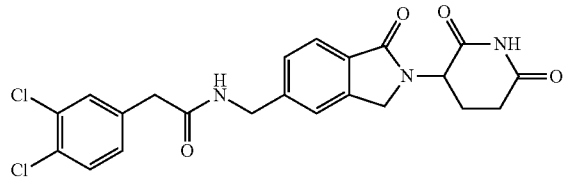 [SMILES: O=C(Cc1ccc(Cl)c(Cl)c1)NCc1ccc2c(c1)CN(C1CCC(=O)NC1=O)C2=O]

A mixture of 3,4-dichlorophenyl-acetic acid (0.31 g, 1.5 mmol) and CDI (0.26 g, 1.6 mmol) in DMF (20 mL) was stirred at 70° C. under N₂. After 4 h, 3-(5-(aminomethyl)-1-oxoisoindolin-2-yl)piperidine-2,6-dione hydrochloride (0.47 g, 1.5 mmol) was added. The mixture was cooled to 40° C. and was stirred at this temperature for an additional 16 h. Water (30 mL) was added resulting in precipitation of the product. The solid precipitate was filtered, washed with water (50 mL) and dried in vacuo providing 2-(3,4-dichlorophenyl)-N-[2-(2,6-dioxo-piperidin-3-yl)-1-oxo-2,3-dihydro-1H-isoindol-5-ylmethyl]-acetamide as a yellow solid (0.24 g, 34% yield); mp 191-193° C.; HPLC, Waters Symmetry C₁₈, 5 μm, 3.9×150 mm, 1 ml/min, 240 nm, 40/60 CH₃CN/0.1% H₃PO₄, 4.17 (98.19%); ¹H NMR (DMSO-d6) δ 1.98-2.02 (m, 1H), 2.32-2.45 (m, 1H), 2.57-2.73 (m, 1H), 2.86-2.98 (m, 1H), 3.54 (s, 2H), 4.45-5.14 (m, 4H), 5.11 (dd, 1H, J=13.2, J=5.1), 7.24 (dd, 1H, J=8.4, J=6.3), 7.29-7.47 (m, 2H), 7.48-7.59 (m, 2H), 7.67 (d, 1H, J=7.8), 8.72 (t, 1H, J=5.7), 10.99 (s, 1H); ¹³C NMR (DMSO-d₆) δ 22.5, 31.2, 41.0, 42.3, 47.1, 51.6, 122.1, 123.0, 127.1, 129.1, 129.5, 130.3, 130.4, 130.6, 131.1, 137.3, 142.3, 143.6, 168.0, 169.4, 170.9, 172.8; LCMS: MH=461,463; Anal. Calcd for C₂₂H₁₉Cl₂N₃O₄+0.5H₂O: C, 56.30; H, 4.30; N, 8.95. Found: C, 56.19; H, 3.91; N, 8.56.

5.64 N-[2-(2,6-dioxo-piperidin-3-yl)-1-oxo-2,3-dihydro-1H-isoindol-5-ylmethyl]-2-(4-trifluoromethylsulfanyl-phenyl)-acetamide

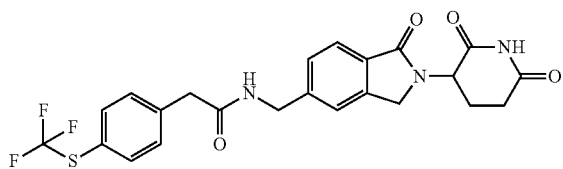 [SMILES: O=C(Cc1ccc(SC(F)(F)F)cc1)NCc1ccc2c(c1)CN(C1CCC(=O)NC1=O)C2=O]

A stirred mixture of 4-(trifluoromethylthio)phenylacetic acid (0.38 g, 1.6 mmol), and CDI-(0.27 g, 1.7 mmol) in DMF (20 ml) was heated at 40° C. for 2 hrs. Then, 3-(5-(aminomethyl)-1-oxoisoindolin-2-yl)piperidine-2,6-dione hydrochloride (0.5 g, 1.6 mmol) was added to the mixture and allowed to stir for 3 h. The mixture was quenched with 4% aqueous HCl (30 mL). The precipitate was filtered and washed with H₂O (50 mL) and dried in vacuo, providing N-[2-(2,6-dioxo-piperidin-3-yl)-1-oxo-2,3-dihydro-1H-isoindol-5-ylmethyl]-2-(4-trifluoromethylsulfanyl-phenyl)-acetamide as a white solid (0.36 g, 46% yield); mp 208-210° C.; HPLC: Waters Symmetry C₁₈, 5 μm, 3.9×150 mm, 1 ml/min, 240 nm, 40/60 CH₃CN/0.1% H₃PO₄, 6.30 (98.81%); ¹H NMR (DMSO-d₆) δ 1.97-2.03 (m, 1H), 2.36-2.44 (m, 1H), 2.58-2.63 (m, 1H), 2.86-2.98 (m, 1H), 3.60 (s, 2H), 4.28 (d, 1H, J=17.4), 4.38-4.45 (m, 3H), 5.11 (dd, 1H, J=13.2, J=5.1), 7.38 (d, 1H, J=8.1), 7.44-7.46 (m, 3H), 7.65-7.68 (m, 3H), 8.75 (t, 1H, J=5.7), 10.99 (s, 1H); ¹³C NMR (DMSO-d₆) δ 22.5, 31.2, 41.8, 42.3, 47.0, 51.5, 120.7 (q, J=1.9), 122.1, 122.9, 127.0, 129.6 (q, J=306), 130.4, 136.1, 140.2, 142.3, 143.6, 167.9, 169.5, 171.0, 172.9; LCMS: MH=492; Anal. Calcd for C₂₃H₂₀F₃N₃O₄S+0.15H₂O: C, 55.90; H, 4.14; N, 8.50. Found: C, 55.56; H, 4.09; N, 8.37.

5.65 4-chloro-N-[2-(2,6-dioxo-piperidin-3-yl)-1-oxo-2,3-dihydro-1H-isoindol-5-ylmethyl]-benzamide

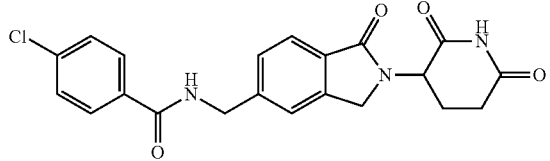 [SMILES: O=C1CCC(N2Cc3cc(CNC(=O)c4ccc(Cl)cc4)ccc3C2=O)C(=O)N1]

TEA (0.28 g, 2.8 mmol) was added to a mixture of 3-(5-aminomethyl-1-oxo-1,3-dihydro-isoindol-2-yl)-piperidine-2,6-dione methanesulfonate (0.5 g, 1.4 mmol) and 4-chlorobenzoyl chloride (0.25 g, 1.4 mmol) in DMF (30 mL) at 0° C. The mixture was stirred at 0° C. for 2 h, then, 4% aqueous HCl (30 mL) was added. The solid precipitate was filtered and dried in vacuo providing 4-chloro-N-[2-(2,6-dioxo-piperidin-3-yl)-1-oxo-2,3-dihydro-1H-isoindol-5-ylmethyl]-benzamide as a white solid (0.22 g, 40% yield); mp 278-280° C.; HPLC, Waters Symmetry C-18, 3.9×150 mm, 5 μm, 1 ml/min, 240 nm, 40/60 CH₃CN/0.1% H₃PO₄, 3.10 (95.66%); ¹H NMR (DMSO-d₆) δ 1.97-2.03 (m, 1H), 2.31-2.45 (m, 1H), 2.57-2.62 (m, 1H), 2.85-2.97 (m, 1H), 4.30 (d, 1H, J=17.3 Hz), 4.45 (d, 1H, J=17.3 Hz), 4.59 (d, 2H, J=5.7 Hz), 5.11 (dd, 1H, J=13.2 Hz, J=5.1 Hz), 7.47 (d, 1H, J=8.1 Hz), 7.54-7.58 (m, 3H), 7.70 (d, 1H, J=7.8 Hz), 7.91-7.96 (m, 2H), 9.23 (t, 1H, J=6.0 Hz). ¹³C NMR (DMSO-d₆) δ 22.5, 31.2, 42.8, 47.1, 51.6, 122.1, 122.9, 127.1, 128.4, 129.2, 130.4, 132.9, 136.1, 142.4, 143.7, 165.2, 167.9, 170.9, 172.8; LCMS: MH=412, 414; Anal. Calcd for C₂₁H₁₈ClN₃O₄+0.5 CH₂Cl₂: C, 56.84; H, 4.22; N, 9.25. Found: C, 56.79; H, 4.30; N, 9.33.

5.66 N-[2-(2,6-dioxo-piperidin-3-yl)-1-oxo-2,3-dihydro-1H-isoindol-5-ylmethyl]-4-fluoro-benzamide

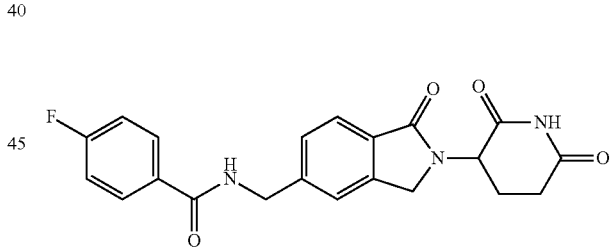

To a stirred mixture of 3-(5-aminomethyl-1-oxo-1,3-dihydro-isoindol-2-yl)-piperidine-2,6-dione hydrochloride (0.50 g, 1.60 mmol) and 4-fluorobenzoyl chloride (0.19 mL, 1.60 mmol) in N,N-dimethylformamide (10 mL), was added triethylamine (0.45 mL, 3.20 mmol) at room temperature under nitrogen. After 18 h, water (200 mL) was added and the solids were isolated by filtration. The crude product was triturated in 1 N aq. HCl (50 mL) for 2 h then in EtOAc (50 mL) for 18 h. The product was isolated by filtration, washed with EtOAc (25 mL) and dried in vacuo to give N-[2-(2,6-dioxo-piperidin-3-yl)-1-oxo-2,3-dihydro-1H-isoindol-5-ylmethyl]-4-fluoro-benzamide as a white solid (0.34 g, 53% yield): HPLC: Waters Symmetry C₁₈, 5 μm, 3.9×150 mm, 1 mL/min, 240 nm, 30/70 CH₃CN/0.1% H₃PO₄, 4.06 min (94.63%); mp: 295-297° C.; ¹H NMR (DMSO-d₆) δ 1.85-2.12 (m, 1H, CHH), 2.22-2.47 (m, 1H, CHH), 2.54-2.70 (m, 1H, CHH), 2.79-3.03 (m, 1H, CHH), 4.31 (d, J=17.4 Hz, 1H, CHH), 4.45 (d, J=17.4 Hz, 1H, CHH), 4.59 (d, J=5.7 Hz, 2H, CH$_2$), 5.11 (dd, J=5.1, 13.2 Hz, 1H, CH), 7.32 (t, J=8.9 Hz, 2H, Ar), 7.47 (d, J=7.7 Hz, 1H, Ar), 7.54 (s, 1H, Ar), 7.70 (d, J=7.7 Hz, 1H, Ar), 7.99 (dd, J=5.6, 8.8 Hz, 2H, Ar), 9.18 (t, J=5.9 Hz, 1H, NH), 10.98 (br. s., 1H, NH); $^{13}$C NMR (DMSO-d$_6$) δ 22.50, 31.21, 42.78, 47.13, 51.59, 115.26 (d, J=22.0 Hz), 122.08, 122.94, 127.08, 129.93 (d, J=8.8 Hz), 130.39, 130.64 (d, J=2.2 Hz), 142.39, 143.85, 163.93 (d, J=248.7 Hz), 165.22, 167.92, 170.98, 172.85; LCMS: MH=396; Anal Calcd for C$_{21}$H$_{18}$N$_3$O$_4$+0.1H$_2$O: C, 63.50; H, 4.62; N, 10.58. Found: C, 63.19; H, 4.54; N, 10.55.

5.67 N-[2-(2,6-dioxo-piperidin-3-yl)-1-oxo-2,3-dihydro-1H-isoindol-5-ylmethyl]-acetamide

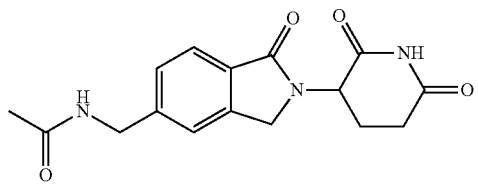 [SMILES: CC(=O)NCc1ccc2c(c1)CN(C1CCC(=O)NC1=O)C2=O]

To a stirred mixture of 3-(5-aminomethyl-1-oxo-1,3-dihydro-isoindol-2-yl)-piperidine-2,6-dione methane sulfonate (0.75 g, 2.0 mmol) and acetic anhydride (0.19 mL, 2.0 mmol) in acetonitrile (20 mL), was added triethylamine (0.56 mL, 4.0 mmol) at room temperature under nitrogen. After 1 h, the solids were isolated by filtration. The crude product was triturated in water (20 mL) for 1.0 h, then isolated by filtration and dried in vacuo to give N-[2-(2,6-dioxo-piperidin-3-yl)-1-oxo-2,3-dihydro-1H-isoindol-5-ylmethyl]-acetamide as a white solid (0.47 g, 75% yield): HPLC: Waters Symmetry C$_{18}$, 5 μm, 3.9×150 mm, 1 mL/min, 240 nm, 10/90 to 90/10 CH$_3$CN/0.1% H$_3$PO$_4$ gradient over 15 mins, 3.28 min (96.26%); mp: 183-185° C.; $^1$H NMR (DMSO-d$_6$) δ 1.89 (s, 3H, CH$_3$), 1.93-2.07 (m, 1H, CHH), 2.26-2.48 (m, 1H, CHH), 2.54-2.70 (m, 1H, CHH), 2.77-3.04 (m, 1H, CHH), 4.22-4.51 (m, 4H, CH$_2$, CH$_2$), 5.11 (dd, J=5.1, 13.2 Hz, 1H, CH), 7.39 (d, J=7.9 Hz, 1H, Ar), 7.47 (s, 1H, Ar), 7.68 (d, J=7.9 Hz, 1H, Ar), 8.45 (t, J=5.8 Hz, 1H, NH), 10.98 (s, 1H, NH); $^{13}$C NMR (DMSO-d$_6$) δ 22.49, 22.56, 31.21, 42.14, 47.10, 51.59, 122.08, 122.90, 127.05, 130.32, 142.36, 143.95, 167.93, 169.25, 171.00, 172.86; LCMS: MH=316; Anal Calcd for C$_{16}$H$_{17}$N$_3$O$_4$: C, 60.94; H, 5.43; N, 13.33. Found: C, 60.61; H, 5.31; N, 13.30.

5.68 2-chloro-N-[2,6-dioxo-piperidin-3yl)-1-oxo-2,3-dihydro-1H-isoindol-5-ylmethyl]-benzamide

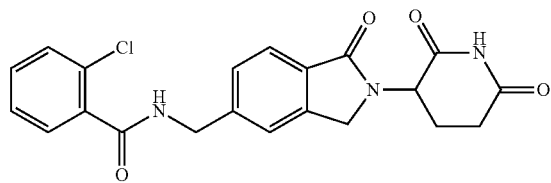 [SMILES: O=C1CCC(N2Cc3cc(CNC(=O)c4ccccc4Cl)ccc3C2=O)C(=O)N1]

TEA (0.28 g, 2.8 mmol) was added to a stirred mixture of 3-(5-aminomethyl-1-oxo-1,3-dihydro-isoindol-2-yl)-piperidine-2,6-dione methanesulfonate (0.50 g, 1.4 mmol) and chlorobenzoyl chloride (0.25 g, 1.4 mmol) in acetonitrile (30 ml) at 0° C. The mixture was stirred at 0° C. for 2 h, and then 4% aqueous HCl (30 ml) was added. The solid precipitate was filtered and dried in vacuo providing 2-chloro-N-[2,6-dioxo-piperidin-3yl)-1-oxo-2,3-dihydro-1H-isoindol-5-ylmethyl]-benzamide as a white solid, (0.33 g, 59% yield); mp 194-196° C.; HPLC, Waters Symmetry C-18, 3.9×150 mm, 5 μm, 1 ml/min, 240 nm, 30/70 CH$_3$CN/0.1% H$_3$PO$_4$, 3.33 (99.10%); $^1$H NMR (DMSO-d$_6$) δ 1.98-2.04 (m, 1H), 2.33-2.43 (m, 1H), 2.46-2.63 (m, 1H), 2.86-2.98 (m, 1H), 4.33 (d, 1H, J=17.4 Hz), 4.46 (d, 1H, J=17.4 Hz), 4.57 (d, 2H, J=6.0 Hz), 5.12 (dd, 1H, J=13.2 Hz, J=5.1 Hz), 7.38-7.53 (m, 5H), 7.58 (s, 1H), 7.71 (d, 1H, J=7.8 Hz), 9.09 (t, 1H, J=6.0 Hz), 10.99 (s, 1H); $^{13}$C NMR (DMSO-d$_6$) δ 22.5, 31.2, 40.3, 42.5, 47.1, 51.6, 122.1, 122.9, 127.1, 127.2, 128.9, 129.6, 130.4, 130.8, 136.7, 142.4, 143.4, 166.5, 167.9, 170.9, 172.9; LCMS: MH=412, 414; Anal. Calcd for C$_{21}$H$_{18}$ClN$_3$O$_4$+0.1H$_2$O: C, 60.98; H, 4.43; N, 10.16. Found: C, 60.76; H, 4.40; N, 10.11.

5.69 3-chloro-N-[2-(2,6-dioxo-piperidin-3yl)-1-oxo-2,3-dihydro-1H-isoindol-5-ylmethyl]-benzamide

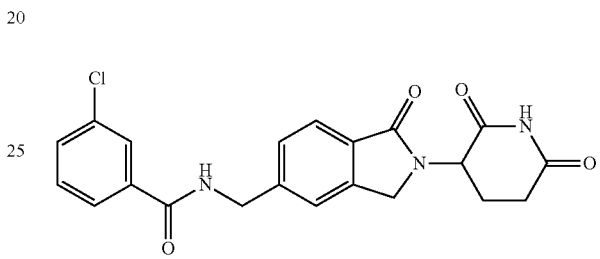

TEA (0.28 g, 2.8 mmol) was added to a mixture of 3-(5-aminomethyl-1-oxo-1,3-dihydro-isoindol-2-yl)-piperidine-2,6-dione methanesulfonate (0.50 g, 1.4 mmol) and 3-chlorobenzoyl chloride (0.25 g, 1.4 mmol) in acetonitrile (30 mL) at 0° C. The mixture was stirred at 0° C. for 2 h, then 4% aqueous HCl (30 mL) was added. The solid precipitate was filtered and dried in vacuo providing 3-chloro-N-[2-(2,6-dioxo-piperidin-3yl)-1-oxo-2,3-dihydro-1H-isoindol-5-ylmethyl]-benzamide as a white solid (0.49 g, 88% yield); mp 293-295° C.; HPLC, Waters Symmetry C-18, 3.9×150 mm, 5 μm, 1 ml/min, 240 nm, 40/60 CH$_3$CN/0.1% H$_3$PO$_4$, 3.50 (98.62%); $^1$H NMR (DMSO-d$_6$) δ 1.96-2.03 (m, 1H), 2.31-2.45 (m, 1H), 2.57-2.63 (m, 1H), 2.85-2.98 (m, 1H), 4.31 (d, 1H, J=17.4 Hz), 4.45 (d, 1H, J=17.4 Hz), 4.60 (d, 2H, J=6.0 Hz), 5.11 (dd, 1H, J=13.2 Hz, J=5.1 Hz), 7.46-7.50 (m, 1H), 7.53-7.55 (m, 2H), 7.61-7.65 (m, 1H), 7.70 (d, 1H, J=7.8 Hz), 7.85-7.89 (m, 1H), 7.95 (t, 1H, J=1.7 Hz), 9.27 (t, 1H, J=6.0 Hz), 10.98 (s, 1H); $^{13}$C NMR (DMSO-d$_6$) δ 22.5, 31.2, 42.8, 47.1, 51.6, 122.1, 122.9, 126.0, 127.1, 127.2, 130.4, 130.5, 131.2, 133.2, 136.1, 142.2, 143.6, 164.9, 167.9, 170.9, 172.8; LCMS: MH=412, 414; Anal. Calcd for C$_{21}$H$_{18}$ClN$_3$O$_4$+0.1H$_2$O: C, 60.98; H, 4.43; N, 10.16. Found: C, 60.71; H, 4.36; N, 10.30.

5.70 N-[2-(2,6-dioxo-piperidin-3-yl)-1-oxo-2,3-dihydro-1H-isoindol-5-ylmethyl]-4-methanesulfonyl-benzamide

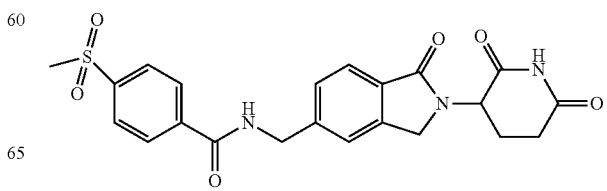

A mixture of 4-methylsulphonylbenzoic acid (0.28 g, 1.4 mmol) and CDI (0.24 g, 1.5 mmol) was stirred in DMF (30 mL) at 40° C. for 4 hours. 3-(5-Aminomethyl-1-oxo-1,3-dihydro-isoindol-2-yl)-piperidine-2,6-dione methanesulfonate (0.50 g, 1.4 mmol) was added and the mixture was stirred at 40° C. for 2 h. The mixture was quenched with 4% aqueous HCl (30 mL) and the resulting precipitate was filtered, washed with water (30 mL) and dried in vacuo providing N-[2-(2,6-dioxo-piperidin-3-yl)-1-oxo-2,3-dihydro-1H-isoindol-5-ylmethyl]-4-methanesulfonyl-benzamide as a white solid, (0.44 g, 71% yield); mp 260-262° C.; HPLC, Waters Symmetry C-18, 3.9×150 mm, 5 µm, 1 ml/min, 240 nm, 50/50 CH$_3$CN/0.1% H$_3$PO$_4$, 4.08 (98.31%); $^1$H NMR (DMSO-d$_6$) δ 1.96-2.03 (m, 1H), 2.31-2.46 (m, 1H), 2.57-2.63 (m, 1H), 2.86-2.98 (m, 1H), 3.27 (s, 3H), 4.31 (d, 1H, J=17.4 Hz), 4.45 (d, 1H, J=17.4 Hz), 4.63 (d, 2H, J=5.7 Hz), 5.11 (dd, 1H, J=13.2 Hz, J=4.8 Hz), 7.48 (d, 1H, J=8.1 Hz), 7.56 (s, 1H), 7.71 (d, 1H, J=7.8 Hz), 8.05 (d, 2H, J=8.4 Hz), 8.14 (d, 2H, J=8.4 Hz), 9.42 (t, 1H, J=6.0 Hz), 10.99 (s, 1H). $^{13}$C NMR (DMSO-d$_6$) δ 22.5, 31.2, 42.9, 43.3, 47.1, 51.6, 122.1, 123.0, 127.1, 128.3, 130.4, 138.6, 142.4, 143.0, 143.5, 165.0, 167.9, 171.0, 172.8; LCMS: MH=456; Anal. Calcd for C$_{22}$H$_{21}$N$_3$O$_6$S: C, 58.01; H, 4.65; N, 9.23. Found: C, 58.15; H, 4.52; N, 9.04.

5.71 N-[2-(2,6-dioxo-piperidin-3-yl)-1-oxo-2,3-dihydro-1H-isoindol-5-ylmethyl]-4-ethylsulfanyl-benzamide

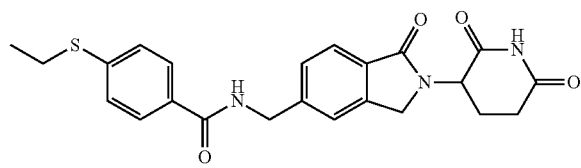 [SMILES: CCSc1ccc(C(=O)NCc2ccc3c(c2)CN(C2CCC(=O)NC2=O)C3=O)cc1]

A mixture of 4-(ethylthio) benzoic acid (0.26 g, 1.4 mmol) and CDI (0.24 g, 1.5 mmol) in DMF (30 ml) was stirred at 40° C. for 4 hours. 3-(5-Aminomethyl-1-oxo-1,3-dihydro-isoindol-2-yl)-piperidine-2,6-dione methanesulfonate (0.50 g, 1.4 mmol) was added and the mixture was stirred at 40° C. for 2 h. 4% Aqueous HCl (30 mL) was added and the resulting precipitate was filtered, washed with water (30 mL) and dried in vacuo providing N-[2-(2,6-dioxo-piperidin-3-yl)-1-oxo-2,3-dihydro-1H-isoindol-5-ylmethyl]-4-ethylsulfanyl-benzamide as a white solid, (0.39 g, 66% yield); mp 217-219° C.; HPLC, Waters Symmetry C-18, 3.9×150 mm, 5 µm, 1 ml/min, 240 nm, 35/65 CH$_3$CN/0.1% H$_3$PO$_4$, 5.75 (99.03%); $^1$H NMR (DMSO-d$_6$) δ 1.26 (t, 3H, J=7.2 Hz), 1.97-2.01 (m, 1H), 2.03-2.45 (m, 1H), 2.57-2.62 (m, 1H), 2.85-2.97 (m, 1H), 3.05 (q, 2H, J=7.2 Hz), 4.30 (d, 1H, J=17.4 Hz), 4.44 (d, 1H, J=17.4 Hz), 4.58 (d, 1H, J=7.8 Hz), 5.11 (dd, 1H, J=13.2 Hz, J=5.1 Hz), 7.37 (d, 2H, J=8.4 Hz), 7.46 (d, 1H, J=7.8 Hz), 7.53 (s, 1H), 7.69 (d, 1H, J=7.8 Hz), 7.85 (d, 2H, J=8.7 Hz), 9.12 (t, 1H, J=5.7 Hz), 10.99 (s, 1H); $^{13}$C NMR (DMSO-d$_6$) δ 13.9, 22.5, 25.2, 31.2, 42.7, 47.1, 51.5, 122.0, 122.9, 126.3, 127.0, 127.8, 130.3, 130.6, 140.9, 142.3, 143.9, 165.7, 167.9, 170.9, 172.8; LCMS: MH=438; Anal. Calcd for C$_{23}$H$_{23}$N$_3$O$_4$S: C, 62.37; H, 5.37; N, 9.49. Found: C, 62.30; H, 5.29; N, 9.60.

5.72 N-[2-(2,6-dioxo-piperidin-3-yl)-1-oxo-2,3-dihydro-1H-isoindol-5-ylmethyl]-4-ethanesulfonyl-benzamide

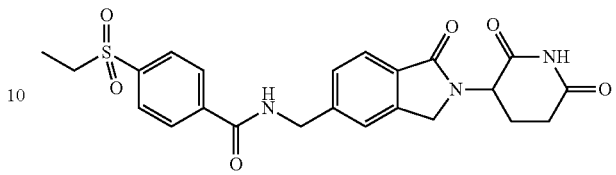

A mixture of 4-(ethylsulfonyl) benzoic acid (0.30 g, 1.4 mmol) and CDI (0.24 g, 1.5 mmol) in DMF (30 ml) was stirred at 40° C. for 4 hours. 3-(5-Aminomethyl-1-oxo-1,3-dihydro-isoindol-2-yl)-piperidine-2,6-dione methanesulfonate (0.50 g, 1.4 mmol) was added and the mixture was stirred at 40° C. for 2 h. 4% Aqueous HCl (30 mL) was added and the resulting precipitate was filtered, washed with water (30 mL) and dried in vacuo providing N-[2-(2,6-dioxo-piperidin-3-yl)-1-oxo-2,3-dihydro-1H-isoindol-5-ylmethyl]-4-ethanesulfonyl-benzamide as a white solid, (0.39 g, 66% yield); mp 222-224° C.; HPLC, Waters Symmetry C-18, 3.9×150 mm, 5 µm, 1 ml/min, 240 nm, 20/80 CH$_3$CN/0.1% H$_3$PO$_4$, 6.39 (98.78%); $^1$H NMR (DMSO-d$_6$) δ 1.11 (t, J=7.3 Hz, 3H, CH$_3$), 1.92-2.09 (m, 1H, CHH), 2.28-2.46 (m, 1H, CHH), 2.54-2.67 (m, 1H, CHH), 2.82-3.02 (m, 1H, CHH), 3.37 (q, 2H, CH$_2$), 4.31 (d, 1H, CHH), 4.42 (d, 1H, CHH), 4.62 (d, J=5.3 Hz, 2H, CHH), 5.11 (dd, J=4.8, 13.1 Hz, 1H, CH), 7.48 (d, 1H, Ar), 7.57 (s, 1H, Ar), 7.71 (d, 1H, Ar), 8.02 (s, 2H, Ar), 8.15 (d, J=8.1 Hz, 2H, Ar), 9.45 (t, 1H, NH), 10.96 (s, 1H, NH); $^{13}$C NMR (DMSO-d$_6$) δ 7.05, 22.49, 31.20, 42.89, 47.13, 49.01, 51.58, 122.15, 122.97, 127.13, 127.94, 128.31, 130.46, 138.75, 140.71, 142.42, 143.45, 165.06, 167.89, 170.98, 172.85; LCMS: MH=470; Anal. Calcd for C$_{23}$H$_{23}$N$_3$O$_6$S+0.3 CH$_2$Cl$_2$: C, 56.54; H, 4.81; N, 8.49. Found: C, 56.51; H, 4.90; N, 8.84.

5.73 6-ethoxy-pyridazine-3-carboxylic acid [2-(2,6-dioxo-piperidin-3-yl)-1-oxo-2,3-dihydro-1H-isoindol-5-ylmethyl]-amide

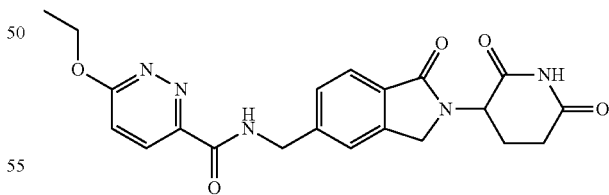

A stirred mixture of 6-ethoxy-pyridazine-3-carboxylic acid (0.23 g, 1.40 mmol) and CDI (0.24 g, 1.50 mmol) in N,N-dimethylformamide (10 mL) was heated to 40° C. under nitrogen. After 1 h, 3-(5-aminomethyl-1-oxo-1,3-dihydro-isoindol-2-yl)-piperidine-2,6-dione methane sulfonate (0.5 g, 1.40 mmol) was added and the mixture was heated at 50° C. for 1.5 h. Water (20 mL) was added and the solids were isolated by filtration. The product was triturated in EtOAc (20 mL) for 18 h, then filtered and dried in vacuo to give 6-ethoxy-pyridazine-3-carboxylic acid [2-(2,6-dioxo-piperidin-3-yl)-1-oxo-2,3-dihydro-1H-isoindol-5-ylmethyl]-amide as a white solid (0.48 g, 84% yield): HPLC: Waters Symmetry $C_{18}$, 5 μm, 3.9×150 mm, 1 mL/min, 240 nm, 10/90 to 90/10 $CH_3CN/0.1\%$ $H_3PO_4$ gradient over 15 mins, 7.15 min (97.48%); mp: 243-245° C.; $^1H$ NMR (DMSO-$d_6$) δ 1.41 (t, J=7.0 Hz, 3H, $CH_3$), 1.86-2.11 (m, 1H, CHH), 2.24-2.47 (m, 1H, CHH), 2.59 (d, J=16.8 Hz, 1H, CHH), 2.79-3.04 (m, 1H, CHH), 4.30 (d, J=17.4 Hz, 1H, CHH), 4.44 (d, J=17.4 Hz, 1H, CHH), 4.51-4.76 (m, 4H, $CH_2$, $CH_2$), 5.10 (dd, J=4.9, 13.2 Hz, 1H, CH), 7.35 (d, J=9.3 Hz, 1H, Ar), 7.49 (d, J=7.9 Hz, 1H, Ar), 7.56 (s, 1H, Ar), 7.69 (d, J=7.7 Hz, 1H, Ar), 8.09 (d, J=9.1 Hz, 1H, Ar), 9.73 (t, J=6.2 Hz, 1H, NH), 10.98 (s, 1H, NH); $^{13}C$ NMR (DMSO-$d_6$) δ 14.28, 22.49, 31.18, 42.52, 47.10, 51.56, 63.44, 117.87, 122.14, 122.91, 127.15, 128.80, 130.38, 142.33, 143.63, 149.23, 162.74, 165.80, 167.90, 170.98, 172.85; LCMS: MH=424; Anal Calcd for $C_{21}H_{21}N_5O_5$: C, 59.57; H, 5.00; N, 16.54. Found: C, 59.26; H, 4.95; N, 16.53.

5.74 N-[2-(2,6-dioxo-piperidin-3-yl)-1-oxo-2,3-dihydro-1H-isoindol-5-ylmethyl]-6-ethoxy-nicotinamide

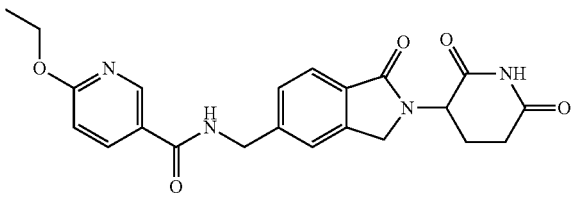 [SMILES: CCOc1ccc(C(=O)NCc2ccc3c(c2)CN(C2CCC(=O)NC2=O)C3=O)cn1]

A stirred mixture of 6-ethoxy-nicotinic acid (0.23 g, 1.40 mmol) and CDI (0.24 g, 1.50 mmol) in N,N-dimethylformamide (10 mL) was heated to 40° C. under nitrogen. After 1 h, 3-(5-aminomethyl-1-oxo-1,3-dihydro-isoindol-2-yl)-piperidine-2,6-dione methane sulfonate (0.5 g, 1.40 mmol) was added and the mixture was heated at 50° C. for 1.5 h. The mixture was cooled to rt and water (20 mL) was added. The solids were isolated by filtration and then triturated in EtOAc (20 mL) for 18 h. The product was filtered and dried in vacuo to give 6-ethoxy-pyridazine-3-carboxylic acid N-[2-(2,6-dioxo-piperidin-3-yl)-1-oxo-2,3-dihydro-1H-isoindol-5-ylmethyl]-6-ethoxy-nicotinamide as a white solid (0.30 g, 53% yield): HPLC: Waters Symmetry $C_{18}$, 5 μm, 3.9×150 mm, 1 mL/min, 240 nm, 10/90 to 90/10 $CH_3CN/0.1\%$ $H_3PO_4$ gradient over 15 mins, 7.12 min (95.33%); mp: 255-257° C.; $^1H$ NMR (DMSO-$d_6$) δ 1.33 (t, J=7.1 Hz, 3H, $CH_3$), 1.84-2.14 (m, 1H, CHH), 2.27-2.47 (m, 1H, CHH), 2.60 (d, J=16.8 Hz, 1H, CHH), 2.80-3.09 (m, 1H, CHH), 4.21-4.52 (m, 4H, $CH_2$, $CH_2$), 4.59 (d, J=5.9 Hz, 2H, $CH_2$), 5.11 (dd, J=5.1, 13.2 Hz, 1H, CH), 6.88 (d, J=8.7 Hz, 1H, Ar), 7.47 (d, J=7.9 Hz, 1H, Ar), 7.55 (s, 1H, Ar), 7.70 (d, J=7.7 Hz, 1H, Ar), 8.16 (dd, J=2.5, 8.7 Hz, 1H, Ar), 8.71 (d, J=2.3 Hz, 1H, Ar), 9.14 (t, J=5.9 Hz, 1H, NH), 10.98 (s, 1H, NH); $^{13}C$ NMR (DMSO-$d_6$) δ 14.40, 22.49, 31.20, 42.60, 47.12, 51.58, 61.80, 110.19, 122.07, 122.94, 123.26, 127.07, 130.39, 138.18, 142.40, 143.80, 147.10, 164.61, 164.91, 167.92, 170.98, 172.85; LCMS: MH=423; Anal Calcd for $C_{22}H_{22}N_4O_5$: C, 62.55; H, 5.25; N, 13.26. Found: C, 62.24; H, 5.19; N, 13.15.

5.75 N-[2-(2,6-dioxo-piperidin-3-yl)-1-oxo-2,3-dihydro-1H-isoindol-5-ylmethyl]-4-ethoxy-benzamide

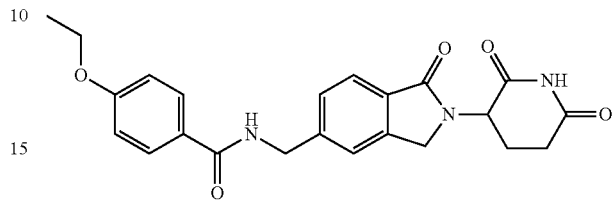

To a stirred mixture of 3-(5-aminomethyl-1-oxo-1,3-dihydro-isoindol-2-yl)-piperidine-2,6-dione methanesulfonate (0.50 g, 1.4 mmol) and 4-ethoxybenzoyl chloride (0.26 g, 1.4 mmol) in acetonitrile (30 mL) at 0° C. was added TEA (0.28 g, 2.8 mmol) dropwise over 10 min. The mixture was stirred at ambient temperature for 2 h and then 10% aqueous HCl solution (30 mL) was added. The solid precipitate was filtered and purified by column chromatography (C18 reverse phase column). The product fractions were combined, concentrated and dried in vacuo providing N-[2-(2,6-dioxo-piperidin-3-yl)-1-oxo-2,3-dihydro-1H-isoindol-5-ylmethyl]-4-ethoxy-benzamide as a white solid (0.26 g, 46% yield); mp 269-271° C.; HPLC, Waters Symmetry C-18, 3.9×150 mm, 5 μm, 1 ml/min, 240 nm, 30/70 $CH_3CN/0.1\%$ $H_3PO_4$, 5.75 (96.56%); $^1H$ NMR (DMSO-$d_6$) δ 1.34 (t, 3H, $CH_3$), 1.90-2.08 (m, 1H, CHH), 2.27-2.45 (m, 1H, CHH), 2.55-2.68 (m, 1H, CHH), 2.80-3.03 (m, 1H, CHH), 4.09 (q, 2H, $CH_2$), 4.30 (d, 1H, CHH), 4.41 (d, 1H, CHH), 4.58 (d, 2H, $CH_2$ and CHH), 5.10 (dd, J=4.5, 13.0 Hz, 1H, CH), 6.99 (d, J=8.3 Hz, 2H, Ar), 7.44 (d, 1H, Ar), 7.54 (s, 1H, Ar), 7.69 (d, 1H, Ar), 7.87 (d, J=8.5 Hz, 2H, Ar), 8.99 (t, 1H, NH), 10.98 (s, 1H, NH); $^{13}C$ NMR (DMSO-$d_6$) δ 14.53, 22.49, 31.18, 42.64, 47.12, 51.56, 63.28, 113.92, 122.01, 122.90, 126.19, 127.02, 129.09, 130.30, 142.35, 144.20, 160.92, 165.75, 167.93, 170.98, 172.85; LCMS: MH=422; Anal. Calcd for $C_{23}H_{23}N_3O_5+0.5H_2O$: C, 64.18; H, 5.62; N, 9.76. Found: C, 64.03; H, 5.45; N, 9.63.

5.76 4-tert-butyl-N-[2-(2,6-dioxo-piperidin-3-yl)-1-oxo-2,3-dihydro-1H-isoindol-5-ylmethyl]-benzamide

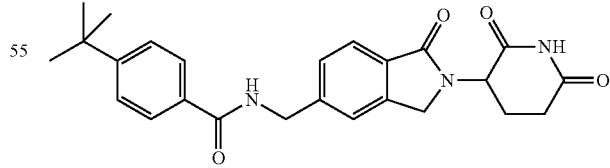

To a stirred mixture of 3-(5-aminomethyl-1-oxo-1,3-dihydro-isoindol-2-yl)-piperidine-2,6-dione methanesulfonate (0.50 g, 1.4 mmol) and 4-tert-butylbenzoyl chloride (0.28 g, 1.4 mmol) in acetonitrile (30 mL) at 0° C. was added TEA (0.28 g, 2.8 mmol) dropwise over 10 min. The mixture was stirred at ambient temperature for 2 h and then 10% aqueous HCl solution (30 mL) was added. The solid precipitate was filtered, washed with water (30 mL) and dried in vacuo providing 4-tert-butyl-N-[2-(2,6-dioxo-piperidin-3-yl)-1-oxo-2,3-dihydro-1H-isoindol-5-ylmethyl]-benzamide as a white solid (0.54 g, 92% yield); mp 238-240° C.; HPLC, Waters Symmetry C-18, 3.9×150 mm, 5 μm, 1 ml/min, 240 nm, 40/60 CH$_3$CN/0.1% H$_3$PO$_4$, 4.89 (99.23%); $^1$H NMR (DMSO-d$_6$) δ 1.30 (s, 9H, t-butyl), 1.91-2.08 (m, 1H, CHH), 2.27-2.45 (m, 1H, CHH), 2.54-2.67 (m, 1H, CHH), 2.81-3.01 (m, 1H, CHH), 4.30 (d, 1H, CHH), 4.44 (d, 1H, CHH), 4.59 (d, J=5.5 Hz, 2H, CH$_2$ and CHH), 5.10 (dd, 1H, CH), 7.40-7.58 (m, 4H, Ar), 7.69 (d, 1H, Ar), 7.85 (d, J=8.1 Hz, 2H, Ar), 9.08 (t, 1H, NH), 10.99 (s, 1H, NH); $^{13}$C NMR (DMSO-d$_6$) δ 22.49, 30.92, 31.20, 34.59, 42.63, 47.12, 51.56, 121.95, 122.91, 125.08, 125.35, 126.97, 127.11, 129.17, 130.32, 131.38, 142.36, 144.10, 154.11, 166.12, 167.93, 170.98, 172.85; LCMS: MH=434; Anal. Calcd for C$_{25}$H$_{27}$N$_3$O$_4$+3.0H$_2$O: C, 68.41; H, 6.34; N, 9.57. Found: C, 68.54; H, 6.47; N, 9.18.

5.77 6-ethoxy-N-[2-(3-methyl-2,6-dioxo-piperidin-3-yl)-1,3-dioxo-2,3-dihydro-1H-isoindol-5-ylmethyl]-nicotinamide

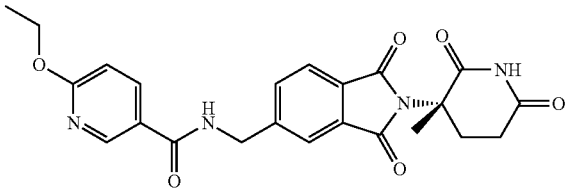 [SMILES: CCOc1ccc(C(=O)NCc2ccc3c(c2)C(=O)N([C@@]2(C)CCC(=O)NC2=O)C3=O)cn1]

A stirred mixture of 6-ethoxy-nicotinic acid (0.33 g, 2.00 mmol) and CDI (0.36 g, 2.20 mmol) in N,N-dimethylformamide (20 mL) was heated to 40° C. under nitrogen. After 1 h, 5-aminomethyl-2-(3-methyl-2,6-dioxo-piperidin-3-yl)-isoindole-1,3-dione hydrochloride (0.68 g, 2.00 mmol) was added and the mixture was heated at 40° C. for 1.5 h. The mixture was cooled to rt and water (40 mL) was added. The solvent was removed in vacuo and the crude product was purified by column chromatography (80/20, EtOAc/hexanes). The product fractions were combined, concentrated and the residue was triturated in Et$_2$O. The product was isolated by filtration and dried in vacuo to give 6-ethoxy-N-[2-(3-methyl-2,6-dioxo-piperidin-3-yl)-1,3-dioxo-2,3-dihydro-1H-isoindol-5-ylmethyl]-nicotinamide as a white solid (0.77 g, 86% yield): HPLC: Waters Symmetry C$_{18}$, 5 μm, 3.9×150 mm, 1 mL/min, 240 nm, 40/60 CH$_3$CN/0.1% H$_3$PO$_4$, 3.56 min (99.14%); mp: 174-176° C.; $^1$H NMR (DMSO-d$_6$) δ 1.33 (t, J=6.9 Hz, 3H), 1.89 (s, 3H), 2.02-2.08 (m, 1H), 2.54-2.73 (m, 3H), 4.34 (dd, J=7.2, 14.1 Hz, 2H), 4.62 (d, J=6.0 Hz, 2H), 6.88 (d, J=8.7 Hz, 1H), 7.77-7.83 (m, 3H), 8.14 (dd, J=2.4, 8.7 Hz, 1H), 8.70 (d, J=2.1 Hz, 1H), 9.20 (t, J=6.0 Hz, 1H), 11.01 (s, 1H); $^{13}$C NMR (DMSO-d$_6$) δ 14.40, 21.00, 28.60, 29.10, 42.50, 58.70, 61.80, 110.30, 121.60, 123.00, 123.20, 129.60, 131.40, 133.40, 138.10, 147.10, 147.30, 164.70, 165.00, 167.70, 167.90, 172.10, 172.20; LCMS: MH=451; Anal Calcd for C$_{23}$H$_{22}$N$_4$O$_6$+0.3H$_2$O: C, 60.60; H, 5.00; N, 12.29. Found: C, 60.24; H, 4.86; N, 12.15.

5.78 5-methylsulfanyl-pyridine-2-carboxylic acid [2-(2,6-dioxo-piperidin-3-yl)-1,3-dioxo-2,3-dihydro-1H-isoindol-5-ylmethyl]-amide

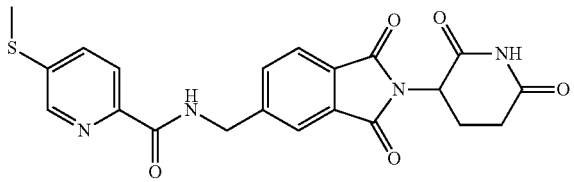 [SMILES: CSc1ccc(C(=O)NCc2ccc3c(c2)C(=O)N(C2CCC(=O)NC2=O)C3=O)nc1]

A stirred mixture of 5-methylsulfanyl-pyridine-2-carboxylic acid (0.34 g, 2.00 mmol) and CDI (0.34 g, 2.10 mmol) in N,N-dimethylformamide (15 mL) was heated to 40° C. under nitrogen. After 2 h, 5-aminomethyl-2-(2,6-dioxo-piperidin-3-yl)-isoindole-1,3-dione methane sulfonate (0.77 g, 2.00 mmol) was added and the mixture was heated at 40° C. for 2 h. The mixture was cooled to rt and EtOAc (75 mL) was added. The organic layer was washed with sat. aq. NaHCO$_3$ (3×75 mL) then concentrated in vacuo. The crude residue was purified by column chromatography (EtOAc/hexanes, gradient, product eluted at 90% EtOAc). The product fractions were combined and concentrated to give 5-methylsulfanyl-pyridine-2-carboxylic acid [2-(2,6-dioxo-piperidin-3-yl)-1,3-dioxo-2,3-dihydro-1H-isoindol-5-ylmethyl]-amide as a white solid (0.55 g, 63% yield): HPLC: Waters Symmetry C$_{18}$, 5 μm, 3.9×150 mm, 1 mL/min, 240 nm, 50/50 CH$_3$CN/0.1% H$_3$PO$_4$, 2.89 min (98.58%); mp: 185-187° C.; $^1$H NMR (DMSO-d$_6$) δ 1.83-2.18 (m, 1H), 2.52-2.68 (m, 5H), 2.78-3.02 (m, 1H), 4.64 (d, J=6.4 Hz, 2H), 5.14 (dd, J=5.4, 12.9 Hz, 1H), 7.76-7.91 (m, 4H), 7.92-8.00 (m, 1H), 8.53 (d, J=1.9 Hz, 1H), 9.52 (t, J=6.3 Hz, 1H), 11.11 (s, 1H); $^{13}$C NMR (DMSO-d$_6$) δ 13.93, 21.99, 30.93, 42.36, 48.99, 122.08, 123.51, 129.78, 131.56, 133.56, 133.83, 139.66, 145.03, 145.90, 147.57, 164.11, 166.99, 167.13, 169.80, 172.72; LCMS: MH=439; Anal Calcd for C$_{21}$H$_{18}$N$_4$O$_5$S: C, 57.53; H, 4.14; N, 12.78. Found: C, 57.17; H, 4.04; N, 12.54.

5.79 5-methanesulfonyl-pyridine-2-carboxylic acid [2-(2,6-dioxo-piperidin-3-yl)-1,3-dioxo-2,3-dihydro-1H-isoindol-5-ylmethyl]-amide

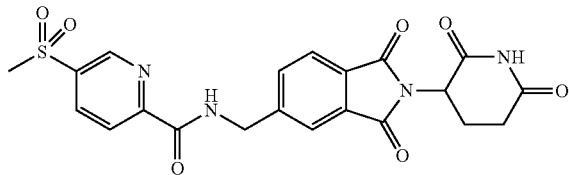 [SMILES: CS(=O)(=O)c1ccc(C(=O)NCc2ccc3c(c2)C(=O)N(C2CCC(=O)NC2=O)C3=O)nc1]

To a stirred mixture of 5-methylsulfanyl-pyridine-2-carboxylic acid [2-(2,6-dioxo-piperidin-3-yl)-1,3-dioxo-2,3-dihydro-1H-isoindol-5-ylmethyl]-amide (0.25 g, 0.57 mmol) in CH$_2$Cl$_2$ (70 mL) was added mCPBA (0.17 g, 0.74 mmol) at rt under nitrogen. After 2 h, the solids were filtered and triturated in MeCN (15 mL). The product was isolated by filtration and dried in vacuo to give 5-methanesulfonyl-pyridine-2-carboxylic acid [2-(2,6-dioxo-piperidin-3-yl)-1,3-dioxo-2,3-dihydro-1H-isoindol-5-ylmethyl]-amide as an off-white solid (0.22 g, 84% yield): HPLC: Waters Symmetry $C_{18}$, 5 μm, 3.9×150 mm, 1 mL/min, 240 nm, 40/60 $CH_3CN/0.1\%$ $H_3PO_4$, 2.53 min (97.80%); mp: 276-278° C.; $^1H$ NMR (DMSO-$d_6$) δ 2.00-2.12 (m, 1H), 2.53-2.68 (m, 2H), 2.80-3.01 (m, 1H), 3.40 (s, 3H), 4.69 (d, J=6.2 Hz, 2H), 5.14 (dd, J=5.4, 12.7 Hz, 1H), 7.74-7.96 (m, 3H), 8.28 (d, J=8.1 Hz, 1H), 8.53 (dd, J=2.2, 8.2 Hz, 1H), 9.15 (d, J=1.7 Hz, 1H), 9.86 (t, J=6.2 Hz, 1H), 11.11 (s, 1H); $^{13}C$ NMR (DMSO-$d_6$) δ 21.99, 30.93, 42.57, 43.56, 49.01, 122.11, 122.61, 123.54, 129.87, 131.59, 133.59, 137.30, 139.20, 147.01, 147.11, 153.21, 163.02, 166.97, 167.12, 169.80, 172.72; LCMS: MH=471; Anal Calcd for $C_{21}H_{18}N_4O_7S$+ 0.35$H_2O$: C, 52.90; H, 3.95; N, 11.75. Found: C, 52.92; H, 3.77; N, 11.70.

5.80 5-ethylsulfanyl-pyridine-2-carboxylic acid [2-(2,6-dioxo-piperidin-3-yl)-1,3-dioxo-2,3-dihydro-1H-isoindol-5-ylmethyl]-amide

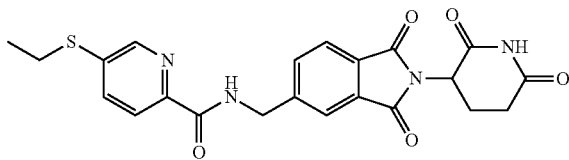 [SMILES: CCSc1ccc(C(=O)NCc2ccc3c(c2)C(=O)N(C2CCC(=O)NC2=O)C3=O)nc1]

A stirred mixture of 5-ethylsulfanyl-pyridine-2-carboxylic acid (0.48 g, 2.60 mmol) and CDI (0.44 g, 2.70 mmol) in N,N-dimethylformamide (20 mL) was heated to 40° C. under nitrogen. After 2 h, 3-(5-aminomethyl-1-oxo-1,3-dihydro-isoindol-2-yl)-piperidine-2,6-dione methane sulfonate (1.0 g, 2.60 mmol) was added and the mixture was heated at 40° C. for 2 h. The mixture was cooled to rt and EtOAc (75 mL) was added. The organic layer was washed with sat. aq. $NaHCO_3$ (3×75 mL) then concentrated in vacuo. The crude residue was purified by column chromatography (hexanes/EtOAc, gradient, product eluted at ~85% EtOAc). The product fractions were combined and concentrated to give 5-ethylsulfanyl-pyridine-2-carboxylic acid [2-(2,6-dioxo-piperidin-3-yl)-1,3-dioxo-2,3-dihydro-1H-isoindol-5-ylmethyl]-amide as a white solid (0.65 g, 60% yield): HPLC: Waters Symmetry $C_{18}$, 5 μm, 3.9×150 mm, 1 mL/min, 240 nm, 50/50 $CH_3CN/0.1\%$ $H_3PO_4$, 7.53 min (97.70%); mp: 198-200° C.; $^1H$ NMR (DMSO-$d_6$) δ 1.28 (t, J=7.4 Hz, 3H), 2.00-2.16 (m, 1H), 2.53-2.67 (m, 2H), 2.79-3.02 (m, 1H), 3.13 (q, J=7.2 Hz, 2H), 4.65 (d, J=6.4 Hz, 2H), 5.14 (dd, J=5.4, 12.9 Hz, 1H), 7.72-8.06 (m, 5H), 8.54 (d, J=1.5 Hz, 1H), 9.53 (t, J=6.3 Hz, 1H), 11.12 (s, 1H); $^{13}C$ NMR (DMSO-$d_6$) δ 13.84, 21.99, 25.27, 30.93, 42.36, 48.99, 122.08, 122.18, 123.51, 129.78, 131.56, 133.56, 135.42, 137.99, 146.30, 146.37, 147.54, 164.07, 166.99, 167.13, 169.80, 172.72; LCMS: MH=453; Anal Calcd for $C_{22}H_{20}N_4O_5S$: C, 58.40; H, 4.46; N, 12.38. Found: C, 58.27; H, 4.35; N, 12.30.

5.81 5-ethanesulfonyl-pyridine-2-carboxylic acid [2-(2,6-dioxo-piperidin-3-yl)-1,3-dioxo-2,3-dihydro-1H-isoindol-5-ylmethyl]-amide

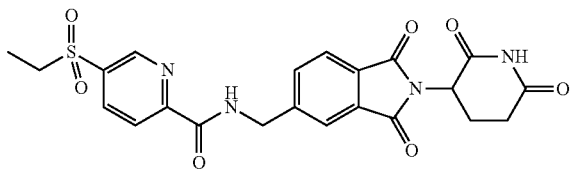 [SMILES: CCS(=O)(=O)c1ccc(C(=O)NCc2ccc3c(c2)C(=O)N(C2CCC(=O)NC2=O)C3=O)nc1]

A stirred mixture of 5-ethanesulfonyl-pyridine-2-carboxylic acid (0.34 g, 1.60 mmol) and CDI (0.27 g, 1.70 mmol) in N,N-dimethylformamide (15 mL) was heated to 40° C. under nitrogen. After 2 h, 5-aminomethyl-2-(2,6-dioxo-piperidin-3-yl)-isoindole-1,3-dione methane sulfonate (0.61 g, 1.60 mmol) was added and the mixture was heated at 40° C. for 2 h. The mixture was cooled to rt and EtOAc (75 mL) was added. The organic layer was washed with sat. aq. $NaHCO_3$ (3×75 mL) then concentrated in vacuo. The crude residue was purified by column chromatography (EtOAc/hexanes, gradient, product eluted at 80-90% EtOAc). The product fractions were combined and concentrated to give 5-ethanesulfonyl-pyridine-2-carboxylic acid [2-(2,6-dioxo-piperidin-3-yl)-1,3-dioxo-2,3-dihydro-1H-isoindol-5-ylmethyl]-amide as a white solid (0.25 g, 32% yield): HPLC: Waters Symmetry $C_{18}$, 5 μm, 3.9×150 mm, 1 mL/min, 240 nm, 30/70 $CH_3CN/0.1\%$ $H_3PO_4$, 6.15 min (96.20%); mp: 265-267° C.; $^1H$ NMR (DMSO-$d_6$) δ 1.15 (t, J=7.4 Hz, 3H), 2.00-2.20 (m, 1H), 2.52-2.67 (m, 2H), 2.77-3.01 (m, 1H), 3.48 (q, J=7.4 Hz, 2H), 4.69 (d, J=6.2 Hz, 2H), 5.14 (dd, J=5.4, 12.7 Hz, 1H), 7.73-8.04 (m, 3H), 8.29 (d, J=8.3 Hz, 1H), 8.49 (dd, J=2.3, 8.1 Hz, 1H), 9.10 (d, J=1.7 Hz, 1H), 9.86 (t, J=6.3 Hz, 1H), 11.12 (s, 1H); $^{13}C$ NMR (DMSO-$d_6$) δ 6.83, 21.99, 30.93, 42.58, 49.01, 49.34, 122.17, 122.68, 123.54, 129.87, 131.59, 133.63, 137.04, 138.13, 147.09, 147.60, 153.38, 163.02, 166.97, 167.12, 169.80, 172.72; LCMS: MH=485; Anal Calcd for $C_{22}H_{20}N_4O_7S$: C, 54.54; H, 4.16; N, 11.56. Found: C, 54.82; H, 3.92; N, 11.57.

5.82 4-ethylsulfanyl-N-[2-(3-methyl-2,6-dioxo-piperidin-3-yl)-1,3-dioxo-2,3-dihydro-1H-isoindol-5-ylmethyl]-benzamide

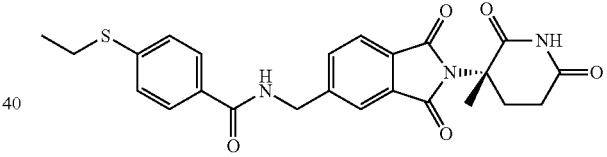

A stirred mixture of 4-(ethylthio)benzoic acid (0.36 g, 2.00 mmol) and CDI (0.34 g, 2.10 mmol) in N,N-dimethylformamide (20 mL) was heated to 40° C. under nitrogen. After 2 h, 5-aminomethyl-2-(3-methyl-2,6-dioxo-piperidin-3-yl)-isoindole-1,3-dione hydrochloride (0.670 g, 2.00 mmol) was added and the mixture was heated at 40° C. for 2 h. The mixture was cooled to rt and EtOAc (75 mL) was added. The organic layer was washed with sat. aq. $NaHCO_3$ (3×100 mL) then concentrated in vacuo. The crude residue was purified by column chromatography (hexanes/EtOAc, gradient, product eluted at ~95% EtOAc). The product fractions were combined and concentrated to give 4-ethylsulfanyl-N-[2-(3-methyl-2,6-dioxo-piperidin-3-yl)-1,3-dioxo-2,3-dihydro-1H-isoindol-5-ylmethyl]-benzamide as a white solid (0.37 g, 61% yield): HPLC: Waters Symmetry $C_{18}$, 5 μm, 3.9×150 mm, 1 mL/min, 240 nm, 50/50 $CH_3CN/0.1\%$ $H_3PO_4$, 4.03 min (99.73%); mp: 135-137° C.; $^1H$ NMR (DMSO-$d_6$) δ 1.27 (t, J=7.3 Hz, 3H), 1.89 (s, 3H), 1.95-2.11 (m, 1H), 2.53-2.61 (m, 2H), 2.61-2.77 (m, 1H), 3.06 (q, J=7.3 Hz, 2H), 4.61 (d, J=5.7 Hz, 2H), 7.38 (d, J=8.3 Hz, 2H), 7.72-7.88 (m, 5H), 9.18 (t, J=5.9 Hz, 1H), 11.01 (s, 1H); $^{13}C$ NMR (DMSO-$d_6$) δ 13.92, 21.02, 25.19, 28.57, 29.11, 42.58, 58.76, 121.60, 123.18, 126.32, 127.83, 129.59, 130.38, 131.38, 133.38, 141.22, 147.51, 165.86, 167.73, 167.88, 172.13, 172.19; LCMS: MH=466; Anal Calcd for $C_{21}H_{23}N_3O_5S+0.3H_2O$: C, 61.21; H, 5.05; N, 8.92. Found: C, 61.27; H, 5.13; N, 8.80.

5.83 4-ethoxy-N-[2-(3-methyl-2,6-dioxo-piperidin-3-yl)-1,3-dioxo-2,3-dihydro-1H-isoindol-5-ylmethyl]-benzamide

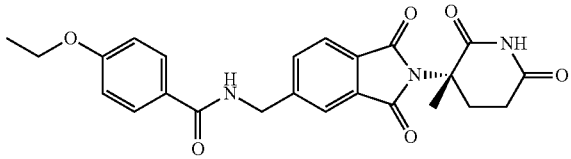 [SMILES: CCOc1ccc(C(=O)NCc2ccc3c(c2)C(=O)N([C@@]2(C)CCC(=O)NC2=O)C3=O)cc1]

A stirred mixture of 4-ethoxybenzoic acid (0.33 g, 2.00 mmol) and CDI (0.34 g, 2.10 mmol) in N,N-dimethylformamide (20 mL) was heated to 40° C. under nitrogen. After 2 h, 5-aminomethyl-2-(3-methyl-2,6-dioxo-piperidin-3-yl)-isoindole-1,3-dione hydrochloride (0.67 g, 2.00 mmol) was added and the mixture was heated at 40° C. for 18 h. The mixture was cooled to rt and EtOAc (75 mL) was added. The organic layer was washed with sat. aq. NaHCO$_3$ (3×100 mL) then concentrated. The residue was triturated in Et$_2$O, then EtOAc and isolated by filtration followed by drying in vacuo to give 4-ethoxy-N-[2-(3-methyl-2,6-dioxo-piperidin-3-yl)-1,3-dioxo-2,3-dihydro-1H-isoindol-5-ylmethyl]-benzamide as a white solid (0.27 g, 30% yield): HPLC: Waters Symmetry C$_{18}$, 5 μm, 3.9×150 mm, 1 mL/min, 240 nm, 40/60 CH$_3$CN/0.1% H$_3$PO$_4$, 5.73 min (97.04%); mp: 163-165° C.; $^1$H NMR (DMSO-d$_6$) δ 1.34 (t, J=7.0 Hz, 3H), 1.81-1.95 (m, 3H), 1.97-2.12 (m, 1H), 2.53-2.61 (m, 2H), 2.61-2.78 (m, 1H), 4.09 (q, J=6.9 Hz, 3H), 4.60 (d, J=5.9 Hz, 2H), 7.00 (d, J=8.7 Hz, 2H), 7.44-8.44 (m, 5H), 9.06 (t, J=5.9 Hz, 1H), 11.01 (s, 1H); $^{13}$C NMR (DMSO-d$_6$) δ 14.53, 21.02, 28.57, 29.11, 42.52, 58.76, 63.31, 113.99, 121.56, 123.16, 125.97, 129.09, 129.55, 131.37, 133.35, 147.73, 161.02, 165.89, 167.75, 167.89, 172.13, 172.19; LCMS: MH=450; Anal Calcd for $C_{24}H_{23}N_3O_6+0.75H_2O$: C, 62.26; H, 5.33; N, 9.08. Found: C, 62.25; H, 5.13; N, 9.17.

5.84 5-ethanesulfonyl-pyridine-2-carboxylic acid [2-(3-methyl-2,6-dioxo-piperidin-3-yl)-1,3-dioxo-2,3-dihydro-1H-isoindol-5-ylmethyl]-amide

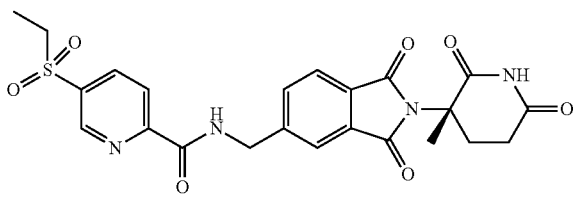 [SMILES: CCS(=O)(=O)c1ccc(C(=O)NCc2ccc3c(c2)C(=O)N([C@@]2(C)CCC(=O)NC2=O)C3=O)nc1]

To a stirred mixture of 5-ethylsulfanyl-pyridine-2-carboxylic acid [2-(3-methyl-2,6-dioxo-piperidin-3-yl)-1,3-dioxo-2,3-dihydro-1H-isoindol-5-ylmethyl]-amide (0.80 g, 1.71 mmol) in CH$_2$Cl$_2$ (100 mL) was added mCPBA (0.73 g, 3.25 mmol) at rt under nitrogen. After 1 h, the solution was washed with sat. aq. NaHCO$_3$ (3×100 mL) and the organic layer was concentrated. The residue was dissolved in EtOAc (75 mL) and washed with water (2×100 mL). The organic layer was separated, dried (MgSO$_4$) then concentrated to give 5-ethanesulfonyl-pyridine-2-carboxylic acid [2-(3-methyl-2,6-dioxo-piperidin-3-yl)-1,3-dioxo-2,3-dihydro-1H-isoindol-5-ylmethyl]-amide as an off-white solid (0.65 g, 76% yield): HPLC: Waters Symmetry C$_{18}$, 5 μm, 3.9×150 mm, 1 mL/min, 240 nm, 40/60 CH$_3$CN/0.1% H$_3$PO$_4$, 3.28 min (97.40%); mp: 145-147° C.; $^1$H NMR (DMSO-d$_6$) δ 1.15 (t, J=7.3 Hz, 3H), 1.88 (s, 3H), 1.97-2.16 (m, 1H), 2.53-2.61 (m, 2H), 2.61-2.79 (m, 1H), 3.48 (q, J=7.4 Hz, 2H), 4.66 (d, J=6.2 Hz, 2H), 7.81 (s, 3H), 8.28 (d, J=8.1 Hz, 1H), 8.49 (dd, J=2.3, 8.1 Hz, 1H), 9.10 (d, J=1.5 Hz, 1H), 9.85 (t, J=6.3 Hz, 1H), 11.01 (s, 1H); $^{13}$C NMR (DMSO-d$_6$) δ 6.83, 21.00, 28.57, 29.09, 42.57, 49.34, 58.76, 121.82, 122.67, 123.18, 129.69, 131.37, 133.59, 137.04, 138.13, 146.91, 147.58, 153.38, 162.98, 167.72, 167.86, 172.15; LCMS: MH=499; Anal Calcd for $C_{23}H_{22}N_4O_7S+1.0$ MeOH: C, 54.33; H, 4.94; N, 10.56. Found: C, 54.40; H, 4.85; N, 10.54.

5.85 N-[2-(3-methyl-2,6-dioxo-piperidin-3-yl)-1,3-dioxo-2,3-dihydro-1H-isoindol-5-ylmethyl]-4-methylsulfanyl-benzamide

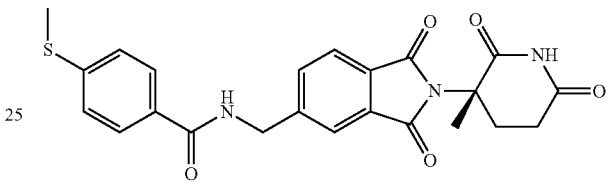

A stirred mixture of 4-(methylthio)benzoic acid (0.34 g, 2.00 mmol) and CDI (0.34 g, 2.10 mmol) in N,N-dimethylformamide (20 mL) was heated to 40° C. under nitrogen. After 2 h, 5-aminomethyl-2-(3-methyl-2,6-dioxo-piperidin-3-yl)-isoindole-1,3-dione hydrochloride (0.68 g, 2.00 mmol) was added and the mixture was heated at 40° C. for 2 h. The mixture was cooled to rt and EtOAc (75 mL) was added. The organic layer was washed with sat. aq. NaHCO$_3$ (3×100 mL) then concentrated in vacuo. The crude residue was purified by column chromatography (CH$_2$Cl$_2$/MeOH, gradient, product eluted after 4.7 min). The product fractions were combined and concentrated to give N-[2-(3-methyl-2,6-dioxo-piperidin-3-yl)-1,3-dioxo-2,3-dihydro-1H-isoindol-5-ylmethyl]-4-methylsulfanyl-benzamide as a white solid (0.24 g, 26% yield): HPLC: Waters Symmetry C$_{18}$, 5 μm, 3.9×150 mm, 1 mL/min, 240 nm, 40/60 CH$_3$CN/0.1% H$_3$PO$_4$, 4.74 min (98.27%); mp: 218-220° C.; $^1$H NMR (DMSO-d$_6$) δ 1.88 (s, 3H), 1.99-2.10 (m, 1H), 2.51-2.61 (m, 5H), 2.62-2.78 (m, 1H), 4.61 (d, J=5.9 Hz, 2H), 7.34 (d, J=8.3 Hz, 2H), 7.64-7.96 (m, 5H), 9.17 (t, J=5.9 Hz, 1H), 11.01 (s, 1H); $^{13}$C NMR (DMSO-d$_6$) δ 14.12, 21.02, 28.57, 29.09, 42.57, 58.76, 121.60, 123.19, 124.95, 127.74, 129.59, 129.93, 131.38, 133.38, 142.84, 147.52, 165.86, 167.73, 167.88, 172.13, 172.19; LCMS: MH=452; Anal Calcd for $C_{23}H_{21}N_3O_5S$: C, 61.18; H, 4.69; N, 9.31. Found: C, 60.82; H, 4.85; N, 8.96.

5.86 5-methylsulfanyl-pyridine-2-carboxylic acid [2-(3-methyl-2,6-dioxo-piperidin-3-yl)-1,3-dioxo-2,3-dihydro-1H-isoindol-5-ylmethyl]-amide

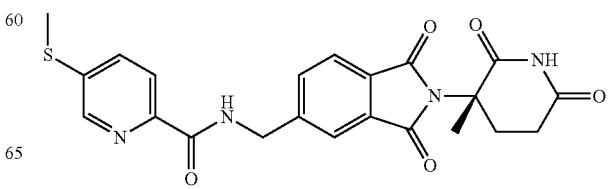

A stirred mixture of 5-methylsulfanyl-pyridine-2-carboxylic acid (0.34 g, 2.00 mmol) and CDI (0.34 g, 2.10 mmol) in N,N-dimethylformamide (20 mL) was heated to 40° C. under nitrogen. After 2 h, 5-aminomethyl-2-(3-methyl-2,6-dioxo-piperidin-3-yl)-isoindole-1,3-dione hydrochloride (0.68 g, 2.00 mmol) was added and the mixture was heated at 40° C. for 2 h. The mixture was cooled to rt and EtOAc (75 mL) was added. The organic layer was washed with sat. aq. NaHCO$_3$ (3×100 mL) then concentrated in vacuo. The crude residue was purified by column chromatography (0-5% gradient, MeOH/CH$_2$Cl$_2$, 0-5% gradient, product eluted after 4.7 min). The product fractions were combined, concentrated and the residue was triturated in MeCN (50 mL) for 1.5 h. The product was isolated by filtration and dried in vacuo to give 5-methylsulfanyl-pyridine-2-carboxylic acid [2-(3-methyl-2,6-dioxo-piperidin-3-yl)-1,3-dioxo-2,3-dihydro-1H-isoindol-5-ylmethyl]-amide as a white solid (0.52 g, 57% yield): HPLC: Waters Symmetry C$_{18}$, 5 µm, 3.9×150 mm, 1 mL/min, 240 nm, 40/60 CH$_3$CN/0.1% H$_3$PO$_4$, 4.89 min (98.54%); mp: 210-212° C.; $^1$H NMR (DMSO-d$_6$) δ 1.88 (s, 3H), 1.97-2.12 (m, 1H), 2.53-2.78 (m, 6H), 4.62 (d, J=6.2 Hz, 2H), 7.68-7.90 (m, 4H), 7.91-8.04 (m, 1H), 8.52 (d, J=1.7 Hz, 1H), 9.51 (t, J=6.3 Hz, 1H), 11.01 (s, 1H); $^{13}$C NMR (DMSO-d$_6$) δ 13.93, 21.02, 28.57, 29.09, 42.35, 58.73, 121.75, 122.05, 123.15, 129.59, 131.34, 133.53, 133.82, 139.65, 145.00, 145.90, 147.39, 164.07, 167.73, 167.88, 172.15; LCMS: MH=453; Anal Calcd for C$_{22}$H$_{20}$N$_4$O$_5$S: C, 58.40; H, 4.46; N, 12.38. Found: C, 58.24; H, 4.33; N, 12.16.

5.87 4-ethanesulfonyl-N-[2-(3-methyl-2,6-dioxo-piperidin-3-yl)-1,3-dioxo-2,3-dihydro-1H-isoindol-5-ylmethyl]-benzamide

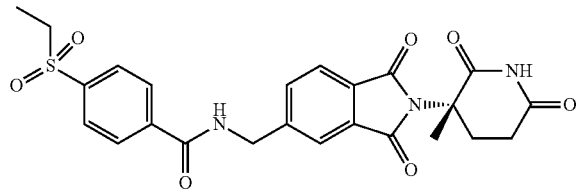 [SMILES: CCS(=O)(=O)c1ccc(C(=O)NCc2ccc3c(c2)C(=O)N([C@@]2(C)CCC(=O)NC2=O)C3=O)cc1]

A stirred mixture of 4-ethylsulfonylbenzoic acid (0.43 g, 2.00 mmol) and CDI (0.34 g, 2.10 mmol) in N,N-dimethylformamide (20 mL) was heated to 40° C. under nitrogen. After 2 h, 5-aminomethyl-2-(3-methyl-2,6-dioxo-piperidin-3-yl)-isoindole-1,3-dione hydrochloride (0.68 g, 2.00 mmol) was added and the mixture was heated at 40° C. for 2 h. The mixture was cooled to rt and EtOAc (75 mL) was added. The organic layer was washed with sat. aq. NaHCO$_3$ (3×100 mL) then concentrated in vacuo. The crude residue was purified by column chromatography (EtOAc/hexanes, gradient). The product fractions were combined and concentrated to give 5-methylsulfanyl-pyridine-2-carboxylic acid 4-ethanesulfonyl-N-[2-(3-methyl-2,6-dioxo-piperidin-3-yl)-1,3-dioxo-2,3-dihydro-1H-isoindol-5-ylmethyl]-benzamide as a white solid (0.31 g, 32% yield): HPLC: Waters Symmetry C$_{18}$, 5 µm, 3.9×150 mm, 1 mL/min, 240 nm, 40/60 CH$_3$CN/0.1% H$_3$PO$_4$, 2.40 min (98.51%); mp: 178-180° C.; $^1$H NMR (DMSO-d$_6$) δ 1.10 (t, J=7.2, 7.4 Hz, 3H), 1.89 (s, 3H), 2.00-2.15 (m, 1H), 2.54-2.77 (m, 3H), 3.35 (q, J=7.4 Hz, 2H), 4.66 (d, J=5.9 Hz, 2H), 7.73-7.86 (m, 3H), 7.97-8.07 (m, 2H), 8.07-8.21 (m, 2H), 9.48 (t, J=5.9 Hz, 1H), 11.01 (s, 1H); $^{13}$C NMR (DMSO-d$_6$) δ 7.06, 21.00, 28.57, 29.09, 42.75, 49.04, 58.78, 121.70, 123.22, 128.02, 128.29, 129.71, 131.41, 133.47, 138.51, 140.85, 146.97, 165.21, 167.72, 167.85, 172.13, 172.19; LCMS: MH=498; Anal Calcd for C$_{24}$H$_{23}$N$_3$O$_7$S+0.15 CH$_2$Cl$_2$: C, 56.85; H, 4.60; N, 8.23. Found: C, 57.11; H, 4.87; N, 7.85.

5.88 N-[2-(2,6-dioxo-piperidin-3-yl)-1,3-dioxo-2,3-dihydro-1H-isoindol-5-ylmethyl]-4-ethanesulfonyl-benzamide

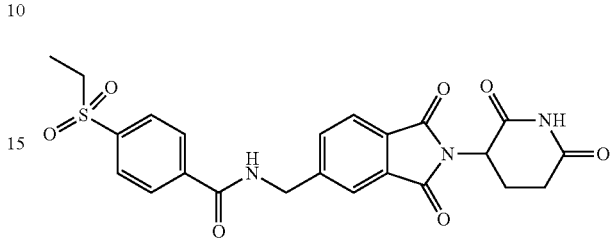

A stirred mixture of 4-ethylsulfonylbenzoic acid (0.64 g, 3.00 mmol) and CDI (0.51 g, 3.15 mmol) in N,N-dimethylformamide (34 mL) was heated to 40° C. under nitrogen. After 2 h, 5-aminomethyl-2-(2,6-dioxo-piperidin-3-yl)-isoindole-1,3-dione methane sulfonate (1.15 g, 3.00 mmol) was added and the mixture was heated at 40° C. for 2 h. The mixture was cooled to rt and EtOAc (150 mL) was added. The organic layer was washed with sat. aq. NaHCO$_3$ (3×100 mL) then concentrated in vacuo. The crude residue was purified by column chromatography (EtOAc/hexanes, gradient). The product fractions were combined and concentrated to give N-[2-(2,6-dioxo-piperidin-3-yl)-1,3-dioxo-2,3-dihydro-1H-isoindol-5-ylmethyl]-4-ethanesulfonyl-benzamide as a white solid (0.63 g, 44% yield): HPLC: Waters Symmetry C$_{18}$, 5 µm, 3.9×150 mm, 1 mL/min, 240 nm, 40/60 CH$_3$CN/0.1% H$_3$PO$_4$, 2.66 min (97.99%); mp: 182-184° C.; $^1$H NMR (DMSO-d$_6$) δ 1.11 (t, J=7.4 Hz, 3H), 2.00-2.18 (m, 1H), 2.54-2.68 (m, 2H), 2.80-2.99 (m, 1H), 3.35 (q, J=7.4 Hz, 2H), 4.68 (d, J=5.7 Hz, 2H), 5.15 (dd, J=5.3, 12.8 Hz, 1H), 7.77-7.97 (m, 3H), 7.98-8.07 (m, 2H), 8.08-8.25 (m, 2H), 9.49 (t, J=5.8 Hz, 1H), 11.12 (s, 1H); $^{13}$C NMR (DMSO-d$_6$) δ 7.06, 21.99, 30.93, 42.77, 49.02, 122.08, 123.58, 128.03, 128.32, 129.90, 131.63, 133.53, 138.50, 140.85, 147.11, 165.24, 166.96, 167.10, 169.82, 172.75; LCMS: MH=484; Anal Calcd for C$_{23}$H$_{21}$N$_3$O$_7$S+0.45H$_2$O: C, 56.19; H, 4.49; N, 8.55. Found: C, 55.87; H, 4.47; N, 8.28.

5.89 N-((2-(2,6-dioxopiperidin-3-yl)-1-oxoisoindolin-5-yl)methyl)-2-(quinolin-6-yl)acetamide

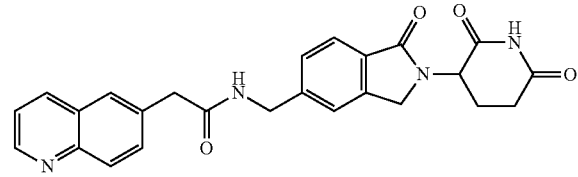 [SMILES: O=C(Cc1ccc2ncccc2c1)NCc1ccc2c(c1)CN(C1CCC(=O)NC1=O)C2=O]

To a solution of quinolin-6-yl-acetic acid (0.19 g, 1.02 mmol) in dry DMF (5 mL) was added CDI (0.16 g, 1.02 mmol). After 1 h of stirring at rt, 3-(5-aminomethyl-1-oxo-1,3-dihydro-isoindol-2-yl)-piperidine-2,6-dione methanesulfonate (0.30 g, 0.81 mmol) was added. After 18 h, water (20 mL) was added. The solids were collected by filtration, washed with water and dried in vacuo for 18 h to give N-((2-(2,6-dioxopiperidin-3-yl)-1-oxoisoindolin-5-yl)

methyl)-2-(quinolin-6-yl)acetamide as a white solid (355 mg, 99%). HPLC: Waters Symmetry $C_{18}$, 5 μm, 3.9×150 mm, 1 ml/min, 240 nm, 10/90, $CH_3CN/0.1\%$ $H_3PO_4$, 4.54 min (95.6%); mp: 205-207° C.; $^1H$ NMR (DMSO-$d_6$) δ 1.89-2.10 (m, 1H), 2.37 (qd, J=4.3, 13.2 Hz, 1H), 2.63 (br. s., 1H), 2.80-3.02 (m, 1H), 3.73 (s, 2H), 4.12-4.30 (m, 1H), 4.30-4.48 (m, 3H), 5.10 (dd, J=5.1, 13.2 Hz, 1H), 7.29-7.47 (m, 2H), 7.52 (dd, J=4.2, 8.3 Hz, 1H), 7.60-7.76 (m, 2H), 7.84 (s, 1H), 7.97 (d, J=8.7 Hz, 1H), 8.32 (d, J=7.7 Hz, 1H), 8.75 (t, J=5.9 Hz, 1H), 8.87 (dd, J=1.7, 4.2 Hz, 1H), 10.99 (s, 1H); $^{13}C$ NMR (DMSO-$d_6$) δ 22.48, 31.18, 42.16, 42.31, 47.03, 51.55, 121.53, 122.02, 122.91, 127.07, 127.52, 127.72, 128.72, 130.36, 131.21, 134.66, 135.61, 142.32, 143.73, 146.73, 150.07, 167.87, 169.99, 170.98, 172.86. LCMS: MH=443; Anal Calcd for $C_{25}H_{22}N_4O_4 + 1.6H_2O$: C, 63.71%; H, 5.39%; N, 11.89%. Found: C, 63.71%; H, 5.25%; N, 11.99%.

5.90 cyclopropanecarboxylic acid [2-(2,6-dioxo-piperidin-3-yl)-1,3-dioxo-2,3-dihydro-1H-isoindol-5-ylmethyl]-amide

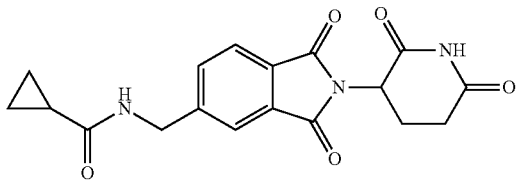 [SMILES: O=C1CCC(N2C(=O)c3ccc(CNC(=O)C4CC4)cc3C2=O)C(=O)N1]

To a stirred mixture of 5-aminomethyl-2-(2,6-dioxo-piperidin-3-yl)-isoindole-1,3-dione hydrochloride (1.00 g, 3.10 mmol) and cyclopropanecarbonyl chloride (0.32 g, 3.10 mmol) in THF (35 mL), was added triethylamine (0.88 mL, 6.20 mmol) at room temperature under nitrogen. The mixture was heated to 40° C. for 6 h then cooled to rt. The mixture was filtered and the filtrate diluted with EtOAc (100 mL). The organic layer was washed with dil. aq. HCl (100 mL), water (2×75 mL), dried (MgSO$_4$) and concentrated in vacuo to give cyclopropanecarboxylic acid [2-(2,6-dioxo-piperidin-3-yl)-1,3-dioxo-2,3-dihydro-1H-isoindol-5-ylmethyl]-amide as a white solid (0.69 g, 63% yield): HPLC: Waters Symmetry $C_{18}$, 5 μm, 3.9×150 mm, 1 mL/min, 240 nm, 25/75 $CH_3CN/0.1\%$ $H_3PO_4$, 2.96 min (98.96%); mp: 163-165° C.; $^1H$ NMR (DMSO-$d_6$) δ 0.62-0.78 (m, 4H), 1.63 (m, 1H), 1.95-2.17 (m, 1H), 2.53-2.67 (m, 2H), 2.79-3.00 (m, 1H), 4.46 (d, J=6.0 Hz, 2H), 5.15 (dd, J=5.4, 12.9 Hz, 1H), 7.67-7.79 (m, 2H), 7.89 (d, J=7.6 Hz, 1H), 8.77 (t, J=5.9 Hz, 1H), 11.13 (s, 1H); $^{13}C$ NMR (DMSO-$d_6$) δ 6.44, 13.57, 21.99, 30.93, 42.05, 48.99, 121.83, 123.54, 129.74, 131.60, 133.35, 147.77, 166.99, 167.13, 169.82, 172.73, 172.94; Anal Calcd for $C_{18}H_{17}N_3O_5 + 0.2H_2O$: C, 60.23; H, 4.89; N, 11.71. Found: C, 60.16; H, 4.54; N, 11.70.

5.91 5-ethoxy-pyridine-2-carboxylic acid [2-(3-methyl-2,6-dioxo-piperidin-3-yl)-1,3-dioxo-2,3-dihydro-1H-isoindol-5-ylmethyl]-amide

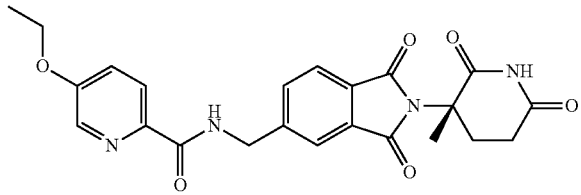

A stirred mixture of 5-ethoxy-pyridine-2-carboxylic acid (0.33 g, 2.00 mmol) and CDI (0.36 g, 2.20 mmol) in N,N-dimethylformamide (20 mL) was heated to 40° C. under nitrogen. After 1 h, 5-aminomethyl-2-(3-methyl-2,6-dioxo-piperidin-3-yl)-isoindole-1,3-dione hydrochloride (0.68 g, 2.00 mmol) was added and the mixture was heated at 40° C. for 1.5 h. The mixture was cooled to rt and water (40 mL) was added. The solids were filtered and dissolved in $CH_2Cl_2$ (10 mL). The crude product was purified by column chromatography (0-5% $MeOH/CH_2Cl_2$, gradient, product eluted at 3% MeOH). The product fractions were combined and concentrated to give 5-ethoxy-pyridine-2-carboxylic acid[2-(3-methyl-2,6-dioxo-piperidin-3-yl)-1,3-dioxo-2,3-dihydro-1H-isoindol-5-ylmethyl]-amide as a white solid (0.69 g, 77% yield): HPLC: Waters Symmetry $C_{18}$, 5 μm, 3.9×150 mm, 1 mL/min, 240 nm, 40/60 $CH_3CN/0.1\%$ $H_3PO_4$, 4.98 min (95.90%); mp: 145-147° C.; $^1H$ NMR (DMSO-$d_6$) δ 1.37 (t, J=7.2 Hz, 3H), 1.88 (s, 3H), 2.01-2.07 (m, 1H), 2.54-2.71 (m, 3H), 4.19 (dd, J=6.9, 13.8 Hz, 2H), 4.61 (d, J=6.3 Hz, 2H), 7.53 (dd, J=3.0, 8.7 Hz, 1H), 7.77-7.82 (m, 3H), 7.99 (d, J=8.7 Hz, 1H), 8.31 (d, J=2.4 Hz, 1H), 9.40 (t, J=6.3 Hz, 1H), 11.00 (s, 1H); $^{13}C$ NMR (DMSO-$d_6$) δ12.70, 19.30, 26.90, 27.40, 40.60, 57.00, 62.40, 119.60, 120.00, 121.40, 121.70, 127.80, 129.60, 131.80, 135.10, 14.050, 145.90, 155.30, 162.30, 166.10, 166.20, 170.40, 170.50; LCMS: MH=451; Anal Calcd for $C_{23}H_{22}N_4O_6 + 0.5H_2O$: C, 60.13; H, 5.05; N, 12.19. Found: C, 59.95; H, 4.91; N, 12.04.

5.92 N-[2-(2,6-dioxo-piperidin-3-yl)-1,3-dioxo-2,3-dihydro-1H-isoindol-5-ylmethyl]-3,3-dimethyl-butyramide

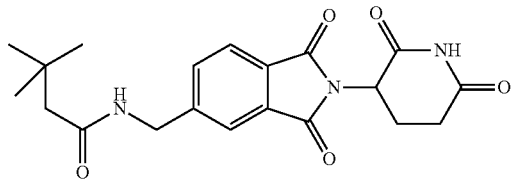 [SMILES: CC(C)(C)CC(=O)NCc1ccc2c(c1)C(=O)N(C1CCC(=O)NC1=O)C2=O]

To a stirred mixture of 5-aminomethyl-2-(2,6-dioxo-piperidin-3-yl)-isoindole-1,3-dione hydrochloride (0.97 g, 3.00 mmol) and t-butylacetyl chloride (0.40 g, 3.00 mmol) in $CH_2Cl_2$ (20 mL), was added DIPEA (1.05 mL, 6.00 mmol) at room temperature under nitrogen. After 18 h, solution was washed with dil. aq. HCl (2×50 mL), water (2×50 mL), dried (MgSO$_4$) and then concentrated. The crude product was purified by column chromatography (0-5% $MeOH/CH_2Cl_2$). The product fractions were combined, concentrated and triturated in EtOAc for 18 h. The product was dried in vacuo to give N-[2-(2,6-dioxo-piperidin-3-yl)-1,3-dioxo-2,3-dihydro-1H-isoindol-5-ylmethyl]-3,3-dimethyl-butyramide as a white solid (0.39 g, 34% yield): HPLC: Waters Symmetry $C_{18}$, 5 μm, 3.9×150 mm, 1 mL/min, 240 nm, 40/60 $CH_3CN/0.1\%$ $H_3PO_4$, 3.13 min (95.97%); mp: 232-234° C.; $^1H$ NMR (DMSO-$d_6$) δ 0.97 (s, 9H, $CH_3$, $CH_3$, $CH_3$), 1.97-2.17 (m, 3H, CHH, $CH_2$), 2.53-2.69 (m, 2H, CHH, CHH), 2.77-3.01 (m, 1H, CHH), 4.43 (d, J=5.9 Hz, 2H, $CH_2$), 5.14 (dd, J=5.4, 12.7 Hz, 1H, CH), 7.71-7.83 (m, 2H, Ar), 7.89 (d, J=7.6 Hz, 1H, Ar), 8.46 (t, J=5.9 Hz, 1H, NH), 11.12 (s, 1H, NH); $^{13}C$ NMR (DMSO-$d_6$) δ 21.99, 29.68, 30.52, 30.93, 41.87, 48.66, 48.99, 121.91, 123.45, 129.69, 131.57, 133.41, 147.87, 166.97, 167.10, 169.83, 171.11, 172.73; LCMS:

MH=386; Anal Calcd for $C_{20}H_{23}N_3O_5$: C, 62.33; H, 6.02; N, 10.90. Found: C, 61.96; H, 5.95; N, 10.75.

5.93 pyridine-2-carboxylic acid [2-(2,6-dioxo-piperidin-3-yl)-1,3-dioxo-2,3-dihydro-1H-isoindol-5-ylmethyl]-amide

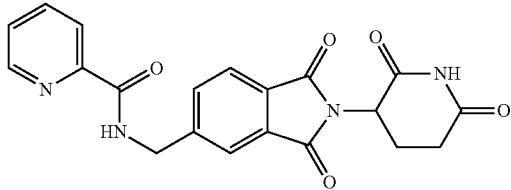 [SMILES: O=C1CCC(N2C(=O)c3ccc(CNC(=O)c4ccccn4)cc3C2=O)C(=O)N1]

To a stirred mixture of 5-aminomethyl-2-(2,6-dioxo-piperidin-3-yl)-isoindole-1,3-dione hydrochloride (0.97 g, 3.00 mmol) and pyridine-2-carbonyl chloride hydrochloride (0.64 g, 3.60 mmol) in THF (50 mL), was added TEA (1.46 mL, 10.50 mmol) at room temperature under nitrogen. The solvent was removed in vacuo and the residue was dissolved in $CH_2Cl_2$ (100 mL). The organic layer was washed with water (100 mL), brine (100 mL), dried ($MgSO_4$) and then concentrated. The crude product was purified by column chromatography (0-5% $MeOH/CH_2Cl_2$). The product fractions were combined, concentrated and dried in vacuo to give pyridine-2-carboxylic acid [2-(2,6-dioxo-piperidin-3-yl)-1,3-dioxo-2,3-dihydro-1H-isoindol-5-ylmethyl]-amide as a white solid (0.58 g, 49% yield): HPLC: Waters Symmetry $C_{18}$, 5 µm, 3.9×150 mm, 1 mL/min, 240 nm, 40/60 $CH_3CN/0.1\%$ $H_3PO_4$, 2.17 min (99.35%); mp: 212-214° C.; $^1$H NMR (DMSO-$d_6$) δ 2.02-2.06 (m, 1H, CHH), 2.43-2.62 (m, 2H, CHH, CHH), 2.81-2.96 (m, 1H, CHH), 4.66 (d, J=6.4 Hz, 2H, $CH_2$), 5.14 (dd, J=5.3, 12.6 Hz, 1H, CH), 7.61-7.66 (m, 1H, Ar), 7.80-7.90 (m, 3H, Ar), 7.97-8.07 (m, 2H, Ar), 8.67-8.69 (m, 1H, Ar), 9.64 (t, J=6.4 Hz, 1H, NH), 11.12 (s, 1H, NH); $^{13}$C NMR (DMSO-$d_6$) δ 21.99, 30.92, 42.37, 48.98, 122.07, 122.11, 123.52, 126.73, 129.79, 131.57, 133.58, 137.86, 147.49, 148.54, 149.71, 164.29, 166.99, 167.14, 169.81, 172.72; Anal Calcd for $C_{20}H_{16}N_4O_5+0.05H_2O$: C, 61.08; H, 4.13; N, 14.25. Found: C, 60.81; H, 3.82; N, 14.15.

5.94 3,4-dichloro-N-[2-(2,6-dioxo-piperidin-3-yl)-1,3-dioxo-2,3-dihydro-1H-isoindol-5-ylmethyl]-benzamide

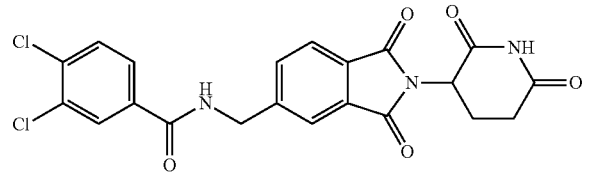 [SMILES: O=C1CCC(N2C(=O)c3ccc(CNC(=O)c4ccc(Cl)c(Cl)c4)cc3C2=O)C(=O)N1]

To a stirred mixture of 5-aminomethyl-2-(2,6-dioxo-piperidin-3-yl)-isoindole-1,3-dione hydrochloride (0.97 g, 3.00 mmol) and 3,4-dichlorobenzoyl chloride (0.69 g, 3.30 mmol) in THF (20 mL), was added DIPEA (1.05 mL, 6.00 mmol) at room temperature under nitrogen. The mixture was heated to 40° C. for 18 h then cooled to rt. The solvent was removed in vacuo and the residue was dissolved in EtOAc (100 mL). The organic layer was washed with dil. aq. HCl (2×150 mL), sat. $NaHCO_3$ (2×150 mL), water (100 mL), dried ($MgSO_4$) and then concentrated. The product was dried in vacuo to give 3,4-dichloro-N-[2-(2,6-dioxo-piperidin-3-yl)-1,3-dioxo-2,3-dihydro-1H-isoindol-5-ylmethyl]-benzamide as a white solid (1.23 g, 89% yield): HPLC: Waters Symmetry $C_{18}$, 5 µm, 3.9×150 mm, 1 mL/min, 240 nm, 40/60 $CH_3CN/0.1\%$ $H_3PO_4$, 9.40 min (98.44%); mp: 253-255° C.; $^1$H NMR (DMSO-$d_6$) δ 2.03-2.07 (m, 1H, CHH), 2.43-2.62 (m, 2H, CHH, CHH), 2.81-2.96 (m, 1H, CHH), 4.65 (d, J=5.7 Hz, 2H, $CH_2$), 5.15 (dd, J=5.2, 12.5 Hz, 1H, CH), 7.77-7.92 (m, 5H, Ar), 8.14 (d, J=1.8 Hz, 1H, Ar), 9.40 (t, J=5.7 Hz, 1H, NH), 11.13 (s, 1H, NH); $^{13}$C NMR (DMSO-$d_6$) δ 21.99, 30.93, 42.77, 49.01, 122.14, 123.57, 127.62, 129.27, 129.90, 130.81, 131.36, 131.62, 133.55, 134.23, 134.29, 147.07; Anal Calcd for $C_{21}H_{15}N_3O_5Cl_2$: C, 54.80; H, 3.28; N, 9.13. Found: C, 54.76; H, 3.29; N, 8.87.

5.95 pentanoic acid [2-(2,6-dioxo-piperidin-3-yl)-1,3-dioxo-2,3-dihydro-1H-isoindol-5-ylmethyl]-amide

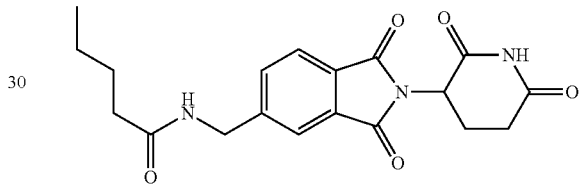

To a stirred mixture of 5-aminomethyl-2-(2,6-dioxo-piperidin-3-yl)-isoindole-1,3-dione hydrochloride (0.97 g, 3.00 mmol) and pentanoyl chloride (0.36 g, 3.00 mmol) in MeCN (20 mL), was added DIPEA (1.05 mL, 6.00 mmol) at room temperature under nitrogen. After 1 h, the solvent was removed in vacuo and the residue was dissolved in EtOAc (100 mL). The organic layer was washed with dil. aq. HCl (2×150 mL), water (100 mL), dried ($MgSO_4$) and then concentrated. The crude product was purified by column chromatography (0-5% $MeOH/CH_2Cl_2$). The product fractions were combined, concentrated and triturated in $Et_2O$ for 18 h. The product was dried in vacuo to give pentanoic acid [2-(2,6-dioxo-piperidin-3-yl)-1,3-dioxo-2,3-dihydro-1H-isoindol-5-ylmethyl]-amide as a white solid (0.77 g, 35% yield): HPLC: Waters Symmetry $C_{18}$, 5 µm, 3.9×150 mm, 1 mL/min, 240 nm, 40/60 $CH_3CN/0.1\%$ $H_3PO_4$, 2.71 min (95.58%); mp: 184-186° C.; $^1$H NMR (DMSO-$d_6$) δ 0.81-0.95 (m, 3H, $CH_3$), 1.28 (dq, J=7.3, 14.8 Hz, 2H, $CH_2$), 1.41-1.64 (m, 2H, $CH_2$), 1.97-2.13 (m, 1H, CHH), 2.17 (t, J=7.5 Hz, 2H, $CH_2$), 2.53-2.70 (m, 2H, CHH, CHH), 2.77-2.99 (m, 1H, CHH), 4.43 (d, J=6.0 Hz, 2H, $CH_2$), 5.15 (dd, J=5.4, 12.9 Hz, 1H, CH), 7.67-7.81 (m, 2H, Ar), 7.88 (d, J=7.7 Hz, 1H, Ar), 8.50 (t, J=5.9 Hz, 1H, NH), 11.13 (s, 1H, NH); $^{13}$C NMR (DMSO-$d_6$) δ 13.68, 21.79, 21.99, 27.37, 30.93, 34.98, 41.87, 48.99, 121.78, 123.48, 129.71, 131.59, 133.28, 147.84, 166.97, 167.12, 169.82, 172.47, 172.73; LCMS: MH=372; Anal Calcd for $C_{19}H_{21}N_3O_5$: C, 61.45; H, 5.70; N, 11.31. Found: C, 61.12; H, 5.54; N, 11.15.

5.96 quinoline-2-carboxylic acid [2-(2,6-dioxo-piperidin-3-yl)-1,3-dioxo-2,3-dihydro-1H-isoindol-5-ylmethyl]-amide

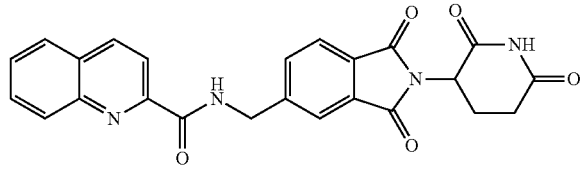 [SMILES: O=C1CCC(N2C(=O)c3ccc(CNC(=O)c4ccc5ccccc5n4)cc3C2=O)C(=O)N1]

To a stirred mixture of 5-aminomethyl-2-(2,6-dioxo-piperidin-3-yl)-isoindole-1,3-dione hydrochloride (0.97 g, 3.00 mmol) and quinoline-2-carbonyl chloride (0.57 g, 3.00 mmol) in MeCN (20 mL), was added DIPEA (1.05 mL, 6.00 mmol) at room temperature under nitrogen. The solvent was removed in vacuo and the residue was dissolved in $CH_2Cl_2$ (100 mL). The organic layer was washed with water (100 mL), brine (100 mL), dried ($MgSO_4$) and then concentrated. The crude product was purified by column chromatography (0-5% $MeOH/CH_2Cl_2$). The product fractions were combined, concentrated and triturated in $Et_2O$ for 18 h. The product was isolated by filtration and dried in vacuo to give quinoline-2-carboxylic acid [2-(2,6-dioxo-piperidin-3-yl)-1,3-dioxo-2,3-dihydro-1H-isoindol-5-ylmethyl]-amide as a white solid (1.15 g, 76% yield): HPLC: Waters Symmetry $C_{18}$, 5 µm, 3.9×150 mm, 1 mL/min, 240 nm, 40/60 $CH_3CN/0.1\%$ $H_3PO_4$, 2.08 min (96.58%); mp: 205-207° C.; $^1H$ NMR (DMSO-$d_6$) δ 1.93-2.16 (m, 1H, CHH), 2.53-2.70 (m, 2H, CHH, CHH), 2.77-3.02 (m, 1H, CHH), 4.74 (d, J=6.4 Hz, 2H, $CH_2$), 5.15 (dd, J=5.3, 12.8 Hz, 1H, CH), 7.66-7.82 (m, 1H, Ar), 7.82-7.99 (m, 4H, Ar), 8.03-8.25 (m, 3H, Ar), 8.59 (d, J=8.1 Hz, 1H, Ar), 9.75 (t, J=6.4 Hz, 1H, NH), 11.12 (s, 1H, NH); $^{13}C$ NMR (DMSO-$d_6$) δ 21.99, 30.92, 42.55, 48.99, 118.74, 122.24, 123.55, 128.15, 128.89, 129.15, 129.84, 130.60, 131.59, 133.67, 137.94, 146.05, 147.44, 149.89, 164.48, 169.82, 172.73; LCMS: MH=448; Anal Calcd for $C_{24}H_{18}N_4O_5$: C, 65.15; H, 4.10; N, 12.68. Found: C, 65.05; H, 4.05; N, 12.58.

5.97 6-ethylsulfanyl-pyridazine-3-carboxylic acid [2-(3-methyl-2,6-dioxo-piperidin-3-yl)-1,3-dioxo-2,3-dihydro-1H-isoindol-5-ylmethyl]amide

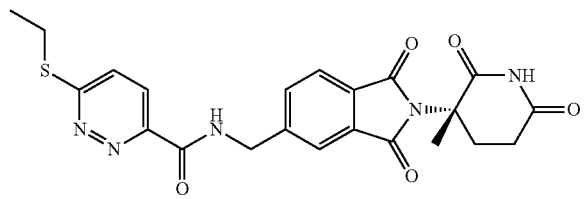 [SMILES: CCSc1ccc(C(=O)NCc2ccc3c(c2)C(=O)N([C@@]2(C)CCC(=O)NC2=O)C3=O)nn1]

A stirred mixture of 6-ethylsulfanyl-pyridazine-3-carboxylic acid (0.37 g, 2.00 mmol) and CDI (0.36 g, 2.20 mmol) in N,N-dimethylformamide (20 mL) was heated to 40° C. under nitrogen. After 1 h, 5-Aminomethyl-2-(3-methyl-2,6-dioxo-piperidin-3-yl)-isoindole-1,3-dione hydrochloride (0.68 g, 2.00 mmol) was added and the mixture was heated at 40° C. for 1.5 h. The mixture was cooled to rt and water (40 mL) was added. After 3 h, the product was isolated by filtration, washed with water (10 mL) and dried in vacuo to give 6-ethylsulfanyl-pyridazine-3-carboxylic acid [2-(3-methyl-2,6-dioxo-piperidin-3-yl)-1,3-dioxo-2,3-dihydro-1H-isoindol-5-ylmethyl]amide as a white solid (0.76 g, 81% yield): HPLC: Waters Symmetry $C_{18}$, 5 µm, 3.9×150 mm, 1 mL/min, 240 nm, 40/60 $CH_3CN/0.1\%$ $H_3PO_4$, 5.24 min (95.32%); mp: 160-162° C.; $^1H$ NMR (DMSO-$d_6$) δ 1.38 (t, J=7.3 Hz, 3H, $CH_3$), 1.88 (s, 3H, $CH_3$), 1.95-2.14 (m, 1H, CHH), 2.52-2.61 (m, 2H, CHH, CHH), 2.61-2.79 (m, 1H, CHH), 3.24-3.43 (m, 2H, $CH_2$), 4.66 (d, J=6.2 Hz, 2H, $CH_2$), 7.74-7.87 (m, 4H, Ar), 7.96 (d, J=8.9 Hz, 1H, Ar), 9.97 (t, J=6.2 Hz, 1H, NH), 11.02 (s, 1H, NH); $^{13}C$ NMR (DMSO-$d_6$) δ 12.67, 19.51, 22.51, 27.07, 27.60, 40.92, 57.25, 120.31, 121.67, 123.40, 125.41, 128.17, 129.87, 132.06, 145.52, 148.23, 161.45, 163.51, 166.22, 166.37, 170.65, 170.71; LCMS: MH=468; Anal Calcd for $C_{22}H_{21}N_5O_5S+0.2H_2O$: C, 56.09; H, 4.58; N, 14.87. Found: C, 55.86; H, 4.59; N, 14.72.

5.98 4-chloro-N-[2-(2,6-dioxo-piperidin-3-yl)-1,3-dioxo-2,3-dihydro-1H-isoindol-5-ylmethyl]-benzamide

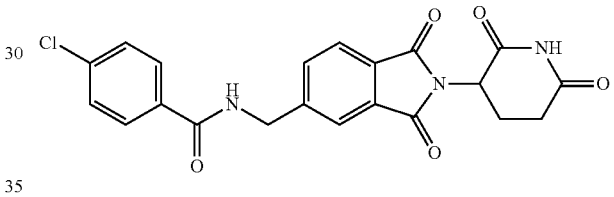

To a stirred mixture of 5-aminomethyl-2-(2,6-dioxo-piperidin-3-yl)-isoindole-1,3-dione hydrochloride (0.97 g, 3.00 mmol) and 4-chlorobenzoyl chloride (0.53 g, 3.30 mmol) in THF (20 mL), was added DIPEA (1.05 mL, 6.00 mmol) at room temperature under nitrogen. The mixture was heated to 40° C. for 18 h then cooled to rt. The solvent was removed in vacuo and the residue was dissolved in EtOAc (100 mL). The organic layer was washed with dil. aq. HCl (2×150 mL), water (100 mL), dried ($MgSO_4$) and then concentrated. The crude product was purified by column chromatography (0-5% $MeOH/CH_2Cl_2$). The product fractions were combined, concentrated and triturated in $Et_2O$ (50 mL) for 18 h. The product was isolated by filtration and dried in vacuo to give 4-chloro-N-[2-(2,6-dioxo-piperidin-3-yl)-1,3-dioxo-2,3-dihydro-1H-isoindol-5-ylmethyl]-benzamide as a white solid (0.80 g, 63% yield): HPLC: Waters Symmetry $C_{18}$, 5 µm, 3.9×150 mm, 1 mL/min, 240 nm, 40/60 $CH_3CN/0.1\%$ $H_3PO_4$, 4.97 min (97.05%); mp: 178-180° C.; $^1H$ NMR (DMSO-$d_6$) δ 1.92-2.15 (m, 1H, CHH), 2.54-2.71 (m, 2H, CHH, CHH), 2.77-3.02 (m, 1H, CHH), 4.65 (d, J=5.9 Hz, 2H, $CH_2$), 5.15 (dd, J=5.5, 12.8 Hz, 1H, CH), 7.53-7.63 (m, 2H, Ar), 7.74-7.87 (m, 2H, Ar), 7.87-8.03 (m, 3H, Ar), 9.31 (t, J=5.9 Hz, 1H, NH), 11.13 (s, 1H, NH); $^{13}C$ NMR (DMSO-$d_6$) δ 21.99, 30.93, 42.67, 48.99, 122.01, 123.55, 128.50, 129.21, 129.84, 131.62, 132.64, 133.47, 136.30, 147.38, 165.40, 166.96, 167.10, 169.80, 172.72; LCMS: MH=426/428; Anal Calcd for $C_{21}H_{16}N_3O_5Cl$: C, 58.98; H, 3.82; N, 9.83. Found: C, 58.67; H, 3.67; N, 9.53.

5.99 furan-2-carboxylic acid [2-(2,6-dioxo-piperidin-3-yl)-1,3-dioxo-2,3-dihydro-1H-isoindol-5-ylmethyl]-amide

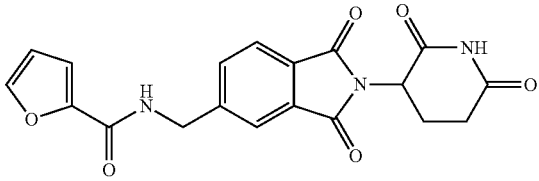

To a stirred mixture of 5-aminomethyl-2-(2,6-dioxo-piperidin-3-yl)-isoindole-1,3-dione hydrochloride (0.97 g, 3.00 mmol) and furan-2-carbonyl chloride (0.39 g, 3.00 mmol) in CH$_2$Cl$_2$ (20 mL), was added DIPEA (1.05 mL, 6.00 mmol) at room temperature under nitrogen. After 18 h, the product was isolated by filtration, washed with CH$_2$Cl$_2$ (10 mL) and dried in vacuo to give furan-2-carboxylic acid [2-(2,6-dioxo-piperidin-3-yl)-1,3-dioxo-2,3-dihydro-1H-isoindol-5-ylmethyl]-amide as a white solid (0.86 g, 75% yield): HPLC: Waters Symmetry C$_{18}$, 5 μm, 3.9×150 mm, 1 mL/min, 240 nm, 40/60 CH$_3$CN/0.1% H$_3$PO$_4$, 2.11 min (96.16%); mp: 180-182° C.; $^1$H NMR (DMSO-d$_6$) δ 1.94-2.17 (m, 1H, CHH), 2.53-2.70 (m, 2H, CHH, CHH), 2.77-3.02 (m, 1H, CHH), 4.59 (d, J=6.0 Hz, 2H, CH$_2$), 5.15 (dd, J=5.4, 12.7 Hz, 1H, CH), 6.65 (dd, J=1.8, 3.5 Hz, 1H, Ar), 7.15 (d, J=3.6 Hz, 1H, Ar), 7.74-7.85 (m, 2H, Ar), 7.85-7.97 (m, 2H, Ar), 9.12 (t, J=6.1 Hz, 1H, NH), 11.12 (s, 1H, NH); $^{13}$C NMR (DMSO-d$_6$) δ 21.99, 30.93, 41.87, 48.99, 111.93, 113.86, 121.97, 123.54, 129.81, 131.59, 133.44, 145.28, 147.39, 147.52, 157.93, 166.97, 167.10, 169.80, 172.72; LCMS: MH=382; Anal Calcd for C$_{19}$H$_{15}$N$_3$O$_6$+0.1H$_2$O: C, 59.56; H, 4.00; N, 10.97. Found: C, 59.26; H, 3.45; N, 10.80.

5.100 benzo[b]thiophene-2-carboxylic acid [2-(2,6-dioxo-piperidin-3-yl)-1,3-dioxo-2,3-dihydro-1H-isoindol-5-ylmethyl]-amide

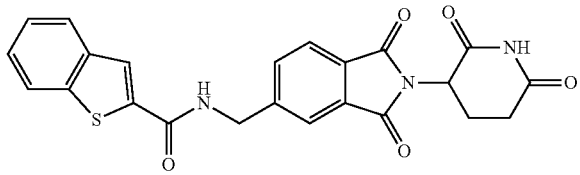 [SMILES: O=C1CCC(N2C(=O)c3ccc(CNC(=O)c4cc5ccccc5s4)cc3C2=O)C(=O)N1]

To a stirred mixture of 5-aminomethyl-2-(2,6-dioxo-piperidin-3-yl)-isoindole-1,3-dione hydrochloride (0.97 g, 3.00 mmol) and benzo[b]thiophene-2-carbonyl chloride (0.59 g, 3.00 mmol) in MeCN (20 mL), was added DIPEA (1.05 mL, 6.00 mmol) at room temperature under nitrogen. After 1 h, the solvent was removed in vacuo and the residue was dissolved in EtOAc (100 mL). The organic layer was washed with dil. aq. HCl (2×150 mL), water (100 mL), dried (MgSO$_4$) and then concentrated. The product was dried in vacuo to give benzo[b]thiophene-2-carboxylic acid[2-(2,6-dioxo-piperidin-3-yl)-1,3-dioxo-2,3-dihydro-1H-isoindol-5-ylmethyl]-amide as a white solid (0.75 g, 56% yield): HPLC: Waters Symmetry C$_{18}$, 5 μm, 3.9×150 mm, 1 mL/min, 240 nm, 40/60 CH$_3$CN/0.1% H$_3$PO$_4$, 7.03 min (96.23%); mp: 318-320° C.; $^1$H NMR (DMSO-d$_6$) δ 1.96-2.17 (m, 1H, CHH), 2.54-2.68 (m, 2H, CHH, CHH), 2.78-3.00 (m, 1H, CHH), 4.68 (d, J=5.9 Hz, 2H, CH$_2$), 5.15 (dd, J=5.4, 12.7 Hz, 1H, CH), 7.39-7.55 (m, 2H, Ar), 7.79-8.10 (m, 5H, Ar), 8.16 (s, 1H, Ar), 9.50 (t, J=5.9 Hz, 1H, NH), 11.13 (s, 1H, NH); $^{13}$C NMR (DMSO-d$_6$) δ 21.99, 30.93, 42.64, 49.01, 122.07, 122.83, 123.63, 124.97, 125.25, 126.32, 129.93, 131.66, 133.54, 139.10, 139.27, 140.25, 147.13, 161.80, 166.96, 167.10, 169.82, 172.73; LCMS: MH=448; Anal Calcd for C$_{23}$H$_{17}$N$_3$O$_5$S: C, 61.74; H, 3.83; N, 9.39. Found: C, 61.59; H, 3.53; N, 9.29.

5.101 N-[2-(2,6-dioxo-piperidin-3-yl)-1,3-dioxo-2,3-dihydro-1H-isoindol-5-ylmethyl]-4-methoxy-benzamide

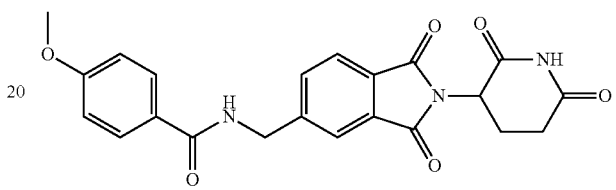

To a stirred mixture of 5-aminomethyl-2-(2,6-dioxo-piperidin-3-yl)-isoindole-1,3-dione hydrochloride (0.97 g, 3.00 mmol) and 4-methoxy-benzoyl chloride (0.51 g, 3.00 mmol) in MeCN (20 mL), was added DIPEA (1.05 mL, 6.00 mmol) at room temperature under nitrogen. After 1 h, the product was isolated by filtration, washed with MeCN (10 mL) and dried in vacuo to give N-[2-(2,6-dioxo-piperidin-3-yl)-1,3-dioxo-2,3-dihydro-1H-isoindol-5-ylmethyl]-4-methoxy-benzamide as a white solid (0.99 g, 79% yield): HPLC: Waters Symmetry C$_{18}$, 5 μm, 3.9×150 mm, 1 mL/min, 240 nm, 40/60 CH$_3$CN/0.1% H$_3$PO$_4$, 3.58 min (97.92%); mp: 215-217° C.; $^1$H NMR (DMSO-d$_6$) δ 1.94-2.20 (m, 1H, CHH), 2.39-2.70 (m, 2H, CHH, CHH), 2.78-3.04 (m, 1H, CHH), 3.82 (s, 3H, CH$_3$), 4.63 (d, J=5.9 Hz, 2H, CH$_2$), 5.14 (dd, J=5.4, 12.7 Hz, 1H, CH), 7.02 (d, J=8.9 Hz, 2H, Ar), 7.76-7.97 (m, 5H, Ar), 9.08 (t, J=5.9 Hz, 1H, NH), 11.12 (s, 1H, NH); $^{13}$C NMR (DMSO-d$_6$) δ 21.99, 30.93, 42.55, 48.99, 55.37, 113.60, 121.91, 123.53, 126.11, 129.11, 129.74, 131.59, 133.40, 147.87, 161.75, 165.91, 167.00, 167.15, 169.82, 172.73; LCMS: MH=422; Anal Calcd for C$_{22}$H$_{19}$N$_3$O$_6$: C, 62.70; H, 4.54; N, 9.97. Found: C, 62.40; H, 4.46; N, 10.12.

5.102 N-[2-(2,6-dioxo-piperidin-3-yl)-1,3-dioxo-2,3-dihydro-1H-isoindol-5-ylmethyl]-4-methyl-benzamide

To a stirred mixture of 5-aminomethyl-2-(2,6-dioxo-piperidin-3-yl)-isoindole-1,3-dione hydrochloride (0.97 g, 3.00 mmol) and 4-methyl-benzoyl chloride (0.46 g, 3.00 mmol) in MeCN (20 mL), was added DIPEA (1.05 mL, 6.00 mmol) at room temperature under nitrogen. After 1 h, the solvent was removed in vacuo and the residue was dissolved in EtOAc (100 mL). The organic layer was washed with dil. aq. HCl (2×150 mL), water (100 mL), dried (MgSO$_4$) and then concentrated. The product was triturated in Et$_2$O (50 mL) for 18 h then filtered and dried in vacuo to give N-[2-(2,6-dioxo-piperidin-3-yl)-1,3-dioxo-2,3-dihydro-1H-isoindol-5-ylmethyl]-4-methyl-benzamide as a white solid (0.85 g, 70% yield): HPLC: Waters Symmetry C$_{18}$, 5 µm, 3.9×150 mm, 1 mL/min, 240 nm, 40/60 CH$_3$CN/0.1% H$_3$PO$_4$, 4.48 min (96.54%); mp: 194-196° C.; $^1$H NMR (DMSO-d$_6$) δ 1.97-2.14 (m, 1H, CHH), 2.36 (s, 3H, CH$_3$), 2.44-2.71 (m, 2H, M$_{01}$), 2.78-3.04 (m, 1H, CHH), 4.63 (d, J=5.9 Hz, 2H, CH$_2$), 5.14 (dd, J=5.4, 12.9 Hz, 1H, CH), 7.30 (d, J=7.9 Hz, 2H, Ar), 7.75-7.86 (m, 4H, Ar), 7.90 (d, J=7.6 Hz, 1H, Ar), 9.14 (t, J=5.9 Hz, 1H, NH), 11.12 (s, 1H, NH); $^{13}$C NMR (DMSO-d$_6$) δ 20.96, 21.99, 30.93, 42.57, 49.01, 121.95, 123.53, 127.27, 128.91, 129.77, 131.14, 131.60, 133.42, 141.37, 147.73, 166.30, 166.99, 167.13, 169.80, 172.72; LCMS: MH=406; Anal Calcd for C$_{22}$H$_{19}$N$_3$O$_5$+0.1H$_2$O: C, 64.89; H, 4.75; N, 10.32. Found: C, 64.72; H, 4.70; N, 10.15.

5.103 5-ethoxy-pyridine-2-carboxylic acid[2-(2,6-dioxo-piperidin-3-yl)-1,3-dioxo-2,3-dihydro-1H-isoindol-5-ylmethyl]-amide

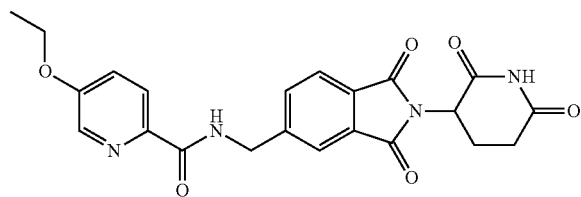 [SMILES: CCOc1ccc(C(=O)NCc2ccc3c(c2)C(=O)N(C2CCC(=O)NC2=O)C3=O)nc1]

A stirred mixture of 5-ethoxy-pyridine-2-carboxylic acid (0.50 g, 3.00 mmol) and CDI (0.54 g, 3.30 mmol) in N,N-dimethylformamide (20 mL) was heated to 40° C. under nitrogen. After 1 h, 5-aminomethyl-2-(2,6-dioxo-piperidin-3-yl)-isoindole-1,3-dione methane sulfonate (1.15 g, 3.00 mmol) was added and the mixture was heated at 40° C. for 1.5 h. The mixture was cooled to rt and water (40 mL) was added. After 2 h, the solids were isolated by filtration. The product was dissolved in MeOH (200 mL) and treated with decolorizing carbon. The carbon was removed by filtration and the filtrate was concentrated until precipitation was observed. The product was isolated by filtration, washed with MeOH (5 mL) and dried in vacuo to give 5-ethoxy-pyridine-2-carboxylic acid[2-(2,6-dioxo-piperidin-3-yl)-1,3-dioxo-2,3-dihydro-1H-isoindol-5-ylmethyl]-amide as a white solid (0.89 g, 68% yield): HPLC: Waters Symmetry C$_{18}$, 5 µm, 3.9×150 mm, 1 mL/min, 240 nm, 40/60 CH$_3$CN/ 0.1% H$_3$PO$_4$, 4.24 min (99.33%); mp: 185-187° C.; $^1$H $^1$H NMR (DMSO-d$_6$) δ 1.37 (t, J=7.0 Hz, 3H, CH$_3$), 1.95-2.16 (m, 1H, CHH), 2.40-2.70 (m, 2H, CHH, CHH), 2.78-3.01 (m, 1H, CHH), 4.19 (q, J=7.0 Hz, 2H, CH$_2$), 4.63 (d, J=6.2 Hz, 2H, CH$_2$), 5.14 (dd, J=5.4, 12.9 Hz, 1H, CH), 7.53 (dd, J=2.9, 8.8 Hz, 1H, Ar), 7.74-7.93 (m, 3H, Ar), 8.00 (d, J=8.7 Hz, 1H, Ar), 8.32 (d, J=2.5 Hz, 1H, Ar), 9.42 (t, J=6.4 Hz, 1H, NH), 11.11 (s, 1H, NH); $^{13}$C NMR (DMSO-d$_6$) δ 14.40, 21.99, 30.93, 42.30, 48.99, 64.07, 121.27, 122.07, 123.39, 123.50, 129.74, 131.54, 133.54, 136.79, 142.16, 147.74, 156.99, 164.09, 167.00, 167.15, 169.80, 172.73; LCMS: MH=437; Anal Calcd for C$_{22}$H$_{20}$N$_4$O$_6$: C, 60.55; H, 4.62; N, 12.84. Found: C, 60.19; H, 4.53; N, 12.71.

5.104 N-[2-(2,6-dioxo-piperidin-3-yl)-1,3-dioxo-2,3-dihydro-1H-isoindol-5-ylmethyl]-6-ethoxy-nicotinamide

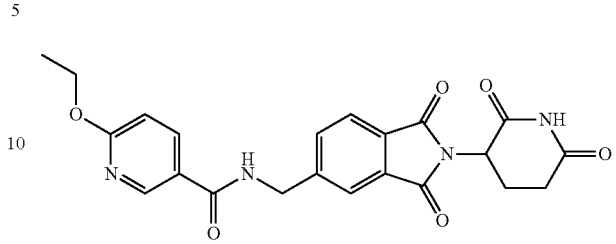

A stirred mixture of 6-ethoxy-nicotinic acid (0.50 g, 3.00 mmol) and CDI (0.54 g, 3.30 mmol) in N,N-dimethylformamide (20 mL) was heated to 40° C. under nitrogen. After 1 h, 5-aminomethyl-2-(2,6-dioxo-piperidin-3-yl)-isoindole-1,3-dione methane sulfonate (1.15 g, 3.00 mmol) was added and the mixture was heated at 40° C. for 1.5 h. The mixture was cooled to rt and water (40 mL) was added. The solvent was removed in vacuo and the crude product was purified by column chromatography (EtOAc/hexanes). The product fractions were combined, concentrated and the residue was triturated in Et$_2$O (20 mL) for 18 h. The product was isolated by filtration and dried in vacuo to give N-[2-(2,6-dioxo-piperidin-3-yl)-1,3-dioxo-2,3-dihydro-1H-isoindol-5-ylmethyl]-6-ethoxy-nicotinamide as a white solid (1.11 g, 85% yield): HPLC: Waters Symmetry C$_{18}$, 5 µm, 3.9×150 mm, 1 mL/min, 240 nm, 40/60 CH$_3$CN/0.1% H$_3$PO$_4$, 3.04 min (98.73%); mp: 243-245° C.; $^1$H NMR (DMSO-d$_6$) δ 1.33 (t, J=7.1 Hz, 3H, CH$_3$), 1.96-2.16 (m, 1H, CHH), 2.41-2.69 (m, 2H, CHH, CHH), 2.79-3.00 (m, 1H, CHH), 4.37 (q, J=7.1 Hz, 2H, CH$_2$), 4.65 (d, J=5.9 Hz, 2H, CH$_2$), 5.15 (dd, J=5.4, 12.7 Hz, 1H, CH), 6.88 (dd, J=0.7, 8.8 Hz, 1H, Ar), 7.77-7.94 (m, 3H, Ar), 8.16 (dd, J=2.6, 8.7 Hz, 1H, Ar), 8.71 (dd, J=0.8, 2.5 Hz, 1H, Ar), 9.21 (t, J=5.9 Hz, 1H, NH), 11.12 (s, 1H, NH); $^{13}$C NMR (DMSO-d$_6$) δ 14.41, 21.99, 30.93, 42.51, 49.01, 61.84, 110.27, 121.99, 123.04, 123.55, 129.82, 131.62, 133.44, 138.18, 147.13, 147.48, 164.79, 165.00, 166.97, 167.12, 169.80, 172.72; LCMS: MH=437; Anal Calcd for C$_{22}$H$_{20}$N$_4$O$_6$+0.1H$_2$O: C, 60.30; H, 4.65; N, 12.78. Found: C, 60.08; H, 4.62; N, 12.77.

5.105 6-ethoxy-pyridazine-3-carboxylic acid [2-(2,6-dioxo-piperidin-3-yl)-1,3-dioxo-2,3-dihydro-1H-isoindol-5-ylmethyl]-amide

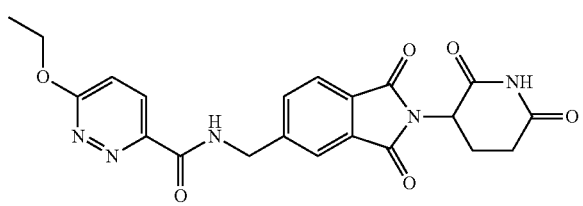 [SMILES: CCOc1ccc(C(=O)NCc2ccc3c(c2)C(=O)N(C2CCC(=O)NC2=O)C3=O)nn1]

A stirred mixture of 6-ethoxy-pyridazine-3-carboxylic acid (0.50 g, 3.00 mmol) and CDI (0.54 g, 3.30 mmol) in N,N-dimethylformamide (20 mL) was heated to 40° C. under nitrogen. After 1 h, 5-aminomethyl-2-(2,6-dioxo-piperidin-3-yl)-isoindole-1,3-dione methane sulfonate (1.15 g, 3.00 mmol) was added and the mixture was heated at 40° C. for 1.5 h. The mixture was cooled to rt and water (40 mL)

was added. After 1 h, the product was isolated by filtration, washed with water (10 mL) and dried in vacuo to give 6-ethoxy-pyridazine-3-carboxylic acid [2-(2,6-dioxo-piperidin-3-yl)-1,3-dioxo-2,3-dihydro-1H-isoindol-5-ylmethyl]-amide as a white solid (1.15 g, 88% yield): HPLC: Waters Symmetry $C_{18}$, 5 μm, 3.9×150 mm, 1 mL/min, 240 nm, 30/70 $CH_3CN$/0.1% $H_3PO_4$, 6.89 min (98.61%); mp: 238-240° C.; $^1$H NMR (DMSO-$d_6$) δ 1.42 (t, J=7.1 Hz, 3H, $CH_3$), 1.96-2.14 (m, 1H, CHH), 2.42-2.69 (m, 2H, CHH, CHH), 2.78-3.01 (m, 1H, CHH), 4.58 (q, J=7.0 Hz, 2H, $CH_2$), 4.68 (d, J=6.2 Hz, 2H, $CH_2$), 5.14 (dd, J=5.4, 12.9 Hz, 1H, CH), 7.35 (d, J=9.1 Hz, 1H, Ar), 7.76-7.95 (m, 3H, Ar), 8.09 (d, J=9.1 Hz, 1H, Ar), 9.85 (t, J=6.2 Hz, 1H, NH), 11.12 (s, 1H, NH); $^{13}$C NMR (DMSO-$d_6$) δ 14.28, 21.99, 30.93, 42.39, 48.99, 63.47, 117.91, 122.10, 123.53, 128.83, 129.82, 131.59, 133.57, 147.30, 149.11, 162.93, 165.86, 166.99, 167.13, 169.83, 172.75; LCMS: MH=438; Anal Calcd for $C_{21}H_{19}N_5O_6$: C, 57.66; H, 4.38; N, 16.01. Found: C, 57.32; H, 4.16; N, 15.80.

5.106 6-ethoxy-pyridazine-3-carboxylic acid [2-(3-methyl-2,6-dioxo-piperidin-3-yl)-1,3-dioxo-2,3-dihydro-1H-isoindol-5-ylmethyl]-amide

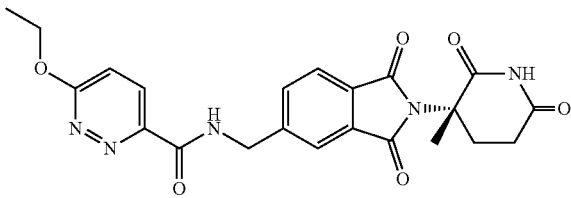 [SMILES: CCOc1ccc(C(=O)NCc2ccc3c(c2)C(=O)N([C@@]2(C)CCC(=O)NC2=O)C3=O)nn1]

A stirred mixture of 6-ethoxy-pyridazine-3-carboxylic acid (0.34 g, 2.00 mmol) and CDI (0.36 g, 2.20 mmol) in N,N-dimethylformamide (20 mL) was heated to 40° C. under nitrogen. After 1 h, 5-Aminomethyl-2-(3-methyl-2,6-dioxo-piperidin-3-yl)-isoindole-1,3-dione hydrochloride (0.68 g, 2.00 mmol) was added and the mixture was heated at 40° C. for 1.5 h. The mixture was cooled to rt and water (40 mL) was added. After 1 h, the product was isolated by filtration, washed with water (10 mL) and dried in vacuo to give 6-ethoxy-pyridazine-3-carboxylic acid [2-(3-methyl-2,6-dioxo-piperidin-3-yl)-1,3-dioxo-2,3-dihydro-1H-isoindol-5-ylmethyl]-amide as a white solid (0.54 g, 60% yield): HPLC: Waters Symmetry $C_{18}$, 5 μm, 3.9×150 mm, 1 mL/min, 240 nm, 30/70 $CH_3CN$/0.1% $H_3PO_4$, 9.24 min (99.01%); mp: 126-128° C.; $^1$H NMR (DMSO-$d_6$) δ 1.41 (t, J=7.1 Hz, 3H, $CH_3$), 1.88 (s, 3H, $CH_3$), 1.97-2.13 (m, 1H, CHH), 2.52-2.62 (m, 2H, CHH, CHH), 2.61-2.78 (m, 1H, CHH), 4.58 (q, J=7.1 Hz, 2H, $CH_2$), 4.65 (d, J=6.2 Hz, 2H, $CH_2$), 7.35 (d, J=9.1 Hz, 1H, Ar), 7.81 (s, 3H, Ar), 8.08 (d, J=9.1 Hz, 1H, Ar), 9.84 (t, J=6.3 Hz, 1H, NH), 11.01 (s, 1H, NH); $^{13}$C NMR (DMSO-$d_6$) δ 14.28, 21.00, 28.57, 29.09, 42.38, 58.75, 63.47, 117.91, 121.75, 123.16, 128.80, 129.65, 131.37, 133.53, 147.14, 149.10, 162.90, 165.86, 167.73, 167.88, 172.14, 172.19; LCMS: MH=452; Anal Calcd for $C_{22}H_{21}N_5O_6$+0.25$H_2O$: C, 57.96; H, 4.75; N, 15.36. Found: C, 57.66; H, 4.61; N, 15.14.

5.107 6-ethylsulfanyl-pyridazine-3-carboxylic acid [2-(2,6-dioxo-piperidin-3-yl)-1,3-dioxo-2,3-dihydro-1H-isoindol-5-ylmethyl]-amide

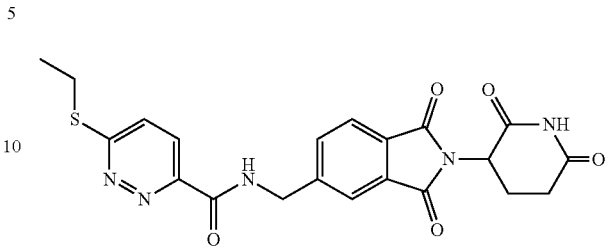

A stirred mixture of 6-ethylsulfanyl-pyridazine-3-carboxylic acid (0.37 g, 2.00 mmol) and CDI (0.36 g, 2.20 mmol) in N,N-dimethylformamide (20 mL) was heated to 40° C. under nitrogen. After 1 h, 5-aminomethyl-2-(2,6-dioxo-piperidin-3-yl)-isoindole-1,3-dione methane sulfonate (0.77 g, 2.00 mmol) was added and the mixture was heated at 40° C. for 1.5 h. The mixture was cooled to rt and water (40 mL) was added. After 2 h, the product was isolated by filtration, washed with water (10 mL) and dried in vacuo to give 6-Ethylsulfanyl-pyridazine-3-carboxylic acid [2-(2,6-dioxo-piperidin-3-yl)-1,3-dioxo-2,3-dihydro-1H-isoindol-5-ylmethyl]-amide as a white solid (0.78 g, 86% yield): HPLC: Waters Symmetry $C_{18}$, 5 μm, 3.9×150 mm, 1 mL/min, 240 nm, 40/60 $CH_3CN$/0.1% $H_3PO_4$, 4.43 min (96.78%); mp: 205-207° C.; $^1$H NMR (DMSO-$d_6$) δ 1.38 (t, J=7.3 Hz, 3H, $CH_3$), 1.98-2.13 (m, 1H, CHH), 2.43-2.69 (m, 2H, CHH, CHH), 2.79-3.00 (m, 1H, CHH), 3.24-3.42 (m, 2H, $CH_2$), 4.69 (d, J=6.2 Hz, 2H, $CH_2$), 5.15 (dd, J=5.3, 12.8 Hz, 1H, CH), 7.75-7.93 (m, 4H, Ar), 7.97 (d, J=9.1 Hz, 1H, Ar), 9.98 (t, J=6.3 Hz, 5H, NH), 11.13 (s, 1H, NH); $^{13}$C NMR (DMSO-$d_6$) δ 14.18, 21.99, 24.01, 30.93, 42.42, 48.99, 122.15, 123.53, 124.92, 126.89, 129.85, 131.57, 133.60, 147.19, 149.74, 162.99, 165.00, 166.97, 167.12, 169.82, 172.73; LCMS: MH=454; Anal Calcd for $C_{21}H_{19}N_5O_5S$: C, 55.62; H, 4.22; N, 15.44. Found: C, 55.43; H, 4.09; N, 15.22.

5.108 morpholine-4-carboxylic acid [2-(2,6-dioxo-piperidin-3-yl)-1-oxo-2,3-dihydro-1H-isoindol-5-ylmethyl]-amide

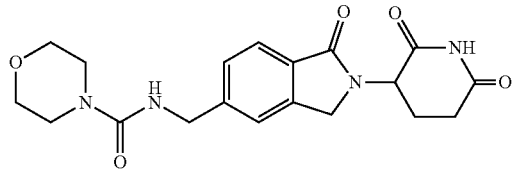 [SMILES: O=C1CCC(N2Cc3cc(CNC(=O)N4CCOCC4)ccc3C2=O)C(=O)N1]

To a stirred mixture of 3-(5-aminomethyl-1-oxo-1,3-dihydro-isoindol-2-yl)-piperidine-2,6-dione (0.37 g, 1 mmol) and triethylamine (0.30 mL, 2.2 mmol) in acetonitrile (10 mL) was added morpholine-4-carbonyl chloride (012 mL, 1.05 mmol) at room temperature under nitrogen. After 4 h, the reaction mixture was filtered and rinsed with acetonitrile (30 mL) and the filtrate was concentrate on the rota-vap. The residue was stirred with 20 mL of acetonitrile and water mixture (1:1). The resulted suspension was filtered to give morpholine-4-carboxylic acid [2-(2,6-dioxo-piperidin-3-yl)-1-oxo-2,3-dihydro-1H-isoindol-5-ylmethyl]-amide as a white solid (0.08 g, 20% yield): HPLC: Waters Nova-Pak C18 column, 3.9×150 mm, 4 μm; gradient CH$_3$CN/0.1% aq H$_3$PO$_4$, 10 min, 1.0 mL/min, 4.8 min (96%); mp: 208-210° C.; $^1$H NMR (DMSO-d$_6$) δ 1.92-2.07 (m, 1H, CHH), 2.39 (qd, J=4.4, 13.3 Hz, 1H, CHH), 2.55-2.66 (m, 1H, CHH), 2.84-2.99 (m, 1H, CHH), 3.27-3.32 (m, 4H, CH$_2$+CH$_2$), 3.52-3.59 (m, 4H, CH$_2$+CH$_2$), 4.25-4.49 (m, 4H, CH$_2$+CH$_2$), 5.11 (dd, J=5.0, 13.3 Hz, 1H, CHN), 7.22 (t, J=5.8 Hz, 1H, Ar), 7.40 (d, J=7.9 Hz, 1H, Ar), 7.47 (s, 1H, NH), 7.67 (d, J=7.9 Hz, 1H, Ar), 10.98 (s, 1H, NH); $^{13}$C NMR (DMSO-d$_6$) δ 22.51, 31.20, 43.54, 43.86, 47.10, 51.56, 65.92, 121.88, 122.77, 126.89, 130.11, 142.23, 145.28, 157.57, 168.02, 171.01, 172.86; LCMS: MH=387; Anal Calcd for C$_{19}$H$_{22}$N$_4$O$_5$+0.6H2O: C, 57.45; H, 5.89; N, 14.10. Found: C, 57.10; H, 6.07; N, 13.97.

5.109 General Synthetic Scheme A

A mixture of appropriate carboxylic acid (1.0 mmol) and CDI (0.17 g, 1.05 mmol) in DMF (10 mL) are heated at 40° C. for 2 hours. Then, 3-(5-aminomethyl-1-oxo-1,3-dihydro-isoindol-2-yl)-piperidine-2,6-dione methane sulfonate (0.37 g, 1.0 mmol) is added, and the mixture is stirred for an additional 6 hours. The mixture is cooled and evaporated under vacuum, and the residue is purified by preparative HPLC. Synthetic Scheme A may be used to prepare the following compounds.

5.109.1 2-(3-chloro-4-methylphenyl)-N-((2-(2,6-dioxopiperidin-3-yl)-1-oxoisoindolin-5-yl)methyl) acetamide

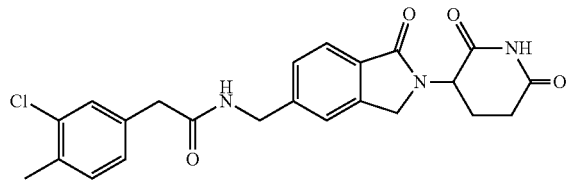 [SMILES: Cc1ccc(CC(=O)NCc2ccc3c(c2)CN(C2CCC(=O)NC2=O)C3=O)cc1Cl]

Using synthetic Scheme A, 2-(3-chloro-4-methylphenyl)-N-((2-(2,6-dioxopiperidin-3-yl)-1-oxoisoindolin-5-yl)methyl)acetamide can be prepared from 2-(3-chloro-4-methylphenyl)acetic acid.

5.109.2 2-(3,4-dimethylphenyl)-N-((2-(2,6-dioxopiperidin-3-yl)-1-oxoisoindolin-5-yl)methyl)acetamide

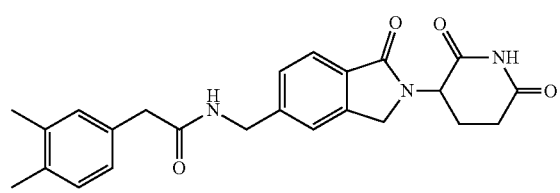 [SMILES: Cc1ccc(CC(=O)NCc2ccc3c(c2)CN(C2CCC(=O)NC2=O)C3=O)cc1C]

Using Synthetic Scheme A, 2-(3,4-dimethylphenyl)-N-((2-(2,6-dioxopiperidin-3-yl)-1-oxoisoindolin-5-yl)methyl) acetamide can be prepared from 2-(3,4-dimethylphenyl) acetic acid.

5.109.3 2-(3-chloro-4-(trifluoromethyl)phenyl)-N-((2-(2,6-dioxopiperidin-3-yl)-1-oxoisoindolin-5-yl) methyl) acetamide

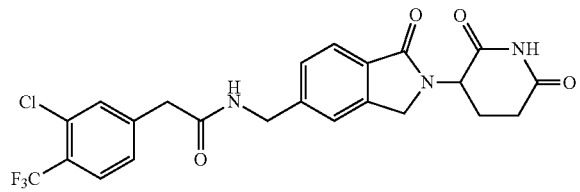 [SMILES: O=C(Cc1ccc(C(F)(F)F)c(Cl)c1)NCc1ccc2c(c1)CN(C1CCC(=O)NC1=O)C2=O]

Using Synthetic Scheme A, 2-(3-chloro-4-(trifluoromethyl)phenyl)-N-((2-(2,6-dioxopiperidin-3-yl)-1-oxoisoindolin-5-yl)methyl)acetamide can be prepared from 2-(3-chloro-4-(trifluoromethyl)phenyl)acetic acid.

5.109.4 2-(3-chlorophenyl)-N-((2-(2,6-dioxopiperidin-3-yl)-1-oxoisoindolin-5-yl)methyl)acetamide

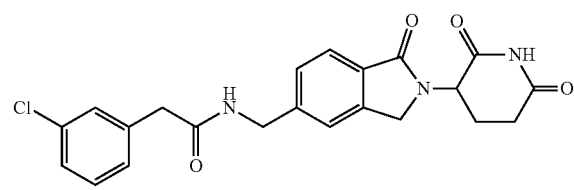 [SMILES: O=C(Cc1cccc(Cl)c1)NCc1ccc2c(c1)CN(C1CCC(=O)NC1=O)C2=O]

Using Synthetic Scheme A, 2-(3-chlorophenyl)-N-((2,6-dioxopiperidin-3-yl)-1-oxoisoindolin-5-yl)methyl)acetamide can be prepared from 2-(3-chlorophenyl)acetic acid.

5.109.5 2-(2-chlorophenyl)-N-((2-(2,6-dioxopiperidin-3-yl)-1-oxoisoindolin-5-yl)methyl)acetamide

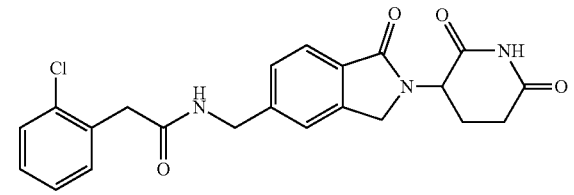 [SMILES: O=C(Cc1ccccc1Cl)NCc1ccc2c(c1)CN(C1CCC(=O)NC1=O)C2=O]

Using Synthetic Scheme A, 2-(2-chlorophenyl)-N-((2,6-dioxopiperidin-3-yl)-1-oxoisoindolin-5-yl)methyl)acetamide can be prepared from 2-(3-chlorophenyl)acetic acid.

5.109.6 N-((2-(2,6-dioxopiperidin-3-yl)-1-oxoisoindolin-5-yl)methyl)-2-o-tolylacetamide

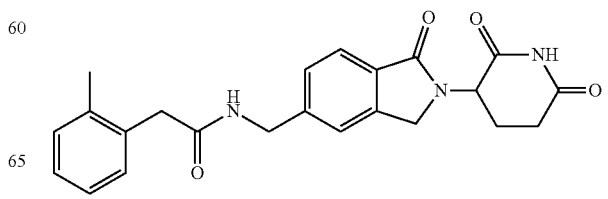

Using Synthetic Scheme A, N-((2-(2,6-dioxopiperidin-3-yl)-1-oxoisoindolin-5-yl)methyl)-2-o-tolylacetamide can be prepared from o-tolylacetic acid.

5.109.7 N-((2-(2,6-dioxopiperidin-3-yl)-1-oxoisoindolin-5-yl)methyl)-2-m-tolylacetamide

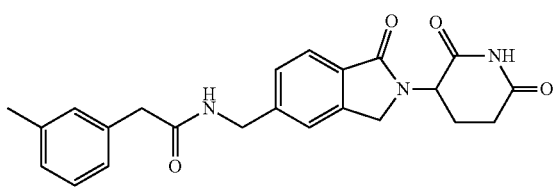 [SMILES: Cc1cccc(CC(=O)NCc2ccc3c(c2)CN(C2CCC(=O)NC2=O)C3=O)c1]

Using Synthetic Scheme A, N-((2-(2,6-dioxopiperidin-3-yl)-1-oxoisoindolin-5-yl)methyl)-2-m-tolylacetamide can be prepared from m-tolylacetic acid.

5.109.8 N-((2-(2,6-dioxopiperidin-3-yl)-1-oxoisoindolin-5-yl)methyl)-2-p-tolylacetamide

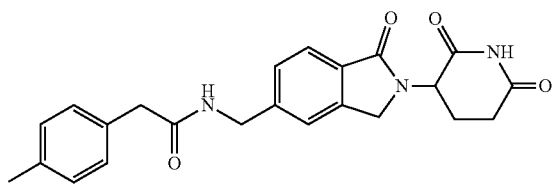 [SMILES: Cc1ccc(CC(=O)NCc2ccc3c(c2)CN(C2CCC(=O)NC2=O)C3=O)cc1]

Using Synthetic Scheme A, N-((2-(2,6-dioxopiperidin-3-yl)-1-oxoisoindolin-5-yl)methyl)-2-p-tolylacetamide can be prepared from p-tolylacetic acid.

5.109.9 2-(4-bromophenyl)-N-((2-(2,6-dioxopiperidin-3-yl)-1-oxoisoindolin-5-yl)methyl)acetamide

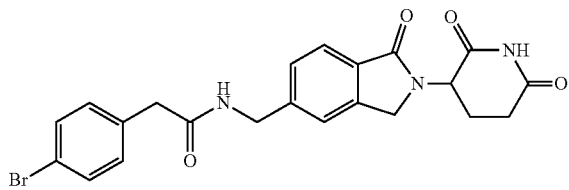 [SMILES: O=C(Cc1ccc(Br)cc1)NCc1ccc2c(c1)CN(C1CCC(=O)NC1=O)C2=O]

Using Synthetic Scheme A, 2-(4-bromophenyl)-N-((2-(2,6-dioxopiperidin-3-yl)-1-oxoisoindolin-5-yl)methyl)acetamide can be prepared from 2-(4-bromophenyl)acetic acid.

5.109.10 N-((2-(2,6-dioxopiperidin-3-yl)-1-oxoisoindolin-5-yl)methyl)-2-(4-(methylsulfonyl)phenyl) acetamide

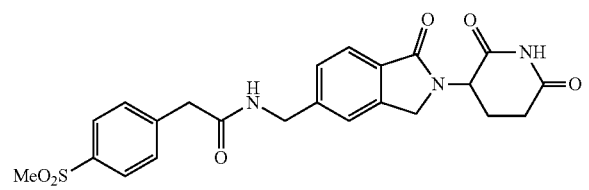 [SMILES: CS(=O)(=O)c1ccc(CC(=O)NCc2ccc3c(c2)CN(C2CCC(=O)NC2=O)C3=O)cc1]

Using Synthetic Scheme A, N-((2-(2,6-dioxopiperidin-3-yl)-1-oxoisoindolin-5-yl)methyl)-2-(4-(methylsulfonyl)phenyl)acetamide can be prepared from 2-(4-(methylsulfonyl)phenyl)acetic acid.

5.109.11 2-(2,3-dihydrobenzofuran-5-yl)-N-((2-(2,6-dioxopiperidin-3-yl)-1-oxoisoindolin-5-yl)methyl) acetamide

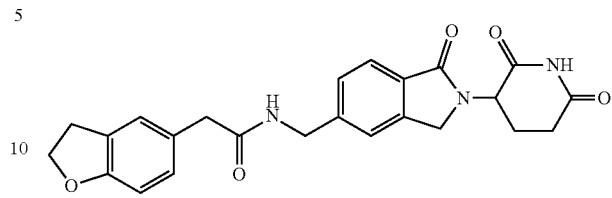

Using Synthetic Scheme A, 2-(2,3-dihydrobenzofuran-5-yl)-N-((2-(2,6-dioxopiperidin-3-yl)-1-oxoisoindolin-5-yl)methyl)acetamide can be prepared from 2-(2,3-dihydrobenzofuran-5-yl)acetic acid.

5.109.12 2-(4-tert-butylphenyl)-N-((2-(2,6-dioxopiperidin-3-yl)-1-oxoisoindolin-5-yl)methyl)acetamide

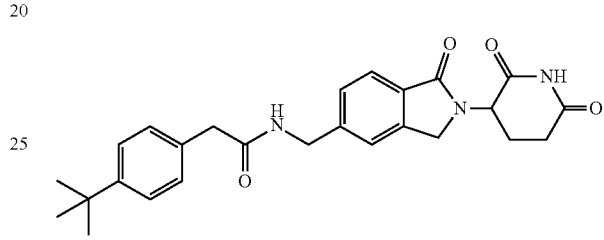

Using Synthetic Scheme A, 2-(4-tert-butylphenyl)-N-((2-(2,6-dioxopiperidin-3-yl)-1-oxoisoindolin-5-yl)methyl)acetamide can be prepared from 2-(4-tert-butylphenyl)acetic acid.

5.109.13 2-(4-iso-propylphenyl)-N-((2-(2,6-dioxopiperidin-3-yl)-1-oxoisoindolin-5-yl)methyl)acetamide

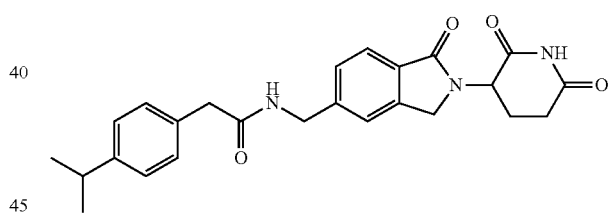

Using Synthetic Scheme A, 2-(4-iso-propylphenyl)-N-((2-(2,6-dioxopiperidin-3-yl)-1-oxoisoindolin-5-yl)methyl)acetamide can be prepared from 2-(4-iso-propylphenyl)acetic acid.

5.109.14 N-((2-(2,6-dioxopiperidin-3-yl)-1-oxoisoindolin-5-yl)methyl)-2-(4-(ethylthio)phenyl) acetamide

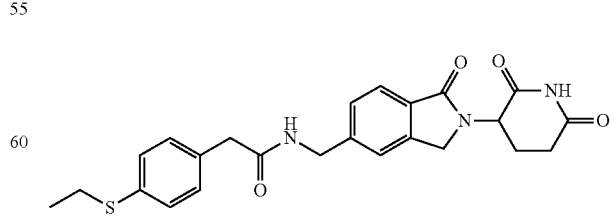

Using Synthetic Scheme A, N-((2-(2,6-dioxopiperidin-3-yl)-1-oxoisoindolin-5-yl)methyl)-2-(4-(ethylthio)phenyl)acetamide can be prepared from 2-(4-(ethylthio)phenyl)acetic acid.

5.109.15 N-((2-(2,6-dioxopiperidin-3-yl)-1-ox-oisoindolin-5-yl)methyl)isoquinoline-7-carboxamide

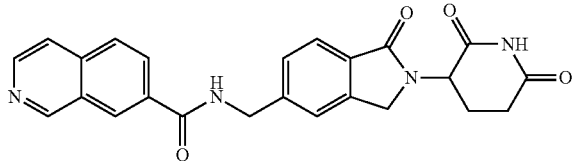 [SMILES: O=C1CCC(N2Cc3cc(CNC(=O)c4ccc5ccncc5c4)ccc3C2=O)C(=O)N1]

Using Synthetic Scheme A, N-((2-(2,6-dioxopiperidin-3-yl)-1-oxoisoindolin-5-yl)methyl)isoquinoline-7-carboxamide can be prepared from isoquinoline-7-carboxylic acid.

5.109.16 N-((2-(2,6-dioxopiperidin-3-yl)-1-ox-oisoindolin-5-yl)methyl)quinoline-7-carboxamide

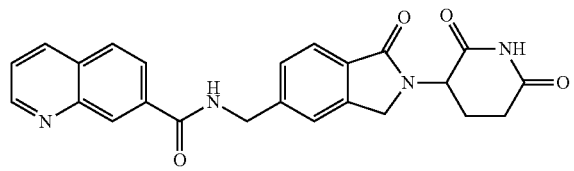 [SMILES: O=C1CCC(N2Cc3cc(CNC(=O)c4ccc5cccnc5c4)ccc3C2=O)C(=O)N1]

Using Synthetic Scheme A, N-((2-(2,6-dioxopiperidin-3-yl)-1-oxoisoindolin-5-yl)methyl)quinoline-7-carboxamide can be prepared from quinoline-7-carboxylic acid.

5.109.17 N-((2-(2,6-dioxopiperidin-3-yl)-1-ox-oisoindolin-5-yl)methyl)isoquinoline-6-carboxamide

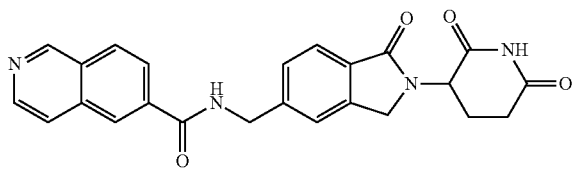 [SMILES: O=C1CCC(N2Cc3cc(CNC(=O)c4ccc5cnccc5c4)ccc3C2=O)C(=O)N1]

Using Synthetic Scheme A, N-((2-(2,6-dioxopiperidin-3-yl)-1-oxoisoindolin-5-yl)methyl)isoquinoline-6-carboxamid can be prepared from isoquinoline-6-carboxylic acid.

5.109.18 N-((2-(2,6-dioxopiperidin-3-yl)-1-ox-oisoindolin-5-yl)methyl)-2-methyl-1,2,3,4-tetrahy-droisoquinoline-7-carboxamide

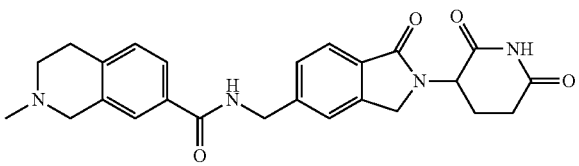 [SMILES: CN1CCc2ccc(C(=O)NCc3ccc4c(c3)CN(C3CCC(=O)NC3=O)C4=O)cc2C1]

Using Synthetic Scheme A, N-((2-(2,6-dioxopiperidin-3-yl)-1-oxoisoindolin-5-yl)methyl)-2-methyl-1,2,3,4-tetrahy-droisoquinoline-7-carboxamide can be prepared from 2-methyl-1,2,3,4-tetrahydroisoquinoline-7-carboxylic acid.

5.109.19 N-((2-(2,6-dioxopiperidin-3-yl)-1-ox-oisoindolin-5-yl)methyl)-2-isobutyl-1,2,3,4-tetrahy-droisoquinoline-7-carboxamide

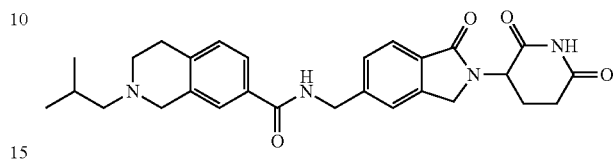

Using Synthetic Scheme A, N-((2-(2,6-dioxopiperidin-3-yl)-1-oxoisoindolin-5-yl)methyl)-2-isobutyl-1,2,3,4-tetra-hydroisoquinoline-7-carboxamide can be prepared from 2-isobutyl-1,2,3,4-tetrahydroisoquinoline-7-carboxylic acid.

5.109.20 N-((2-(2,6-dioxopiperidin-3-yl)-1-ox-oisoindolin-5-yl)methyl)-1,2,3,4-tetrahydroisoquino-line-7-carboxamide

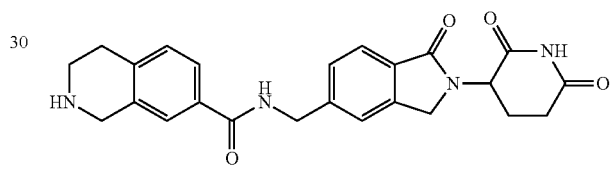

Step 1: Using Synthetic Scheme A, tert-butyl 7-((2-(2,6-dioxopiperidin-3-yl)-1-oxoisoindolin-5-yl)methylcarbam-oyl)-3,4-dihydroisoquinoline-2(1H)-carboxylate can be prepared from 2-(tert-butoxycarbonyl)-1,2,3,4-tetrahydroisoquinoline-7-carboxylic acid.

Step 2: A mixture of tert-butyl 7-((2-(2,6-dioxopiperidin-3-yl)-1-oxoisoindolin-5-yl)methylcarbamoyl)-3,4-dihy-droisoquinoline-2(1H)-carboxylate (0.53 g, 1.0 mmol) in methylene chloride (100 mL) is treated with HCl (5 mL of a 2N solution in diethyl ether), and stirred at ambient temperature for 48 hours. The mixture is evaporated under vacuum, and triturated in ethyl acetate (10 mL), filtered, and dried under vacuum.

5.109.21 N-((2-(2,6-dioxopiperidin-3-yl)-1-ox-oisoindolin-5-yl)methyl)-1-isobutylpiperidine-4-carboxamide

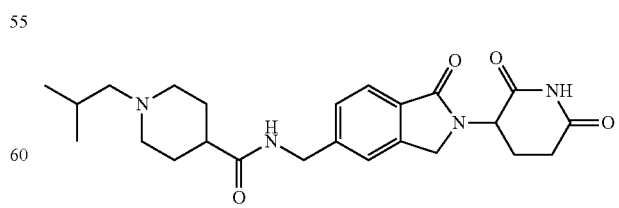

Using Synthetic Scheme A, N-((2-(2,6-dioxopiperidin-3-yl)-1-oxoisoindolin-5-yl)methyl)-1-isobutylpiperidine-4-carboxamide will be prepared from 1-isobutylpiperidine-4-carboxylic acid.

5.109.22 N-((2-(2,6-dioxopiperidin-3-yl)-1-ox-oisoindolin-5-yl)methyl)piperidine-4-carboxamide

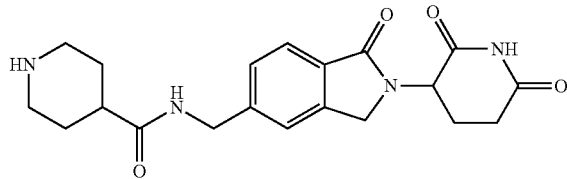 [SMILES: O=C1CCC(N2Cc3cc(CNC(=O)C4CCNCC4)ccc3C2=O)C(=O)N1]

Step 1: Using Synthetic Scheme A, tert-butyl 4-((2-(2,6-dioxopiperidin-3-yl)-1-oxoisoindolin-5-yl)methylcarbamoyl)piperidine-1-carboxylate can be prepared from 1-(tert-butoxycarbonyl)piperidine-4-carboxylic acid.

Step 2: A mixture of tert-butyl 4-((2-(2,6-dioxopiperidin-3-yl)-1-oxoisoindolin-5-yl)methylcarbamoyl)piperidine-1-carboxylate (0.48 g, 1.0 mmol) in methylene chloride (100 mL) is treated with HCl (5 mL of a 2N solution in diethyl ether), and stirred at ambient temperature for 48 hours. The mixture is evaporated under vacuum, and triturated in ethyl acetate (10 mL), filtered, and dried under vacuum.

5.110 General Synthetic Scheme B

A mixture of the appropriate amino starting material (4.0 mmol), TEA (0.80 g, 8.0 mmol), and pyridine (0.31 g, 4.0 mmol) is cooled to 0° C. Then, either phosgene (1.9 mL of a 20% solution in toluene) or p-nitrophenyl chloroformate (0.77 g, 3.8 mmol) is added, and stirring proceeds for 30 minutes. Then, 3-(5-aminomethyl-1-oxo-1,3-dihydro-isoindol-2-yl)-piperidine-2,6-dione methane sulfonate (1.1 g, 3.0 mmol) and TEA (0.80 g, 8.0 mmol) are added, and the mixture is stirred for an additional 6 hours. The mixture is cooled and evaporated under vacuum, and the residue is purified by preparative HPLC. The following compounds can be made using the Synthetic Scheme B

5.110.1 N-((2-(2,6-dioxopiperidin-3-yl)-1-oxoisoindolin-5-yl)methyl)-4-methylpiperazine-1-carboxamide

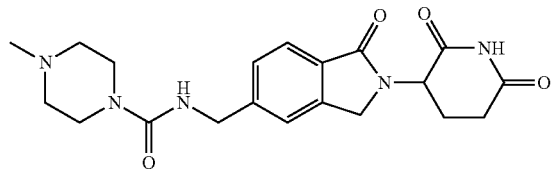 [SMILES: CN1CCN(C(=O)NCc2ccc3c(c2)CN(C2CCC(=O)NC2=O)C3=O)CC1]

Using Synthetic Scheme B, N-((2-(2,6-dioxopiperidin-3-yl)-1-oxoisoindolin-5-yl)methyl)-4-methylpiperazine-1-carboxamide can be prepared from 1-methylpiperazine.

5.110.2 N-((2-(2,6-dioxopiperidin-3-yl)-1-oxoisoindolin-5-yl)methyl)piperazine-1-carboxamide

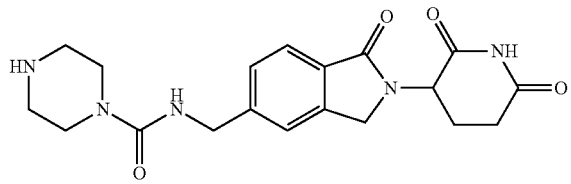 [SMILES: O=C1CCC(N2Cc3cc(CNC(=O)N4CCNCC4)ccc3C2=O)C(=O)N1]

Step 1: Using Synthetic Scheme A, tert-butyl 4-((2-(2,6-dioxopiperidin-3-yl)-1-oxoisoindolin-5-yl)methylcarbamoyl)piperazine-1-carboxylate can be prepared from tert-butyl piperazine-1-carboxylate.

Step 2: A mixture of tert-butyl 4-((2-(2,6-dioxopiperidin-3-yl)-1-oxoisoindolin-5-yl)methylcarbamoyl)piperazine-1-carboxylate (0.49 g, 1.0 mmol) in methylene chloride (100 mL) is treated with HCl (5 mL of a 2N solution in diethyl ether), and stirred at ambient temperature for 48 hours. The mixture is evaporated under vacuum, and triturated in ethyl acetate (10 mL), filtered, and dried under vacuum.

5.111 1-(2-chloro-phenyl)-3-[2-(2,6-dioxo-piperidin-3-yl)-1,3-dioxo-2,3-dihydro-1H-isoindol-5-ylmethyl]-urea

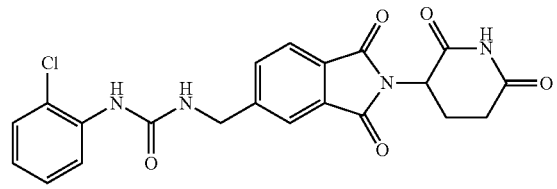 [SMILES: O=C1CCC(N2C(=O)c3ccc(CNC(=O)Nc4ccccc4Cl)cc3C2=O)C(=O)N1]

Step 1: A mixture of 4-bromophthalic anhydride (10.0 g, 44.1 mmol), rac-α-aminoglutarimide hydrochloride (7.25 g, 44.0 mmol) and sodium acetate (3.61 g, 44.0 mmol) in acetic acid (150 mL) was heated to reflux overnight. The reaction mixture was cooled to room temperature, and the solvent was evaporated under vacuum. The residue was stirred in water (170 mL) for 3 hours, and the resulting solid was filtered, washed with additional water (80 mL), and dried under vacuum, to afford 13.8 g of 5-bromo-2-(2,6-dioxopiperidin-3-yl)-isoindole-1,3-dione, in 93% yield; $^1$H NMR (DMSO-$d_6$) δ 2.03-2.10 (m, 1H), 2.43-2.63 (m, 2H), 2.82-2.97 (m, 1H), 5.17 (dd, J=12.8 Hz, J=5.3 Hz, 1H), 7.85-7.88 (d, J=7.9 Hz, 1H), 8.10 (dd, J=7.9 Hz, J=1.7 Hz, 1H), 8.16 (d, J=1.7 Hz, 1H), 11.15 (s, 1H); $^{13}$C NMR (DMSO-$d_6$) δ 21.9, 30.9, 49.2, 125.3, 126.4, 128.5, 130.1, 133.2, 137.6, 165.9, 166.4, 169.7, 172.7; Anal. Calcd for $C_{13}H_9N_2O_4Br$: C, 46.32; H, 2.69; N, 8.31. Found: C, 46.23; H, 2.47; N, 8.41.

Step 2: DMF (300 mL) was degassed via nitrogen sparge for 1 hour and 5-bromo-2-(2,6-dioxo-piperidin-3-yl)-isoindole-1,3-dione (13.7 g, 40.6 mmol), zinc cyanide (2.86 g, 24.4 mmol), tris(dibenzylideneacetone)dipalladium (0.74 g, 0.80 mmol) and 1,1'-bis(diphenylphosphino)ferrocene (0.90 g, 1.6 mmol) were added. The reaction mixture was heated to 120° C. for 3 hours, cooled to 60° C., and filtered through Celite. The filter was washed with additional DMF (160 mL), and the filtrate was evaporated under vacuum. The residue was stirred in water (300 mL) for 2 days and filtered, washed with additional water, and dried under vacuum. The resulting solid was triturated with acetone (300 mL) for 1 hour and filtered, and the solid was washed with additional acetone (300 mL) and dried under vacuum. The resulting solid was refluxed in methanol for 1 hour, cooled to room temperature, filtered, washed with additional methanol, and dried to give 11.1 g of 2-(2,6-dioxo-piperidin-3-yl)-1,3-dioxo-2,3-dihydro-1H-isoindole-5-carbonitrile, in 96% yield; mp>260° C.; $^1$H NMR (DMSO-$d_6$) δ 2.03-2.12 (m, 1H), 2.43-2.64 (m, 2H), 2.83-2.97 (m, 1H), 5.22 (dd, J=12.8 Hz, J=5.2 Hz, 1H), 8.12 (d, J=7.8 Hz, 1H), 8.38 (dd, J=7.8 Hz, J=1.4 Hz, 1H), 8.49 (s, 1H), 11.17 (s, 1H); $^{13}$C NMR (DMSO-$d_6$) δ 21.8, 30.9, 49.3, 117.0, 117.4, 124.2, 127.3, 131.8, 134.5, 139.1, 165.6, 165.9, 169.5, 172.7; Anal. Calcd for $C_{14}H_9N_3O_4$+0.3$H_2O$: C, 58.26; H, 3.35; N, 14.56. Found: C, 58.01; H, 3.01; N, 14.37.

Step 3: A mixture of 2-(2,6-dioxo-piperidin-3-yl)-1,3-dioxo-2,3-dihydro-1H-isoindole-5-carbonitrile (1.00 g, 3.53 mmol), 4N HCl (4.5 mL), 10% Pd—C (0.1 g) and decolorizing carbon (0.06 g) in DMF (30 mL) was hydrogenated at 50 psi overnight. Water (5 mL) was added, and the reaction mixture was filtered through Celite. The filter was washed with methanol (10 mL). The filtrate was concentrated, and the residue was co-evaporated with ethanol (4×5 mL). The resulting solid was triturated with ethanol (5 mL) for 1 hour, filtered, washed with additional ethanol (10 mL), and dried to give 0.97 g of 5-aminomethyl-2-(2,6-dioxo-piperidin-3-yl)-isoindole-1,3-dione hydrochloride as a white solid, in 85% yield; mp>260° C.; $^1$H NMR (DMSO-$d_6$) δ 2.05-2.12 (m, 1H), 2.45-2.63 (m, 2H), 2.83-2.98 (m, 1H), 4.24 (s, 2H), 5.18 (dd, J=12.6 Hz, J=5.4 Hz, 1H), 7.96-8.03 (m, 2H), 8.11 (s, 1H), 8.73 (br, 3H), 11.15 (s, 1H); $^{13}$C NMR (DMSO-$d_6$) δ 22.0, 30.9, 41.7, 49.1, 123.6, 123.9, 131.0, 131.5, 135.4, 141.5, 166.8, 166.9, 169.8, 172.7; Anal. Calcd for $C_{14}H_{14}N_3O_4Cl$+0.15$H_2O$: C, 51.51; H, 4.42; N, 12.87. Found: C, 51.16; H, 4.40; N, 12.59.

Step 4: A mixture of 5-aminomethyl-2-(2,6-dioxo-piperidin-3-yl)-isoindole-1,3-dione hydrochloride (0.97 g, 3.0 mmol), 2-chlorophenyl isocyanate (0.36 mL, 3.0 mmol) and N,N-diisopropylethylamine (1.05 mL, 6.00 mmol) in THF (20 mL) was stirred at 40° C. overnight. The reaction mixture was cooled to room temperature, and the solvent was removed under vacuum. The residue was dissolved in ethyl acetate (100 mL) and washed with dilute aqueous HCl (2×150 mL) and water (2×150 mL). During this wash, a solid precipitated. It was filtered and washed with additional water. The organic phase of the filtrate was dried (MgSO$_4$), and the solvent was removed under vacuum. The combined solids were stirred in ether for 3 hours and filtered, to give 1.2 g of the product, in 92% yield; mp 238-240° C.; HPLC, Waters Symmetry C-18, 3.9×150 mm, 5 µm, 1 mL/min, 240 nm, 40/60 CH$_3$CN/0.1% H$_3$PO$_4$, 4.34 (98.10%); $^1$H NMR (DMSO-$d_6$) δ 1.99-2.08 (m, 1H), 2.50-2.63 (m, 2H), 2.82-2.95 (m, 1H), 4.51 (d, J=5.8 Hz, 2H), 5.15 (dd, J=12.6 Hz, J=5.3 Hz, 1H), 6.94-7.43 (m, 3H), 7.65 (t, J=5.8 Hz, 1H), 7.79-8.14 (m, 4H), 8.24 (s, 1H), 11.13 (s, 1H); $^{13}$C NMR (DMSO-$d_6$) δ 22.0, 30.9, 42.6, 49.0, 121.1, 121.6, 121.7, 122.8, 123.6, 127.5, 129.1, 129.8, 131.7, 133.3, 136.5, 148.2, 154.9, 167.0, 167.2, 169.8, 172.7; Anal. Calcd for $C_{21}H_{17}N_4O_5Cl$+0.1$H_2O$: C, 56.98; H, 3.92; N, 12.66. Found: C, 56.71; H, 4.05; N, 12.33.

5.112 1-(3-chloro-phenyl)-3-[2-(2,6-dioxo-piperidin-3-yl)-1,3-dioxo-2,3-dihydro-1H-isoindol-5-ylmethyl]-urea

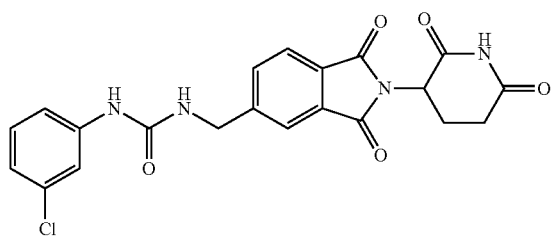 [SMILES: O=C1CCC(N2C(=O)c3ccc(CNC(=O)Nc4cccc(Cl)c4)cc3C2=O)C(=O)N1]

A mixture of 5-aminomethyl-2-(2,6-dioxo-piperidin-3-yl)-isoindole-1,3-dione hydrochloride (0.97 g, 3.0 mmol), 3-chlorophenyl isocyanate (0.37 mL, 3.0 mmol) and N,N-diisopropylethylamine (1.05 mL, 6.00 mmol) in THF (20 mL) was stirred at 40° C. overnight. The reaction mixture was cooled to room temperature, and the solvent was removed under vacuum. The residue was dissolved in ethyl acetate (150 mL), washed with dilute aqueous HCl (2×150 mL) and water (2×150 mL), dried (MgSO$_4$), and evaporated. The resulting solid was stirred in ether for 3 hours and filtered, to give 1.2 g of the product, in 92% yield; mp 214-216° C.; HPLC, Waters Symmetry C-18, 3.9×150 mm, 5 µm, 1 mL/min, 240 nm, 40/60 CH$_3$CN/0.1% H$_3$PO$_4$, 4.58 (98.39%); $^1$H NMR (DMSO-$d_6$) δ 1.99-2.07 (m, 1H), 2.50-2.62 (m, 2H), 2.82-2.95 (m, 1H), 4.47 (d, J=5.5 Hz, 2H), 5.14 (dd, J=12.5 Hz, J=5.1 Hz, 1H), 6.93-6.98 (m, 2H), 7.22-7.28 (m, 2H), 7.66-7.91 (m, 4H), 8.96 (s, 1H), 11.12 (s, 1H); $^{13}$C NMR (DMSO-$d_6$) δ 22.0, 30.9, 42.7, 49.0, 116.2, 117.2, 120.8, 121.7, 123.5, 129.7, 130.2, 131.6, 133.1, 133.2, 141.9, 148.5, 155.1, 167.0, 167.2, 169.8, 172.7; Anal. Calcd for $C_{21}H_{17}N_4O_5Cl$+0.1$H_2O$: C, 56.98; H, 3.92; N, 12.66. Found: C, 56.96; H, 3.70; N, 12.29.

5.113 1-(4-chloro-phenyl)-3-[2-(2,6-dioxo-piperidin-3-yl)-1,3-dioxo-2,3-dihydro-1H-isoindol-5-ylmethyl]-urea

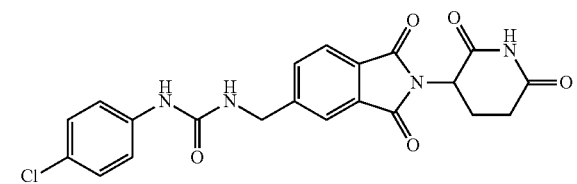

A mixture of 5-aminomethyl-2-(2,6-dioxo-piperidin-3-yl)-isoindole-1,3-dione hydrochloride (0.97 g, 3.0 mmol), 4-chlorophenyl isocyanate (0.38 mL, 3.0 mmol) and N,N-diisopropylethylamine (1.05 mL, 6.00 mmol) in THF (20 mL) was stirred at 40° C. for 2 days. The reaction mixture was cooled to room temperature. The solid was filtered, washed with water (20 mL), washed with ethyl acetate (20 mL), and dried, to give 0.64 g of the product, in 48% yield; mp 278-280° C.; HPLC, Waters Symmetry C-18, 3.9×150 mm, 5 µm, 1 mL/min, 240 nm, 40/60 CH$_3$CN/0.1% H$_3$PO$_4$, 4.18 (98.85%); $^1$H NMR (DMSO-$d_6$) δ 2.03-2.07 (m, 1H), 2.46-2.62 (m, 2H), 2.82-2.96 (m, 1H), 4.47 (d, J=5.8 Hz, 2H), 5.14 (dd, J=12.5 Hz, J=5.2 Hz, 1H), 6.91 (t, J=5.8 Hz, 1H), 7.26 (d, J=8.8 Hz, 2H), 7.44 (d, J=8.9 Hz, 2H), 7.77-7.91 (m, 3H), 8.89 (s, 1H), 11.13 (s, 1H); $^{13}$C NMR (DMSO-$d_6$) δ 22.0, 30.9, 42.7, 49.0, 119.3, 121.7, 123.5, 124.7, 128.5, 129.7, 131.6, 133.2, 139.3, 148.6, 155.1, 167.0, 167.2, 169.8, 172.7; Anal. Calcd for $C_{21}H_{17}N_4O_5Cl$+0.3$H_2O$: C, 56.52; H, 3.98; N, 12.55. Found: C, 56.19; H, 3.78; N, 12.28.

5.114 1-[2-(2,6-dioxo-piperidin-3-yl)-1,3-dioxo-2,3-dihydro-1H-isoindol-5-ylmethyl]-3-(2-methoxyphenyl)-urea

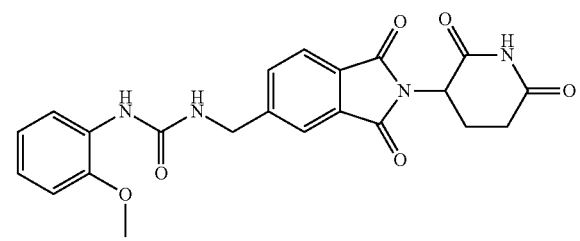 [SMILES: COc1ccccc1NC(=O)NCc1ccc2c(c1)C(=O)N(C1CCC(=O)NC1=O)C2=O]

A mixture of 5-aminomethyl-2-(2,6-dioxo-piperidin-3-yl)-isoindole-1,3-dione hydrochloride (0.97 g, 3.0 mmol), 2-methoxyphenyl isocyanate (0.40 mL, 3.0 mmol) and N,N-diisopropylethylamine (1.05 mL, 6.00 mmol) in THF (20 mL) was stirred at 40° C. overnight. The reaction mixture was cooled to room temperature, and the solvent was removed under vacuum. The residue was suspended in a biphasic mixture of ethyl acetate (150 mL) and diluted aqueous HCl (150 mL). The solid was filtered and washed with water (50 mL). The resulting solid was chromatographed using a methanol-$CH_2Cl_2$ gradient, eluting the product at 5:95 methanol-$CH_2Cl_2$ to give the product (0.090 g, 7% yield); mp 276-278° C.; HPLC, Waters Symmetry C-18, 3.9×150 mm, 5 μm, 1 mL/min, 240 nm, 30/70 $CH_3CN$/0.1% $H_3PO_4$, 8.93 (98.32%); $^1H$ NMR (DMSO-$d_6$) δ 2.02-2.09 (m, 1H), 2.46-2.62 (m, 2H), 2.83-2.95 (m, 1H), 3.84 (s, 3H), 4.48 (d, J=5.8 Hz, 2H), 5.15 (dd, J=12.8 Hz, J=5.3 Hz, 1H), 6.83-6.99 (m, 3H), 7.51 (t, J=6.0 Hz, 1H), 7.78-8.11 (m, 5H), 11.13 (s, 1H); $^{13}C$ NMR (DMSO-$d_6$) δ 22.0, 30.9, 42.5, 49.0, 55.6, 110.59, 118.11, 120.4, 121.3, 121.6, 123.5, 129.1, 129.7, 131.6, 133.2, 147.4, 148.6, 155.2, 167.0, 167.2, 169.8, 172.7; Anal. Calcd for $C_{22}H_{20}N_4O_6$+1.2$H_2O$: C, 57.69; H, 4.93; N, 12.23. Found: C, 57.63; H, 4.19; N, 11.84.

5.115 1-[2-(2,6-dioxo-piperidin-3-yl)-1,3-dioxo-2,3-dihydro-1H-isoindol-5-ylmethyl]-3-(4-methoxy-phenyl)-urea

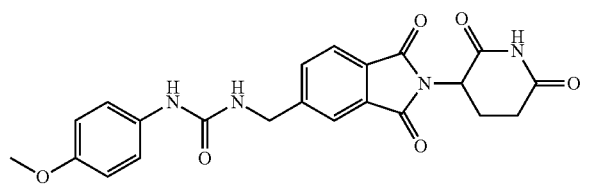 [SMILES: COc1ccc(NC(=O)NCc2ccc3c(c2)C(=O)N(C2CCC(=O)NC2=O)C3=O)cc1]

A mixture of 5-aminomethyl-2-(2,6-dioxo-piperidin-3-yl)-isoindole-1,3-dione hydrochloride (0.97 g, 3.0 mmol), 4-methoxyphenyl isocyanate (0.39 mL, 3.0 mmol) and N,N-diisopropylethylamine (1.05 mL, 6.00 mmol) in THF (20 mL) was stirred at 40° C. for 2 days. The reaction mixture was cooled to room temperature, and the solvent was removed under vacuum. The residue was dissolved in ethyl acetate (150 mL) and washed with dilute aqueous HCl (2×150 mL) and water (2×150 mL). The solvent was removed under vacuum, and the resulting solid was chromatographed using a methanol-$CH_2Cl_2$ gradient, eluting the product at 5:95 methanol-$CH_2Cl_2$, to give 0.57 g of the product, in 44% yield; mp 241-243° C.; HPLC, Waters Symmetry C-18, 3.9×150 mm, 5 μm, 1 mL/min, 240 nm, 30/70 $CH_3CN$/0.1% $H_3PO_4$, 5.69 (98.79%); $^1H$ NMR (DMSO-$d_6$) δ 2.04-2.08 (m, 1H), 2.49-2.63 (m, 2H), 2.85-2.90 (m, 1H), 3.69 (s, 3H), 4.45 (d, J=6.0 Hz, 2H), 5.15 (dd, J=12.6 Hz, J=5.1 Hz, 1H), 6.75 (t, J=6.0 Hz, 1H), 6.80-6.84 (m, 2H), 7.29-7.32 (m, 2H), 7.77-7.91 (m, 3H), 8.51 (s, 1H), 11.13 (s, 1H); $^{13}C$ NMR (DMSO-$d_6$) δ 22.0, 30.9, 42.6, 49.0, 55.1, 113.8, 119.6, 121.7, 123.5, 129.6, 131.6, 133.2, 133.3, 148.9, 154.1, 155.5, 167.0, 167.2, 169.8, 172.7; Anal. Calcd for $C_{22}H_{20}N_4O_6$: C, 60.55; H, 4.62; N, 12.84. Found: C, 60.22; H, 4.35; N, 12.62.

5.116 1-[2-(2,6-dioxo-piperidin-3-yl)-1,3-dioxo-2,3-dihydro-1H-isoindol-5-ylmethyl]-3-m-tolyl-urea

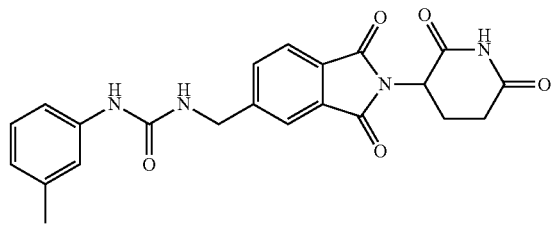 [SMILES: Cc1cccc(NC(=O)NCc2ccc3c(c2)C(=O)N(C2CCC(=O)NC2=O)C3=O)c1]

A mixture of 5-aminomethyl-2-(2,6-dioxo-piperidin-3-yl)-isoindole-1,3-dione hydrochloride (0.97 g, 3.0 mmol), m-tolyl isocyanate (0.38 mL, 3.0 mmol) and N,N-diisopropylethylamine (1.05 mL, 6.00 mmol) in acetonitrile (20 mL) was stirred at room temperature for 1 hour. The solid was filtered, washed with additional acetonitrile (20 mL), and dried under vacuum, providing 0.72 g of the product, in 57% yield; mp 220-222° C.; HPLC, Waters Symmetry C-18, 3.9×150 mm, 5 μm, 1 mL/min, 240 nm, 40/60 $CH_3CN$/0.1% $H_3PO_4$, 5.21 (95.95%); $^1H$ NMR (DMSO-$d_6$) δ 2.02-2.10 (m, 1H), 2.24 (s, 3H), 2.48-2.63 (m, 2H), 2.83-2.95 (m, 1H), 4.47 (d, J=6.0 Hz, 2H), 5.15 (dd, J=12.6 Hz, J=5.1 Hz, 1H), 6.72 (d, J=7.2 Hz, 1H), 6.83 (t, J=6.0 Hz, 1H), 7.07-7.25 (m, 3H), 7.78-7.82 (m, 2H), 7.90 (d, J=7.8 Hz, 1H), 8.64 (s, 1H), 11.12 (s, 1H); $^{13}C$ NMR (DMSO-$d_6$) δ 21.2, 22.0, 30.9, 42.6, 49.0, 115.0, 118.4, 121.7, 122.0, 123.5, 128.5, 129.6, 131.6, 133.2, 137.7, 140.2, 148.8, 155.3, 167.0, 167.2, 169.8, 172.7; Anal. Calcd for $C_{22}H_{20}N_4O_5$: C, 62.85; H, 4.79; N, 13.33. Found: C, 62.54; H, 4.60; N, 13.38.

5.117 1-[2-(2,6-dioxo-piperidin-3-yl)-1,3-dioxo-2,3-dihydro-1H-isoindol-5-ylmethyl]-3-p-tolyl-urea

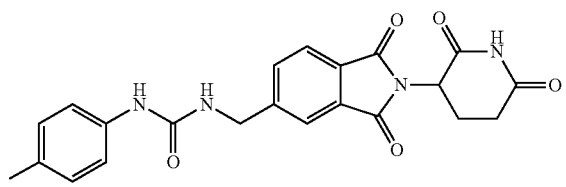 [SMILES: Cc1ccc(NC(=O)NCc2ccc3c(c2)C(=O)N(C2CCC(=O)NC2=O)C3=O)cc1]

A mixture of 5-aminomethyl-2-(2,6-dioxo-piperidin-3-yl)-isoindole-1,3-dione hydrochloride (0.97 g, 3.0 mmol), p-tolyl isocyanate (0.38 mL, 3.0 mmol) and N,N-diisopropylethylamine (1.05 mL, 6.00 mmol) in $CH_2Cl_2$ (20 mL) was stirred at room temperature overnight. The solid was filtered and washed with additional $CH_2Cl_2$ (20 mL). The solid was stirred in methanol overnight, heated to reflux for 3 hours and filtered. The filtrate was concentrated, and the residue was stirred in ethyl acetate and filtered. The solids were combined to give 0.70 g of the product, in 56% yield; mp 238-240° C.; HPLC, Waters Symmetry C-18, 3.9×150 mm, 5 μm, 1 mL/min, 240 nm, 40/60 $CH_3CN$/0.1% $H_3PO_4$, 4.66 (98.56%); $^1H$ NMR (DMSO-$d_6$) δ 1.99-2.10 (m, 1H), 2.21 (s, 3H), 2.47-2.63 (m, 2H), 2.83-2.95 (m, 1H), 4.46 (d, J=5.7 Hz, 2H), 5.15 (dd, J=12.6 Hz, J=5.1 Hz, 1H), 6.79 (t, J=6.0 Hz, 1H), 7.03 (d, J=8.4 Hz, 2H), 7.29 (d, J=8.4 Hz, 2H), 7.78-7.91 (m, 3H), 8.59 (s, 1H), 11.12 (s, 1H); $^{13}C$ NMR (DMSO-$d_6$) δ 20.3, 22.0, 30.9, 42.6, 49.0, 117.94, 121.7, 123.5, 129.0, 129.6, 130.0, 131.6, 133.2, 137.7, 148.9, 155.3, 167.0, 167.2, 169.8, 172.7; Anal. Calcd for C$_{22}$H$_{20}$N$_4$O$_5$+0.1H$_2$O: C, 62.58; H, 4.82; N, 13.27. Found: C, 62.37; H, 4.55; N, 12.92.

5.118 1-[2-(2,6-dioxo-piperidin-3-yl)-1,3-dioxo-2,3-dihydro-1H-isoindol-5-ylmethyl]-3-(4-trifluoromethoxy-phenyl)-urea

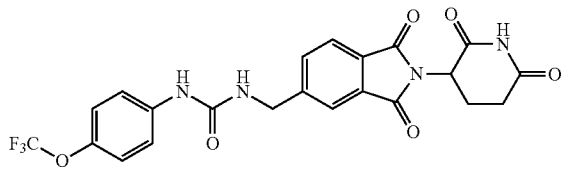 [SMILES: O=C1CCC(N2C(=O)c3ccc(CNC(=O)Nc4ccc(OC(F)(F)F)cc4)cc3C2=O)C(=O)N1]

A mixture of 5-aminomethyl-2-(2,6-dioxo-piperidin-3-yl)-isoindole-1,3-dione hydrochloride (0.97 g, 3.0 mmol), 4-(trifluoromethoxy)-phenyl isocyanate (0.45 mL, 3.0 mmol) and N,N-diisopropylethylamine (1.05 mL, 6.00 mmol) in THF (20 mL) was stirred at 40° C. overnight. The reaction mixture was cooled to room temperature, and the solvent was removed under vacuum. The residue was dissolved in ethyl acetate (150 mL) and washed with dilute aqueous HCl (2×150 mL) and water (2×150 mL). The solvent was removed under vacuum, and the residue was stirred in ether (20 mL) overnight. The resulting solid was filtered to give the product (1.3 g, 89% yield); mp 226-228° C.; HPLC, Waters Symmetry C-18, 3.9×150 mm, 5 µm, 1 mL/min, 240 nm, 40/60 CH$_3$CN/0.1% H$_3$PO$_4$, 9.50 (98.37%); $^1$H NMR (DMSO-d$_6$) δ 2.02-2.09 (m, 1H), 2.47-2.63 (m, 2H), 2.83-2.95 (m, 1H), 4.48 (d, J=6.0 Hz, 2H), 5.15 (dd, J=12.6 Hz, J=5.1 Hz, 1H), 6.93 (t, J=6.0 Hz, 1H), 7.23 (d, J=8.4 Hz, 2H), 7.49-7.54 (m, 2H), 7.79-7.91 (m, 3H), 8.96 (s, 1H), 11.13 (s, 1H); $^{13}$C NMR (DMSO-d$_6$) δ 22.0, 30.9, 42.6, 49.0, 118.9, 120.16 (q, J=254 Hz), 121.6, 121.7, 123.5, 129.7, 131.6, 133.2, 139.59, 142.1, 148.6, 155.2, 167.0, 167.2, 169.8, 172.7; Anal. Calcd for C$_{22}$H$_{17}$N$_4$O$_6$F$_3$: C, 53.88; H, 3.49; N, 11.42. Found: C, 53.80; H, 3.15; N, 11.25.

5.119 1-(4-cyano-phenyl)-3-[2-(2,6-dioxo-piperidin-3-yl)-1,3-dioxo-2,3-dihydro-1H-isoindol-5-ylmethyl]-urea

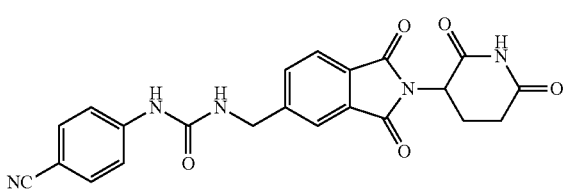 [SMILES: N#Cc1ccc(NC(=O)NCc2ccc3c(c2)C(=O)N(C2CCC(=O)NC2=O)C3=O)cc1]

A mixture of 5-aminomethyl-2-(2,6-dioxo-piperidin-3-yl)-isoindole-1,3-dione hydrochloride (0.97 g, 3.0 mmol), 4 cyanophenyl isocyanate (0.43 g, 3.0 mmol) and N,N-diisopropylethylamine (1.05 mL, 6.00 mmol) in CH$_2$Cl$_2$ (20 mL) was stirred at room temperature for 2 days. The solid was filtered and washed with additional CH$_2$Cl$_2$ (20 mL). The solid was stirred in ethyl acetate for 3 hours and filtered. The residue was purified by preparative HPLC using an acetonitrile-water gradient, eluting the product at 35:65 acetonitrile-water, providing 0.56 g of the product, in 43% yield; mp 265-267° C.; HPLC, Waters Symmetry C-18, 3.9×150 mm, 5 µm, 1 mL/min, 240 nm, 30/70 CH$_3$CN/0.1% H$_3$PO$_4$, 8.97 (97.25%); $^1$H NMR (DMSO-d$_6$) δ 2.04-2.08 (m, 1H), 2.50-2.63 (m, 2H), 2.83-2.95 (m, 1H), 4.49 (d, J=6.0 Hz, 2H), 5.15 (dd, J=12.9 Hz, J=5.4 Hz, 1H), 7.18 (t, J=5.7 Hz, 1H), 7.58-7.69 (m, 4H), 7.79-7.91 (m, 3H), 9.38 (s, 1H), 11.12 (s, 1H); $^{13}$C NMR (DMSO-d$_6$) δ 22.0, 30.9, 42.6, 49.0, 102.6, 117.6, 119.4, 121.7, 123.5, 129.7, 131.6, 133.1, 133.2, 144.8, 148.3, 154.8, 167.0, 167.2, 169.8, 172.7; Anal. Calcd for C$_{22}$H$_{17}$N$_5$O$_5$+0.4H$_2$O: C, 60.25; H, 4.09; N, 15.97. Found: C, 59.87; H, 3.70; N, 15.87.

5.120 1-(4-tert-butyl-phenyl)-3-[2-(2,6-dioxo-piperidin-3-yl)-1,3-dioxo-2,3-dihydro-1H-isoindol-5-ylmethyl]-urea

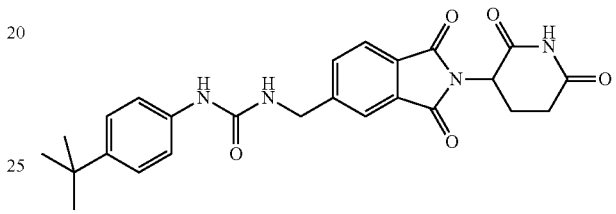

A mixture of 5-aminomethyl-2-(2,6-dioxo-piperidin-3-yl)-isoindole-1,3-dione hydrochloride (0.97 g, 3.0 mmol), 4-(tert-butyl)-phenyl isocyanate (0.52 g, 3.0 mmol) and N,N-diisopropylethylamine (1.05 mL, 6.00 mmol) in THF (20 mL) was stirred at 40° C. overnight. The reaction mixture was cooled to room temperature, and the solvent was removed under vacuum. The residue was dissolved in ethyl acetate (100 mL), washed with dilute aqueous HCl (2×150 mL) and water (2×150 mL), dried (MgSO$_4$), and evaporated. The solid was stirred in ether overnight and filtered to give 0.34 g of the product, in 24% yield; mp 207-209° C.; HPLC, Waters Symmetry C-18, 3.9×150 mm, 5 µm, 1 mL/min, 240 nm, 50/50 CH$_3$CN/0.1% H$_3$PO$_4$, 4.87 (95.56%); $^1$H NMR (DMSO-d$_6$) δ 1.24 (s, 9H), 2.02-2.09 (m, 1H), 2.49-2.63 (m, 2H), 2.83-2.95 (m, 1H), 4.47 (d, J=5.7 Hz, 2H), 5.15 (dd, J=12.6 Hz, J=5.1 Hz, 1H), 6.79 (t, J=6.0 Hz, 1H), 7.22-7.33 (m, 4H), 7.78-7.91 (m, 3H), 8.96 (s, 1H), 11.12 (s, 1H); $^{13}$C NMR (DMSO-d$_6$) δ 22.0, 30.9, 31.2, 33.8, 42.6, 49.0, 117.7, 121.6, 123.5, 125.2, 129.6, 131.6, 133.2, 137.6, 143.5, 148.9, 155.3, 167.0, 167.2, 169.8, 172.7; Anal. Calcd for C$_{25}$H$_{26}$N$_4$O$_5$+0.15H$_2$O: C, 64.55; H, 5.70; N, 12.04. Found: C, 64.17; H, 5.44; N, 11.90.

5.121 1-(3,4-dichloro-phenyl)-3-[2-(2,6-dioxo-piperidin-3-yl)-1,3-dioxo-2,3-dihydro-1H-isoindol-5-ylmethyl]-urea

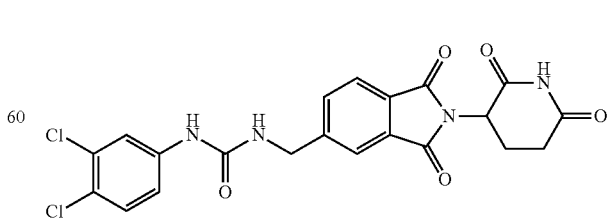

A mixture of 5-aminomethyl-2-(2,6-dioxo-piperidin-3-yl)-isoindole-1,3-dione hydrochloride (0.97 g, 3.0 mmol), 3,4-dichlorophenyl isocyanate (0.56 g, 3.0 mmol) and N,N-diisopropylethylamine (1.05 mL, 6.00 mmol) in pyridine (20 mL) was stirred at 40° C. overnight. The reaction mixture was cooled to room temperature, and the solvent was removed under vacuum. The residue was suspended in a biphasic mixture of CH$_2$Cl$_2$ (150 mL) and water (150 mL) and stirred for 2 hours. The solid was filtered, washed with additional water (50 mL), and dried. The resulting solid was stirred in methanol (200 mL) at room temperature for 1 hour, filtered, and dried. This material was refluxed in methanol (2×200 mL) for 3 hours, filtered, and dried. The resulting solid was chromatographed using a methanol-CH$_2$Cl$_2$ (with 0.1% of triethylamine) gradient, eluting 0.23 g of the product at 7:93 methanol-CH$_2$Cl$_2$ (with 0.1% of triethylamine), in 16% yield; mp 290-292° C.; HPLC, Waters Symmetry C-18, 3.9×150 mm, 5 μm, 1 mL/min, 240 nm, 40/60 CH$_3$CN/0.1% H$_3$PO$_4$, 10.50 (97.00%); $^1$H NMR (DMSO-d$_6$) δ 2.03-2.07 (m, 1H), 2.56-2.62 (m, 2H), 2.82-2.94 (m, 1H), 4.47 (d, J=5.9 Hz, 2H), 5.15 (dd, J=12.6 Hz, J=5.4 Hz, 1H), 7.05 (t, J=6.1 Hz, 1H), 7.29 (dd, J=8.8 Hz, J=2.4 Hz, 1H), 7.46 (d, J=8.8 Hz, 1H), 7.77-7.91 (m, 4H), 9.11 (s, 1H), 11.13 (s, 1H); $^{13}$C NMR (DMSO-d$_6$) δ 22.0, 30.9, 42.7, 49.0, 117.9, 118.9, 121.7, 122.4, 123.5, 129.7, 130.4, 130.9, 131.6, 133.3, 140.6, 148.4, 155.0, 167.0, 167.2, 169.8, 172.7; Anal. Calcd for C$_{21}$H$_{16}$N$_4$O$_5$Cl$_2$+0.25H$_2$O: C, 52.57; H, 3.47; N, 11.68. Found: C, 52.22; H, 3.25; N, 11.56.

5.122 1-(3,4-dimethyl-phenyl)-3-[2-(2,6-dioxo-piperidin-3-yl)-1,3-dioxo-2,3-dihydro-1H-isoindol-5-ylmethyl]-urea

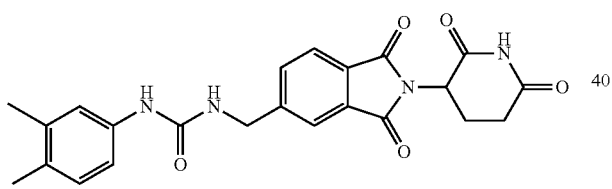

A mixture of 5-aminomethyl-2-(2,6-dioxo-piperidin-3-yl)-isoindole-1,3-dione hydrochloride (0.97 g, 3.0 mmol), 3,4-dimethylphenyl isocyanate (0.42 mL, 3.0 mmol) and N,N-diisopropylethylamine (1.05 mL, 6.00 mmol) in THF (20 mL) was stirred at 40° C. for 2 days. The reaction mixture was cooled to room temperature. The solid was filtered, washed with water (20 mL), washed with ethyl acetate (20 mL), and dried to give 1.0 g of the product, in 78% yield; mp 238-240° C.; HPLC, Waters Symmetry C-18, 3.9×150 mm, 5 μm, 1 mL/min, 240 nm, 40/60 CH$_3$CN/0.1% H$_3$PO$_4$, 5.35 (98.53%); $^1$H NMR (DMSO-d$_6$) δ 2.03-2.07 (m, 1H), 2.12 (s, 3H), 2.15 (s, 3H), 2.46-2.62 (m, 2H), 2.82-2.96 (m, 1H), 4.45 (d, J=5.9 Hz, 2H), 5.14 (dd, J=12.6 Hz, J=5.3 Hz, 1H), 6.77 (t, J=5.9 Hz, 1H), 6.96 (d, J=7.0 Hz, 1H), 7.09-7.18 (m, 2H), 7.77-7.91 (m, 3H), 8.52 (s, 1H), 11.12 (s, 1H); $^{13}$C NMR (DMSO-d$_6$) δ 18.6, 19.6, 22.0, 30.9, 42.6, 49.0, 115.5, 119.3, 121.7, 123.5, 128.8, 129.5, 129.6, 131.6, 133.2, 136.1, 137.9, 148.9, 155.3, 167.0, 167.2, 169.8, 172.7; Anal. Calcd for C$_{23}$H$_{22}$N$_4$O$_5$+0.4H$_2$O: C, 62.55; H, 5.20; N, 12.69. Found: C, 62.22; H, 5.12; N, 12.39.

5.123 1-(3-chloro-4-methyl-phenyl)-3-[2-(2,6-dioxo-piperidin-3-yl)-1,3-dioxo-2,3-dihydro-1H-isoindol-5-ylmethyl]-urea

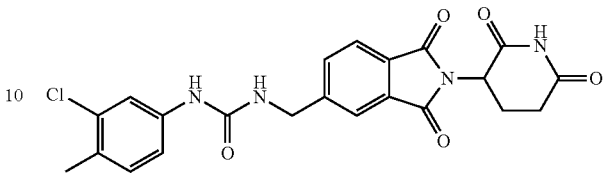

A mixture of 5-aminomethyl-2-(2,6-dioxo-piperidin-3-yl)-isoindole-1,3-dione hydrochloride (0.97 g, 3.0 mmol), 3-chloro-4-methylphenyl isocyanate (0.41 mL, 3.0 mmol) and N,N-diisopropylethylamine (1.05 mL, 6.00 mmol) in THF (20 mL) was stirred at 40° C. overnight. The reaction mixture was cooled to room temperature, and the solvent was removed under vacuum. The residue was stirred in a biphasic mixture of CH$_2$Cl$_2$ (150 mL) and water (150 mL), and the organic solvent was removed under vacuum. The resulting solid was filtered and stirred in methanol (100 mL) at room temperature overnight, filtered and dried to give the product as a white solid (1.2 g, 88% yield); mp 243-245° C.; HPLC, Waters Symmetry C-18, 3.9×150 mm, 5 μm, 1 mL/min, 240 nm, 40/60 CH$_3$CN/0.1% H$_3$PO$_4$, 8.42 (98.48%); $^1$H NMR (DMSO-d$_6$) δ 2.04-2.09 (m, 1H), 2.24 (s, 3H), 2.47-2.64 (m, 2H), 2.83-2.96 (m, 1H), 4.47 (d, J=5.6 Hz, 2H), 5.16 (dd, J=12.3 Hz, J=4.9 Hz, 1H), 6.92 (t, J=5.7 Hz, 1H), 7.13-7.21 (m, 2H), 7.66-7.92 (m, 4H), 8.86 (s, 1H), 11.14 (s, 1H); $^{13}$C NMR (DMSO-d$_6$) δ 18.7, 22.0, 30.9, 42.7, 49.0, 116.5, 117.8, 121.7, 123.5, 127.5, 129.7, 131.0, 131.6, 133.0, 133.2, 139.5, 148.6, 155.1, 167.0, 167.2, 169.8, 172.7; Anal. Calcd for C$_{22}$H$_{19}$N$_4$O$_5$Cl+0.4H$_2$O: C, 57.19; H, 4.32; N, 12.12. Found: C, 56.80; H, 4.12; N, 11.75.

5.124 1-(4-chloro-3-methyl-phenyl)-3-[2-(2,6-dioxo-piperidin-3-yl)-1,3-dioxo-2,3-dihydro-1H-isoindol-5-ylmethyl]-urea

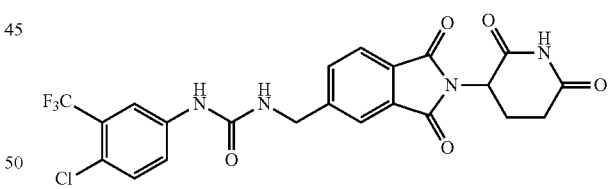

A mixture of 5-aminomethyl-2-(2,6-dioxo-piperidin-3-yl)-isoindole-1,3-dione hydrochloride (0.97 g, 3.0 mmol), 4-chloro-3-(trifluoromethyl)-phenyl isocyanate (0.66 g, 3.0 mmol) and N,N-diisopropylethylamine (1.05 mL, 6.00 mmol) in CH$_2$Cl$_2$ (20 mL) was stirred at room temperature for 2 days. The solid was filtered, washed with additional CH$_2$Cl$_2$ (20 mL), and dried to give 1.0 g of the product, in 68% yield; mp 285-287° C.; HPLC, Waters Symmetry C-18, 3.9×150 mm, 5 μm, 1 mL/min, 240 nm, 50/50 CH$_3$CN/0.1% H$_3$PO$_4$, 6.01 (95.01%); $^1$H NMR (DMSO-d$_6$) δ 2.02-2.09 (m, 1H), 2.46-2.63 (m, 2H), 2.84-2.94 (m, 1H), 4.49 (d, J=6.0 Hz, 2H), 5.15 (dd, J=12.6 Hz, J=5.4 Hz, 1H), 7.09 (t, J=6.0 Hz, 1H), 7.54-7.65 (m, 2H), 7.79-7.94 (m, 3H), 8.06 (d, J=2.4 Hz, 1H), 9.29 (s, 1H), 11.13 (s, 1H); $^{13}$C NMR (DMSO-d$_6$) δ 22.0, 30.9, 42.7, 49.0, 116.3 (q, J=6.0 Hz), 122.8 (q, J=270 Hz), 121.6, 121.7, 122.5, 123.5, 126.6 (q, J=30 Hz), 129.7, 131.8, 131.6, 133.2, 139.9, 148.4, 155.0, 167.0, 167.2, 169.8, 172.7; Anal. Calcd for $C_{20}H_{16}N_4O_5ClF_3+0.5H_2O$: C, 51.03; H, 3.31; N, 10.82. Found: C, 50.68; H, 2.96; N, 10.55.

5.125 1-benzo[1,3]dioxol-5-YL-3-[2-(2,6-dioxo-piperidin-3-yl)-1,3-dioxo-2,3-dihydro-1H-isoindol-5-ylmethyl]-urea

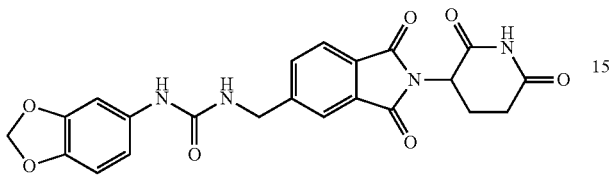

A mixture of 5-aminomethyl-2-(2,6-dioxo-piperidin-3-yl)-isoindole-1,3-dione hydrochloride (0.97 g, 3.0 mmol), 3,4-(methylenedioxy)-phenyl isocyanate (0.49 g, 3.0 mmol) and N,N-diisopropylethylamine (1.05 mL, 6.00 mmol) in methylene chloride (20 mL) was stirred at room temperature for 1 hour. The solid was filtered, washed with additional methylene chloride (20 mL), and dried under vacuum, to provide 0.86 g of the product, in 64% yield; mp 200-202° C.; HPLC, Waters Symmetry C-18, 3.9×150 mm, 5 μm, 1 mL/min, 240 nm, 40/60 CH$_3$CN/0.1% H$_3$PO$_4$, 3.10 (96.75%); $^1$H NMR (DMSO-d$_6$) δ 2.02-2.09 (m, 1H), 2.48-2.63 (m, 2H), 2.83-2.94 (m, 1H), 4.45 (d, J=6.0 Hz, 2H), 5.15 (dd, J=12.6 Hz, J=5.1 Hz, 1H), 5.93 (s, 2H), 6.70-6.80 (m, 3H), 7.16 (d, J=1.8 Hz, 1H), 7.77-7.91 (m, 3H), 8.62 (s, 1H), 11.13 (s, 1H); $^{13}$C NMR (DMSO-d$_6$) δ 22.0, 30.9, 42.6, 49.0, 110.6, 100.6, 108.0, 110.5, 121.7, 123.5, 129.6, 131.6, 133.2, 134.7, 141.6, 147.1, 148.8, 155.4, 167.0, 167.2, 169.8, 172.7; Anal. Calcd for $C_{22}K_8N_4O_7+0.1H_2O$: C, 58.43; H, 4.06; N, 12.39. Found: C, 58.20; H, 3.78; N, 12.21.

5.126 1-[2-(2,6-dioxo-piperidin-3-yl)-1,3-dioxo-2,3-dihydro-1H-isoindol-5-ylmethyl]-3-naphthalen-1-yl-urea

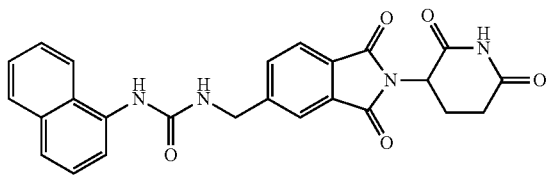 [SMILES: O=C1CCC(N2C(=O)c3ccc(CNC(=O)Nc4cccc5ccccc45)cc3C2=O)C(=O)N1]

A mixture of 5-aminomethyl-2-(2,6-dioxo-piperidin-3-yl)-isoindole-1,3-dione hydrochloride (1.0 g, 3.1 mmol), 1-naphthyl isocyanate (0.52 g, 3.1 mmol), and triethylamine (0.63 g, 6.2 mmol) in THF (35 mL) was heated to 40° C. under nitrogen, with stirring, for 21 hours. The mixture was cooled to room temperature and partitioned between ethyl acetate (100 mL) and dilute aqueous HCl (100 mL), and the organic phase was washed with water (2×100 mL), dried (MgSO$_4$), and evaporated. The residue was chromatographed using a methylene chloride-methanol gradient, eluting the product at 19:1 methylene chloride-methanol. This material was further purified by preparative HPLC, using a 40-60 acetonitrile-water isocrat, and providing 0.3 g as a white solid (21%); mp 229-231° C.; HPLC, Waters Symmetry C-18, 3.9×150 mm, 5 urn, 1 mL/min, 240 nm, 40/60 CH$_3$CN/0.1% H$_3$PO$_4$, 4.76 (96.81%); $^1$H NMR (DMSO-d$_6$) δ 1.96-2.03 (m, 1H), 2.40-2.56 (m, 2H), 2.76-2.89 (m, 1H), 4.48 (d, J=6.0 Hz, 2H), 5.09 (dd, J=12.6 Hz, J=5.4 Hz, 1H), 7.17 (t, J=6.0 Hz, 1H), 7.36 (t, J=8.0 Hz, 1H), 7.44-7.54 (m, 3H), 7.76-7.89 (m, 5H), 8.04 (d, J=7.8 Hz, 1H), 8.68 (s, 1H), 11.06 (s, 1H); $^{13}$C NMR (DMSO-d$_6$) δ 22.0, 30.9, 42.7, 49.0, 117.2, 121.5, 121.7, 122.5, 123.5, 125.5, 125.8, 125.9, 128.3, 129.7, 131.6, 133.2, 133.7, 134.8, 148.7, 155.8, 167.0, 167.2, 169.8, 172.7; Anal. Calcd for $C_{25}H_{26}N_4O_5+0.2H_2O$: C, 65.27; H, 4.47; N, 12.18. Found: C, 65.32; H, 4.17; N, 12.14.

5.127 1-butyl-3-[2-(2,6-dioxo-piperidin-3-yl)-1,3-dioxo-2,3-dihydro-1H-isoindol-5-ylmethyl]-urea

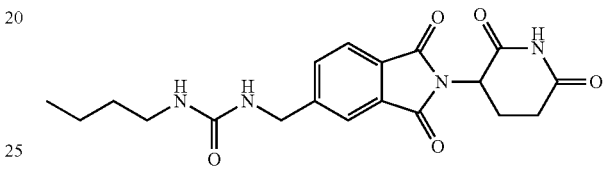

A mixture of 5-aminomethyl-2-(2,6-dioxo-piperidin-3-yl)-isoindole-1,3-dione hydrochloride (0.97 g, 3.0 mmol), butyl isocyanate (0.33 mL, 3.0 mmol) and N,N-diisopropylethylamine (1.05 mL, 6.00 mmol) in acetonitrile (20 mL) was stirred at room temperature for 1 hour. The reaction mixture was concentrated. The residue was dissolved in ethyl acetate (100 mL), and washed with dilute aqueous HCl (2×150 mL) and water (2×150 mL), dried (MgSO$_4$), and evaporated under vacuum. The residue was purified by preparative HPLC using a 35:65 acetonitrile-water isocrat, providing 0.20 g of the product, in 17% yield; mp 171-173° C.; HPLC, Waters Symmetry C-18, 3.9×150 mm, 5 μm, 1 mL/min, 240 nm, 35/65 CH$_3$CN/0.1% H$_3$PO$_4$, 3.13 (97.37%); $^1$H NMR (DMSO-d$_6$) δ 0.87 (t, J=6.9 Hz, 3H), 1.21-1.41 (m, 4H), 2.02-2.10 (m, 1H), 2.46-2.63 (m, 2H), 2.83-2.91 (m, 1H), 2.94-3.04 (m, 2H), 4.36 (d, J=6.0 Hz, 2H), 5.14 (dd, J=12.6 Hz, J=5.4 Hz, 1H), 6.07 (t, J=5.7 Hz, 1H), 6.51 (t, J=6.0 Hz, 1H), 7.71-7.88 (m, 3H), 11.12 (s, 1H); $^{13}$C NMR (DMSO-d$_6$) δ 13.7, 19.5, 22.0, 30.9, 32.1, 39.0, 42.7, 49.0, 121.5, 123.4, 129.5, 131.5, 133.0, 149.5, 158.0, 167.0, 167.2, 169.8, 172.7; Anal. Calcd for $C_{19}H_{22}N_4O_5$: C, 59.06; H, 5.74; N, 14.50. Found: C, 58.84; H, 5.73; N, 14.29.

5.128 1-[2-(2,6-dioxo-piperidin-3-yl)-1,3-dioxo-2,3-dihydro-1H-isoindol-5-ylmethyl]-3-pentyl-urea

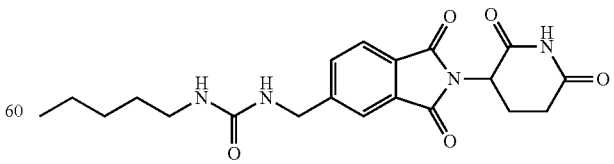

A mixture of 5-aminomethyl-2-(2,6-dioxo-piperidin-3-yl)-isoindole-1,3-dione hydrochloride (0.97 g, 3.0 mmol), pentyl isocyanate (0.39 mL, 3.0 mmol) and N,N-diisopropylethylamine (1.05 mL, 6.00 mmol) in CH$_2$Cl$_2$ (20 mL)

was stirred at room temperature overnight. The solid was filtered, washed with additional CH$_2$Cl$_2$ (20 mL), and with methanol (20 mL). It was dried to give 0.54 g of the product, in 45% yield; mp 176-178° C.; HPLC, Waters Symmetry C-18, 3.9×150 mm, 5 μm, 1 mL/min, 240 nm, 40/60 CH$_3$CN/0.1% H$_3$PO$_4$, 3.15 (98.59%); $^1$H NMR (DMSO-d$_6$) δ 0.86 (t, J=6.6 Hz, 3H), 1.18-1.42 (m, 6H), 2.02-2.10 (m, 1H), 2.46-2.63 (m, 2H), 2.83-3.03 (m, 3H), 4.46 (d, J=6.3 Hz, 2H), 5.15 (dd, J=12.9 Hz, J=5.4 Hz, 1H), 6.07 (t, J=5.7 Hz, 1H), 6.51 (t, J=6.0 Hz, 1H), 7.71-7.88 (m, 3H), 11.12 (s, 1H); $^{13}$C NMR (DMSO-d$_6$) δ 13.9, 21.9, 22.0, 28.6, 29.6, 30.9, 39.3, 42.7, 48.9, 121.5, 123.4, 129.5, 131.5, 133.1, 149.5, 158.0, 167.0, 167.2, 169.8, 172.7; Anal. Calcd for C$_{20}$H$_{24}$N$_4$O$_5$: C, 59.99; H, 6.04; N, 13.99. Found: C, 59.65; H, 5.89; N, 13.86.

5.129 1-[2-(2,6-dioxo-piperidin-3-yl)-1,3-dioxo-2,3-dihydro-1H-isoindol-5-yl methyl]-3-hexyl-urea

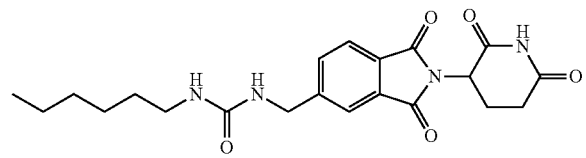 [SMILES: CCCCCCNC(=O)NCc1ccc2c(c1)C(=O)N(C1CCC(=O)NC1=O)C2=O]

A mixture of 5-aminomethyl-2-(2,6-dioxo-piperidin-3-yl)-isoindole-1,3-dione hydrochloride (0.97 g, 3.0 mmol), hexyl isocyanate (0.43 mL, 3.0 mmol) and N,N-diisopropylethylamine (1.05 mL, 6.00 mmol) in THF (20 mL) was stirred at 40° C. overnight. The reaction mixture was cooled to room temperature, and the solvent was removed under vacuum. The residue was dissolved in ethyl acetate (150 mL), washed with dilute aqueous HCl (2×150 mL) and water (2×150 mL), dried (MgSO$_4$), and evaporated. The residue was purified by preparative HPLC using a 55:45 acetonitrile-water isocrat, affording 0.67 g of the product, in 54% yield; mp 162-164° C.; HPLC, Waters Symmetry C-18, 3.9×150 mm, 5 μm, 1 mL/min, 240 nm, 40/60 CH$_3$CN/0.1% H$_3$PO$_4$, 3.41 (99.34%); $^1$H NMR (DMSO-d$_6$) δ 0.85 (t, J=6.3 Hz, 3H), 1.24-1.36 (m, 8H), 2.03-2.07 (m, 1H), 2.45-2.62 (m, 2H), 2.82-2.91 (m, 1H), 2.96-3.03 (m, 2H), 4.36 (d, J=5.9 Hz, 2H), 5.14 (dd, J=12.5 Hz, J=5.3 Hz, 1H), 6.07 (t, J=5.6 Hz, 1H), 6.52 (t, J=6.0 Hz, 1H), 7.71-7.76 (m, 2H), 7.87 (d, J=7.7 Hz, 1H), 11.12 (s, 1H); $^{13}$C NMR (DMSO-d$_6$) δ 13.9, 22.0, 22.1, 26.0, 29.9, 30.9, 31.0, 39.37, 42.8, 49.0, 121.6, 123.4, 129.5, 131.5, 133.1, 149.5, 158.0, 167.1, 167.2, 169.8, 172.7; Anal. Calcd for C$_{21}$H$_{26}$N$_4$O$_5$+0.15H$_2$O: C, 60.46; H, 6.35; N, 13.43. Found: C, 60.17; H, 6.23; N, 13.57.

5.130 1-(4-chloro-phenyl)-3-[2-(2,6-dioxo-piperidin-3-yl)-1,3-dioxo-2,3-dihydro-1H-isoindol-5-ylmethyl]-thiourea

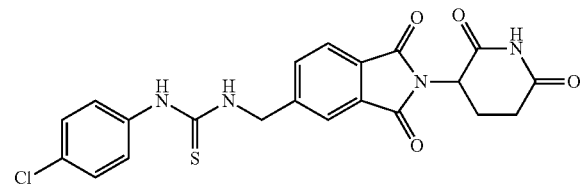 [SMILES: O=C1CCC(N2C(=O)c3ccc(CNC(=S)Nc4ccc(Cl)cc4)cc3C2=O)C(=O)N1]

A mixture of 5-aminomethyl-2-(2,6-dioxo-piperidin-3-yl)-isoindole-1,3-dione hydrochloride (0.97 g, 3.0 mmol), 4-chlorophenyl isothiocyanate (0.51 g, 3.0 mmol) and N,N-diisopropylethylamine (1.05 mL, 6.00 mmol) in THF (20 mL) was stirred at 40° C. overnight. The reaction mixture was cooled to room temperature, and the solvent was removed under vacuum. The residue was dissolved in ethyl acetate (100 mL) and washed with dilute aqueous HCl (2×150 mL) and water (2×150 mL), dried (MgSO$_4$), and evaporated under vacuum. The resulting solid was stirred in ether overnight and filtered. The solid was purified by preparative HPLC using a 40:60 acetonitrile-water isocrat. The solid thus obtained was stirred in ether and filtered to give 0.75 g of the product, in 55% yield; mp 239-241° C.; HPLC, Waters Symmetry C-18, 3.9×150 mm, 5 μm, 1 mL/min, 240 nm, 40/60 CH$_3$CN/0.1% H$_3$PO$_4$, 6.19 (95.49%); $^1$H NMR (DMSO-d$_6$) δ 2.03-2.10 (m, 1H), 2.46-2.63 (m, 2H), 2.84-2.96 (m, 1H), 4.91 (d, J=5.4 Hz, 2H), 5.15 (dd, J=12.9 Hz, J=5.4 Hz, 1H), 7.37-7.40 (m, 2H), 7.45-7.48 (m, 2H), 7.80-7.84 (m, 2H), 7.89-7.91 (m, 1H), 8.46 (s, 1H), 9.89 (s, 1H), 11.13 (s, 1H); $^{13}$C NMR (DMSO-d$_6$) δ 22.0, 30.9, 46.8, 49.0, 121.9, 123.4, 125.1, 128.3, 128.5, 129.7, 131.4, 133.4, 138.0, 147.2, 167.0, 167.2, 169.8, 172.7, 181.2; Anal. Calcd for C$_{21}$H$_{17}$N$_4$O$_4$SCl: C, 55.20; H, 3.75; N, 12.26. Found: C, 54.81; H, 3.51; N, 12.05.

5.131 1-[2-(2,6-dioxo-piperidin-3-yl)-1,3-dioxo-2,3-dihydro-1H-isoindol-5-ylmethyl]-3-p-tolyl-thiourea

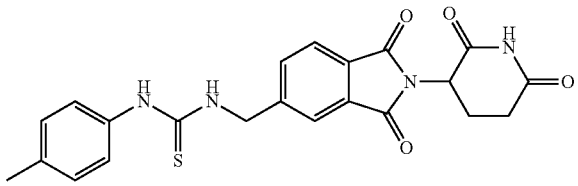 [SMILES: Cc1ccc(NC(=S)NCc2ccc3c(c2)C(=O)N(C2CCC(=O)NC2=O)C3=O)cc1]

A mixture of 5-aminomethyl-2-(2,6-dioxo-piperidin-3-yl)-isoindole-1,3-dione hydrochloride (0.97 g, 3.0 mmol), p-tolylisothiocyanate (0.45 g, 3.0 mmol) and N,N-diisopropylethylamine (1.05 mL, 6.00 mmol) in THF (20 mL) was warmed to 40° C. and stirred overnight. The reaction mixture was cooled to room temperature, and the solvent was removed under vacuum. The residue was dissolved in ethyl acetate (100 mL) and washed with dilute aqueous HCl (2×150 mL) and water (2×150 mL). The solid was filtered. The organic layer of the biphasic filtrate was evaporated, and the residue was combined with the solid that had been filtered. This solid was stirred in ether overnight and filtered. The resulting solid was stirred in DMF (10 mL), filtered, washed with additional DMF and water. The solid was stirred in ether and filtered, providing 0.31 g of the product, in 24% yield; mp 246-248° C.; HPLC, Waters Symmetry C-18, 3.9×150 mm, 5 μm, 1 mL/min, 240 nm, 40/60 CH$_3$CN/0.1% H$_3$PO$_4$, 6.47 (96.05%); $^1$H NMR (DMSO-d$_6$) δ 2.02-2.10 (m, 1H), 2.38 (s, 3H), 2.46-2.63 (m, 2H), 2.83-2.96 (m, 1H), 4.89 (d, J=5.7 Hz, 2H), 5.15 (dd, J=12.9 Hz, J=5.4 Hz, 1H), 7.12-7.26 (m, 4H), 7.79-7.95 (m, 3H), 8.23 (t, 1H), 9.71 (s, 1H), 11.13 (s, 1H); $^{13}$C NMR (DMSO-d$_6$) δ 20.5, 22.0, 30.9, 46.9, 49.0, 121.9, 123.4, 124.1, 129.3, 129.6, 131.4, 133.4, 134.1, 136.0, 147.6, 167.0, 167.2, 169.8, 172.7, 181.1; Anal. Calcd for C$_{22}$H$_{20}$N$_4$O$_4$S+0.1H$_2$O: C, 60.29; H, 4.65; N, 12.78. Found: C, 60.10; H, 4.36; N, 12.67.

5.132 1-(4-chloro-phenyl)-3-[2-(3S)-(3-methyl-2,6-dioxo-piperidin-3-yl)-1,3-dioxo-2,3-dihydro-1H-isoindol-5-ylmethyl]-urea

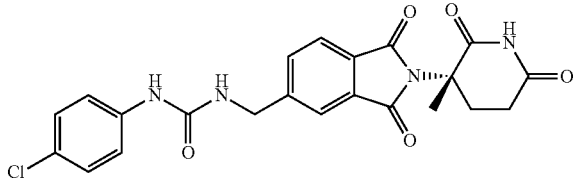 [SMILES: C[C@]1(N2C(=O)c3ccc(CNC(=O)Nc4ccc(Cl)cc4)cc3C2=O)CCC(=O)NC1=O]

Step 1: A mixture of 4-bromophthalic anhydride (7.53 g, 33.2 mmol), amino-3-methyl-piperidine-2,6-dione hydrobromide (8.00 g, 44.1 mmol) and sodium acetate (2.72 g, 33.2 mmol) in acetic acid (150 mL) was heated to reflux for 24 hours. The reaction mixture was cooled to room temperature, and the solvent was evaporated under vacuum. The residue was stirred in water (170 mL) for 3 hours, and the resulting solid was filtered, washed with additional water (80 mL), and dried, to afford 6.3 g of 5-bromo-2-[(3S)-3-methyl-2,6-dioxo-piperidin-3-yl]-isoindole-1,3-dione, in 54% yield; $^1$H NMR (DMSO-$d_6$) δ 1.89 (s, 3H), 2.01-2.09 (m, 1H), 2.53-2.73 (m, 3H), 7.79 (dd, J=5.7 Hz, J=2.7 Hz, 1H), 8.06 (m, 2H), 11.04 (s, 1H); $^{13}$C NMR (DMSO-$d_6$) δ 21.0, 28.5, 29.0, 58.9, 124.9, 125.9, 128.3, 130.0, 133.0, 137.4, 166.6, 167.2, 172.0, 172.1.

Step 2: DMF (160 mL) was degassed via nitrogen sparge for 1 hour and 5-bromo-2-[(3S)-3-methyl-2,6-dioxo-piperidin-3-yl]-isoindole-1,3-dione (6.31 g, 18.0 mmol), zinc cyanide (1.26 g, 10.8 mmol), tris(dibenzylideneacetone)dipalladium (0) (0.33 g, 0.40 mmol) and 1,1′-bis(diphenylphosphino)ferrocene (0.4 g, 0.7 mmol) were added. The reaction mixture was heated to 120° C. for 3 hours, cooled to 60° C., and filtered through Celite. The filter was washed with additional DMF (100 mL), and the filtrate was evaporated under vacuum. The residue was stirred in water (200 mL) for 2 days and filtered, washed with additional water (50 mL), and dried. The resulting solid was triturated with acetone (50 mL) and stirred for 1 hour, and filtered and washed with additional acetone (40 mL). Drying provided 4.7 g of 2-[(3S)-3-methyl-2,6-dioxo-piperidin-3-yl]-1,3-dioxo-2,3-dihydro-1H-isoindole-5-carbonitrile, in 88% yield; HPLC, Waters Symmetry C-18, 3.9×150 mm, 5 μm, 1 mL/min, 240 nm, 30/70 CH$_3$CN/0.1% H$_3$PO$_4$, 5.21 (98.40%); $^1$H NMR (DMSO-$d_6$) δ 1.89 (s, 3H), 2.02-2.10 (m, 1H), 2.51-2.73 (m, 3H), 8.03 (d, J=7.8 Hz, 1H), 8.33 (dd, J=7.8 Hz, J=1.5 Hz, 1H), 8.40 (s, 1H), 11.06 (s, 1H); $^{13}$C NMR (DMSO-$d_6$) δ 21.0, 28.5, 28.9, 59.1, 116.7, 117.4, 123.8, 126.9, 131.7, 134.4, 138.8, 166.3, 166.6, 171.8, 172.2.

Step 3: A mixture of 2-[(3S)-3-methyl-2,6-dioxo-piperidin-3-yl]-1,3-dioxo-2,3-dihydro-1H-isoindole-5-carbonitrile (4.70 g, 15.8 mmol), 4N HCl (21 mL), and 10% Pd—C (1.88 g) in CH$_3$OH (200 mL) was hydrogenated under 50 psi of H$_2$ for 16 hours. Water (24 mL) was added, and the reaction mixture was filtered through Celite. The filter was washed with additional methanol (50 mL). The filtrate was concentrated and dried to give 3.5 g of 5-aminomethyl-2-[(3S)-3-methyl-2,6-dioxo-piperidin-3-yl]-isoindole-1,3-dione hydrochloride, in 66% yield; HPLC, Waters Symmetry C-18, 3.9×150 mm, 5 μm, 1 mL/min, 240 nm, 30/70 CH$_3$CN/0.1% H$_3$PO$_4$, 1.00 (97.70%); $^1$H NMR (DMSO-$d_6$) δ 1.91 (s, 3H), 2.03-2.10 (m, 1H), 2.49-2.61 (m, 2H), 2.66-2.75 (m, 1H), 4.23 (s, 2H), 7.89-8.03 (m, 3H), 8.68 (br, 3H), 11.04 (s, 1H); $^{13}$C NMR (DMSO-$d_6$) δ 20.9, 28.6, 29.0, 41.6, 58.9, 123.2, 123.5, 130.8, 131.4, 135.3, 141.2, 167.5, 167.6, 172.1, 172.2.

Step 4: A mixture of 5-aminomethyl-2-[(3S)-3-methyl-2,6-dioxo-piperidin-3-yl]-isoindole-1,3-dione hydrochloride (0.51 g, 1.5 mmol), 4-chlorophenyl isocyanate (0.19 mL, 1.5 mmol) and N,N-diisopropylethylamine (0.52 mL, 3.0 mmol) in acetonitrile (20 mL) was stirred at room temperature for 1 hour. The reaction mixture was concentrated, and the residue was dissolved in ethyl acetate (100 mL), washed with dilute aqueous HCl (2×150 mL) and water (2×150 mL), dried (MgSO$_4$), and evaporated under vacuum. The residue was chromatographed using a methanol-CH$_2$Cl$_2$ gradient, eluting the product at 4:96 methanol-CH$_2$Cl$_2$. The resulting solid was stirred in ether overnight, filtered and dried to give 0.39 g of the product, in 57% yield; mp 245-247° C.; HPLC, Waters Symmetry C-18, 3.9×150 mm, 5 μm, 1 mL/min, 240 nm, 45/55 CH$_3$CN/0.1% H$_3$PO$_4$, 4.76 (99.33%); $^1$H NMR (DMSO-$d_6$) δ 1.89 (s, 3H), 1.99-2.08 (m, 1H), 2.54-2.60 (m, 2H), 2.63-2.72 (m, 1H), 4.45 (d, J=6.0 Hz, 2H), 6.89 (t, J=6.0 Hz, 1H), 7.25-7.29 (m, 2H), 7.42-7.46 (m, 2H), 7.75-7.83 (m, 3H), 8.87 (s, 1H), 11.02 (s, 1H); $^{13}$C NMR (DMSO-$d_6$) δ 21.0, 28.6, 29.1, 42.6, 58.7, 119.3, 121.3, 123.1, 124.7, 128.4, 129.5, 131.3, 133.2, 139.3, 148.4, 155.1, 167.8, 167.9, 172.1, 172.2; Anal. Calcd for C$_{22}$H$_{19}$N$_4$O$_5$Cl: C, 58.09; H, 4.21; N, 12.32. Found: C, 57.70; H, 4.20; N, 11.99.

5.133 1-[2-[(3S)-3-methyl-2,6-dioxo-piperidin-3-yl]-1,3-dioxo-2,3-dihydro-1H-isoindol-5-ylmethyl]-3-(4-trifluoromethoxy-phenyl)-urea

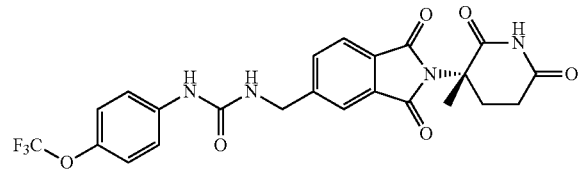 [SMILES: C[C@]1(N2C(=O)c3ccc(CNC(=O)Nc4ccc(OC(F)(F)F)cc4)cc3C2=O)CCC(=O)NC1=O]

A mixture of 5-aminomethyl-2-[(3S)-3-methyl-2,6-dioxo-piperidin-3-yl]-isoindole-1,3-dione hydrochloride (0.40 g, 1.2 mmol), 4-(trifluoromethoxy)phenyl isocyanate (0.18 mL, 1.2 mmol) and N,N-diisopropylethylamine (0.41 mL, 2.4 mmol) in acetonitrile (20 mL) was stirred at room temperature for 1 hour. The reaction mixture was concentrated, and the residue was dissolved in ethyl acetate (100 mL). The organic phase was washed with dilute aqueous HCl (2×150 mL) and water (2×150 mL), dried (MgSO$_4$), and evaporated under vacuum. The resulting solid was stirred in ether overnight, filtered and dried to give 0.54 g of the product, in 90% yield; mp 168-170° C.; HPLC, Waters Symmetry C-18, 3.9×150 mm, 5 μm, 1 mL/min, 240 nm, 50/50 CH$_3$CN/0.1% H$_3$PO$_4$, 6.04 (98.93%); $^1$H NMR (DMSO-$d_6$) δ 1.89 (s, 3H), 2.02-2.08 (m, 1H), 2.52-2.60 (m, 2H), 2.63-2.72 (m, 1H), 4.46 (d, J=6.0 Hz, 2H), 6.91 (t, J=6.0 Hz, 1H), 7.22 (d, J=8.1 Hz, 2H), 7.48-7.53 (m, 2H), 7.75-7.83 (m, 3H), 8.95 (s, 1H), 11.02 (s, 1H); $^{13}$C NMR (DMSO-$d_6$) δ 21.0, 28.6, 29.1, 42.6, 58.7, 118.9, 120.2 (q, J=254 Hz), 121.3, 121.6, 123.1, 129.5, 131.4, 133.2, 139.6, 142.1, 148.4, 155.1, 167.8, 167.9, 172.1, 172.2; Anal. Calcd for C$_{23}$H$_{19}$N$_4$O$_6$F$_3$: C, 54.77; H, 3.80; N, 11.11. Found: C, 54.57; H, 3.44; N, 10.93.

5.134 1-hexyl-3-[2-[(3S)-3-methyl-2,6-dioxo-piperidin-3-yl]-1,3-dioxo-2,3-dihydro-1H-isoindol-5-ylmethyl]-urea

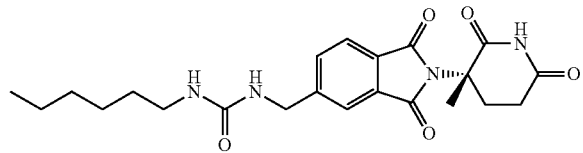 [SMILES: CCCCCCNC(=O)NCc1ccc2c(c1)C(=O)N([C@@]1(C)CCC(=O)NC1=O)C2=O]

A mixture of 5-aminomethyl-2-[(3S)-3-methyl-2,6-dioxo-piperidin-3-yl]-isoindole-1,3-dione hydrochloride (0.51 g, 1.5 mmol), hexyl isocyanate (0.22 mL, 1.5 mmol) and N,N-diisopropylethylamine (0.52 mL, 3.00 mmol) in acetonitrile (20 mL) was stirred at room temperature for 1 hour. The reaction mixture was concentrated and the residue was dissolved in ethyl acetate (100 mL), washed with dilute aqueous HCl (2×150 mL) and water (2×150 mL), dried (MgSO$_4$), and evaporated under vacuum. The resulting solid was stirred in ether overnight, filtered and dried to give 0.50 g of the product, in 78% yield; mp 195-197° C.; HPLC, Waters Symmetry C-18, 3.9×150 mm, 5 µm, 1 mL/min, 240 nm, 45/55 CH$_3$CN/0.1% H$_3$PO$_4$, 4.25 (98.51%); $^1$H NMR (DMSO-d$_6$) δ 0.85 (t, J=6.6 Hz, 3H), 1.24-1.30 (m, 6H), 1.32-1.38 (m, 2H), 1.89 (s, 3H), 2.02-2.08 (m, 1H), 2.53-2.60 (m, 2H), 2.63-2.76 (m, 1H), 2.99 (dd, J=12.9 Hz, J=6.6 Hz, 2H), 4.34 (d, J=6.0 Hz, 2H), 6.06 (t, J=5.7 Hz, 1H), 6.50 (t, J=6.3 Hz, 1H), 7.68-7.80 (m, 3H), 11.02 (s, 1H); $^{13}$C NMR (DMSO-d$_6$) δ 13.9, 21.0, 22.0, 26.0, 28.6, 29.1, 29.9, 31.0, 39.3, 42.7, 58.7, 121.2, 123.0, 129.3, 131.3, 133.0, 149.4, 158.0, 167.8, 167.9, 172.1, 172.2; Anal. Calcd for C$_{22}$H$_{28}$N$_4$O$_5$+0.10H$_2$O: C, 61.41; H, 6.61; N, 13.02. Found: C, 61.16; H, 6.66; N, 12.70.

5.135 1-(3-chloro-4-methyl-phenyl)-3-[2-(2,6-dioxo-piperidin-3-yl)-1-oxo-2,3-dihydro-1H-isoindol-5-ylmethyl]-urea

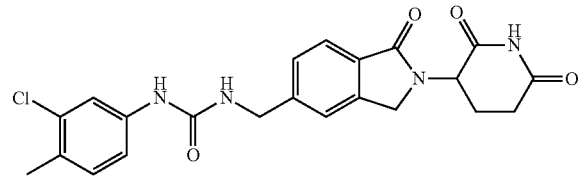 [SMILES: Cc1ccc(NC(=O)NCc2ccc3c(c2)CN(C2CCC(=O)NC2=O)C3=O)cc1Cl]

Step 1: A mechanically stirred mixture of 4-bromo-2-methyl-benzoic acid (100 g, 465 mmol), iodomethane (95 g, 670 mmol) and sodium bicarbonate (112 g, 1340 mmol) in DMF (325 mL) was heated at 80° C. overnight. The reaction mixture was cooled to room temperature and partitioned between water (1500 mL) and 4:1 hexanes:ethyl acetate (1500 mL). The organic layer was washed with water and dried (Na$_2$SO$_4$). The solvent was removed under vacuum to give 110 g of 4-bromo-2-methyl-benzoic acid methyl ester as an oil, in 100% yield; $^1$H NMR (DMSO-d$_6$) δ 2.51 (s, 3H), 3.84 (s, 3H), 7.40-7.78 (m, 3H).

Step 2: A mechanically stirred mixture of 4-bromo-2-methyl-benzoic acid methyl ester (115 g, 500 mmol), N-bromosuccinimide (90 g, 500 mmol) and AIBN (3.1 g) in acetonitrile (700 mL) was warmed over 45 minutes to a gentle reflux, and held at reflux for 21 hours. The reaction mixture was cooled to room temperature, diluted with saturated aqueous sodium bisulfite, and concentrated in vacuo. The residue was partitioned between water and 1:1 hexanes:ethyl acetate. The organic phase was washed with water, brine, and filtered through a pad of silica gel. The solvent was removed under vacuum to give an oil/solid mixture, which was digested in ether and filtered. The filtrate was chromatographed on silica gel using a hexanes-ethyl acetate gradient, eluting the product at 4:1 hexanes-ethyl acetate and providing 102 g of 4-bromo-2-bromomethyl-benzoic acid methyl ester, in 66% yield; $^1$H NMR (DMSO-d$_6$) δ 3.87 (s, 3H), 4.99 (s, 2H), 7.67-7.97 (m, 3H).

Step 3: A mechanically stirred mixture of 4-bromo-2-bromomethyl-benzoic acid methyl ester (121 g, 390 mmol) and 3-amino-piperidine-2,6-dione hydrochloride (64.2 g, 390 mmol) in DMF (400 mL) was treated dropwise with triethylamine (98.5 g, 980 mmol) over 75 minutes. After the addition was completed, the reaction mixture was stirred at room temperature overnight. The mixture was quenched sequentially with acetic acid (50 mL), water (2500 mL) and a 1:1 mixture of ethyl acetate and hexanes (600 mL). After stirring the mixture for 20 minutes, the solid was filtered, washed with water and air dried overnight. The solid was stirred in acetic acid (200 mL) and refluxed for 2 hours. The mixture was cooled to room temperature and filtered. The solid was washed with additional acetic acid, hexanes and air dried overnight to give 25.4 g of 3-(5-bromo-1-oxo-1,3-dihydro-isoindol-2-yl)-piperidine-2,6-dione as a grey solid, in 20% yield; $^1$H NMR (DMSO-d$_6$) δ 1.97-2.04 (m, 1H), 2.32-2.46 (m, 1H), 2.56-2.63 (m, 1H), 2.85-2.97 (m, 1H), 4.34 (d, J=17.7 Hz, 1H), 4.47 (d, J=17.7 Hz, 1H), 5.11 (dd, J=13.2 Hz, J=5.1 Hz, 1H), 7.67 (d, J=8.1 Hz, 1H), 7.72 (dd, J=8.1 Hz, J=1.5 Hz, 1H), 7.89 (d, J=0.9 Hz, 1H), 11.00 (s, 1H).

Step 4: A mechanically stirred mixture of 3-(5-bromo-1-oxo-1,3-dihydro-isoindol-2-yl)-piperidine-2,6-dione (25.2 g, 78 mmol), bis(diphenylphosphino)ferrocene (2.0 g), tris(dibenzylideneacetone)dipalladium (2.0 g) and zinc cyanide (9.4 g, 80 mmol) in DMF (300 mL) was heated to 120° C. and stirred at this temperature for 19 hours. The reaction mixture was cooled to 40° C., and another 9.4 g of zinc cyanide, 2 g of bis(diphenylphosphino)ferrocene and 2 g of tris(dibenzylideneacetone)dipalladium were added. The mixture was stirred at 120° C. for 2 hours, cooled to room temperature and quenched with water (900 mL). The solid was filtered, washed with additional water and air dried overnight. The solid was stirred in hot acetic acid (200 mL) for 20 minutes. The solid was filtered, washed with additional acetic acid, ethyl acetate and hexanes, and air dried to give 30.8 g of crude 2-(2,6-dioxo-piperidin-3-yl)-1-oxo-2,3-dihydro-1H-isoindole-5-carbonitrile as a gray solid; $^1$H NMR (DMSO-d$_6$) δ 1.99-2.06 (m, 1H), 2.35-2.45 (m, 1H), 2.57-2.63 (m, 1H), 2.86-2.98 (m, 1H), 4.42 (d, J=17.7 Hz, 1H), 4.55 (d, J=17.7 Hz, 1H), 5.15 (dd, J=13.2 Hz, J=5.1 Hz, 1H), 7.91 (d, J=7.8 Hz, 1H), 7.99 (dd, J=7.8 Hz, J=0.9 Hz, 1H), 8.16 (s, 1H), 11.03 (s, 1H).

Step 5: A mixture of 2-(2,6-dioxo-piperidin-3-yl)-1-oxo-2,3-dihydro-1H-isoindole-5-carbonitrile (9.2 g, 34 mmol), 10% Pd—C (1.7 g) and concentrated HCl (5.3 g) in N-methylpyrrolidone (300 mL) was hydrogenated at 58 psi overnight. The crude reaction mixture was filtered through Celite, and the catalyst washed with water. The combined filtrate was concentrated in vacuo, and the product, 3-(5-aminomethyl-1-oxo-1,3-dihydro-isoindol-2-yl)-piperidine-2,6-dione hydrochloride, was isolated by fractional crystallization of the residue from isopropanol-water (1.9 g, 18%); $^1$H NMR (DMSO-d$_6$) δ 1.85-2.20 (m, 1H), 2.35-2.45 (m, 1H), 2.58-2.80 (m, 1H), 2.87-2.99 (m, 1H), 4.16 (s, 2H), 4.35 (d, J=17.5 Hz, 1H), 4.49 (d, J=17.5 Hz, 1H), 5.13 (dd, J=13.2 Hz, J=4.8 Hz, 1H), 7.63 (d, J=7.8 Hz, 1H), 7.72 (s, 1H), 7.79 (d, J=7.8 Hz, 1H), 8.43 (br, 3H), 11.01 (s, 1H).

Step 6: A mixture of 3-(5-aminomethyl-1-oxo-1,3-dihydro-isoindol-2-yl)-piperidine-2,6-dione hydrochloride (0.50 g, 1.6 mmol), 3-chloro-4-methylphenyl isocyanate (0.27 g, 1.6 mmol) and TEA (0.32 g, 3.2 mmol) in THF (25 mL) was heated to 40° C. with stirring under $N_2$. After 3 hours, an additional portion of 3-chloro-4-methylisocyanate (0.17 g, 1.1 mmol) was added, and stirring proceeded for 2 hours. The mixture was filtered, and the filter was washed with ethyl acetate. The solid was triturated with 10 mL of 1:1 acetone-DMF and filtered. The filter was washed with acetone, and the solid was dried under vacuum, providing 430 mg of the product, in 60% yield; mp 258-260° C.; HPLC, Waters Symmetry C-18, 3.9×150 mm, 5 µm, 1 mL/min, 240 nm, 40/60 $CH_3CN/0.1\%$ $H_3PO_4$, 4.49 (98.75%); $^1H$ NMR (DMSO-$d_6$) δ 1.90-1.96 (m, 1H), 2.16 (s, 3H), 2.25-2.39 (m, 1H), 2.50-2.55 (m, 1H), 2.78-2.91 (m, 1H), 4.24 (d, J=18.0 Hz, 1H), 4.33-4.41 (m, 3H), 5.04 (dd, J=13.5 Hz, J=4.5 Hz, 1H), 6.73 (t, J=6.0 Hz, 1H), 7.04-7.13 (m, 2H), 7.36-7.44 (m, 2H), 7.59-7.44 (m, 2H), 8.69 (s, 1H), 10.92 (s, 1H); $^{13}C$ NMR (DMSO-$d_6$) δ 18.7, 22.5, 31.2, 42.8, 47.1, 51.5, 116.4, 117.6, 121.9, 122.9, 126.9, 127.4, 130.3, 131.0, 133.0, 139.6, 142.4, 144.7, 155.1, 167.9, 171.0, 172.9; Anal. Calcd for $C_{22}H_{21}ClN_4O_4$: C, 59.93; H, 4.80; N, 12.71. Found: C, 59.77; H, 4.61; N, 12.69.

5.136 1-(4-chloro-phenyl)-3-[2-(2,6-dioxo-piperidin-3-yl)-1-oxo-2,3-dihydro-1H-isoindol-5-ylmethyl]-urea

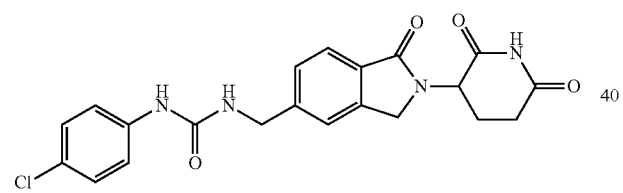

A mixture of 3-(5-aminomethyl-1-oxo-1,3-dihydro-isoindol-2-yl)-piperidine-2,6-dione hydrochloride (0.50 g, 1.6 mmol), 4-chlorophenyl isocyanate (0.25 g, 1.6 mmol) and TEA (0.32 g, 3.2 mmol) in THF (25 mL) was heated to 40° C. with stirring under $N_2$. After 3 hours, an additional portion of 4-chlorophenyl isocyanate (0.17 g, 1.1 mmol) was added, and stirring proceeded for 2 hours. The mixture was filtered, and the filter was washed with ethyl acetate. The solid was purified by preparative HPLC, using a 35:65 acetonitrile-water isocrat, and providing 0.22 g of the product, in 32% yield; mp 270-272° C.; HPLC, Waters Symmetry C-18, 3.9×150 mm, 5 µm, 1 mL/min, 240 nm, 40/60 $CH_3CN/0.1\%$ $H_3PO_4$, 3.28 (95.95%); $^1H$ NMR (DMSO-$d_6$) δ 1.96-2.03 (m, 1H), 2.35-2.41 (m, 1H), 2.57-2.62 (m, 1H), 2.85-2.96 (m, 1H), 4.31 (d, J=15.0 Hz, 1H), 4.41-4.48 (m, 3H), 5.11 (dd, J=13.5 Hz, J=4.5 Hz, 1H), 6.81 (t, J=6.0 Hz, 1H), 7.24-7.52 (m, 6H), 7.70 (d, J=9.0 Hz, 1H), 8.81 (s, 1H), 10.99 (s, 1H); $^{13}C$ NMR (DMSO-$d_6$) δ 22.5, 31.2, 42.8, 47.1, 51.5, 119.2, 121.9, 122.9, 124.6, 126.9, 128.4, 130.3, 139.4, 142.4, 144.7, 155.1, 167.9, 171.0, 172.9; Anal. Calcd for $C_{21}H_{19}ClN_4O_4+0.2H_2O$: C, 58.60; H, 4.54; N, 13.02. Found: C, 58.50; H, 4.15; N, 12.69.

5.137 1-[2-(2,6-dioxo-piperidin-3-yl)-1-oxo-2,3-dihydro-1H-isoindol-5-ylmethyl]-3-hexyl-urea

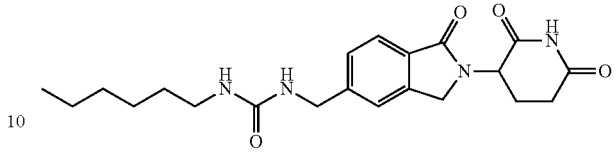

A mixture of 3-(5-aminomethyl-1-oxo-1,3-dihydro-isoindol-2-yl)-piperidine-2,6-dione hydrochloride (0.50 g, 1.6 mmol), hexyl isocyanate (0.20 g, 1.6 mmol) and TEA (0.32 g, 3.2 mmol) in THF (25 mL) was heated to 40° C. with stirring under $N_2$. After 3 hours, an additional portion of hexyl isocyanate (0.20 g, 1.6 mmol) was added, and stirring proceeded for 20 hours. The mixture was filtered, and the filtered solid was washed with ethyl acetate and dried under vacuum, providing 0.60 g of the product, in 92% yield; mp 234-236° C.; HPLC, Waters Symmetry C-18, 3.9×150 mm, 5 µm, 1 mL/min, 240 nm, 35/65 $CH_3CN/0.1\%$ $H_3PO_4$, 3.57 (96.04%); $^1H$ NMR (DMSO-$d_6$) δ 0.86 (t, J=7.5 Hz, 3H), 1.25-1.38 (m, 8H), 1.99-2.02 (m, 1H), 2.37-2.41 (m, 1H), 2.56-2.62 (m, 1H), 2.87-3.03 (m, 3H), 4.26-4.32 (m, 3H), 4.43 (d, J=18.0 Hz, 1H), 5.10 (dd, J=13.5 Hz, J=4.5 Hz, 1H), 5.96 (t, J=6.0 Hz, 1H), 6.39 (t, J=6.0 Hz, 1H), 7.38 (d, J=7.5, 1H), 7.44 (s, 1H), 7.66 (d, J=6.0 Hz, 1H), 10.98 (s, 1H); $^{13}C$ NMR (DMSO-$d_6$) δ 13.9, 22.1, 22.5, 26.0, 29.9, 31.0, 31.1, 39.3, 42.9, 47.0, 51.5, 121.7, 122.8, 126.8, 130.1, 142.3, 145.6, 158.0, 168.0, 171.0, 172.9; Anal. Calcd for $C_{21}H_{28}N_4O_4+0.1H_2O$: C, 62.70; H, 7.07; N, 13.93. Found: C, 62.66; H, 6.89; N, 13.87.

5.138 (3'S)-3-(3'-methoxy-phenyl)-1-methyl-1-[2-(3-methyl-2',6'-dioxo-piperidin-3'-yl)-1,3-dioxo-2,3-dihydro-1H-isoindol-4-ylmethyl]-urea

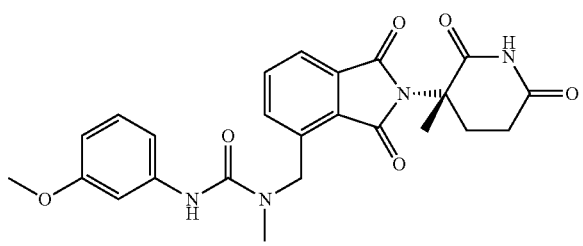

5.138.1 (3'S)-4-methylaminomethyl-2-(3'-methyl-2',6'-dioxo-piperidin-3'-yl)-isoindole-1,3-dione hydrochloride

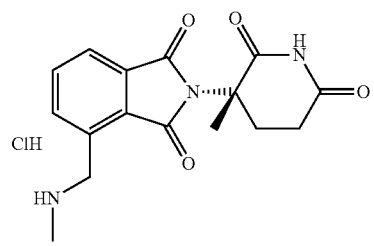

Step 1: A solution of potassium hydroxide (1.3 g, 23.1 mmol) in water (5 mL) was added to a stirred solution of 3[(t-butoxycarbonyl-methyl-amino)-methyl]phthalic dimethyl ester (2.6 g, 7.7 mmol) in methanol (35 mL). The resulting solution was stirred at room temperature overnight. The mixture was concentrated, and water (30 mL) was added. The resulting mixture was washed with ether (30 mL). The aqueous layer was acidified with 4N HCl to pH=2. The mixture was extracted with $CH_2Cl_2$ (3×40 mL) and dried. Solvent was removed to give a mixture of 3-[(t-butoxycarbonyl-methyl-amino)-methyl]-phthalic acid and monomethyl ester, which was used in the next step without further purification.

Step 2: A mixture of 3[(t-butoxycarbonyl-methyl-amino)-methyl]phthalic acid (2.5 g, 7.71 mmol) and (3S)-3-amino-3-methylpiperidine-2,6-dione hydrobromide monohydrate (2.0 g, 8.48 mmol) in pyridine (40 mL) was refluxed for overnight. The mixture was cooled and concentrated. The residue was dissolved in EtOAc (100 mL) and water (50 mL). The EtOAc solution was washed with water (50 mL), 1N citric acid (50 mL), water (50 mL), sat. $NaHCO_3$ (50 mL), water (50 mL), and brine (50 mL), and dried ($MgSO_4$). Solvent was removed, and the residue was purified by chromatography ($SiO_2$, $CH_2Cl_2$:EtOAc 9:1) to give (3'S)-methyl-[2-(3'-methyl-2',6'-dioxo-piperidin-3'-yl)-1,3-dioxo-2,3-dihydro-1H-isoindol-4-ylmethyl]-carbamic acid tert-butylester (0.99 g, 31%).

Step 3: 2NHCl/ether (3 mL) was added to a stirred solution of (3S)-methyl-[2-(3'-methyl-2',6'-dioxo-piperidin-3'-yl)-1,3-dioxo-2,3-dihydro-1H-isoindol-4-ylmethyl]-carbamic acid tert-butylester (0.99 g, 2.4 mmol) in methylene chloride (20 mL). The mixture was stirred at room temperature overnight. Ether (20 mL) was added and the mixture was filtered and dried to afford (3'S)-4-methylaminomethyl-2-(3'-methyl-2',6'-dioxo-piperidin-3'-yl)-isoindole-1,3-dione hydrochloride (0.73 g, 87%): $^1$H NMR (DMSO-$d_6$) δ11.04 (s, 1H), 9.56 (s, 2H), 8.05-7.88 (m, 3H), 4.56-4.45 (m, 2H), 2.73-2.53 (m, 6H), 2.10-2.04 (m, 1H), 2.02 (s, 3H); $^{13}$C NMR (DMSO-$d_6$) δ 172.15, 171.96, 168.08, 167.31, 136.48, 134.68, 131.26, 130.23, 129.05, 123.59, 58.84, 54.88, 45.73, 32.42, 29.09, 28.55, 21.04.

5.138.2 (3'S)-3-(3-methoxy-phenyl)-1-methyl-1-[2-(3'-methyl-isoindol-4-ylmethyl]-urea

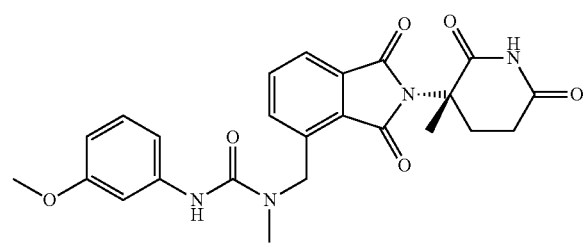

3-Methoxyphenylisocyanate (0.4 g, 2.6 mmol) was added to a stirred suspension of (3'S)-4-methylamino-methyl-2-(3'-methyl-2',6'-dioxo-piperidin-3'-yl)-isoindole-1,3-dione hydrochloride and triethylamine (0.3 g, 3.0 mmol) in THF (30 mL). The resulting mixture was stirred at room temperature for 2 hours. Reaction mixture was concentrated, and residue was dissolved in methylene chloride (70 mL), washed with 1N HCl (30 mL), water (2×30 mL), and brine (30 mL), and dried ($MgSO_4$). Solvent was removed, and residue was purified by chromatography ($SiO_2$, $CH_2Cl_2$: EtOAc 8:2) to give (3'S)-3-(3-methoxy-phenyl)-1-methyl-1-[2-(3'-methyl-2'-6'-dioxo-piperidin-3'-yl)-1,3-dioxo-2,3-dihydro-1H-isoindol-4-ylmethyl]-urea (0.7 g, 74%): mp 166-168° C.; $^1$H NMR (DMSO-$d_6$) δ 11.03 (s, 1H), 8.46 (s, 1H), 7.83 (t, J=7.5 Hz, 1H), 7.75 (d, J=6.6 Hz, 1H), 7.58 (d, J=7.3 Hz, 1H), 7.19-7.07 (m, 3H), 6.55-6.51 (m, 1H), 4.98 (s, 2H), 3.70 (s, 3H), 3.03 (s, 3H), 2.72-2.51 (m, 3H), 2.10-2.04 (m, 1H), 1.91 (s, 3H); $^{13}$C NMR (DMSO-$d_6$) δ 172.46, 172.44, 168.70, 167.99, 159.59, 155.88, 141.87, 138.74, 135.11, 132.51, 131.98, 129.20, 127.57, 121.78, 112.38, 107.68, 105.78, 59.01, 55.15, 47.67, 35.39, 29.38, 28.86, 21.31; Anal. Calcd. for $C_{24}H_{24}N_4O_6$: C, 62.06; H, 5.21; N, 12.06. Found: C, 62.15; H, 5.32; N, 11.71.

5.139 1-(2,6-dichloro-phenyl)-3-[2-(2,6-dioxo-piperidin-3-yl)-1-oxo-2,3-dihydro-1H-isoindol-5-ylmethyl]-urea

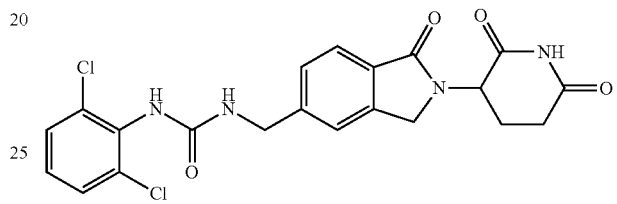

To a stirred mixture of 3-(5-Aminomethyl-1-oxo-1,3-dihydro-isoindol-2-yl)-piperidine-2,6-dione hydrochloride (0.423 g, 1.15 mmol) and 2,6-dichlorophenyl isocyanate (0.216 g, 1.15 mmol) in acetonitrile (10 mL), was added triethylamine (0.32 mL, 2.30 mmol) at room temperature under nitrogen. After 1 h, 1N aq. HCl (10 mL) was added and the mixture was stirred for 10 min. The product was isolated by filtration, washed with 1N aq. HCl (20 mL), acetonitrile (20 mL) and dried overnight in vacuo to give 1-(2,6-dichloro-phenyl)-3-[2-(2,6-dioxo-piperidin-3-yl)-1-oxo-2,3-dihydro-1H-isoindol-5-ylmethyl]-urea as a white solid (0.156 g, 29% yield): HPLC: Waters Symmetry $C_{18}$, 5 μm, 3.9×150 mm, 1 mL/min, 240 nm, 30/70 $CH_3CN$/0.1% $H_3PO_4$, 3.74 min (99.7%); mp: 238-240° C.; $^1$H NMR (DMSO-$d_6$) δ 1.93-2.08 (m, 1H, CH), 2.31-2.47 (m, 1H, CH), 2.60 (d, J=17.0 Hz, 1H, CH), 2.84-3.01 (m, 1H, CH), 4.24-4.51 (m, 4H, $CH_2$, $CH_2$), 5.11 (dd, J=5.0, 13.3 Hz, 1H, NCH), 6.96 (t, J=5.9 Hz, 1H, NH), 7.23-7.33 (m, 1H, Ar), 7.42-7.57 (m, 4H, Ar), 7.69 (d, J=7.7 Hz, 1H, Ar), 8.19 (s, 1H, NH), 10.99 (s, 1H, NH); $^{13}$C NMR (DMSO-$d_6$) δ 22.48, 31.20, 43.02, 47.07, 51.56, 121.66, 122.85, 126.73, 128.12, 128.38, 130.23, 133.88, 134.07, 142.30, 144.96, 155.13, 167.96, 171.01, 172.86; LCMS: MH=461, 463; Anal Calcd for $C_{21}H_{18}N_4O_4Cl_2$+0.1$H_2O$: C, 54.47; H, 3.96; N, 12.10; Cl, 15.31. Found: C, 54.12; H, 3.71; N, 11.85; Cl, 15.31.

5.140 1-[2-(2,6-dioxo-piperidin-3-yl)-1-oxo-2,3-dihydro-1H-isoindol-5-ylmethyl]-3-(4-fluoro-phenyl)-urea

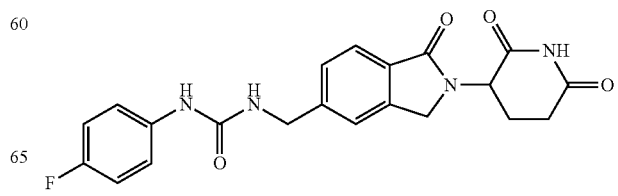

To a stirred mixture of 3-(5-aminomethyl-1-oxo-1,3-dihydro-isoindol-2-yl)-piperidine-2,6-dione methane sulfonate (0.50 g, 1.80 mmol) and 4-fluorophenylisocyanate (0.25 g, 1.80 mmol) in acetonitrile (20 mL), was added triethylamine (0.51 mL, 3.60 mmol) at room temperature under nitrogen. After 1 h, 1N aq. HCl (20 mL) was added and the mixture was stirred for 10 min. The product was isolated by filtration, washed with 1N aq. HCl (20 mL), acetonitrile (20 mL) and dried overnight in vacuo to give 1-[2-(2,6-dioxo-piperidin-3-yl)-1-oxo-2,3-dihydro-1H-isoindol-5-ylmethyl]-3-(4-fluoro-phenyl)-urea as an off-white solid (0.51 g, 68% yield): HPLC: Waters Symmetry $C_{18}$, 5 μm, 3.9×150 mm, 1 mL/min, 240 nm, 40/60 $CH_3CN$/0.1% $H_3PO_4$, 2.13 min (98.98%); mp: 262-264° C.; $^1H$ NMR (DMSO-$d_6$) δ 1.92-2.13 (m, 1H), 2.29-2.47 (m, 1H), 2.54-2.69 (m, 1H), 2.82-3.00 (m, 1H), 4.31 (d, J=17.4 Hz, 1H), 4.37-4.55 (m, 3H), 5.11 (dd, J=13.2, 5.1 Hz, 1H), 6.73 (t, J=5.9 Hz, 1H), 7.06 (t, J=8.9 Hz, 2H), 7.37-7.48 (m, 3H), 7.52 (s, 1H), 7.70 (d, J=7.9 Hz, 1H), 8.67 (s, 1H), 10.99 (s, 1H); $^{13}C$ NMR (DMSO-$d_6$) δ 22.5, 31.2, 42.8, 47.1, 51.6, 115.1 (d, J=22.0 Hz), 119.4 (d, J=6.6 Hz), 121.9, 122.9, 126.9, 130.3, 136.8, 142.4, 144.9, 155.3 (d, J=4.4 Hz), 158.5, 168.0, 171.0, 172.9; LCMS: MH=411; Anal Calcd for $C_{21}H_{19}FN_4O_4$: C, 61.46; H, 4.67; N, 13.65. Found: C, 61.44; H, 4.53; N, 13.46.

5.141 1-(3-chloro-4-fluoro-phenyl)-3-[2-(2,6-dioxo-piperidin-3-yl)-1-oxo-2,3-dihydro-1H-isoindol-5-ylmethyl]-urea To a stirred mixture of 3-(5-aminomethyl-1-oxo-1,3-dihydro-isoindol-2-yl)-piperidine-2,6-dione methane sulfonate (0.50 g, 1.80 mmol) and 3-chloro-4-fluorophenylisocyanate (0.31 g, 1.80 mmol) in acetonitrile (20 mL), was added triethylamine (0.51 mL, 3.60 mmol) at room temperature under nitrogen. After 1 h, 1N aq. HCl (20 mL) was added and the mixture was stirred for 10 min. The product was isolated by filtration, washed with 1N aq. HCl (20 mL), acetonitrile (20 mL) and dried overnight in vacuo to give 1-(3-chloro-4-fluoro-phenyl)-3-[2-(2,6-dioxo-piperidin-3-yl)-1-oxo-2,3-dihydro-1H-isoindol-5-ylmethyl]-urea as a white solid (0.47 g, 78% yield): HPLC: Waters Symmetry $C_{18}$, 5 μm, 3.9×150 mm, 1 mL/min, 240 nm, 40/60 $CH_3CN$/0.1% $H_3PO_4$, 3.40 min (98.65%); mp: 224-226° C.; $^1H$ NMR (DMSO-$d_6$) δ 1.93-2.08 (m, 1H), 2.29-2.47 (m, 1H), 2.55-2.66 (m, 1H), 2.81-3.01 (m, 1H), 4.31 (m, J=17.2 Hz, 1H), 4.37-4.53 (m, 3H), 5.11 (dd, J=13.2, 5.1 Hz, 1H), 6.86 (t, J=5.9 Hz, 1H), 7.18-7.33 (m, 2H), 7.44 (d, J=7.9 Hz, 1H), 7.52 (s, 1H), 7.70 (d, J=7.9 Hz, 1H), 7.78 (dd, J=6.8, J=1.7 Hz, 1H), 8.88 (s, 1H), 10.99 (s, 1H); $^{13}C$ NMR (DMSO-$d_6$) δ 22.5, 31.1, 42.7, 47.0, 51.5, 116.6 (d, J=22.0 Hz), 117.8 (d, J=6.6 Hz), 119.0 (d, J=11.0 Hz), 121.9, 122.9, 126.9, 130.3, 137.7 (d, J=3.3 Hz), 142.3, 144.6, 150.2, 153.4, 155.0, 167.9, 170.9, 172.8; LCMS: MH=445/447; Anal Calcd for $C_{21}H_{18}ClFN_4O_4$: C, 56.70; H, 4.08; N, 12.59. Found: C, 56.54; H, 3.93; N, 12.23.

5.142 1-(3,4-dimethyl-phenyl)-3-[2-(2,6-dioxo-piperidin-3-yl)-1-oxo-2,3-dihydro-1H-isoindol-5-ylmethyl]-urea

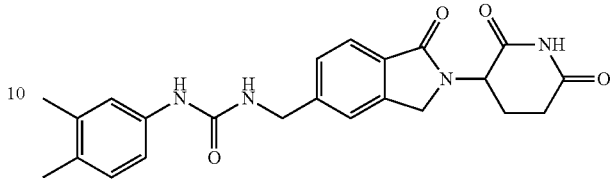

To a stirred mixture of 3-(5-aminomethyl-1-oxo-1,3-dihydro-isoindol-2-yl)-piperidine-2,6-dione methane sulfonate (0.37 g, 1.00 mmol) and 3,4-dimethylphenylisocyanate (0.15 g, 1.00 mmol) in acetonitrile (10 mL), was added triethylamine (0.28 mL, 2.00 mmol) at room temperature under nitrogen. After 1 h, 1N aq. HCl (20 mL) was added and the mixture was stirred for 10 min. The product was isolated by filtration, washed with 1N aq. HCl (20 mL), acetonitrile (20 mL) and dried overnight in vacuo to give 1-(3,4-dimethyl-phenyl)-3-[2-(2,6-dioxo-piperidin-3-yl)-1-oxo-2,3-dihydro-1H-isoindol-5-ylmethyl]-urea as a white solid (0.30 g, 71% yield): HPLC: Waters Symmetry $C_{18}$, 5 μm, 3.9×150 mm, 1 mL/min, 240 nm, 40/60 $CH_3CN$/0.1% $H_3PO_4$, 3.02 min (97.86%); mp: 254-256° C.; $^1H$ NMR (DMSO-$d_6$) δ 1.93-2.06 (m, 1H), 2.12 (s, 3H), 2.15 (s, 3H), 2.30-2.47 (m, 1H), 2.60 (d, J=17.2 Hz, 1H), 2.82-3.00 (m, 1H), 4.31 (d, J=17.4 Hz, 1H), 4.36-4.50 (m, 3H), 5.11 (dd, J=5.0, 13.3 Hz, 1H), 6.66 (t, J=5.9 Hz, 1H), 6.96 (d, J=8.3 Hz, 1H), 7.11 (dd, J=1.7, 8.1 Hz, 1H), 7.18 (s, 1H), 7.44 (d, J=7.9 Hz, 1H), 7.51 (s, 1H), 7.69 (d, J=7.7 Hz, 1H), 8.41 (s, 1H), 10.98 (s, 1H); $^{13}C$ NMR (DMSO-$d_6$) δ 18.60, 19.62, 22.49, 31.20, 42.77, 47.10, 51.56, 115.35, 119.15, 121.86, 122.91, 126.89, 128.67, 129.49, 130.26, 136.08, 138.03, 142.36, 144.96, 155.26, 167.95, 170.98, 172.85; Anal Calcd for $C_{23}H_{24}N_4O_4$: C, 65.70; H, 5.75; N, 13.33. Found: C, 65.48; H, 5.62; N, 13.20.

5.143 1-(3,4-dimethoxy-phenyl)-3-[2-(2,6-dioxo-piperidin-3-yl)-1-oxo-2,3-dihydro-1H-isoindol-5-ylmethyl]-urea

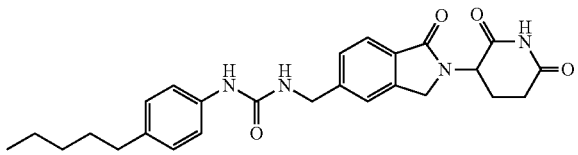 [SMILES: CCCCCc1ccc(NC(=O)NCc2ccc3c(c2)CN(C2CCC(=O)NC2=O)C3=O)cc1]

TEA (0.28 ml, 2 mmol) was added to a stirred mixture of 3-(5-aminomethyl-1-oxo-1,3-dihydro-isoindol-2-yl)-piperidine-2,6-dione (0.37 g, 1 mmol) and 1-isocyanato-4-pentylbenzene (0.16 ml, 1 mmol) in acetonitrile (10 mL) under nitrogen. The mixture was stirred at ambient temperature for 1 h, during which time it remained a suspension. The reaction was then monitored and determined to be complete. A 3.5% aqueous HCl solution (10 mL) was added, and the mixture stirred for 10 minutes. The solid was isolated by filtration, and the solid was washed with additional 3.5% aq. HCl (20 mL) and acetonitrile (20 mL), yielding 1-(3,4-dimethoxy-phenyl)-3-[2-(2,6-dioxo-piperidin-3-yl)-1-oxo- 2,3-dihydro-1H-isoindol-5-ylmethyl]-urea as a white solid (370 mg, 80%). HPLC: Waters Symmetry C-18, 3.9×150 mm, 5 micro, 1 mL/min, 240 nm, 50/50 CH$_3$CN/0.1% H$_3$PO$_4$ in H$_2$O: t$_R$=6.40 min (97%); mp. 286-288° C. $^1$H NMR (DMSO-d$_6$) δ 0.85 (t, J=6.9 Hz, 3H, CH$_3$), 1.12-1.38 (m, 4H, CH$_2$+CH$_2$), 1.52 (quin, J=7.3 Hz, 2H, CH$_2$), 1.86-2.09 (m, 1H, CHH), 2.29-2.43 (m, 1H, CHH), 2.44-2.48 (m, 2H, CH$_2$), 2.62 (br. s., 1H, CHH), 2.82-3.01 (m, 1H, CHH), 4.24-4.50 (m, 4H, CH$_2$+CH$_2$), 5.11 (dd, J=5.0, 13.1 Hz, 1H, CHN), 6.67 (t, J=5.9 Hz, 1H, Ar), 7.03 (d, J=8.5 Hz, 2H, Ar), 7.30 (d, J=8.5 Hz, 2H, Ar), 7.44 (d, J=7.9 Hz, 1H, Ar), 7.51 (s, 1H, NH), 7.69 (d, J=7.9 Hz, 1H, Ar), 8.50 (s, 1H, NH), 10.98 (s, 1H, NH); $^{13}$C NMR (DMSO-d$_6$) δ 13.92, 21.94, 22.49, 30.80, 31.18, 34.39, 42.76, 47.10, 51.56, 117.87, 121.85, 122.91, 126.88, 128.35, 130.26, 135.00, 137.99, 142.38, 144.94, 155.28, 167.95, 170.99, 172.85. LCMS MH=463. Anal Calcd for: C$_{26}$H$_{30}$N$_4$O$_4$+0.1H$_2$O: C, 67.25; H, 6.56; N, 12.07. found: C, 67.08; H, 6.33; N, 12.01.

5.144 1-(3,4-dimethoxy-phenyl)-3-[2-(2,6-dioxo-piperidin-3-yl)-1-oxo-2,3-dihydro-1H-isoindol-5-ylmethyl]-urea

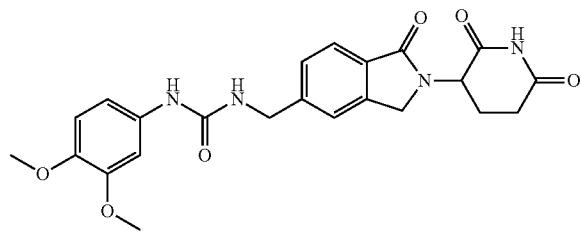 [SMILES: COc1ccc(NC(=O)NCc2ccc3c(c2)CN(C2CCC(=O)NC2=O)C3=O)cc1OC]

TEA (0.28 ml, 2 mmol) was added to a stirred mixture of 3-(5-aminomethyl-1-oxo-1,3-dihydro-isoindol-2-yl)-piperidine-2,6-dione (0.37 g, 1 mmol) and 4-isocyanato-1,2-dimethoxy-benzene (0.15 ml, 1 mmol) in acetonitrile (10 mL) under nitrogen. The mixture was stirred at ambient temperature for 1 h, during which time it remained a suspension. The reaction was then monitored and determined to be complete. A 3.5% aqueous HCl solution (10 mL) was added, and the mixture stirred for 10 minutes. The solid was isolated by filtration, and the solid was washed with additional 3.5% aq. HCl (20 mL) and acetonitrile (20 mL), yielding the 1-(3,4-Dimethoxy-phenyl)-3-[2-(2,6-dioxo-piperidin-3-yl)-1-oxo-2,3-dihydro-1H-isoindol-5-ylmethyl]-urea as a white solid (400 mg, 91%). HPLC: Waters Symmetry C-18, 3.9×150 mm, 5 micro, 1 mL/min, 240 nm, 30/70 CH$_3$CN/0.1% H$_3$PO$_4$ in H$_2$O: t$_R$=2.43 min (97%); mp. 216-218° C. $^1$H NMR (DMSO-d$_6$) δ 1.79-2.12 (m, 1H, CHH), 2.25-2.47 (m, 1H, CHH), 2.62 (br. s., 1H, CHH), 2.81-3.01 (m, 1H, CHH), 3.69 (d, J=6.0 Hz, 6H, OCH$_3$+OCH$_3$), 4.24-4.53 (m, 4H, CH$_2$+CH$_2$), 5.11 (dd, J=5.0, 13.1 Hz, 1H, CHN), 6.64 (t, J=5.9 Hz, 1H, Ar), 6.82 (s, 2H, Ar), 7.18 (s, 1H, Ar), 7.44 (d, J=7.7 Hz, 1H, Ar), 7.51 (s, 1H, NH), 7.69 (d, J=7.9 Hz, 1H, Ar), 8.46 (s, 1H, NH), 10.98 (s, 1H, NH); $^{13}$C NMR (DMSO-d$_6$) δ 22.49, 31.20, 42.77, 47.12, 51.56, 55.28, 55.88, 103.55, 109.60, 112.56, 121.83, 122.91, 126.85, 130.25, 134.15, 142.36, 143.51, 145.03, 148.73, 155.35, 167.95, 170.99, 172.85. LCMS MH=453. Anal Calcd for: C$_{23}$H$_{24}$N$_4$O$_6$: C, 61.06; H, 5.35; N, 12.38. found: C, 59.84; H, 4.87; N, 12.13.

5.145 1-(3-chloro-2-methyl-phenyl)-3-[2-(2,6-dioxo-piperidin-3-yl)-1-oxo-2,3-dihydro-1H-isoindol-5-ylmethyl]-urea

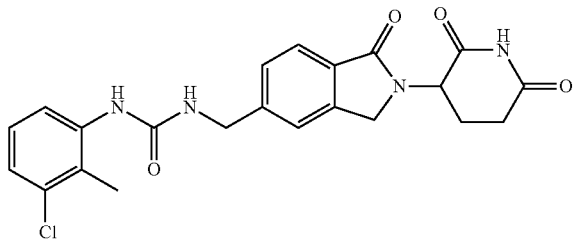 [SMILES: Cc1c(Cl)cccc1NC(=O)NCc1ccc2c(c1)CN(C1CCC(=O)NC1=O)C2=O]

TEA (0.28 ml, 2 mmol) was added to a stirred mixture of 3-(5-aminomethyl-1-oxo-1,3-dihydro-isoindol-2-yl)-piperidine-2,6-dione (0.37 g, 1 mmol) and 1-chloro-3-isocyanato-2-methyl-benzene (0.13 ml, 1 mmol) in acetonitrile (10 mL) under nitrogen. The mixture was stirred at ambient temperature for 1 h, during which time it remained a suspension. The reaction was then monitored and determined to be complete. A 3.5% aqueous HCl solution (10 mL) was added, and the mixture stirred for 10 minutes. The solid was isolated by filtration, and the solid was washed with additional 3.5% aq. HCl (20 mL) and acetonitrile (20 mL), yielding 1-(3-chloro-2-methyl-phenyl)-3-[2-(2,6-dioxo-piperidin-3-yl)-1-oxo-2,3-dihydro-1H-isoindol-5-ylmethyl]-urea as a white solid (400 mg, 91%). HPLC: Waters Symmetry C-18, 3.9×150 mm, 5 micro, 1 mL/min, 240 nm, 40/60 CH$_3$CN/0.1% H$_3$PO$_4$ in H$_2$O: t$_R$=3.23 min (97%); mp. 252-254° C. $^1$H NMR (DMSO-d$_6$) δ 1.93-2.08 (m, 5H, CHH), 2.25 (s, 3H, CH3), 2.33-2.47 (m, 1H, CHH), 2.61-2.64 (m., 1H, CHH), 2.82-3.01 (m, 1H, CHH), 4.25-4.55 (m, 4H, CH2+CH2), 5.11 (dd, J=5.1, 13.2 Hz, 1H, NCH), 6.98-7.20 (m, 3H, Ar), 7.46 (d, J=7.9 Hz, 1H, Ar), 7.53 (s, 1H, NH), 7.67-7.83 (m, 2H, Ar), 8.02 (s, 1H, NH), 10.99 (s, 1H, NH); $^{13}$C NMR (DMSO-d$_6$) δ 14.62, 22.49, 31.20, 42.90, 47.12, 51.58, 120.32, 121.96, 123.01, 125.74, 126.78, 126.95, 130.35, 133.39, 139.61, 142.42, 144.61, 155.31, 167.93, 170.99, 172.86. LCMS MH=441. Anal Calcd for: C$_{22}$H$_{21}$ClN$_4$O$_3$+ 0.05 HCl: C, 59.69; H, 4.79; N, 12.66; Cl, 8.41. found: C, 59.44; H, 4.57; N, 12.51; Cl, 8.43.

5.146 1-(2-chloro-5-trifluoromethyl-phenyl)-3-[2-(2,6-dioxo piperidin-3-yl)-1-oxo-2,3-dihydro-1H-isoindol-5-ylmethyl]-urea

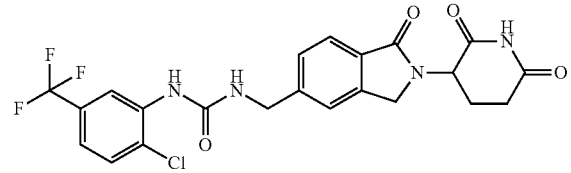 [SMILES: O=C1CCC(N2Cc3cc(CNC(=O)Nc4cc(C(F)(F)F)ccc4Cl)ccc3C2=O)C(=O)N1]

TEA (0.28 ml, 2 mmol) was added to a stirred mixture of 3-(5-aminomethyl-1-oxo-1,3-dihydro-isoindol-2-yl)-piperidine-2,6-dione (0.37 g, 1 mmol) and 1-chloro-2-isocyanato-4-trifluoromethyl-benzene (0.15 ml, 1 mmol) in acetonitrile (10 mL) under nitrogen. The mixture was stirred at ambient temperature for 1 h, during which time it remained a suspension. The reaction was then monitored and determined to be complete. A 3.5% aqueous HCl solution (10 mL) was added, and the mixture stirred for 10 minutes. The solid was isolated by filtration, and the solid was washed with additional 3.5% aq. HCl (20 mL) and acetonitrile (20 mL), yielding the 1-(2-chloro-5-trifluoromethyl-phenyl)-3-[2-(2,6-dioxo-piperidin-3-yl)-1-oxo-2,3-dihydro-1H-isoindol-5-ylmethyl]-urea as a white solid (240 mg, 49%). HPLC: Waters Symmetry C-18, 3.9×150 mm, 5 micro, 1 mL/min, 240 nm, 40/60 $CH_3CN$/0.1% $H_3PO_4$ in $H_2O$: $t_R$=7.88 min (99%); mp. 240-242° C.; $^1$H NMR (DMSO-$d_6$) δ 1.93-2.06 (m, 1H, CHH), 2.39 (qd, J=4.3, 13.2 Hz, 1H, CHH), 2.63 (br. s., 1H, CHH), 2.82-3.02 (m, 1H, CHH), 4.24-4.55 (m, 4H, CH2+CH2), 5.12 (dd, J=5.0, 13.1 Hz, 1H, NCH), 7.30 (dd, J=1.6, 8.4 Hz, 1H, Ar), 7.47 (d, J=7.9 Hz, 1H, Ar), 7.55 (s, 1H, Ar), 7.69 (dd, J=8.0, 15.4 Hz, 2H, Ar), 7.78 (t, J=5.7 Hz, 1H, Ar), 8.49 (s, 1H, NH), 8.66 (s, 1H, NH), 10.99 (s, 1H, NH). $^{13}$C NMR (DMSO-$d_6$) δ 22.49, 31.20, 42.80, 47.13, 51.58, 116.19, 116.25, 118.54, 122.07, 123.06, 124.60, 125.64, 127.02, 127.90, 128.32, 130.23, 130.49, 137.51, 142.49, 143.95, 154.67, 167.89, 170.98, 172.85. LCMS MH=495; Anal Calcd for: $C_{22}H_{18}ClF_3N_4O_4$+0.05 HCl: C, 53.20; H, 3.66; N, 7.49; Cl, 11.28. found: C, 53.08; H, 3.39; N, 7.64; Cl, 11.29.

5.147 1-[2-(2,6-dioxo-piperidin-3-yl)-1-oxo-2,3-dihydro-1H-isoindol-5-ylmethyl]-3-(4-ethyl-phenyl)-urea

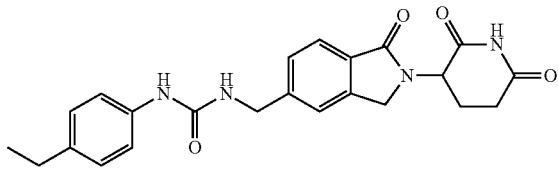 [SMILES: CCc1ccc(NC(=O)NCc2ccc3c(c2)CN(C2CCC(=O)NC2=O)C3=O)cc1]

TEA (0.3 ml, 2.2 mmol) was added to a stirred mixture of 3-(5-aminomethyl-1-oxo-1,3-dihydro-isoindol-2-yl)-piperidine-2,6-dione (0.32 g, 0.85 mmol) and 1-ethyl-4-isocyanato-benzene (0.14 ml, 1 mmol) in acetonitrile (20 mL) under nitrogen. The mixture was stirred at ambient temperature for 1 h, during which time it remained a suspension. The reaction was then monitored and determined to be complete. A 3.5% aqueous HCl solution (10 mL) was added, and the mixture stirred for 10 minutes. The solid was isolated by filtration, and the solid was washed with additional 3.5% aq. HCl (20 mL) and acetonitrile (20 mL), yielding the 1-[2-(2,6-dioxo-piperidin-3-yl)-1-oxo-2,3-dihydro-1H-isoindol-5-ylmethyl]-3-(4-ethyl-phenyl)-urea as a white solid (230 mg, 64%). HPLC: Waters Symmetry C-18, 3.9×150 mm, 5 micro, 1 mL/min, 240 nm, 40/60 $CH_3CN$/0.1% $H_3PO_4$ in $H_2O$: $t_R$=3.53 min (98%); mp. 263-265° C. $^1$H NMR (DMSO-$d_6$) δ 1.94-2.06 (m, 1H, CHH), 2.38 (qd, J=4.2, 13.1 Hz, 1H, CHH), 2.60 (d, J=17.0 Hz, 1H, CHH), 2.84-3.00 (m, 1H, CHH), 4.26-4.50 (m, 4H, CH2+CH2), 5.03 (s, 2H, CH2), 5.11 (dd, J=5.0, 13.1 Hz, 1H, CHN), 6.64 (t, J=5.9 Hz, 1H, Ar), 6.90 (d, J=8.9 Hz, 2H, Ar), 7.26-7.48 (m, 8H, Ar), 7.51 (s, 1H, NH), 7.69 (d, J=7.9 Hz, 1H, Ar), 8.43 (s, 1H, NH), 10.99 (s, 1H, NH); $^{13}$C NMR (DMSO-$d_6$) δ 22.49, 31.20, 42.79, 47.10, 51.56, 69.38, 114.92, 119.44, 121.85, 122.91, 126.88, 127.59, 127.68, 128.35, 130.25, 133.73, 137.26, 142.36, 145.00, 153.02, 155.41, 167.95, 170.99, 172.86; LCMS MH=421. Anal Calcd for: $C_{23}H_{24}N_4O_4$+0.15 $CH_3CN$: C, 65.60; H, 5.78; N, 13.62. found: C, 65.42; H, 5.69; N, 13.24.

5.148 1-(4-chloro-2-methyl-phenyl)-3-[2-(2,6-dioxo-piperidin-3-yl)-1-oxo-2,3-dihydro-1H-isoindol-5-ylmethyl]-urea

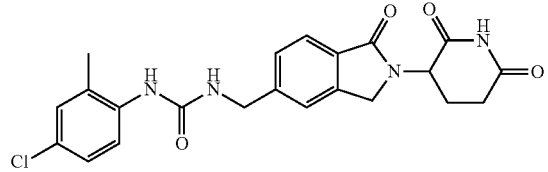 [SMILES: Cc1cc(Cl)ccc1NC(=O)NCc1ccc2c(c1)CN(C1CCC(=O)NC1=O)C2=O]

TEA (0.28 ml, 2 mmol) was added to a stirred mixture of 3-(5-aminomethyl-1-oxo-1,3-dihydro-isoindol-2-yl)-piperidine-2,6-dione (0.37 g, 1 mmol) and 4-chloro-1-isocyanato-2-methyl-benzene (0.17 mgl, 1 mmol) in acetonitrile (10 mL) under nitrogen. The mixture was stirred at ambient temperature for 1 h, during which time it remained a suspension. The reaction was then monitored and determined to be complete. A 3.5% aqueous HCl solution (10 mL) was added, and the mixture was stirred for 10 minutes. The solid was isolated by filtration, and the solid was washed with additional 3.5% aq. HCl (20 mL) and acetonitrile (20 mL), yielding 1-(4-chloro-2-methyl-phenyl)-3-[2-(2,6-dioxo-piperidin-3-yl)-1-oxo-2,3-dihydro-1H-isoindol-5-ylmethyl]-urea as a white solid (380 mg, 90%). HPLC: Waters Symmetry C-18, 3.9×150 mm, 5 micro, 1 mL/min, 240 nm, 40/60 $CH_3CN$/0.1% $H_3PO_4$ in $H_2O$: $t_R$=3.6 min (99%); mp. 256-258° C. $^1$H NMR (DMSO-$d_6$) δ 1.93-2.08 (m, 1H, CHH), 2.19 (s, 3H, $CH_3$), 2.31-2.47 (m, 1H, CHH), 2.63 (br. s., 1H, CHH), 2.82-3.00 (m, 1H, CHH), 4.27-4.51 (m, 4H, $CH_2$, $CH_2$), 5.11 (dd, J=5.2, 13.3 Hz, 1H, CHN), 7.09-7.24 (m, 3H, Ar), 7.46 (d, J=7.7 Hz, 1H, Ar), 7.53 (s, 1H, NH), 7.71 (d, J=7.7 Hz, 1H, Ar), 7.87 (d, J=3.4 Hz, 1H, Ar), 7.90 (s, 1H, NH), 10.99 (s, 1H, NH); $^{13}$C NMR (DMSO-$d_6$) δ 17.61, 22.49, 31.20, 42.83, 47.12, 51.58, 121.64, 121.98, 122.99, 125.36, 125.77, 126.97, 129.04, 129.46, 130.36, 137.14, 142.42, 144.58, 155.22, 167.92, 170.99, 172.85; LCMS MH=441. Anal Calcd for: $C_{22}H_{21}ClN_4O_4$+0.2$H_2O$: C, 59.45; H, 4.85; N, 12.60; Cl, 7.98. found: C, 59.21; H, 4.71; N, 12.46; Cl, 8.21.

5.149 1-(3,5-dimethyl-phenyl)-3-[2-(2,6-dioxo-piperidin-3-yl)-1-oxo-2,3-dihydro-1H-isoindol-5-ylmethyl]-urea

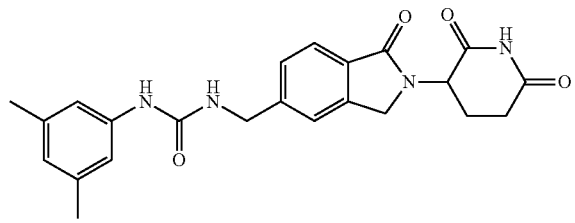 [SMILES: Cc1cc(C)cc(NC(=O)NCc2ccc3c(c2)CN(C2CCC(=O)NC2=O)C3=O)c1]

TEA (0.28 ml, 2 mmol) was added to a stirred mixture of 3-(5-aminomethyl-1-oxo-1,3-dihydro-isoindol-2-yl)-piperidine-2,6-dione (0.37 g, 1 mmol) and 1-isocyanato-3,5-dimethyl-benzene (0.17 mg, 1 mmol) in acetonitrile (10 mL) under nitrogen. The mixture was stirred at ambient temperature for 1 h, during which time it remained a suspension. The reaction was then monitored and determined to be complete. A 3.5% aqueous HCl solution (10 mL) was added, and the mixture was stirred for 10 minutes. The solid was isolated by filtration, and the solid was washed with additional 3.5% aq. HCl (20 mL) and acetonitrile (20 mL), yielding 1-(3,5-dimethyl-phenyl)-3-[2-(2,6-dioxo-piperidin-3-yl)-1-oxo-2,3-dihydro-1H-isoindol-5-ylmethyl]-urea as a white solid (280 mg, 67%). HPLC: Waters Symmetry C-18, 3.9×150 mm, 5 micro, 1 mL/min, 240 nm, 40/60 $CH_3CN/0.1\%$ $H_3PO_4$ in $H_2O$: $t_R$=3.4 min (96%); mp. 289-291° C. $^1H$ NMR (DMSO-$d_6$) δ 1.92-2.06 (m, 1H, CHH), 2.19 (s, 6H, $CH_3+CH_3$), 2.38 (qd, J=4.4, 13.1 Hz, 1H, CHH), 2.54-2.66 (m, 1H, CHH), 2.80-3.02 (m, 1H, CHH), 4.17-4.58 (m, 4H, $CH_2+CH_2$), 5.11 (dd, J=5.2, 13.3 Hz, 1H, CHN), 6.54 (s, 1H, Ar), 6.69 (t, J=5.9 Hz, 1H, Ar), 7.03 (s, 2H, Ar), 7.44 (d, J=7.9 Hz, 1H, Ar), 7.51 (s, 1H, NH), 7.69 (d, J=7.7 Hz, 1H, Ar), 8.45 (s, 1H, NH), 10.98 (s, 1H, NH). $^{13}C$ NMR (DMSO-$d_6$) δ 21.12, 22.49, 31.20, 42.76, 47.10, 51.56, 115.54, 121.88, 122.78, 122.93, 126.91, 130.27, 137.49, 140.19, 142.38, 144.93, 155.21, 167.95, 170.99, 172.85; LCMS MH=421. Anal Calcd for: $C_{23}H_{24}N_4O_4$+0.1$H_2O$: C, 65.42; H, 5.78; N, 13.27. found: C, 65.15; H, 5.58; N, 13.18.

5.150 1-(3,4-dichloro-phenyl)-3-[2-(2,6-dioxo-piperidin-3-yl)-1-oxo-2,3-dihydro-1H-isoindol-5-ylmethyl]-urea

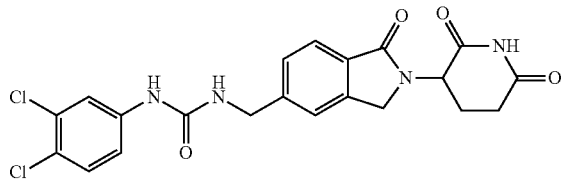 [SMILES: O=C1CCC(N2Cc3cc(CNC(=O)Nc4ccc(Cl)c(Cl)c4)ccc3C2=O)C(=O)N1]

3,4-Dichlorophenylisocyanate (0.19 g, 1.0 mmol) was added to a mixture of 3-(5-(aminomethyl)-1-oxoisoindolin-2-yl)piperidine-2,6-dione hydrochloride (0.31 g, 1.0 mmol) in DMF (20 mL), followed by dropwise addition of triethylamine (0.31 mL). After 1 h, water (20 mL) was added. The solid precipitate was filtered and washed with 4% aqueous HCl, and dried in vacuo providing 1-(3,4-dichloro-phenyl)-3-[2-(2,6-dioxo-piperidin-3-yl)-1-oxo-2,3-dihydro-1H-isoindol-5-ylmethyl]-urea as a white solid (0.43 g, 60% yield); mp 238-240° C.; HPLC, Waters Symmetry $C_{18}$, 5 μm, 3.9×150 mm, 1 ml/min, 240 nm, 40/60 $CH_3CN/0.1\%$ $H_3PO_4$, 7.87 (99.70%) $^1H$ NMR (DMSO-d6) δ 1.98-2.01 (m, 1H), 2.33-2.46 (m, 1H), 2.57-2.62 (m, 1H), 2.86-3.00 (m, 1H), 4.34 (d, 1H, J=17.4), 4.35-4.79 (m, 3H), 5.11 (dd, 1H, J=13.2, J=5.4), 6.93 (t, 1H, J=5.7), 7.27 (dd, 1H, J=8.7, J=2.4), 7.46 (m, 3H), 7.70 (d, 1H, J=7.8), 7.86 (d, 1H, J=2.1), 9.00 (s, 1H), 10.97 (s, 1H). $^{13}C$ NMR (DMSO-$d_6$) δ 22.5, 31.2, 42.8, 47.1, 51.5, 117.8, 118.9, 121.9, 122.3, 122.9, 123.0, 127.0, 130.3, 130.9, 140.6, 142.4, 144.5, 154.9, 167.9, 171.0, 172.9. Anal. Calcd for $C_{21}H_{18}Cl_2N_4O_4$+0.9 $CH_2Cl_2$: C, 48.92; H, 3.71; N, 10.42. Found: C, 48.87; H, 3.48; N, 10.73.

5.151 1-tert-butyl-3-[2-(2,6-dioxo-piperidin-3-yl)-1-oxo-2,3-dihydro-1H-isoindol-5-ylmethyl]-urea

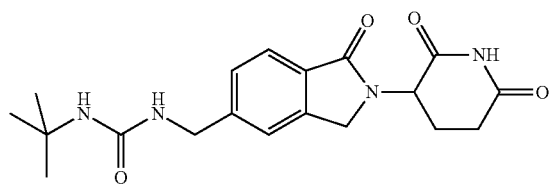 [SMILES: CC(C)(C)NC(=O)NCc1ccc2c(c1)CN(C1CCC(=O)NC1=O)C2=O]

To a stirred mixture of 3-(5-aminomethyl-1-oxo-1,3-dihydro-isoindol-2-yl)-piperidine-2,6-dione hydrochloride (0.50 g, 1.60 mmol) and tert-butylisocyanate (0.19 mL, 1.60 mmol) in N,N-dimethylformamide (10 mL), was added triethylamine (0.45 mL, 3.20 mmol) at room temperature under nitrogen. After 18 h, water (200 mL) was added and the product was extracted with $CH_2Cl_2$ (5×100 mL). The organic layers were combined, dried (MgSO$_4$) and concentrated in vacuo. The resulting residue was triturated in $Et_2O$ (50 mL) for 18 h. The product was isolated by filtration and dried in vacuo to give 1-tert-butyl-3-[2-(2,6-dioxo-piperidin-3-yl)-1-oxo-2,3-dihydro-1H-isoindol-5-ylmethyl]-urea as a white solid (0.24 g, 40% yield): HPLC: Waters Symmetry $C_{18}$, 5 μm, 3.9×150 mm, 1 mL/min, 240 nm, 20/80 $CH_3CN/0.1\%$ $H_3PO_4$, 7.51 min (98.18%); mp: 260-262° C.; $^1H$ NMR (DMSO-$d_6$) δ 1.24 (s, 9H, 3 $CH_3$), 1.89-2.11 (m, 1H, CHH), 2.28-2.48 (m, 1H, CHH), 2.60 (d, J=17.6 Hz, 1H, CHH), 2.80-3.04 (m, 1H, CHH), 4.17-4.36 (m, 3H, CHH, $CH_2$), 4.44 (d, J=17.4 Hz, 1H, CHH), 5.11 (dd, J=5.0, 13.1 Hz, 1H, CH), 5.78 (s, 1H, Ar), 6.20 (t, J=5.9 Hz, 1H, NH), 7.37 (d, J=7.9 Hz, 1H, Ar), 7.44 (s, 1H, NH), 7.67 (d, J=7.7 Hz, 1H, Ar), 10.98 (s, 1H, NH); $^{13}C$ NMR (DMSO-$d_6$) δ 22.50, 29.30, 31.21, 42.58, 47.10, 49.11, 51.56, 121.73, 122.87, 126.75, 130.14, 142.32, 145.55, 157.28, 167.98, 171.00, 172.85; LCMS: MH=373; Anal Calcd for $C_{19}H_{24}N_4O_4$: C, 61.28; H, 6.50; N, 15.04. Found: C, 61.00; H, 6.57; N, 15.03.

5.152 1-(4-tert-butyl-phenyl)-3-[2-(2,6-dioxo-piperidin-3-yl)-1-oxo-2,3-dihydro-1H-isoindol-5-ylmethyl]-urea

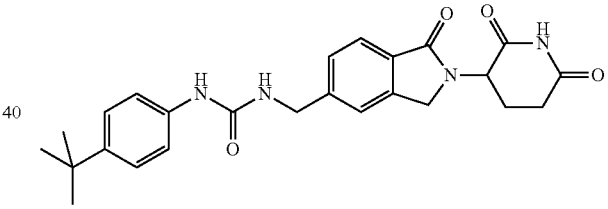

To a stirred mixture of 3-(5-aminomethyl-1-oxo-1,3-dihydro-isoindol-2-yl)-piperidine-2,6-dione methanesulfonate (0.37 g, 1.0 mmol) and 4-(tert-butyl) phenyl isocyanate (0.18 g, 1.0 mmol) in DMF (20 mL) was added triethylamine (0.22 g, 2.2 mmol) at rt under nitrogen. After 2 h, 4% aqueous HCl (30 ml) was added and the solids were filtered and dried in vacuo providing 1-(4-tert-butyl-phenyl)-3-[2-(2,6-dioxo-piperidin-3-yl)-1-oxo-2,3-dihydro-1H-isoindol-5-ylmethyl]-urea as a white solid, (0.34 g, 76% yield); mp 254-256° C.; HPLC, Waters Symmetry C-18, 3.9×150 mm, 5 μm, 1 ml/min, 240 nm, 40/60 $CH_3CN/0.1\%$ $H_3PO_4$, 7.71 (96.94%); $^1H$ NMR (DMSO-$d_6$) δ 1.24 (s, 9H), 1.97-2.01 (m, 1H), 2.35-2.45 (m, 1H), 2.54-2.62 (m, 1H), 2.85-2.97 (m, 1H), 4.30 (d, 2H, J=17.3 Hz), 4.45 (d, 2H, J=17.3 Hz), 5.10 (dd, 1H, J=12.9 Hz, J=4.5 Hz), 6.68 (t, 1H, J=4.8 Hz), 7.23 (dd, 2H, J=8.4 Hz, J=1.5), 7.31 (dd, 2H, J=8.4 Hz, J=1.5 Hz), 7.44 (d, 1H, J=7.8 Hz), 7.51 (s, 1H), 7.69 (d, 1H, J=7.8 Hz), 8.54 (s, 1H), 10.98 (s, 1H); $^{13}C$ NMR (DMSO-$d_6$) δ 22.5, 31.2, 31.3, 33.8, 42.7, 47.1, 51.6, 117.6, 121.8, 122.9, 125.2, 126.9, 130.3, 137.7, 142.4, 143.4, 144.9, 155.5, 167.9, 170.9, 172.8; LCMS: MH=449; Anal. Calcd for $C_{25}H_{28}N_4O_4$+0.5$H_2O$: C, 65.63; H, 6.39; N, 12.25. Found: C, 65.24; H, 6.17; N, 12.29.

5.153 1-(2-chloro-phenyl)-3-[2-(2,6-dioxo-piperidin-3-yl)-1-oxo-2,3-dihydro-1H-isoindol-5-ylmethyl]-urea

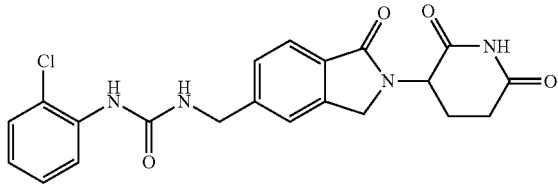 [SMILES: O=C1CCC(N2Cc3cc(CNC(=O)Nc4ccccc4Cl)ccc3C2=O)C(=O)N1]

To a stirred mixture of 3-(5-aminomethyl-1-oxo-1,3-dihydro-isoindol-2-yl)-piperidine-2,6-dione hydrochloride (0.50 g, 1.40 mmol) and 2-chlorophenylisocyanate (0.16 mL, 1.40 mmol) in N,N-dimethylformamide (10 mL), was added triethylamine (0.38 mL, 2.7 mmol) at room temperature under nitrogen. After 2 h, 1 N aq. HCl (40 mL) was added and the solids were isolated by filtration and washed with water (20 mL). The crude product was triturated in EtOAc (50 mL) for 0.5 h. The product was isolated by filtration and dried in vacuo to give 1-(2-chloro-phenyl)-3-[2-(2,6-dioxo-piperidin-3-yl)-1-oxo-2,3-dihydro-1H-isoindol-5-ylmethyl]-urea as a white solid (0.56 g, 97% yield): HPLC: Waters Symmetry $C_{18}$, 5 µm, 3.9×150 mm, 1 mL/min, 240 nm, 30/70 $CH_3CN$/0.1% $H_3PO_4$, 6.35 min (98.37%); mp: 235-237° C.; $^1$H NMR (DMSO-$d_6$) δ 1.77-2.14 (m, 1H, CHH), 2.23-2.47 (m, 1H, CHH), 2.60 (d, J=17.2 Hz, 1H, CHH), 2.77-3.04 (m, 1H, CHH), 4.32 (d, J=17.4 Hz, 1H, CHH), 4.39-4.61 (m, 3H, CHH, $CH_2$), 5.11 (dd, J=4.9, 13.2 Hz, 1H, CH), 6.88-7.04 (m, 1H, Ar), 7.15-7.32 (m, 1H, Ar), 7.34-7.50 (m, 2H, Ar), 7.54 (s, 1H, NH), 7.58 (t, J=5.8 Hz, 1H, NH), 7.71 (d, J=7.7 Hz, 1H, Ar), 8.17 (d, J=6.0 Hz, 2H, Ar), 10.98 (s, 1H, NH); $^{13}$C NMR (DMSO-$d_6$) δ 22.50, 31.21, 42.83, 47.14, 51.59, 120.86, 121.28, 122.01, 122.61, 123.03, 127.00, 127.45, 129.08, 130.44, 136.57, 142.48, 144.30, 154.83, 167.92, 171.00, 172.85; LCMS: MH=427/429; Anal Calcd for $C_{21}H_{19}N_4O_4Cl$: C, 59.09; H, 4.49; N, 13.13; Cl, 8.31. Found: C, 58.86; H, 4.26; N, 12.88; Cl, 8.32.

5.154 1-(3-chloro-phenyl)-3-[2-(2,6-dioxo-piperidin-3-yl)-1-oxo-2,3-dihydro-1H-isoindol-5-ylmethyl]-urea

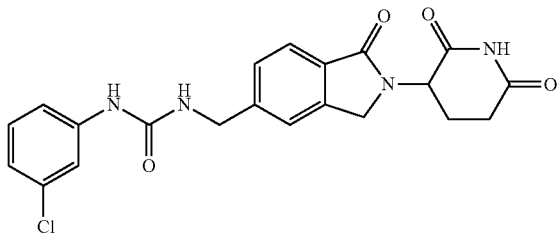 [SMILES: O=C1CCC(N2Cc3cc(CNC(=O)Nc4cccc(Cl)c4)ccc3C2=O)C(=O)N1]

To a stirred mixture of 3-(5-aminomethyl-1-oxo-1,3-dihydro-isoindol-2-yl)-piperidine-2,6-dione hydrochloride (0.50 g, 1.40 mmol) and 3-chlorophenylisocyanate (0.16 mL, 1.40 mmol) in N,N-dimethylformamide (10 mL), was added triethylamine (0.38 mL, 2.7 mmol) at room temperature under nitrogen. After 2 h, 1 N aq. HCl (40 mL) was added and the solids were isolated by filtration and washed with water (20 mL). The crude product was triturated in EtOAc (50 mL) for 0.5 h. The product was isolated by filtration and dried in vacuo to give 1-(3-chloro-phenyl)-3-[2-(2,6-dioxo-piperidin-3-yl)-1-oxo-2,3-dihydro-1H-isoindol-5-ylmethyl]-urea as an off-white solid (0.52 g, 90% yield): HPLC: Waters Symmetry $C_{18}$, 5 µm, 3.9×150 mm, 1 mL/min, 240 nm, 30/70 $CH_3CN$/0.1% $H_3PO_4$, 9.26 min (96.05%); mp: 215-217° C.; $^1$H NMR (DMSO-$d_6$) δ 1.88-2.12 (m, 1H, CHH), 2.27-2.47 (m, 1H, CHH), 2.60 (d, J=17.2 Hz, 1H, CHH), 2.77-3.03 (m, 1H, CHH), 4.31 (d, J=17.4 Hz, 1H, CHH), 4.37-4.54 (m, 3H, CHH, $CH_2$), 5.11 (dd, J=5.1, 13.2 Hz, 1H, CH), 6.85 (t, J=5.9 Hz, 1H, NH), 6.90-7.07 (m, 1H, Ar), 7.10-7.34 (m, 2H, Ar), 7.45 (d, J=7.9 Hz, 1H, Ar), 7.52 (s, 1H, Ar), 7.61-7.78 (m, 2H, Ar), 8.88 (s, 1H, NH), 10.98 (s, 1H, NH); $^{13}$C NMR (DMSO-$d_6$) δ 22.50, 31.21, 42.80, 47.13, 51.59, 116.12, 117.10, 120.73, 121.91, 122.94, 126.91, 130.22, 130.33, 133.09, 141.95, 142.39, 144.64, 155.00, 167.93, 171.00, 172.85; LCMS: MH=427/429; Anal Calcd for $C_{21}H_{19}N_4O_4Cl$: C, 59.09; H, 4.49; N, 13.13; Cl, 8.31. Found: C, 58.82; H, 4.22; N, 13.03; Cl, 8.32.

5.155 1-(4-chloro-3-trifluoromethyl-phenyl)-3-[2-(2,6-dioxo-piperidin-3-yl)-1-oxo-2,3-dihydro-1H-isoindol-5-ylmethyl]-urea

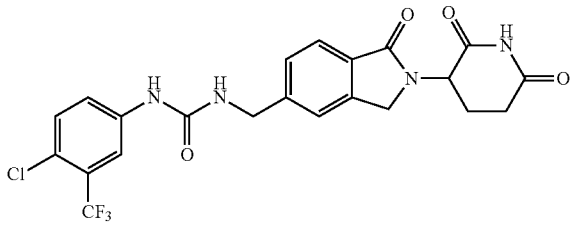 [SMILES: O=C1CCC(N2Cc3cc(CNC(=O)Nc4ccc(Cl)c(C(F)(F)F)c4)ccc3C2=O)C(=O)N1]

TEA (0.28 g, 2.8 mmol) was added to a mixture of 3-(5-aminomethyl-1-oxo-1,3-dihydro-isoindol-2-yl)-piperidine-2,6-dione methanesulfonate (0.5 g, 1.4 mmol) and 4-chloro-3-(trifluoromethyl)phenyl isocyanate (0.31 g, 1.4 mmol) in DMF (30 mL) at 0° C. The mixture stirred at 0° C. for 3 h, and then 4% aqueous HCl (30 mL) was added. The solid precipitate was filtered and dried in vacuo providing 1-(4-chloro-3-trifluoromethyl-phenyl)-3-[2-(2,6-dioxo-piperidin-3-yl)-1-oxo-2,3-dihydro-1H-isoindol-5-ylmethyl]-urea as a white solid, (0.57 g, 86% yield); mp 261-263° C.; HPLC, Waters Symmetry C-18, 3.9×150 mm, 5 µm, 1 ml/min, 240 nm, 40/60 $CH_3CN$/0.1% $H_3PO_4$, 8.57 (98.52%); $^1$H NMR (DMSO-$d_6$) δ 1.98-2.02 (m, 1H), 2.13-2.46 (m, 1H), 2.58-2.63 (m, 1H), 2.86-2.98 (m, 1H), 4.28-4.48 (m, 4H), 5.11 (dd, 1H, J=13.2 Hz, J=5.1 Hz), 6.98 (t, 1H, J=6.0 Hz), 7.45 (d, 1H, J=8.1 Hz), 7.54 (d, 2H, J=11.7 Hz), 7.61 (dd, 1H, J=8.7 Hz, J=2.1 Hz), 7.70 (d, 1H, J=7.8 Hz), 8.09 (d, 1H, J=2.4 Hz), 9.18 (s, 1H), 10.99 (s, 1H); $^{13}$C NMR (DMSO-$d_6$) δ 22.5, 31.2, 42.8, 47.1, 51.6, 116.2 (q, J=5.6 Hz), 121.5, 121.9, 122.4, 122.8 (q, J=271 Hz), 122.9, 126.6 (q, J=30 Hz), 126.9, 130.3, 131.8, 140.0, 142.4, 144.5, 154.9, 167.9, 171.0, 172.8; LCMS: MH=495, 497; Anal. Calcd for $C_{22}H_{18}ClF_3N_4O_4$+0.1$H_2O$: C, 53.20; H, 3.69; N, 11.28. Found: C, 52.83; H, 3.47; N, 11.15.

5.156 1-[2-(2,6-dioxo-piperidin-3-yl)-1-oxo-2,3-dihydro-1H-isoindol-5-ylmethyl]-3-(4-trifluoromethylsulfanyl-phenyl)-urea

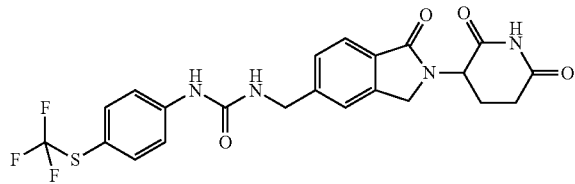 [SMILES: O=C1CCC(N2Cc3cc(CNC(=O)Nc4ccc(SC(F)(F)F)cc4)ccc3C2=O)C(=O)N1]

TEA (0.28 g, 2.8 mmol) was added to a mixture of 3-(5-aminomethyl-1-oxo-1,3-dihydro-isoindol-2-yl)-piperidine-2,6-dione methanesulfonate (0.50 g, 1.4 mmol) and 4-(trifluoromethylthio)phenyl isocyanate (0.31 g, 1.4 mmol) in acetonitrile (30 mL) at 0° C. The reaction was stirred at 0° C. for 2 h and then 4% aqueous HCl (30 mL) was added. The solid precipitate was filtered and dried in vacuo providing 1-[2-(2,6-dioxo-piperidin-3-yl)-1-oxo-2,3-dihydro-1H-isoindol-5-ylmethyl]-3-(4-trifluoromethylsulfanyl-phenyl)-urea as a white solid (0.34 g, 51% yield); mp 218-220° C.; HPLC, Waters Symmetry C-18, 3.9×150 mm, 5 µm, 1 ml/min, 240 nm, 50/50 CH$_3$CN/0.1% H$_3$PO$_4$, 3.18 (97.19%), $^1$H NMR (DMSO-d$_6$) δ 1.97-2.02 (m, 1H), 2.31-2.46 (m, 1H), 2.57-2.63 (m, 1H), 2.87-2.98 (m, 1H), 4.28-4.48 (m, 4H), 5.11 (dd, 1H, J=13.2 Hz, J=5.1 Hz), 6.92 (t, 1H, J=6.0 Hz), 7.45 (d, 1H, J=8.1 Hz), 7.52-7.64 (m, 5H), 7.70 (d, 1H, J=7.8 Hz), 9.08 (s, 1H), 10.98 (s, 1H); $^{13}$C NMR (DMSO-d$_6$) δ 22.5, 31.2, 42.8, 47.1, 51.5, 113.0, 118.4, 121.9, 122.9, 126.9, 129.6 (q, J=306 Hz), 130.3, 137.3, 142.4, 143.6, 144.5, 154.8, 167.9, 171.0, 172.8; LCMS: MH=493; Anal. Calcd for C$_{22}$H$_{19}$F$_3$N$_4$O$_4$S+0.2H$_2$O: C, 53.27; H, 3.94; N, 11.29. Found: C, 53.06; H, 3.59; N, 11.12.

5.157 1-[2-(2,6-dioxo-piperidin-3-yl)-1-oxo-2,3-dihydro-1H-isoindol-5-ylmethyl]-3-(4-methyl-3-trifluoromethyl-phenyl)-thiourea

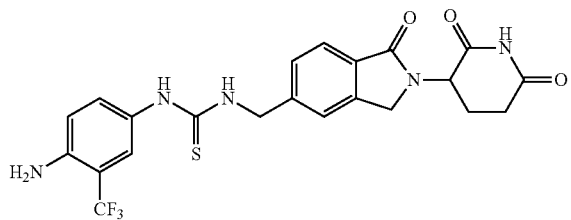 [SMILES: Nc1ccc(NC(=S)NCc2ccc3c(c2)CN(C2CCC(=O)NC2=O)C3=O)cc1C(F)(F)F]

TEA (0.28 g, 2.8 mmol) was added to a mixture of 3-(5-aminomethyl-1-oxo-1,3-dihydro-isoindol-2-yl)-piperidine-2,6-dione methanesulfonate (0.50 g, 1.4 mmol) and -(trifluoromethyl)-4-methylphenyl isothiocyanate (0.30 g, 1.4 mmol) in acetonitrile (30 mL) at 0° C. The mixture was stirred at ambient temperature for 60 h and then 10% aqueous HCl solution (30 mL) was added. The solid precipitate was filtered and dried in vacuo providing 1-[2-(2,6-dioxo-piperidin-3-yl)-1-oxo-2,3-dihydro-1H-isoindol-5-ylmethyl]-3-(4-methyl-3-trifluoromethyl-phenyl)-thiourea as a white solid (0.50 g, 76% yield); mp 238-240° C.; HPLC, Waters Symmetry C-18, 3.9×150 mm, 5 µm, 1 ml/min, 240 nm, 40/60 CH$_3$CN/0.1% H$_3$PO$_4$, 8.02 (98.09%); $^1$H NMR (DMSO-d$_6$) δ 1.99-2.07 (m, 1H), 2.27-2.47 (m, 4H), 2.58-2.63 (m, 1H), 2.86-2.98 (m, 1H), 4.32 (d, 1H, J=17.4 Hz), 4.46 (d, 1H, J=17.4 Hz), 4.87 (d, 2H, J=5.4 Hz), 5.11 (dd, 1H, J=13.2 Hz, J=5.1 Hz), 7.38 (d, 1H, J=8.4 Hz), 7.48 (d, 1H, J=7.8 Hz), 7.55-7.60 (m, 2H), 7.71 (d, 1H, J=7.8 Hz), 7.85 (s, 1H), 8.44 (s, 1H), 9.83 (s, 1H), 10.99 (s, 1H); $^{13}$C NMR (DMSO-d$_6$) δ 18.1, 22.5, 31.2, 47.1, 51.6, 120.4, 122.1, 122.9, 124.3 (q, J=272), 126.6, 126.8, 127.0, 127.1, 127.4, 130.4, 131.3, 132.4, 137.5, 143.2, 167.9, 171.0, 172.8, 181.2; LCMS: MH=491; Anal. Calcd for C$_{22}$H$_{19}$F$_3$N$_4$O$_4$S: C, 56.32; H, 4.32; N, 11.42. Found: C, 56.31; H, 4.12; N, 11.36.

5.158 1-[2-(2,6-dioxo-piperidin-3-yl)-1-oxo-2,3-dihydro-1H-isoindol-5-ylmethyl]-3-(4-trifluoromethylsulfanyl-phenyl)-thiourea

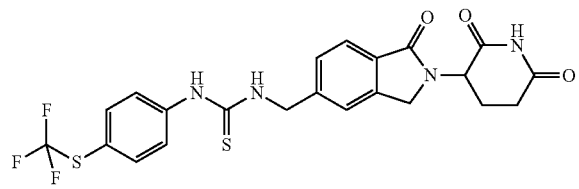

TEA (0.28 g, 2.8 mmol) was added to a mixture of 3-(5-aminomethyl-1-oxo-1,3-dihydro-isoindol-2-yl)-piperidine-2,6-dione methanesulfonate (0.50 g, 1.4 mmol) and -(trifluoromethylthio)phenyl isothiocyanate (0.33 g, 1.4 mmol) in acetonitrile (30 mL) at 0° C. The mixture stirred at 0° C. for 16 h, and then 4% aqueous HCl solution (30 mL) was added. The solid precipitate was filtered and dried in vacuo providing 1-[2-(2,6-dioxo-piperidin-3-yl)-1-oxo-2,3-dihydro-1H-isoindol-5-ylmethyl]-3-(4-trifluoromethylsulfanyl-phenyl)-thiourea as a white solid (0.33 g, 48% yield); mp 229-231° C.; HPLC, Waters Symmetry C-18, 3.9×150 mm, 5 µm, 1 ml/min, 240 nm, 50/50 CH$_3$CN/0.1% H$_3$PO$_4$, 4.08 (98.31%); $^1$H NMR (DMSO-d$_6$) δ 1.98-2.04 (m, 1H), 2.32-2.47 (m, 1H), 2.57-2.63 (m, 1H), 2.86-2.98 (m, 1H), 4.32 (d, 1H, J=17.4 Hz), 4.46 (d, 1H, J=17.4 Hz), 4.89 (d, 2H, J=5.4 Hz), 5.12 (dd, 1H, J=13.2 Hz, J=5.1 Hz), 7.48 (d, 1H, J=8.4 Hz), 7.56 (s, 1H), 7.64-7.73 (m, 5H), 8.60 (s, 1H), 10.02 (s, 1H), 10.99 (s, 1H); $^{13}$C NMR (DMSO-d$_6$) δ 22.5, 31.2, 47.0, 47.1, 51.6, 116.2, 122.2, 122.8, 122.9, 127.2, 129.6 (q, J=306), 130.5, 136.8, 142.3, 142.7, 143.0, 167.9, 171.0, 172.8, 180.8; LCMS: MH=509; Anal. Calcd for C$_{22}$H$_{19}$F$_3$N$_4$O$_3$S$_2$+0.1H$_2$O: C, 51.78; H, 3.79; N, 10.98. Found: C, 51.55; H, 3.55; N, 10.85.

5.159 1-[2-(2,6-dioxo-piperidin-3-yl)-1-oxo-2,3-dihydro-1H-isoindol-5-ylmethyl]-3-(4-ethoxy-phenyl)-urea

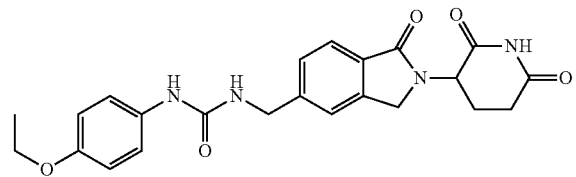 [SMILES: CCOc1ccc(NC(=O)NCc2ccc3c(c2)CN(C2CCC(=O)NC2=O)C3=O)cc1]

To a stirred mixture of 3-(5-aminomethyl-1-oxo-1,3-dihydro-isoindol-2-yl)-piperidine-2,6-dione methane sulfonate (0.50 g, 1.40 mmol) and 4-ethoxyphenylisocyanate (0.20 mL, 1.40 mmol) in N,N-dimethylformamide (10 mL), was added triethylamine (0.38 mL, 2.7 mmol) at room temperature under nitrogen. After 2 h, 1 N aq. HCl (15 mL) was added and the solids were isolated by filtration, washed with water (30 mL). The crude solids were slurried in EtOAc (15 mL) for 4 h then filtered, washed with EtOAc (15 mL) and dried in vacuo to give 1-[2-(2,6-dioxo-piperidin-3-yl)-1-oxo-2,3-dihydro-1H-isoindol-5-ylmethyl]-3-(4-ethoxy-phenyl)-urea as an off-white solid (0.66 g, 100% yield): HPLC: Waters Symmetry $C_{18}$, 5 µm, 3.9×150 mm, 1 mL/min, 240 nm, 10/90 to 90/10 $CH_3CN/0.1\%$ $H_3PO_4$ gradient over 15 mins, 7.43 min (99.34%); mp: 277-279° C.; $^1H$ NMR (DMSO-$d_6$) δ 1.29 (t, J=7.0 Hz, 3H, $CH_3$), 1.85-2.14 (m, 1H, CHH), 2.23-2.47 (m, 1H, CHH), 2.59 (d, J=17.6 Hz, 1H, CHH), 2.79-3.07 (m, 1H, CHH), 3.94 (q, J=7.0 Hz, 2H, $CH_2$), 4.23-4.36 (m, 1H, CHH), 4.36-4.55 (m, 3H, CHH, $CH_2$), 5.11 (dd, J=4.9, 13.2 Hz, 1H, CH), 6.62 (t, J=5.9 Hz, 1H, NH), 6.80 (d, J=8.9 Hz, 2H, Ar), 7.29 (d, J=8.9 Hz, 2H, Ar), 7.44 (d, J=7.9 Hz, 1H, Ar), 7.51 (s, 1H, Ar), 7.69 (d, J=7.7 Hz, 1H, Ar), 8.40 (s, 1H, NH), 10.98 (s, 1H, NH); $^{13}C$ NMR (DMSO-$d_6$) δ 14.72, 22.49, 31.20, 42.79, 47.10, 51.56, 63.04, 114.44, 119.52, 121.85, 122.91, 126.88, 130.25, 133.39, 142.36, 145.03, 153.24, 155.44, 167.96, 170.99, 172.86; LCMS: MH=437; Anal Calcd for $C_{23}H_{24}N_4O_5$: C, 63.29; H, 5.54; N, 12.84. Found: C, 63.27; H, 5.46; N, 12.73.

5.160 1-[2-(2,6-dioxo-piperidin-3-yl)-1-oxo-2,3-dihydro-1H-isoindol-5-ylmethyl]-3-(4-trifluoromethoxy-phenyl)-urea

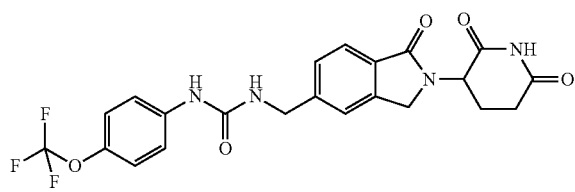 [SMILES: O=C1CCC(N2Cc3cc(CNC(=O)Nc4ccc(OC(F)(F)F)cc4)ccc3C2=O)C(=O)N1]

To a stirred mixture of 3-(5-aminomethyl-1-oxo-1,3-dihydro-isoindol-2-yl)-piperidine-2,6-dione methane sulfonate (0.50 g, 1.40 mmol) and 4-(trifluoromethoxy)phenylisocyanate (0.20 mL, 1.40 mmol) in N,N-dimethylformamide (10 mL), was added triethylamine (0.38 mL, 2.7 mmol) at room temperature under nitrogen. After 2 h, 1 N aq. HCl (15 mL) was added and the solids were isolated by filtration and washed with water (30 mL). The crude solids were slurried in EtOAc (15 mL) for 4 h then filtered, washed with EtOAc (15 mL) and dried in vacuo to give 1-[2-(2,6-dioxo-piperidin-3-yl)-1-oxo-2,3-dihydro-1H-isoindol-5-ylmethyl]-3-(4-trifluoromethoxy-phenyl)-urea as an off-white solid (0.43 g, 67% yield): HPLC: Waters Symmetry $C_{18}$, 5 µm, 3.9×150 mm, 1 mL/min, 240 nm, 10/90 to 90/10 $CH_3CN/0.1\%$ $H_3PO_4$ gradient over 15 mins, 8.87 min (98.89%); mp: 269-271° C.; $^1H$ NMR (DMSO-$d_6$) δ 1.85-2.13 (m, 1H, CHH), 2.25-2.47 (m, 1H, CHH), 2.60 (d, J=17.2 Hz, 1H, CHH), 2.79-3.08 (m, 1H, CHH), 4.22-4.38 (d, J=17.4 Hz, 1H, CHH), 4.38-4.57 (m, 3H, CHH, $CH_2$), 5.11 (dd, J=5.0, 13.1 Hz, 1H, CH), 6.81 (t, J=5.9 Hz, 1H, NH), 7.23 (d, J=8.7 Hz, 2H, Ar), 7.45 (d, J=7.9 Hz, 1H, Ar), 7.48-7.60 (m, 3H, Ar), 7.70 (d, J=7.7 Hz, 1H, Ar), 8.87 (s, 1H, NH), 10.99 (s, 1H, NH); $^{13}C$ NMR (DMSO-$d_6$) δ 22.49, 31.18, 42.79, 47.12, 51.56, 120.08 (q, $M_{03}$), 118.80, 120.08 (q, J=250 Hz), 121.56, 121.86, 122.93, 126.88, 130.30, 139.71, 142.07, 142.38, 144.69, 155.10, 167.93, 170.99, 172.85; LCMS: MH=477; Anal Calcd for $C_{22}H_{19}N_4O_5F_3$: C, 55.47; H, 4.02; N, 11.76; F, 11.96. Found: C, 55.27; H, 3.88; N, 11.73; F, 11.99.

5.161 1-(3-chloro-4-methyl-phenyl)-3-[2-(2,6-dioxo-piperidin-3-yl)-1-oxo-2,3-dihydro-1H-isoindol-5-ylmethyl]-thiourea

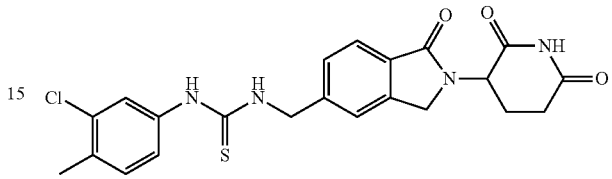

TEA (0.28 g, 2.8 mmol) was added to a mixture of 3-(5-aminomethyl-1-oxo-1,3-dihydro-isoindol-2-yl)-piperidine-2,6-dione methanesulfonate (0.50 g, 1.4 mmol) and 3-chloro-4-methylphenyl isothiocyanate (0.26 g, 1.4 mmol) in acetonitrile (30 mL) at 0° C. The mixture was stirred at ambient temperature for 3 h and then 10% aqueous HCl solution (30 mL) was added. The solid precipitate was filtered and dried in vacuo providing 1-(3-chloro-4-methyl-phenyl)-3-[2-(2,6-dioxo-piperidin-3-yl)-1-oxo-2,3-dihydro-1H-isoindol-5-ylmethyl]-thiourea as a white solid (0.52 g, 84% yield); mp 240-242° C.; HPLC, Waters Symmetry C-18, 3.9×150 mm, 5 µm, 1 ml/min, 240 nm, 40/60 $CH_3CN/0.1\%$ $H_3PO_4$, 7.11 (97.48%); $^1H$ NMR (DMSO-$d_6$) δ 1.95-2.06 (m, 1H, CHH), 2.29 (s, 3H, $CH_3$), 2.35-2.47 (m, 1H, CHH), 2.55-2.67 (m, 1H, CHH), 2.84-3.00 (m, 1H, CHH), 4.32 (d, 1H, CHH), 4.46 (d, 1H, CHH), 4.86 (d, J=5.1 Hz, 2H, $CH_2$ and CHH), 5.11 (dd, 1H, CH), 7.25 (dd, 1H, Ar), 7.28 (d, 1H, Ar), 7.47 (d, 1H, Ar), 7.54 (s, 1H, Ar), 7.61 (s, 1H, Ar), 7.70 (d, 1H, Ar), 8.37 (t, 1H, NH), 9.73 (s, 1H, NH), 11.00 (s, 1H, NH); $^{13}C$ NMR (DMSO-$d_6$) δ 18.96, 22.49, 31.20, 47.13, 51.58, 122.14, 122.88, 123.48, 127.13, 130.39, 130.97, 131.12, 132.67, 138.29, 142.27, 143.32, 167.92, 170.99, 172.86, 181.00; LCMS: MH=457/459; Anal. Calcd for $C_{22}H_{21}ClN_4O_3S$: C, 57.83; H, 4.63; N, 12.26. Found: C, 57.57; H, 4.51; N, 12.21.

5.162 1-[2-(2,6-dioxo-piperidin-3-yl)-1-oxo-2,3-dihydro-1H-isoindol-5-ylmethyl]-3-(4-methoxyphenyl)-urea

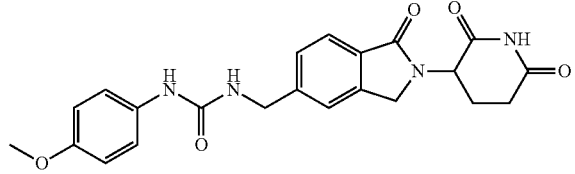 [SMILES: COc1ccc(NC(=O)NCc2ccc3c(c2)CN(C2CCC(=O)NC2=O)C3=O)cc1]

TEA (0.28 g, 2.8 mmol) was added to a mixture of 3-(5-aminomethyl-1-oxo-1,3-dihydro-isoindol-2-yl)-piperidine-2,6-dione methanesulfonate (0.50 g, 1.4 mmol) and 4-methoxyphenylisocyanate (0.21 g, 1.4 mmol) in acetonitrile (30 mL) at 0° C. The mixture was stirred at ambient temperature for 2 h and then 10% aqueous HCl solution (30 mL) was added. The solid precipitate was filtered and dried in vacuo providing 1-[2-(2,6-dioxo-piperidin-3-yl)-1-oxo-2,3-dihydro-1H-isoindol-5-ylmethyl]-3-(4-methoxy-phenyl)-urea as a white solid (0.48 g, 84% yield); mp 255-257° C.; HPLC, Waters Symmetry C-18, 3.9×150 mm, 5 μm, 1 ml/min, 240 nm, 30/70 CH$_3$CN/0.1% H$_3$PO$_4$, 6.39 (99.34%); $^1$H NMR (DMSO-d$_6$) δ 1.93-2.06 (m, 1H, CHH), 2.29-2.47 (m, 1H, CHH), 2.54-2.66 (m, 1H, CHH), 2.83-2.99 (m, 1H, CHH), 3.69 (s, 3H, CH$_3$), 4.30 (d, 1H, CHH), 4.36-4.50 (m, 3H, CH$_2$ and CHH), 5.11 (dd, 1H, CH), 6.65 (t, 1H, NH), 6.81 (d, J=8.9 Hz, 2H, Ar), 7.31 (d, 2H, Ar), 7.44 (d, 1H, Ar), 7.51 (s, 1H, Ar), 7.69 (d, 1H, Ar), 8.44 (s, 1H, NH), 10.99 (s, 1H, NH); $^{13}$C NMR (DMSO-d$_6$) δ 8.60, 22.49, 31.20, 42.79, 45.69, 47.10, 51.56, 55.12, 113.86, 119.50, 121.85, 122.91, 126.88, 130.25, 133.50, 142.36, 145.03, 153.98, 155.45, 167.96, 170.99, 172.86; LCMS: MH=423; Anal. Calcd for C$_{22}$H$_{22}$N$_4$O$_5$+0.1H$_2$O: C, 62.55; H, 5.25; N, 13.26. Found: C, 62.12; H, 5.36; N, 13.21.

5.163 1-(3,5-dichloro-phenyl)-3-[2-(2,6-dioxo-piperidin-3-yl)-1-oxo-2,3-dihydro-1H-isoindol-5-ylmethyl]-urea

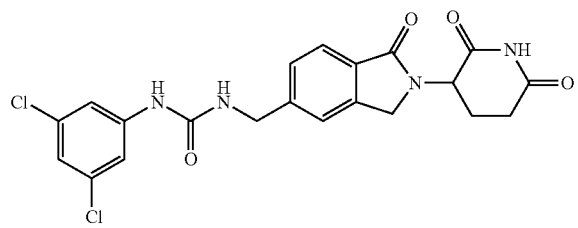 [SMILES: O=C1CCC(N2Cc3cc(CNC(=O)Nc4cc(Cl)cc(Cl)c4)ccc3C2=O)C(=O)N1]

To a stirred mixture of 3-(5-aminomethyl-1-oxo-1,3-dihydro-isoindol-2-yl)-piperidine-2,6-dione methane sulfonate (0.37 g, 1.0 mmol) and 3,5-dichlorophenylisocyanate (0.19 g, 1.0 mmol) in acetonitrile (10 mL), was added triethylamine (0.28 mL, 2.0 mmol) at room temperature under nitrogen. After 18 h, 1 N aq. HCl (10 mL) was added and the solids were isolated by filtration and washed with water (40 mL). The solids were triturated in EtOAc (10 mL) for 18 h, then isolated by filtration, washed with EtOAc (40 mL) and dried in vacuo to give 1-(3,5-dichloro-phenyl)-3-[2-(2,6-dioxo-piperidin-3-yl)-1-oxo-2,3-dihydro-1H-isoindol-5-ylmethyl]-urea as a white solid (0.36 g, 78% yield): HPLC: Waters Symmetry C$_{18}$, 5 μm, 3.9×150 mm, 1 mL/min, 240 nm, 10/90 to 90/10 CH$_3$CN/0.1% H$_3$PO$_4$ gradient over 15 mins, 9.14 min (96.29%); mp: 274-276° C.; $^1$H NMR (DMSO-d$_6$) δ 1.86-2.12 (m, 1H, CHH), 2.24-2.47 (m, 1H, CHH), 2.60 (d, J=16.4 Hz, 1H, CHH), 2.77-3.05 (m, 1H, CHH), 4.31 (d, J=17.4 Hz, 1H, CHH), 4.38-4.56 (m, 3H, CHH, CH$_2$), 5.11 (dd, J=5.1, 13.2 Hz, 1H, CH), 7.00 (t, J=5.9 Hz, 1H, NH), 7.08 (t, J=1.7 Hz, 1H, Ar), 7.44 (d, J=7.7 Hz, 1H, Ar), 7.48-7.59 (m, 3H, Ar), 7.70 (d, J=7.7 Hz, 1H, Ar), 9.08 (s, 1H, NH), 10.99 (s, 1H, NH); $^{13}$C NMR (DMSO-d$_6$) δ 22.49, 31.20, 42.83, 47.12, 51.58, 115.78, 120.16, 121.92, 122.94, 126.92, 130.35, 133.93, 142.39, 142.93, 144.43, 154.77, 167.92, 170.98, 172.85; LCMS: MH=461/463/465; Anal Calcd for C$_{21}$H$_{18}$N$_4$O$_4$Cl$_2$: C, 54.68; H, 3.93; N, 12.15; Cl, 15.37. Found: C, 54.61; H, 3.78; N, 11.84; Cl, 15.10.

5.164 1-[2-(2,6-dioxo-piperidin-3-yl)-1-oxo-2,3-dihydro-1H-isoindol-5-ylmethyl]-3-phenyl-urea

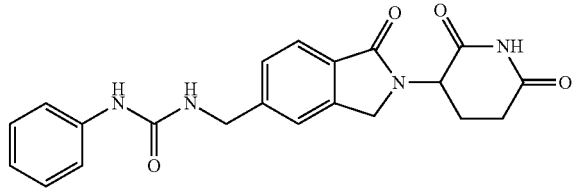 [SMILES: O=C1CCC(N2Cc3cc(CNC(=O)Nc4ccccc4)ccc3C2=O)C(=O)N1]

To a stirred mixture of 3-(5-aminomethyl-1-oxo-1,3-dihydro-isoindol-2-yl)-piperidine-2,6-dione methane sulfonate (0.37 g, 1.0 mmol) and phenylisocyanate (0.12 g, 1.0 mmol) in acetonitrile (10 mL), was added triethylamine (0.28 mL, 2.0 mmol) at room temperature under nitrogen. After 2 h, 1 N aq. HCl (10 mL) was added and the solids were isolated by filtration and washed with water (20 mL). The solids were triturated in EtOAc (10 mL) for 18 h, then isolated by filtration, washed with EtOAc (40 mL) and dried in vacuo to give 1-[2-(2,6-dioxo-piperidin-3-yl)-1-oxo-2,3-dihydro-1H-isoindol-5-ylmethyl]-3-phenyl-urea as a white solid (0.38 g, 97% yield): HPLC: Waters Symmetry C$_{18}$, 5 μm, 3.9×150 mm, 1 mL/min, 240 nm, 10/90 to 90/10 CH$_3$CN/0.1% H$_3$PO$_4$ gradient over 15 mins, 6.94 min (96.31%); mp: 243-245° C.; $^1$H NMR (DMSO-d$_6$) δ 1.88-2.12 (m, 1H, CHH), 2.27-2.47 (m, 1H, CHH), 2.59 (d, J=17.6 Hz, 1H, CHH), 2.77-3.06 (m, 1H, CHH), 4.31 (d, J=17.4 Hz, 1H, CHH), 4.37-4.56 (m, 3H, CHH, CH$_2$), 5.11 (dd, J=5.0, 13.1 Hz, 1H, CH), 6.73 (t, J=5.9 Hz, 1H, Ar), 6.82-6.98 (m, 1H, Ar), 7.22 (t, J=7.9 Hz, 2H, Ar), 7.33-7.49 (m, 3H, Ar), 7.52 (s, 1H, NH), 7.70 (d, J=7.7 Hz, 1H, Ar), 8.62 (s, 1H, NH), 10.98 (s, 1H, NH); $^{13}$C NMR (DMSO-d$_6$) δ 22.49, 31.20, 42.76, 47.12, 51.56, 117.72, 121.13, 121.86, 122.93, 126.88, 128.61, 130.29, 140.36, 142.39, 144.85, 155.22, 167.95, 170.99, 172.85; LCMS: MH=393; Anal Calcd for C$_{21}$H$_{20}$N$_4$O$_4$: C, 64.28; H, 5.14; N, 14.28. Found: C, 64.23; H, 4.94; N, 14.20.

5.165 1-[2-(2,6-dioxo-piperidin-3-yl)-1-oxo-2,3-dihydro-1H-isoindol-5-ylmethyl]-3-naphthalen-1-YL-urea

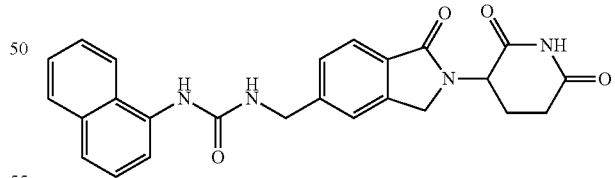

To a stirred mixture of 3-(5-aminomethyl-1-oxo-1,3-dihydro-isoindol-2-yl)-piperidine-2,6-dione methanesulfonate (0.37 g, 1.00 mmol) and 1-naphthylisocyanate (0.17 g, 1.00 mmol) in acetonitrile (30 mL) at 0° C. was added TEA (0.20 g, 2.0 mmol) dropwise over 10 min. The mixture was stirred at ambient temperature for 3 h and then 10% aqueous HCl solution (30 mL) was added. The solid precipitate was filtered and dried in vacuo providing 1-[2-(2,6-dioxo-piperidin-3-yl)-1-oxo-2,3-dihydro-1H-isoindol-5-ylmethyl]-3-naphthalen-1-yl-urea as a white solid (0.39 g, 89% yield); mp 250-252° C.; HPLC, Waters Symmetry C-18, 3.9×150 mm, 5 μm, 1 ml/min, 240 nm, 40/60 CH$_3$CN/0.1% H$_3$PO$_4$, 6.96 (97.91%); $^1$H NMR (DMSO-d$_6$) δ 1.94-2.06 (m, 1H, CHH), 2.29-2.47 (m, 1H, CHH), 2.54-2.67 (m, 1H, CHH), 2.84-3.00 (m, 1H, CHH), 4.26-4.46 (m, 2H, CHH), 4.50 (d, J=4.9 Hz, 2H, CH$_2$ and CHH), 5.11 (dd, 1H, CH), 7.17 (t, 1H, NH), 7.38-7.62 (m, 6H, Ar), 7.72 (d, J=7.7 Hz, 1H, Ar), 7.90 (d, 1H, Ar), 8.01 (d, 1H, Ar), 8.12 (d, 1H, Ar), 8.69 (s, 1H, NH), 10.99 (s, 1H, NH); $^{13}$C NMR (DMSO-d$_6$) δ 22.49, 31.20, 42.95, 47.13, 51.58, 116.73, 121.38, 121.98, 122.26, 123.00, 125.43, 125.61, 125.74, 125.89, 126.97, 128.34, 130.36, 133.69, 134.98, 142.45, 144.72, 155.66, 167.95, 170.99, 172.85; LCMS: MH=443; Anal. Calcd for C$_{25}$H$_{22}$N$_4$O$_4$: C, 67.86; H, 5.01; N, 12.66. Found: C, 67.50; H, 4.96; N, 12.34.

5.166 1-[2-(2,6-dioxo-piperidin-3-yl)-1-oxo-2,3-dihydro-1H-isoindol-5-ylmethyl]-3-p-tolyl-urea

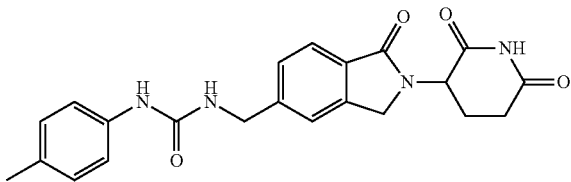 [SMILES: Cc1ccc(NC(=O)NCc2ccc3c(c2)CN(C2CCC(=O)NC2=O)C3=O)cc1]

To a stirred mixture of 3-(5-aminomethyl-1-oxo-1,3-dihydro-isoindol-2-yl)-piperidine-2,6-dione methanesulfonate (0.37 g, 1.00 mmol) and p-tolyl-isocyanate (0.13 g, 1.00 mmol) in acetonitrile (30 mL) at 0° C. was added TEA (0.20 g, 2.0 mmol) dropwise over 10 min. The mixture was stirred at ambient temperature for 1.5 h and then 10% aqueous HCl solution (30 mL) was added. The solid precipitate was filtered, washed with water (20 mL) and dried in vacuo providing 1-[2-(2,6-dioxo-piperidin-3-yl)-1-oxo-2,3-dihydro-1H-isoindol-5-ylmethyl]-3-p-tolyl-urea as a white solid (0.19 g, 46% yield); mp 267-269° C.; HPLC, Waters Symmetry C-18, 3.9×150 mm, 5 μm, 1 ml/min, 240 nm, 30/70 CH$_3$CN/0.1% H$_3$PO$_4$, 4.30 (99.66%); $^1$H NMR (DMSO-d$_6$) δ 1.91-2.08 (m, 1H, CHH), 2.21 (s, 3H, CH$_3$), 2.28-2.47 (m, 1H, CHH), 2.53-2.68 (m, 1H, CHH), 2.80-3.02 (m, 1H, CHH), 4.31 (d, 1H, CHH), 4.36-4.52 (m, 3H, CH$_2$ and CHH), 5.11 (dd, J=4.8, 13.1 Hz, 1H, CH), 6.69 (t, 1H, NH), 7.02 (d, 2H, Ar), 7.29 (d, J=8.1 Hz, 2H, Ar), 7.42 (d, 1H, Ar), 7.51 (s, 1H, Ar), 7.69 (d, 1H, Ar), 8.52 (s, 1H, NH), 10.98 (s, 1H, NH); $^{13}$C NMR (DMSO-d$_6$) δ 20.28, 22.49, 31.20, 42.76, 45.72, 47.12, 51.56, 117.84, 121.86, 122.91, 126.89, 129.01, 129.84, 130.27, 137.81, 142.38, 144.93, 155.28, 167.95, 170.99, 172.85; LCMS: MH=407; Anal. Calcd for C$_{22}$H$_{22}$N$_4$O$_4$: C, 65.01; H, 5.46; N, 13.78. Found: C, 64.75; H, 5.48; N, 13.66.

5.167 1-(4-bromo-phenyl)-3-[2-(2,6-dioxo-piperidin-3-yl)-1-oxo-2,3-dihydro-1H-isoindol-5-ylmethyl]-urea

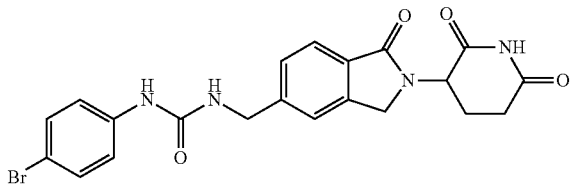

To a stirred mixture of 3-(5-aminomethyl-1-oxo-1,3-dihydro-isoindol-2-yl)-piperidine-2,6-dione methanesulfonate (0.37 g, 1.00 mmol) and 4-bromophenylisocyanate (0.20 g, 1.00 mmol) in acetonitrile (30 mL) at 0° C. was added TEA (0.20 g, 2.0 mmol) dropwise over 10 min. The mixture was stirred at ambient temperature for 2 h and then 10% aqueous HCl solution (30 mL) was added. The solid precipitate was filtered, washed with water (30 mL) and dried in vacuo providing 1-(4-bromo-phenyl)-3-[2-(2,6-dioxo-piperidin-3-yl)-1-oxo-2,3-dihydro-1H-isoindol-5-ylmethyl]-urea as a white solid (0.42 g, 89% yield); mp 278-280° C.; HPLC, Waters Symmetry C-18, 3.9×150 mm, 5 μm, 1 ml/min, 240 nm, 40/60 CH$_3$CN/0.1% H$_3$PO$_4$, 3.00 (99.50%); $^1$H NMR (DMSO-d$_6$) δ 1.93-2.06 (m, 1H, CHH), 2.29-2.46 (m, 1H, CHH), 2.54-2.67 (m, 1H, CHH), 2.81-3.02 (m, 1H, CHH), 4.30 (d, 1H, CHH), 4.36-4.52 (m, 3H, CH$_2$ and CHH), 5.11 (dd, J=4.8, 13.1 Hz, 1H, CH), 6.80 (t, J=5.7 Hz, 1H, NH), 7.31-7.47 (m, 5H, Ar), 7.51 (s, 1H, Ar), 7.69 (d, 1H, Ar), 8.81 (s, 1H, NH), 10.98 (s, 1H, NH); $^{13}$C NMR (DMSO-d$_6$) δ 22.49, 31.20, 42.77, 47.12, 51.56, 112.42, 119.66, 121.88, 122.93, 126.89, 130.30, 131.32, 139.81, 142.38, 144.69, 155.03, 167.93, 170.99, 172.85 LCMS: MH=472; Anal. Calcd for C$_{21}$H$_{19}$BrN$_4$O$_4$: C, 53.52; H, 4.06; N, 11.89. Found: C, 53.32; H, 3.97; N, 11.77.

5.168 1-(4-cyano-phenyl)-3-[2-(2,6-dioxo-piperidin-3-yl)-1-oxo-2,3-dihydro-1H-isoindol-5-ylmethyl]-urea

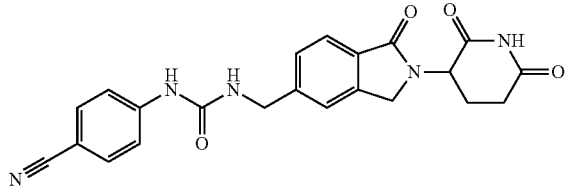 [SMILES: N#Cc1ccc(NC(=O)NCc2ccc3c(c2)CN(C2CCC(=O)NC2=O)C3=O)cc1]

To a stirred mixture of 3-(5-aminomethyl-1-oxo-1,3-dihydro-isoindol-2-yl)-piperidine-2,6-dione methane sulfonate (0.37 g, 1.0 mmol) and 4-cyanophenylisocyanate (0.14 g, 1.0 mmol) in acetonitrile (10 mL), was added triethylamine (0.28 mL, 2.0 mmol) at room temperature under nitrogen. After 18 h, 1 N aq. HCl (15 mL) was added and the solids were isolated by filtration, washed with water (40 mL). The crude product was purified by prep-HPLC (MeCN/H$_2$O, 10/90 to 90/10 gradient over 15 min). The product fractions were combined, triturated in Et$_2$O then filtered and dried in vacuo to give 1-(4-cyano-phenyl)-3-[2-(2,6-dioxo-piperidin-3-yl)-1-oxo-2,3-dihydro-1H-isoindol-5-ylmethyl]-urea as a white solid (0.16 g, 38% yield): HPLC: Waters Symmetry C$_{18}$, 5 μm, 3.9×150 mm, 1 mL/min, 240 nm, 10/90 to 90/10 CH$_3$CN/0.1% H$_3$PO$_4$ gradient over 15 mins, 7.31 min (97.64%); mp: 258-260° C.; $^1$H NMR (DMSO-d$_6$) δ 1.86-2.06 (m, 1H, CHH), 2.27-2.47 (m, 1H, CHH), 2.60 (d, J=17.0 Hz, 1H, CHH), 2.78-3.03 (m, 1H, CHH), 4.31 (d, J=17.2 Hz, 1H, CHH), 4.38-4.59 (m, 3H, CHH, CH$_2$), 5.11 (dd, J=4.9, 13.2 Hz, 1H, CH), 7.00 (t, J=5.7 Hz, 1H, NH), 7.45 (d, J=7.9 Hz, 1H, Ar), 7.52 (s, 1H, Ar), 7.56-7.63 (m, 2H, Ar), 7.64-7.82 (m, 3H, Ar), 9.23 (s, 1H, NH), 10.99 (s, 1H, NH); $^{13}$C NMR (DMSO-d$_6$) δ 22.49, 31.20, 42.79, 47.12, 51.56, 102.50, 117.56, 119.40, 121.89, 122.96, 126.91, 130.36, 133.15, 142.39, 144.39, 144.84, 154.68, 167.92, 170.98, 172.85; LCMS: MH=418; Anal Calcd for $C_{22}H_{19}N_5O_4$: C, 62.76; H, 4.64; N, 16.63. Found: C, 62.65; H, 4.55; N, 16.69.

5.169 1-(2,4-dichloro-phenyl)-3-[2-(2,6-dioxo-piperidin-3-yl)-1-oxo-2,3-dihydro-1H-isoindol-5-ylmethyl]-urea

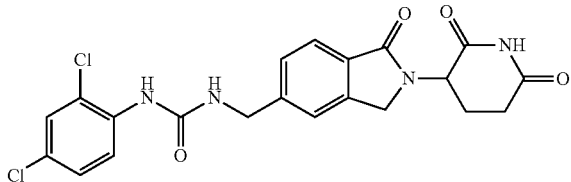 [SMILES: O=C1CCC(N2Cc3cc(CNC(=O)Nc4ccc(Cl)cc4Cl)ccc3C2=O)C(=O)N1]

To a stirred mixture of 3-(5-aminomethyl-1-oxo-1,3-dihydro-isoindol-2-yl)-piperidine-2,6-dione methane sulfonate (0.37 g, 1.0 mmol) and 2,4-dichlorophenylisocyanate (0.19 g, 1.0 mmol) in acetonitrile (10 mL), was added triethylamine (0.28 mL, 2.0 mmol) at room temperature under nitrogen. After 2 h, 1 N aq. HCl (15 mL) was added and the solids were isolated by filtration, washed with water (3×20 mL) and dried in vacuo to give 1-(2,4-dichlorophenyl)-3-[2-(2,6-dioxo-piperidin-3-yl)-1-oxo-2,3-dihydro-1H-isoindol-5-ylmethyl]-urea as a white solid (0.44 g, 96% yield): HPLC: Waters Symmetry $C_{18}$, 5 µm, 3.9×150 mm, 1 mL/min, 240 nm, 10/90 to 90/10 $CH_3CN$/0.1% $H_3PO_4$ gradient over 15 mins, 8.99 min (96.51%); mp: 265-267° C.; $^1$H NMR (DMSO-$d_6$) δ 1.89-2.06 (m, 1H, CHH), 2.29-2.47 (m, 1H, CHH), 2.54-2.70 (m, 1H, CHH), 2.78-3.06 (m, 1H, CHH), 4.32 (d, J=17.4 Hz, 1H, CHH), 4.38-4.53 (m, 3H, CHH, $CH_2$), 5.11 (dd, J=5.0, 13.3 Hz, 1H, CH), 7.33 (dd, J=2.5, 9.1 Hz, 1H, Ar), 7.46 (d, J=7.7 Hz, 1H, Ar), 7.53 (s, 1H, Ar), 7.57 (d, J=2.5 Hz, 1H, Ar), 7.62 (t, J=5.8 Hz, 1H, NH), 7.71 (d, J=7.7 Hz, 1H, Ar), 8.20 (d, J=8.9 Hz, 1H, Ar), 8.26 (s, 1H, NH), 10.99 (br. s., 1H, NH); $^{13}$C NMR (DMSO-$d_6$) δ 22.49, 31.20, 42.82, 47.13, 51.58, 121.63, 121.92, 122.02, 123.04, 125.33, 126.99, 127.50, 128.39, 130.45, 135.81, 142.48, 144.12, 154.67, 167.90, 170.99, 172.86; LCMS: MH=461/463/465; Anal Calcd for $C_{21}H_{18}N_4O_4Cl_2$: C, 54.68; H, 3.93; N, 12.15; Cl, 15.37. Found: C, 54.37; H, 3.84; N, 12.15; Cl, 15.50.

5.170 1-[2-(2,6-dioxo-piperidin-3-yl)-1-oxo-2,3-dihydro-1H-isoindol-5-ylmethyl]-3-propyl-urea

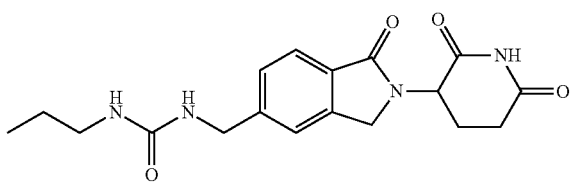 [SMILES: CCCNC(=O)NCc1ccc2c(c1)CN(C1CCC(=O)NC1=O)C2=O]

To a stirred mixture of 3-(5-aminomethyl-1-oxo-1,3-dihydro-isoindol-2-yl)-piperidine-2,6-dione methane sulfonate (0.37 g, 1.0 mmol) and propylisocyanate (0.09 mL, 1.0 mmol) in acetonitrile (10 mL), was added triethylamine (0.28 mL, 2.0 mmol) at room temperature under nitrogen. After 2 h, 1 N aq. HCl (15 mL) was added and the solids were isolated by filtration, washed with water (2×20 mL). The product was extracted with EtOAc (3×50 mL) and $CH_2Cl_2$ (3×50 mL). The organic layers were combined, concentrated and the residue was triturated in $Et_2O$ (20 mL). The product was isolated by filtration and dried in vacuo to give 1-[2-(2,6-dioxo-piperidin-3-yl)-1-oxo-2,3-dihydro-1H-isoindol-5-ylmethyl]-3-propyl-urea as a white solid (0.20 g, 53% yield): HPLC: Waters Symmetry $C_{18}$, 5 µm, 3.9×150 mm, 1 mL/min, 240 nm, 10/90 to 90/10 $CH_3CN$/0.1% $H_3PO_4$ gradient over 15 mins, 5.84 min (98.91%); mp: 250-252° C.; $^1$H NMR (DMSO-$d_6$) δ 0.84 (t, J=7.4 Hz, 3H, $CH_3$), 1.22-1.59 (m, 2H, $CH_2$), 1.85-2.10 (m, 1H, CHH), 2.25-2.47 (m, 1H, CHH), 2.60 (d, J=17.4 Hz, 1H, CHH), 2.78-3.10 (m, 3H, $CH_2$, CHH), 4.21-4.37 (m, 3H, $CH_2$, CHH), 4.44 (d, J=17.4 Hz, 1H, CHH), 5.11 (dd, J=5.1, 13.2 Hz, 1H, CH), 5.99 (t, J=5.7 Hz, 1H, NH), 6.40 (t, J=5.9 Hz, 1H, NH), 7.38 (d, J=7.7 Hz, 1H, Ar), 7.45 (s, 1H, Ar), 7.67 (d, J=7.9 Hz, 1H, Ar), 10.98 (s, 1H, NH); $^{13}$C NMR (DMSO-$d_6$) δ 11.32, 22.49, 23.19, 31.20, 41.18, 42.92, 47.09, 51.55, 121.73, 122.83, 126.78, 130.11, 142.29, 145.55, 158.02, 167.98, 171.01, 172.86; LCMS: MH=359; Anal Calcd for $C_{18}H_{22}N_4O_4$: C, 60.32; H, 6.19; N, 15.63. Found: C, 60.21; H, 6.15; N, 15.51.

5.171 1-tert-butyl-3-[2-(2,6-dioxo-piperidin-3-yl)-1,3-dioxo-2,3-dihydro-1H-isoindol-5-ylmethyl]-urea

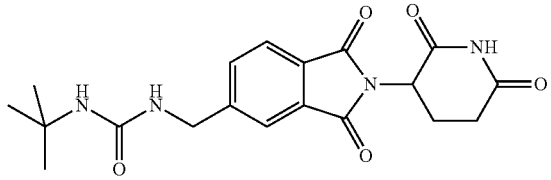 [SMILES: CC(C)(C)NC(=O)NCc1ccc2c(c1)C(=O)N(C1CCC(=O)NC1=O)C2=O]

To a stirred mixture of 5-aminomethyl-2-(2,6-dioxo-piperidin-3-yl)-isoindole-1,3-dione hydrochloride (1.00 g, 3.10 mmol) and t-butylisocyanate (0.31 g, 3.10 mmol) in THF (35 mL), was added triethylamine (0.88 mL, 6.20 mmol) at room temperature under nitrogen. The mixture was heated to 40° C. for 18 h then cooled to rt. The mixture was filtered and the filtrate diluted with EtOAc (100 mL). The organic layer was washed with dil. aq. HCl (100 mL), water (2×100 mL), dried (MgSO$_4$) and concentrated. The crude product was purified by prep-HPLC (35/65 $CH_3CN/H_2O$). The product fractions were combined, concentrated and dried in vacuo to give 1-tert-butyl-3-[2-(2,6-dioxo-piperidin-3-yl)-1,3-dioxo-2,3-dihydro-1H-isoindol-5-ylmethyl]-urea as a white solid (0.40 g, 84% yield): HPLC: Waters Symmetry $C_{18}$, 5 µm, 3.9×150 mm, 1 mL/min, 240 nm, 30/70 $CH_3CN$/0.1% $H_3PO_4$, 4.89 min (97.00%); mp: 202-204° C.; $^1$H NMR (DMSO-$d_6$) δ 1.24 (s, 9H), 1.97-2.14 (m, 1H), 2.53-2.71 (m, 2H), 2.79-3.02 (m, 1H), 4.34 (d, J=5.9 Hz, 2H), 5.14 (dd, J=5.4, 12.9 Hz, 1H), 5.89 (s, 1H), 6.34 (t, J=6.0 Hz, 1H), 7.65-7.79 (m, 2H), 7.87 (d, J=7.7 Hz, 1H), 11.08 (s, 1H); $^{13}$C NMR (DMSO-$d_6$) δ 22.0, 29.2, 30.9, 42.3, 48.9, 49.2, 121.4, 123.4, 129.5, 131.5, 133.0, 149.6, 157.3, 167.0, 167.2, 169.8, 172.7; Anal Calcd for $C_{19}H_{22}N_4O_5$+0.3$H_2O$: C, 58.24; H, 5.81; N, 14.30. Found: C, 58.15; H, 5.52; N, 14.16.

5.172 1-cyclohexyl-3-[2-(2,6-dioxo-piperidin-3-yl)-1,3-dioxo-2,3-dihydro-1H-isoindol-5-ylmethyl]-urea

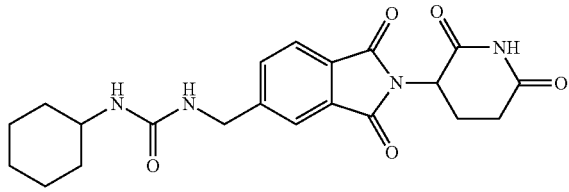 [SMILES: O=C1CCC(N2C(=O)c3ccc(CNC(=O)NC4CCCCC4)cc3C2=O)C(=O)N1]

To a stirred mixture of 5-aminomethyl-2-(2,6-dioxo-piperidin-3-yl)-isoindole-1,3-dione hydrochloride (1.00 g, 3.10 mmol) and cyclohexylisocyanate (0.39 g, 3.10 mmol) in THF (35 mL), was added triethylamine (0.88 mL, 6.20 mmol) at room temperature under nitrogen. The mixture was heated to 40° C. for 18 h then cooled to rt. The mixture was filtered and the filtrate diluted with EtOAc (100 mL). The organic layer was washed with dil. aq. HCl (100 mL), water (2×100 mL), dried (MgSO$_4$) and concentrated. The crude product was purified by prep-HPLC (40/60 CH$_3$CN/H$_2$O). The product fractions were combined, concentrated and dried in vacuo to give 1-cyclohexyl-3-[2-(2,6-dioxo-piperidin-3-yl)-1,3-dioxo-2,3-dihydro-1H-isoindol-5-ylmethyl]-urea as a white solid (0.65 g, 77% yield): HPLC: Waters Symmetry C$_{18}$, 5 μm, 3.9×150 mm, 1 mL/min, 240 nm, 40/60 CH$_3$CN/0.1% H$_3$PO$_4$, 3.16 min (99.05%); mp: 208-210° C.; $^1$H NMR (DMSO-d$_6$) δ 1.01-1.36 (m, 5H), 1.46-1.83 (m, 5H), 2.00-2.14 (m, 1H), 2.53-2.66 (m, 2H), 2.79-3.01 (m, 1H), 3.34-3.44 (m, 1H), 4.36 (d, J=6.0 Hz, 2H), 5.14 (dd, J=5.3, 12.8 Hz, 1H), 6.00 (d, J=7.9 Hz, 1H), 6.42 (t, J=5.9 Hz, 1H), 7.67-7.79 (m, 2H), 7.87 (d, J=7.6 Hz, 1H), 11.12 (s, 1H); $^{13}$C NMR (DMSO-d$_6$) δ 22.01, 24.50, 25.27, 30.93, 33.23, 42.67, 47.97, 48.97, 121.54, 123.39, 129.50, 131.53, 133.07, 149.49, 157.28, 167.05, 167.22, 169.83, 172.73; LCMS: MH=413; Anal Calcd for C$_{21}$H$_{24}$N$_4$O$_5$+0.2H$_2$O: C, 60.76; H, 5.90; N, 13.47. Found: C, 60.61; H, 5.74; N, 13.31.

5.173 1-(3-chloro-4-(trifluoromethyl)phenyl)-3-((2-(2,6-dioxopiperidin-3-yl)-1-oxoisoindolin-5-yl)methyl)urea

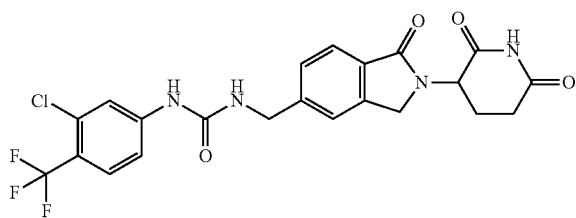 [SMILES: O=C1CCC(N2Cc3cc(CNC(=O)Nc4ccc(C(F)(F)F)c(Cl)c4)ccc3C2=O)C(=O)N1]

To a solution of 3-chloro-4-(trifluoromethyl)aniline (0.60 g, 3.07 mmol), pyridine (0.24 g, 3.07 mmol), and DIEA (1.10 ml, 6.14 mmol) in acetonitrile (5 mL) was added phosgene (1.54 mL, 2.91 mmol, 20% in toluene) via syringe at 0° C. After 30 min, (2-(2,6-dioxopiperidin-3-yl)-1-oxoisoindolin-5-yl)methanaminium methanesulfonate (0.84 g, 2.27 mmol) was added in one portion followed by additional DIEA (1.1 ml, 6.14 mmol). The resulting suspension was stirred for 1.5 h and allowed to warm to room temperature. After 1.5 h, the reaction was quenched by the addition of 1 N HCl (20 ml) and the precipitated solid was filtered, washed with water and air-dried. The crude product was purified further by reslurrying with acetonitrile (10 mL) followed by precipitation from DMF (5 mL)/water. The product was isolated by filtration, washed with Et$_2$O and dried in vacuo to give 1-(3-chloro-4-(trifluoromethyl)phenyl)-3-((2-(2,6-dioxopiperidin-3-yl)-1-oxoisoindolin-5-yl)methyl)urea as an off-white solid (420 mg, 40%). HPLC: Waters Symmetry C$_{18}$, 5 μm, 3.9×150 mm, 1 ml/min, 240 nm, 45/55, CH$_3$CN/0.1% H$_3$PO$_4$, 4.76 min (98.7%); mp: 274-276° C.; $^1$H NMR (DMSO-d$_6$) δ 1.90-2.16 (m, 1H), 2.26-2.45 (m, 1H), 2.59 (d, J=19.6 Hz, 1H), 2.82-3.00 (m, 1H), 4.25-4.52 (m, 4H), 5.11 (dd, J=5.0, 13.3 Hz, 1H), 7.05 (t, J=5.9 Hz, 1H), 7.39-7.49 (m, 2H), 7.53 (s, 1H), 7.69 (dd, J=4.2, 8.2 Hz, 2H), 7.91 (s, 1H), 9.32 (s, 1H), 10.98 (s, 1H); $^{13}$C NMR (DMSO-d$_6$) δ 22.50, 31.20, 42.83, 47.12, 51.58, 115.58, 118.19, 118.60, 118.98, 121.44, 121.94, 122.96, 125.05, 126.93, 128.31, 128.38, 130.38, 131.14, 142.41, 144.32, 145.28, 154.66, 167.92, 171.00, 172.85. LCMS: MH=495; Anal Calcd for C$_{22}$H$_{18}$ClF$_3$N$_4$O$_4$+0.28H$_2$O: C, 52.86%; H, 3.74%; N, 11.21%; Cl, 7.09%; F; 11.40%. Found: C, 52.60%; H, 3.41% N, 11.01%; Cl, 7.23%; F, 11.63%.

5.174 1-(3-chloro-4-methyl-phenyl)-3-[2-(3-methyl-2,6-dioxo-piperidin-3-yl)-1,3-dioxo-2,3-dihydro-1H-isoindol-5-ylmethyl]-urea

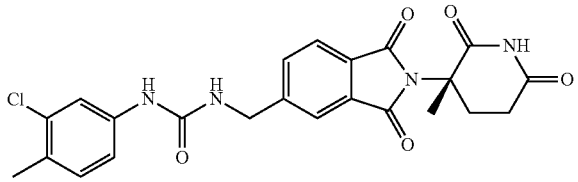 [SMILES: Cc1ccc(NC(=O)NCc2ccc3c(c2)C(=O)N([C@@]2(C)CCC(=O)NC2=O)C3=O)cc1Cl]

To a stirred mixture of 5-aminomethyl-2-(3-methyl-2,6-dioxo-piperidin-3-yl)-isoindole-1,3-dione hydrochloride (0.50 g, 1.50 mmol) and 3-chloro-4-methyl-phenyl isocyanate (0.25 g, 1.50 mmol) in THF (25 mL), was added triethylamine (0.42 mL, 3.00 mmol) at room temperature under nitrogen. After 2 h, 2% aq. HCl (75 mL) was added. The product was extracted with EtOAc (75 mL) and the organic layer was separated and washed with water (2×75 mL), dried (MgSO$_4$) and concentrated in vacuo to give 1-(3-chloro-4-methyl-phenyl)-3-[2-(3-methyl-2,6-dioxo-piperidin-3-yl)-1,3-dioxo-2,3-dihydro-1H-isoindol-5-ylmethyl]-urea as a white solid (0.40 g, 58% yield): HPLC: Waters Symmetry C$_{18}$, 5 μm, 3.9×150 mm, 1 mL/min, 240 nm, 50/50 CH$_3$CN/0.1% H$_3$PO$_4$, 4.37 min (98.73%); mp: 232-234° C.; $^1$H NMR (DMSO-d$_6$) δ 1.89 (s, 3H), 1.98-2.13 (m, 1H), 2.23 (s, 3H), 2.52-2.79 (m, 3H), 4.44 (d, J=6.0 Hz, 2H), 6.89 (t, J=5.9 Hz, 1H), 7.08-7.21 (m, 2H), 7.64 (d, J=1.9 Hz, 1H), 7.72-7.88 (m, 3H), 8.82 (s, 1H), 11.01 (s, 1H); $^{13}$C NMR (DMSO-d$_6$) δ 18.74, 21.02, 28.58, 29.11, 42.65, 58.76, 116.53, 117.74, 121.37, 123.13, 127.53, 129.49, 131.02, 131.37, 132.97, 133.21, 139.49, 148.47, 155.10, 167.77, 167.93, 172.13, 172.21; LCMS: MH=469/471; Anal Calcd for C$_{23}$H$_{21}$ClN$_4$O$_5$: C, 58.91; H, 4.51; N, 11.95. Found: C, 58.63; H, 4.40; N, 11.82.

5.175 1-[2-(2,6-dioxo-piperidin-3-yl)-1,3-dioxo-2,3-dihydro-1H-isoindol-5-ylmethyl]-3-phenyl-urea

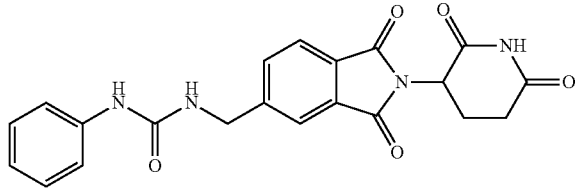 [SMILES: O=C1CCC(N2C(=O)c3ccc(CNC(=O)Nc4ccccc4)cc3C2=O)C(=O)N1]

To a stirred mixture of 5-aminomethyl-2-(2,6-dioxo-piperidin-3-yl)-isoindole-1,3-dione hydrochloride (0.97 g, 3.00 mmol) and phenylisocyanate (0.36 g, 3.30 mmol) in THF (20 mL), was added DIPEA (1.05 mL, 6.00 mmol) at room temperature under nitrogen. The mixture was heated to 40° C. for 18 h then cooled to rt. The solvent was removed in vacuo and the residue was dissolved in EtOAc (100 mL). The organic layer was washed with dil. aq. HCl (2×150 mL), water (100 mL), dried (MgSO$_4$) and then concentrated. The product was dried in vacuo to give 1-[2-(2,6-dioxo-piperidin-3-yl)-1,3-dioxo-2,3-dihydro-1H-isoindol-5-ylmethyl]-3-phenyl-urea as a white solid (0.77 g, 63% yield): HPLC: Waters Symmetry C$_{18}$, 5 µm, 3.9×150 mm, 1 mL/min, 240 nm, 40/60 CH$_3$CN/0.1% H$_3$PO$_4$, 2.38 min (99.57%); mp: 288-290° C.; $^1$H NMR (DMSO-d$_6$) δ 1.99-2.07 (m, 1H, CHH), 2.44-2.62 (m, 2H, CHH, CHH), 2.82-2.96 (m, 3H, CHH, CH$_2$), 4.47 (d, J=5.9 Hz, 2H, CH$_2$), 5.15 (dd, J=5.3, 12.5 Hz, 1H, CH), 6.82-6.93 (m, 2H, Ar), 7.22 (t, J=7.6 Hz, 2H, Ar), 7.40 (d, J=8.0 Hz, 2H, Ar), 7.78-7.91 (m, 3H, Ar, NH), 8.72 (s, 1H, NH), 11.13 (s, 1H, NH); $^{13}$C NMR (DMSO-d$_6$) δ 22.01, 30.93, 42.62, 48.99, 117.83, 121.26, 121.69, 123.48, 128.64, 129.67, 131.60, 133.21, 140.27, 148.79, 155.28, 167.03, 167.20, 169.83, 172.74; LCMS: MH=407; Anal Calcd for C$_{21}$H$_{18}$N$_4$O$_5$+0.2H$_2$O: C, 61.52; H, 4.52; N, 13.66. Found: C, 61.33; H, 4.36; N, 13.46.

5.176 1-[2-(2,6-dioxo-piperidin-3-yl)-1,3-dioxo-2,3-dihydro-1H-isoindol-5-ylmethyl]-3-(3-methoxy-phenyl)-urea

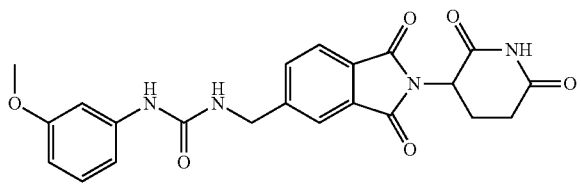 [SMILES: COc1cccc(NC(=O)NCc2ccc3c(c2)C(=O)N(C2CCC(=O)NC2=O)C3=O)c1]

To a stirred mixture of 5-aminomethyl-2-(2,6-dioxo-piperidin-3-yl)-isoindole-1,3-dione hydrochloride (0.97 g, 3.00 mmol) and 3-methoxyphenylisocyanate (0.45 g, 3.30 mmol) in THF (20 mL), was added DIPEA (1.05 mL, 6.00 mmol) at room temperature under nitrogen. The mixture was heated to 40° C. for 18 h then cooled to rt. The solvent was removed in vacuo and the residue was dissolved in EtOAc (100 mL). The organic layer was washed with dil. aq. HCl (2×150 mL), water (100 mL), dried (MgSO$_4$) and then concentrated. The residue was triturated in Et$_2$O (50 mL) for 3 h at rt, then refluxed in acetone (50 mL) for 1 h. The product was isolated by filtration and dried in vacuo to give 1-[2-(2,6-dioxo-piperidin-3-yl)-1,3-dioxo-2,3-dihydro-1H-isoindol-5-ylmethyl]-3-(3-methoxy-phenyl)-urea as a white solid (0.08 g, 6% yield): HPLC: Waters Symmetry C$_{18}$, 5 µm, 3.9×150 mm, 1 mL/min, 240 nm, 30/70 CH$_3$CN/0.1% H$_3$PO$_4$, 8.01 min (99.44%); mp: 323-325° C.; $^1$H NMR (DMSO-d$_6$) δ 2.03-2.09 (m, 1H, CHH), 2.49-2.63 (m, 2H, CHH, CHH), 2.85-2.91 (m, 1H, CHH), 3.70 (s, 3H, CH$_3$), 4.47 (d, J=6.0 Hz, 2H, CH$_2$), 5.15 (dd, J=5.4, 13.5 Hz, 1H, CH), 6.47-6.50 (m, 1H, Ar or NH), 6.82-6.91 (m, 2H, Ar or NH), 7.09-7.15 (m, 2H, Ar or NH), 7.78-7.91 (m, 3H, Ar or NH), 8.74 (s, 1H, NH), 11.12 (s, 1H, NH); $^{13}$C NMR (DMSO-d$_6$) δ 21.98, 30.90, 42.57, 48.96, 54.81, 103.52, 106.72, 110.14, 121.63, 123.47, 129.36, 129.65, 131.57, 133.17, 141.49, 143.07, 148.75, 155.16, 159.60, 167.02, 167.18, 169.80, 172.72; LCMS: MH=437; Anal Calcd for C$_{22}$H$_{20}$N$_4$O$_6$: C, 58.38; H, 4.85; N, 12.38. Found: C, 58.36; H, 4.45; N, 11.98.

5.177 1-(2-chloro-6-methyl-phenyl)-3-[2-(2,6-dioxo-piperidin-3-yl)-1-oxo-2,3-dihydro-1H-isoindol-5-ylmethyl]-urea

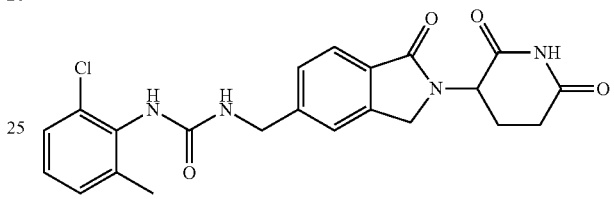

To a stirred mixture of CC-16313 (0.412 g, 1.11 mmol) and 2-chloro-6-methylphenyl isocyanate (0.152 mL, 1.11 mmol) in acetonitrile (10 mL), was added triethylamine (0.31 mL, 2.23 mmol) at room temperature under nitrogen. After 1 h, 1N aq. HCl (10 mL) was added and the mixture was stirred for 10 min. The product was isolated by filtration, washed with 1N aq. HCl (20 mL), acetonitrile (20 mL) and dried overnight in vacuo to give 1-(2-Chloro-6-methyl-phenyl)-3-[2-(2,6-dioxo-piperidin-3-yl)-1-oxo-2,3-dihydro-1H-isoindol-5-ylmethyl]-urea as a white solid (0.37 g, 75% yield): HPLC: Waters Symmetry C$_{18}$, 5 µm, 3.9×150 mm, 1 mL/min, 240 nm, 30/70 CH$_3$CN/0.1% H$_3$PO$_4$, 3.55 min (99.6%); mp: 243-245° C.; $^1$H NMR (DMSO-d$_6$) δ 1.90-2.10 (m, 1H, CH), 2.22 (s, 3H, CH$_3$), 2.32-2.47 (m, 1H, CH), 2.60 (d, J=17.4 Hz, 1H, CH), 2.84-3.00 (m, 1H, CH), 4.25-4.50 (m, 4H, CH$_2$CH$_2$), 5.11 (dd, J=5.1, 13.2 Hz, 1H, NCH), 6.88 (t, J=5.9 Hz, 1H, NH), 7.09-7.24 (m, 2H, Ar), 7.31 (dd, J=1.2, 7.6 Hz, 1H, Ar), 7.45 (d, J=7.7 Hz, 1H, Ar), 7.51 (s, 1H, Ar), 7.69 (d, J=7.7 Hz, 1H, Ar), 7.90 (s, 1H, NH), 10.99 (s, 1H, NH); $^{13}$C NMR (DMSO-d$_6$) δ 18.57, 22.48, 31.20, 43.02, 47.09, 51.56, 121.67, 122.85, 126.73, 126.94, 128.96, 130.20, 131.92, 134.59, 138.63, 142.30, 145.15, 155.60, 167.96, 171.01, 172.86; LCMS: MH=441, 443; Anal Calcd for C$_{22}$H$_{21}$N$_4$O$_4$Cl: C, 59.93; H, 4.80; N, 12.71; Cl, 8.04. Found: C, 59.61; H, 4.78; N, 12.55; Cl, 7.87.

5.178 1-(2,5-dichloro-phenyl)-3-[2-(2,6-dioxo-piperidin-3-yl)-1-oxo-2,3-dihydro-1H-isoindol-5-ylmethyl]-urea

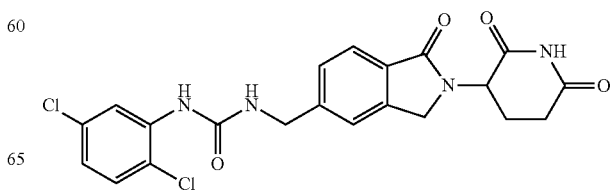

To a stirred mixture of CC-16313 (0.421 g, 1.14 mmol) and 2,5-dichlorophenyl isocyanate (0.214 g, 1.14 mmol) in acetonitrile (10 mL), was added triethylamine (0.31 mL, 2.28 mmol) at room temperature under nitrogen. After 1 h, 1N aq. HCl (10 mL) was added and the mixture was stirred for 10 min. The product was isolated by filtration, washed with 1N aq. HCl (20 mL), acetonitrile (20 mL) and dried overnight in vacuo to give 1-(2,5-Dichloro-phenyl)-3-[2-(2,6-dioxo-piperidin-3-yl)-1-oxo-2,3-dihydro-1H-isoindol-5-ylmethyl]-urea as a white solid (0.41 g, 78% yield): HPLC: Waters Symmetry $C_{18}$, 5 μm, 3.9×150 mm, 1 mL/min, 240 nm, 40/60 $CH_3CN$/0.1% $H_3PO_4$, 5.34 min (99.3%); mp: 269-271° C.; $^1$H NMR (DMSO-$d_6$) δ 1.94-2.06 (m, 1H, CH), 2.30-2.47 (m, 1H, CH), 2.60 (d, J=17.0 Hz, 1H, CH), 2.83-3.01 (m, 1H, CH), 4.27-4.52 (m, 4H, $CH_2$, $CH_2$), 5.12 (dd, J=5.0, 13.3 Hz, 1H, NCH), 7.02 (dd, J=2.5, 8.6 Hz, 1H, Ar), 7.41-7.51 (m, 2H, Ar), 7.54 (s, 1H, Ar), 7.67-7.79 (m, 2H, Ar and $NHCH_2$), 8.27-8.39 (m, 2H, NH and Ar), 10.99 (s, 1H, NH); $^{13}$C NMR (DMSO-$d_6$) δ 22.49, 31.20, 42.80, 47.13, 51.58, 101.19, 119.43, 121.92, 122.05, 123.06, 127.02, 130.38, 130.48, 131.83, 137.81, 142.49, 143.99, 154.58, 167.89, 170.98, 172.86, 183.55; LCMS: MH=461, 463; Anal Calcd for $C_{21}H_{18}N_4O_4Cl_2$: C, 54.68; H, 3.93; N, 12.15; Cl, 15.37. Found: C, 54.46; H, 3.73; N, 12.00; Cl, 15.11.

5.179 1-[2-(2,6-dioxo-piperidin-3-yl)-1-oxo-2,3-dihydro-1H-isoindol-5-ylmethyl]-3-(4-methyl-3-trifluoromethyl-phenyl)-urea

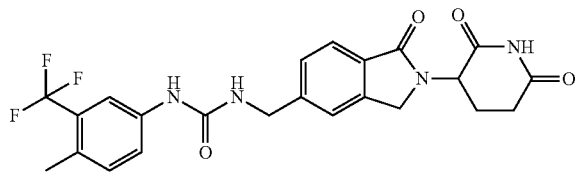 [SMILES: Cc1ccc(NC(=O)NCc2ccc3c(c2)CN(C2CCC(=O)NC2=O)C3=O)cc1C(F)(F)F]

To a stirred mixture of CC-16313 (0.419 g, 1.13 mmol) and 3-(trifluoromethyl)-4-methyl-phenyl isocyanate (0.177 mL, 1.13 mmol) in acetonitrile (10 mL), was added triethylamine (0.31 mL, 2.27 mmol) at room temperature under nitrogen. After 1 h, 1N aq. HCl (10 mL) was added and the mixture was stirred for 10 min. The product was isolated by filtration, washed with 1N aq. HCl (20 mL), acetonitrile (20 mL) and dried overnight in vacuo to give 1-[2-(2,6-Dioxo-piperidin-3-yl)-1-oxo-2,3-dihydro-1H-isoindol-5-ylmethyl]-3-(4-methyl-3-trifluoromethyl-phenyl)-urea as a white solid (0.36 g, 67% yield): HPLC: Waters Symmetry $C_{18}$, 5 μm, 3.9×150 mm, 1 mL/min, 240 nm, 40/60 $CH_3CN$/0.1% $H_3PO_4$, 5.88 min (99.5%); mp: 273-275° C.; $^1$H NMR (DMSO-$d_6$) δ 1.93-2.06 (m, 1H, CH), 2.27-2.46 (m, 4H, $CH_3$, CH), 2.60 (d, J=17.0 Hz, 1H, CH), 2.82-3.01 (m, 1H, CH), 4.24-4.52 (m, 4H, $CH_2$, $CH_2$), 5.11 (dd, J=5.0, 13.3 Hz, 1H, NCH), 6.84 (t, J=5.9 Hz, 1H, NH), 7.27 (d, J=8.5 Hz, 1H, Ar), 7.40-7.50 (m, 2H, Ar), 7.52 (s, 1H, Ar), 7.70 (d, J=7.7 Hz, 1H, Ar), 7.90 (d, J=2.1 Hz, 1H, Ar), 8.91 (s, 1H, NH), 10.99 (s, 1H, NH); $^{13}$C NMR (DMSO-$d_6$) δ 18.00, 22.49, 31.18, 42.79, 47.10, 51.56, 114.62 (q, $J_{C-CF3}$=5.8 Hz), 121.10, 121.88, 122.93, 124.52 (q, $J_{CF3}$=274 Hz), 126.89, 127.15, 127.53, 127.80, 130.30, 132.48, 138.69, 142.38, 144.71, 155.15, 167.93, 170.99, 172.85; LCMS: MH=475; Anal Calcd for $C_{23}H_{21}N_4O_4F_3$: C, 58.23; H, 4.46; N, 11.81; F, 12.01. Found: C, 57.99; H, 4.28; N, 11.83; F, 11.88.

5.180 1-(5-chloro-2-methoxy-phenyl)-3-[2-(2,6-dioxo-piperidin-3-yl)-1-oxo-2,3-dihydro-1H-isoindol-5-ylmethyl]-urea

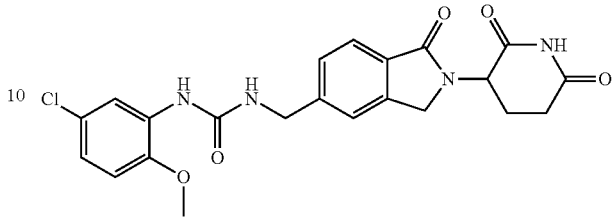

To a stirred mixture of CC-16313 (0.433 g, 1.17 mmol) and 5-chloro-2-methoxyphenyl isocyanate (0.215 g, 1.17 mmol) in acetonitrile (10 mL), was added triethylamine (0.33 mL, 2.34 mmol) at room temperature under nitrogen. After 1.5 h, 1N aq. HCl (10 mL) was added and the mixture was stirred for 10 min. The product was isolated by filtration, washed with 1N aq. HCl (20 mL), acetonitrile (20 mL) and dried overnight in vacuo to give 1-(5-Chloro-2-methoxy-phenyl)-3-[2-(2,6-dioxo-piperidin-3-yl)-1-oxo-2,3-dihydro-1H-isoindol-5-ylmethyl]-urea as a white solid (0.49 g, 91% yield): HPLC: Waters Symmetry $C_{18}$, 5 μm, 3.9×150 mm, 1 mL/min, 240 nm, 40/60 $CH_3CN$/0.1% $H_3PO_4$, 3.95 min (99.4%); mp: 283-285° C.; $^1$H NMR (DMSO-$d_6$) δ 1.92-2.05 (m, 1H, CH), 2.27-2.47 (m, 1H, CH), 2.60 (d, J=16.8 Hz, 1H, CH), 2.82-3.01 (m, 1H, CH), 3.84 (s, 3H, $OCH_3$), 4.24-4.53 (m, 4H, $CH_2$, $CH_2$), 5.11 (dd, J=4.9, 13.2 Hz, 1H, NCH), 6.85-7.04 (m, 2H, Ar), 7.44 (d, J=7.9 Hz, 1H, Ar), 7.49-7.60 (m, 2H, Ar and NH), 7.71 (d, J=7.7 Hz, 1H, Ar), 8.22 (d, J=2.5 Hz, 1H, Ar), 8.25 (s, 1H, NH), 10.99 (s, 1H, NH); $^{13}$C NMR (DMSO-$d_6$) δ 22.49, 31.20, 42.70, 47.12, 51.58, 56.05, 111.79, 117.02, 120.13, 121.94, 123.01, 124.28, 126.92, 130.39, 130.64, 142.46, 144.36, 146.01, 154.96, 167.90, 170.98, 172.85; LCMS: MH=457, 459; Anal Calcd for $C_{22}H_{21}N_4O_5Cl$: C, 57.84; H, 4.63; N, 12.26; Cl, 7.76. Found: C, 57.77; H, 4.55; N, 12.55; Cl, 7.74.

5.181 1-(2-chloro-5-methyl-phenyl)-3-[2-(2,6-dioxo-piperidin-3-yl)-1-oxo-2,3-dihydro-1H-isoindol-5-ylmethyl]-urea

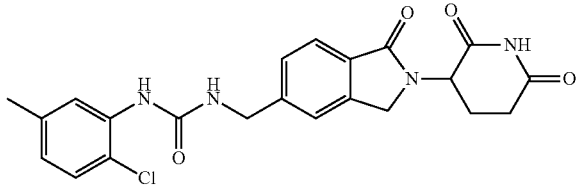 [SMILES: Cc1ccc(Cl)c(NC(=O)NCc2ccc3c(c2)CN(C2CCC(=O)NC2=O)C3=O)c1]

To a stirred mixture of CC-16313 (0.426 g, 1.15 mmol) and 2-chloro-5-methylphenyl isocyanate (0.193 g, 1.15 mmol) in acetonitrile (10 mL), was added triethylamine (0.32 mL, 2.31 mmol) at room temperature under nitrogen. After 1.2 h, 1N aq. HCl (10 mL) was added and the mixture was stirred for 10 min. The product was isolated by filtration, washed with 1N aq. HCl (20 mL), acetonitrile (20 mL) and dried overnight in vacuo to give 1-(2-Chloro-5-methyl-phenyl)-3-[2-(2,6-dioxo-piperidin-3-yl)-1-oxo-2,3-dihydro-1H-isoindol-5-ylmethyl]-urea as a white solid (0.46 g, 90% yield): HPLC: Waters Symmetry $C_{18}$, 5 μm, 3.9×150 mm, 1 mL/min, 240 nm, 40/60 CH₃CN/0.1% H₃PO₄, 3.75 min (99.5%); mp: 278-280° C.; ¹H NMR (DMSO-d₆) δ 1.94-2.06 (m, 1H, CH), 2.25 (s, 3H, CH₃), 2.30-2.47 (m, 1H, CH), 2.60 (d, J=16.8 Hz, 1H, CH), 2.83-3.02 (m, 1H, CH), 4.24-4.54 (m, 4H, CH₂, CH₂), 5.12 (dd, J=5.0, 13.3 Hz, 1H, NCH), 6.78 (dd, J=1.5, 8.1 Hz, 1H, Ar), 7.27 (d, J=8.1 Hz, 1H, Ar), 7.46 (d, J=7.9 Hz, 1H, Ar), 7.53 (s, 1H, Ar), 7.58 (t, J=5.9 Hz, 1H, NH), 7.71 (d, J=7.9 Hz, 1H, Ar), 8.01 (d, J=1.3 Hz, 1H, Ar), 8.08 (s, 1H, NH), 10.99 (s, 1H, NH); ¹³C NMR (DMSO-d₆) δ 20.90, 22.49, 31.20, 42.82, 47.13, 51.58, 118.33, 121.28, 121.99, 123.01, 123.29, 126.99, 128.64, 130.41, 136.16, 136.86, 142.46, 144.34, 154.81, 167.92, 170.99, 172.85; LCMS: MH=441, 443; Anal Calcd for $C_{22}H_{21}N_4O_4Cl$: C, 59.93; H, 4.80; N, 12.71; Cl, 8.04. Found: C, 59.89; H, 4.63; N, 12.87; Cl, 7.95.

5.182 1-(5-chloro-2-methyl-phenyl)-3-[2-(2,6-dioxo-piperidin-3-yl)-1-oxo-2,3-dihydro-1H-isoindol-5-ylmethyl]-urea

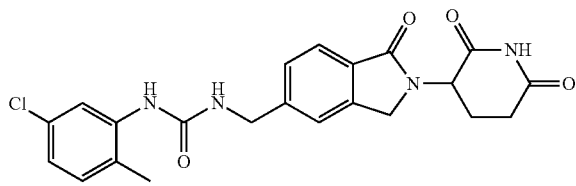 [SMILES: Cc1ccc(Cl)cc1NC(=O)NCc1ccc2c(c1)CN(C1CCC(=O)NC1=O)C2=O]

To a stirred mixture of CC-16313 (0.432 g, 1.17 mmol) and 5-chloro-2-methylphenyl isocyanate (0.16 mL, 1.15 mmol) in acetonitrile (10 mL), was added triethylamine (0.33 mL, 2.34 mmol) at room temperature under nitrogen. After 1 h, 1N aq. HCl (10 mL) was added and the mixture was stirred for 10 min. The product was isolated by filtration, washed with 1N aq. HCl (20 mL), acetonitrile (20 mL) and dried overnight in vacuo to give 1-(5-Chloro-2-methyl-phenyl)-3-[2-(2,6-dioxo-piperidin-3-yl)-1-oxo-2,3-dihydro-1H-isoindol-5-ylmethyl]-urea as a white solid (0.48 g, 93% yield): HPLC: Waters Symmetry C₁₈, 5 μm, 3.9×150 mm, 1 mL/min, 240 nm, 40/60 CH₃CN/0.1% H₃PO₄, 3.67 min (99.1%); mp: 358-360° C.; ¹H NMR (DMSO-d₆) δ 1.94-2.06 (m, 1H, CH), 2.17 (s, 3H, CH₃), 2.29-2.47 (m, 1H, CH), 2.60 (d, J=17.0 Hz, 1H, CH), 2.83-3.01 (m, 1H, CH), 4.26-4.54 (m, 4H, CH₂, CH₂), 5.12 (dd, J=4.9, 13.2 Hz, 1H, NCH), 6.90 (dd, J=2.2, 8.0 Hz, 1H, Ar), 7.14 (d, J=8.3 Hz, 1H, Ar), 7.30 (t, J=5.8 Hz, 1H, NH), 7.46 (d, J=7.9 Hz, 1H, Ar), 7.54 (s, 1H, Ar), 7.71 (d, J=7.9 Hz, 1H, Ar), 7.91 (s, 1H, NH), 8.07 (d, J=2.3 Hz, 1H, Ar), 10.99 (s, 1H, NH); ¹³C NMR (DMSO-d₆) δ 17.36, 22.49, 31.20, 42.80, 47.13, 51.58, 118.74, 121.03, 122.02, 123.00, 124.62, 126.99, 130.29, 130.41, 131.37, 139.52, 142.45, 144.42, 155.09, 167.92, 170.98, 172.85; LCMS: MH=441, 443; Anal Calcd for $C_{22}H_{21}N_4O_4Cl$: C, 59.93; H, 4.80; N, 12.71; Cl, 8.04. Found: C, 59.96; H, 4.64; N, 12.83; Cl, 7.95.

5.183 1-[2-(2,6-dioxo-piperidin-3-yl)-1-oxo-2,3-dihydro-1H-isoindol-5-ylmethyl]-3-(2,4,6-trichloro-phenyl)-urea

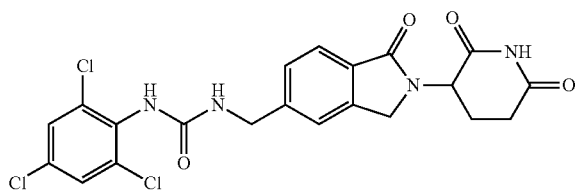 [SMILES: O=C1CCC(N2Cc3cc(CNC(=O)Nc4c(Cl)cc(Cl)cc4Cl)ccc3C2=O)C(=O)N1]

To a stirred mixture of CC-16313 (0.450 g, 1.22 mmol) and 2,4,6-trichlorophenyl isocyanate (0.271 g, 1.22 mmol) in acetonitrile (10 mL), was added triethylamine (0.34 mL, 2.44 mmol) at room temperature under nitrogen. After 1 h, 1N aq. HCl (10 mL) was added and the mixture was stirred for 10 min. The product was isolated by filtration, washed with 1N aq. HCl (20 mL), acetonitrile (20 mL) and dried overnight in vacuo to give 1-[2-(2,6-Dioxo-piperidin-3-yl)-1-oxo-2,3-dihydro-1H-isoindol-5-ylmethyl]-3-(2,4,6-trichloro-phenyl)-urea as a white solid (0.42 g, 69% yield): HPLC: Waters Symmetry C₁₈, 5 μm, 3.9×150 mm, 1 mL/min, 240 nm, 40/60 CH₃CN/0.1% H₃PO₄, 3.22 min (99.7%); mp: 264-266° C.; ¹H NMR (DMSO-d₆) δ 1.91-2.06 (m, 1H, CH), 2.31-2.47 (m, 1H, CH), 2.60 (d, J=17.0 Hz, 1H, CH), 2.83-3.02 (m, 1H, CH), 4.21-4.54 (m, 4H, CH₂, CH₂), 5.11 (dd, J=4.9, 13.2 Hz, 1H, NCH), 7.01 (t, J=5.9 Hz, 1H, NH), 7.44 (d, J=7.9 Hz, 1H, Ar), 7.51 (s, 1H, Ar), 7.66-7.75 (m, 3H, Ar), 8.24 (s, 1H, NH), 10.99 (s, 1H, NH); ¹³C NMR (DMSO-d₆) δ 22.48, 31.20, 43.02, 47.07, 51.56, 121.66, 122.87, 126.72, 128.09, 130.23, 131.24, 133.34, 134.87, 142.29, 144.84, 154.97, 167.95, 170.99, 172.86; LCMS: MH=495, 497; Anal Calcd for $C_{21}H_{17}N_4O_4Cl_3$: C, 50.51; H, 3.45; N, 11.22; Cl, 22.01. Found: C, 50.28; H, 3.17; N, 11.13; Cl, 21.96.

5.184 1-[2-(2,6-dioxo-piperidin-3-yl)-1,3-dioxo-2,3-dihydro-1H-isoindol-5-ylmethyl]-3-propyl-urea

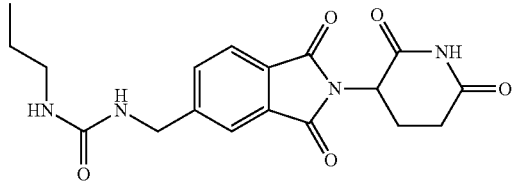 [SMILES: CCCNC(=O)NCc1ccc2c(c1)C(=O)N(C1CCC(=O)NC1=O)C2=O]

To a stirred mixture of 5-aminomethyl-2-(2,6-dioxo-piperidin-3-yl)-isoindole-1,3-dione hydrochloride (0.97 g, 3.00 mmol) and propylisocyanate (0.26 g, 3.30 mmol) in THF (20 mL), was added DIPEA (1.05 mL, 6.00 mmol) at room temperature under nitrogen. The mixture was heated to 40° C. for 18 h then cooled to rt. The solvent was removed in vacuo and the residue was dissolved in EtOAc (100 mL). The organic layer was washed with dil. aq. HCl (2×150 mL), water (2×150 mL), dried (MgSO₄) and then concentrated. The crude product was purified by column chromatography (0-5% MeOH/CH₂Cl₂, gradient over 15 min). The product fractions were combined, concentrated and triturated in Et₂O/CH₂Cl₂ (50 mL) for 18 h. The product was isolated by filtration dried in vacuo to give 1-[2-(2,6-dioxo-piperidin-3-yl)-1,3-dioxo-2,3-dihydro-1H-isoindol-5-ylmethyl]-3-propyl-urea as a white solid (0.24 g, 29% yield): HPLC: Waters Symmetry C₁₈, 5 μm, 3.9×150 mm, 1 mL/min, 240 nm, 40/60 CH₃CN/0.1% H₃PO₄, 1.63 min (98.92%); mp: 166-168° C.; ¹H NMR (DMSO-d₆) δ 0.83 (t, J=7.3 Hz, 3H, CH₃), 1.31-1.46 (m, 2H, CH₂), 2.03-2.08 (m, 1H, CHH), 2.45-2.62 (m, 2H, CHH, CHH), 2.82-3.01 (m, 3H, CHH, CH₂), 4.36 (d, J=5.9 Hz, 2H, CH₂), 5.14 (dd, J=5.3, 12.6 Hz, 1H, CH), 6.10 (t, J=5.7 Hz, 1H, NH), 6.53 (t, J=6.0 Hz, 1H, NH), 7.71-7.89 (m, 3H, Ar), 11.13 (s, 1H, NH); ¹³C NMR (DMSO-d₆) δ 11.31, 22.01, 23.16, 30.94, 41.20, 42.74, 48.98, 121.54, 123.39, 129.51, 131.53, 133.07, 149.53, 158.03, 167.06, 167.24, 169.84, 172.74; LCMS: MH=373;

Anal Calcd for $C_{18}H_{20}N_4O_5 + 0.1H_2O$: C, 57.78; H, 5.44; N, 14.97. Found: C, 57.52; H, 5.37; N, 14.76.

5.185 1-(2,3-dihydro-benzo[1,4]dioxin-6-yl)-3-[2-(2,6-dioxo-piperidin-3-yl)-1-oxo-2,3-dihydro-1H-isoindol-5-ylmethyl]-urea

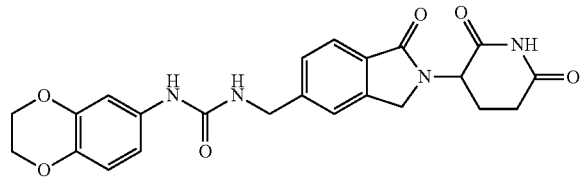 [SMILES: O=C1CCC(N2Cc3cc(CNC(=O)Nc4ccc5c(c4)OCCO5)ccc3C2=O)C(=O)N1]

To a stirred mixture of 3-(5-aminomethyl-1-oxo-1,3-dihydro-isoindol-2-yl)-piperidine-2,6-dione (0.37 g, 1.00 mmol) and 6-isocyanato-2,3-dihydro-benzo[1,4]dioxine (0.18 g, 1.00 mmol) in acetonitrile (10 mL), was added triethylamine (0.28 mL, 2.00 mmol) at room temperature under nitrogen. After 2 h, dil. aq. HCl (25 mL) was added. The solids were collected by filtration and washed with water (3×30 mL). The product was slurried in EtOAc for 24 h, then filtered and dried in vacuo to give 1-(2,3-dihydro-benzo[1,4]dioxin-6-yl)-3-[2-(2,6-dioxo-piperidin-3-yl)-1-oxo-2,3-dihydro-1H-isoindol-5-ylmethyl]-urea as a white solid (0.41 g, 91% yield): HPLC: Waters Nova-Pak C18 column, 3.9×150 mm, 4 μm; 10/90 to 90/10 $CH_3CN/0.1\%$ aq $H_3PO_4$, Gradient over 15 min, 1.0 mL/min, 7.26 min (99.20%); mp: 230-232° C.; $^1H$ NMR (DMSO-$d_6$) δ 1.86-2.10 (m, 1H, CHH), 2.27-2.47 (m, 1H, CHH), 2.59 (d, J=17.6 Hz, 1H, CHH), 2.79-3.04 (m, 1H, CHH), 4.17 (q, J=4.8 Hz, 4H, $CH_2$, $CH_2$), 4.30 (d, J=17.4 Hz, 1H, CHH), 4.36-4.53 (m, 3H, CHH, $CH_2$), 5.11 (dd, J=5.1, 13.2 Hz, 1H, CH), 6.62 (t, J=5.9 Hz, 1H, NH), 6.66-6.83 (m, 2H, Ar), 7.05 (d, J=2.1 Hz, 1H, Ar), 7.43 (d, J=7.7 Hz, 1H, Ar), 7.50 (s, 1H, Ar), 7.69 (d, J=7.7 Hz, 1H, Ar), 8.41 (s, 1H, NH), 10.98 (s, 1H, NH); $^{13}C$ NMR (DMSO-$d_6$) δ 22.49, 31.18, 42.76, 47.10, 51.56, 63.81, 64.19, 107.05, 111.15, 116.66, 121.85, 122.91, 126.86, 130.26, 134.08, 137.90, 142.36, 142.99, 144.94, 155.28, 167.95, 170.99, 172.85; LCMS: MH=451; Anal Calcd for $C_{23}H_{22}N_4O_6$: C, 61.33; H, 4.92; N, 12.44. Found: C, 61.14; H, 4.82; N, 12.40.

5.186 1-cyclohexyl-3-[2-(2,6-dioxo-piperidin-3-yl)-1-oxo-2,3-dihydro-1H-isoindol-5-ylmethyl]-urea

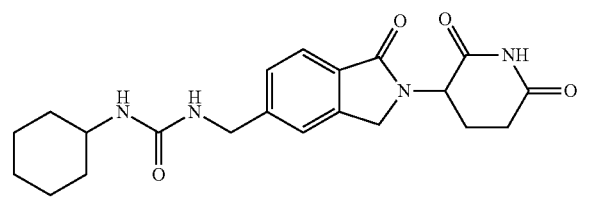 [SMILES: O=C1CCC(N2Cc3cc(CNC(=O)NC4CCCCC4)ccc3C2=O)C(=O)N1]

To a stirred mixture of 3-(5-aminomethyl-1-oxo-1,3-dihydro-isoindol-2-yl)-piperidine-2,6-dione methane sulfonate (0.43 g, 1.16 mmol) and cyclohexylisocyanate (0.148 mL, 1.16 mmol) in acetonitrile (8 mL), was added triethylamine (0.32 mL, 2.33 mmol) at room temperature under nitrogen. After 2 h, dil. aq. HCl (10 mL) was added. The solids were collected by filtration and washed with dil. aq. HCl (20 mL) and acetonitrile (10 mL). The product was dried in vacuo to give 1-cyclohexyl-3-[2-(2,6-dioxo-piperidin-3-yl)-1-oxo-2,3-dihydro-1H-isoindol-5-ylmethyl]-urea as a white solid (0.24 g, 52% yield): HPLC: Waters Nova-Pak C18 column, 3.9×150 mm, 4 μm; 25/75 $CH_3CN/0.1\%$ aq $H_3PO_4$, 10 min, 1.0 mL/min, 5.94 min (99.50%); mp: 265-267° C.; $^1H$ NMR (DMSO-$d_6$) δ 0.99-1.36 (m, 5H, $CH_2$, $CH_2$, CH), 1.44-1.84 (m, 5H, $CH_2$, $CH_2$, CH), 1.92-2.06 (m, 1H, CH), 2.25-2.47 (m, 1H, CH), 2.59 (d, J=17.4 Hz, 1H, CH), 2.82-3.02 (m, 1H, CH), 3.33-3.47 (m, 1H, CH), 4.22-4.50 (m, 4H, $CH_2$ and $CH_2$), 5.10 (dd, J=5.0, 13.3 Hz, 1H, NCH), 5.88 (d, J=7.9 Hz, 1H, NH), 6.29 (t, J=5.9 Hz, 1H, NH), 7.38 (d, J=7.7 Hz, 1H, Ar), 7.44 (s, 1H, Ar), 7.67 (d, J=7.7 Hz, 1H, Ar), 10.98 (s, 1H, NH); $^{13}C$ NMR (DMSO-$d_6$) δ 22.49, 24.49, 25.28, 31.20, 33.28, 42.86, 47.09, 47.89, 51.55, 121.76, 122.84, 126.81, 130.13, 142.30, 145.51, 157.26, 167.98, 170.99, 172.85; LCMS: MH=399; Anal Calcd for $C_{21}H_{26}N_4O_4$: C, 63.30; H, 6.58; N, 14.06. Found: C, 63.30; H, 6.51; N, 13.76.

5.187 General Synthetic Scheme B

The following compounds may be made using Synthetic Scheme B, described above in Section 5.110.

5.187.1 1-(3-chloro-4-(trifluoromethylthio)phenyl)-3-((2-(2,6-dioxopiperidin-3-yl)-1-oxoisoindolin-5-yl)methyl)urea

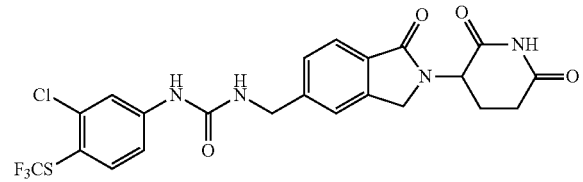

Using Synthetic Scheme B, 1-(3-chloro-4-(trifluoromethylthio)phenyl)-3-((2-(2,6-dioxopiperidin-3-yl)-1-oxoisoindolin-5-yl)methyl)urea can be prepared from 3-chloro-4-(trifluoromethylthio)aniline.

5.187.2 1-(4-bromo-3-methylphenyl)-3-((2-(2,6-dioxopiperidin-3-yl)-1-oxoisoindolin-5-yl)methyl)urea

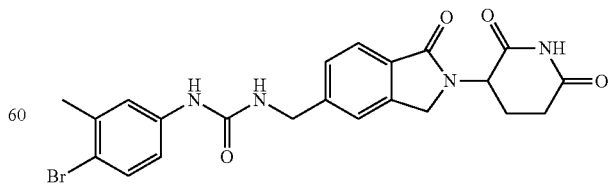

Using Synthetic Scheme B, 1-(4-bromo-3-methylphenyl)-3-((2-(2,6-dioxopiperidin-3-yl)-1-oxoisoindolin-5-yl)methyl)urea can be prepared from 4-bromo-3-methylaniline.

5.187.3 1-((2-(2,6-dioxopiperidin-3-yl)-1-oxoisoindolin-5-yl)methyl)-3-(4-methylpyridin-2-yl)urea

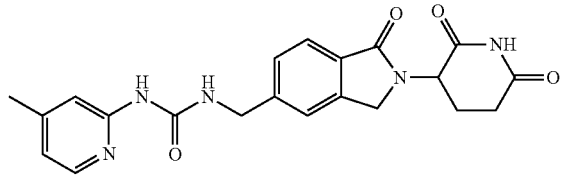 [SMILES: Cc1ccnc(NC(=O)NCc2ccc3c(c2)CN(C2CCC(=O)NC2=O)C3=O)c1]

Using Synthetic Scheme B, 1-((2-(2,6-dioxopiperidin-3-yl)-1-oxoisoindolin-5-yl)methyl)-3-(4-methylpyridin-2-yl)urea can be prepared from 4-methylpyridin-2-amine.

5.187.4 1-(4,5-dimethylpyridin-2-yl)-3-((2-(2,6-dioxopiperidin-3-yl)-1-oxoisoindolin-5-yl)methyl)urea

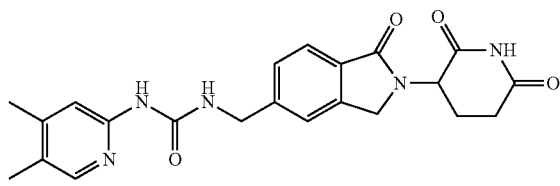 [SMILES: Cc1cnc(NC(=O)NCc2ccc3c(c2)CN(C2CCC(=O)NC2=O)C3=O)cc1C]

Using Synthetic Scheme B, 1-(4,5-dimethylpyridin-2-yl)-3-((2-(2,6-dioxopiperidin-3-yl)-1-oxoisoindolin-5-yl)methyl)urea can be prepared from 4,5-dimethylpyridin-2-amine.

5.187.5 1-(4,5-dichloropyridin-2-yl)-3-((2-(2,6-dioxopiperidin-3-yl)-1-oxoisoindolin-5-yl)methyl)urea

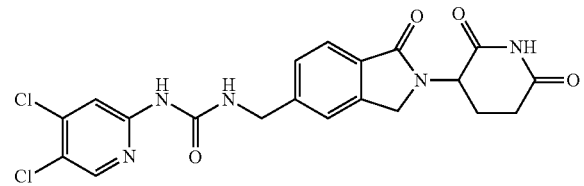

Using Synthetic Scheme B, 1-(4,5-dichloropyridin-2-yl)-3-((2-(2,6-dioxopiperidin-3-yl)-1-oxoisoindolin-5-yl)methyl)urea can be prepared from 4,5-dichloropyridin-2-amine.

5.187.6 1-((2-(2,6-dioxopiperidin-3-yl)-1-oxoisoindolin-5-yl)methyl)-3-(4-fluoropyridin-2-yl)urea

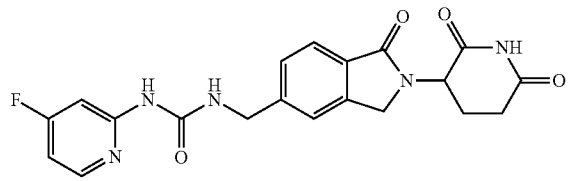 [SMILES: O=C1CCC(N2Cc3cc(CNC(=O)Nc4cc(F)ccn4)ccc3C2=O)C(=O)N1]

Using Synthetic Scheme B, 1-((2-(2,6-dioxopiperidin-3-yl)-1-oxoisoindolin-5-yl)methyl)-3-(4-fluoropyridin-2-yl)urea can be prepared from 4-fluoropyridin-2-amine.

5.187.7 1-((2-(2,6-dioxopiperidin-3-yl)-1-oxoisoindolin-5-yl)methyl)-3-(1-methylisoquinolin-6-yl)urea

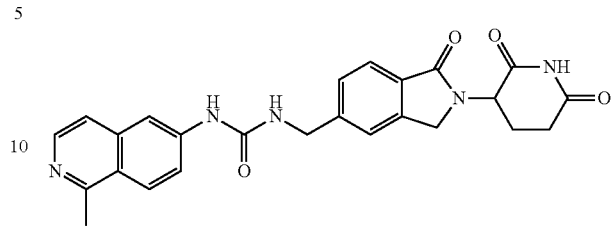

Using Synthetic Scheme B, 1-((2-(2,6-dioxopiperidin-3-yl)-1-oxoisoindolin-5-yl)methyl)-3-(1-methylisoquinolin-6-yl)urea can be prepared from 1-methylisoquinolin-6-amine.

5.187.8 1-((2-(2,6-dioxopiperidin-3-yl)-1-oxoisoindolin-5-yl)methyl)-3-(isoquinolin-6-yl)urea

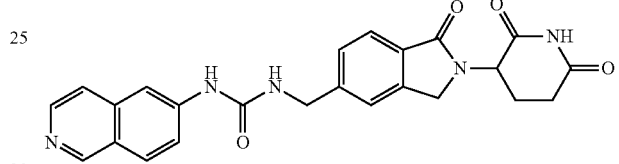

Using Synthetic Scheme B, 1-((2-(2,6-dioxopiperidin-3-yl)-1-oxoisoindolin-5-yl)methyl)-3-(isoquinolin-6-yl)urea can be prepared from isoquinolin-6-amine.

5.187.9 1-((2-(2,6-dioxopiperidin-3-yl)-1-oxoisoindolin-5-yl)methyl)-3-(quinolin-6-yl)urea

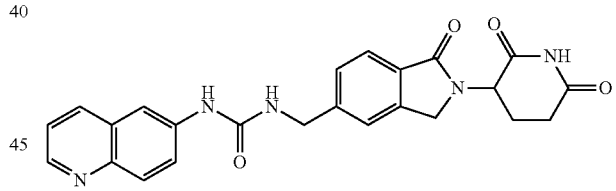

Using Synthetic Scheme B, 1-((2-(2,6-dioxopiperidin-3-yl)-1-oxoisoindolin-5-yl)methyl)-3-(quinolin-6-yl)urea can be prepared from quinolin-6-amine.

5.187.10 1-((2-(2,6-dioxopiperidin-3-yl)-1-oxoisoindolin-5-yl)methyl)-3-(naphthalen-2-yl)urea

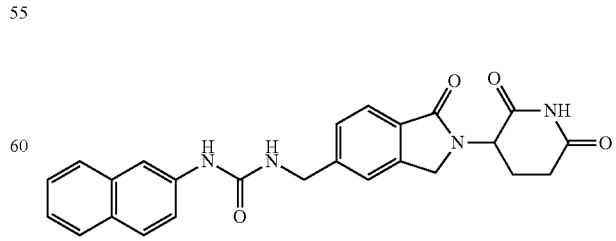

Using Synthetic Scheme B, 1-((2-(2,6-dioxopiperidin-3-yl)-1-oxoisoindolin-5-yl)methyl)-3-(naphthalen-2-yl)urea can be prepared from naphthalen-2-amine.

5.187.11 1-((2-(2,6-dioxopiperidin-3-yl)-1-oxoisoindolin-5-yl)methyl)-3-(quinazolin-7-yl)urea

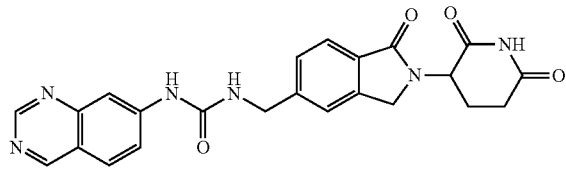 [SMILES: O=C1CCC(N2Cc3cc(CNC(=O)Nc4ccc5cncnc5c4)ccc3C2=O)C(=O)N1]

Using Synthetic Scheme B, 1-((2-(2,6-dioxopiperidin-3-yl)-1-oxoisoindolin-5-yl)methyl)-3-(quinazolin-7-yl)urea can be prepared from quinazolin-7-amine.

5.187.12 1-((2-(2,6-dioxopiperidin-3-yl)-1-oxoisoindolin-5-yl)methyl)-3-(2-methylquinazolin-7-yl)urea

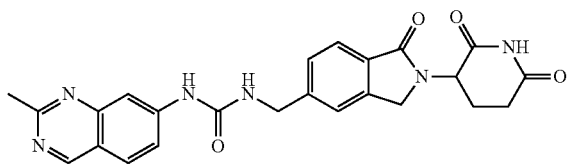 [SMILES: Cc1ncc2ccc(NC(=O)NCc3ccc4c(c3)CN(C3CCC(=O)NC3=O)C4=O)cc2n1]

Using Synthetic Scheme B, 1-((2-(2,6-dioxopiperidin-3-yl)-1-oxoisoindolin-5-yl)methyl)-3-(2-methylquinazolin-7-yl)urea can be prepared from 2-methylquinazolin-7-amine.

5.187.13 1-((2-(2,6-dioxopiperidin-3-yl)-1-oxoisoindolin-5-yl)methyl)-3-(quinazolin-2-yl)urea

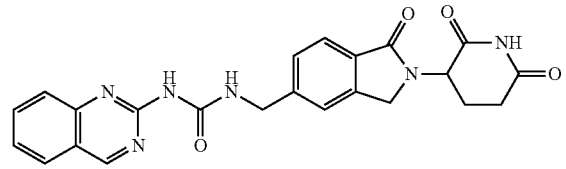 [SMILES: O=C1CCC(N2Cc3cc(CNC(=O)Nc4ncc5ccccc5n4)ccc3C2=O)C(=O)N1]

Using Synthetic Scheme B, 1-((2-(2,6-dioxopiperidin-3-yl)-1-oxoisoindolin-5-yl)methyl)-3-(quinazolin-2-yl)urea can be prepared from quinazolin-2-amine.

5.187.14 1-((2-(2,6-dioxopiperidin-3-yl)-1-oxoisoindolin-5-yl)methyl)-3-(4-methylquinazolin-2-yl)urea

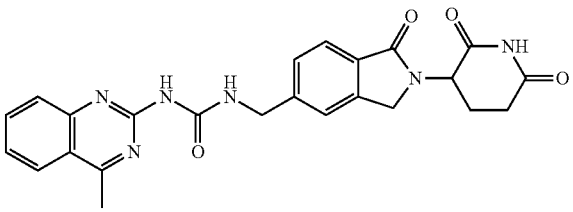 [SMILES: Cc1nc(NC(=O)NCc2ccc3c(c2)CN(C2CCC(=O)NC2=O)C3=O)nc2ccccc12]

Using Synthetic Scheme B, 1-((2-(2,6-dioxopiperidin-3-yl)-1-oxoisoindolin-5-yl)methyl)-3-(4-methylquinazolin-2-yl)urea can be prepared from 4-methylquinazolin-2-amine.

5.187.15 1-((2-(2,6-dioxopiperidin-3-yl)-1-oxoisoindolin-5-yl)methyl)-3-(1,2,3,4-tetrahydroisoquinolin-6-yl)urea

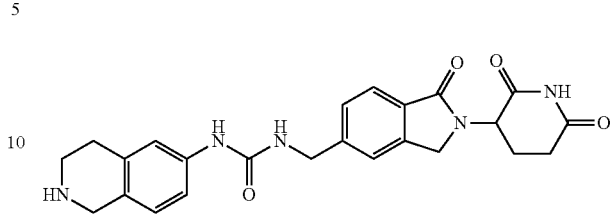

Step 1: Using Synthetic Scheme B, tert-butyl 6-(3-((2-(2,6-dioxopiperidin-3-yl)-1-oxoisoindolin-5-yl)methyl)ureido)-3,4-dihydroisoquinoline-2(1H)-carboxylate can be prepared from tert-butyl 6-amino-3,4-dihydroisoquinoline-2(1H)-carboxylate.

Step 2: A mixture of tert-butyl 6-(3-((2-(2,6-dioxopiperidin-3-yl)-1-oxoisoindolin-5-yl)methyl)ureido)-3,4-dihydroisoquinoline-2(1H)-carboxylate (0.55 g, 1.0 mmol) in methylene chloride (100 mL) is treated with HCl (5 mL of a 2N solution in diethyl ether), and stirred at ambient temperature for 48 hours. The mixture is evaporated under vacuum, and triturated in ethyl acetate (10 mL), filtered, and dried under vacuum.

5.188 Assays

5.188.1 TNFα Inhibition Assay in PMBC

Peripheral blood mononuclear cells (PBMC) from normal donors are obtained by Ficoll Hypaque (Pharmacia, Piscataway, N.J., USA) density centrifugation. Cells are cultured in RPMI 1640 (Life Technologies, Grand Island, N.Y., USA) supplemented with 10% AB+human serum (Gemini Bioproducts, Woodland, Calif., USA), 2 mM L-glutamine, 100 U/ml penicillin, and 100 µg/ml streptomycin (Life Technologies).

PBMC ($2 \times 10^5$ cells) are plated in 96-well flat-bottom Costar tissue culture plates (Corning, N.Y., USA) in triplicate. Cells are stimulated with LPS (from *Salmonella abortus* equi, Sigma cat. no. L-1887, St. Louis, Mo., USA) at 1 ng/ml final in the absence or presence of compounds. Compounds of the invention are dissolved in DMSO (Sigma) and further dilutions are done in culture medium immediately before use. The final DMSO concentration in all assays can be about 0.25%. Compounds are added to cells 1 hour before LPS stimulation. Cells are then incubated for 18-20 hours at 37° C. in 5% $CO_2$, and supernatants are then collected, diluted with culture medium and assayed for TNFα levels by ELISA (Endogen, Boston, Mass., USA). $IC_{50}$s are calculated using non-linear regression, sigmoidal dose-response, constraining the top to 100% and bottom to 0%, allowing variable slope (GraphPad Prism v3.02).

5.188.2 IL-2 and MIP-3α Production by T Cells

PBMC are depleted of adherent monocytes by placing $1 \times 10^8$ PBMC in 10 ml complete medium (RPMI 1640 supplemented with 10% heat-inactivated fetal bovine serum, 2 mM L-glutamine, 100 U/ml penicillin, and 100 µg/ml streptomycin) per 10 cm tissue culture dish, in 37° C., 5% $CO_2$ incubator for 30-60 minutes. The dish is rinsed with medium to remove all non-adherent PBMC. T cells are purified by negative selection using the following antibody (Pharmingen) and Dynabead (Dynal) mixture for every 1×10⁸ non-adherent PBMC: 0.3 ml Sheep anti-mouse IgG beads, 15 µl anti-CD16, 15 µl anti-CD33, 15 µl anti-CD56, 0.23 ml anti-CD19 beads, 0.23 ml anti-HLA class II beads, and 56 µl anti-CD14 beads. The cells and bead/antibody mixture is rotated end-over-end for 30-60 minutes at 4° C. Purified T cells are removed from beads using a Dynal magnet. Typical yield is about 50% T cells, 87-95% $CD3^+$ by flow cytometry.

Tissue culture 96-well flat-bottom plates are coated with anti-CD3 antibody OKT3 at 5 µg/ml in PBS, 100 µl per well, incubated at 37° C. for 3-6 hours, then washed four times with complete medium 100 µl/well just before T cells are added. Compounds are diluted to 20 times of final in a round bottom tissue culture 96-well plate. Final concentrations are about 10 µM to about 0.00064 µM. A 10 mM stock of compounds of the invention is diluted 1:50 in complete for the first 20× dilution of 200 µM in 2% DMSO and serially diluted 1:5 into 2% DMSO. Compound is added at 10 µl per 200 µl culture, to give a final DMSO concentration of 0.1%. Cultures are incubated at 37° C., 5% $CO_2$ for 2-3 days, and supernatants analyzed for IL-2 and MIP-3α by ELISA (R&D Systems). IL-2 and MIP-3α levels are normalized to the amount produced in the presence of an amount of a compound of the invention, and $EC_{50}$s calculated using non-linear regression, sigmoidal dose-response, constraining the top to 100% and bottom to 0%, allowing variable slope (GraphPad Prism v3.02).

5.188.3 Cell Proliferation Assay

Cell lines Namalwa, MUTZ-5, and UT-7 are obtained from the Deutsche Sammlung von Mikroorganismen and Zellkulturen GmbH (Braunschweig, Germany). The cell line KG-1 is obtained from the American Type Culture Collection (Manassas, Va., USA). Cell proliferation as indicated by ³H-thymidine incorporation is measured in all cell lines as follows.

Cells are plated in 96-well plates at 6000 cells per well in media. The cells are pre-treated with compounds at about 100, 10, 1, 0.1, 0.01, 0.001, 0.0001 and 0 µM in a final concentration of about 0.25% DMSO in triplicate at 37° C. in a humidified incubator at 5% $CO_2$ for 72 hours. One microcurie of ³H-thymidine (Amersham) is then added to each well, and cells are incubated again at 37° C. in a humidified incubator at 5% $CO_2$ for 6 hours. The cells are harvested onto UniFilter GF/C filter plates (Perkin Elmer) using a cell harvester (Tomtec), and the plates are allowed to dry overnight. Microscint 20 (Packard) (25 µl/well) is added, and plates are analyzed in TopCount NXT (Packard). Each well is counted for one minute. Percent inhibition of cell proliferation is calculated by averaging all triplicates and normalizing to the DMSO control (0% inhibition). Each compound is tested in each cell line in three separate experiments. Final $IC_{50}$s are calculated using non-linear regression, sigmoidal dose-response, constraining the top to 100% and bottom to 0%, allowing variable slope. (GraphPad Prism v3.02).

5.188.4 Immunoprecipitation and Immunoblot

Namalwa cells are treated with DMSO or an amount of a compound of the invention for 1 hour, then stimulated with 10 U/ml of Epo (R&D Systems) for 30 minutes. Cell lysates are prepared and either immunoprecipitated with Epo receptor Ab or separated immediately by SDS-PAGE. Immunoblots are probed with Akt, phospo-Akt (Ser473 or Thr308), phospho-Gab1 (Y627), Gab1, IRS2, actin and IRF-1 Abs and analyzed on a Storm 860 Imager using ImageQuant software (Molecular Dynamics).

5.188.5 Cell Cycle Analysis

Cells are treated with DMSO or an amount of a compound of the invention overnight. Propidium iodide staining for cell cycle is performed using CycleTEST PLUS (Becton Dickinson) according to manufacturer's protocol. Following staining, cells are analyzed by a FACSCalibur flow cytometer using ModFit LT software (Becton Dickinson).

5.188.6 Apoptosis Analysis

Cells are treated with DMSO or an amount of a compound of the invention at various time points, then washed with annexin-V wash buffer (BD Biosciences). Cells are incubated with annexin-V binding protein and propidium iodide (BD Biosciences) for 10 minutes. Samples are analyzed using flow cytometry.

5.188.7 Luciferase Assay

Namalwa cells are transfected with 4 µg of AP1-luciferase (Stratagene) per 1×10⁶ cells and 3 µl Lipofectamine 2000 (Invitrogen) reagent according to manufacturer's instructions. Six hours post-transfection, cells are treated with DMSO or an amount of a compound of the invention. Luciferase activity is assayed using luciferase lysis buffer and substrate (Promega) and measured using a luminometer (Turner Designs).

5.188.8 Screening for Anti-Proliferation Activity

Anti-proliferation activity of compounds disclosed herein can be assessed using the following exemplary protocol:

Day1: The cells are seeded to 96-well plate with 50 ul/well in 10% FBS RPMI (w/Glutamine, w/o pen-strip) for overnight, with the following cells:
   Colorectal cancer cell: Colo 205 3200 cells/well; positive control irinotecan
   Pancreatic cancer cell: BXPC-3 1200 cells/well; positive control gemcitabine
   Prostate cancer cell: PC3 1200 cells/well; positive control docetaxel
   Breast cancer cell: MDA-MB-231 2400 cells/well; positive control paclitaxel Day2: The compounds are serially diluted from 0.00001 µm~10 µm with 50 µl/well (of 2×) and added to the plates in duplicate with relative positive control. The plates are then incubated at 37° C. for 72 hours.

Day5: The results were detected by CellTiter Glo method. 100 µl/well of CellTiter Glo reagent is added to the plates and incubated for 10 minutes at room temperature, and then analyzed on the Top Count reader. The $IC_{50}$ of each compound is based on the result of two individually experiments.

5.189 TNFα Inhibition Assay (I)

In one experiment, TNFα inhibitory effect of certain compounds provided herein were tested according to the assay substantially similar to that described in 5.188.1, above.

Tested compounds included the following: 5-{[(benzofuran-2-ylmethyl)-amino]-methyl}-2-(2,6-dioxo-piperidin-3-yl)-isoindole-1,3-dione; 3,4-dichloro-N-[2-(2,6-dioxo-piperidin-3-yl)-1-oxo-2,3-dihydro-1H-isoindol-5-ylmethyl]- benzamide; [2-(2,6-dioxo-piperidin-3-yl)-1,3-dioxo-2,3-dihydro-1H-isoindol-5-ylmethyl]-carbamic acid hexyl ester; hexanoic acid [2-(2,6-dioxo-piperidin-3-yl)-1,3-dioxo-2,3-dihydro-1H-isoindol-5-ylmethyl]-amide; N-[2-(2,6-dioxo-piperidin-3-yl)-1,3-dioxo-2,3-dihydro-1H-isoindol-5-ylmethyl]-4-trifluoromethoxybenzamide; thiophene-2-carboxylic acid [2-(2,6-dioxo-piperidin-3-yl)-1,3-dioxo-2,3-dihydro-1H-isoindol-5-ylmethyl]-amide; N-[2-(2,6-dioxo-piperidin-3-yl)-1,3-dioxo-2,3-dihydro-1H-isoindol-5-ylmethyl]-4-methyl-benzamide; 5-{[2-(2,6-dioxo-piperidin-3-yl)-1,3-dioxo-2,3-dihydro-1H-isoindol-5-ylmethyl]-carbamoyl}-pentanoic acidtert-butyl ester; 5-{[2-(2,6-dioxo-piperidin-3-yl)-1,3-dioxo-2,3-dihydro-1H-isoindol-5-ylmethyl]-carbamoyl}-pentanoic acid; hexanoic acid [2-[(3S)-3-methyl-2,6-dioxo-piperidin-3-yl]-1,3-dioxo-2,3-dihydro-1H-isoindol-5-ylmethyl]-amide; heptanoic acid [2-(2,6-dioxo-piperidin-3-yl)-1,3-dioxo-2,3-dihydro-1H-isoindol-5-ylmethyl]-amide; 4-chloro-N-[2-[(3S)-3-methyl-2,6-dioxo-piperidin-3-yl]-1,3-dioxo-2,3-dihydro-1H-isoindol-5-ylmethyl]-benzamide; {2-[(3S)-3-Methyl-2,6-dioxo-piperidin-3-yl]-1,3-dioxo-2,3-dihydro-1H-isoindol-5-ylmethyl}-carbamic acid hexyl ester; N-[2-(2,6-dioxo-piperidin-3-yl)-1-oxo-2,3-dihydro-1H-isoindol-5-ylmethyl]-4-trifluoromethoxy-benzamide; N-[2-[(3S)-3-methyl-2,6-dioxo-piperidin-3-yl]-1,3-dioxo-2,3-dihydro-1H-isoindol-5-ylmethyl]-4-trifluoromethoxy-benzamide; furan-2-carboxylic acid [2-(2,6-dioxo-piperidin-3-yl)-1-oxo-2,3-dihydro-1H-isoindol-5-ylmethyl]amide; 2-(4-chloro-phenyl)-N-[2-(2,6-dioxo-piperidin-3-yl)-1-oxo-2,3-dihydro-1H-isoindol-5-ylmethyl]-acetamide; hexanoic acid [2-(2,6-dioxo-piperidin-3-yl)-1-oxo-2,3-dihydro-1H-isoindol-5-ylmethyl]-amide; pyridine-2-carboxylic acid [2-[(3S)-3-methyl-2,6-dioxo-piperidin-3-yl]-1,3-dioxo-2,3-dihydro-1H-isoindol-5-ylmethyl]-amide; N-[2-[(3S)-3-methyl-2,6-dioxo-piperidin-3-yl]-1,3-dioxo-2,3-dihydro-1H-isoindol-5-ylmethyl]-4-trifluoromethyl-benzamide; N-[2-[(3S)-3-methyl-2,6-dioxo-piperidin-3-yl]-1,3-dioxo-2,3-dihydro-1H-isoindol-5-ylmethyl]-isonicotinamide; 4-fluoro-N-[2-[(3S)-3-methyl-2,6-dioxo-piperidin-3-yl]-1,3-dioxo-2,3-dihydro-1H-isoindol-5-ylmethyl]-benzamide; N-[2-(3S)-(3-methyl-2,6-dioxo-piperidin-3-yl)-1,3-dioxo-2,3-dihydro-1H-isoindol-5-ylmethyl]-6-trifluoromethyl nicotinamide; thiophene-2-carboxylic acid [2-[(3S)-3-methyl-2,6-dioxo-piperidin-3-yl]-1,3-dioxo-2,3-dihydro-1H-isoindol-5-ylmethyl]-amide; N-((2-(2,6-dioxopiperidin-3-yl)-1,3-dioxoisoindolin-5-yl)methyl)-4-(trifluoromethylthio)benzamide; N-((2-(2,6-dioxopiperidin-3-yl)-1,3-dioxoisoindolin-5-yl)methyl)-4-(1,1,2,2-tetrafluoroethoxy)benzamide; 4-bromo-N-[2-(2,6-dioxo-piperidin-3-yl)-1,3-dioxo-2,3-dihydro-1H-isoindol-5-ylmethyl]-benzamide; N-[2-(2,6-dioxo-piperidin-3-yl)-1,3-dioxo-2,3-dihydro-1H-isoindol-5-ylmethyl]-4-ethyl-benzamide; N-[2-(2,6-dioxo-piperidin-3-yl)-1,3-dioxo-2,3-dihydro-1H-isoindol-5-ylmethyl]-4-ethoxy-benzamide; N-[2-(2,6-dioxo-piperidin-3-yl)-1,3-dioxo-2,3-dihydro-1H-isoindol-5-ylmethyl]-4-methanesulfonyl-benzamide; N-[2-(2,6-dioxo-piperidin-3-yl)-1,3-dioxo-2,3-dihydro-1H-isoindol-5-ylmethyl]-4-iodo-benzamide; N-[2-(2,6-dioxo-piperidin-3-yl)-1,3-dioxo-2,3-dihydro-1H-isoindol-5-ylmethyl]-4-methyl sulfanyl-benzamide; N-[2-(2,6-dioxo-piperidin-3-yl)-1,3-dioxo-2,3-dihydro-1H-isoindol-5-ylmethyl]-4-ethylsulfanyl-benzamide; N-((2-(2,6-dioxopiperidin-3-yl)-1,3-dioxoisoindolin-5-yl)methyl)-2-(4-(trifluoromethylthio) phenyl) acetamide; 4-tert-butyl-N-((2-(2,6-dioxopiperidin-3-yl)-1,3-dioxoisoindolin-5-yl)methyl)benzamide; 5-bromo-N-[[2-[(3S)-3-methyl-2,6-dioxopiperidin-3-yl]-1,3-dioxoisoindolin-5-yl]methyl]picolinamide; N-[[2-[(3S)-3-methyl-2,6-dioxopiperidin-3-yl]-1,3-dioxoisoindolin-5-yl]methyl]-4-(methylsulfonyl)benzamide; 4-ethyl-N-[[2-[(3S)-3-methyl-2,6-dioxopiperidin-3-yl]-1,3-dioxoisoindolin-5-yl]methyl]benzamide; N-[[2-[(3S)-3-methyl-2,6-dioxopiperidin-3-yl]-1,3-dioxoisoindolin-5-yl]methyl]-4-(trifluoromethylthio)benzamide; N-[[2-(2,6-dioxopiperidin-3-yl)-1-oxoisoindolin-5-yl]methyl]-4-(trifluoromethylthio) benzamide; 4-ethylsulfanyl-N-[[2-[(3S)-3-methyl-2,6-dioxopiperidin-3-yl]-1,3-dioxo-2,3-dihydro-1H-isoindol-5-ylmethyl]-benzamide; 4-ethoxy-N-[[2-[(3S)-3-methyl-2,6-dioxopiperidin-3-yl]-1,3-dioxo-2,3-dihydro-1H-isoindol-5-ylmethyl]-benzamide; 1-(3,4-dichloro-phenyl)-3-[2-(2,6-dioxo-piperidin-3-yl)-1,3-dioxo-2,3-dihydro-1H-isoindol-5-ylmethyl]-urea; 1-(3,4-dimethyl-phenyl)-3-[2-(2,6-dioxo-piperidin-3-yl)-1,3-dioxo-2,3-dihydro-1H-isoindol-5-ylmethyl]-urea; 1-(3-chloro-4-methyl-phenyl)-3-[2-(2,6-dioxo-piperidin-3-yl)-1,3-dioxo-2,3-dihydro-1H-isoindol-5-ylmethyl]-urea; 1-[2-(2,6-Dioxo-piperidin-3-yl)-1,3-dioxo-2,3-dihydro-1H-isoindol-5-yl methyl]-3-hexyl-urea; 1-(3-chloro-phenyl)-3-[2-(2,6-dioxo-piperidin-3-yl)-1,3-dioxo-2,3-dihydro-1H-isoindol-5-ylmethyl]-urea; 1-(4-chloro-phenyl)-3-[2-(2,6-dioxo-piperidin-3-yl)-1,3-dioxo-2,3-dihydro-1H-isoindol-5-ylmethyl]-urea; 1-(3-chloro-4-methyl-phenyl)-3-[2-(2,6-dioxo-piperidin-3-yl)-1-oxo-2,3-dihydro-1H-isoindol-5-ylmethyl]-urea; 1-(4-chloro-phenyl)-3-[2-(2,6-dioxo-piperidin-3-yl)-1-oxo-2,3-dihydro-1H-isoindol-5-ylmethyl]-urea; 1-[2-(2,6-dioxo-piperidin-3-yl)-1-oxo-2,3-dihydro-1H-isoindol-5-ylmethyl]-3-hexyl-urea; 1-[2-(2,6-dioxo-piperidin-3-yl)-1,3-dioxo-2,3-dihydro-1H-isoindol-5-ylmethyl]-3-(4-methoxy-phenyl)-urea; 1-[2-(2,6-dioxo-piperidin-3-yl)-1,3-dioxo-2,3-dihydro-1H-isoindol-5-ylmethyl]-3-(2-methoxy-phenyl)-urea; 1-[2-(2,6-dioxo-piperidin-3-yl)-1,3-dioxo-2,3-dihydro-1H-isoindol-5-ylmethyl]-3-(4-trifluoromethoxy-phenyl)-urea; 1-[2-(2,6-dioxo-piperidin-3-yl)-1,3-dioxo-2,3-dihydro-1H-isoindol-5-ylmethyl]-3-naphthalen-1-yl-urea; 1-[2-(2,6-Dioxo-piperidin-3-yl)-1,3-dioxo-2,3-dihydro-1H-isoindol-5-ylmethyl]-3-hexyl-urea; 1-(4-chloro-3-methyl-phenyl)-3-[2-(2,6-dioxo-piperidin-3-yl)-1,3-dioxo-2,3-dihydro-1H-isoindol-5-ylmethyl]-urea; 1-(4-cyano-phenyl)-3-[2-(2,6-dioxo-piperidin-3-yl)-1,3-dioxo-2,3-dihydro-1H-isoindol-5-ylmethyl]-urea; 1-[2-(2,6-dioxo-piperidin-3-yl)-1,3-dioxo-2,3-dihydro-1H-isoindol-5-ylmethyl]-3-p-tolyl-urea; 1-[2-(2,6-dioxo-piperidin-3-yl)-1,3-dioxo-2,3-dihydro-1H-isoindol-5-ylmethyl]-3-m-tolyl-urea; 1-butyl-3-[2-(2,6-dioxo-piperidin-3-yl)-1,3-dioxo-2,3-dihydro-1H-isoindol-5-ylmethyl]-urea; 1-(4-chloro-phenyl)-3-[2-(3S)-(3-methyl-2,6-dioxo-piperidin-3-yl)-1,3-dioxo-2,3-dihydro-1H-isoindol-5-ylmethyl]-urea; 1-hexyl-3-[2-[(3S)-3-methyl-2,6-dioxo-piperidin-3-yl]-1,3-dioxo-2,3-dihydro-1H-isoindol-5-ylmethyl]-urea; and 1-[2-[(3S)-3-methyl-2,6-dioxo-piperidin-3-yl]-1,3-dioxo-2,3-dihydro-1H-isoindol-5-ylmethyl]-3-(4-trifluoromethoxy-phenyl)-urea.

These compounds exhibited $IC_{50}$ values in the range of 0.002 to 15 µM.

5.190 TNFα Inhibition Assay (II)

In another experiment, TNFα inhibitory effect of certain compounds provided herein were tested according to the assay substantially similar to that described in 5.188.1, above.

Tested compounds included the following: N-[2-(2,6-dioxo-piperidin-3-yl)-1-oxo-2,3-dihydro-1H-isoindol-5-ylmethyl]-4-trifluoromethyl-benzamide; N-[2-(2,6-dioxo-piperidin-3-yl)-1-oxo-2,3-dihydro-1H-isoindol-5-ylmethyl]-6-trifluoromethyl-nicotinamide; N-[2-(2,6-dioxo-piperidin-3- yl)-1-oxo-2,3-dihydro-1H-isoindol-5-ylmethyl]-3-trifluoromethyl-benzamide; 3,4-dichloro-N-[2-(3-methyl-2,6-dioxo-piperidin-3-yl)-1-oxo-2,3-dihydro-1H-isoindol-5-ylmethyl]-benzamide; N-[2-(3-methyl-2,6-dioxo-piperidin-3-yl)-1-oxo-2,3-dihydro-1H-isoindol-5-ylmethyl]-4-trifluoromethoxy-benzamide; 2-(4-chloro-phenyl)-N-[2-(3-methyl-2,6-dioxo-piperidin-3-yl)-1-oxo-2,3-dihydro-1H-isoindol-5-ylmethyl]-acetamide; 5-methanesulfonyl-pyridine-2-carboxylic acid [2-(2,6-dioxo-piperidin-3-yl)-1,3-dioxo-2,3-dihydro-1H-isoindol-5-ylmethyl]-amide; 5-ethylsulfanyl-pyridine-2-carboxylic acid [2-(2,6-dioxo-piperidin-3-yl)-1,3-dioxo-2,3-dihydro-1H-isoindol-5-ylmethyl]-amide; 5-ethanesulfonyl-pyridine-2-carboxylic acid [2-(2,6-dioxo-piperidin-3-yl)-1,3-dioxo-2,3-dihydro-1H-isoindol-5-ylmethyl]-amide; 5-ethanesulfonyl-pyridine-2-carboxylic acid [2-(3-methyl-2,6-dioxo-piperidin-3-yl)-1,3-dioxo-2,3-dihydro-1H-isoindol-5-ylmethyl]-amide; 5-ethoxy-pyridine-2-carboxylic acid[2-(2,6-dioxo-piperidin-3-yl)-1,3-dioxo-2,3-dihydro-1H-isoindol-5-ylmethyl]-amide; 5-ethoxy-pyridine-2-carboxylic acid[2-(3-methyl-2,6-dioxo-piperidin-3-yl)-1,3-dioxo-2,3-dihydro-1H-isoindol-5-ylmethyl]-amide; N-[2-(3-methyl-2,6-dioxo-piperidin-3-yl)-1,3-dioxo-2,3-dihydro-1H-isoindol-5-ylmethyl]-4-methylsulfanyl-benzamide; 5-methylsulfanyl-pyridine-2-carboxylic acid [2-(3-methyl-2,6-dioxo-piperidin-3-yl)-1,3-dioxo-2,3-dihydro-1H-isoindol-5-ylmethyl]-amide; 6-ethoxy-N-[2-(3-methyl-2,6-dioxo-piperidin-3-yl)-1,3-dioxo-2,3-dihydro-1H-isoindol-5-ylmethyl]-nicotinamide; 4-ethanesulfonyl-N-[2-(3-methyl-2,6-dioxo-piperidin-3-yl)-1,3-dioxo-2,3-dihydro-1H-isoindol-5-ylmethyl]-benzamide; N-[2-(2,6-dioxo-piperidin-3-yl)-1,3-dioxo-2,3-dihydro-1H-isoindol-5-ylmethyl]-4-ethanesulfonyl-benzamide; 6-ethoxy-pyridazine-3-carboxylic acid [2-(3-methyl-2,6-dioxo-piperidin-3-yl)-1,3-dioxo-2,3-dihydro-1H-isoindol-5-ylmethyl]-amide; 6-ethylsulfanyl-pyridazine-3-carboxylic acid [2-(3-methyl-2,6-dioxo-piperidin-3-yl)-1,3-dioxo-2,3-dihydro-1H-isoindol-5-ylmethyl]amide; N-[2-(2,6-dioxo-piperidin-3-yl)-1-oxo-2,3-dihydro-1H-isoindol-5-ylmethyl]-2-(4-trifluoromethylsulfanyl-phenyl)-acetamide; N-[2-(2,6-dioxo-piperidin-3-yl)-1-oxo-2,3-dihydro-1H-isoindol-5-ylmethyl]-2-(4-trifluoromethyl-phenyl)-acetamide; 3-chloro-N-[2-(2,6-dioxo-piperidin-3-yl)-1-oxo-2,3-dihydro-1H-isoindol-5-ylmethyl]-4-methyl-benzamide; 2-(3,4-dichloro-phenyl)-N-[2-(2,6-dioxo-piperidin-3-yl)-1-oxo-2,3-dihydro-1H-isoindol-5-ylmethyl]-acetamide; 4-chloro-N-[2-(2,6-dioxo-piperidin-3-yl)-1-oxo-2,3-dihydro-1H-isoindol-5-ylmethyl]-benzamide; N-[2-(2,6-dioxo-piperidin-3-yl)-1-oxo-2,3-dihydro-1H-isoindol-5-ylmethyl]-4-fluoro-benzamide; 3-chloro-N-[2-(2,6-dioxo-piperidin-3yl)-1-oxo-2,3-dihydro-1H-isoindol-5-ylmethyl]-benzamide; N-[2-(2,6-dioxo-piperidin-3-yl)-1-oxo-2,3-dihydro-1H-isoindol-5-ylmethyl]-4-methanesulfonyl-benzamide; N-[2-(2,6-dioxo-piperidin-3-yl)-1-oxo-2,3-dihydro-1H-isoindol-5-ylmethyl]-4-ethylsulfanyl-benzamide; N-[2-(2,6-dioxo-piperidin-3-yl)-1-oxo-2,3-dihydro-1H-isoindol-5-ylmethyl]-4-ethanesulfonyl-benzamide; 6-ethoxy-pyridazine-3-carboxylic acid [2-(2,6-dioxo-piperidin-3-yl)-1-oxo-2,3-dihydro-1H-isoindol-5-ylmethyl]-amide; N-[2-(2,6-dioxo-piperidin-3-yl)-1-oxo-2,3-dihydro-1H-isoindol-5-ylmethyl]-6-ethoxy-nicotinamide; N-((2-(2,6-dioxopiperidin-3-yl)-1-oxoisoindolin-5-yl)methyl)-2-(quinolin-6-yl)acetamide; N-[2-(2,6-dioxo-piperidin-3-yl)-1-oxo-2,3-dihydro-1H-isoindol-5-ylmethyl]-benzamide; N-[2-(2,6-dioxo-piperidin-3-yl)-1-oxo-2,3-dihydro-1H-isoindol-5-ylmethyl]-4-ethoxy-benzamide; 4-tert-butyl-N-[2-(2,6-dioxo-piperidin-3-yl)-1-oxo-2,3-dihydro-1H-isoindol-5-ylmethyl]-benzamide; 1-(3,4-Di-chloro-phenyl)-3-[2-(2,6-dioxo-piperidin-3-yl)-1-oxo-2,3-dihydro-1H-isoindol-5-ylmethyl]-urea; 1-(3-chloro-4-(trifluoromethyl)phenyl)-3-((2-(2,6-dioxopiperidin-3-yl)-1-oxoisoindolin-5-yl)methyl)urea; 1-(3-chloro-4-methyl-phenyl)-3-[2-(3-methyl-2,6-dioxo-piperidin-3-yl)-1,3-dioxo-2,3-dihydro-1H-isoindol-5-ylmethyl]-urea; 1-(4-tert-butyl-phenyl)-3-[2-(2,6-dioxo-piperidin-3-yl)-1-oxo-2,3-dihydro-1H-isoindol-5-ylmethyl]-urea; 1-(2-chloro-phenyl)-3-[2-(2,6-dioxo-piperidin-3-yl)-1-oxo-2,3-dihydro-1H-isoindol-5-ylmethyl]-urea; 1-(3-chloro-phenyl)-3-[2-(2,6-dioxo-piperidin-3-yl)-1-oxo-2,3-dihydro-1H-isoindol-5-ylmethyl]-urea; 1-(4-chloro-3-trifluoromethyl-phenyl)-3-[2-(2,6-dioxo-piperidin-3-yl)-1-oxo-2,3-dihydro-1H-isoindol-5-ylmethyl]-urea; 1-[2-(2,6-dioxo-piperidin-3-yl)-1-oxo-2,3-dihydro-1H-isoindol-5-ylmethyl]-3-(4-trifluoromethylsulfanyl-phenyl)-urea; 1-[2-(2,6-dioxo-piperidin-3-yl)-1-oxo-2,3-dihydro-1H-isoindol-5-ylmethyl]-3-(4-methyl-3-trifluoromethyl-phenyl)-thiourea; 1-[2-(2,6-dioxo-piperidin-3-yl)-1-oxo-2,3-dihydro-1H-isoindol-5-ylmethyl]-3-(4-trifluoromethylsulfanyl-phenyl)-thiourea; 1-[2-(2,6-dioxo-piperidin-3-yl)-1-oxo-2,3-dihydro-1H-isoindol-5-ylmethyl]-3-(4-ethoxy-phenyl)-urea; 1-[2-(2,6-dioxo-piperidin-3-yl)-1-oxo-2,3-dihydro-1H-isoindol-5-ylmethyl]-3-(4-trifluoromethoxy-phenyl)-urea; 1-(3-chloro-4-methyl-phenyl)-3-[2-(2,6-dioxo-piperidin-3-yl)-1-oxo-2,3-dihydro-1H-isoindol-5-ylmethyl]-thiourea; 1-[2-(2,6-dioxo-piperidin-3-yl)-1-oxo-2,3-dihydro-1H-isoindol-5-ylmethyl]-3-(4-methoxy-phenyl)-urea; 1-[2-(2,6-dioxo-piperidin-3-yl)-1-oxo-2,3-dihydro-1H-isoindol-5-ylmethyl]-3-(4-fluoro-phenyl)-urea; 1-(3-chloro-4-fluoro-phenyl)-3-[2-(2,6-dioxo-piperidin-3-yl)-1-oxo-2,3-dihydro-1H-isoindol-5-ylmethyl]-urea; 1-(3,4-dimethyl-phenyl)-3-[2-(2,6-dioxo-piperidin-3-yl)-1-oxo-2,3-dihydro-1H-isoindol-5-ylmethyl]-urea; 1-(3,4-dimethoxy-phenyl)-3-[2-(2,6-dioxo-piperidin-3-yl)-1-oxo-2,3-dihydro-1H-isoindol-5-ylmethyl]-urea; 1-(4-chloro-2-methyl-phenyl)-3-[2-(2,6-dioxo-piperidin-3-yl)-1-oxo-2,3-dihydro-1H-isoindol-5-ylmethyl]-urea; 1-(3,5-dichloro-phenyl)-3-[2-(2,6-dioxo-piperidin-3-yl)-1-oxo-2,3-dihydro-1H-isoindol-5-ylmethyl]-urea; 1-[2-(2,6-dioxo-piperidin-3-yl)-1-oxo-2,3-dihydro-1H-isoindol-5-ylmethyl]-3-phenyl-urea; 1-(3,4-dimethoxy-phenyl)-3-[2-(2,6-dioxo-piperidin-3-yl)-1-oxo-2,3-dihydro-1H-isoindol-5-ylmethyl]-urea; 1-[2-(2,6-dioxo-piperidin-3-yl)-1-oxo-2,3-dihydro-1H-isoindol-5-ylmethyl]-3-naphthalen-1-yl-urea; 1-[2,5-dichloro-phenyl)-3-[2-(2,6-dioxo-piperidin-3-yl)-1-oxo-2,3-dihydro-1H-isoindol-5-ylmethyl]-urea; 1-[2-(2,6-dioxo-piperidin-3-yl)-1-oxo-2,3-dihydro-1H-isoindol-5-ylmethyl]-3-(4-methyl-3-trifluoromethyl-phenyl)-urea; 1-(5-chloro-2-methoxy-phenyl)-3-[2-(2,6-dioxo-piperidin-3-yl)-1-oxo-2,3-dihydro-1H-isoindol-5-ylmethyl]-urea; 1-(2-chloro-5-methyl-phenyl)-3-[2-(2,6-dioxo-piperidin-3-yl)-1-oxo-2,3-dihydro-1H-isoindol-5-ylmethyl]-urea; 1-(5-chloro-2-methyl-phenyl)-3-[2-(2,6-dioxo-piperidin-3-yl)-1-oxo-2,3-dihydro-1H-isoindol-5-ylmethyl]-urea; 1-[2-(2,6-dioxo-piperidin-3-yl)-1-oxo-2,3-dihydro-1H-isoindol-5-ylmethyl]-3-(2,4,6-trichloro-phenyl)-urea; 1-[2-(2,6-dioxo-piperidin-3-yl)-1-oxo-2,3-dihydro-1H-isoindol-5-ylmethyl]-3-p-tolyl-urea; 1-(4-bromo-phenyl)-3-[2-(2,6-dioxo-piperidin-3-yl)-1-oxo-2,3-dihydro-1H-isoindol-5-ylmethyl]-urea; 1-(4-cyano-phenyl)-3-[2-(2,6-dioxo-piperidin-3-yl)-1-oxo-2,3-dihydro-1H-isoindol-5-ylmethyl]-urea; 1-(2,4-dichloro-phenyl)-3-[2-(2,6-dioxo-piperidin-3-yl)-1-oxo-2,3-dihydro-1H-isoindol-5-ylmethyl]-urea; 1-[2-(2,6-dioxo-piperidin-3-yl)-1-oxo-2,3-dihydro-1H-isoindol-5-ylmethyl]-3-propyl-urea; 1-(3-chloro-2-methyl-phenyl)-3-[2-(2,6-dioxo-piperidin-3-yl)-1-oxo-2,3-dihydro-1H-isoindol-5-ylmethyl]-urea; 1-(2- chloro-5-trifluoromethyl-phenyl)-3-[2-(2,6-dioxopiperidin-3-yl)-1-oxo-2,3-dihydro-1H-isoindol-5-ylmethyl]-urea; 1-[2-(2,6-dioxo-piperidin-3-yl)-1-oxo-2,3-dihydro-1H-isoindol-5-ylmethyl]-3-(4-ethyl-phenyl)-urea; and 1-(3,5-dimethyl-phenyl)-3-[2-(2,6-dioxo-piperidin-3-yl)-1-oxo-2,3-dihydro-1H-isoindol-5-ylmethyl]-urea.

These compounds exhibited $IC_{50}$ values in the range of 0.0001 to 15 μM.

5.191 IL-2 Production Assay (I)

In one experiment, IL-2 production effect of certain compounds provided herein were tested according to the assay substantially similar to that described in 5.188.2, above.

Tested compounds included the following: hexanoic acid [2-[(3S)-3-methyl-2,6-dioxo-piperidin-3-yl]-1,3-dioxo-2,3-dihydro-1H-isoindol-5-ylmethyl]-amide; 4-chloro-N-[2-[(3S)-3-methyl-2,6-dioxo-piperidin-3-yl]-1,3-dioxo-2,3-dihydro-1H-isoindol-5-ylmethyl]-benzamide; {2-[(3S)-3-Methyl-2,6-dioxo-piperidin-3-yl]-1,3-dioxo-2,3-dihydro-1H-isoindol-5-ylmethyl}-carbamic acid hexyl ester; N-[2-[(3S)-3-methyl-2,6-dioxo-piperidin-3-yl]-1,3-dioxo-2,3-dihydro-1H-isoindol-5-ylmethyl]-4-trifluoromethoxy-benzamide; furan-2-carboxylic acid [2-(2,6-dioxo-piperidin-3-yl)-1-oxo-2,3-dihydro-1H-isoindol-5-ylmethyl]amide; pyridine-2-carboxylic acid [2-[(3S)-3-methyl-2,6-dioxo-piperidin-3-yl]-1,3-dioxo-2,3-dihydro-1H-isoindol-5-ylmethyl]-amide; N-[2-[(3S)-3-methyl-2,6-dioxo-piperidin-3-yl]-1,3-dioxo-2,3-dihydro-1H-isoindol-5-ylmethyl]-4-trifluoromethyl-benzamide; N-[2-[(3S)-3-methyl-2,6-dioxo-piperidin-3-yl]-1,3-dioxo-2,3-dihydro-1H-isoindol-5-ylmethyl]-isonicotinamide; 4-fluoro-N-[2-[(3S)-3-methyl-2,6-dioxo-piperidin-3-yl]-1,3-dioxo-2,3-dihydro-1H-isoindol-5-ylmethyl]-benzamide; N-[2-(3S)-(3-methyl-2,6-dioxo-piperidin-3-yl)-1,3-dioxo-2,3-dihydro-1H-isoindol-5-ylmethyl]-6-trifluoromethyl nicotinamide; 3,4-dichloro-N-[2-[(3S)-3-methyl-2,6-dioxo-piperidin-3-yl]-1,3-dioxo-2,3-dihydro-1H-isoindol-5-ylmethyl]-benzamide; thiophene-2-carboxylic acid [2-[(3S)-3-methyl-2,6-dioxo-piperidin-3-yl]-1,3-dioxo-2,3-dihydro-1H-isoindol-5-ylmethyl]-amide; isoquinoline-3-carboxylic acid p-[(3S)-3-methyl-2,6-dioxo-piperidin-3-yl]-1,3-dioxo-2,3-dihydro-1H-isoindol-5-ylmethyl]-amide; 5-bromo-N-[[2-[(3S)-3-methyl-2,6-dioxopiperidin-3-yl]-1,3-dioxoisoindolin-5-yl]methyl]picolinamide; N-[[2-[(3S)-3-methyl-2,6-dioxopiperidin-3-yl]-1,3-dioxoisoindolin-5-yl]methyl]-4-(methylsulfonyl)benzamide; 4-ethyl-N-[[2-[(3S)-3-methyl-2,6-dioxopiperidin-3-yl]-1,3-dioxoisoindolin-5-yl]methyl]benzamide; N-[[2-[(3S)-3-methyl-2,6-dioxopiperidin-3-yl]-1,3-dioxoisoindolin-5-yl]methyl]-4-(trifluoromethylthio)benzamide; 4-ethylsulfanyl-N-[p-[(3S)-3-methyl-2,6-dioxopiperidin-3-yl]-1,3-dioxo-2,3-dihydro-1H-isoindol-5-ylmethyl]-benzamide; 4-ethoxy-N-[[2-[(3S)-3-methyl-2,6-dioxopiperidin-3-yl]-1,3-dioxo-2,3-dihydro-1H-isoindol-5-ylmethyl]-benzamide; 1-[2-(2,6-dioxo-piperidin-3-yl)-1,3-dioxo-2,3-dihydro-1H-isoindol-5-ylmethyl]-3-(4-trifluoromethoxy-phenyl)-urea; 1-(4-cyano-phenyl)-3-[2-(2,6-dioxo-piperidin-3-yl)-1,3-dioxo-2,3-dihydro-1H-isoindol-5-ylmethyl]-urea; 1-(4-chloro-phenyl)-3-[2-(3S)-(3-methyl-2,6-dioxo-piperidin-3-yl)-1,3-dioxo-2,3-dihydro-1H-isoindol-5-ylmethyl]-urea; 1-hexyl-3-[2-[(3S)-3-methyl-2,6-dioxo-piperidin-3-yl]-1,3-dioxo-2,3-dihydro-1H-isoindol-5-ylmethyl]-urea; and 1-[2-[(3S)-3-methyl-2,6-dioxo-piperidin-3-yl]-1,3-dioxo-2,3-dihydro-1H-isoindol-5-ylmethyl]-3-(4-trifluoromethoxy-phenyl)-urea.

These compounds exhibited $EC_{50}$ values in the range of 0.015 to 3 μM.

5.192 IL-2 Production Assay (II)

In another experiment, IL-2 production effect of certain compounds provided herein were tested according to the assay substantially similar to that described in 5.188.2, above.

Tested compounds included the following: furan-2-carboxylic acid [2-(2,6-dioxo-piperidin-3-yl)-1,3-dioxo-2,3-dihydro-1H-isoindol-5-ylmethyl]-amide; N-[2-(3-methyl-2,6-dioxo-piperidin-3-yl)-1-oxo-2,3-dihydro-1H-isoindol-5-ylmethyl]-4-trifluoromethoxy-benzamide; 5-ethanesulfonyl-pyridine-2-carboxylic acid [2-(3-methyl-2,6-dioxo-piperidin-3-yl)-1,3-dioxo-2,3-dihydro-1H-isoindol-5-ylmethyl]-amide; N-[2-(3-methyl-2,6-dioxo-piperidin-3-yl)-1,3-dioxo-2,3-dihydro-1H-isoindol-5-ylmethyl]-4-methylsulfanyl-benzamide; 5-methylsulfanyl-pyridine-2-carboxylic acid [2-(3-methyl-2,6-dioxo-piperidin-3-yl)-1,3-dioxo-2,3-dihydro-1H-isoindol-5-ylmethyl]-amide; 5-ethoxy-pyridine-2-carboxylic acid[2-(3-methyl-2,6-dioxo-piperidin-3-yl)-1,3-dioxo-2,3-dihydro-1H-isoindol-5-ylmethyl]-amide; 6-ethoxy-N-[2-(3-methyl-2,6-dioxo-piperidin-3-yl)-1,3-dioxo-2,3-dihydro-1H-isoindol-5-ylmethyl]-nicotinamide; 4-ethanesulfonyl-N-[2-(3-methyl-2,6-dioxo-piperidin-3-yl)-1,3-dioxo-2,3-dihydro-1H-isoindol-5-ylmethyl]-benzamide; 6-ethoxy-pyridazine-3-carboxylic acid [2-(3-methyl-2,6-dioxo-piperidin-3-yl)-1,3-dioxo-2,3-dihydro-1H-isoindol-5-ylmethyl]-amide; 6-ethylsulfanyl-pyridazine-3-carboxylic acid [2-(3-methyl-2,6-dioxo-piperidin-3-yl)-1,3-dioxo-2,3-dihydro-1H-isoindol-5-ylmethyl]amide; N-[2-(2,6-dioxo-piperidin-3-yl)-1-oxo-2,3-dihydro-1H-isoindol-5-ylmethyl]-2-(4-trifluoromethylsulfanyl-phenyl)-acetamide; N-[2-(2,6-dioxo-piperidin-3-yl)-1-oxo-2,3-dihydro-1H-isoindol-5-ylmethyl]-2-(4-trifluoromethyl-phenyl)-acetamide; 4-chloro-N-[2-(2,6-dioxo-piperidin-3-yl)-1-oxo-2,3-dihydro-1H-isoindol-5-ylmethyl]-benzamide; N-[2-(2,6-dioxo-piperidin-3-yl)-1-oxo-2,3-dihydro-1H-isoindol-5-ylmethyl]-4-fluoro-benzamide; 3-chloro-N-[2-(2,6-dioxo-piperidin-3yl)-1-oxo-2,3-dihydro-1H-isoindol-5-ylmethyl]-benzamide; N-[2-(2,6-dioxo-piperidin-3-yl)-1-oxo-2,3-dihydro-1H-isoindol-5-ylmethyl]-4-methanesulfonyl-benzamide; N-[2-(2,6-dioxo-piperidin-3-yl)-1-oxo-2,3-dihydro-1H-isoindol-5-ylmethyl]-4-ethanesulfonyl-benzamide; N-((2-(2,6-dioxopiperidin-3-yl)-1-oxoisoindolin-5-yl)methyl)-2-(quinolin-6-yl)acetamide; N-[2-(2,6-dioxo-piperidin-3-yl)-1-oxo-2,3-dihydro-1H-isoindol-5-ylmethyl]-benzamide; N-[2-(2,6-dioxo-piperidin-3-yl)-1-oxo-2,3-dihydro-1H-isoindol-5-ylmethyl]-4-ethoxy-benzamide; 1-[2-(2,6-dioxo-piperidin-3-yl)-1,3-dioxo-2,3-dihydro-1H-isoindol-5-ylmethyl]-3-propyl-urea; and 1-tert-butyl-3-[2-(2,6-dioxo-piperidin-3-yl)-1-oxo-2,3-dihydro-1H-isoindol-5-ylmethyl]-urea.

These compounds exhibited $EC_{50}$ values in the range of 0.003 to 5 μM.

5.192 Anti-Proliferative Activity Against Prostate Tumor (I)

In one experiment, anti-proliferative effect of certain compounds provided herein were tested using PC3 cells (prostate tumor) according to the cell proliferation assay substantially similar to that described in 5.188.8, above.

Tested compounds included the following: 3,4-dichloro-N-[2-(2,6-dioxo-piperidin-3-yl)-1-oxo-2,3-dihydro-1H- isoindol-5-ylmethyl]-benzamide; 2-(4-chloro-phenyl)-N-[2-(2,6-dioxo-piperidin-3-yl)-1-oxo-2,3-dihydro-1H-isoindol-5-ylmethyl]-acetamide; N-[[2-(2,6-dioxopiperidin-3-yl)-1-oxoisoindolin-5-yl]methyl]-4-(trifluoromethylthio)benzamide; 1-(3,4-dichloro-phenyl)-3-[2-(2,6-dioxo-piperidin-3-yl)-1,3-dioxo-2,3-dihydro-1H-isoindol-5-ylmethyl]-urea; 1-(3,4-dimethyl-phenyl)-3-[2-(2,6-dioxo-piperidin-3-yl)-1,3-dioxo-2,3-dihydro-1H-isoindol-5-ylmethyl]-urea; 1-(4-chloro-phenyl)-3-[2-(2,6-dioxo-piperidin-3-yl)-1,3-dioxo-2,3-dihydro-1H-isoindol-5-ylmethyl]-urea; 1-(3-chloro-4-methyl-phenyl)-3-[2-(2,6-dioxo-piperidin-3-yl)-1-oxo-2,3-dihydro-1H-isoindol-5-ylmethyl]-urea; 1-(4-chloro-phenyl)-3-[2-(2,6-dioxo-piperidin-3-yl)-1-oxo-2,3-dihydro-1H-isoindol-5-ylmethyl]-urea; 1-[2-(2,6-dioxo-piperidin-3-yl)-1-oxo-2,3-dihydro-1H-isoindol-5-ylmethyl]-3-hexyl-urea; 1-(4-tert-butyl-phenyl)-3-[2-(2,6-dioxo-piperidin-3-yl)-1,3-dioxo-2,3-dihydro-1H-isoindol-5-ylmethyl]-urea; 1-(4-chloro-phenyl)-3-[2-(2,6-dioxo-piperidin-3-yl)-1,3-dioxo-2,3-dihydro-1H-isoindol-5-ylmethyl]-thiourea; 1-(4-chloro-3-methyl-phenyl)-3-[2-(2,6-dioxo-piperidin-3-yl)-1,3-dioxo-2,3-dihydro-1H-isoindol-5-ylmethyl]-urea; and 1-[2-(2,6-dioxo-piperidin-3-yl)-1,3-dioxo-2,3-dihydro-1H-isoindol-5-ylmethyl]-3-m-tolyl-urea.

These compounds exhibited $IC_{50}$ values in the range of 0.006-11 µM.

5.193 Anti-Proliferative Activity Against Prostate Tumor (II)

In another experiment, anti-proliferative effect of certain compounds provided herein were tested using PC3 cells (prostate tumor) according to the cell proliferation assay substantially similar to that described in 5.188.8, above.

Tested compounds included the following: N-[2-(2,6-dioxo-piperidin-3-yl)-1-oxo-2,3-dihydro-1H-isoindol-5-yl-methyl]-2-(4-trifluoromethylsulfanyl-phenyl)-acetamide; 3-chloro-N-[2-(2,6-dioxo-piperidin-3-yl)-1-oxo-2,3-dihydro-1H-isoindol-5-ylmethyl]-4-methyl-benzamide; 2-(3,4-dichloro-phenyl)-N-[2-(2,6-dioxo-piperidin-3-yl)-1-oxo-2,3-dihydro-1H-isoindol-5-ylmethyl]-acetamide; N-[2-(2,6-dioxo-piperidin-3-yl)-1-oxo-2,3-dihydro-1H-isoindol-5-ylmethyl]-4-ethylsulfanyl-benzamide; 4-tert-butyl-N-[2-(2,6-dioxo-piperidin-3-yl)-1-oxo-2,3-dihydro-1H-isoindol-5-ylmethyl]-benzamide; 1-(3,4-dichloro-phenyl)-3-[2-(2,6-dioxo-piperidin-3-yl)-1-oxo-2,3-dihydro-1H-isoindol-5-ylmethyl]-urea; 1-(3-chloro-4-(trifluoromethyl)phenyl)-3-((2-(2,6-dioxopiperidin-3-yl)-1-oxoisoindolin-5-yl)methyl)urea; 1-(4-tert-butyl-phenyl)-3-[2-(2,6-dioxo-piperidin-3-yl)-1-oxo-2,3-dihydro-1H-isoindol-5-ylmethyl]-urea; 1-(2-chloro-phenyl)-3-[2-(2,6-dioxo-piperidin-3-yl)-1-oxo-2,3-dihydro-1H-isoindol-5-ylmethyl]-urea; 1-(3-chloro-phenyl)-3-[2-(2,6-dioxo-piperidin-3-yl)-1-oxo-2,3-dihydro-1H-isoindol-5-ylmethyl]-urea; 1-(4-chloro-3-trifluoromethyl-phenyl)-3-[2-(2,6-dioxo-piperidin-3-yl)-1-oxo-2,3-dihydro-1H-isoindol-5-ylmethyl]-urea; 1-[2-(2,6-dioxo-piperidin-3-yl)-1-oxo-2,3-dihydro-1H-isoindol-5-ylmethyl]-3-(4-trifluoromethylsulfanyl-phenyl)-urea; 1-[2-(2,6-dioxo-piperidin-3-yl)-1-oxo-2,3-dihydro-1H-isoindol-5-ylmethyl]-3-(4-methyl-3-trifluoromethyl-phenyl)-thiourea; 1-[2-(2,6-dioxo-piperidin-3-yl)-1-oxo-2,3-dihydro-1H-isoindol-5-ylmethyl]-3-(4-trifluoromethylsulfanyl-phenyl)-thiourea; 1-[2-(2,6-dioxo-piperidin-3-yl)-1-oxo-2,3-dihydro-1H-isoindol-5-ylmethyl]-3-(4-trifluoromethoxy-phenyl)-urea; 1-(3-chloro-4-methyl-phenyl)-3-[2-(2,6-dioxo-piperidin-3-yl)-1-oxo-2,3-dihydro-1H-isoindol-5-ylmethyl]-thiourea; 1-[2-(2,6-dioxo-piperidin-3-yl)-1-oxo-2,3-dihydro-1H-isoindol-5-ylmethyl]-3-(4-methoxy-phenyl)-urea; 1-[2-(2,6-dioxo-piperidin-3-yl)-1-oxo-2,3-dihydro-1H-isoindol-5-ylmethyl]-3-(4-fluoro-phenyl)-urea; 1-(3-chloro-4-fluoro-phenyl)-3-[2-(2,6-dioxo-piperidin-3-yl)-1-oxo-2,3-dihydro-1H-isoindol-5-ylmethyl]-urea; 1-(3,4-dimethyl-phenyl)-3-[2-(2,6-dioxo-piperidin-3-yl)-1-oxo-2,3-dihydro-1H-isoindol-5-ylmethyl]-urea; 1-(3,5-dichloro-phenyl)-3-[2-(2,6-dioxo-piperidin-3-yl)-1-oxo-2,3-dihydro-1H-isoindol-5-ylmethyl]-urea; 1-[2-(2,6-dioxo-piperidin-3-yl)-1-oxo-2,3-dihydro-1H-isoindol-5-ylmethyl]-3-phenyl-urea; 1-(4-chloro-2-methyl-phenyl)-3-[2-(2,6-dioxo-piperidin-3-yl)-1-oxo-2,3-dihydro-1H-isoindol-5-ylmethyl]-urea; 1-(3,4-dimethoxy-phenyl)-3-[2-(2,6-dioxo-piperidin-3-yl)-1-oxo-2,3-dihydro-1H-isoindol-5-ylmethyl]-urea; 1-[2-(2,6-dioxo-piperidin-3-yl)-1-oxo-2,3-dihydro-1H-isoindol-5-ylmethyl]-3-naphthalen-1-yl-urea; 1-(2,5-dichloro-phenyl)-3-[2-(2,6-dioxo-piperidin-3-yl)-1-oxo-2,3-dihydro-1H-isoindol-5-ylmethyl]-urea; 1-[2-(2,6-dioxo-piperidin-3-yl)-1-oxo-2,3-dihydro-1H-isoindol-5-ylmethyl]-3-(4-methyl-3-trifluoromethyl-phenyl)-urea; 1-(5-chloro-2-methoxy-phenyl)-3-[2-(2,6-dioxo-piperidin-3-yl)-1-oxo-2,3-dihydro-1H-isoindol-5-ylmethyl]-urea; 1-(2-chloro-5-methyl-phenyl)-3-[2-(2,6-dioxo-piperidin-3-yl)-1-oxo-2,3-dihydro-1H-isoindol-5-ylmethyl]-urea; 1-(5-chloro-2-methyl-phenyl)-3-[2-(2,6-dioxo-piperidin-3-yl)-1-oxo-2,3-dihydro-1H-isoindol-5-ylmethyl]-urea; 1-[2-(2,6-dioxo-piperidin-3-yl)-1-oxo-2,3-dihydro-1H-isoindol-5-ylmethyl]-3-(2,4,6-trichloro-phenyl)-urea; 1-[2-(2,6-dioxo-piperidin-3-yl)-1-oxo-2,3-dihydro-1H-isoindol-5-ylmethyl]-3-p-tolyl-urea; 1-(4-bromo-phenyl)-3-[2-(2,6-dioxo-piperidin-3-yl)-1-oxo-2,3-dihydro-1H-isoindol-5-ylmethyl]-urea; 1-(2,4-dichloro-phenyl)-3-[2-(2,6-dioxo-piperidin-3-yl)-1-oxo-2,3-dihydro-1H-isoindol-5-ylmethyl]-urea; 1-(3-chloro-2-methyl-phenyl)-3-[2-(2,6-dioxo-piperidin-3-yl)-1-oxo-2,3-dihydro-1H-isoindol-5-ylmethyl]-urea; 1-(2-chloro-5-trifluoromethyl-phenyl)-3-[2-(2,6-dioxopiperidin-3-yl)-1-oxo-2,3-dihydro-1H-isoindol-5-ylmethyl]-urea; 1-[2-(2,6-dioxo-piperidin-3-yl)-1-oxo-2,3-dihydro-1H-isoindol-5-ylmethyl]-3-(4-ethyl-phenyl)-urea; and 1-(3,5-dimethyl-phenyl)-3-[2-(2,6-dioxo-piperidin-3-yl)-1-oxo-2,3-dihydro-1H-isoindol-5-ylmethyl]-urea.

These compounds exhibited $IC_{50}$ values in the range of 0.005-3 µM.

5.194 Anti-Proliferative Activity Against Colon Tumor (I)

In one experiment, anti-proliferative effect of certain compounds provided herein were tested using Colo 205 cells (colon tumor) according to the cell proliferation assay substantially similar to that described in 5.188.8, above.

Tested compounds included the following: N-[2-(2,6-dioxo-piperidin-3-yl)-1-oxo-2,3-dihydro-1H-isoindol-5-yl-methyl]-4-trifluoromethoxy-benzamide; 3,4-dichloro-N-[2-(2,6-dioxo-piperidin-3-yl)-1-oxo-2,3-dihydro-1H-isoindol-5-ylmethyl]-benzamide; 2-(4-chloro-phenyl)-N-[2-(2,6-dioxo-piperidin-3-yl)-1-oxo-2,3-dihydro-1H-isoindol-5-ylmethyl]-acetamide; N-[[2-(2,6-dioxopiperidin-3-yl)-1-oxoisoindolin-5-yl]methyl]-4-(trifluoromethylthio)benzamide; 4-tert-butyl-N-((2-(2,6-dioxopiperidin-3-yl)-1,3-dioxoisoindolin-5-yl)methyl)benzamide; 1-(3,4-dichloro-phenyl)-3-[2-(2,6-dioxo-piperidin-3-yl)-1,3-dioxo-2,3-dihydro-1H-isoindol-5-ylmethyl]-urea; 1-(3,4-dimethyl-phenyl)-3-[2-(2,6-dioxo-piperidin-3-yl)-1,3-dioxo-2,3-dihydro-1H-isoindol-5-ylmethyl]-urea; 1-(4-chloro-phenyl)-3-[2-(2,6-dioxo-piperidin-3-yl)-1,3-dioxo-2,3- dihydro-1H-isoindol-5-ylmethyl]-urea; 1-(3-chloro-4-methyl-phenyl)-3-[2-(2,6-dioxo-piperidin-3-yl)-1-oxo-2,3-dihydro-1H-isoindol-5-ylmethyl]-urea; 1-(4-chloro-phenyl)-3-[2-(2,6-dioxo-piperidin-3-yl)-1-oxo-2,3-dihydro-1H-isoindol-5-ylmethyl]-urea; 1-[2-(2,6-dioxo-piperidin-3-yl)-1-oxo-2,3-dihydro-1H-isoindol-5-ylmethyl]-3-hexyl-urea; 1-(4-tert-butyl-phenyl)-3-[2-(2,6-dioxo-piperidin-3-yl)-1,3-dioxo-2,3-dihydro-1H-isoindol-5-ylmethyl]-urea; 1-[2-(2,6-dioxo-piperidin-3-yl)-1,3-dioxo-2,3-dihydro-1H-isoindol-5-ylmethyl]-3-(4-trifluoromethoxy-phenyl)-urea; 1-(4-chloro-phenyl)-3-[(2-(2,6-dioxo-piperidin-3-yl)-1,3-dioxo-2,3-dihydro-1H-isoindol-5-ylmethyl]-thiourea; 1-(4-chloro-3-methyl-phenyl)-3-[2-(2,6-dioxo-piperidin-3-yl)-1,3-dioxo-2,3-dihydro-1H-isoindol-5-ylmethyl]-urea; and 1-[2-(2,6-dioxo-piperidin-3-yl)-1,3-dioxo-2,3-dihydro-1H-isoindol-5-ylmethyl]-3-m-tolyl-urea.

These compounds exhibited $IC_{50}$ values in the range of 0.003 to 3.5 µM.

5.195 Anti-Proliferative Activity Against Colon Tumor (II)

In another experiment, anti-proliferative effect of certain compounds provided herein were tested using Colo 205 cells (colon tumor) according to the cell proliferation assay substantially similar to that described in 5.188.8, above.

Tested compounds included the following: N-[2-(2,6-dioxo-piperidin-3-yl)-1-oxo-2,3-dihydro-1H-isoindol-5-ylmethyl]-2-(4-trifluoromethylsulfanyl-phenyl)-acetamide; N-[2-(2,6-dioxo-piperidin-3-yl)-1-oxo-2,3-dihydro-1H-isoindol-5-ylmethyl]-2-(4-trifluoromethyl-phenyl)-acetamide; 3-chloro-N-[2-(2,6-dioxo-piperidin-3-yl)-1-oxo-2,3-dihydro-1H-isoindol-5-ylmethyl]-4-methyl-benzamide; 2-(3,4-dichloro-phenyl)-N-[2-(2,6-dioxo-piperidin-3-yl)-1-oxo-2,3-dihydro-1H-isoindol-5-ylmethyl]-acetamide; N-[2-(2,6-dioxo-piperidin-3-yl)-1-oxo-2,3-dihydro-1H-isoindol-5-ylmethyl]-4-ethylsulfanyl-benzamide; 4-tert-butyl-N-[2-(2,6-dioxo-piperidin-3-yl)-1-oxo-2,3-dihydro-1H-isoindol-5-ylmethyl]-benzamide; 1-(3,4-dichloro-phenyl)-3-[2-(2,6-dioxo-piperidin-3-yl)-1-oxo-2,3-dihydro-1H-isoindol-5-ylmethyl]-urea; 1-(3-chloro-4-(trifluoromethyl)phenyl)-3-((2-(2,6-dioxopiperidin-3-yl)-1-oxoisoindolin-5-yl)methyl)urea; 1-(3-chloro-4-methyl-phenyl)-3-[2-(3-methyl-2,6-dioxo-piperidin-3-yl)-1,3-dioxo-2,3-dihydro-1H-isoindol-5-ylmethyl]-urea; 1-(4-tert-butyl-phenyl)-3-[2-(2,6-dioxo-piperidin-3-yl)-1-oxo-2,3-dihydro-1H-isoindol-5-ylmethyl]-urea; 1-(2-chloro-phenyl)-3-[2-(2,6-dioxo-piperidin-3-yl)-1-oxo-2,3-dihydro-1H-isoindol-5-ylmethyl]-urea; 1-(3-chloro-phenyl)-3-[2-(2,6-dioxo-piperidin-3-yl)-1-oxo-2,3-dihydro-1H-isoindol-5-ylmethyl]-urea; 1-(4-chloro-3-trifluoromethyl-phenyl)-3-[2-(2,6-dioxo-piperidin-3-yl)-1-oxo-2,3-dihydro-1H-isoindol-5-ylmethyl]-urea; 1-[2-(2,6-dioxo-piperidin-3-yl)-1-oxo-2,3-dihydro-1H-isoindol-5-ylmethyl]-3-(4-trifluoromethylsulfanyl-phenyl)-urea; 1-[2-(2,6-dioxo-piperidin-3-yl)-1-oxo-2,3-dihydro-1H-isoindol-5-ylmethyl]-3-(4-methyl-3-trifluoromethyl-phenyl)-thiourea; 1-[2-(2,6-dioxo-piperidin-3-yl)-1-oxo-2,3-dihydro-1H-isoindol-5-ylmethyl]-3-(4-trifluoromethylsulfanyl-phenyl)-thiourea; 1-[2-(2,6-dioxo-piperidin-3-yl)-1-oxo-2,3-dihydro-1H-isoindol-5-ylmethyl]-3-(4-ethoxy-phenyl)-urea; 1-[2-(2,6-dioxo-piperidin-3-yl)-1-oxo-2,3-dihydro-1H-isoindol-5-ylmethyl]-3-(4-trifluoromethoxy-phenyl)-urea; 1-(3-chloro-4-methyl-phenyl)-3-[2-(2,6-dioxo-piperidin-3-yl)-1-oxo-2,3-dihydro-1H-isoindol-5-ylmethyl]-thiourea; 1-[2-(2,6-dioxo-piperidin-3-yl)-1-oxo-2,3-dihydro-1H-isoindol-5-ylmethyl]-3-(4-methoxy-phenyl)-urea; 1-[2-(2,6-dioxo-piperidin-3-yl)-1-oxo-2,3-dihydro-1H-isoindol-5-ylmethyl]-3-(4-fluoro-phenyl)-urea; 1-(3-chloro-4-fluoro-phenyl)-3-[2-(2,6-dioxo-piperidin-3-yl)-1-oxo-2,3-dihydro-1H-isoindol-5-ylmethyl]-urea; 1-(3,4-dimethyl-phenyl)-3-[2-(2,6-dioxo-piperidin-3-yl)-1-oxo-2,3-dihydro-1H-isoindol-5-ylmethyl]-urea; 1-(3,5-dichloro-phenyl)-3-[2-(2,6-dioxo-piperidin-3-yl)-1-oxo-2,3-dihydro-1H-isoindol-5-ylmethyl]-urea; 1-[2-(2,6-dioxo-piperidin-3-yl)-1-oxo-2,3-dihydro-1H-isoindol-5-ylmethyl]-3-phenyl-urea; 1-(4-chloro-2-methyl-phenyl)-3-[2-(2,6-dioxo-piperidin-3-yl)-1-oxo-2,3-dihydro-1H-isoindol-5-ylmethyl]-urea; N-[2-(2,6-dioxo-piperidin-3-yl)-1-oxo-2,3-dihydro-1H-isoindol-5-ylmethyl]-4-ethoxy-benzamide; 1-(3,4-dimethoxy-phenyl)-3-[2-(2,6-dioxo-piperidin-3-yl)-1-oxo-2,3-dihydro-1H-isoindol-5-ylmethyl]-urea; 1-(2-Chloro-6-methyl-phenyl)-3-[2-(2,6-dioxo-piperidin-3-yl)-1-oxo-2,3-dihydro-1H-isoindol-5-ylmethyl]-urea; 1-[2-(2,6-dioxo-piperidin-3-yl)-1-oxo-2,3-dihydro-1H-isoindol-5-ylmethyl]-3-naphthalen-1-yl-urea; 1-(2,5-dichloro-phenyl)-3-[2-(2,6-dioxo-piperidin-3-yl)-1-oxo-2,3-dihydro-1H-isoindol-5-ylmethyl]-urea; 1-[2-(2,6-dioxo-piperidin-3-yl)-1-oxo-2,3-dihydro-1H-isoindol-5-ylmethyl]-3-(4-methyl-3-trifluoromethyl-phenyl)-urea; 1-(5-chloro-2-methoxy-phenyl)-3-[2-(2,6-dioxo-piperidin-3-yl)-1-oxo-2,3-dihydro-1H-isoindol-5-ylmethyl]-urea; 1-(2-chloro-5-methyl-phenyl)-3-[2-(2,6-dioxo-piperidin-3-yl)-1-oxo-2,3-dihydro-1H-isoindol-5-ylmethyl]-urea; 1-(5-chloro-2-methyl-phenyl)-3-[2-(2,6-dioxo-piperidin-3-yl)-1-oxo-2,3-dihydro-1H-isoindol-5-ylmethyl]-urea; 1-[2-(2,6-dioxo-piperidin-3-yl)-1-oxo-2,3-dihydro-1H-isoindol-5-ylmethyl]-3-(2,4,6-trichloro-phenyl)-urea; 1-(2,6-dichloro-phenyl)-3-[2-(2,6-dioxo-piperidin-3-yl)-1-oxo-2,3-dihydro-1H-isoindol-5-ylmethyl]-urea; 1-[2-(2,6-dioxo-piperidin-3-yl)-1-oxo-2,3-dihydro-1H-isoindol-5-ylmethyl]-3-p-tolyl-urea; 1-(4-bromo-phenyl)-3-[2-(2,6-dioxo-piperidin-3-yl)-1-oxo-2,3-dihydro-1H-isoindol-5-ylmethyl]-urea; 1-(2,4-dichloro-phenyl)-3-[2-(2,6-dioxo-piperidin-3-yl)-1-oxo-2,3-dihydro-1H-isoindol-5-ylmethyl]-urea; 1-(3-chloro-2-methyl-phenyl)-3-[2-(2,6-dioxo-piperidin-3-yl)-1-oxo-2,3-dihydro-1H-isoindol-5-ylmethyl]-urea; 1-(2-chloro-5-trifluoromethyl-phenyl)-3-[2-(2,6-dioxopiperidin-3-yl)-1-oxo-2,3-dihydro-1H-isoindol-5-ylmethyl]-urea; 1-[2-(2,6-dioxo-piperidin-3-yl)-1-oxo-2,3-dihydro-1H-isoindol-5-ylmethyl]-3-(4-ethyl-phenyl)-urea; and 1-(3,5-dimethyl-phenyl)-3-[2-(2,6-dioxo-piperidin-3-yl)-1-oxo-2,3-dihydro-1H-isoindol-5-ylmethyl]-urea.

These compounds exhibited $IC_{50}$ values in the range of 0.001 to 2.5 µM.

5.196 Anti-Proliferative Activity Against Pancreatic Tumor (I)

In one experiment, anti-proliferative effect of certain compounds provided herein were tested using BxPC3 cells (pancreatic tumor) according to the cell proliferation assay substantially similar to that described in 5.188.8, above.

Tested compounds included the following: 3,4-dichloro-N-[2-(2,6-dioxo-piperidin-3-yl)-1-oxo-2,3-dihydro-1H-isoindol-5-ylmethyl]-benzamide; 2-(4-chloro-phenyl)-N-[2-(2,6-dioxo-piperidin-3-yl)-1-oxo-2,3-dihydro-1H-isoindol-5-ylmethyl]-acetamide; N-[[2-(2,6-dioxopiperidin-3-yl)-1-oxoisoindolin-5-yl]methyl]-4-(trifluoromethylthio)benzamide; 1-(3,4-dichloro-phenyl)-3-[2-(2,6-dioxo-piperidin-3-yl)-1,3-dioxo-2,3-dihydro-1H-isoindol-5-ylmethyl]-urea; 1-(3,4-dimethyl-phenyl)-3-[2-(2,6-dioxo-piperidin-3-yl)-1,3-dioxo-2,3-dihydro-1H-isoindol-5-ylmethyl]-urea; 1-(4-chloro-phenyl)-3-[2-(2,6-dioxo-piperidin-3-yl)-1,3-dioxo-2,3-dihydro-1H-isoindol-5-ylmethyl]-urea; 1-(3-chloro-4-methyl-phenyl)-3-[2-(2,6-dioxo-piperidin-3-yl)-1-oxo-2,3-dihydro-1H-isoindol-5-ylmethyl]-urea; 1-(4-chloro-phenyl)-3-[2-(2,6-dioxo-piperidin-3-yl)-1-oxo-2,3-dihydro-1H-isoindol-5- ylmethyl]-urea; 1-[2-(2,6-dioxo-piperidin-3-yl)-1-oxo-2,3-dihydro-1H-isoindol-5-ylmethyl]-3-hexyl-urea; 1-(4-tert-butyl-phenyl)-3-[2-(2,6-dioxo-piperidin-3-yl)-1,3-dioxo-2,3-dihydro-1H-isoindol-5-ylmethyl]-urea; 1-(4-chloro-3-methyl-phenyl)-3-[2-(2,6-dioxo-piperidin-3-yl)-1,3-dioxo-2,3-dihydro-1H-isoindol-5-ylmethyl]-urea; and 1-[2-(2,6-dioxo-piperidin-3-yl)-1,3-dioxo-2,3-dihydro-1H-isoindol-5-ylmethyl]-3-m-tolyl-urea.

These compounds exhibited $IC_{50}$ values in the range of 0.01 to 10 µM.

5.197 Anti-Proliferative Activity Against Pancreatic Tumor (II)

In another experiment, anti-proliferative effect of certain compounds provided herein were tested using BxPC3 cells (pancreatic tumor) according to the cell proliferation assay substantially similar to that described in 5.188.8, above.

Tested compounds included the following: 3-chloro-N-[2-(2,6-dioxo-piperidin-3-yl)-1-oxo-2,3-dihydro-1H-isoindol-5-ylmethyl]-4-methyl-benzamide; 2-(3,4-dichloro-phenyl)-N-[2-(2,6-dioxo-piperidin-3-yl)-1-oxo-2,3-dihydro-1H-isoindol-5-ylmethyl]-acetamide; N-[2-(2,6-dioxo-piperidin-3-yl)-1-oxo-2,3-dihydro-1H-isoindol-5-ylmethyl]-4-ethylsulfanyl-benzamide; 4-tert-butyl-N-[2-(2,6-dioxo-piperidin-3-yl)-1-oxo-2,3-dihydro-1H-isoindol-5-ylmethyl]-benzamide; 1-(3,4-dichloro-phenyl)-3-[2-(2,6-dioxo-piperidin-3-yl)-1-oxo-2,3-dihydro-1H-isoindol-5-ylmethyl]-urea; 1-(3-chloro-4-(trifluoromethyl)phenyl)-3-((2-(2,6-dioxopiperidin-3-yl)-1-oxoisoindolin-5-yl)methyl)urea; 1-(4-tert-butyl-phenyl)-3-[2-(2,6-dioxo-piperidin-3-yl)-1-oxo-2,3-dihydro-1H-isoindol-5-ylmethyl]-urea; 1-(2-chloro-phenyl)-3-[2-(2,6-dioxo-piperidin-3-yl)-1-oxo-2,3-dihydro-1H-isoindol-5-ylmethyl]-urea; 1-(3-chloro-phenyl)-3-[2-(2,6-dioxo-piperidin-3-yl)-1-oxo-2,3-dihydro-1H-isoindol-5-ylmethyl]-urea; 1-(4-chloro-3-trifluoromethyl-phenyl)-3-[2-(2,6-dioxo-piperidin-3-yl)-1-oxo-2,3-dihydro-1H-isoindol-5-ylmethyl]-urea; 1-[2-(2,6-dioxo-piperidin-3-yl)-1-oxo-2,3-dihydro-1H-isoindol-5-ylmethyl]-3-(4-trifluoromethylsulfanyl-phenyl)-urea; 1-[2-(2,6-dioxo-piperidin-3-yl)-1-oxo-2,3-dihydro-1H-isoindol-5-ylmethyl]-3-(4-methyl-3-trifluoromethyl-phenyl)-thiourea; 1-[2-(2,6-dioxo-piperidin-3-yl)-1-oxo-2,3-dihydro-1H-isoindol-5-ylmethyl]-3-(4-trifluoromethylsulfanyl-phenyl)-thiourea; 1-[2-(2,6-dioxo-piperidin-3-yl)-1-oxo-2,3-dihydro-1H-isoindol-5-ylmethyl]-3-(4-trifluoromethoxy-phenyl)-urea; 1-(3-chloro-4-methyl-phenyl)-3-[2-(2,6-dioxo-piperidin-3-yl)-1-oxo-2,3-dihydro-1H-isoindol-5-ylmethyl]-thiourea; 1-[2-(2,6-dioxo-piperidin-3-yl)-1-oxo-2,3-dihydro-1H-isoindol-5-ylmethyl]-3-(4-methoxy-phenyl)-urea; 1-[2-(2,6-dioxo-piperidin-3-yl)-1-oxo-2,3-dihydro-1H-isoindol-5-ylmethyl]-3-(4-fluoro-phenyl)-urea; 1-(3-chloro-4-fluoro-phenyl)-3-[2-(2,6-dioxo-piperidin-3-yl)-1-oxo-2,3-dihydro-1H-isoindol-5-ylmethyl]-urea; 1-(3,4-dimethyl-phenyl)-3-[2-(2,6-dioxo-piperidin-3-yl)-1-oxo-2,3-dihydro-1H-isoindol-5-ylmethyl]-urea; 1-(3,5-dichloro-phenyl)-3-[2-(2,6-dioxo-piperidin-3-yl)-1-oxo-2,3-dihydro-1H-isoindol-5-ylmethyl]-urea; 1-[2-(2,6-dioxo-piperidin-3-yl)-1-oxo-2,3-dihydro-1H-isoindol-5-ylmethyl]-3-phenyl-urea; 1-(4-chloro-2-methyl-phenyl)-3-[2-(2,6-dioxo-piperidin-3-yl)-1-oxo-2,3-dihydro-1H-isoindol-5-ylmethyl]-urea; 1-(3,4-dimethoxy-phenyl)-3-[2-(2,6-dioxo-piperidin-3-yl)-1-oxo-2,3-dihydro-1H-isoindol-5-ylmethyl]-urea; 1-[2-(2,6-dioxo-piperidin-3-yl)-1-oxo-2,3-dihydro-1H-isoindol-5-ylmethyl]-3-naphthalen-1-yl-urea; 1-(2,5-dichloro-phenyl)-3-[2-(2,6-dioxo-piperidin-3-yl)-1-oxo-2,3-dihydro-1H-isoindol-5-ylmethyl]-urea; 1-[2-(2,6-dioxo-piperidin-3-yl)-1-oxo-2,3-dihydro-1H-isoindol-5-ylmethyl]-3-(4-methyl-3-trifluoromethyl-phenyl)-urea; 1-(5-chloro-2-methoxy-phenyl)-3-[2-(2,6-dioxo-piperidin-3-yl)-1-oxo-2,3-dihydro-1H-isoindol-5-ylmethyl]-urea; 1-(2-chloro-5-methyl-phenyl)-3-[2-(2,6-dioxo-piperidin-3-yl)-1-oxo-2,3-dihydro-1H-isoindol-5-ylmethyl]-urea; 1-(5-chloro-2-methyl-phenyl)-3-[2-(2,6-dioxo-piperidin-3-yl)-1-oxo-2,3-dihydro-1H-isoindol-5-ylmethyl]-urea; 1-[2-(2,6-dioxo-piperidin-3-yl)-1-oxo-2,3-dihydro-1H-isoindol-5-ylmethyl]-3-(2,4,6-trichloro-phenyl)-urea; 1-[2-(2,6-dioxo-piperidin-3-yl)-1-oxo-2,3-dihydro-1H-isoindol-5-ylmethyl]-3-p-tolyl-urea; 1-(4-bromo-phenyl)-3-[2-(2,6-dioxo-piperidin-3-yl)-1-oxo-2,3-dihydro-1H-isoindol-5-ylmethyl]-urea; 1-(2,4-dichloro-phenyl)-3-[2-(2,6-dioxo-piperidin-3-yl)-1-oxo-2,3-dihydro-1H-isoindol-5-ylmethyl]-urea; 1-(3-chloro-2-methyl-phenyl)-3-[2-(2,6-dioxo-piperidin-3-yl)-1-oxo-2,3-dihydro-1H-isoindol-5-ylmethyl]-urea; 1-(2-chloro-5-trifluoromethyl-phenyl)-3-[2-(2,6-dioxopiperidin-3-yl)-1-oxo-2,3-dihydro-1H-isoindol-5-ylmethyl]-urea; 1-[2-(2,6-dioxo-piperidin-3-yl)-1-oxo-2,3-dihydro-1H-isoindol-5-ylmethyl]-3-(4-ethyl-phenyl)-urea; and 1-(3,5-dimethyl-phenyl)-3-[2-(2,6-dioxo-piperidin-3-yl)-1-oxo-2,3-dihydro-1H-isoindol-5-ylmethyl]-urea.

These compounds exhibited $IC_{50}$ values in the range of 0.01 to 5 µM.

5.198 Anti-Proliferative Activity Against Breast Tumor (I)

In one experiment, anti-proliferative effect of certain compounds provided herein were tested using MDAMB321 cells (breast cancer) according to the cell proliferation assay substantially similar to that described in 5.188.8, above.

Tested compounds included the following: 3,4-dichloro-N-[2-(2,6-dioxo-piperidin-3-yl)-1-oxo-2,3-dihydro-1H-isoindol-5-ylmethyl]-benzamide; 2-(4-chloro-phenyl)-N-[2-(2,6-dioxo-piperidin-3-yl)-1-oxo-2,3-dihydro-1H-isoindol-5-ylmethyl]-acetamide; N-[[2-(2,6-dioxopiperidin-3-yl)-1-oxoisoindolin-5-yl]methyl]-4-(trifluoromethylthio)benzamide; 4-tert-butyl-N-((2-(2,6-dioxopiperidin-3-yl)-1,3-dioxoisoindolin-5-yl)methyl)benzamide; 1-(3,4-dichloro-phenyl)-3-[2-(2,6-dioxo-piperidin-3-yl)-1,3-dioxo-2,3-dihydro-1H-isoindol-5-ylmethyl]-urea; 1-(3,4-dimethyl-phenyl)-3-[2-(2,6-dioxo-piperidin-3-yl)-1,3-dioxo-2,3-dihydro-1H-isoindol-5-ylmethyl]-urea; 1-(4-chloro-phenyl)-3-[2-(2,6-dioxo-piperidin-3-yl)-1,3-dioxo-2,3-dihydro-1H-isoindol-5-ylmethyl]-urea; 1-(3-chloro-4-methyl-phenyl)-3-[2-(2,6-dioxo-piperidin-3-yl)-1-oxo-2,3-dihydro-1H-isoindol-5-ylmethyl]-urea; 1-(4-chloro-phenyl)-3-[2-(2,6-dioxo-piperidin-3-yl)-1-oxo-2,3-dihydro-1H-isoindol-5-ylmethyl]-urea; 1-[2-(2,6-dioxo-piperidin-3-yl)-1-oxo-2,3-dihydro-1H-isoindol-5-ylmethyl]-3-hexyl-urea; 1-(4-tert-butyl-phenyl)-3-[2-(2,6-dioxo-piperidin-3-yl)-1,3-dioxo-2,3-dihydro-1H-isoindol-5-ylmethyl]-urea; 1-[2-(2,6-dioxo-piperidin-3-yl)-1,3-dioxo-2,3-dihydro-1H-isoindol-5-ylmethyl]-3-(4-trifluoromethoxy-phenyl)-urea; 1-(4-chloro-phenyl)-3-[2-(2,6-dioxo-piperidin-3-yl)-1,3-dioxo-2,3-dihydro-1H-isoindol-5-ylmethyl]-thiourea; 1-(4-chloro-3-methyl-phenyl)-3-[2-(2,6-dioxo-piperidin-3-yl)-1,3-dioxo-2,3-dihydro-1H-isoindol-5-ylmethyl]-urea; and 1-[2-(2,6-dioxo-piperidin-3-yl)-1,3-dioxo-2,3-dihydro-1H-isoindol-5-ylmethyl]-3-m-tolyl-urea.

These compounds exhibited $IC_{50}$ values in the range of 0.0004 to 4.5 µM.

5.199 Anti-Proliferative Activity Against Breast Tumor (II)

In another experiment, anti-proliferative effect of certain compounds provided herein were tested using MDAMB321 cells (breast cancer) according to the cell proliferation assay substantially similar to that described in 5.188.8, above.

Tested compounds included the following: N-[2-(2,6-dioxo-piperidin-3-yl)-1-oxo-2,3-dihydro-1H-isoindol-5-ylmethyl]-2-(4-trifluoromethylsulfanyl-phenyl)-acetamide; 3-chloro-N-[2-(2,6-dioxo-piperidin-3-yl)-1-oxo-2,3-dihydro-1H-isoindol-5-ylmethyl]-4-methyl-benzamide; 2-(3,4-dichloro-phenyl)-N-[2-(2,6-dioxo-piperidin-3-yl)-1-oxo-2,3-dihydro-1H-isoindol-5-ylmethyl]-acetamide; N-[2-(2,6-dioxo-piperidin-3-yl)-1-oxo-2,3-dihydro-1H-isoindol-5-ylmethyl]-4-ethylsulfanyl-benzamide; 4-tert-butyl-N-[2-(2,6-dioxo-piperidin-3-yl)-1-oxo-2,3-dihydro-1H-isoindol-5-ylmethyl]-benzamide; 1-(3,4-dichloro-phenyl)-3-[2-(2,6-dioxo-piperidin-3-yl)-1-oxo-2,3-dihydro-1H-isoindol-5-ylmethyl]-urea; 1-(3-chloro-4-(trifluoromethyl)phenyl)-3-((2-(2,6-dioxopiperidin-3-yl)-1-oxoisoindolin-5-yl)methyl)urea; 1-(3-chloro-4-methyl-phenyl)-3-[2-(3-methyl-2,6-dioxo-piperidin-3-yl)-1,3-dioxo-2,3-dihydro-1H-isoindol-5-ylmethyl]-urea; 1-(4-tert-butyl-phenyl)-3-[2-(2,6-dioxo-piperidin-3-yl)-1-oxo-2,3-dihydro-1H-isoindol-5-ylmethyl]-urea; 1-(2-chloro-phenyl)-3-[2-(2,6-dioxo-piperidin-3-yl)-1-oxo-2,3-dihydro-1H-isoindol-5-ylmethyl]-urea; 1-(3-chloro-phenyl)-3-[2-(2,6-dioxo-piperidin-3-yl)-1-oxo-2,3-dihydro-1H-isoindol-5-ylmethyl]-urea; 1-(4-chloro-3-trifluoromethyl-phenyl)-3-[2-(2,6-dioxo-piperidin-3-yl)-1-oxo-2,3-dihydro-1H-isoindol-5-ylmethyl]-urea; 1-[2-(2,6-dioxo-piperidin-3-yl)-1-oxo-2,3-dihydro-1H-isoindol-5-ylmethyl]-3-(4-trifluoromethylsulfanyl-phenyl)-urea; 1-[2-(2,6-dioxo-piperidin-3-yl)-1-oxo-2,3-dihydro-1H-isoindol-5-ylmethyl]-3-(4-methyl-3-trifluoromethyl-phenyl)-thiourea; 1-[2-(2,6-dioxo-piperidin-3-yl)-1-oxo-2,3-dihydro-1H-isoindol-5-ylmethyl]-3-(4-trifluoromethylsulfanyl-phenyl)-thiourea; 1-[2-(2,6-dioxo-piperidin-3-yl)-1-oxo-2,3-dihydro-1H-isoindol-5-ylmethyl]-3-(4-ethoxy-phenyl)-urea; 1-[2-(2,6-dioxo-piperidin-3-yl)-1-oxo-2,3-dihydro-1H-isoindol-5-ylmethyl]-3-(4-trifluoromethoxy-phenyl)-urea; 1-(3-chloro-4-methyl-phenyl)-3-[2-(2,6-dioxo-piperidin-3-yl)-1-oxo-2,3-dihydro-1H-isoindol-5-ylmethyl]-thiourea; 1-[2-(2,6-dioxo-piperidin-3-yl)-1-oxo-2,3-dihydro-1H-isoindol-5-ylmethyl]-3-(4-methoxy-phenyl)-urea; 1-[2-(2,6-dioxo-piperidin-3-yl)-1-oxo-2,3-dihydro-1H-isoindol-5-ylmethyl]-3-(4-fluoro-phenyl)-urea; 1-(3-chloro-4-fluoro-phenyl)-3-[2-(2,6-dioxo-piperidin-3-yl)-1-oxo-2,3-dihydro-1H-isoindol-5-ylmethyl]-urea; 1-(3,4-dimethyl-phenyl)-3-[2-(2,6-dioxo-piperidin-3-yl)-1-oxo-2,3-dihydro-1H-isoindol-5-ylmethyl]-urea; 1-(3,5-dichloro-phenyl)-3-[2-(2,6-dioxo-piperidin-3-yl)-1-oxo-2,3-dihydro-1H-isoindol-5-ylmethyl]-urea; 1-[2-(2,6-dioxo-piperidin-3-yl)-1-oxo-2,3-dihydro-1H-isoindol-5-ylmethyl]-3-phenyl-urea; 1-(4-chloro-2-methyl-phenyl)-3-[2-(2,6-dioxo-piperidin-3-yl)-1-oxo-2,3-dihydro-1H-isoindol-5-ylmethyl]-urea; 1-(3,4-dimethoxy-phenyl)-3-[2-(2,6-dioxo-piperidin-3-yl)-1-oxo-2,3-dihydro-1H-isoindol-5-ylmethyl]-urea; 1-(2-Chloro-6-methyl-phenyl)-3-[2-(2,6-dioxo-piperidin-3-yl)-1-oxo-2,3-dihydro-1H-isoindol-5-ylmethyl]-urea; 1-[2-(2,6-dioxo-piperidin-3-yl)-1-oxo-2,3-dihydro-1H-isoindol-5-ylmethyl]-3-naphthalen-1-yl-urea; 1-(2,5-dichloro-phenyl)-3-[2-(2,6-dioxo-piperidin-3-yl)-1-oxo-2,3-dihydro-1H-isoindol-5-ylmethyl]-urea; 1-[2-(2,6-dioxo-piperidin-3-yl)-1-oxo-2,3-dihydro-1H-isoindol-5-ylmethyl]-3-(4-methyl-3-trifluoromethyl-phenyl)-urea; 1-(5-chloro-2-methoxy-phenyl)-3-[2-(2,6-dioxo-piperidin-3-yl)-1-oxo-2,3-dihydro-1H-isoindol-5-ylmethyl]-urea; 1-(2-chloro-5-methyl-phenyl)-3-[2-(2,6-dioxo-piperidin-3-yl)-1-oxo-2,3-dihydro-1H-isoindol-5-ylmethyl]-urea; 1-(5-chloro-2-methyl-phenyl)-3-[2-(2,6-dioxo-piperidin-3-yl)-1-oxo-2,3-dihydro-1H-isoindol-5-ylmethyl]-urea; 1-[2-(2,6-dioxo-piperidin-3-yl)-1-oxo-2,3-dihydro-1H-isoindol-5-ylmethyl]-3-(2,4,6-trichloro-phenyl)-urea; 1-[2-(2,6-dioxo-piperidin-3-yl)-1-oxo-2,3-dihydro-1H-isoindol-5-ylmethyl]-3-p-tolyl-urea; 1-(4-bromo-phenyl)-3-[2-(2,6-dioxo-piperidin-3-yl)-1-oxo-2,3-dihydro-1H-isoindol-5-ylmethyl]-urea; 1-(2,4-dichloro-phenyl)-3-[2-(2,6-dioxo-piperidin-3-yl)-1-oxo-2,3-dihydro-1H-isoindol-5-ylmethyl]-urea; 1-(3-chloro-2-methyl-phenyl)-3-[2-(2,6-dioxo-piperidin-3-yl)-1-oxo-2,3-dihydro-1H-isoindol-5-ylmethyl]-urea; 1-(2-chloro-5-trifluoromethyl-phenyl)-3-[2-(2,6-dioxopiperidin-3-yl)-1-oxo-2,3-dihydro-1H-isoindol-5-ylmethyl]-urea; 1-[2-(2,6-dioxo-piperidin-3-yl)-1-oxo-2,3-dihydro-1H-isoindol-5-ylmethyl]-3-(4-ethyl-phenyl)-urea; and 1-(3,5-dimethyl-phenyl)-3-[2-(2,6-dioxo-piperidin-3-yl)-1-oxo-2,3-dihydro-1H-isoindol-5-ylmethyl]-urea.

These compounds exhibited $IC_{50}$ values in the range of 0.001 to 3 µM.

5.200 Additional Anti-Proliferative Activity

In other experiments, anti-proliferative effect of certain compounds provided herein were tested using Namalwa, HN 5q, HT-1080, SK-MES-1, and PC-3 cells according to the cell proliferation assay substantially similar to that described in 5.188.3, above.

The tested compounds exhibited $IC_{50}$ values in the ranges of: 0.5 to 200 µM for Namalwa cells; 0.0001 to 10 µM for HN 5q cells; 0.01 to 20 µM for HT-1080 cells; 0.001 to 30 µM for SK-MES-1 cells; and 0.005 to 10 µM for PC-3 cells. These results show that compounds provided herein exhibit anti-proliferative effect on various cancer cells.

In another experiment, two human glioblastoma cell lines, T98G (glioblastoma multiforme; mutant p53) and U87MG (brain grade III glioblastoma-astrocytoma; wildtype p53), and two human neuroblastoma cell lines, SH-SY5Y (derived from bone marrow metastatic site; trisomy of chromosome 1q; MYCN amplified) and SK-N-MC (derived from supraorbital area metastatic site; pseudodiploid with modal chromosome number of 46; tumorigenic in nude mice) were obtained from ATCC. These cell lines were grown up; low-passage number stocks were frozen down in liquid nitrogen. Compounds were reconstituted in DMSO to obtain a 10 mM stock. Cells were plated in 96 well plates at $5 \times 10^3$ cells/100 µl media per well. Cells were allowed to adhere overnight at 37° C. in a 94% humidified incubator with 5% $CO_2$. Following overnight incubation, cells were treated in triplicate with the lead CC compounds at 100, 10, 0.1, 0.01, 0.001 and 0.0001 and 0 µM in a final concentration of 0.1% DMSO for a 72 hour treatment period. Cell proliferation was determined by the $^3$H-thymidine cell proliferation assay. $IC_{50}$s were calculated from the transformed data using non-linear regression, sigmoidal dose response using GraphPad Prism v4.0.

The tested compounds exhibited $IC_{50}$ values in the ranges of: 0.1 µM to about 1 mM for T98G cells; 0.05 to about 150 µM for U87MG cells; 0.0001 to 0.5 µM for SH-SY5Y; and 0.0001 to 0.1 µM for SK-N-MC cells. These results also show that compounds provided herein possess anti-proliferative activity against various cancer cells.

The embodiments of the invention described above are intended to be merely exemplary, and those skilled in the art will recognize, or will be able to ascertain using no more than routine experimentation, numerous equivalents of specific compounds, materials, and procedures. All such equivalents are considered to be within the scope of the invention and are encompassed by the appended claims.

All of the patents, patent applications and publications referred to herein are incorporated herein in their entireties. Citation or identification of any reference in this application is not an admission that such reference is available as prior art to this invention. The full scope of the invention is better understood with reference to the appended claims.

What is claimed is:

1. A method of treating or managing a disease or disorder which comprises administering to a patient in need of such treatment or management a therapeutically effective amount of a compound of formula (I):

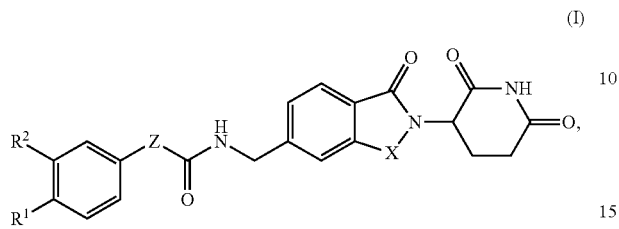

or a pharmaceutically acceptable salt, solvate, or stereoisomer thereof, wherein:
X is $CH_2$ or $C=O$;
Z is: $(CH_2)_m$, wherein m is 0 or 1; or NH;
$R^1$ is halogen or $(C_1-C_6)$alkyl, itself optionally substituted with one or more halogen; and
$R^2$ is hydrogen; halogen; or $(C_1-C_6)$alkyl, itself optionally substituted with one or more halogen; and
wherein the disease or disorder is cancer or a disorder associated with angiogenesis.

2. The method of claim 1, wherein the disease or disorder is cancer.

3. The method of claim 2, wherein the cancer is a cancer of the skin, lung, ovary, prostate, colon, rectum, brain, head and neck, throat, pancreas, blood, bone, liver or bladder.

* * * * *